(12) United States Patent
Paramithiotis et al.

(10) Patent No.: US 9,857,378 B2
(45) Date of Patent: Jan. 2, 2018

(54) TUBERCULOSIS BIOMARKERS AND USES THEREOF

(71) Applicants: CAPRION PROTEOMICS, Montreal (CA); Albert Einstein College of Medicine, Inc., Bronx, NY (US)

(72) Inventors: Eustache Paramithiotis, Boucherville (CA); Pascal Croteau, Laval (CA); Jacqueline Michele Achkar, Brooklyn, NY (US)

(73) Assignees: Caprion Proteomics Inc., Montreal (CA); Albert Einstein College of Medicine, Inc., Bronx, NY (US)

(*) Notice: Subject to any disclaimer, the term of this patent is extended or adjusted under 35 U.S.C. 154(b) by 0 days.

(21) Appl. No.: 14/835,939

(22) Filed: Aug. 26, 2015

(65) Prior Publication Data
US 2016/0154005 A1 Jun. 2, 2016

Related U.S. Application Data

(63) Continuation of application No. PCT/US2014/017289, filed on Feb. 20, 2014.

(60) Provisional application No. 61/770,432, filed on Feb. 28, 2013.

(51) Int. Cl.
| | |
|---|---|
| *A61K 39/04* | (2006.01) |
| *A61K 39/02* | (2006.01) |
| *A61K 39/40* | (2006.01) |
| *G01N 33/68* | (2006.01) |
| *G01N 33/569* | (2006.01) |

(52) U.S. Cl.
CPC ..... *G01N 33/6848* (2013.01); *G01N 33/5695* (2013.01); *G01N 2500/04* (2013.01); *G01N 2560/00* (2013.01); *G01N 2800/52* (2013.01); *G01N 2800/60* (2013.01)

(58) Field of Classification Search
CPC ......... A61K 39/00; A61K 39/02; A61K 39/04
USPC ......... 424/130.1, 164.1, 234.1, 248.1; 435/4, 435/7.1
See application file for complete search history.

(56) References Cited

U.S. PATENT DOCUMENTS

| | | |
|---|---|---|
| 2009/0104602 A1 | 4/2009 | Fernandez-Reyes et al. |
| 2011/0015087 A1* | 1/2011 | Nagore Casas ...... G01N 33/689 506/9 |
| 2011/0129817 A1 | 6/2011 | Banchereau et al. |
| 2011/0151490 A1* | 6/2011 | Hillman ............... C12Q 1/6886 435/7.92 |
| 2011/0165146 A1* | 7/2011 | Westbrook ......... G01N 33/6896 424/130.1 |
| 2011/0196614 A1 | 8/2011 | Banchereau et al. |
| 2011/0236411 A1 | 9/2011 | Scholler et al. |

FOREIGN PATENT DOCUMENTS

| | | |
|---|---|---|
| WO | WO-2000/066143 A1 | 11/2000 |
| WO | WO-2006/125973 A2 | 11/2006 |
| WO | WO-2011/101787 A1 | 8/2011 |
| WO | WO-2012/085652 A2 | 6/2012 |
| WO | WO-2012/115885 A1 | 8/2012 |

OTHER PUBLICATIONS

Wallis et al.,"Biomarkers and diagnostics for tuberculosis: progress, needs, and translation into practice", Lancet, May 19, 2010, pp. 1920-1937.
Walzl et al., "Immunological biomarkers of tuberculosis", Nature Reviews Immunology, vol. 11, No. 5, Apr. 8, 2011, pp. 343-354.
Matsuyama et al., "Increased Serum Level of Vascular Endothelial Growth Factor in Pulmonary Tuberculosis", American Journal of Respiratory and Critical Care Medicine, vol. 162, No. 3, Sep. 1, 2000, pp. 1120-1122.
International Search Report from PCT/US2014/017289, dated Jun. 20, 2014.
Liu et al., Proteomic Analysis of Pericardial Effusion: Characteristics of Tuberculosis-Related Proteins, Proteomics Clin Appl., 2008; 2(4):458-66.
Ayaslioglu et al., "The Role of CD14 Gene Promoter Polymorphism in Tuberculosis Susceptibility", Journal of Microbiology, Immunology and Infection, 2013, 46, 158-163.
Lawn et al., "Elevated serum concentrations of soluble CD14 in HIV- and HIV+ patients with tuberculosis in Africa: Prolonged elevation during anti-tuberculosis treatment," Clin Exp Immunol, 2000, 120(3):483-7.
Achkar et al."Host Protein Biomarkers Identify Active Tuberculosis in HIV Uninfected and Co-infected Individuals," EBioMedicine, 2015, 2:1160-1168.
Paulette, "14-3-3 proteins—an update," Cell Research, 15(4):228-236, Apr. 2005.

* cited by examiner

*Primary Examiner* — Rodney P Swartz
(74) *Attorney, Agent, or Firm* — McCarter & English, LLP; Jonathan M. Sparks; Deborah L. Nagle

(57) ABSTRACT

The present invention provides biomarkers, methods and kits for diagnosing active tuberculosis in a subject, methods and kits for monitoring the effectiveness of treatment for active TB, as well as methods for identifying a compound that can treat TB reduce or inhibit the development of complications associated with the disease in a subject, and methods to treat active TB.

13 Claims, 6 Drawing Sheets

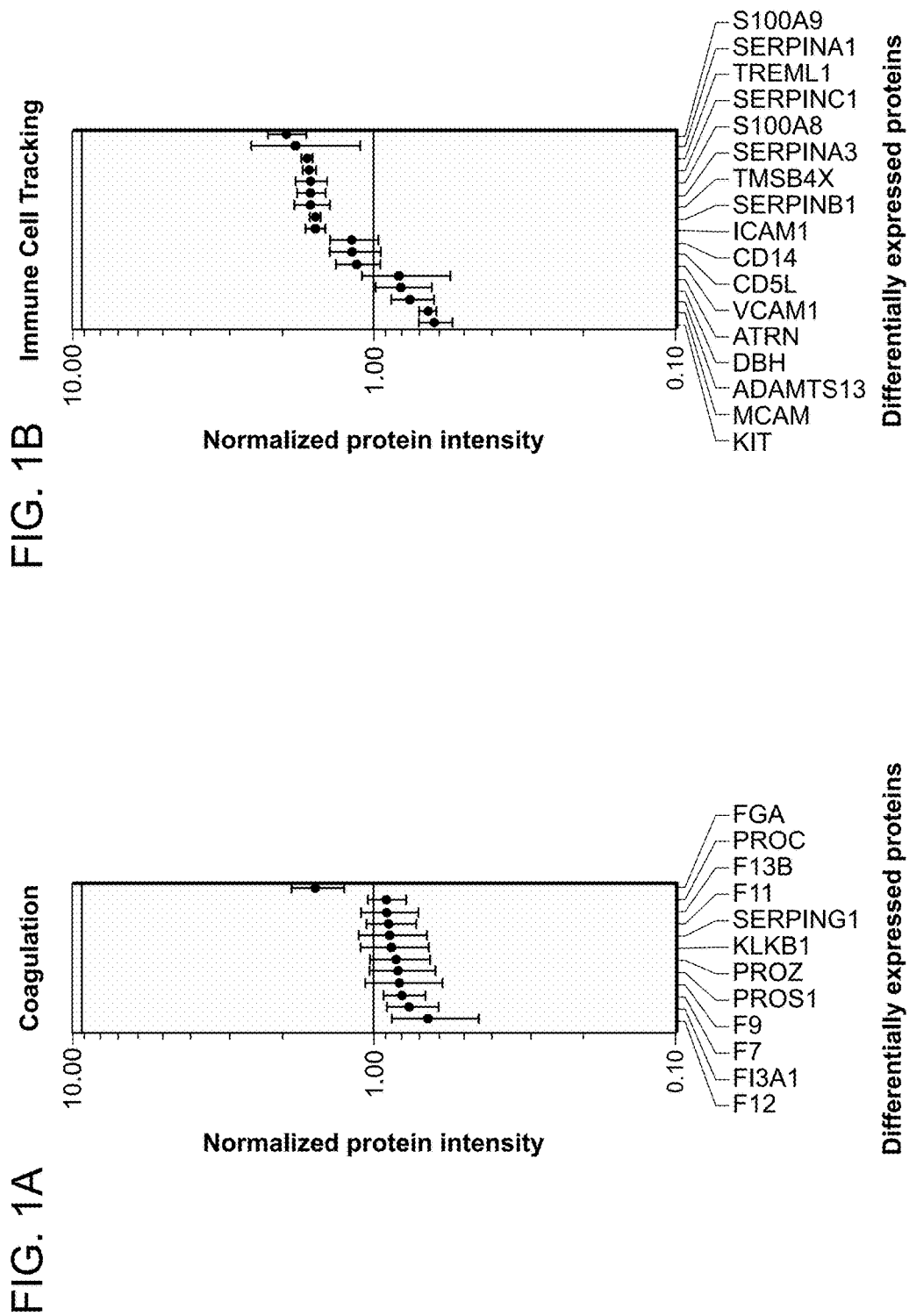

Figure 2

TUBERCULOSIS BIOMARKERS AND USES THEREOF

RELATED APPLICATIONS

This application is a 35 U.S.C. 111(a) continuation application, which claims the benefit of priority to PCT/US2014/017289, filed on Feb. 20, 2014 and U.S. Provisional Patent Application Ser. No. 61/770,432, filed on Feb. 28, 2013, the entire contents of each of which is incorporated herein by reference.

BACKGROUND OF THE INVENTION

Tuberculosis (TB) remains a major global public health problem. About a third of the world's population is latently infected with *Mycobacterium tuberculosis*, and an estimated 8.7 million new TB cases were diagnosed in 2011 (World Health Organization, Global tuberculosis control: WHO report 2011, 2011: Geneva, Switzerland). In addition, in 2011 almost one million TB-associated deaths occurred among HIV uninfected (HIV−) individuals and about 0.43 million deaths among HIV-infected (HIV+) individuals.

In addition to prevention, the cornerstones of TB control are reduction of transmission, morbidity, and mortality all of which require early treatment initiation. This in turn necessitates timely TB diagnosis, underlining the need for new rapid diagnostic tests. Rapid identification of active TB is the key unmet need in TB disease management.

Currently, TB diagnostic tests depend on the detection of *M. tuberculosis* which, thus, require a specimen from the site of disease which is not always easy to obtain. Furthermore, the current tests for TB are limited by lack of sensitivity (microscopy of sputum smears) or require amplification of *M. tuberculosis* which takes weeks (culture) and/or is expensive (molecular detection). Moreover, these gold standard tests (culture and molecular detection) require laboratory infrastructure which is not accessible in many endemic regions.

Accordingly, there is a need in the art for novel TB biomarkers that are easily detectable, and neither require a specimen from the site of infection, nor laboratory infrastructure to provide rapid TB diagnosis and limit the spread of the disease.

SUMMARY OF THE INVENTION

The present invention is based, at least in part, on the discovery of markers that are associated with the presence of active tuberculosis (TB). Accordingly, the present invention provides sensitive and facile methods and kits for determining whether a subject has active TB, as well as methods for identifying a compound that can treat active TB, methods of monitoring the effectiveness of a therapy for treating active TB in a subject, and methods for treating a subject having active TB by measuring and identifying particular markers, or particular combinations of markers.

Accordingly, in one aspect the present invention provides methods for determining whether a subject has active tuberculosis (TB). The methods include determining the level of one or more markers listed in Table 1 in a sample(s) from the subject; comparing the level of the one or more markers in the subject sample(s) with a level of the one or more markers in a control sample(s), wherein a difference in the level of the one or more markers in the subject sample(s) as compared to the level of the one or more markers in the control sample(s) indicates that the subject has active TB.

In one aspect the present invention provides methods for monitoring the effectiveness of a treatment in a subject having active tuberculosis (TB). The methods include determining the level of one or more markers listed in Table 1 in a first sample(s) from the subject prior to the initiation of the treatment; determining the level of one or more markers listed in Table 1 in a second sample(s) from the subject after at least a portion of the treatment has been administered; comparing the level of the one or more markers in the first sample(s) with a level of the one or more markers in the second sample(s), wherein a difference in the level of the one or more markers in the first sample(s) as compared to the level of the one or more markers in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers listed in Table 1 in each of the aliquots; and selecting a member of the library of compounds which modulates the level and/or the activity of the one or more markers listed in Table 1 in an aliquot as compared to the level and/or activity of the one or more markers of the invention in a control sample, thereby identifying a compound that is useful for treating a subject having active TB.

In one aspect the present invention provides methods for treating a subject having active tuberculosis (TB). The methods include administering to the subject an effective amount of an agent that modulates the level and/or activity of any one or more of the markers listed in Table 1, thereby treating the subject.

In one embodiment, the subject is HIV positive (HIV+). In another embodiment, the subject is HIV negative (HIV−).

In one embodiment, the level of the marker is an expression level and/or activity of the marker.

In one embodiment, the level in the subject sample(s) is determined by mass spectrometry. In one embodiment, the mass spectrometry is matrix assisted laser desorption/time of flight (MALDI/TOF) mass spectrometry, liquid chromatography quadruple ion trap electrospray (LCQ-MS), or surface enhanced laser desorption ionization/time of flight (SELDI/TOF) mass spectrometry. In another embodiment, the level in the subject sample(s) is determined by immunoassay.

In one embodiment, the sample(s) from the subject is a fluid sample(s). In another embodiment, the sample(s) from the subject is a tissue sample(s).

In one embodiment, the subject resides in North America or Europe.

In one embodiment, the one or more markers is selected from the group consisting of APOE, SELL, TNXB, COMP, LUM, PGLYRP2, HABP2, LRG1, QSOX1, S100A8, APOC3, LCP1, VASN, PFN1, IGFBP6, LRG1, APOA4, BCHE, PI16, SEPP1, APOA1, IGFALS, CD14, TAGLN2, CPN2, APOC1, PEPD, GP1BA and PTGDS.

In another embodiment, the methods further comprise determining the level of one or CPB2, GP1BA, GP5, GPX3, PROCR, VWF, ATRN, CD14, DBH, SELL, VCAM1, S100A8, S100A9, CD163, CPN1, FCN3, HIST2H2BE, KNG1, MASP1, MASP2, PROS1, YWHAZ, CA1, ORM1, PDLIM1, PGLYRP2, LCAT, LPA, PCSK9, PON1, PTGDS, APOA1, APOA4, APOC1, APOC3, APOE, ANPEP, BCHE, BTD, CDH5, CLEC3B, CLU, CNTN1, ECM1, GPLD1, HABP2, HGFAC, HYOU1, IGFALS, IGFBP3, IGFBP6, LCP1, LGALS3BP, LUM, MINPP1, MST1, NCAM1, NID1, PEPD, PFN1, PRG4, QSOX1, SEPP1, SHBG, SPARC, TGFBI, THBS1, TLN1, TNXB, VASN, VTN, YWHAE, CA2, CKM, CNDP1, COMP, IGF2, LRG1, PI16, PRDX2, PTPRG, SPP2, TAGLN2, ZYX, MTB81, MTB51, CACNA2D1, CPN2, and MAN1A1.

In one aspect the present invention provides methods for determining whether a subject has active tuberculosis (TB). The methods include determining the level of CD14 and the level of APOE in a sample(s) from the subject; comparing the level of CD14 and the level of APOE in the subject sample(s) with a level of CD14 and a level of APOE in a control sample(s), wherein a difference in the level of CD14 and a difference in the level of APOE in the subject sample(s) as compared to the level of CD14 and the level of APOE in the control sample(s) indicates that the subject has active TB.

In one aspect the present invention provides methods for monitoring the effectiveness of a treatment in a subject having active tuberculosis (TB). The methods include determining the level of CD14 and the level of APOE in a first sample(s) from the subject prior to the initiation of the treatment; determining the level of CD14 and the level of APOE in a second sample(s) from the subject after at least a portion of the treatment has been administered; comparing the level of CD14 and the level of APOE in the first sample(s) with a level of CD14 and the level of APOE in the second sample(s), wherein a difference in the level of CD14 and a difference in the level of APOE in the first sample(s) as compared to the level of the CD14 and the level of APOE in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14 and the level and/or activity of APOE in each of the aliquots; and selecting a member of the library of compounds which modulates the level and/or the activity of CD14 and the level and/or activity of APOE in an aliquot as compared to the level and/or activity of CD14 and the level and/or activity of APOE in a control sample, thereby identifying a compound that is useful for treating a subject having active TB.

In one aspect the present invention provides methods for treating a subject having active tuberculosis (TB). The methods include administering to the subject an effective amount of an agent that modulates the level and/or activity of CD14 and the level and/or activity of APOE, thereby treating the subject.

In one aspect the present invention provides methods for determining whether a subject has active tuberculosis (TB). The methods include determining the level of PEPD and the level of SELL in a sample(s) from the subject; comparing the level of PEPD and the level of SELL in the subject sample(s) with a level of PEPD and a level of SELL in a control sample(s), wherein a difference in the level of PEPD and a difference in the level of SELL in the subject sample(s) as compared to the level of PEPD and the level of SELL in the control sample(s) indicates that the subject has active TB.

In one aspect the present invention provides methods for monitoring the effectiveness of a treatment in a subject having active tuberculosis (TB). The methods include determining the level of PEPD and the level of SELL in a first sample(s) from the subject prior to the initiation of the treatment; determining the level of PEPD and the level of SELL in a second sample(s) from the subject after at least a portion of the treatment has been administered; comparing the level of PEPD and the level of SELL in the first sample(s) with a level of PEPD and the level of SELL in the second sample(s), wherein a difference in the level of PEPD and the level of SELL in the first sample(s) as compared to the level of PEPD and the level of SELL in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PEPD and the level and/or activity of SELL in each of the aliquots; and selecting a member of the library of compounds which modulates the level and/or the activity of PEPD and the level and/or activity of SELL in an aliquot as compared to the level and/or activity of PEPD and the level and/or activity of SELL of the invention in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PEPD and the level and/or activity of SELL, thereby treating the subject.

In one aspect the present invention provides methods for determining whether a subject has active tuberculosis (TB). The methods include determining the level of PEPD, the level of SELL, and the level of TNXB in a sample(s) from the subject; comparing the level of PEPD, the level of SELL, and the level of TNXB in the subject sample(s) with a level of PEPD, a level of SELL, and a level of TNXB in a control sample(s), wherein a difference in the level of PEPD, a difference in the level of SELL, and a difference in the level of TNXB in the subject sample(s) as compared to the level of PEPD, the level of SELL, and the level of TNXB in the control sample(s) indicates that the subject has active TB.

In one aspect the present invention provides methods for monitoring the effectiveness of a treatment in a subject having active tuberculosis (TB). The methods include determining the level of PEPD, the level of SELL, and the level of TNXB in a first sample(s) from the subject prior to the initiation of the treatment; determining the level of PEPD, the level of SELL, and the level of TNXB in a second sample(s) from the subject after at least a portion of the treatment has been administered; comparing the level of PEPD, the level of SELL, and the level of TNXB in the first sample(s) with a level of PEPD, the level of SELL, and the level of TNXB in the second sample(s), wherein a difference in the level of PEPD, the level of SELL, and the level of TNXB in the first sample(s) as compared to the level of PEPD, the level of SELL, and the level of TNXB in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PEPD, the level and/or activity of SELL, and the level and/or activity of TNXB in each of the aliquots; and selecting a member of the library of compounds which modulates the level and/or the activity of PEPD, the level and/or activity of SELL, and the level and/or activity of TNXB in an aliquot as compared to the level and/or activity of PEPD, the level and/or activity of SELL, and the level and/or activity of TNXB in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PEPD, the level and/or activity of SELL, and the level and/or activity of TNXB, thereby treating the subject.

In one aspect the present invention provides methods for determining whether a subject has active tuberculosis (TB). The methods include determining the level of PEPD, the level of SELL, and the level of COMP in a sample(s) from the subject; comparing the level of PEPD, the level of SELL, and the level of COMP in the subject sample(s) with a level of PEPD, a level of SELL, and a level of COMP in a control sample(s), wherein a difference in the level of PEPD, a difference in the level of SELL, and a difference in the level of COMP in the subject sample(s) as compared to the level of PEPD, the level of SELL, and the level of COMP in the control sample(s) indicates that the subject has active TB.

In one aspect the present invention provides methods for monitoring the effectiveness of a treatment in a subject having active tuberculosis (TB). The methods include determining the level of PEPD, the level of SELL, and the level of COMP in a first sample(s) from the subject prior to the initiation of the treatment; determining the level of PEPD, the level of SELL, and the level of COMP in a second sample(s) from the subject after at least a portion of the treatment has been administered; comparing the level of PEPD, the level of SELL, and the level of COMP in the first sample(s) with a level of PEPD, the level of SELL, and the level of COMP in the second sample(s), wherein a difference in the level of PEPD, the level of SELL, and the level of COMP in the first sample(s) as compared to the level of PEPD, the level of SELL, and the level of COMP in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PEPD, the level and/or activity of SELL, and the level and/or activity of COMP in each of the aliquots; and selecting a member of the library of compounds which modulates the level and/or the activity of PEPD, the level and/or activity of SELL, and the level and/or activity of COMP in an aliquot as compared to the level and/or activity of PEPD, the level and/or activity of SELL, and the level and/or activity of COMP in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PEPD, the level and/or activity of SELL, and the level and/or activity of COMP, thereby treating the subject.

In one aspect the present invention provides methods for determining whether a subject has active tuberculosis (TB). The methods include determining the level of PEPD, the level of SELL, and the level of QSOX1 in a sample(s) from the subject; comparing the level of PEPD, the level of SELL, and the level of QSOX1 in the subject sample(s) with a level of PEPD, a level of SELL, and a level of QSOX1 in a control sample(s), wherein a difference in the level of PEPD, a difference in the level of SELL, and a difference in the level of QSOX1 in the subject sample(s) as compared to the level of PEPD, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of PEPD, the level of SELL, and the level of QSOX1 in a first sample(s) from the subject prior to the initiation of the treatment; determining the level of PEPD, the level of SELL, and the level of QSOX1 in a second sample(s) from the subject after at least a portion of the treatment has been administered; comparing the level of PEPD, the level of SELL, and the level of QSOX1 in the first sample(s) with a level of PEPD, the level of SELL, and the level of QSOX1 in the second sample(s), wherein a difference in the level of PEPD, the level of SELL, and the level of QSOX1 in the first sample(s) as compared to the level of PEPD, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PEPD, the level and/or activity of SELL, and the level and/or activity of QSOX1 in each of the aliquots; and selecting a member of the library of compounds which modulates the level and/or the activity of PEPD, the level and/or activity of SELL, and the level and/or activity of QSOX1 in an aliquot as compared to the level and/or activity of PEPD, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PEPD, the level and/or activity of SELL, and the level and/or activity of QSOX1, thereby treating the subject.

In one aspect the present invention provides methods for determining whether a subject has active tuberculosis (TB). The methods include determining the level of PEPD, the level of SELL, and the level of CD14 in a sample(s) from the subject; comparing the level of PEPD, the level of SELL, and the level of CD14 in the subject sample(s) with a level of PEPD, a level of SELL, and a level of CD14 in a control sample(s), wherein a difference in the level of PEPD, a difference in the level of SELL, and a difference in the level of CD14 in the subject sample(s) as compared to the level of PEPD, the level of SELL, and the level of CD14 in the control sample(s) indicates that the subject has active TB.

In one aspect the present invention provides methods for monitoring the effectiveness of a treatment in a subject having active tuberculosis (TB). The methods include determining the level of PEPD, the level of SELL, and the level of CD14 in a first sample(s) from the subject prior to the initiation of the treatment; determining the level of PEPD, the level of SELL, and the level of CD14 in a second sample(s) from the subject after at least a portion of the treatment has been administered; comparing the level of PEPD, the level of SELL, and the level of CD14 in the first sample(s) with a level of PEPD, the level of SELL, and the level of CD14 in the second sample(s), wherein a difference in the level of PEPD, the level of SELL, and the level of CD14 in the first sample(s) as compared to the level of PEPD, the level of SELL, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PEPD, the level and/or activity of SELL, and the level and/or activity of CD14 in each of the aliquots; and selecting a member of the library of compounds which modulates the level and/or the activity of PEPD, the level and/or activity of SELL, and the level and/or activity of CD14 in an aliquot as compared to the level and/or activity of PEPD, the level and/or activity of SELL, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PEPD, the level and/or activity of SELL, and the level and/or activity of CD14, thereby treating the subject.

In one aspect the present invention provides methods for determining whether a subject has active tuberculosis (TB). The methods include determining the level of PEPD, the level of SELL, and the level of SEPP1 in a sample(s) from the subject; comparing the level of PEPD, the level of SELL, and the level of SEPP1 in the subject sample(s) with a level of PEPD, a level of SELL, and a level of SEPP1 in a control sample(s), wherein a difference in the level of PEPD, a difference in the level of SELL, and a difference in the level of SEPP1 in the subject sample(s) as compared to the level of PEPD, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of PEPD, the level of SELL, and the level of SEPP1 in a first sample(s) from the subject prior to the initiation of the treatment; determining the level of PEPD, the level of SELL, and the level of SEPP1 in a second sample(s) from the subject after at least a portion of the treatment has been administered; comparing the level of PEPD, the level of SELL, and the level of SEPP1 in the first sample(s) with a level of PEPD, the level of SELL, and the level of SEPP1 in the second sample(s), wherein a difference in the level of PEPD, the level of SELL, and the level of SEPP1 in the first sample(s) as compared to the level of PEPD, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PEPD, the level and/or activity of SELL, and the level and/or activity of SEPP1 in each of the aliquots; and selecting a member of the library of compounds which modulates the level and/or the activity of PEPD, the level and/or activity of SELL, and the level and/or activity of SEPP1 in an aliquot as compared to the level and/or activity of PEPD, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PEPD, the level and/or activity of SELL, and the level and/or activity of SEPP1, thereby treating the subject.

In one aspect the present invention provides methods for determining whether a subject has active tuberculosis (TB). The methods include determining the level of PEPD, the level of SELL, and the level of LUM in a sample(s) from the subject; comparing the level of PEPD, the level of SELL, and the level of LUM in the subject sample(s) with a level of PEPD, a level of SELL, and a level of LUM in a control sample(s), wherein a difference in the level of PEPD, a difference in the level of SELL, and a difference in the level of LUM in the subject sample(s) as compared to the level of PEPD, the level of SELL, and the level of LUM in the control sample(s) indicates that the subject has active TB.

In one aspect the present invention provides methods for monitoring the effectiveness of a treatment in a subject having active tuberculosis (TB). The methods include determining the level of PEPD, the level of SELL, and the level of LUM in a first sample(s) from the subject prior to the initiation of the treatment; determining the level of PEPD, the level of SELL, and the level of LUM in a second sample(s) from the subject after at least a portion of the treatment has been administered; comparing the level of PEPD, the level of SELL, and the level of LUM in the first sample(s) with a level of PEPD, the level of SELL, and the level of LUM in the second sample(s), wherein a difference in the level of PEPD, the level of SELL, and the level of LUM in the first sample(s) as compared to the level of PEPD, the level of SELL, and the level of LUM in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PEPD, the level and/or activity of SELL, and the level and/or activity of LUM in each of the aliquots; and selecting a member of the library of compounds which modulates the level and/or the activity of PEPD, the level and/or activity of SELL, and the level and/or activity of LUM in an aliquot as compared to the level and/or activity of PEPD, the level and/or activity of SELL, and the level and/or activity of LUM in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PEPD, the level and/or activity of SELL, and the level and/or activity of LUM, thereby treating the subject.

In one aspect the present invention provides methods for determining whether a subject has active tuberculosis (TB). The methods include determining the level of TNXB, the level of SELL, and the level of SEPP1 in a sample(s) from the subject; comparing the level of TNXB, the level of SELL, and the level of SEPP1 in the subject sample(s) with a level of TNXB, a level of SELL, and a level of SEPP1 in a control sample(s), wherein a difference in the level of TNXB, a difference in the level of SELL, and a difference in the level of SEPP1 in the subject sample(s) as compared to the level of TNXB, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of TNXB, the level of SELL, and the level of SEPP1 in a first sample(s) from the subject prior to the initiation of the treatment; determining the level of TNXB, the level of SELL, and the level of SEPP1 in a second sample(s) from the subject after at least a portion of the treatment has been administered; comparing the level of TNXB, the level of SELL, and the level of SEPP1 in the first sample(s) with a level of TNXB, the level of SELL, and the level of SEPP1 in the second sample(s), wherein a difference in the level of TNXB, the level of SELL, and the level of SEPP1 in the first sample(s) as compared to the level of TNXB, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of TNXB, the level and/or activity of SELL, and the level and/or activity of SEPP1 in each of the aliquots; and selecting a member of the library of compounds which modulates the level and/or the activity of TNXB, the level and/or activity of SELL, and the level and/or activity of SEPP1 in an aliquot as compared to the level and/or activity of TNXB, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TNXB, the level and/or activity of SELL, and the level and/or activity of SEPP1, thereby treating the subject.

In one aspect the present invention provides methods for determining whether a subject has active tuberculosis (TB). The methods include determining the level of APOC1, the level of SELL, and the level of QSOX1 in a sample(s) from the subject; comparing the level of APOC1, the level of SELL, and the level of QSOX1 in the subject sample(s) with a level of APOC1, a level of SELL, and a level of QSOX1 in a control sample(s), wherein a difference in the level of APOC1, a difference in the level of SELL, and a difference in the level of QSOX1 in the subject sample(s) as compared to the level of APOC1, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of APOC1, the level of SELL, and the level of QSOX1 in a first sample(s) from the subject prior to the initiation of the treatment; determining the level of APOC1, the level of SELL, and the level of QSOX1 in a second sample(s) from the subject after at least a portion of the treatment has been administered; comparing the level of APOC1, the level of SELL, and the level of QSOX1 in the first sample(s) with a level of APOC1, the level of SELL, and the level of QSOX1 in the second sample(s), wherein a difference in the level of APOC1, the level of SELL, and the level of QSOX1 in the first sample(s) as compared to the level of APOC1, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of APOC1, the level and/or activity of SELL, and the level and/or activity of QSOX1 in each of the aliquots; and selecting a member of the library of compounds which modulates the level and/or the activity of APOC1, the level and/or activity of SELL, and the level and/or activity of QSOX1 in an aliquot as compared to the level and/or activity of APOC1, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of SELL, and the level and/or activity of QSOX1, thereby treating the subject.

In one aspect the present invention provides methods for determining whether a subject has active tuberculosis (TB). The methods include determining the level of TNXB, the level of SELL, and the level of QSOX1 in a sample(s) from the subject; comparing the level of TNXB, the level of SELL, and the level of QSOX1 in the subject sample(s) with a level of TNXB, a level of SELL, and a level of QSOX1 in a control sample(s), wherein a difference in the level of TNXB, a difference in the level of SELL, and a difference in the level of QSOX1 in the subject sample(s) as compared to the level of TNXB, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of TNXB, the level of SELL, and the level of QSOX1 in a first sample(s) from the subject prior to the initiation of the treatment; determining the level of TNXB, the level of SELL, and the level of QSOX1 in a second sample(s) from the subject after at least a portion of the treatment has been administered; comparing the level of TNXB, the level of SELL, and the level of QSOX1 in the first sample(s) with a level of TNXB, the level of SELL, and the level of QSOX1 in the second sample(s), wherein a difference in the level of TNXB, the level of SELL, and the level of QSOX1 in the first sample(s) as compared to the level of TNXB, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of TNXB, the level and/or activity of SELL, and the level and/or activity of QSOX1 in each of the aliquots; and selecting a member of the library of compounds which modulates the level and/or the activity of TNXB, the level and/or activity of SELL, and the level and/or activity of QSOX1 in an aliquot as compared to the level and/or activity of TNXB, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TNXB, the level and/or activity of SELL, and the level and/or activity of QSOX1, thereby treating the subject.

In one aspect the present invention provides methods for determining whether a subject has active tuberculosis (TB). The methods include determining the level of COMP, the level of SELL, and the level of SEPP1 in a sample(s) from the subject; comparing the level of COMP, the level of SELL, and the level of SEPP1 in the subject sample(s) with a level of COMP, a level of SELL, and a level of SEPP1 in a control sample(s), wherein a difference in the level of COMP, a difference in the level of SELL, and a difference in the level of SEPP1 in the subject sample(s) as compared to the level of COMP, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of COMP, the level of SELL, and the level of SEPP1 in a first sample(s) from the subject prior to the initiation of the treatment; determining the level of COMP, the level of SELL, and the level of SEPP1 in a second sample(s) from the subject after at least a portion of the treatment has been administered; comparing the level of COMP, the level of SELL, and the level of SEPP1 in the first sample(s) with a level of COMP, the level of SELL, and the level of SEPP1 in the second sample(s), wherein a difference in the level of COMP, the level of SELL, and the level of SEPP1 in the first sample(s) as compared to the level of COMP, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of COMP, the level and/or activity of SELL, and the level and/or activity of SEPP1 in each of the aliquots; and selecting a member of the library of compounds which modulates the level and/or the activity of COMP, the level and/or activity of SELL, and the level and/or activity of SEPP1 in an aliquot as compared to the level and/or activity of COMP, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of SELL, and the level and/or activity of SEPP1, thereby treating the subject.

In one aspect the present invention provides methods for determining whether a subject has active tuberculosis (TB). The methods include determining the level of LUM, the level of SELL, and the level of SEPP1 in a sample(s) from the subject; comparing the level of LUM, the level of SELL, and the level of SEPP1 in the subject sample(s) with a level of LUM, a level of SELL, and a level of SEPP1 in a control sample(s), wherein a difference in the level of LUM, a difference in the level of SELL, and a difference in the level of SEPP1 in the subject sample(s) as compared to the level of LUM, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of LUM, the level of SELL, and the level of SEPP1 in a first sample(s) from the subject prior to the initiation of the treatment; determining the level of LUM, the level of SELL, and the level of SEPP1 in a second sample(s) from the subject after at least a portion of the treatment has been administered; comparing the level of LUM, the level of SELL, and the level of SEPP1 in the first sample(s) with a level of LUM, the level of SELL, and the level of SEPP1 in the second sample(s), wherein a difference in the level of LUM, the level of SELL, and the level of SEPP1 in the first sample(s) as compared to the level of LUM, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LUM, the level and/or activity of SELL, and the level and/or activity of SEPP1 in each of the aliquots; and selecting a member of the library of compounds which modulates the level and/or the activity of LUM, the level and/or activity of SELL, and the level and/or activity of SEPP1 in an aliquot as compared to the level and/or activity of LUM, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LUM, the level and/or activity of SELL, and the level and/or activity of SEPP1, thereby treating the subject.

In one aspect the present invention provides methods for determining whether a subject has active tuberculosis (TB). The methods include determining the level of QSOX1, the level of SELL, and the level of SEPP1 in a sample(s) from the subject; comparing the level of QSOX1, the level of SELL, and the level of SEPP1 in the subject sample(s) with a level of QSOX1, a level of SELL, and a level of SEPP1 in a control sample(s), wherein a difference in the level of QSOX1, a difference in the level of SELL, and a difference in the level of SEPP1 in the subject sample(s) as compared to the level of QSOX1, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of QSOX1, the level of SELL, and the level of SEPP1 in a first sample(s) from the subject prior to the initiation of the treatment; determining the level of QSOX1, the level of SELL, and the level of SEPP1 in a second sample(s) from the subject after at least a portion of the treatment has been administered; comparing the level of QSOX1, the level of SELL, and the level of SEPP1 in the first sample(s) with a level of QSOX1, the level of SELL, and the level of SEPP1 in the second sample(s), wherein a difference in the level of QSOX1, the level of SELL, and the level of SEPP1 in the first sample(s) as compared to the level of QSOX1, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of QSOX1, the level and/or activity of SELL, and the level and/or activity of SEPP1 in each of the aliquots; and selecting a member of the library of compounds which modulates the level and/or the activity of QSOX1, the level and/or activity of SELL, and the level and/or activity of SEPP1 in an aliquot as compared to the level and/or activity of QSOX1, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of QSOX1, the level and/or activity of SELL, and the level and/or activity of SEPP1, thereby treating the subject.

In one aspect the present invention provides methods for determining whether a subject has active tuberculosis (TB). The methods include determining the level of PEPD, the level of APOC1, and the level of CD14 in a sample(s) from the subject; comparing the level of PEPD, the level of APOC1, and the level of CD14 in the subject sample(s) with a level of PEPD, a level of APOC1, and a level of CD14 in a control sample(s), wherein a difference in the level of PEPD, a difference in the level of APOC1, and a difference in the level of CD14 in the subject sample(s) as compared to the level of PEPD, the level of APOC1, and the level of CD14 in the control sample(s) indicates that the subject has active TB.

In one aspect the present invention provides methods for monitoring the effectiveness of a treatment in a subject having active tuberculosis (TB). The methods include determining the level of PEPD, the level of APOC1, and the level of CD14 in a first sample(s) from the subject prior to the initiation of the treatment; determining the level of PEPD, the level of APOC1, and the level of CD14 in a second sample(s) from the subject after at least a portion of the treatment has been administered; comparing the level of PEPD, the level of APOC1, and the level of CD14 in the first sample(s) with a level of PEPD, the level of APOC1, and the level of CD14 in the second sample(s), wherein a difference in the level of PEPD, the level of APOC1, and the level of CD14 in the first sample(s) as compared to the level of PEPD, the level of APOC1, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PEPD, the level and/or activity of APOC1, and the level and/or activity of CD14 in each of the aliquots; and selecting a member of the library of compounds which modulates the level and/or the activity of PEPD, the level and/or activity of APOC1, and the level and/or activity of CD14 in an aliquot as compared to the level and/or activity of PEPD, the level and/or activity of APOC1, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PEPD, the level and/or activity of APOC1, and the level and/or activity of CD14, thereby treating the subject.

In one aspect the present invention provides methods for determining whether a subject has active tuberculosis (TB). The methods include determining the level of COMP, the level of SELL, and the level of APOC1 in a sample(s) from the subject; comparing the level of COMP, the level of SELL, and the level of APOC1 in the subject sample(s) with a level of COMP, a level of SELL, and a level of APOC1 in a control sample(s), wherein a difference in the level of COMP, a difference in the level of SELL, and a difference in the level of APOC1 in the subject sample(s) as compared to the level of COMP, the level of SELL, and the level of APOC1 in the control sample(s) indicates that the subject has active TB.

In one aspect the present invention provides methods for monitoring the effectiveness of a treatment in a subject having active tuberculosis (TB). The methods include determining the level of COMP, the level of SELL, and the level of APOC1 in a first sample(s) from the subject prior to the initiation of the treatment; determining the level of COMP, the level of SELL, and the level of APOC1 in a second sample(s) from the subject after at least a portion of the treatment has been administered; comparing the level of COMP, the level of SELL, and the level of APOC1 in the first sample(s) with a level of COMP, the level of SELL, and the level of APOC1 in the second sample(s), wherein a difference in the level of COMP, the level of SELL, and the level of APOC1 in the first sample(s) as compared to the level of COMP, the level of SELL, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of COMP, the level and/or activity of SELL, and the level and/or activity of APOC1 in each of the aliquots; and selecting a member of the library of compounds which modulates the level and/or the activity of COMP, the level and/or activity of SELL, and the level and/or activity of APOC1 in an aliquot as compared to the level and/or activity of COMP, the level and/or activity of SELL, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of SELL, and the level and/or activity of APOC1, thereby treating the subject.

In one aspect the present invention provides methods for determining whether a subject has active tuberculosis (TB). The methods include determining the level of QSOX1, the level of APOC1, and the level of CD14 in a sample(s) from the subject; comparing the level of QSOX1, the level of APOC1, and the level of CD14 in the subject sample(s) with a level of QSOX1, a level of APOC1, and a level of CD14 in a control sample(s), wherein a difference in the level of QSOX1, a difference in the level of APOC1, and a difference in the level of CD14 in the subject sample(s) as compared to the level of QSOX1, the level of APOC1, and the level of CD14 in the control sample(s) indicates that the subject has active TB.

In one aspect the present invention provides methods for monitoring the effectiveness of a treatment in a subject having active tuberculosis (TB). The methods include determining the level of QSOX1, the level of APOC1, and the level of CD14 in a first sample(s) from the subject prior to the initiation of the treatment; determining the level of QSOX1, the level of APOC1, and the level of CD14 in a second sample(s) from the subject after at least a portion of the treatment has been administered; comparing the level of QSOX1, the level of APOC1, and the level of CD14 in the first sample(s) with a level of QSOX1, the level of APOC1, and the level of CD14 in the second sample(s), wherein a difference in the level of QSOX1, the level of APOC1, and the level of CD14 in the first sample(s) as compared to the level of QSOX1, the level of APOC1, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of QSOX1, the level and/or activity of APOC1, and the level and/or activity of CD14 in each of the aliquots; and selecting a member of the library of compounds which modulates the level and/or the activity of QSOX1, the level and/or activity of APOC1, and the level and/or activity of CD14 in an aliquot as compared to the level and/or activity of QSOX1, the level and/or activity of APOC1, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of QSOX1, the level and/or activity of APOC1, and the level and/or activity of CD14, thereby treating the subject.

In one aspect the present invention provides methods for determining whether a subject has active tuberculosis (TB). The methods include determining the level of PEPD, the level of SELL, and the level of APOC1 in a sample(s) from the subject; comparing the level of PEPD, the level of SELL, and the level of APOC1 in the subject sample(s) with a level of PEPD, a level of SELL, and a level of APOC1 in a control sample(s), wherein a difference in the level of PEPD, a difference in the level of SELL, and a difference in the level of APOC1 in the subject sample(s) as compared to the level of PEPD, the level of SELL, and the level of APOC1 in the control sample(s) indicates that the subject has active TB.

In one aspect the present invention provides methods for monitoring the effectiveness of a treatment in a subject having active tuberculosis (TB). The methods include determining the level of PEPD, the level of SELL, and the level of APOC1 in a first sample(s) from the subject prior to the initiation of the treatment; determining the level of PEPD, the level of SELL, and the level of APOC1 in a second sample(s) from the subject after at least a portion of the treatment has been administered; comparing the level of PEPD, the level of SELL, and the level of APOC1 in the first sample(s) with a level of PEPD, the level of SELL, and the level of APOC1 in the second sample(s), wherein a difference in the level of PEPD, the level of SELL, and the level of APOC1 in the first sample(s) as compared to the level of PEPD, the level of SELL, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PEPD, the level and/or activity of SELL, and the level and/or activity of APOC1 in each of the aliquots; and selecting a member of the library of compounds which modulates the level and/or the activity of PEPD, the level and/or activity of SELL, and the level and/or activity of APOC1 in an aliquot as compared to the level and/or activity of PEPD, the level and/or activity of SELL, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PEPD, the level and/or activity of SELL, and the level and/or activity of APOC1, thereby treating the subject.

In one aspect the present invention provides methods for determining whether a subject has active tuberculosis (TB). The methods include determining the level of CD14, the level of APOE, and the level of SELL in a sample(s) from the subject; comparing the level of CD14, the level of APOE, and the level of SELL in the subject sample(s) with a level of CD14, a level of APOE, and a level of SELL in a control sample(s), wherein a difference in the level of CD14, a difference in the level of APOE, and a difference in the level of SELL in the subject sample(s) as compared to the level of CD14, the level of APOE, and the level of SELL in the control sample(s) indicates that the subject has active TB.

In one aspect the present invention provides methods for monitoring the effectiveness of a treatment in a subject having active tuberculosis (TB). The methods include determining the level CD14, the level of APOE, and the level of SELL in a first sample(s) from the subject prior to the initiation of the treatment; determining the level of CD14, the level of APOE, and the level of SELL in a second sample(s) from the subject after at least a portion of the treatment has been administered; comparing the level of the CD14, the level of APOE, and the level of SELL with a level of CD14, the level of APOE, and the level of SELL in the second sample(s), wherein a difference in the level of CD14, the level of APOE, and the level of SELL in the first sample(s) as compared to the level of CD14, the level of APOE, and the level of SELL in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of APOE, and the level and/or activity of SELL of the invention in each of the aliquots; and selecting a member of the library of compounds which modulates the level and/or the activity of CD14, the level of APOE, and the level of SELL in an aliquot as compared to the level and/or activity of CD14, the level and/or activity of APOE, and the level and/or activity of SELL in a control sample, thereby identifying a compound that is useful for treating a subject having active TB.

In one aspect the present invention provides methods for treating a subject having active tuberculosis (TB). The methods include administering to the subject an effective amount of an agent that modulates the level and/or activity of CD14, the level and/or activity of APOE, and the level and/or activity of SELL, thereby treating the subject.

In one aspect the present invention provides methods for determining whether a subject has active tuberculosis (TB). The methods include determining the level of GP1BA, the level of PEPD, the level of SELL, and the level of TNXB in a sample(s) from the subject; comparing the level of GP1BA, the level of PEPD, the level of SELL, and the level of TNXB in the subject sample(s) with a level of GP1BA, a level of PEPD, a level of SELL, and a level of TNXB in a control sample(s), wherein a difference in the level of GP1BA, a difference in the level of PEPD, a difference in the level of SELL, and a difference in the level of TNXB in the subject sample(s) as compared to the level of GP1BA, the level of PEPD, the level of SELL, and the level of TNXB in the control sample(s) indicates that the subject has active TB.

In one aspect the present invention provides methods for monitoring the effectiveness of a treatment in a subject having active tuberculosis (TB). The methods include determining the level of GP1BA, the level of PEPD, the level of SELL, and the level of TNXB in a first sample(s) from the subject prior to the initiation of the treatment; determining the level of GP1BA, the level of PEPD, the level of SELL, and the level of TNXB in a second sample(s) from the subject after at least a portion of the treatment has been administered; comparing the level of GP1BA, the level of PEPD, the level of SELL, and the level of TNXB in the first sample(s) with a level of GP1BA, the level of PEPD, the level of SELL, and the level of TNXB in the second sample(s), wherein a difference in the level of GP1BA, the level of PEPD, the level of SELL, and the level of TNXB in the first sample(s) as compared to the level of GP1BA, the level of PEPD, the level of SELL, and the level of TNXB in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of GP1BA, the level and/or activity of PEPD, the level and/or activity of SELL, and the level and/or activity of TNXB in an aliquot as compared to the level and/or activity of GP1BA, the level and/or activity of PEPD, the level and/or activity of SELL, and the level and/or activity of TNXB in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of GP1BA, the level and/or activity of PEPD, the level and/or activity of SELL, and the level and/or activity of TNXB, thereby treating the subject.

In one aspect the present invention provides methods for determining whether a subject has active tuberculosis (TB). The methods include determining the level of COMP, the level of PEPD, the level of SELL, and the level of TNXB in a sample(s) from the subject; comparing the level of COMP, the level of PEPD, the level of SELL, and the level of TNXB in the subject sample(s) with a level of COMP, a level of PEPD, a level of SELL, and a level of TNXB in a control sample(s), wherein a difference in the level of COMP, a difference in the level of PEPD, a difference in the level of SELL, and a difference in the level of TNXB in the subject sample(s) as compared to the level of COMP, the level of PEPD, the level of SELL, and the level of TNXB in the control sample(s) indicates that the subject has active TB.

In one aspect the present invention provides methods for monitoring the effectiveness of a treatment in a subject having active tuberculosis (TB). The methods include determining the level of COMP, the level of PEPD, the level of SELL, and the level of TNXB in a first sample(s) from the subject prior to the initiation of the treatment; determining the level of COMP, the level of PEPD, the level of SELL, and the level of TNXB in a second sample(s) from the subject after at least a portion of the treatment has been administered; comparing the level of COMP, the level of PEPD, the level of SELL, and the level of TNXB in the first sample(s) with a level of COMP, the level of PEPD, the level of SELL, and the level of TNXB in the second sample(s), wherein a difference in the level of COMP, the level of PEPD, the level of SELL, and the level of TNXB in the first sample(s) as compared to the level of COMP, the level of PEPD, the level of SELL, and the level of TNXB in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of PEPD, the level and/or activity of SELL, and the level and/or activity of TNXB in an aliquot as compared to the level and/or activity of COMP, the level and/or activity of PEPD, the level and/or activity of SELL, and the level and/or activity of TNXB in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of PEPD, the level and/or activity of SELL, and the level and/or activity of TNXB, thereby treating the subject.

In one aspect the present invention provides methods for determining whether a subject has active tuberculosis (TB). The methods include determining the level of COMP, the level of PEPD, the level of SELL, and the level of QSOX1 in a sample(s) from the subject; comparing the level of COMP, the level of PEPD, the level of SELL, and the level of QSOX1 in the subject sample(s) with a level of COMP, a level of PEPD, a level of SELL, and a level of QSOX1 in a control sample(s), wherein a difference in the level of COMP, a difference in the level of PEPD, a difference in the level of SELL, and a difference in the level of QSOX1 in the subject sample(s) as compared to the level of COMP, the level of PEPD, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of COMP, the level of PEPD, the level of SELL, and the level of QSOX1 in a first sample(s) from the subject prior to the initiation of the treatment; determining the level of COMP, the level of PEPD, the level of SELL, and the level of QSOX1 in a second sample(s) from the subject after at least a portion of the treatment has been administered; comparing the level of COMP, the level of PEPD, the level of SELL, and the level of QSOX1 in the first sample(s) with a level of COMP, the level of PEPD, the level of SELL, and the level of QSOX1 in the second sample(s), wherein a difference in the level of COMP, the level of PEPD, the level of SELL, and the level of QSOX1 in the first sample(s) as compared to the level of COMP, the level of PEPD, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of PEPD, the level and/or activity of SELL, and the level and/or activity of QSOX1 in an aliquot as compared to the level and/or activity of COMP, the level and/or activity of PEPD, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of PEPD, the level and/or activity of SELL, and the level and/or activity of QSOX1, thereby treating the subject.

In one aspect the present invention provides methods for determining whether a subject has active tuberculosis (TB). The methods include determining the level of COMP, the level of PEPD, the level of SELL, and the level of LUM in a sample(s) from the subject; comparing the level of COMP, the level of PEPD, the level of SELL, and the level of LUM in the subject sample(s) with a level of COMP, a level of PEPD, a level of SELL, and a level of LUM in a control sample(s), wherein a difference in the level of COMP, a difference in the level of PEPD, a difference in the level of SELL, and a difference in the level of LUM in the subject sample(s) as compared to the level of COMP, the level of PEPD, the level of SELL, and the level of LUM in the control sample(s) indicates that the subject has active TB.

In one aspect the present invention provides methods for monitoring the effectiveness of a treatment in a subject having active tuberculosis (TB). The methods include determining the level of COMP, the level of PEPD, the level of SELL, and the level of LUM in a first sample(s) from the subject prior to the initiation of the treatment; determining the level of COMP, the level of PEPD, the level of SELL, and the level of LUM in a second sample(s) from the subject after at least a portion of the treatment has been administered; comparing the level of COMP, the level of PEPD, the level of SELL, and the level of LUM in the first sample(s) with a level of COMP, the level of PEPD, the level of SELL, and the level of LUM in the second sample(s), wherein a difference in the level of COMP, the level of PEPD, the level of SELL, and the level of LUM in the first sample(s) as compared to the level of COMP, the level of PEPD, the level of SELL, and the level of LUM in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of PEPD, the level and/or activity of SELL, and the level and/or activity of LUM in an aliquot as compared to the level and/or activity of COMP, the level and/or activity of PEPD, the level and/or activity of SELL, and the level and/or activity of LUM in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of PEPD, the level and/or activity of SELL, and the level and/or activity of LUM, thereby treating the subject.

In one aspect the present invention provides methods for determining whether a subject has active tuberculosis (TB). The methods include determining the level of CD14, the level of PEPD, the level of SELL, and the level of TNXB in a sample(s) from the subject; comparing the level of CD14, the level of PEPD, the level of SELL, and the level of TNXB in the subject sample(s) with a level of CD14, a level of PEPD, a level of SELL, and a level of TNXB in a control sample(s), wherein a difference in the level of CD14, a difference in the level of PEPD, a difference in the level of SELL, and a difference in the level of TNXB in the subject sample(s) as compared to the level of CD14, the level of PEPD, the level of SELL, and the level of TNXB in the control sample(s) indicates that the subject has active TB.

In one aspect the present invention provides methods for monitoring the effectiveness of a treatment in a subject having active tuberculosis (TB). The methods include determining the level of CD14, the level of PEPD, the level of SELL, and the level of TNXB in a first sample(s) from the subject prior to the initiation of the treatment; determining the level of CD14, the level of PEPD, the level of SELL, and the level of TNXB in a second sample(s) from the subject after at least a portion of the treatment has been administered; comparing the level of CD14, the level of PEPD, the level of SELL, and the level of TNXB in the first sample(s) with a level of CD14, the level of PEPD, the level of SELL, and the level of TNXB in the second sample(s), wherein a difference in the level of CD14, the level of PEPD, the level of SELL, and the level of TNXB in the first sample(s) as compared to the level of CD14, the level of PEPD, the level of SELL, and the level of TNXB in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of CD14, the level and/or activity of PEPD, the level and/or activity of SELL, and the level and/or activity of TNXB in an aliquot as compared to the level and/or activity of CD14, the level and/or activity of PEPD, the level and/or activity of SELL, and the level and/or activity of TNXB in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of PEPD, the level and/or activity of SELL, and the level and/or activity of TNXB, thereby treating the subject.

In one aspect the present invention provides methods for determining whether a subject has active tuberculosis (TB). The methods include determining the level of CD14, the level of PEPD, the level of SELL, and the level of SEPP1 in a sample(s) from the subject; comparing the level of CD14, the level of PEPD, the level of SELL, and the level of SEPP1 in the subject sample(s) with a level of CD14, a level of PEPD, a level of SELL, and a level of SEPP1 in a control sample(s), wherein a difference in the level of CD14, a difference in the level of PEPD, a difference in the level of SELL, and a difference in the level of SEPP1 in the subject sample(s) as compared to the level of CD14, the level of PEPD, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of CD14, the level of PEPD, the level of SELL, and the level of SEPP1 in a first sample(s) from the subject prior to the initiation of the treatment; determining the level of CD14, the level of PEPD, the level of SELL, and the level of SEPP1 in a second sample(s) from the subject after at least a portion of the treatment has been administered; comparing the level of CD14, the level of PEPD, the level of SELL, and the level of SEPP1 in the first sample(s) with a level of CD14, the level of PEPD, the level of SELL, and the level of SEPP1 in the second sample(s), wherein a difference in the level of CD14, the level of PEPD, the level of SELL, and the level of SEPP1 in the first sample(s) as compared to the level of CD14, the level of PEPD, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of CD14, the level and/or activity of PEPD, the level and/or activity of SELL, and the level and/or activity of SEPP1 in an aliquot as compared to the level and/or activity of CD14, the level and/or activity of PEPD, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of PEPD, the level and/or activity of SELL, and the level and/or activity of SEPP1, thereby treating the subject.

In one aspect the present invention provides methods for determining whether a subject has active tuberculosis (TB). The methods include determining the level of CD14, the level of PEPD, the level of SELL, and the level of QSOX1 in a sample(s) from the subject; comparing the level of CD14, the level of PEPD, the level of SELL, and the level of QSOX1 in the subject sample(s) with a level of CD14, a level of PEPD, a level of SELL, and a level of QSOX1 in a control sample(s), wherein a difference in the level of CD14, a difference in the level of PEPD, a difference in the level of SELL, and a difference in the level of QSOX1 in the subject sample(s) as compared to the level of CD14, the level of PEPD, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of CD14, the level of PEPD, the level of SELL, and the level of QSOX1 in a first sample(s) from the subject prior to the initiation of the treatment; determining the level of CD14, the level of PEPD, the level of SELL, and the level of QSOX1 in a second sample(s) from the subject after at least a portion of the treatment has been administered; comparing the level of CD14, the level of PEPD, the level of SELL, and the level of QSOX1 in the first sample(s) with a level of CD14, the level of PEPD, the level of SELL, and the level of QSOX1 in the second sample(s), wherein a difference in the level of CD14, the level of PEPD, the level of SELL, and the level of QSOX1 in the first sample(s) as compared to the level of CD14, the level of PEPD, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of CD14, the level and/or activity of PEPD, the level and/or activity of SELL, and the level and/or activity of QSOX1 in an aliquot as compared to the level and/or activity of CD14, the level and/or activity of PEPD, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of PEPD, the level and/or activity of SELL, and the level and/or activity of QSOX1, thereby treating the subject.

In one aspect the present invention provides methods for determining whether a subject has active tuberculosis (TB). The methods include determining the level of COMP, the level of PEPD, the level of SELL, and the level of GP1BA in a sample(s) from the subject; comparing the level of COMP, the level of PEPD, the level of SELL, and the level of GP1BA in the subject sample(s) with a level of COMP, a level of PEPD, a level of SELL, and a level of GP1BA in a control sample(s), wherein a difference in the level of COMP, a difference in the level of PEPD, a difference in the level of SELL, and a difference in the level of GP1BA in the subject sample(s) as compared to the level of COMP, the level of PEPD, the level of SELL, and the level of GP1BA in the control sample(s) indicates that the subject has active TB.

In one aspect the present invention provides methods for monitoring the effectiveness of a treatment in a subject having active tuberculosis (TB). The methods include determining the level of COMP, the level of PEPD, the level of SELL, and the level of GP1BA in a first sample(s) from the subject prior to the initiation of the treatment; determining the level of COMP, the level of PEPD, the level of SELL, and the level of GP1BA in a second sample(s) from the subject after at least a portion of the treatment has been administered; comparing the level of COMP, the level of PEPD, the level of SELL, and the level of GP1BA in the first sample(s) with a level of COMP, the level of PEPD, the level of SELL, and the level of GP1BA in the second sample(s), wherein a difference in the level of COMP, the level of PEPD, the level of SELL, and the level of GP1BA in the first sample(s) as compared to the level of COMP, the level of PEPD, the level of SELL, and the level of GP1BA in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of PEPD, the level and/or activity of SELL, and the level and/or activity of GP1BA in an aliquot as compared to the level and/or activity of COMP, the level and/or activity of PEPD, the level and/or activity of SELL, and the level and/or activity of GP1BA in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of PEPD, the level and/or activity of SELL, and the level and/or activity of GP1BA, thereby treating the subject.

In one aspect the present invention provides methods for determining whether a subject has active tuberculosis (TB). The methods include determining the level of COMP, the level of PEPD, the level of SELL, and the level of APOC1 in a sample(s) from the subject; comparing the level of COMP, the level of PEPD, the level of SELL, and the level of APOC1 in the subject sample(s) with a level of COMP, a level of PEPD, a level of SELL, and a level of APOC1 in a control sample(s), wherein a difference in the level of COMP, a difference in the level of PEPD, a difference in the level of SELL, and a difference in the level of APOC1 in the subject sample(s) as compared to the level of COMP, the level of PEPD, the level of SELL, and the level of APOC1 in the control sample(s) indicates that the subject has active TB.

In one aspect the present invention provides methods for monitoring the effectiveness of a treatment in a subject having active tuberculosis (TB). The methods include determining the level of COMP, the level of PEPD, the level of SELL, and the level of APOC1 in a first sample(s) from the subject prior to the initiation of the treatment; determining the level of COMP, the level of PEPD, the level of SELL, and the level of APOC1 in a second sample(s) from the subject after at least a portion of the treatment has been administered; comparing the level of COMP, the level of PEPD, the level of SELL, and the level of APOC1 in the first sample(s) with a level of COMP, the level of PEPD, the level of SELL, and the level of APOC1 in the second sample(s), wherein a difference in the level of COMP, the level of PEPD, the level of SELL, and the level of APOC1 in the first sample(s) as compared to the level of COMP, the level of PEPD, the level of SELL, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of PEPD, the level and/or activity of SELL, and the level and/or activity of APOC1 in an aliquot as compared to the level and/or activity of COMP, the level and/or activity of PEPD, the level and/or activity of SELL, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of PEPD, the level and/or activity of SELL, and the level and/or activity of APOC1, thereby treating the subject.

In one aspect the present invention provides methods for determining whether a subject has active tuberculosis (TB). The methods include determining the level of TNXB, the level of PEPD, the level of SELL, and the level of LUM in a sample(s) from the subject; comparing the level of TNXB, the level of PEPD, the level of SELL, and the level of LUM in the subject sample(s) with a level of TNXB, a level of PEPD, a level of SELL, and a level of LUM in a control sample(s), wherein a difference in the level of TNXB, a difference in the level of PEPD, a difference in the level of SELL, and a difference in the level of LUM in the subject sample(s) as compared to the level of TNXB, the level of PEPD, the level of SELL, and the level of LUM in the control sample(s) indicates that the subject has active TB.

In one aspect the present invention provides methods for monitoring the effectiveness of a treatment in a subject having active tuberculosis (TB). The methods include determining the level of TNXB, the level of PEPD, the level of SELL, and the level of LUM in a first sample(s) from the subject prior to the initiation of the treatment; determining the level of TNXB, the level of PEPD, the level of SELL, and the level of LUM in a second sample(s) from the subject after at least a portion of the treatment has been administered; comparing the level of TNXB, the level of PEPD, the level of SELL, and the level of LUM in the first sample(s) with a level of TNXB, the level of PEPD, the level of SELL, and the level of LUM in the second sample(s), wherein a difference in the level of TNXB, the level of PEPD, the level of SELL, and the level of LUM in the first sample(s) as compared to the level of TNXB, the level of PEPD, the level of SELL, and the level of LUM in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of TNXB, the level and/or activity of PEPD, the level and/or activity of SELL, and the level and/or activity of LUM in an aliquot as compared to the level and/or activity of TNXB, the level and/or activity of PEPD, the level and/or activity of SELL, and the level and/or activity of LUM in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TNXB, the level and/or activity of PEPD, the level and/or activity of SELL, and the level and/or activity of LUM, thereby treating the subject.

In one aspect the present invention provides methods for determining whether a subject has active tuberculosis (TB). The methods include determining the level of CD14, the level of PEPD, the level of SELL, and the level of APOC1 in a sample(s) from the subject; comparing the level of CD14, the level of PEPD, the level of SELL, and the level of APOC1 in the subject sample(s) with a level of CD14, a level of PEPD, a level of SELL, and a level of APOC1 in a control sample(s), wherein a difference in the level of CD14, a difference in the level of PEPD, a difference in the level of SELL, and a difference in the level of APOC1 in the subject sample(s) as compared to the level of CD14, the level of PEPD, the level of SELL, and the level of APOC1 in the control sample(s) indicates that the subject has active TB.

In one aspect the present invention provides methods for monitoring the effectiveness of a treatment in a subject having active tuberculosis (TB). The methods include determining the level of CD14, the level of PEPD, the level of SELL, and the level of APOC1 in a first sample(s) from the subject prior to the initiation of the treatment; determining the level of CD14, the level of PEPD, the level of SELL, and the level of APOC1 in a second sample(s) from the subject after at least a portion of the treatment has been administered; comparing the level of CD14, the level of PEPD, the level of SELL, and the level of APOC1 in the first sample(s) with a level of CD14, the level of PEPD, the level of SELL, and the level of APOC1 in the second sample(s), wherein a difference in the level of CD14, the level of PEPD, the level of SELL, and the level of APOC1 in the first sample(s) as compared to the level of CD14, the level of PEPD, the level of SELL, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of CD14, the level and/or activity of PEPD, the level and/or activity of SELL, and the level and/or activity of APOC1 in an aliquot as compared to the level and/or activity of CD14, the level and/or activity of PEPD, the level and/or activity of SELL, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of PEPD, the level and/or activity of SELL, and the level and/or activity of APOC1, thereby treating the subject.

In one aspect the present invention provides methods for determining whether a subject has active tuberculosis (TB). The methods include determining the level of COMP, the level of PEPD, the level of SELL, and the level of SEPP1 in a sample(s) from the subject; comparing the level of COMP, the level of PEPD, the level of SELL, and the level of SEPP1 in the subject sample(s) with a level of COMP, a level of PEPD, a level of SELL, and a level of SEPP1 in a control sample(s), wherein a difference in the level of COMP, a difference in the level of PEPD, a difference in the level of SELL, and a difference in the level of SEPP1 in the subject sample(s) as compared to the level of COMP, the level of PEPD, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of COMP, the level of PEPD, the level of SELL, and the level of SEPP1 in a first sample(s) from the subject prior to the initiation of the treatment; determining the level of COMP, the level of PEPD, the level of SELL, and the level of SEPP1 in a second sample(s) from the subject after at least a portion of the treatment has been administered; comparing the level of COMP, the level of PEPD, the level of SELL, and the level of SEPP1 in the first sample(s) with a level of COMP, the level of PEPD, the level of SELL, and the level of SEPP1 in the second sample(s), wherein a difference in the level of COMP, the level of PEPD, the level of SELL, and the level of SEPP1 in the first sample(s) as compared to the level of COMP, the level of PEPD, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of PEPD, the level and/or activity of SELL, and the level and/or activity of SEPP1 in an aliquot as compared to the level and/or activity of COMP, the level and/or activity of PEPD, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of PEPD, the level and/or activity of SELL, and the level and/or activity of SEPP1, thereby treating the subject.

In one aspect the present invention provides methods for determining whether a subject has active tuberculosis (TB). The methods include determining the level of TNXB, the level of PEPD, the level of SELL, and the level of QSOX1 in a sample(s) from the subject; comparing the level of TNXB, the level of PEPD, the level of SELL, and the level of QSOX1 in the subject sample(s) with a level of TNXB, a level of PEPD, a level of SELL, and a level of QSOX1 in a control sample(s), wherein a difference in the level of TNXB, a difference in the level of PEPD, a difference in the level of SELL, and a difference in the level of QSOX1 in the subject sample(s) as compared to the level of TNXB, the level of PEPD, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of TNXB, the level of PEPD, the level of SELL, and the level of QSOX1 in a first sample(s) from the subject prior to the initiation of the treatment; determining the level of TNXB, the level of PEPD, the level of SELL, and the level of QSOX1 in a second sample(s) from the subject after at least a portion of the treatment has been administered; comparing the level of TNXB, the level of PEPD, the level of SELL, and the level of QSOX1 in the first sample(s) with a level of TNXB, the level of PEPD, the level of SELL, and the level of QSOX1 in the second sample(s), wherein a difference in the level of TNXB, the level of PEPD, the level of SELL, and the level of QSOX1 in the first sample(s) as compared to the level of TNXB, the level of PEPD, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of TNXB, the level and/or activity of PEPD, the level and/or activity of SELL, and the level and/or activity of QSOX1 in an aliquot as compared to the level and/or activity of TNXB, the level and/or activity of PEPD, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TNXB, the level and/or activity of PEPD, the level and/or activity of SELL, and the level and/or activity of QSOX1, thereby treating the subject.

In one aspect the present invention provides methods for determining whether a subject has active tuberculosis (TB). The methods include determining the level of LUM, the level of PEPD, the level of SELL, and the level of SEPP1 in a sample(s) from the subject; comparing the level of LUM, the level of PEPD, the level of SELL, and the level of SEPP1 in the subject sample(s) with a level of LUM, a level of PEPD, a level of SELL, and a level of SEPP1 in a control sample(s), wherein a difference in the level of LUM, a difference in the level of PEPD, a difference in the level of SELL, and a difference in the level of SEPP1 in the subject sample(s) as compared to the level of LUM, the level of PEPD, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of LUM, the level of PEPD, the level of SELL, and the level of SEPP1 in a first sample(s) from the subject prior to the initiation of the treatment; determining the level of LUM, the level of PEPD, the level of SELL, and the level of SEPP1 in a second sample(s) from the subject after at least a portion of the treatment has been administered; comparing the level of LUM, the level of PEPD, the level of SELL, and the level of SEPP1 in the first sample(s) with a level of LUM, the level of PEPD, the level of SELL, and the level of SEPP1 in the second sample(s), wherein a difference in the level of LUM, the level of PEPD, the level of SELL, and the level of SEPP1 in the first sample(s) as compared to the level of LUM, the level of PEPD, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of LUM, the level and/or activity of PEPD, the level and/or activity of SELL, and the level and/or activity of SEPP1 in an aliquot as compared to the level and/or activity of LUM, the level and/or activity of PEPD, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LUM, the level and/or activity of PEPD, the level and/or activity of SELL, and the level and/or activity of SEPP1, thereby treating the subject.

In one aspect the present invention provides methods for determining whether a subject has active tuberculosis (TB). The methods include determining the level of COMP, the level of PEPD, the level of SELL, and the level of CD14 in a sample(s) from the subject; comparing the level of COMP, the level of PEPD, the level of SELL, and the level of CD14 in the subject sample(s) with a level of COMP, a level of PEPD, a level of SELL, and a level of CD14 in a control sample(s), wherein a difference in the level of COMP, a difference in the level of PEPD, a difference in the level of SELL, and a difference in the level of CD14 in the subject sample(s) as compared to the level of COMP, the level of PEPD, the level of SELL, and the level of CD14 in the control sample(s) indicates that the subject has active TB.

In one aspect the present invention provides methods for monitoring the effectiveness of a treatment in a subject having active tuberculosis (TB). The methods include determining the level of COMP, the level of PEPD, the level of SELL, and the level of CD14 in a first sample(s) from the subject prior to the initiation of the treatment; determining the level of COMP, the level of PEPD, the level of SELL, and the level of CD14 in a second sample(s) from the subject after at least a portion of the treatment has been administered; comparing the level of COMP, the level of PEPD, the level of SELL, and the level of CD14 in the first sample(s) with a level of COMP, the level of PEPD, the level of SELL, and the level of CD14 in the second sample(s), wherein a difference in the level of COMP, the level of PEPD, the level of SELL, and the level of CD14 in the first sample(s) as compared to the level of COMP, the level of PEPD, the level of SELL, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of PEPD, the level and/or activity of SELL, and the level and/or activity of CD14 in an aliquot as compared to the level and/or activity of COMP, the level and/or activity of PEPD, the level and/or activity of SELL, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of PEPD, the level and/or activity of SELL, and the level and/or activity of CD14, thereby treating the subject.

In one aspect the present invention provides methods for determining whether a subject has active tuberculosis (TB). The methods include determining the level of TNXB, the level of PEPD, the level of SELL, and the level of SEPP1 in a sample(s) from the subject; comparing the level of TNXB, the level of PEPD, the level of SELL, and the level of SEPP1 in the subject sample(s) with a level of TNXB, a level of PEPD, a level of SELL, and a level of SEPP1 in a control sample(s), wherein a difference in the level of TNXB, a difference in the level of PEPD, a difference in the level of SELL, and a difference in the level of SEPP1 in the subject sample(s) as compared to the level of TNXB, the level of PEPD, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of TNXB, the level of PEPD, the level of SELL, and the level of SEPP1 in a first sample(s) from the subject prior to the initiation of the treatment; determining the level of TNXB, the level of PEPD, the level of SELL, and the level of SEPP1 in a second sample(s) from the subject after at least a portion of the treatment has been administered; comparing the level of TNXB, the level of PEPD, the level of SELL, and the level of SEPP1 in the first sample(s) with a level of TNXB, the level of PEPD, the level of SELL, and the level of SEPP1 in the second sample(s), wherein a difference in the level of TNXB, the level of PEPD, the level of SELL, and the level of SEPP1 in the first sample(s) as compared to the level of TNXB, the level of PEPD, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of TNXB, the level and/or activity of PEPD, the level and/or activity of SELL, and the level and/or activity of SEPP1 in an aliquot as compared to the level and/or activity of TNXB, the level and/or activity of PEPD, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TNXB, the level and/or activity of PEPD, the level and/or activity of SELL, and the level and/or activity of SEPP1, thereby treating the subject.

In one aspect the present invention provides methods for determining whether a subject has active tuberculosis (TB). The methods include determining the level of GP1BA, the level of PEPD, the level of SELL, and the level of CD14 in a sample(s) from the subject; comparing the level of GP1BA, the level of PEPD, the level of SELL, and the level of CD14 in the subject sample(s) with a level of GP1BA, a level of PEPD, a level of SELL, and a level of CD14 in a control sample(s), wherein a difference in the level of GP1BA, a difference in the level of PEPD, a difference in the level of SELL, and a difference in the level of CD14 in the subject sample(s) as compared to the level of GP1BA, the level of PEPD, the level of SELL, and the level of CD14 in the control sample(s) indicates that the subject has active TB.

In one aspect the present invention provides methods for monitoring the effectiveness of a treatment in a subject having active tuberculosis (TB). The methods include determining the level of GP1BA, the level of PEPD, the level of SELL, and the level of CD14 in a first sample(s) from the subject prior to the initiation of the treatment; determining the level of GP1BA, the level of PEPD, the level of SELL, and the level of CD14 in a second sample(s) from the subject after at least a portion of the treatment has been administered; comparing the level of GP1BA, the level of PEPD, the level of SELL, and the level of CD14 in the first sample(s)

with a level of GP1BA, the level of PEPD, the level of SELL, and the level of CD14 in the second sample(s), wherein a difference in the level of GP1BA, the level of PEPD, the level of SELL, and the level of CD14 in the first sample(s) as compared to the level of GP1BA, the level of PEPD, the level of SELL, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of GP1BA, the level and/or activity of PEPD, the level and/or activity of SELL, and the level and/or activity of CD14 in an aliquot as compared to the level and/or activity of GP1BA, the level and/or activity of PEPD, the level and/or activity of SELL, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of GP1BA, the level and/or activity of PEPD, the level and/or activity of SELL, and the level and/or activity of CD14, thereby treating the subject.

In one aspect the present invention provides methods for determining whether a subject has active tuberculosis (TB). The methods include determining the level of TNXB, the level of PEPD, the level of SELL, and the level of APOC1 in a sample(s) from the subject; comparing the level of TNXB, the level of PEPD, the level of SELL, and the level of APOC1 in the subject sample(s) with a level of TNXB, a level of PEPD, a level of SELL, and a level of APOC1 in a control sample(s), wherein a difference in the level of TNXB, a difference in the level of PEPD, a difference in the level of SELL, and a difference in the level of APOC1 in the subject sample(s) as compared to the level of TNXB, the level of PEPD, the level of SELL, and the level of APOC1 in the control sample(s) indicates that the subject has active TB.

In one aspect the present invention provides methods for monitoring the effectiveness of a treatment in a subject having active tuberculosis (TB). The methods include determining the level of TNXB, the level of PEPD, the level of SELL, and the level of APOC1 in a first sample(s) from the subject prior to the initiation of the treatment; determining the level of TNXB, the level of PEPD, the level of SELL, and the level of APOC1 in a second sample(s) from the subject after at least a portion of the treatment has been administered; comparing the level of TNXB, the level of PEPD, the level of SELL, and the level of APOC1 in the first sample(s) with a level of TNXB, the level of PEPD, the level of SELL, and the level of APOC1 in the second sample(s), wherein a difference in the level of TNXB, the level of PEPD, the level of SELL, and the level of APOC1 in the first sample(s) as compared to the level of TNXB, the level of PEPD, the level of SELL, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of TNXB, the level and/or activity of PEPD, the level and/or activity of SELL, and the level and/or activity of APOC1 in an aliquot as compared to the level and/or activity of TNXB, the level and/or activity of PEPD, the level and/or activity of SELL, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TNXB, the level and/or activity of PEPD, the level and/or activity of SELL, and the level and/or activity of APOC1, thereby treating the subject.

In one aspect the present invention provides methods for determining whether a subject has active tuberculosis (TB). The methods include determining the level of QSOX1, the level of PEPD, the level of SELL, and the level of SEPP1 in a sample(s) from the subject; comparing the level of QSOX1, the level of PEPD, the level of SELL, and the level of SEPP1 in the subject sample(s) with a level of QSOX1, a level of PEPD, a level of SELL, and a level of SEPP1 in a control sample(s), wherein a difference in the level of QSOX1, a difference in the level of PEPD, a difference in the level of SELL, and a difference in the level of SEPP1 in the subject sample(s) as compared to the level of QSOX1, the level of PEPD, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of QSOX1, the level of PEPD, the level of SELL, and the level of SEPP1 in a first sample(s) from the subject prior to the initiation of the treatment; determining the level of QSOX1, the level of PEPD, the level of SELL, and the level of SEPP1 in a second sample(s) from the subject after at least a portion of the treatment has been administered; comparing the level of QSOX1, the level of PEPD, the level of SELL, and the level of SEPP1 in the first sample(s) with a level of QSOX1, the level of PEPD, the level of SELL, and the level of SEPP1 in the second sample(s), wherein a difference in the level of QSOX1, the level of PEPD, the level of SELL, and the level of SEPP1 in the first sample(s) as compared to the level of QSOX1, the level of PEPD, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of QSOX1, the level and/or activity of PEPD, the level and/or activity of SELL, and the level and/or activity of SEPP1 in an aliquot as compared to the level and/or activity of QSOX1, the level and/or activity of PEPD, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of QSOX1, the level and/or activity of PEPD, the level and/or activity of SELL, and the level and/or activity of SEPP1, thereby treating the subject.

In one aspect the present invention provides methods for determining whether a subject has active tuberculosis (TB). The methods include determining the level of LUM, the level of PEPD, the level of SELL, and the level of CD14 in a sample(s) from the subject; comparing the level of LUM, the level of PEPD, the level of SELL, and the level of CD14 in the subject sample(s) with a level of LUM, a level of PEPD, a level of SELL, and a level of CD14 in a control sample(s), wherein a difference in the level of LUM, a difference in the level of PEPD, a difference in the level of SELL, and a difference in the level of CD14 in the subject sample(s) as compared to the level of LUM, the level of PEPD, the level of SELL, and the level of CD14 in the control sample(s) indicates that the subject has active TB.

In one aspect the present invention provides methods for monitoring the effectiveness of a treatment in a subject having active tuberculosis (TB). The methods include determining the level of LUM, the level of PEPD, the level of SELL, and the level of CD14 in a first sample(s) from the subject prior to the initiation of the treatment; determining the level of LUM, the level of PEPD, the level of SELL, and the level of CD14 in a second sample(s) from the subject after at least a portion of the treatment has been administered; comparing the level of LUM, the level of PEPD, the level of SELL, and the level of CD14 in the first sample(s) with a level of LUM, the level of PEPD, the level of SELL, and the level of CD14 in the second sample(s), wherein a difference in the level of LUM, the level of PEPD, the level of SELL, and the level of CD14 in the first sample(s) as compared to the level of LUM, the level of PEPD, the level of SELL, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of LUM, the level and/or activity of PEPD, the level and/or activity of SELL, and the level and/or activity of CD14 in an aliquot as compared to the level and/or activity of LUM, the level and/or activity of PEPD, the level and/or activity of SELL, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LUM, the level and/or activity of PEPD, the level and/or activity of SELL, and the level and/or activity of CD14, thereby treating the subject.

In one aspect the present invention provides methods for determining whether a subject has active tuberculosis (TB). The methods include determining the level of LUM, the level of PEPD, the level of SELL, and the level of QSOX1 in a sample(s) from the subject; comparing the level of LUM, the level of PEPD, the level of SELL, and the level of QSOX1 in the subject sample(s) with a level of LUM, a level of PEPD, a level of SELL, and a level of QSOX1 in a control sample(s), wherein a difference in the level of LUM, a difference in the level of PEPD, a difference in the level of SELL, and a difference in the level of QSOX1 in the subject sample(s) as compared to the level of LUM, the level of PEPD, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of LUM, the level of PEPD, the level of SELL, and the level of QSOX1 in a first sample(s) from the subject prior to the initiation of the treatment; determining the level of LUM, the level of PEPD, the level of SELL, and the level of QSOX1 in a second sample(s) from the subject after at least a portion of the treatment has been administered; comparing the level of LUM, the level of PEPD, the level of SELL, and the level of QSOX1 in the first sample(s) with a level of LUM, the level of PEPD, the level of SELL, and the level of QSOX1 in the second sample(s), wherein a difference in the level of LUM, the level of PEPD, the level of SELL, and the level of QSOX1 in the first sample(s) as compared to the level of LUM, the level of PEPD, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of LUM, the level and/or activity of PEPD, the level and/or activity of SELL, and the level and/or activity of QSOX1 in an aliquot as compared to the level and/or activity of LUM, the level and/or activity of PEPD, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LUM, the level and/or activity of PEPD, the level and/or activity of SELL, and the level and/or activity of QSOX1, thereby treating the subject.

In one aspect the present invention provides methods for determining whether a subject has active tuberculosis (TB). The methods include determining the level of COMP, the level of APOC1, the level of SELL, and the level of SEPP1 in a sample(s) from the subject; comparing the level of COMP, the level of APOC1, the level of SELL, and the level of SEPP1 in the subject sample(s) with a level of COMP, a level of APOC1, a level of SELL, and a level of SEPP1 in a control sample(s), wherein a difference in the level of COMP, a difference in the level of APOC1, a difference in the level of SELL, and a difference in the level of SEPP1 in the subject sample(s) as compared to the level of COMP, the level of APOC1, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of COMP, the level of APOC1, the level of SELL, and the level of SEPP1 in a first sample(s) from the subject prior to the initiation of the treatment; determining the level of COMP, the level of APOC1, the level of SELL, and the level of SEPP1 in a second sample(s) from the subject after at least a portion of the treatment has been administered; comparing the level of COMP, the level of APOC1, the level of SELL, and the level of SEPP1 in the first sample(s) with a level of COMP, the level of APOC1, the level of SELL, and the level of SEPP1 in the second sample(s), wherein a difference in the level of COMP, the level of APOC1, the level of SELL, and the level of SEPP1 in the first sample(s) as compared to the level of COMP, the level of APOC1, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of APOC1, the level and/or activity of SELL, and the level and/or activity of SEPP1 in an aliquot as compared to the level and/or activity of COMP, the level and/or activity of APOC1, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of APOC1, the level and/or activity of SELL, and the level and/or activity of SEPP1, thereby treating the subject.

In one aspect the present invention provides methods for determining whether a subject has active tuberculosis (TB). The methods include determining the level of GP1BA, the level of PEPD, the level of SELL, and the level of QSOX1 in a sample(s) from the subject; comparing the level of GP1BA, the level of PEPD, the level of SELL, and the level of QSOX1 in the subject sample(s) with a level of GP1BA, a level of PEPD, a level of SELL, and a level of QSOX1 in a control sample(s), wherein a difference in the level of GP1BA, a difference in the level of PEPD, a difference in the level of SELL, and a difference in the level of QSOX1 in the subject sample(s) as compared to the level of GP1BA, the level of PEPD, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of GP1BA, the level of PEPD, the level of SELL, and the level of QSOX1 in a first sample(s) from the subject prior to the initiation of the treatment; determining the level of GP1BA, the level of PEPD, the level of SELL, and the level of QSOX1 in a second sample(s) from the subject after at least a portion of the treatment has been administered; comparing the level of GP1BA, the level of PEPD, the level of SELL, and the level of QSOX1 in the first sample(s) with a level of GP1BA, the level of PEPD, the level of SELL, and the level of QSOX1 in the second sample(s), wherein a difference in the level of GP1BA, the level of PEPD, the level of SELL, and the level of QSOX1 in the first sample(s) as compared to the level of GP1BA, the level of PEPD, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of GP1BA, the level and/or activity of PEPD, the level and/or activity of SELL, and the level and/or activity of QSOX1 in an aliquot as compared to the level and/or activity of GP1BA, the level and/or activity of PEPD, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of GP1BA, the level and/or activity of PEPD, the level and/or activity of SELL, and the level and/or activity of QSOX1, thereby treating the subject.

In one aspect the present invention provides methods for determining whether a subject has active tuberculosis (TB). The methods include determining the level of LUM, the level of PEPD, the level of SELL, and the level of APOC1 in a sample(s) from the subject; comparing the level of LUM, the level of PEPD, the level of SELL, and the level of APOC1 in the subject sample(s) with a level of LUM, a level of PEPD, a level of SELL, and a level of APOC1 in a control sample(s), wherein a difference in the level of LUM, a difference in the level of PEPD, a difference in the level of SELL, and a difference in the level of APOC1 in the subject sample(s) as compared to the level of LUM, the level of PEPD, the level of SELL, and the level of APOC1 in the control sample(s) indicates that the subject has active TB.

In one aspect the present invention provides methods for monitoring the effectiveness of a treatment in a subject having active tuberculosis (TB). The methods include determining the level of LUM, the level of PEPD, the level of SELL, and the level of APOC1 in a first sample(s) from the subject prior to the initiation of the treatment; determining the level of LUM, the level of PEPD, the level of SELL, and the level of APOC1 in a second sample(s) from the subject after at least a portion of the treatment has been administered; comparing the level of LUM, the level of PEPD, the level of SELL, and the level of APOC1 in the first sample(s) with a level of LUM, the level of PEPD, the level of SELL, and the level of APOC1 in the second sample(s), wherein a difference in the level of LUM, the level of PEPD, the level of SELL, and the level of APOC1 in the first sample(s) as compared to the level of LUM, the level of PEPD, the level of SELL, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of LUM, the level and/or activity of PEPD, the level and/or activity of SELL, and the level and/or activity of APOC1 in an aliquot as compared to the level and/or activity of LUM, the level and/or activity of PEPD, the level and/or activity of SELL, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LUM, the level and/or activity of PEPD, the level and/or activity of SELL, and the level and/or activity of APOC1, thereby treating the subject.

In one aspect the present invention provides methods for determining whether a subject has active tuberculosis (TB). The methods include determining the level of APOC1, the level of PEPD, the level of SELL, and the level of QSOX1 in a sample(s) from the subject; comparing the level of APOC1, the level of PEPD, the level of SELL, and the level of QSOX1 in the subject sample(s) with a level of APOC1, a level of PEPD, a level of SELL, and a level of QSOX1 in a control sample(s), wherein a difference in the level of APOC1, a difference in the level of PEPD, a difference in the level of SELL, and a difference in the level of QSOX1 in the subject sample(s) as compared to the level of APOC1, the level of PEPD, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of APOC1, the level of PEPD, the level of SELL, and the level of QSOX1 in a first sample(s) from the subject prior to the initiation of the treatment; determining the level of APOC1, the level of PEPD, the level of SELL, and the level of QSOX1 in a second sample(s) from the subject after at least a portion of the treatment has been administered; comparing the level of APOC1, the level of PEPD, the level of SELL, and the level of QSOX1 in the first sample(s) with a level of APOC1, the level of PEPD, the level of SELL, and the level of QSOX1 in the second sample(s), wherein a difference in the level of APOC1, the level of PEPD, the level of SELL, and the level of QSOX1 in the first sample(s) as compared to the level of APOC1, the level of PEPD, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of PEPD, the level and/or activity of SELL, and the level and/or activity of QSOX1 in an aliquot as compared to the level and/or activity of APOC1, the level and/or activity of PEPD, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of PEPD, the level and/or activity of SELL, and the level and/or activity of QSOX1, thereby treating the subject.

In one aspect the present invention provides methods for determining whether a subject has active tuberculosis (TB). The methods include determining the level of SEPP1, the level of PEPD, the level of SELL, and the level of APOC1 in a sample(s) from the subject; comparing the level of SEPP1, the level of PEPD, the level of SELL, and the level of APOC1 in the subject sample(s) with a level of SEPP1, a level of PEPD, a level of SELL, and a level of APOC1 in a control sample(s), wherein a difference in the level of SEPP1, a difference in the level of PEPD, a difference in the level of SELL, and a difference in the level of APOC1 in the subject sample(s) as compared to the level of SEPP1, the level of PEPD, the level of SELL, and the level of APOC1 in the control sample(s) indicates that the subject has active TB.

In one aspect the present invention provides methods for monitoring the effectiveness of a treatment in a subject having active tuberculosis (TB). The methods include determining the level of SEPP1, the level of PEPD, the level of SELL, and the level of APOC1 in a first sample(s) from the subject prior to the initiation of the treatment; determining the level of SEPP1, the level of PEPD, the level of SELL, and the level of APOC1 in a second sample(s) from the subject after at least a portion of the treatment has been administered; comparing the level of SEPP1, the level of PEPD, the level of SELL, and the level of APOC1 in the first sample(s) with a level of SEPP1, the level of PEPD, the level of SELL, and the level of APOC1 in the second sample(s), wherein a difference in the level of SEPP1, the level of PEPD, the level of SELL, and the level of APOC1 in the first sample(s) as compared to the level of SEPP1, the level of PEPD, the level of SELL, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of PEPD, the level and/or activity of SELL, and the level and/or activity of APOC1 in an aliquot as compared to the level and/or activity of SEPP1, the level and/or activity of PEPD, the level and/or activity of SELL, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of PEPD, the level and/or activity of SELL, and the level and/or activity of APOC1, thereby treating the subject.

In one aspect the present invention provides methods for determining whether a subject has active tuberculosis (TB). The methods include determining the level of APOC1, the level of COMP, the level of SELL, and the level of QSOX1 in a sample(s) from the subject; comparing the level of APOC1, the level of COMP, the level of SELL, and the level of QSOX1 in the subject sample(s) with a level of APOC1, a level of COMP, a level of SELL, and a level of QSOX1 in a control sample(s), wherein a difference in the level of APOC1, a difference in the level of COMP, a difference in the level of SELL, and a difference in the level of QSOX1 in the subject sample(s) as compared to the level of APOC1, the level of COMP, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of APOC1, the level of COMP, the level of SELL, and the level of QSOX1 in a first sample(s) from the subject prior to the initiation of the treatment; determining the level of APOC1, the level of COMP, the level of SELL, and the level of QSOX1 in a second sample(s) from the subject after at least a portion of the treatment has been administered; comparing the level of APOC1, the level of COMP, the level of SELL, and the level of QSOX1 in the first sample(s) with a level of APOC1, the level of COMP, the level of SELL, and the level of QSOX1 in the second sample(s), wherein a difference in the level of APOC1, the level of COMP, the level of SELL, and the level of QSOX1 in the first sample(s) as compared to the level of APOC1, the level of COMP, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of COMP, the level and/or activity of SELL, and the level and/or activity of QSOX1 in an aliquot as compared to the level and/or activity of APOC1, the level and/or activity of COMP, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of COMP, the level and/or activity of SELL, and the level and/or activity of QSOX1, thereby treating the subject.

In one aspect the present invention provides methods for determining whether a subject has active tuberculosis (TB). The methods include determining the level of APOC1, the level of CD14, the level of SELL, and the level of QSOX1 in a sample(s) from the subject; comparing the level of APOC1, the level of CD14, the level of SELL, and the level of QSOX1 in the subject sample(s) with a level of APOC1, a level of CD14, a level of SELL, and a level of QSOX1 in a control sample(s), wherein a difference in the level of APOC1, a difference in the level of CD14, a difference in the level of SELL, and a difference in the level of QSOX1 in the subject sample(s) as compared to the level of APOC1, the level of CD14, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of APOC1, the level of CD14, the level of SELL, and the level of QSOX1 in a first sample(s) from the subject prior to the initiation of the treatment; determining the level of APOC1, the level of CD14, the level of SELL, and the level of QSOX1 in a second sample(s) from the subject after at least a portion of the treatment has been administered; comparing the level of APOC1, the level of CD14, the level of SELL, and the level of QSOX1 in the first sample(s) with a level of APOC1, the level of CD14, the level of SELL, and the level of QSOX1 in the second sample(s), wherein a difference in the level of APOC1, the level of CD14, the level of SELL, and the level of QSOX1 in the first sample(s) as compared to the level of APOC1, the level of CD14, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of CD14, the level and/or activity of SELL, and the level and/or activity of QSOX1 in an aliquot as compared to the level and/or activity of APOC1, the level and/or activity of CD14, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of CD14, the level and/or activity of SELL, and the level and/or activity of QSOX1, thereby treating the subject.

In one aspect the present invention provides methods for determining whether a subject has active tuberculosis (TB). The methods include determining the level of APOC1, the level of SEPP1, the level of SELL, and the level of QSOX1 in a sample(s) from the subject; comparing the level of APOC1, the level of SEPP1, the level of SELL, and the level of QSOX1 in the subject sample(s) with a level of APOC1, a level of SEPP1, a level of SELL, and a level of QSOX1 in a control sample(s), wherein a difference in the level of APOC1, a difference in the level of SEPP1, a difference in the level of SELL, and a difference in the level of QSOX1 in the subject sample(s) as compared to the level of APOC1, the level of SEPP1, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of APOC1, the level of SEPP1, the level of SELL, and the level of QSOX1 in a first sample(s) from the subject prior to the initiation of the treatment; determining the level of APOC1, the level of SEPP1, the level of SELL, and the level of QSOX1 in a second sample(s) from the subject after at least a portion of the treatment has been administered; comparing the level of APOC1, the level of SEPP1, the level of SELL, and the level of QSOX1 in the first sample(s) with a level of APOC1, the level of SEPP1, the level of SELL, and the level of QSOX1 in the second sample(s), wherein a difference in the level of APOC1, the level of SEPP1, the level of SELL, and the level of QSOX1 in the first sample(s) as compared to the level of APOC1, the level of SEPP1, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of SEPP1, the level and/or activity of SELL, and the level and/or activity of QSOX1 in an aliquot as compared to the level and/or activity of APOC1, the level and/or activity of SEPP1, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of SEPP1, the level and/or activity of SELL, and the level and/or activity of QSOX1, thereby treating the subject.

In one aspect the present invention provides methods for determining whether a subject has active tuberculosis (TB). The methods include determining the level of APOC1, the level of LUM, the level of SELL, and the level of QSOX1 in a sample(s) from the subject; comparing the level of APOC1, the level of LUM, the level of SELL, and the level of QSOX1 in the subject sample(s) with a level of APOC1, a level of LUM, a level of SELL, and a level of QSOX1 in a control sample(s), wherein a difference in the level of APOC1, a difference in the level of LUM, a difference in the level of SELL, and a difference in the level of QSOX1 in the subject sample(s) as compared to the level of APOC1, the level of LUM, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of APOC1, the level of LUM, the level of SELL, and the level of QSOX1 in a first sample(s) from the subject prior to the initiation of the treatment; determining the level of APOC1, the level of LUM, the level of SELL, and the level of QSOX1 in a second sample(s) from the subject after at least a portion of the treatment has been administered; comparing the level of APOC1, the level of LUM, the level of SELL, and the level of QSOX1 in the first sample(s) with a level of APOC1, the level of LUM, the level of SELL, and the level of QSOX1 in the second sample(s), wherein a difference in the level of APOC1, the level of LUM, the level of SELL, and the level of QSOX1 in the first sample(s) as compared to the level of APOC1, the level of LUM, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of LUM, the level and/or activity of SELL, and the level and/or activity of QSOX1 in an aliquot as compared to the level and/or activity of APOC1, the level and/or activity of LUM, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of LUM, the level and/or activity of SELL, and the level and/or activity of QSOX1, thereby treating the subject.

In one aspect the present invention provides methods for determining whether a subject has active tuberculosis (TB). The methods include determining the level of GP1BA, the level of CD14, the level of SELL, and the level of QSOX1 in a sample(s) from the subject; comparing the level of GP1BA, the level of CD14, the level of SELL, and the level of QSOX1 in the subject sample(s) with a level of GP1BA, a level of CD14, a level of SELL, and a level of QSOX1 in a control sample(s), wherein a difference in the level of GP1BA, a difference in the level of CD14, a difference in the level of SELL, and a difference in the level of QSOX1 in the subject sample(s) as compared to the level of GP1BA, the level of CD14, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of GP1BA, the level of CD14, the level of SELL, and the level of QSOX1 in a first sample(s) from the subject prior to the initiation of the treatment; determining the level of GP1BA, the level of CD14, the level of SELL, and the level of QSOX1 in a second sample(s) from the subject after at least a portion of the treatment has been administered; comparing the level of GP1BA, the level of CD14, the level of SELL, and the level of QSOX1 in the first sample(s) with a level of GP1BA, the level of CD14, the level of SELL, and the level of QSOX1 in the second sample(s), wherein a difference in the level of GP1BA, the level of CD14, the level of SELL, and the level of QSOX1 in the first sample(s) as compared to the level of GP1BA, the level of CD14, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of GP1BA, the level and/or activity of CD14, the level and/or activity of SELL, and the level and/or activity of QSOX1 in an aliquot as compared to the level and/or activity of GP1BA, the level and/or activity of CD14, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of GP1BA, the level and/or activity of CD14, the level and/or activity of SELL, and the level and/or activity of QSOX1, thereby treating the subject.

In one aspect the present invention provides methods for determining whether a subject has active tuberculosis (TB). The methods include determining the level of LUM, the level of PEPD, the level of SELL, and the level of GP1BA in a sample(s) from the subject; comparing the level of LUM, the level of PEPD, the level of SELL, and the level of GP1BA in the subject sample(s) with a level of LUM, a level of PEPD, a level of SELL, and a level of GP1BA in a control sample(s), wherein a difference in the level of LUM, a difference in the level of PEPD, a difference in the level of SELL, and a difference in the level of GP1BA in the subject sample(s) as compared to the level of LUM, the level of PEPD, the level of SELL, and the level of GP1BA in the control sample(s) indicates that the subject has active TB.

In one aspect the present invention provides methods for monitoring the effectiveness of a treatment in a subject having active tuberculosis (TB). The methods include determining the level of LUM, the level of PEPD, the level of SELL, and the level of GP1BA in a first sample(s) from the subject prior to the initiation of the treatment; determining the level of LUM, the level of PEPD, the level of SELL, and the level of GP1BA in a second sample(s) from the subject after at least a portion of the treatment has been administered; comparing the level of LUM, the level of PEPD, the level of SELL, and the level of GP1BA in the first sample(s) with a level of LUM, the level of PEPD, the level of SELL, and the level of GP1BA in the second sample(s), wherein a difference in the level of LUM, the level of PEPD, the level of SELL, and the level of GP1BA in the first sample(s) as compared to the level of LUM, the level of PEPD, the level of SELL, and the level of GP1BA in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of LUM, the level and/or activity of PEPD, the level and/or activity of SELL, and the level and/or activity of GP1BA in an aliquot as compared to the level and/or activity of LUM, the level and/or activity of PEPD, the level and/or activity of SELL, and the level and/or activity of GP1BA in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LUM, the level and/or activity of PEPD, the level and/or activity of SELL, and the level and/or activity of GP1BA, thereby treating the subject.

In one aspect the present invention provides methods for determining whether a subject has active tuberculosis (TB). The methods include determining the level of APOC1, the level of TNXB, the level of SELL, and the level of QSOX1 in a sample(s) from the subject; comparing the level of APOC1, the level of TNXB, the level of SELL, and the level of QSOX1 in the subject sample(s) with a level of APOC1, a level of TNXB, a level of SELL, and a level of QSOX1 in a control sample(s), wherein a difference in the level of APOC1, a difference in the level of TNXB, a difference in the level of SELL, and a difference in the level of QSOX1 in the subject sample(s) as compared to the level of APOC1, the level of TNXB, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of APOC1, the level of TNXB, the level of SELL, and the level of QSOX1 in a first sample(s) from the subject prior to the initiation of the treatment; determining the level of APOC1, the level of TNXB, the level of SELL, and the level of QSOX1 in a second sample(s) from the subject after at least a portion of the treatment has been administered; comparing the level of APOC1, the level of TNXB, the level of SELL, and the level of QSOX1 in the first sample(s) with a level of APOC1, the level of TNXB, the level of SELL, and the level of QSOX1 in the second sample(s), wherein a difference in the level of APOC1, the level of TNXB, the level of SELL, and the level of QSOX1 in the first sample(s) as compared to the level of APOC1, the level of TNXB, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of TNXB, the level and/or activity of SELL, and the level and/or activity of QSOX1 in an aliquot as compared to the level and/or activity of APOC1, the level and/or activity of TNXB, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of TNXB, the level and/or activity of SELL, and the level and/or activity of QSOX1, thereby treating the subject.

In one aspect the present invention provides methods for determining whether a subject has active tuberculosis (TB). The methods include determining the level of SEPP1, the level of PEPD, the level of SELL, and the level of GP1BA in a sample(s) from the subject; comparing the level of SEPP1, the level of PEPD, the level of SELL, and the level of GP1BA in the subject sample(s) with a level of SEPP1, a level of PEPD, a level of SELL, and a level of GP1BA in a control sample(s), wherein a difference in the level of SEPP1, a difference in the level of PEPD, a difference in the level of SELL, and a difference in the level of GP1BA in the subject sample(s) as compared to the level of SEPP1, the level of PEPD, the level of SELL, and the level of GP1BA in the control sample(s) indicates that the subject has active TB.

In one aspect the present invention provides methods for monitoring the effectiveness of a treatment in a subject having active tuberculosis (TB). The methods include determining the level of SEPP1, the level of PEPD, the level of SELL, and the level of GP1BA in a first sample(s) from the subject prior to the initiation of the treatment; determining the level of SEPP1, the level of PEPD, the level of SELL, and the level of GP1BA in a second sample(s) from the subject after at least a portion of the treatment has been administered; comparing the level of SEPP1, the level of PEPD, the level of SELL, and the level of GP1BA in the first sample(s) with a level of SEPP1, the level of PEPD, the level of SELL, and the level of GP1BA in the second sample(s), wherein a difference in the level of SEPP1, the level of PEPD, the level of SELL, and the level of GP1BA in the first sample(s) as compared to the level of SEPP1, the level of PEPD, the level of SELL, and the level of GP1BA in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of PEPD, the level and/or activity of SELL, and the level and/or activity of GP1BA in an aliquot as compared to the level and/or activity of SEPP1, the level and/or activity of PEPD, the level and/or activity of SELL, and the level and/or activity of GP1BA in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of PEPD, the level and/or activity of SELL, and the level and/or activity of GP1BA, thereby treating the subject.

In one aspect the present invention provides methods for determining whether a subject has active tuberculosis (TB). The methods include determining the level of SEPP1, the level of TNXB, the level of SELL, and the level of QSOX1 in a sample(s) from the subject; comparing the level of SEPP1, the level of TNXB, the level of SELL, and the level of QSOX1 in the subject sample(s) with a level of SEPP1, a level of TNXB, a level of SELL, and a level of QSOX1 in a control sample(s), wherein a difference in the level of SEPP1, a difference in the level of TNXB, a difference in the level of SELL, and a difference in the level of QSOX1 in the subject sample(s) as compared to the level of SEPP1, the level of TNXB, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of SEPP1, the level of TNXB, the level of SELL, and the level of QSOX1 in a first sample(s) from the subject prior to the initiation of the treatment; determining the level of SEPP1, the level of TNXB, the level of SELL, and the level of QSOX1 in a second sample(s) from the subject after at least a portion of the treatment has been administered; comparing the level of SEPP1, the level of TNXB, the level of SELL, and the level of QSOX1 in the first sample(s) with a level of SEPP1, the level of TNXB, the level of SELL, and the level of QSOX1 in the second sample(s), wherein a difference in the level of SEPP1, the level of TNXB, the level of SELL, and the level of QSOX1 in the first sample(s) as compared to the level of SEPP1, the level of TNXB, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of TNXB, the level and/or activity of SELL, and the level and/or activity of QSOX1 in an aliquot as compared to the level and/or activity of SEPP1, the level and/or activity of TNXB, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of TNXB, the level and/or activity of SELL, and the level and/or activity of QSOX1, thereby treating the subject.

In one aspect the present invention provides methods for determining whether a subject has active tuberculosis (TB). The methods include determining the level of SEPP1, the level of LUM, the level of SELL, and the level of QSOX1 in a sample(s) from the subject; comparing the level of SEPP1, the level of LUM, the level of SELL, and the level of QSOX1 in the subject sample(s) with a level of SEPP1, a level of LUM, a level of SELL, and a level of QSOX1 in a control sample(s), wherein a difference in the level of SEPP1, a difference in the level of LUM, a difference in the level of SELL, and a difference in the level of QSOX1 in the subject sample(s) as compared to the level of SEPP1, the level of LUM, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of SEPP1, the level of LUM, the level of SELL, and the level of QSOX1 in a first sample(s) from the subject prior to the initiation of the treatment; determining the level of SEPP1, the level of LUM, the level of SELL, and the level of QSOX1 in a second sample(s) from the subject after at least a portion of the treatment has been administered; comparing the level of SEPP1, the level of LUM, the level of SELL, and the level of QSOX1 in the first sample(s) with a level of SEPP1, the level of LUM, the level of SELL, and the level of QSOX1 in the second sample(s), wherein a difference in the level of SEPP1, the level of LUM, the level of SELL, and the level of QSOX1 in the first sample(s) as compared to the level of SEPP1, the level of LUM, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of LUM, the level and/or activity of SELL, and the level and/or activity of QSOX1 in an aliquot as compared to the level and/or activity of SEPP1, the level and/or activity of LUM, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of LUM, the level and/or activity of SELL, and the level and/or activity of QSOX1, thereby treating the subject.

In one aspect the present invention provides methods for determining whether a subject has active tuberculosis (TB). The methods include determining the level of SEPP1, the level of COMP, the level of SELL, and the level of GP1BA in a sample(s) from the subject; comparing the level of SEPP1, the level of COMP, the level of SELL, and the level of GP1BA in the subject sample(s) with a level of SEPP1, a level of COMP, a level of SELL, and a level of GP1BA in a control sample(s), wherein a difference in the level of SEPP1, a difference in the level of COMP, a difference in the level of SELL, and a difference in the level of GP1BA in the subject sample(s) as compared to the level of SEPP1, the level of COMP, the level of SELL, and the level of GP1BA in the control sample(s) indicates that the subject has active TB.

In one aspect the present invention provides methods for monitoring the effectiveness of a treatment in a subject having active tuberculosis (TB). The methods include determining the level of SEPP1, the level of COMP, the level of SELL, and the level of GP1BA in a first sample(s) from the subject prior to the initiation of the treatment; determining the level of SEPP1, the level of COMP, the level of SELL, and the level of GP1BA in a second sample(s) from the subject after at least a portion of the treatment has been administered; comparing the level of SEPP1, the level of COMP, the level of SELL, and the level of GP1BA in the first sample(s) with a level of SEPP1, the level of COMP, the level of SELL, and the level of GP1BA in the second sample(s), wherein a difference in the level of SEPP1, the level of COMP, the level of SELL, and the level of GP1BA in the first sample(s) as compared to the level of SEPP1, the level of COMP, the level of SELL, and the level of GP1BA in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of COMP, the level and/or activity of SELL, and the level and/or activity of GP1BA in an aliquot as compared to the level and/or activity of SEPP1, the level and/or activity of COMP, the level and/or activity of SELL, and the level and/or activity of GP1BA in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of COMP, the level and/or activity of SELL, and the level and/or activity of GP1BA, thereby treating the subject.

In one aspect the present invention provides methods for determining whether a subject has active tuberculosis (TB). The methods include determining the level of APOC1, the level of PEPD, the level of SELL, and the level of GP1BA in a sample(s) from the subject; comparing the level of APOC1, the level of PEPD, the level of SELL, and the level of GP1BA in the subject sample(s) with a level of APOC1, a level of PEPD, a level of SELL, and a level of GP1BA in a control sample(s), wherein a difference in the level of APOC1, a difference in the level of PEPD, a difference in the level of SELL, and a difference in the level of GP1BA in the subject sample(s) as compared to the level of APOC1, the level of PEPD, the level of SELL, and the level of GP1BA in the control sample(s) indicates that the subject has active TB.

In one aspect the present invention provides methods for monitoring the effectiveness of a treatment in a subject having active tuberculosis (TB). The methods include determining the level of APOC1, the level of PEPD, the level of SELL, and the level of GP1BA in a first sample(s) from the subject prior to the initiation of the treatment; determining the level of APOC1, the level of PEPD, the level of SELL, and the level of GP1BA in a second sample(s) from the subject after at least a portion of the treatment has been administered; comparing the level of APOC1, the level of PEPD, the level of SELL, and the level of GP1BA in the first sample(s) with a level of APOC1, the level of PEPD, the level of SELL, and the level of GP1BA in the second sample(s), wherein a difference in the level of APOC1, the level of PEPD, the level of SELL, and the level of GP1BA in the first sample(s) as compared to the level of APOC1, the level of PEPD, the level of SELL, and the level of GP1BA in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of PEPD, the level and/or activity of SELL, and the level and/or activity of GP1BA in an aliquot as compared to the level and/or activity of APOC1, the level and/or activity of PEPD, the level and/or activity of SELL, and the level and/or activity of GP1BA in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of PEPD, the level and/or activity of SELL, and the level and/or activity of GP1BA, thereby treating the subject.

In one aspect the present invention provides methods for determining whether a subject has active tuberculosis (TB). The methods include determining the level of SEPP1, the level of COMP, the level of SELL, and the level of QSOX1 in a sample(s) from the subject; comparing the level of SEPP1, the level of COMP, the level of SELL, and the level of QSOX1 in the subject sample(s) with a level of SEPP1, a level of COMP, a level of SELL, and a level of QSOX1 in a control sample(s), wherein a difference in the level of SEPP1, a difference in the level of COMP, a difference in the level of SELL, and a difference in the level of QSOX1 in the subject sample(s) as compared to the level of SEPP1, the level of COMP, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of SEPP1, the level of COMP, the level of SELL, and the level of QSOX1 in a first sample(s) from the subject prior to the initiation of the treatment; determining the level of SEPP1, the level of COMP, the level of SELL, and the level of QSOX1 in a second sample(s) from the subject after at least a portion of the treatment has been administered; comparing the level of SEPP1, the level of COMP, the level of SELL, and the level of QSOX1 in the first sample(s) with a level of SEPP1, the level of COMP, the level of SELL, and the level of QSOX1 in the second sample(s), wherein a difference in the level of SEPP1, the level of COMP, the level of SELL, and the level of QSOX1 in the first sample(s) as compared to the level of SEPP1, the level of COMP, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of COMP, the level and/or activity of SELL, and the level and/or activity of QSOX1 in an aliquot as compared to the level and/or activity of SEPP1, the level and/or activity of COMP, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of COMP, the level and/or activity of SELL, and the level and/or activity of QSOX1, thereby treating the subject.

In one aspect the present invention provides methods for determining whether a subject has active tuberculosis (TB). The methods include determining the level of SEPP1, the level of LUM, the level of SELL, and the level of COMP in a sample(s) from the subject; comparing the level of SEPP1, the level of LUM, the level of SELL, and the level of COMP in the subject sample(s) with a level of SEPP1, a level of LUM, a level of SELL, and a level of COMP in a control sample(s), wherein a difference in the level of SEPP1, a difference in the level of LUM, a difference in the level of SELL, and a difference in the level of COMP in the subject sample(s) as compared to the level of SEPP1, the level of LUM, the level of SELL, and the level of COMP in the control sample(s) indicates that the subject has active TB.

In one aspect the present invention provides methods for monitoring the effectiveness of a treatment in a subject having active tuberculosis (TB). The methods include determining the level of SEPP1, the level of LUM, the level of SELL, and the level of COMP in a first sample(s) from the subject prior to the initiation of the treatment; determining the level of SEPP1, the level of LUM, the level of SELL, and the level of COMP in a second sample(s) from the subject after at least a portion of the treatment has been administered; comparing the level of SEPP1, the level of LUM, the level of SELL, and the level of COMP in the first sample(s) with a level of SEPP1, the level of LUM, the level of SELL, and the level of COMP in the second sample(s), wherein a difference in the level of SEPP1, the level of LUM, the level of SELL, and the level of COMP in the first sample(s) as compared to the level of SEPP1, the level of LUM, the level of SELL, and the level of COMP in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of LUM, the level and/or activity of SELL, and the level and/or activity of COMP in an aliquot as compared to the level and/or activity of SEPP1, the level and/or activity of LUM, the level and/or activity of SELL, and the level and/or activity of COMP in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of LUM, the level and/or activity of SELL, and the level and/or activity of COMP, thereby treating the subject.

In one aspect the present invention provides methods for determining whether a subject has active tuberculosis (TB). The methods include determining the level of SEPP1, the level of CD14, the level of SELL, and the level of QSOX1 in a sample(s) from the subject; comparing the level of SEPP1, the level of CD14, the level of SELL, and the level of QSOX1 in the subject sample(s) with a level of SEPP1, a level of CD14, a level of SELL, and a level of QSOX1 in a control sample(s), wherein a difference in the level of SEPP1, a difference in the level of CD14, a difference in the level of SELL, and a difference in the level of QSOX1 in the subject sample(s) as compared to the level of SEPP1, the level of CD14, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of SEPP1, the level of CD14, the level of SELL, and the level of QSOX1 in a first sample(s) from the subject prior to the initiation of the treatment; determining the level of SEPP1, the level of CD14, the level of SELL, and the level of QSOX1 in a second sample(s) from the subject after at least a portion of the treatment has been administered; comparing the level of SEPP1, the level of CD14, the level of SELL, and the level of QSOX1 in the first sample(s) with a level of SEPP1, the level of CD14, the level of SELL, and the level of QSOX1 in the second sample(s), wherein a difference in the level of SEPP1, the level of CD14, the level of SELL, and the level of QSOX1 in the first sample(s) as compared to the level of SEPP1, the level of CD14, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of CD14, the level and/or activity of SELL, and the level and/or activity of QSOX1 in an aliquot as compared to the level and/or activity of SEPP1, the level and/or activity of CD14, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of CD14, the level and/or activity of SELL, and the level and/or activity of QSOX1, thereby treating the subject.

In one aspect the present invention provides methods for determining whether a subject has active tuberculosis (TB). The methods include determining the level of SEPP1, the level of TNXB, the level of SELL, and the level of COMP in a sample(s) from the subject; comparing the level of SEPP1, the level of TNXB, the level of SELL, and the level of COMP in the subject sample(s) with a level of SEPP1, a level of TNXB, a level of SELL, and a level of COMP in a control sample(s), wherein a difference in the level of SEPP1, a difference in the level of TNXB, a difference in the level of SELL, and a difference in the level of COMP in the subject sample(s) as compared to the level of SEPP1, the level of TNXB, the level of SELL, and the level of COMP in the control sample(s) indicates that the subject has active TB.

In one aspect the present invention provides methods for monitoring the effectiveness of a treatment in a subject having active tuberculosis (TB). The methods include determining the level of SEPP1, the level of TNXB, the level of SELL, and the level of COMP in a first sample(s) from the subject prior to the initiation of the treatment; determining the level of SEPP1, the level of TNXB, the level of SELL, and the level of COMP in a second sample(s) from the subject after at least a portion of the treatment has been administered; comparing the level of SEPP1, the level of TNXB, the level of SELL, and the level of COMP in the first sample(s) with a level of SEPP1, the level of TNXB, the level of SELL, and the level of COMP in the second sample(s), wherein a difference in the level of SEPP1, the level of TNXB, the level of SELL, and the level of COMP in the first sample(s) as compared to the level of SEPP1, the level of TNXB, the level of SELL, and the level of COMP in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of TNXB, the level and/or activity of SELL, and the level and/or activity of COMP in an aliquot as compared to the level and/or activity of SEPP1, the level and/or activity of TNXB, the level and/or activity of SELL, and the level and/or activity of COMP in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of TNXB, the level and/or activity of SELL, and the level and/or activity of COMP, thereby treating the subject.

In one aspect the present invention provides methods for determining whether a subject has active tuberculosis (TB). The methods include determining the level of APOC1, the level of CD14, the level of GP1BA, and the level of QSOX1 in a sample(s) from the subject; comparing the level of APOC1, the level of CD14, the level of GP1BA, and the level of QSOX1 in the subject sample(s) with a level of APOC1, a level of CD14, a level of GP1BA, and a level of QSOX1 in a control sample(s), wherein a difference in the level of APOC1, a difference in the level of CD14, a difference in the level of GP1BA, and a difference in the level of QSOX1 in the subject sample(s) as compared to the level of APOC1, the level of CD14, the level of GP1BA, and the level of QSOX1 in the control sample(s) indicates that the subject has active TB.

In one aspect the present invention provides methods for monitoring the effectiveness of a treatment in a subject having active tuberculosis (TB). The methods include determining the level of APOC1, the level of CD14, the level of GP1BA, and the level of QSOX1 in a first sample(s) from the subject prior to the initiation of the treatment; determining the level of APOC1, the level of CD14, the level of GP1BA, and the level of QSOX1 in a second sample(s) from the subject after at least a portion of the treatment has been administered; comparing the level of APOC1, the level of CD14, the level of GP1BA, and the level of QSOX1 in the first sample(s) with a level of APOC1, the level of CD14, the level of GP1BA, and the level of QSOX1 in the second sample(s), wherein a difference in the level of APOC1, the level of CD14, the level of GP1BA, and the level of QSOX1 in the first sample(s) as compared to the level of APOC1, the level of CD14, the level of GP1BA, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of CD14, the level and/or activity of GP1BA, and the level and/or activity of QSOX1 in an aliquot as compared to the level and/or activity of APOC1, the level and/or activity of CD14, the level and/or activity of GP1BA, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of CD14, the level and/or activity of GP1BA, and the level and/or activity of QSOX1, thereby treating the subject.

In one aspect the present invention provides methods for determining whether a subject has active tuberculosis (TB). The methods include determining the level of TNXB, the level of CD14, the level of SELL, and the level of QSOX1 in a sample(s) from the subject; comparing the level of TNXB, the level of CD14, the level of SELL, and the level of QSOX1 in the subject sample(s) with a level of TNXB, a level of CD14, a level of SELL, and a level of QSOX1 in a control sample(s), wherein a difference in the level of TNXB, a difference in the level of CD14, a difference in the level of SELL, and a difference in the level of QSOX1 in the subject sample(s) as compared to the level of TNXB, the level of CD14, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of TNXB, the level of CD14, the level of SELL, and the level of QSOX1 in a first sample(s) from the subject prior to the initiation of the treatment; determining the level of TNXB, the level of CD14, the level of SELL, and the level of QSOX1 in a second sample(s) from the subject after at least a portion of the treatment has been administered; comparing the level of TNXB, the level of CD14, the level of SELL, and the level of QSOX1 in the first sample(s) with a level of TNXB, the level of CD14, the level of SELL, and the level of QSOX1 in the second sample(s), wherein a difference in the level of TNXB, the level of CD14, the level of SELL, and the level of QSOX1 in the first sample(s) as compared to the level of TNXB, the level of CD14, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of TNXB, the level and/or activity of CD14, the level and/or activity of SELL, and the level and/or activity of QSOX1 in an aliquot as compared to the level and/or activity of TNXB, the level and/or activity of CD14, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TNXB, the level and/or activity of CD14, the level and/or activity of SELL, and the level and/or activity of QSOX1, thereby treating the subject.

In one aspect the present invention provides methods for determining whether a subject has active tuberculosis (TB). The methods include determining the level of SEPP1, the level of TNXB, the level of SELL, and the level of APOC1 in a sample(s) from the subject; comparing the level of SEPP1, the level of TNXB, the level of SELL, and the level of APOC1 in the subject sample(s) with a level of SEPP1, a level of TNXB, a level of SELL, and a level of APOC1 in a control sample(s), wherein a difference in the level of SEPP1, a difference in the level of TNXB, a difference in the level of SELL, and a difference in the level of APOC1 in the subject sample(s) as compared to the level of SEPP1, the level of TNXB, the level of SELL, and the level of APOC1 in the control sample(s) indicates that the subject has active TB.

In one aspect the present invention provides methods for monitoring the effectiveness of a treatment in a subject having active tuberculosis (TB). The methods include determining the level of SEPP1, the level of TNXB, the level of SELL, and the level of APOC1 in a first sample(s) from the subject prior to the initiation of the treatment; determining the level of SEPP1, the level of TNXB, the level of SELL, and the level of APOC1 in a second sample(s) from the subject after at least a portion of the treatment has been administered; comparing the level of SEPP1, the level of TNXB, the level of SELL, and the level of APOC1 in the first sample(s) with a level of SEPP1, the level of TNXB, the level of SELL, and the level of APOC1 in the second sample(s), wherein a difference in the level of SEPP1, the level of TNXB, the level of SELL, and the level of APOC1 in the first sample(s) as compared to the level of SEPP1, the level of TNXB, the level of SELL, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of TNXB, the level and/or activity of SELL, and the level and/or activity of APOC1 in an aliquot as compared to the level and/or activity of SEPP1, the level and/or activity of TNXB, the level and/or activity of SELL, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of TNXB, the level and/or activity of SELL, and the level and/or activity of APOC1, thereby treating the subject.

In one aspect the present invention provides methods for determining whether a subject has active tuberculosis (TB). The methods include determining the level of APOC1, the level of SELL, the level of GP1BA, and the level of QSOX1 in a sample(s) from the subject; comparing the level of APOC1, the level of SELL, the level of GP1BA, and the level of QSOX1 in the subject sample(s) with a level of APOC1, a level of SELL, a level of GP1BA, and a level of QSOX1 in a control sample(s), wherein a difference in the level of APOC1, a difference in the level of SELL, a difference in the level of GP1BA, and a difference in the level of QSOX1 in the subject sample(s) as compared to the level of APOC1, the level of SELL, the level of GP1BA, and the level of QSOX1 in the control sample(s) indicates that the subject has active TB.

In one aspect the present invention provides methods for monitoring the effectiveness of a treatment in a subject having active tuberculosis (TB). The methods include determining the level of APOC1, the level of SELL, the level of GP1BA, and the level of QSOX1 in a first sample(s) from the subject prior to the initiation of the treatment; determining the level of APOC1, the level of SELL, the level of GP1BA, and the level of QSOX1 in a second sample(s) from the subject after at least a portion of the treatment has been administered; comparing the level of APOC1, the level of SELL, the level of GP1BA, and the level of QSOX1 in the first sample(s) with a level of APOC1, the level of SELL, the level of GP1BA, and the level of QSOX1 in the second sample(s), wherein a difference in the level of APOC1, the level of SELL, the level of GP1BA, and the level of QSOX1 in the first sample(s) as compared to the level of APOC1, the level of SELL, the level of GP1BA, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of SELL, the level and/or activity of GP1BA, and the level and/or activity of QSOX1 in an aliquot as compared to the level and/or activity of APOC1, the level and/or activity of SELL, the level and/or activity of GP1BA, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of SELL, the level and/or activity of GP1BA, and the level and/or activity of QSOX1, thereby treating the subject.

In one aspect the present invention provides methods for determining whether a subject has active tuberculosis (TB). The methods include determining the level of APOC1, the level of CD14, the level of GP1BA, and the level of PEPD in a sample(s) from the subject; comparing the level of APOC1, the level of CD14, the level of GP1BA, and the level of PEPD in the subject sample(s) with a level of APOC1, a level of CD14, a level of GP1BA, and a level of PEPD in a control sample(s), wherein a difference in the level of APOC1, a difference in the level of CD14, a difference in the level of GP1BA, and a difference in the level of PEPD in the subject sample(s) as compared to the level of APOC1, the level of CD14, the level of GP1BA, and the level of PEPD in the control sample(s) indicates that the subject has active TB.

In one aspect the present invention provides methods for monitoring the effectiveness of a treatment in a subject having active tuberculosis (TB). The methods include determining the level of APOC1, the level of CD14, the level of GP1BA, and the level of PEPD in a first sample(s) from the subject prior to the initiation of the treatment; determining the level of APOC1, the level of CD14, the level of GP1BA, and the level of PEPD in a second sample(s) from the subject after at least a portion of the treatment has been administered; comparing the level of APOC1, the level of CD14, the level of GP1BA, and the level of PEPD in the first sample(s) with a level of APOC1, the level of CD14, the level of GP1BA, and the level of PEPD in the second sample(s), wherein a difference in the level of APOC1, the level of CD14, the level of GP1BA, and the level of PEPD in the first sample(s) as compared to the level of APOC1, the level of CD14, the level of GP1BA, and the level of PEPD in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of CD14, the level and/or activity of GP1BA, and the level and/or activity of PEPD in an aliquot as compared to the level and/or activity of APOC1, the level and/or activity of CD14, the level and/or activity of GP1BA, and the level and/or activity of PEPD in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of CD14, the level and/or activity of GP1BA, and the level and/or activity of PEPD, thereby treating the subject.

In one aspect the present invention provides methods for determining whether a subject has active tuberculosis (TB). The methods include determining the level of COMP, the level of CD14, the level of GP1BA, and the level of SELL in a sample(s) from the subject; comparing the level of COMP, the level of CD14, the level of GP1BA, and the level of SELL in the subject sample(s) with a level of COMP, a level of CD14, a level of GP1BA, and a level of SELL in a control sample(s), wherein a difference in the level of COMP, a difference in the level of CD14, a difference in the level of GP1BA, and a difference in the level of SELL in the subject sample(s) as compared to the level of COMP, the level of CD14, the level of GP1BA, and the level of SELL in the control sample(s) indicates that the subject has active TB.

In one aspect the present invention provides methods for monitoring the effectiveness of a treatment in a subject having active tuberculosis (TB). The methods include determining the level of COMP, the level of CD14, the level of GP1BA, and the level of SELL in a first sample(s) from the subject prior to the initiation of the treatment; determining the level of COMP, the level of CD14, the level of GP1BA, and the level of SELL in a second sample(s) from the subject after at least a portion of the treatment has been administered; comparing the level of COMP, the level of CD14, the level of GP1BA, and the level of SELL in the first sample(s) with a level of COMP, the level of CD14, the level of GP1BA, and the level of SELL in the second sample(s), wherein a difference in the level of COMP, the level of CD14, the level of GP1BA, and the level of SELL in the first sample(s) as compared to the level of COMP, the level of CD14, the level of GP1BA, and the level of SELL in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of CD14, the level and/or activity of GP1BA, and the level and/or activity of SELL in an aliquot as compared to the level and/or activity of COMP, the level and/or activity of CD14, the level and/or activity of GP1BA, and the level and/or activity of SELL in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of CD14, the level and/or activity of GP1BA, and the level and/or activity of SELL, thereby treating the subject.

In one aspect the present invention provides methods for determining whether a subject has active tuberculosis (TB). The methods include determining the level of APOC1, the level of CD14, the level of GP1BA, and the level of TNXB in a sample(s) from the subject; comparing the level of APOC1, the level of CD14, the level of GP1BA, and the level of TNXB in the subject sample(s) with a level of APOC1, a level of CD14, a level of GP1BA, and a level of TNXB in a control sample(s), wherein a difference in the level of APOC1, a difference in the level of CD14, a difference in the level of GP1BA, and a difference in the level of TNXB in the subject sample(s) as compared to the level of APOC1, the level of CD14, the level of GP1BA, and the level of TNXB in the control sample(s) indicates that the subject has active TB.

In one aspect the present invention provides methods for monitoring the effectiveness of a treatment in a subject having active tuberculosis (TB). The methods include determining the level of APOC1, the level of CD14, the level of GP1BA, and the level of TNXB in a first sample(s) from the subject prior to the initiation of the treatment; determining the level of APOC1, the level of CD14, the level of GP1BA, and the level of TNXB in a second sample(s) from the subject after at least a portion of the treatment has been administered; comparing the level of APOC1, the level of CD14, the level of GP1BA, and the level of TNXB in the first sample(s) with a level of APOC1, the level of CD14, the level of GP1BA, and the level of TNXB in the second sample(s), wherein a difference in the level of APOC1, the level of CD14, the level of GP1BA, and the level of TNXB in the first sample(s) as compared to the level of APOC1, the level of CD14, the level of GP1BA, and the level of TNXB in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of CD14, the level and/or activity of GP1BA, and the level and/or activity of TNXB in an aliquot as compared to the level and/or activity of APOC1, the level and/or activity of CD14, the level and/or activity of GP1BA, and the level and/or activity of TNXB in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of CD14, the level and/or activity of GP1BA, and the level and/or activity of TNXB, thereby treating the subject.

In one aspect the present invention provides methods for determining whether a subject has active tuberculosis (TB). The methods include determining the level of APOC1, the level of CD14, the level of GP1BA, and the level of COMP in a sample(s) from the subject; comparing the level of APOC1, the level of CD14, the level of GP1BA, and the level of COMP in the subject sample(s) with a level of APOC1, a level of CD14, a level of GP1BA, and a level of COMP in a control sample(s), wherein a difference in the level of APOC1, a difference in the level of CD14, a difference in the level of GP1BA, and a difference in the level of COMP in the subject sample(s) as compared to the level of APOC1, the level of CD14, the level of GP1BA, and the level of COMP in the control sample(s) indicates that the subject has active TB.

In one aspect the present invention provides methods for monitoring the effectiveness of a treatment in a subject having active tuberculosis (TB). The methods include determining the level of APOC1, the level of CD14, the level of GP1BA, and the level of COMP in a first sample(s) from the subject prior to the initiation of the treatment; determining the level of APOC1, the level of CD14, the level of GP1BA, and the level of COMP in a second sample(s) from the subject after at least a portion of the treatment has been administered; comparing the level of APOC1, the level of CD14, the level of GP1BA, and the level of COMP in the first sample(s) with a level of APOC1, the level of CD14, the level of GP1BA, and the level of COMP in the second sample(s), wherein a difference in the level of APOC1, the level of CD14, the level of GP1BA, and the level of COMP in the first sample(s) as compared to the level of APOC1, the level of CD14, the level of GP1BA, and the level of COMP in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of CD14, the level and/or activity of GP1BA, and the level and/or activity of COMP in an aliquot as compared to the level and/or activity of APOC1, the level and/or activity of CD14, the level and/or activity of GP1BA, and the level and/or activity of COMP in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of CD14, the level and/or activity of GP1BA, and the level and/or activity of COMP, thereby treating the subject.

In one aspect the present invention provides methods for determining whether a subject has active tuberculosis (TB). The methods include determining the level of TNXB, the level of COMP, the level of SELL, and the level of QSOX1 in a sample(s) from the subject; comparing the level of TNXB, the level of COMP, the level of SELL, and the level of QSOX1 in the subject sample(s) with a level of TNXB, a level of COMP, a level of SELL, and a level of QSOX1 in a control sample(s), wherein a difference in the level of TNXB, a difference in the level of COMP, a difference in the level of SELL, and a difference in the level of QSOX1 in the subject sample(s) as compared to the level of TNXB, the level of COMP, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of TNXB, the level of COMP, the level of SELL, and the level of QSOX1 in a first sample(s) from the subject prior to the initiation of the treatment; determining the level of TNXB, the level of COMP, the level of SELL, and the level of QSOX1 in a second sample(s) from the subject after at least a portion of the treatment has been administered; comparing the level of TNXB, the level of COMP, the level of SELL, and the level of QSOX1 in the first sample(s) with a level of TNXB, the level of COMP, the level of SELL, and the level of QSOX1 in the second sample(s), wherein a difference in the level of TNXB, the level of COMP, the level of SELL, and the level of QSOX1 in the first sample(s) as compared to the level of TNXB, the level of COMP, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or activity of TNXB, the level and/or activity of COMP, the level and/or activity of SELL, and the level and/or activity of QSOX1 in an aliquot as compared to the level and/or activity of TNXB, the level and/or activity of COMP, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TNXB, the level and/or activity of COMP, the level and/or activity of SELL, and the level and/or activity of QSOX1, thereby treating the subject.

In one aspect the present invention provides methods for determining whether a subject has active tuberculosis (TB). The methods include determining the level of TNXB, the level of GP1BA, the level of SELL, and the level of QSOX1 in a sample(s) from the subject; comparing the level of TNXB, the level of GP1BA, the level of SELL, and the level of QSOX1 in the subject sample(s) with a level of TNXB, a level of GP1BA, a level of SELL, and a level of QSOX1 in a control sample(s), wherein a difference in the level of TNXB, a difference in the level of GP1BA, a difference in the level of SELL, and a difference in the level of QSOX1 in the subject sample(s) as compared to the level of TNXB, the level of GP1BA, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of TNXB, the level of GP1BA, the level of SELL, and the level of QSOX1 in a first sample(s) from the subject prior to the initiation of the treatment; determining the level of TNXB, the level of GP1BA, the level of SELL, and the level of QSOX1 in a second sample(s) from the subject after at least a portion of the treatment has been administered; comparing the level of TNXB, the level of GP1BA, the level of SELL, and the level of QSOX1 in the first sample(s) with a level of TNXB, the level of GP1BA, the level of SELL, and the level of QSOX1 in the second sample(s), wherein a difference in the level of TNXB, the level of GP1BA, the level of SELL, and the level of QSOX1 in the first sample(s) as compared to the level of TNXB, the level of GP1BA, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of TNXB, the level and/or activity of GP1BA, the level and/or activity of SELL, and the level and/or activity of QSOX1 in an aliquot as compared to the level and/or activity of TNXB, the level and/or activity of GP1BA, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TNXB, the level and/or activity of GP1BA, the level and/or activity of SELL, and the level and/or activity of QSOX1, thereby treating the subject.

In one aspect the present invention provides methods for determining whether a subject has active tuberculosis (TB). The methods include determining the level of TNXB, the level of LUM, the level of SELL, and the level of QSOX1 in a sample(s) from the subject; comparing the level of TNXB, the level of LUM, the level of SELL, and the level of QSOX1 in the subject sample(s) with a level of TNXB, a level of LUM, a level of SELL, and a level of QSOX1 in a control sample(s), wherein a difference in the level of TNXB, a difference in the level of LUM, a difference in the level of SELL, and a difference in the level of QSOX1 in the subject sample(s) as compared to the level of TNXB, the level of LUM, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of TNXB, the level of LUM, the level of SELL, and the level of QSOX1 in a first sample(s) from the subject prior to the initiation of the treatment; determining the level of TNXB, the level of LUM, the level of SELL, and the level of QSOX1 in a second sample(s) from the subject after at least a portion of the treatment has been administered; comparing the level of TNXB, the level of LUM, the level of SELL, and the level of QSOX1 in the first sample(s) with a level of TNXB, the level of LUM, the level of SELL, and the level of QSOX1 in the second sample(s), wherein a difference in the level of TNXB, the level of LUM, the level of SELL, and the level of QSOX1 in the first sample(s) as compared to the level of TNXB, the level of LUM, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of TNXB, the level and/or activity of LUM, the level and/or activity of SELL, and the level and/or activity of QSOX1 in an aliquot as compared to the level and/or activity of TNXB, the level and/or activity of LUM, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TNXB, the level and/or activity of LUM, the level and/or activity of SELL, and the level and/or activity of QSOX1, thereby treating the subject.

In one aspect the present invention provides methods for determining whether a subject has active tuberculosis (TB). The methods include determining the level of SEPP1, the level of GP1BA, the level of SELL, and the level of QSOX1 in a sample(s) from the subject; comparing the level of SEPP1, the level of GP1BA, the level of SELL, and the level of QSOX1 in the subject sample(s) with a level of SEPP1, a level of GP1BA, a level of SELL, and a level of QSOX1 in a control sample(s), wherein a difference in the level of SEPP1, a difference in the level of GP1BA, a difference in the level of SELL, and a difference in the level of QSOX1 in the subject sample(s) as compared to the level of SEPP1, the level of GP1BA, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of SEPP1, the level of GP1BA, the level of SELL, and the level of QSOX1 in a first sample(s) from the subject prior to the initiation of the treatment; determining the level of SEPP1, the level of GP1BA, the level of SELL, and the level of QSOX1 in a second sample(s) from the subject after at least a portion of the treatment has been administered; comparing the level of SEPP1, the level of GP1BA, the level of SELL, and the level of QSOX1 in the first sample(s) with a level of SEPP1, the level of GP1BA, the level of SELL, and the level of QSOX1 in the second sample(s), wherein a difference in the level of SEPP1, the level of GP1BA, the level of SELL, and the level of QSOX1 in the first sample(s) as compared to the level of SEPP1, the level of GP1BA, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of GP1BA, the level and/or activity of SELL, and the level and/or activity of QSOX1 in an aliquot as compared to the level and/or activity of SEPP1, the level and/or activity of GP1BA, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of GP1BA, the level and/or activity of SELL, and the level and/or activity of QSOX1, thereby treating the subject.

In one aspect the present invention provides methods for determining whether a subject has active tuberculosis (TB). The methods include determining the level of SEPP1, the level of LUM, the level of SELL, and the level of APOC1 in a sample(s) from the subject; comparing the level of SEPP1, the level of LUM, the level of SELL, and the level of APOC1 in the subject sample(s) with a level of SEPP1, a level of LUM, a level of SELL, and a level of APOC1 in a control sample(s), wherein a difference in the level of SEPP1, a difference in the level of LUM, a difference in the level of SELL, and a difference in the level of APOC1 in the subject sample(s) as compared to the level of SEPP1, the level of LUM, the level of SELL, and the level of APOC1 in the control sample(s) indicates that the subject has active TB.

In one aspect the present invention provides methods for monitoring the effectiveness of a treatment in a subject having active tuberculosis (TB). The methods include determining the level of SEPP1, the level of LUM, the level of SELL, and the level of APOC1 in a first sample(s) from the subject prior to the initiation of the treatment; determining the level of SEPP1, the level of LUM, the level of SELL, and the level of APOC1 in a second sample(s) from the subject after at least a portion of the treatment has been administered; comparing the level of SEPP1, the level of LUM, the level of SELL, and the level of APOC1 in the first sample(s) with a level of SEPP1, the level of LUM, the level of SELL, and the level of APOC1 in the second sample(s), wherein a difference in the level of SEPP1, the level of LUM, the level of SELL, and the level of APOC1 in the first sample(s) as compared to the level of SEPP1, the level of LUM, the level of SELL, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of LUM, the level and/or activity of SELL, and the level and/or activity of APOC1 in an aliquot as compared to the level and/or activity of SEPP1, the level and/or activity of LUM, the level and/or activity of SELL, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of LUM, the level and/or activity of SELL, and the level and/or activity of APOC1, thereby treating the subject.

In one aspect the present invention provides methods for determining whether a subject has active tuberculosis (TB). The methods include determining the level of APOC1, the level of CD14, the level of GP1BA, and the level of LUM in a sample(s) from the subject; comparing the level of APOC1, the level of CD14, the level of GP1BA, and the level of LUM in the subject sample(s) with a level of APOC1, a level of CD14, a level of GP1BA, and a level of LUM in a control sample(s), wherein a difference in the level of APOC1, a difference in the level of CD14, a difference in the level of GP1BA, and a difference in the level of LUM in the subject sample(s) as compared to the level of APOC1, the level of CD14, the level of GP1BA, and the level of LUM in the control sample(s) indicates that the subject has active TB.

In one aspect the present invention provides methods for monitoring the effectiveness of a treatment in a subject having active tuberculosis (TB). The methods include determining the level of APOC1, the level of CD14, the level of GP1BA, and the level of LUM in a first sample(s) from the subject prior to the initiation of the treatment; determining the level of APOC1, the level of CD14, the level of GP1BA, and the level of LUM in a second sample(s) from the subject after at least a portion of the treatment has been administered; comparing the level of APOC1, the level of CD14, the level of GP1BA, and the level of LUM in the first sample(s) with a level of APOC1, the level of CD14, the level of GP1BA, and the level of LUM in the second sample(s), wherein a difference in the level of APOC1, the level of CD14, the level of GP1BA, and the level of LUM in the first sample(s) as compared to the level of APOC1, the level of CD14, the level of GP1BA, and the level of LUM in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of CD14, the level and/or activity of GP1BA, and the level and/or activity of LUM in an aliquot as compared to the level and/or activity of APOC1, the level and/or activity of CD14, the level and/or activity of GP1BA, and the level and/or activity of LUM in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of CD14, the level and/or activity of GP1BA, and the level and/or activity of LUM, thereby treating the subject.

In one aspect the present invention provides methods for determining whether a subject has active tuberculosis (TB). The methods include determining the level of TNXB, the level of GP1BA, the level of SELL, and the level of SEPP1 in a sample(s) from the subject; comparing the level of TNXB, the level of GP1BA, the level of SELL, and the level of SEPP1 in the subject sample(s) with a level of TNXB, a level of GP1BA, a level of SELL, and a level of SEPP1 in a control sample(s), wherein a difference in the level of TNXB, a difference in the level of GP1BA, a difference in the level of SELL, and a difference in the level of SEPP1 in the subject sample(s) as compared to the level of TNXB, the level of GP1BA, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of TNXB, the level of GP1BA, the level of SELL, and the level of SEPP1 in a first sample(s) from the subject prior to the initiation of the treatment; determining the level of TNXB, the level of GP1BA, the level of SELL, and the level of SEPP1 in a second sample(s) from the subject after at least a portion of the treatment has been administered; comparing the level of TNXB, the level of GP1BA, the level of SELL, and the level of SEPP1 in the first sample(s) with a level of TNXB, the level of GP1BA, the level of SELL, and the level of SEPP1 in the second sample(s), wherein a difference in the level of TNXB, the level of GP1BA, the level of SELL, and the level of SEPP1 in the first sample(s) as compared to the level of TNXB, the level of GP1BA, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of TNXB, the level and/or activity of GP1BA, the level and/or activity of SELL, and the level and/or activity of SEPP1 in an aliquot as compared to the level and/or activity of TNXB, the level and/or activity of GP1BA, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TNXB, the level and/or activity of GP1BA, the level and/or activity of SELL, and the level and/or activity of SEPP1, thereby treating the subject.

In one aspect the present invention provides methods for determining whether a subject has active tuberculosis (TB). The methods include determining the level of SEPP1, the level of LUM, the level of SELL, and the level of CD14 in a sample(s) from the subject; comparing the level of SEPP1, the level of LUM, the level of SELL, and the level of CD14 in the subject sample(s) with a level of SEPP1, a level of LUM, a level of SELL, and a level of CD14 in a control sample(s), wherein a difference in the level of SEPP1, a difference in the level of LUM, a difference in the level of SELL, and a difference in the level of CD14 in the subject sample(s) as compared to the level of SEPP1, the level of LUM, the level of SELL, and the level of CD14 in the control sample(s) indicates that the subject has active TB.

In one aspect the present invention provides methods for monitoring the effectiveness of a treatment in a subject having active tuberculosis (TB). The methods include determining the level of SEPP1, the level of LUM, the level of SELL, and the level of CD14 in a first sample(s) from the subject prior to the initiation of the treatment; determining the level of SEPP1, the level of LUM, the level of SELL, and the level of CD14 in a second sample(s) from the subject after at least a portion of the treatment has been administered; comparing the level of SEPP1, the level of LUM, the level of SELL, and the level of CD14 in the first sample(s) with a level of SEPP1, the level of LUM, the level of SELL, and the level of CD14 in the second sample(s), wherein a difference in the level of SEPP1, the level of LUM, the level of SELL, and the level of CD14 in the first sample(s) as compared to the level of SEPP1, the level of LUM, the level of SELL, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of LUM, the level and/or activity of SELL, and the level and/or activity of CD14 in an aliquot as compared to the level and/or activity of SEPP1, the level and/or activity of LUM, the level and/or activity of SELL, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of LUM, the level and/or activity of SELL, and the level and/or activity of CD14, thereby treating the subject.

In one aspect the present invention provides methods for determining whether a subject has active tuberculosis (TB). The methods include determining the level of TNXB, the level of COMP, the level of SELL, and the level of CD14 in a sample(s) from the subject; comparing the level of TNXB, the level of COMP, the level of SELL, and the level of CD14 in the subject sample(s) with a level of TNXB, a level of COMP, a level of SELL, and a level of CD14 in a control sample(s), wherein a difference in the level of TNXB, a difference in the level of COMP, a difference in the level of SELL, and a difference in the level of CD14 in the subject sample(s) as compared to the level of TNXB, the level of COMP, the level of SELL, and the level of CD14 in the control sample(s) indicates that the subject has active TB.

In one aspect the present invention provides methods for monitoring the effectiveness of a treatment in a subject having active tuberculosis (TB). The methods include determining the level of TNXB, the level of COMP, the level of SELL, and the level of CD14 in a first sample(s) from the subject prior to the initiation of the treatment; determining the level of TNXB, the level of COMP, the level of SELL, and the level of CD14 in a second sample(s) from the subject after at least a portion of the treatment has been administered; comparing the level of TNXB, the level of COMP, the level of SELL, and the level of CD14 in the first sample(s) with a level of TNXB, the level of COMP, the level of SELL, and the level of CD14 in the second sample(s), wherein a difference in the level of TNXB, the level of COMP, the level of SELL, and the level of CD14 in the first sample(s) as compared to the level of TNXB, the level of COMP, the level of SELL, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of TNXB, the level and/or activity of COMP, the level and/or activity of SELL, and the level and/or activity of CD14 in an aliquot as compared to the level and/or activity of TNXB, the level and/or activity of COMP, the level and/or activity of SELL, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TNXB, the level and/or activity of COMP, the level and/or activity of SELL, and the level and/or activity of CD14, thereby treating the subject.

In one aspect the present invention provides methods for determining whether a subject has active tuberculosis (TB). The methods include determining the level of SEPP1, the level of TNXB, the level of SELL, and the level of CD14 in a sample(s) from the subject; comparing the level of SEPP1, the level of TNXB, the level of SELL, and the level of CD14 in the subject sample(s) with a level of SEPP1, a level of TNXB, a level of SELL, and a level of CD14 in a control sample(s), wherein a difference in the level of SEPP1, a difference in the level of TNXB, a difference in the level of SELL, and a difference in the level of CD14 in the subject sample(s) as compared to the level of SEPP1, the level of TNXB, the level of SELL, and the level of CD14 in the control sample(s) indicates that the subject has active TB.

In one aspect the present invention provides methods for monitoring the effectiveness of a treatment in a subject having active tuberculosis (TB). The methods include determining the level of SEPP1, the level of TNXB, the level of SELL, and the level of CD14 in a first sample(s) from the subject prior to the initiation of the treatment; determining the level of SEPP1, the level of TNXB, the level of SELL, and the level of CD14 in a second sample(s) from the subject after at least a portion of the treatment has been administered; comparing the level of SEPP1, the level of TNXB, the level of SELL, and the level of CD14 in the first sample(s) with a level of SEPP1, the level of TNXB, the level of SELL, and the level of CD14 in the second sample(s), wherein a difference in the level of SEPP1, the level of TNXB, the level of SELL, and the level of CD14 in the first sample(s) as compared to the level of SEPP1, the level of TNXB, the level of SELL, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of TNXB, the level and/or activity of SELL, and the level and/or activity of CD14 in an aliquot as compared to the level and/or activity of SEPP1, the level and/or activity of TNXB, the level and/or activity of SELL, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of TNXB, the level and/or activity of SELL, and the level and/or activity of CD14, thereby treating the subject.

In one aspect the present invention provides methods for determining whether a subject has active tuberculosis (TB). The methods include determining the level of LUM, the level of GP1BA, the level of SELL, and the level of SEPP1 in a sample(s) from the subject; comparing the level of LUM, the level of GP1BA, the level of SELL, and the level of SEPP1 in the subject sample(s) with a level of LUM, a level of GP1BA, a level of SELL, and a level of SEPP1 in a control sample(s), wherein a difference in the level of LUM, a difference in the level of GP1BA, a difference in the level of SELL, and a difference in the level of SEPP1 in the subject sample(s) as compared to the level of LUM, the level of GP1BA, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of LUM, the level of GP1BA, the level of SELL, and the level of SEPP1 in a first sample(s) from the subject prior to the initiation of the treatment; determining the level of LUM, the level of GP1BA, the level of SELL, and the level of SEPP1 in a second sample(s) from the subject after at least a portion of the treatment has been administered; comparing the level of LUM, the level of GP1BA, the level of SELL, and the level of SEPP1 in the first sample(s) with a level of LUM, the level of GP1BA, the level of SELL, and the level of SEPP1 in the second sample(s), wherein a difference in the level of LUM, the level of GP1BA, the level of SELL, and the level of SEPP1 in the first sample(s) as compared to the level of LUM, the level of GP1BA, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of LUM, the level and/or activity of GP1BA, the level and/or activity of SELL, and the level and/or activity of SEPP1 in an aliquot as compared to the level and/or activity of LUM, the level and/or activity of GP1BA, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LUM, the level and/or activity of GP1BA, the level and/or activity of SELL, and the level and/or activity of SEPP1, thereby treating the subject.

In one aspect the present invention provides methods for determining whether a subject has active tuberculosis (TB). The methods include determining the level of SEPP1, the level of COMP, the level of SELL, and the level of CD14 in a sample(s) from the subject; comparing the level of SEPP1, the level of COMP, the level of SELL, and the level of CD14 in the subject sample(s) with a level of SEPP1, a level of COMP, a level of SELL, and a level of CD14 in a control sample(s), wherein a difference in the level of SEPP1, a difference in the level of COMP, a difference in the level of SELL, and a difference in the level of CD14 in the subject sample(s) as compared to the level of SEPP1, the level of COMP, the level of SELL, and the level of CD14 in the control sample(s) indicates that the subject has active TB.

In one aspect the present invention provides methods for monitoring the effectiveness of a treatment in a subject having active tuberculosis (TB). The methods include determining the level of SEPP1, the level of COMP, the level of SELL, and the level of CD14 in a first sample(s) from the subject prior to the initiation of the treatment; determining the level of SEPP1, the level of COMP, the level of SELL, and the level of CD14 in a second sample(s) from the subject after at least a portion of the treatment has been administered; comparing the level of SEPP1, the level of COMP, the level of SELL, and the level of CD14 in the first sample(s) with a level of SEPP1, the level of COMP, the level of SELL, and the level of CD14 in the second sample(s), wherein a difference in the level of SEPP1, the level of COMP, the level of SELL, and the level of CD14 in the first sample(s) as compared to the level of SEPP1, the level of COMP, the level of SELL, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of SEPP1, the level and/or activity of COMP, the level and/or activity of SELL, and the level and/or activity of CD14 in an aliquot as compared to the level and/or activity of SEPP1, the level and/or activity of COMP, the level and/or activity of SELL, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of COMP, the level and/or activity of SELL, and the level and/or activity of CD14, thereby treating the subject.

In one aspect the present invention provides methods for determining whether a subject has active tuberculosis (TB). The methods include determining the level of LUM, the level of TNXB, the level of SELL, and the level of SEPP1 in a sample(s) from the subject; comparing the level of LUM, the level of TNXB, the level of SELL, and the level of SEPP1 in the subject sample(s) with a level of LUM, a level of TNXB, a level of SELL, and a level of SEPP1 in a control sample(s), wherein a difference in the level of LUM, a difference in the level of TNXB, a difference in the level of SELL, and a difference in the level of SEPP1 in the subject sample(s) as compared to the level of LUM, the level of TNXB, the level of SELL, and the level of SEPP1 in the control sample(s) indicates that the subject has active TB.

In one aspect the present invention provides methods for monitoring the effectiveness of a treatment in a subject having active tuberculosis (TB). The methods include determining the level of LUM, the level of TNXB, the level of SELL, and the level of SEPP1 in a first sample(s) from the subject prior to the initiation of the treatment; determining the level of LUM, the level of TNXB, the level of SELL, and the level of SEPP1 in a second sample(s) from the subject after at least a portion of the treatment has been administered; comparing the level of LUM, the level of TNXB, the level of SELL, and the level of SEPP1 in the first sample(s) with a level of LUM, the level of TNXB, the level of SELL, and the level of SEPP1 in the second sample(s), wherein a difference in the level of LUM, the level of TNXB, the level of SELL, and the level of SEPP1 in the first sample(s) as compared to the level of LUM, the level of TNXB, the level of SELL, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of LUM, the level and/or activity of TNXB, the level and/or activity of SELL, and the level and/or activity of SEPP1 in an aliquot as compared to the level and/or activity of LUM, the level and/or activity of TNXB, the level and/or activity of SELL, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LUM, the level and/or activity of TNXB, the level and/or activity of SELL, and the level and/or activity of SEPP1, thereby treating the subject.

In one aspect the present invention provides methods for determining whether a subject has active tuberculosis (TB). The methods include determining the level of APOC1, the level of TNXB, the level of SELL, and the level of CD14 in a sample(s) from the subject; comparing the level of APOC1, the level of TNXB, the level of SELL, and the level of CD14 in the subject sample(s) with a level of APOC1, a level of TNXB, a level of SELL, and a level of CD14 in a control sample(s), wherein a difference in the level of APOC1, a difference in the level of TNXB, a difference in the level of SELL, and a difference in the level of CD14 in the subject sample(s) as compared to the level of APOC1, the level of TNXB, the level of SELL, and the level of CD14 in the control sample(s) indicates that the subject has active TB.

In one aspect the present invention provides methods for monitoring the effectiveness of a treatment in a subject having active tuberculosis (TB). The methods include determining the level of APOC1, the level of TNXB, the level of SELL, and the level of CD14 in a first sample(s) from the subject prior to the initiation of the treatment; determining the level of APOC1, the level of TNXB, the level of SELL, and the level of CD14 in a second sample(s) from the subject after at least a portion of the treatment has been administered; comparing the level of APOC1, the level of TNXB, the level of SELL, and the level of CD14 in the first sample(s) with a level of APOC1, the level of TNXB, the level of SELL, and the level of CD14 in the second sample(s), wherein a difference in the level of APOC1, the level of TNXB, the level of SELL, and the level of CD14 in the first sample(s) as compared to the level of APOC1, the level of TNXB, the level of SELL, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of TNXB, the level and/or activity of SELL, and the level and/or activity of CD14 in an aliquot as compared to the level and/or activity of APOC1, the level and/or activity of TNXB, the level and/or activity of SELL, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of TNXB, the level and/or activity of SELL, and the level and/or activity of CD14, thereby treating the subject.

In one aspect the present invention provides methods for determining whether a subject has active tuberculosis (TB). The methods include determining the level of GP1BA, the level of TNXB, the level of SELL, and the level of CD14 in a sample(s) from the subject; comparing the level of GP1BA, the level of TNXB, the level of SELL, and the level of CD14 in the subject sample(s) with a level of GP1BA, a level of TNXB, a level of SELL, and a level of CD14 in a control sample(s), wherein a difference in the level of GP1BA, a difference in the level of TNXB, a difference in the level of SELL, and a difference in the level of CD14 in the subject sample(s) as compared to the level of GP1BA, the level of TNXB, the level of SELL, and the level of CD14 in the control sample(s) indicates that the subject has active TB.

In one aspect the present invention provides methods for monitoring the effectiveness of a treatment in a subject having active tuberculosis (TB). The methods include determining the level of GP1BA, the level of TNXB, the level of SELL, and the level of CD14 in a first sample(s) from the subject prior to the initiation of the treatment; determining the level of GP1BA, the level of TNXB, the level of SELL, and the level of CD14 in a second sample(s) from the subject after at least a portion of the treatment has been administered; comparing the level of GP1BA, the level of TNXB, the level of SELL, and the level of CD14 in the first sample(s) with a level of GP1BA, the level of TNXB, the level of SELL, and the level of CD14 in the second sample(s), wherein a difference in the level of GP1BA, the level of TNXB, the level of SELL, and the level of CD14 in the first sample(s) as compared to the level of GP1BA, the level of TNXB, the level of SELL, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of GP1BA, the level and/or activity of TNXB, the level and/or activity of SELL, and the level and/or activity of CD14 in an aliquot as compared to the level and/or activity of GP1BA, the level and/or activity of TNXB, the level and/or activity of SELL, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of GP1BA, the level and/or activity of TNXB, the level and/or activity of SELL, and the level and/or activity of CD14, thereby treating the subject.

In one aspect the present invention provides methods for determining whether a subject has active tuberculosis (TB). The methods include determining the level of APOC1, the level of CD14, the level of GP1BA, and the level of SEPP1 in a sample(s) from the subject; comparing the level of APOC1, the level of CD14, the level of GP1BA, and the level of SEPP1 in the subject sample(s) with a level of APOC1, a level of CD14, a level of GP1BA, and a level of SEPP1 in a control sample(s), wherein a difference in the level of APOC1, a difference in the level of CD14, a difference in the level of GP1BA, and a difference in the level of SEPP1 in the subject sample(s) as compared to the level of APOC1, the level of CD14, the level of GP1BA, and the level of SEPP1 in the control sample(s) indicates that the subject has active TB.

In one aspect the present invention provides methods for monitoring the effectiveness of a treatment in a subject having active tuberculosis (TB). The methods include determining the level of APOC1, the level of CD14, the level of GP1BA, and the level of SEPP1 in a first sample(s) from the subject prior to the initiation of the treatment; determining the level of APOC1, the level of CD14, the level of GP1BA, and the level of SEPP1 in a second sample(s) from the subject after at least a portion of the treatment has been administered; comparing the level of APOC1, the level of CD14, the level of GP1BA, and the level of SEPP1 in the first sample(s) with a level of APOC1, the level of CD14, the level of GP1BA, and the level of SEPP1 in the second sample(s), wherein a difference in the level of APOC1, the level of CD14, the level of GP1BA, and the level of SEPP1 in the first sample(s) as compared to the level of APOC1, the level of CD14, the level of GP1BA, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of CD14, the level and/or activity of GP1BA, and the level and/or activity of SEPP1 in an aliquot as compared to the level and/or activity of APOC1, the level and/or activity of CD14, the level and/or activity of GP1BA, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of CD14, the level and/or activity of GP1BA, and the level and/or activity of SEPP1, thereby treating the subject.

In one aspect the present invention provides methods for determining whether a subject has active tuberculosis (TB). The methods include determining the level of APOC1, the level of CD14, the level of SELL, and the level of LUM in a sample(s) from the subject; comparing the level of APOC1, the level of CD14, the level of SELL, and the level of LUM in the subject sample(s) with a level of APOC1, a level of CD14, a level of SELL, and a level of LUM in a control sample(s), wherein a difference in the level of APOC1, a difference in the level of CD14, a difference in the level of SELL, and a difference in the level of LUM in the subject sample(s) as compared to the level of APOC1, the level of CD14, the level of SELL, and the level of LUM in the control sample(s) indicates that the subject has active TB.

In one aspect the present invention provides methods for monitoring the effectiveness of a treatment in a subject having active tuberculosis (TB). The methods include determining the level of APOC1, the level of CD14, the level of SELL, and the level of LUM in a first sample(s) from the subject prior to the initiation of the treatment; determining the level of APOC1, the level of CD14, the level of SELL, and the level of LUM in a second sample(s) from the subject after at least a portion of the treatment has been administered; comparing the level of APOC1, the level of CD14, the level of SELL, and the level of LUM in the first sample(s) with a level of APOC1, the level of CD14, the level of SELL, and the level of LUM in the second sample(s), wherein a difference in the level of APOC1, the level of CD14, the level of SELL, and the level of LUM in the first sample(s) as compared to the level of APOC1, the level of CD14, the level of SELL, and the level of LUM in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of CD14, the level and/or activity of SELL, and the level and/or activity of LUM in an aliquot as compared to the level and/or activity of APOC1, the level and/or activity of CD14, the level and/or activity of SELL, and the level and/or activity of LUM in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of CD14, the level and/or activity of SELL, and the level and/or activity of LUM, thereby treating the subject.

In one aspect the present invention provides methods for determining whether a subject has active tuberculosis (TB). The methods include determining the level of COMP, the level of GP1BA, the level of SELL, and the level of APOC1 in a sample(s) from the subject; comparing the level of COMP, the level of GP1BA, the level of SELL, and the level of APOC1 in the subject sample(s) with a level of COMP, a level of GP1BA, a level of SELL, and a level of APOC1 in a control sample(s), wherein a difference in the level of COMP, a difference in the level of GP1BA, a difference in the level of SELL, and a difference in the level of APOC1 in the subject sample(s) as compared to the level of COMP, the level of GP1BA, the level of SELL, and the level of APOC1 in the control sample(s) indicates that the subject has active TB.

In one aspect the present invention provides methods for monitoring the effectiveness of a treatment in a subject having active tuberculosis (TB). The methods include determining the level of COMP, the level of GP1BA, the level of SELL, and the level of APOC1 in a first sample(s) from the subject prior to the initiation of the treatment; determining the level of COMP, the level of GP1BA, the level of SELL, and the level of APOC1 in a second sample(s) from the subject after at least a portion of the treatment has been administered; comparing the level of COMP, the level of GP1BA, the level of SELL, and the level of APOC1 in the first sample(s) with a level of COMP, the level of GP1BA, the level of SELL, and the level of APOC1 in the second sample(s), wherein a difference in the level of COMP, the level of GP1BA, the level of SELL, and the level of APOC1 in the first sample(s) as compared to the level of COMP, the level of GP1BA, the level of SELL, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of GP1BA, the level and/or activity of SELL, and the level and/or activity of APOC1 in an aliquot as compared to the level and/or activity of COMP, the level and/or activity of GP1BA, the level and/or activity of SELL, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of GP1BA, the level and/or activity of SELL, and the level and/or activity of APOC1, thereby treating the subject.

In one aspect the present invention provides methods for determining whether a subject has active tuberculosis (TB). The methods include determining the level of COMP, the level of CD14, the level of SELL, and the level of APOC1 in a sample(s) from the subject; comparing the level of COMP, the level of CD14, the level of SELL, and the level of APOC1 in the subject sample(s) with a level of COMP, a level of CD14, a level of SELL, and a level of APOC1 in a control sample(s), wherein a difference in the level of COMP, a difference in the level of CD14, a difference in the level of SELL, and a difference in the level of APOC1 in the subject sample(s) as compared to the level of COMP, the level of CD14, the level of SELL, and the level of APOC1 in the control sample(s) indicates that the subject has active TB.

In one aspect the present invention provides methods for monitoring the effectiveness of a treatment in a subject having active tuberculosis (TB). The methods include determining the level of COMP, the level of CD14, the level of SELL, and the level of APOC1 in a first sample(s) from the subject prior to the initiation of the treatment; determining the level of COMP, the level of CD14, the level of SELL, and the level of APOC1 in a second sample(s) from the subject after at least a portion of the treatment has been administered; comparing the level of COMP, the level of CD14, the level of SELL, and the level of APOC1 in the first sample(s) with a level of COMP, the level of CD14, the level of SELL, and the level of APOC1 in the second sample(s), wherein a difference in the level of COMP, the level of CD14, the level of SELL, and the level of APOC1 in the first sample(s) as compared to the level of COMP, the level of CD14, the level of SELL, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of CD14, the level and/or activity of SELL, and the level and/or activity of APOC1 in an aliquot as compared to the level and/or activity of COMP, the level and/or activity of CD14, the level and/or activity of SELL, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of CD14, the level and/or activity of SELL, and the level and/or activity of APOC1, thereby treating the subject.

In one aspect the present invention provides methods for determining whether a subject has active tuberculosis (TB). The methods include determining the level of APOC1, the level of CD14, the level of PEPD, and the level of LUM in a sample(s) from the subject; comparing the level of APOC1, the level of CD14, the level of PEPD, and the level of LUM in the subject sample(s) with a level of APOC1, a level of CD14, a level of PEPD, and a level of LUM in a control sample(s), wherein a difference in the level of APOC1, a difference in the level of CD14, a difference in the level of PEPD, and a difference in the level of LUM in the subject sample(s) as compared to the level of APOC1, the level of CD14, the level of PEPD, and the level of LUM in the control sample(s) indicates that the subject has active TB.

In one aspect the present invention provides methods for monitoring the effectiveness of a treatment in a subject having active tuberculosis (TB). The methods include determining the level of APOC1, the level of CD14, the level of PEPD, and the level of LUM in a first sample(s) from the subject prior to the initiation of the treatment; determining the level of APOC1, the level of CD14, the level of PEPD, and the level of LUM in a second sample(s) from the subject after at least a portion of the treatment has been administered; comparing the level of APOC1, the level of CD14, the level of PEPD, and the level of LUM in the first sample(s) with a level of APOC1, the level of CD14, the level of PEPD, and the level of LUM in the second sample(s), wherein a difference in the level of APOC1, the level of CD14, the level of PEPD, and the level of LUM in the first sample(s) as compared to the level of APOC1, the level of CD14, the level of PEPD, and the level of LUM in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of CD14, the level and/or activity of PEPD, and the level and/or activity of LUM in an aliquot as compared to the level and/or activity of APOC1, the level and/or activity of CD14, the level and/or activity of PEPD, and the level and/or activity of LUM in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of CD14, the level and/or activity of PEPD, and the level and/or activity of LUM, thereby treating the subject.

In one aspect the present invention provides methods for determining whether a subject has active tuberculosis (TB). The methods include determining the level of LUM, the level of TNXB, the level of SELL, and the level of COMP in a sample(s) from the subject; comparing the level of LUM, the level of TNXB, the level of SELL, and the level of COMP in the subject sample(s) with a level of LUM, a level of TNXB, a level of SELL, and a level of COMP in a control sample(s), wherein a difference in the level of LUM, a difference in the level of TNXB, a difference in the level of SELL, and a difference in the level of COMP in the subject sample(s) as compared to the level of LUM, the level of TNXB, the level of SELL, and the level of COMP in the control sample(s) indicates that the subject has active TB.

In one aspect the present invention provides methods for monitoring the effectiveness of a treatment in a subject having active tuberculosis (TB). The methods include determining the level of LUM, the level of TNXB, the level of SELL, and the level of COMP in a first sample(s) from the subject prior to the initiation of the treatment; determining the level of LUM, the level of TNXB, the level of SELL, and the level of COMP in a second sample(s) from the subject after at least a portion of the treatment has been administered; comparing the level of LUM, the level of TNXB, the level of SELL, and the level of COMP in the first sample(s) with a level of LUM, the level of TNXB, the level of SELL, and the level of COMP in the second sample(s), wherein a difference in the level of LUM, the level of TNXB, the level of SELL, and the level of COMP in the first sample(s) as compared to the level of LUM, the level of TNXB, the level of SELL, and the level of COMP in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of LUM, the level and/or activity of TNXB, the level and/or activity of SELL, and the level and/or activity of COMP in an aliquot as compared to the level and/or activity of LUM, the level and/or activity of TNXB, the level and/or activity of SELL, and the level and/or activity of COMP in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LUM, the level and/or activity of TNXB, the level and/or activity of SELL, and the level and/or activity of COMP, thereby treating the subject.

In one aspect the present invention provides methods for determining whether a subject has active tuberculosis (TB). The methods include determining the level of GP1BA, the level of SEPP1, the level of SELL, and the level of CD14 in a sample(s) from the subject; comparing the level of GP1BA, the level of SEPP1, the level of SELL, and the level of CD14 in the subject sample(s) with a level of GP1BA, a level of SEPP1, a level of SELL, and a level of CD14 in a control sample(s), wherein a difference in the level of GP1BA, a difference in the level of SEPP1, a difference in the level of SELL, and a difference in the level of CD14 in the subject sample(s) as compared to the level of GP1BA, the level of SEPP1, the level of SELL, and the level of CD14 in the control sample(s) indicates that the subject has active TB.

In one aspect the present invention provides methods for monitoring the effectiveness of a treatment in a subject having active tuberculosis (TB). The methods include determining the level of GP1BA, the level of SEPP1, the level of SELL, and the level of CD14 in a first sample(s) from the subject prior to the initiation of the treatment; determining the level of GP1BA, the level of SEPP1, the level of SELL, and the level of CD14 in a second sample(s) from the subject after at least a portion of the treatment has been administered; comparing the level of GP1BA, the level of SEPP1, the level of SELL, and the level of CD14 in the first sample(s) with a level of GP1BA, the level of SEPP1, the level of SELL, and the level of CD14 in the second sample(s), wherein a difference in the level of GP1BA, the level of SEPP1, the level of SELL, and the level of CD14 in the first sample(s) as compared to the level of GP1BA, the level of SEPP1, the level of SELL, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of GP1BA, the level and/or activity of SEPP1, the level and/or activity of SELL, and the level and/or activity of CD14 in an aliquot as compared to the level and/or activity of GP1BA, the level and/or activity of SEPP1, the level and/or activity of SELL, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of GP1BA, the level and/or activity of SEPP1, the level and/or activity of SELL, and the level and/or activity of CD14, thereby treating the subject.

In one aspect the present invention provides methods for determining whether a subject has active tuberculosis (TB). The methods include determining the level of LUM, the level of TNXB, the level of SELL, and the level of CD14 in a sample(s) from the subject; comparing the level of LUM, the level of TNXB, the level of SELL, and the level of CD14 in the subject sample(s) with a level of LUM, a level of TNXB, a level of SELL, and a level of CD14 in a control sample(s), wherein a difference in the level of LUM, a difference in the level of TNXB, a difference in the level of SELL, and a difference in the level of CD14 in the subject sample(s) as compared to the level of LUM, the level of TNXB, the level of SELL, and the level of CD14 in the control sample(s) indicates that the subject has active TB.

In one aspect the present invention provides methods for monitoring the effectiveness of a treatment in a subject having active tuberculosis (TB). The methods include determining the level of LUM, the level of TNXB, the level of SELL, and the level of CD14 in a first sample(s) from the subject prior to the initiation of the treatment; determining the level of LUM, the level of TNXB, the level of SELL, and the level of CD14 in a second sample(s) from the subject after at least a portion of the treatment has been administered; comparing the level of LUM, the level of TNXB, the level of SELL, and the level of CD14 in the first sample(s) with a level of LUM, the level of TNXB, the level of SELL, and the level of CD14 in the second sample(s), wherein a difference in the level of LUM, the level of TNXB, the level of SELL, and the level of CD14 in the first sample(s) as compared to the level of LUM, the level of TNXB, the level of SELL, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of LUM, the level and/or activity of TNXB, the level and/or activity of SELL, and the level and/or activity of CD14 in an aliquot as compared to the level and/or activity of LUM, the level and/or activity of TNXB, the level and/or activity of SELL, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LUM, the level and/or activity of TNXB, the level and/or activity of SELL, and the level and/or activity of CD14, thereby treating the subject.

In one aspect the present invention provides methods for determining whether a subject has active tuberculosis (TB). The methods include determining the level of GP1BA, the level of LUM, the level of SELL, and the level of CD14 in a sample(s) from the subject; comparing the level of GP1BA, the level of LUM, the level of SELL, and the level of CD14 in the subject sample(s) with a level of GP1BA, a level of LUM, a level of SELL, and a level of CD14 in a control sample(s), wherein a difference in the level of GP1BA, a difference in the level of LUM, a difference in the level of SELL, and a difference in the level of CD14 in the subject sample(s) as compared to the level of GP1BA, the level of LUM, the level of SELL, and the level of CD14 in the control sample(s) indicates that the subject has active TB.

In one aspect the present invention provides methods for monitoring the effectiveness of a treatment in a subject having active tuberculosis (TB). The methods include determining the level of GP1BA, the level of LUM, the level of SELL, and the level of CD14 in a first sample(s) from the subject prior to the initiation of the treatment; determining the level of GP1BA, the level of LUM, the level of SELL, and the level of CD14 in a second sample(s) from the subject after at least a portion of the treatment has been administered; comparing the level of GP1BA, the level of LUM, the level of SELL, and the level of CD14 in the first sample(s) with a level of GP1BA, the level of LUM, the level of SELL, and the level of CD14 in the second sample(s), wherein a difference in the level of GP1BA, the level of LUM, the level of SELL, and the level of CD14 in the first sample(s)

as compared to the level of GP1BA, the level of LUM, the level of SELL, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of GP1BA, the level and/or activity of LUM, the level and/or activity of SELL, and the level and/or activity of CD14 in an aliquot as compared to the level and/or activity of GP1BA, the level and/or activity of LUM, the level and/or activity of SELL, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of GP1BA, the level and/or activity of LUM, the level and/or activity of SELL, and the level and/or activity of CD14, thereby treating the subject.

In one aspect the present invention provides methods for determining whether a subject has active tuberculosis (TB). The methods include determining the level of COMP, the level of LUM, the level of SELL, and the level of APOC1 in a sample(s) from the subject; comparing the level of COMP, the level of LUM, the level of SELL, and the level of APOC1 in the subject sample(s) with a level of COMP, a level of LUM, a level of SELL, and a level of APOC1 in a control sample(s), wherein a difference in the level of COMP, a difference in the level of LUM, a difference in the level of SELL, and a difference in the level of APOC1 in the subject sample(s) as compared to the level of COMP, the level of LUM, the level of SELL, and the level of APOC1 in the control sample(s) indicates that the subject has active TB.

In one aspect the present invention provides methods for monitoring the effectiveness of a treatment in a subject having active tuberculosis (TB). The methods include determining the level of COMP, the level of LUM, the level of SELL, and the level of APOC1 in a first sample(s) from the subject prior to the initiation of the treatment; determining the level of COMP, the level of LUM, the level of SELL, and the level of APOC1 in a second sample(s) from the subject after at least a portion of the treatment has been administered; comparing the level of COMP, the level of LUM, the level of SELL, and the level of APOC1 in the first sample(s) with a level of COMP, the level of LUM, the level of SELL, and the level of APOC1 in the second sample(s), wherein a difference in the level of COMP, the level of LUM, the level of SELL, and the level of APOC1 in the first sample(s) as compared to the level of COMP, the level of LUM, the level of SELL, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of LUM, the level and/or activity of SELL, and the level and/or activity of APOC1 in an aliquot as compared to the level and/or activity of COMP, the level and/or activity of LUM, the level and/or activity of SELL, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of LUM, the level and/or activity of SELL, and the level and/or activity of APOC1, thereby treating the subject.

In one aspect the present invention provides methods for determining whether a subject has active tuberculosis (TB). The methods include determining the level of COMP, the level of TNXB, the level of SELL, and the level of APOC1 in a sample(s) from the subject; comparing the level of COMP, the level of TNXB, the level of SELL, and the level of APOC1 in the subject sample(s) with a level of COMP, a level of TNXB, a level of SELL, and a level of APOC1 in a control sample(s), wherein a difference in the level of COMP, a difference in the level of TNXB, a difference in the level of SELL, and a difference in the level of APOC1 in the subject sample(s) as compared to the level of COMP, the level of TNXB, the level of SELL, and the level of APOC1 in the control sample(s) indicates that the subject has active TB.

In one aspect the present invention provides methods for monitoring the effectiveness of a treatment in a subject having active tuberculosis (TB). The methods include determining the level of COMP, the level of TNXB, the level of SELL, and the level of APOC1 in a first sample(s) from the subject prior to the initiation of the treatment; determining the level of COMP, the level of TNXB, the level of SELL, and the level of APOC1 in a second sample(s) from the subject after at least a portion of the treatment has been administered; comparing the level of COMP, the level of TNXB, the level of SELL, and the level of APOC1 in the first sample(s) with a level of COMP, the level of TNXB, the level of SELL, and the level of APOC1 in the second sample(s), wherein a difference in the level of COMP, the level of TNXB, the level of SELL, and the level of APOC1 in the first sample(s) as compared to the level of COMP, the level of TNXB, the level of SELL, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of TNXB, the level and/or activity of SELL, and the level and/or activity of APOC1 in an aliquot as compared to the level and/or activity of COMP, the level and/or activity of TNXB, the level and/or activity of SELL, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of TNXB, the level and/or activity of SELL, and the level and/or activity of APOC1, thereby treating the subject.

In one aspect the present invention provides methods for determining whether a subject has active tuberculosis (TB). The methods include determining the level of GP1BA, the level of SEPP1, the level of COMP, and the level of CD14 in a sample(s) from the subject; comparing the level of GP1BA, the level of SEPP1, the level of COMP, and the level of CD14 in the subject sample(s) with a level of GP1BA, a level of SEPP1, a level of COMP, and a level of CD14 in a control sample(s), wherein a difference in the level of GP1BA, a difference in the level of SEPP1, a difference in the level of COMP, and a difference in the level of CD14 in the subject sample(s) as compared to the level of GP1BA, the level of SEPP1, the level of COMP, and the level of CD14 in the control sample(s) indicates that the subject has active TB.

In one aspect the present invention provides methods for monitoring the effectiveness of a treatment in a subject having active tuberculosis (TB). The methods include determining the level of GP1BA, the level of SEPP1, the level of COMP, and the level of CD14 in a first sample(s) from the subject prior to the initiation of the treatment; determining the level of GP1BA, the level of SEPP1, the level of COMP, and the level of CD14 in a second sample(s) from the subject after at least a portion of the treatment has been administered; comparing the level of GP1BA, the level of SEPP1, the level of COMP, and the level of CD14 in the first sample(s) with a level of GP1BA, the level of SEPP1, the level of COMP, and the level of CD14 in the second sample(s), wherein a difference in the level of GP1BA, the level of SEPP1, the level of COMP, and the level of CD14 in the first sample(s) as compared to the level of GP1BA, the level of SEPP1, the level of COMP, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of GP1BA, the level and/or activity of SEPP1, the level and/or activity of COMP, and the level and/or activity of CD14 in an aliquot as compared to the level and/or activity of GP1BA, the level and/or activity of SEPP1, the level and/or activity of COMP, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of GP1BA, the level and/or activity of SEPP1, the level and/or activity of COMP, and the level and/or activity of CD14, thereby treating the subject.

In one aspect the present invention provides methods for determining whether a subject has active tuberculosis (TB). The methods include determining the level of GP1BA, the level of SEPP1, the level of LUM, and the level of CD14 in a sample(s) from the subject; comparing the level of GP1BA, the level of SEPP1, the level of LUM, and the level of CD14 in the subject sample(s) with a level of GP1BA, a level of SEPP1, a level of LUM, and a level of CD14 in a control sample(s), wherein a difference in the level of GP1BA, a difference in the level of SEPP1, a difference in the level of LUM, and a difference in the level of CD14 in the subject sample(s) as compared to the level of GP1BA, the level of SEPP1, the level of LUM, and the level of CD14 in the control sample(s) indicates that the subject has active TB.

In one aspect the present invention provides methods for monitoring the effectiveness of a treatment in a subject having active tuberculosis (TB). The methods include determining the level of GP1BA, the level of SEPP1, the level of LUM, and the level of CD14 in a first sample(s) from the subject prior to the initiation of the treatment; determining the level of GP1BA, the level of SEPP1, the level of LUM, and the level of CD14 in a second sample(s) from the subject after at least a portion of the treatment has been administered; comparing the level of GP1BA, the level of SEPP1, the level of LUM, and the level of CD14 in the first sample(s) with a level of GP1BA, the level of SEPP1, the level of LUM, and the level of CD14 in the second sample(s), wherein a difference in the level of GP1BA, the level of SEPP1, the level of LUM, and the level of CD14 in the first sample(s) as compared to the level of GP1BA, the level of SEPP1, the level of LUM, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of GP1BA, the level and/or activity of SEPP1, the level and/or activity of LUM, and the level and/or activity of CD14 in an aliquot as compared to the level and/or activity of GP1BA, the level and/or activity of SEPP1, the level and/or activity of LUM, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of GP1BA, the level and/or activity of SEPP1, the level and/or activity of LUM, and the level and/or activity of CD14, thereby treating the subject.

In one aspect the present invention provides methods for determining whether a subject has active tuberculosis (TB). The methods include determining the level of GP1BA, the level of SEPP1, the level of TNXB, and the level of CD14 in a sample(s) from the subject; comparing the level of GP1BA, the level of SEPP1, the level of TNXB, and the level of CD14 in the subject sample(s) with a level of GP1BA, a level of SEPP1, a level of TNXB, and a level of CD14 in a control sample(s), wherein a difference in the level of GP1BA, a difference in the level of SEPP1, a difference in the level of TNXB, and a difference in the level of CD14 in the subject sample(s) as compared to the level of GP1BA, the level of SEPP1, the level of TNXB, and the level of CD14 in the control sample(s) indicates that the subject has active TB.

In one aspect the present invention provides methods for monitoring the effectiveness of a treatment in a subject having active tuberculosis (TB). The methods include determining the level of GP1BA, the level of SEPP1, the level of TNXB, and the level of CD14 in a first sample(s) from the subject prior to the initiation of the treatment; determining the level of GP1BA, the level of SEPP1, the level of TNXB, and the level of CD14 in a second sample(s) from the subject after at least a portion of the treatment has been administered; comparing the level of GP1BA, the level of SEPP1, the level of TNXB, and the level of CD14 in the first sample(s) with a level of GP1BA, the level of SEPP1, the level of TNXB, and the level of CD14 in the second sample(s), wherein a difference in the level of GP1BA, the level of SEPP1, the level of TNXB, and the level of CD14 in the first sample(s) as compared to the level of GP1BA, the level of SEPP1, the level of TNXB, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of GP1BA, the level and/or activity of SEPP1, the level and/or activity of TNXB, and the level and/or activity of CD14 in an aliquot as compared to the level and/or activity of GP1BA, the level and/or activity of SEPP1, the level and/or activity of TNXB, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of GP1BA, the level and/or activity of SEPP1, the level and/or activity of TNXB, and the level and/or activity of CD14, thereby treating the subject.

In one aspect the present invention provides methods for determining whether a subject has active tuberculosis (TB). The methods include determining the level of APOC1, the level of CD14, the level of QSOX1, and the level of SEPP1 in a sample(s) from the subject; comparing the level of APOC1, the level of CD14, the level of QSOX1, and the level of SEPP1 in the subject sample(s) with a level of APOC1, a level of CD14, a level of QSOX1, and a level of SEPP1 in a control sample(s), wherein a difference in the level of APOC1, a difference in the level of CD14, a difference in the level of QSOX1, and a difference in the level of SEPP1 in the subject sample(s) as compared to the level of APOC1, the level of CD14, the level of QSOX1, and the level of SEPP1 in the control sample(s) indicates that the subject has active TB.

In one aspect the present invention provides methods for monitoring the effectiveness of a treatment in a subject having active tuberculosis (TB). The methods include determining the level of APOC1, the level of CD14, the level of QSOX1, and the level of SEPP1 in a first sample(s) from the subject prior to the initiation of the treatment; determining the level of APOC1, the level of CD14, the level of QSOX1, and the level of SEPP1 in a second sample(s) from the subject after at least a portion of the treatment has been administered; comparing the level of APOC1, the level of CD14, the level of QSOX1, and the level of SEPP1 in the first sample(s) with a level of APOC1, the level of CD14, the level of QSOX1, and the level of SEPP1 in the second sample(s), wherein a difference in the level of APOC1, the level of CD14, the level of QSOX1, and the level of SEPP1 in the first sample(s) as compared to the level of APOC1, the level of CD14, the level of QSOX1, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of CD14, the level and/or activity of QSOX1, and the level and/or activity of SEPP1 in an aliquot as compared to the level and/or activity of APOC1, the level and/or activity of CD14, the level and/or activity of QSOX1, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of CD14, the level and/or activity of QSOX1, and the level and/or activity of SEPP1, thereby treating the subject.

In one aspect the present invention provides methods for determining whether a subject has active tuberculosis (TB). The methods include determining the level of COMP, the level of CD14, the level of PEPD, and the level of APOC1 in a sample(s) from the subject; comparing the level of COMP, the level of CD14, the level of PEPD, and the level of APOC1 in the subject sample(s) with a level of COMP, a level of CD14, a level of PEPD, and a level of APOC1 in a control sample(s), wherein a difference in the level of COMP, a difference in the level of CD14, a difference in the level of PEPD, and a difference in the level of APOC1 in the subject sample(s) as compared to the level of COMP, the level of CD14, the level of PEPD, and the level of APOC1 in the control sample(s) indicates that the subject has active TB.

In one aspect the present invention provides methods for monitoring the effectiveness of a treatment in a subject having active tuberculosis (TB). The methods include determining the level of COMP, the level of CD14, the level of PEPD, and the level of APOC1 in a first sample(s) from the subject prior to the initiation of the treatment; determining the level of COMP, the level of CD14, the level of PEPD, and the level of APOC1 in a second sample(s) from the subject after at least a portion of the treatment has been administered; comparing the level of COMP, the level of CD14, the level of PEPD, and the level of APOC1 in the first sample(s) with a level of COMP, the level of CD14, the level of PEPD, and the level of APOC1 in the second sample(s), wherein a difference in the level of COMP, the level of CD14, the level of PEPD, and the level of APOC1 in the first sample(s) as compared to the level of COMP, the level of CD14, the level of PEPD, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of CD14, the level and/or activity of PEPD, and the level and/or activity of APOC1 in an aliquot as compared to the level and/or activity of COMP, the level and/or activity of CD14, the level and/or activity of PEPD, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of CD14, the level and/or activity of PEPD, and the level and/or activity of APOC1, thereby treating the subject.

In one aspect the present invention provides methods for determining whether a subject has active tuberculosis (TB). The methods include determining the level of COMP, the level of TNXB, the level of SELL, and the level of GP1BA in a sample(s) from the subject; comparing the level of COMP, the level of TNXB, the level of SELL, and the level of GP1BA in the subject sample(s) with a level of COMP, a level of TNXB, a level of SELL, and a level of GP1BA in a control sample(s), wherein a difference in the level of COMP, a difference in the level of TNXB, a difference in the level of SELL, and a difference in the level of GP1BA in the subject sample(s) as compared to the level of COMP, the level of TNXB, the level of SELL, and the level of GP1BA in the control sample(s) indicates that the subject has active TB.

In one aspect the present invention provides methods for monitoring the effectiveness of a treatment in a subject having active tuberculosis (TB). The methods include determining the level of COMP, the level of TNXB, the level of SELL, and the level of GP1BA in a first sample(s) from the subject prior to the initiation of the treatment; determining the level of COMP, the level of TNXB, the level of SELL, and the level of GP1BA in a second sample(s) from the subject after at least a portion of the treatment has been administered; comparing the level of COMP, the level of TNXB, the level of SELL, and the level of GP1BA in the first sample(s) with a level of COMP, the level of TNXB, the level of SELL, and the level of GP1BA in the second sample(s), wherein a difference in the level of COMP, the level of TNXB, the level of SELL, and the level of GP1BA in the first sample(s) as compared to the level of COMP, the level of TNXB, the level of SELL, and the level of GP1BA in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of COMP, the level and/or activity of TNXB, the level and/or activity of SELL, and the level and/or activity of GP1BA in an aliquot as compared to the level and/or activity of COMP, the level and/or activity of TNXB, the level and/or activity of SELL, and the level and/or activity of GP1BA in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of COMP, the level and/or activity of TNXB, the level and/or activity of SELL, and the level and/or activity of GP1BA, thereby treating the subject.

In one aspect the present invention provides methods for determining whether a subject has active tuberculosis (TB). The methods include determining the level of APOC1, the level of CD14, the level of QSOX1, and the level of LUM in a sample(s) from the subject; comparing the level of APOC1, the level of CD14, the level of QSOX1, and the level of LUM in the subject sample(s) with a level of APOC1, a level of CD14, a level of QSOX1, and a level of LUM in a control sample(s), wherein a difference in the level of APOC1, a difference in the level of CD14, a difference in the level of QSOX1, and a difference in the level of LUM in the subject sample(s) as compared to the level of APOC1, the level of CD14, the level of QSOX1, and the level of LUM in the control sample(s) indicates that the subject has active TB.

In one aspect the present invention provides methods for monitoring the effectiveness of a treatment in a subject having active tuberculosis (TB). The methods include determining the level of APOC1, the level of CD14, the level of QSOX1, and the level of LUM in a first sample(s) from the subject prior to the initiation of the treatment; determining the level of APOC1, the level of CD14, the level of QSOX1, and the level of LUM in a second sample(s) from the subject after at least a portion of the treatment has been administered; comparing the level of APOC1, the level of CD14, the level of QSOX1, and the level of LUM in the first sample(s) with a level of APOC1, the level of CD14, the level of QSOX1, and the level of LUM in the second sample(s), wherein a difference in the level of APOC1, the level of CD14, the level of QSOX1, and the level of LUM in the first sample(s) as compared to the level of APOC1, the level of CD14, the level of QSOX1, and the level of LUM in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of APOC1, the level and/or activity of CD14, the level and/or activity of QSOX1, and the level and/or activity of LUM in an aliquot as compared to the level and/or activity of APOC1, the level and/or activity of CD14, the level and/or activity of QSOX1, and the level and/or activity of LUM in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of APOC1, the level and/or activity of CD14, the level and/or activity of QSOX1, and the level and/or activity of LUM, thereby treating the subject.

In one aspect the present invention provides methods for determining whether a subject has active tuberculosis (TB). The methods include determining the level of TNXB, the level of CD14, the level of PEPD, and the level of APOC1 in a sample(s) from the subject; comparing the level of TNXB, the level of CD14, the level of PEPD, and the level of APOC1 in the subject sample(s) with a level of TNXB, a level of CD14, a level of PEPD, and a level of APOC1 in a control sample(s), wherein a difference in the level of TNXB, a difference in the level of CD14, a difference in the level of PEPD, and a difference in the level of APOC1 in the subject sample(s) as compared to the level of TNXB, the level of CD14, the level of PEPD, and the level of APOC1 in the control sample(s) indicates that the subject has active TB.

In one aspect the present invention provides methods for monitoring the effectiveness of a treatment in a subject having active tuberculosis (TB). The methods include determining the level of TNXB, the level of CD14, the level of PEPD, and the level of APOC1 in a first sample(s) from the subject prior to the initiation of the treatment; determining the level of TNXB, the level of CD14, the level of PEPD, and the level of APOC1 in a second sample(s) from the subject after at least a portion of the treatment has been administered; comparing the level of TNXB, the level of CD14, the level of PEPD, and the level of APOC1 in the first sample(s) with a level of TNXB, the level of CD14, the level of PEPD, and the level of APOC1 in the second sample(s), wherein a difference in the level of TNXB, the level of CD14, the level of PEPD, and the level of APOC1 in the first sample(s) as compared to the level of TNXB, the level of CD14, the level of PEPD, and the level of APOC1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of TNXB, the level and/or activity of CD14, the level and/or activity of PEPD, and the level and/or activity of APOC1 in an aliquot as compared to the level and/or activity of TNXB, the level and/or activity of CD14, the level and/or activity of PEPD, and the level and/or activity of APOC1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TNXB, the level and/or activity of CD14, the level and/or activity of PEPD, and the level and/or activity of APOC1, thereby treating the subject.

In one aspect the present invention provides methods for determining whether a subject has active tuberculosis (TB). The methods include determining the level of CD14, the level of APOE, the level of SELL, and the level of TNXB in a sample(s) from the subject; comparing the level of CD14, the level of APOE, the level of SELL, and the level of TNXB in the subject sample(s) with a level of CD14, a level of APOE, a level of SELL, and a level of TNXB in a control sample(s), wherein a difference in the level of CD14, a difference in the level of APOE, a difference in the level of SELL, and a difference in the level of TNXB in the subject sample(s) as compared to the level of CD14, the level of APOE, the level of SELL, and the level of TNXB in the control sample(s) indicates that the subject has active TB.

In one aspect the present invention provides methods for monitoring the effectiveness of a treatment in a subject having active tuberculosis (TB). The methods include determining the level of CD14, the level of APOE, the level of SELL, and the level of TNXB in a first sample(s) from the subject prior to the initiation of the treatment; determining the level of CD14, the level of APOE, the level of SELL, and the level of TNXB in a second sample(s) from the subject after at least a portion of the treatment has been administered; comparing the level of CD14, the level of APOE, the level of SELL, and the level of TNXB in the first sample(s) with a level of CD14, the level of APOE, the level of SELL, and the level of TNXB in the second sample(s), wherein a difference in the level of CD14, the level of APOE, the level of SELL, and the level of TNXB in the first sample(s) as compared to the level of CD14, the level of APOE, the level of SELL, and the level of TNXB in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of APOE, the level and/or activity of SELL, and the level and/or activity of TNXB in each of the aliquots; and selecting a member of the library of compounds which modulates the level and/or the activity of CD14, the level and/or activity of APOE, the level and/or activity of SELL, and the level and/or activity of TNXB in an aliquot as compared to the level and/or activity of CD14, the level and/or activity of APOE, the level and/or activity of SELL, and the level and/or activity of TNXB in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of APOE, the level and/or activity of SELL, and the level and/or activity of TNXB, thereby treating the subject.

In one aspect the present invention provides methods for determining whether a subject has active tuberculosis (TB). The methods include determining the level of CD14, the level of APOE, the level of SELL, and the level of COMP in a sample(s) from the subject; comparing the level of CD14, the level of APOE, the level of SELL, and the level of COMP in the subject sample(s) with a level of CD14, a level of APOE, a level of SELL, and a level of COMP in a control sample(s), wherein a difference in the level of CD14, a difference in the level of APOE, a difference in the level of SELL, and a difference in the level of COMP in the subject sample(s) as compared to the level of CD14, the level of APOE, the level of SELL, and the level of COMP in the control sample(s) indicates that the subject has active TB.

In one aspect the present invention provides methods for monitoring the effectiveness of a treatment in a subject having active tuberculosis (TB). The methods include determining the level of CD14, the level of APOE, the level of SELL, and the level of COMP in a first sample(s) from the subject prior to the initiation of the treatment; determining the level of CD14, the level of APOE, the level of SELL, and the level of COMP in a second sample(s) from the subject after at least a portion of the treatment has been administered; comparing the level of CD14, the level of APOE, the level of SELL, and the level of COMP in the first sample(s) with a level of CD14, the level of APOE, the level of SELL, and the level of COMP in the second sample(s), wherein a difference in the level of CD14, the level of APOE, the level of SELL, and the level of COMP in the first sample(s) as compared to the level of CD14, the level of APOE, the level of SELL, and the level of COMP in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of APOE, the level and/or activity of SELL, and the level and/or activity of COMP in each of the aliquots; and selecting a member of the library of compounds which modulates the level and/or the activity of CD14, the level and/or activity of APOE, the level and/or activity of SELL, and the level and/or activity of COMP in an aliquot as compared to the level and/or activity of CD14, the level and/or activity of APOE, the level and/or activity of SELL, and the level and/or activity of COMP in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of APOE, the level and/or activity of SELL, and the level and/or activity of COMP, thereby treating the subject.

In one aspect the present invention provides methods for determining whether a subject has active tuberculosis (TB). The methods include determining the level of CD14, the level of APOE, the level of SELL, and the level of LUM in a sample(s) from the subject; comparing the level of CD14, the level of APOE, the level of SELL, and the level of LUM in the subject sample(s) with a level of CD14, a level of APOE, a level of SELL, and a level of LUM in a control sample(s), wherein a difference in the level of CD14, a difference in the level of APOE, a difference in the level of SELL, and a difference in the level of LUM in the subject sample(s) as compared to the level of CD14, the level of APOE, the level of SELL, and the level of LUM in the control sample(s) indicates that the subject has active TB.

In one aspect the present invention provides methods for monitoring the effectiveness of a treatment in a subject having active tuberculosis (TB). The methods include determining the level of CD14, the level of APOE, the level of SELL, and the level of LUM in a first sample(s) from the subject prior to the initiation of the treatment; determining the level of CD14, the level of APOE, the level of SELL, and the level of LUM in a second sample(s) from the subject after at least a portion of the treatment has been administered; comparing the level of CD14, the level of APOE, the level of SELL, and the level of LUM in the first sample(s) with a level of CD14, the level of APOE, the level of SELL, and the level of LUM in the second sample(s), wherein a difference in the level of CD14, the level of APOE, the level of SELL, and the level of LUM in the first sample(s) as compared to the level of CD14, the level of APOE, the level of SELL, and the level of LUM in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of APOE, the level and/or activity of SELL, and the level and/or activity of LUM in each of the aliquots; and selecting a member of the library of compounds which modulates the level and/or the activity of CD14, the level and/or activity of APOE, the level and/or activity of SELL, and the level and/or activity of LUM in an aliquot as compared to the level and/or activity of CD14, the level and/or activity of APOE, the level and/or activity of SELL, and the level and/or activity of LUM in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of APOE, the level and/or activity of SELL, and the level and/or activity of LUM, thereby treating the subject.

In one aspect the present invention provides methods for determining whether a subject has active tuberculosis (TB). The methods include determining the level of CD14, the level of APOE, the level of SELL, and the level of PGLYRP2 in a sample(s) from the subject; comparing the level of CD14, the level of APOE, the level of SELL, and the level of PGLYRP2 in the subject sample(s) with a level of CD14, a level of APOE, a level of SELL, and a level of PGLYRP2 in a control sample(s), wherein a difference in the level of CD14, a difference in the level of APOE, a difference in the level of SELL, and a difference in the level of PGLYRP2 in the subject sample(s) as compared to the level of CD14, the level of APOE, the level of SELL, and the level of PGLYRP2 in the control sample(s) indicates that the subject has active TB.

In one aspect the present invention provides methods for monitoring the effectiveness of a treatment in a subject having active tuberculosis (TB). The methods include determining the level of CD14, the level of APOE, the level of SELL, and the level of PGLYRP2 in a first sample(s) from the subject prior to the initiation of the treatment; determining the level of CD14, the level of APOE, the level of SELL, and the level of PGLYRP2 in a second sample(s) from the subject after at least a portion of the treatment has been administered; comparing the level of CD14, the level of APOE, the level of SELL, and the level of PGLYRP2 in the first sample(s) with a level of CD14, the level of APOE, the level of SELL, and the level of PGLYRP2 in the second sample(s), wherein a difference in the level of CD14, the level of APOE, the level of SELL, and the level of PGLYRP2 in the first sample(s) as compared to the level of CD14, the level of APOE, the level of SELL, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of APOE, the level and/or activity of SELL, and the level and/or activity of PGLYRP2 in each of the aliquots; and selecting a member of the library of compounds which modulates the level and/or the activity of CD14, the level and/or activity of APOE, the level and/or activity of SELL, and the level and/or activity of PGLYRP2 in an aliquot as compared to the level and/or activity of CD14, the level and/or activity of APOE, the level and/or activity of SELL, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level of APOE, the level of SELL, and the level of PGLYRP2, thereby treating the subject.

In one aspect the present invention provides methods for determining whether a subject has active tuberculosis (TB). The methods include determining the level of CD14, the level of APOE, the level of SELL, and the level of HABP2 in a sample(s) from the subject; comparing the level of CD14, the level of APOE, the level of SELL, and the level of HABP2 in the subject sample(s) with a level of CD14, a level of APOE, a level of SELL, and a level of HABP2 in a control sample(s), wherein a difference in the level of CD14, a difference in the level of APOE, a difference in the level of SELL, and a difference in the level of HABP2 in the subject sample(s) as compared to the level of CD14, the level of APOE, the level of SELL, and the level of HABP2 in the control sample(s) indicates that the subject has active TB.

In one aspect the present invention provides methods for monitoring the effectiveness of a treatment in a subject having active tuberculosis (TB). The methods include determining the level of CD14, the level of APOE, the level of SELL, and the level of HABP2 in a first sample(s) from the subject prior to the initiation of the treatment; determining the level of CD14, the level of APOE, the level of SELL, and the level of HABP2 in a second sample(s) from the subject after at least a portion of the treatment has been administered; comparing the level of CD14, the level of APOE, the level of SELL, and the level of HABP2 in the first sample(s) with a level of CD14, the level of APOE, the level of SELL, and the level of HABP2 in the second sample(s), wherein a difference in the level of CD14, the level of APOE, the level of SELL, and the level of HABP2 in the first sample(s) as compared to the level of CD14, the level of APOE, the level of SELL, and the level of HABP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of APOE, the level and/or activity of SELL, and the level and/or activity of HABP2 in each of the aliquots; and selecting a member of the library of compounds which modulates the level and/or the activity of CD14, the level and/or activity of APOE, the level and/or activity of SELL, and the level and/or activity of HABP2 in an aliquot as compared to the level and/or activity of CD14, the level and/or activity of APOE, the level and/or activity of SELL, and the level and/or activity of HABP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of APOE, the level and/or activity of SELL, and the level and/or activity of HABP2, thereby treating the subject.

In one aspect the present invention provides methods for determining whether a subject has active tuberculosis (TB). The methods include determining the level of CD14, the level of APOE, the level of SELL, and the level of LRG1 in a sample(s) from the subject; comparing the level of CD14, the level of APOE, the level of SELL, and the level of LRG1 in the subject sample(s) with a level of CD14, a level of APOE, a level of SELL, and a level of LRG1 in a control sample(s), wherein a difference in the level of CD14, a difference in the level of APOE, a difference in the level of SELL, and a difference in the level of LRG1 in the subject sample(s) as compared to the level of CD14, the level of APOE, the level of SELL, and the level of LRG1 in the control sample(s) indicates that the subject has active TB.

In one aspect the present invention provides methods for monitoring the effectiveness of a treatment in a subject having active tuberculosis (TB). The methods include determining the level of CD14, the level of APOE, the level of SELL, and the level of LRG1 in a first sample(s) from the subject prior to the initiation of the treatment; determining the level of CD14, the level of APOE, the level of SELL, and the level of LRG1 in a second sample(s) from the subject after at least a portion of the treatment has been administered; comparing the level of CD14, the level of APOE, the level of SELL, and the level of LRG1 in the first sample(s) with a level of CD14, the level of APOE, the level of SELL, and the level of LRG1 in the second sample(s), wherein a difference in the level of CD14, the level of APOE, the level of SELL, and the level of LRG1 in the first sample(s) as compared to the level of CD14, the level of APOE, the level of SELL, and the level of LRG1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of APOE, the level and/or activity of SELL, and the level and/or activity of LRG1 in each of the aliquots; and selecting a member of the library of compounds which modulates the level and/or the activity of CD14, the level and/or activity of APOE, the level and/or activity of SELL, and the level and/or activity of LRG1 in an aliquot as compared to the level and/or activity of CD14, the level and/or activity of APOE, the level and/or activity of SELL, and the level and/or activity of LRG1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of APOE, the level and/or activity of SELL, and the level and/or activity of LRG1, thereby treating the subject.

In one aspect the present invention provides methods for determining whether a subject has active tuberculosis (TB). The methods include determining the level of CD14, the level of APOE, the level of SELL, and the level of QSOX1 in a sample(s) from the subject; comparing the level of CD14, the level of APOE, the level of SELL, and the level of QSOX1 in the subject sample(s) with a level of CD14, a level of APOE, a level of SELL, and a level of QSOX1 in a control sample(s), wherein a difference in the level of CD14, a difference in the level of APOE, a difference in the level of SELL, and a difference in the level of QSOX1 in the subject sample(s) as compared to the level of CD14, the level of APOE, the level of SELL, and the level of QSOX1 in the control sample(s) indicates that the subject has active TB.

In one aspect the present invention provides methods for monitoring the effectiveness of a treatment in a subject having active tuberculosis (TB). The methods include determining the level of CD14, the level of APOE, the level of SELL, and the level of QSOX1 in a first sample(s) from the subject prior to the initiation of the treatment; determining the level of CD14, the level of APOE, the level of SELL, and the level of QSOX1 in a second sample(s) from the subject after at least a portion of the treatment has been administered; comparing the level of CD14, the level of APOE, the level of SELL, and the level of QSOX1 in the first sample(s) with a level of CD14, the level of APOE, the level of SELL, and the level of QSOX1 in the second sample(s), wherein a difference in the level of CD14, the level of APOE, the level of SELL, and the level of QSOX1 in the first sample(s) as compared to the level of CD14, the level of APOE, the level of SELL, and the level of QSOX1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of APOE, the level of SELL, and the level of QSOX1 in each of the aliquots; and selecting a member of the library of compounds which modulates the level and/or the activity of CD14, the level and/or activity of APOE, the level and/or activity of SELL, and the level and/or activity of QSOX1 in an aliquot as compared to the level and/or activity of CD14, the level and/or activity of APOE, the level and/or activity of SELL, and the level and/or activity of QSOX1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity CD14, the level and/or activity of APOE, the level and/or activity of SELL, and the level and/or activity of QSOX1, thereby treating the subject.

In one aspect the present invention provides methods for determining whether a subject has active tuberculosis (TB). The methods include determining the level of CD14, the level of APOE, the level of SELL, and the level of S100A8 in a sample(s) from the subject; comparing the level of CD14, the level of APOE, the level of SELL, and the level of S100A8 in the subject sample(s) with a level of CD14, a level of APOE, a level of SELL, and a level of S100A8 in a control sample(s), wherein a difference in the level of CD14, a difference in the level of APOE, a difference in the level of SELL, and a difference in the level of S100A8 in the subject sample(s) as compared to the level of CD14, the level of APOE, the level of SELL, and the level of S100A8 in the control sample(s) indicates that the subject has active TB.

In one aspect the present invention provides methods for monitoring the effectiveness of a treatment in a subject having active tuberculosis (TB). The methods include determining the level of CD14, the level of APOE, the level of SELL, and the level of S100A8 in a first sample(s) from the subject prior to the initiation of the treatment; determining the level of CD14, the level of APOE, the level of SELL, and the level of S100A8 in a second sample(s) from the subject after at least a portion of the treatment has been administered; comparing the level of CD14, the level of APOE, the level of SELL, and the level of S100A8 in the first sample(s) with a level of CD14, the level of APOE, the level of SELL, and the level of S100A8 in the second sample(s), wherein a difference in the level of CD14, the level of APOE, the level of SELL, and the level of S100A8 in the first sample(s) as compared to the level of CD14, the level of APOE, the level of SELL, and the level of S100A8 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of CD14, the level level and/or activity of APOE, the level level and/or activity of SELL, and the level level and/or activity of S100A8 in an aliquot as compared to the level and/or activity of CD14, the level level and/or activity of APOE, the level level and/or activity of SELL, and the level level and/or activity of S100A8 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level level and/or activity of APOE, the level level and/or activity of SELL, and the level level and/or activity of S100A8, thereby treating the subject.

In one aspect the present invention provides methods for determining whether a subject has active tuberculosis (TB). The methods include determining the level of CD14, the level of APOE, and the level of APOC3 in a sample(s) from the subject; comparing the level of CD14, the level of APOE, and the level of APOC3 in the subject sample(s) with a level of CD14, a level of APOE, and a level of APOC3 in a control sample(s), wherein a difference in the level of CD14, a difference in the level of APOE, and a difference in the level of APOC3 in the subject sample(s) as compared to the level of CD14, the level of APOE, and the level of APOC3 in the control sample(s) indicates that the subject has active TB.

In one aspect the present invention provides methods for monitoring the effectiveness of a treatment in a subject having active tuberculosis (TB). The methods include determining the level of CD14, the level of APOE, and the level of APOC3 in a first sample(s) from the subject prior to the initiation of the treatment; determining the level of CD14, the level of APOE, and the level of APOC3 in a second sample(s) from the subject after at least a portion of the treatment has been administered; comparing the level of CD14, the level of APOE, and the level of APOC3 in the first sample(s) with a level of CD14, the level of APOE, and the level of APOC3 in the second sample(s), wherein a difference in the level of CD14, the level of APOE, and the level of APOC3 in the first sample(s) as compared to the level of CD14, the level of APOE, and the level of APOC3 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of APOE, and the level and/or activity of APOC3 in each of the aliquots; and selecting a member of the library of compounds which modulates the level and/or the activity of the CD14, the level and/or activity of APOE, and the level and/or activity of APOC3 in an aliquot as compared to the level and/or activity of CD14, the level and/or activity of APOE, and the level and/or activity of APOC3 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of APOE, and the level and/or activity of APOC3, thereby treating the subject.

In one aspect the present invention provides methods for determining whether a subject has active tuberculosis (TB). The methods include determining the level of CD14, the level of APOE, the level of APOC3, and the level of PGLYRP2 in a sample(s) from the subject; comparing the level of CD14, the level of APOE, the level of APOC3, and the level of PGLYRP2 in the subject sample(s) with a level of CD14, a level of APOE, a level of APOC3, and a level of PGLYRP2 in a control sample(s), wherein a difference in the level of CD14, a difference in the level of APOE, a difference in the level of APOC3, and a difference in the level of PGLYRP2 in the subject sample(s) as compared to the level of CD14, the level of APOE, the level of APOC3, and the level of PGLYRP2 in the control sample(s) indicates that the subject has active TB.

In one aspect the present invention provides methods for monitoring the effectiveness of a treatment in a subject having active tuberculosis (TB). The methods include determining the level CD14, the level of APOE, the level of APOC3, and the level of PGLYRP2 in a first sample(s) from the subject prior to the initiation of the treatment; determining the level of CD14, the level of APOE, the level of APOC3, and the level of PGLYRP2 in a second sample(s) from the subject after at least a portion of the treatment has been administered; comparing the level of CD14, the level of APOE, the level of APOC3, and the level of PGLYRP2 in the first sample(s) with a level of CD14, the level of APOE, the level of APOC3, and the level of PGLYRP2 in the second sample(s), wherein a difference in the level CD14, the level of APOE, the level of APOC3, and the level of PGLYRP2 in the first sample(s) as compared to the level of CD14, the level of APOE, the level of APOC3, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of APOE, the level and/or activity of APOC3, and the level and/or activity of PGLYRP2 in each of the aliquots; and selecting a member of the library of compounds which modulates the level and/or the activity of CD14, the level and/or activity of APOE, the level and/or activity of APOC3, and the level and/or activity of PGLYRP2 in an aliquot as compared to the level and/or activity of CD14, the level and/or activity of APOE, the level and/or activity of APOC3, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of APOE, the level and/or activity of APOC3, and the level and/or activity of PGLYRP2, thereby treating the subject.

In one aspect the present invention provides methods for determining whether a subject has active tuberculosis (TB). The methods include determining the level of CD14, the level of APOE, the level of APOC3, and the level of SELL in a sample(s) from the subject; comparing the level of CD14, the level of APOE, the level of APOC3, and the level of SELL in the subject sample(s) with a level of CD14, a level of APOE, a level of APOC3, and a level of SELL in a control sample(s), wherein a difference in the level of CD14, a difference in the level of APOE, a difference in the level of APOC3, and a difference in the level of SELL in the subject sample(s) as compared to the level of CD14, the level of APOE, the level of APOC3, and the level of SELL in the control sample(s) indicates that the subject has active TB.

In one aspect the present invention provides methods for monitoring the effectiveness of a treatment in a subject having active tuberculosis (TB). The methods include determining the level of CD14, the level of APOE, the level of APOC3, and the level of SELL in a first sample(s) from the subject prior to the initiation of the treatment; determining the level of CD14, the level of APOE, the level of APOC3, and the level of SELL in a second sample(s) from the subject after at least a portion of the treatment has been administered; comparing the level of CD14, the level of APOE, the level of APOC3, and the level of SELL in the first sample(s) with a level of CD14, the level of APOE, the level of APOC3, and the level of SELL in the second sample(s), wherein a difference in the level of CD14, the level of APOE, the level of APOC3, and the level of SELL in the first sample(s) as compared to the level of CD14, the level of APOE, the level of APOC3, and the level of SELL in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of CD14, the level and/or activity of APOE, the level and/or activity of APOC3, and the level and/or activity of SELL in an aliquot as compared to the level and/or activity of CD14, the level and/or activity of APOE, the level and/or activity of APOC3, and the level and/or activity of SELL in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of APOE, the level and/or activity of APOC3, and the level and/or activity of SELL, thereby treating the subject.

In one aspect the present invention provides methods for determining whether a subject has active tuberculosis (TB). The methods include determining the level of CD14, the level of APOE, the level of APOC3, and the level of HABP2 in a sample(s) from the subject; comparing the level of CD14, the level of APOE, the level of APOC3, and the level of HABP2 in the subject sample(s) with a level of CD14, a level of APOE, a level of APOC3, and a level of HABP2 in a control sample(s), wherein a difference in the level of CD14, a difference in the level of APOE, a difference in the level of APOC3, and a difference in the level of HABP2 in the subject sample(s) as compared to the level of CD14, the level of APOE, the level of APOC3, and the level of HABP2 in the control sample(s) indicates that the subject has active TB.

In one aspect the present invention provides methods for monitoring the effectiveness of a treatment in a subject having active tuberculosis (TB). The methods include determining the level of CD14, the level of APOE, the level of APOC3, and the level of HABP2 in a first sample(s) from the subject prior to the initiation of the treatment; determining the level of CD14, the level of APOE, the level of APOC3, and the level of HABP2 in a second sample(s) from the subject after at least a portion of the treatment has been administered; comparing the level of CD14, the level of APOE, the level of APOC3, and the level of HABP2 in the first sample(s) with a level of CD14, the level of APOE, the level of APOC3, and the level of HABP2 in the second sample(s), wherein a difference in the level of CD14, the level of APOE, the level of APOC3, and the level of HABP2 in the first sample(s) as compared to the level of CD14, the level of APOE, the level of APOC3, and the level of HABP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of one or more markers of the invention in each of the aliquots; and selecting a member of the library of compounds which modulates the level and/or the activity of CD14, the level and/or activity of APOE, the level and/or activity of APOC3, and the level and/or activity of HABP2 in an aliquot as compared to the level and/or activity of CD14, the level and/or activity of APOE, the level and/or activity of APOC3, and the level and/or activity of HABP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of APOE, the level and/or activity of APOC3, and the level and/or activity of HABP2, thereby treating the subject.

In one embodiment, the subject is HIV−.

In one aspect the present invention provides methods for determining whether a subject has active tuberculosis (TB). The methods include determining the level of LCP1 and the level of PFN1 in a sample(s) from the subject; comparing the level of LCP1 and the level of PFN1 in the subject sample(s) with a level of LCP1 and a level of PFN1 in a control sample(s), wherein a difference in the level of LCP1 and a difference in the level of PFN1 in the subject sample(s) as compared to the level of LCP1 and the level of PFN1 in the control sample(s) indicates that the subject has active TB.

In one aspect the present invention provides methods for monitoring the effectiveness of a treatment in a subject having active tuberculosis (TB). The methods include determining the level of LCP1 and the level of PFN1 in a first sample(s) from the subject prior to the initiation of the treatment; determining the level of LCP1 and the level of PFN1 in a second sample(s) from the subject after at least a portion of the treatment has been administered; comparing the level of LCP1 and the level of PFN1 in the first sample(s) with a level of LCP1 and the level of PFN1 in the second sample(s), wherein a difference in the level of LCP1 and the level of PFN1 in the first sample(s) as compared to the level of LCP1 and the level of PFN1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1 and the level and/or activity of PFN1 in each of the aliquots; and selecting a member of the library of compounds which modulates the level and/or the activity of LCP1 and the level and/or activity of PFN1 in an aliquot as compared to the level and/or activity of LCP1 and the level and/or activity of PFN1 of the invention in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1 and the level and/or activity of PFN1, thereby treating the subject.

In one aspect the present invention provides methods for determining whether a subject has active tuberculosis (TB). The methods include determining the level of LCP1 and the level of VASN in a sample(s) from the subject; comparing the level of LCP1 and the level of VASN in the subject sample(s) with a level of LCP1 and a level of VASN in a control sample(s), wherein a difference in the level of LCP1 and a difference in the level of VASN in the subject sample(s) as compared to the level of LCP1 and the level of VASN in the control sample(s) indicates that the subject has active TB.

In one aspect the present invention provides methods for monitoring the effectiveness of a treatment in a subject having active tuberculosis (TB). The methods include determining the level of LCP1 and the level of VASN in a first sample(s) from the subject prior to the initiation of the treatment; determining the level of LCP1 and the level of VASN in a second sample(s) from the subject after at least a portion of the treatment has been administered; comparing the level of LCP1 and the level of VASN in the first sample(s) with a level of LCP1 and the level of VASN in the second sample(s), wherein a difference in the level of LCP1 and the level of VASN in the first sample(s) as compared to the level of LCP1 and the level of VASN in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1 and the level and/or activity of VASN in each of the aliquots; and selecting a member of the library of compounds which modulates the level and/or the activity of LCP1 and the level and/or activity of VASN in an aliquot as compared to the level and/or activity of LCP1 and the level and/or activity of VASN in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1 and the level and/or activity of VASN, thereby treating the subject.

In one aspect the present invention provides methods for determining whether a subject has active tuberculosis (TB). The methods include determining the level of VASN and the level of PFN1 in a sample(s) from the subject; comparing the level of VASN and the level of PFN1 in the subject sample(s) with a level of VASN and a level of PFN1 in a control sample(s), wherein a difference in the level of VASN and a difference in the level of PFN1 in the subject sample(s) as compared to the level of VASN and the level of PFN1 in the control sample(s) indicates that the subject has active TB.

In one aspect the present invention provides methods for monitoring the effectiveness of a treatment in a subject having active tuberculosis (TB). The methods include determining the level of VASN and the level of PFN1 in a first sample(s) from the subject prior to the initiation of the treatment; determining the level of VASN and the level of PFN1 in a second sample(s) from the subject after at least a portion of the treatment has been administered; comparing the level of VASN and the level of PFN1 in the first sample(s) with a level of VASN and the level of PFN1 in the second sample(s), wherein a difference in the level of VASN and the level of PFN1 in the first sample(s) as compared to the level of VASN and the level of PFN1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of VASN and the level and/or activity of PFN1 in each of the aliquots; and selecting a member of the library of compounds which modulates the level and/or the activity of VASN and the level and/or activity of PFN1 in an aliquot as compared to the level and/or activity of VASN and the level and/or activity of PFN1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of VASN and the level and/or activity of PFN1, thereby treating the subject.

In one aspect the present invention provides methods for determining whether a subject has active tuberculosis (TB). The methods include determining the level of LCP1, the level of VASN, and the level of PFN1 in a sample(s) from the subject; comparing the level of LCP1, the level of VASN, and the level of PFN1 in the subject sample(s) with a level of LCP1, a level of VASN, and a level of PFN1 in a control sample(s), wherein a difference in the level of LCP1, a difference in the level of VASN, and a difference in the level of PFN1 in the subject sample(s) as compared to the level of LCP1, the level of VASN, and the level of PFN1 in the control sample(s) indicates that the subject has active TB.

In one aspect the present invention provides methods for monitoring the effectiveness of a treatment in a subject having active tuberculosis (TB). The methods include determining the level of LCP1, the level of VASN, and the level of PFN1 in a first sample(s) from the subject prior to the initiation of the treatment; determining the level of LCP1, the level of VASN, and the level of PFN1 in a second sample(s) from the subject after at least a portion of the treatment has been administered; comparing the level of LCP1, the level of VASN, and the level of PFN1 in the first sample(s) with a level of LCP1, the level of VASN, and the level of PFN1 in the second sample(s), wherein a difference in the level of LCP1, the level of VASN, and the level of PFN1 in the first sample(s) as compared to the level of LCP1, the level of VASN, and the level of PFN1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, and the level and/or activity of PFN1 in each of the aliquots; and selecting a member of the library of compounds which modulates the level and/or the activity of LCP1, the level and/or activity of VASN, and the level and/or activity of PFN1 in an aliquot as compared to the level and/or activity of LCP1, the level and/or activity of VASN, and the level and/or activity of PFN1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, and the level and/or activity of PFN1, thereby treating the subject.

In one aspect the present invention provides methods for determining whether a subject has active tuberculosis (TB). The methods include determining the level of CD14, the level of CPN2, and the level of PFN1 in a sample(s) from the subject; comparing the level of CD14, the level of CPN2, and the level of PFN1 in the subject sample(s) with a level of CD14, a level of CPN2, and a level of PFN1 in a control sample(s), wherein a difference in the level of CD14, a difference in the level of CPN2, and a difference in the level of PFN1 in the subject sample(s) as compared to the level of CD14, the level of CPN2, and the level of PFN1 in the control sample(s) indicates that the subject has active TB.

In one aspect the present invention provides methods for monitoring the effectiveness of a treatment in a subject having active tuberculosis (TB). The methods include determining the level of CD14, the level of CPN2, and the level of PFN1 in a first sample(s) from the subject prior to the initiation of the treatment; determining the level of CD14, the level of CPN2, and the level of PFN1 in a second sample(s) from the subject after at least a portion of the treatment has been administered; comparing the level of CD14, the level of CPN2, and the level of PFN1 in the first sample(s) with a level of CD14, the level of CPN2, and the level of PFN1 in the second sample(s), wherein a difference in the level of CD14, the level of CPN2, and the level of PFN1 in the first sample(s) as compared to the level of CD14, the level of CPN2, and the level of PFN1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of CPN2, and the level and/or activity of PFN1 in each of the aliquots; and selecting a member of the library of compounds which modulates the level and/or the activity of CD14, the level and/or activity of CPN2, and the level and/or activity of PFN1 in an aliquot as compared to the level and/or activity of CD14, the level and/or activity of CPN2, and the level and/or activity of PFN1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, and the level and/or activity of PFN1, thereby treating the subject.

In one aspect the present invention provides methods for determining whether a subject has active tuberculosis (TB). The methods include determining the level of CD14, the level of CPN2, and the level of TAGLN2 in a sample(s) from the subject; comparing the level of CD14, the level of CPN2, and the level of TAGLN2 in the subject sample(s) with a level of CD14, a level of CPN2, and a level of TAGLN2 in a control sample(s), wherein a difference in the level of CD14, a difference in the level of CPN2, and a difference in the level of TAGLN2 in the subject sample(s) as compared to the level of CD14, the level of CPN2, and the level of TAGLN2 in the control sample(s) indicates that the subject has active TB.

In one aspect the present invention provides methods for monitoring the effectiveness of a treatment in a subject having active tuberculosis (TB). The methods include determining the level of CD14, the level of CPN2, and the level of TAGLN2 in a first sample(s) from the subject prior to the initiation of the treatment; determining the level of CD14, the level of CPN2, and the level of TAGLN2 in a second sample(s) from the subject after at least a portion of the treatment has been administered; comparing the level of CD14, the level of CPN2, and the level of TAGLN2 in the first sample(s) with a level of CD14, the level of CPN2, and the level of TAGLN2 in the second sample(s), wherein a difference in the level of CD14, the level of CPN2, and the level of TAGLN2 in the first sample(s) as compared to the level of CD14, the level of CPN2, and the level of TAGLN2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of CPN2, and the level and/or activity of TAGLN2 in each of the aliquots; and selecting a member of the library of compounds which modulates the level and/or the activity of CD14, the level and/or activity of CPN2, and the level and/or activity of TAGLN2 in an aliquot as compared to the level and/or activity of CD14, the level and/or activity of CPN2, and the level and/or activity of TAGLN2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, and the level and/or activity of TAGLN2, thereby treating the subject.

In one aspect the present invention provides methods for determining whether a subject has active tuberculosis (TB). The methods include determining the level of CD14, the level of PGLYRP2, and the level of PFN1 in a sample(s) from the subject; comparing the level of CD14, the level of PGLYRP2, and the level of PFN1 in the subject sample(s) with a level of CD14, a level of PGLYRP2, and a level of PFN1 in a control sample(s), wherein a difference in the level of CD14, a difference in the level of PGLYRP2, and a difference in the level of PFN1 in the subject sample(s) as compared to the level of CD14, the level of PGLYRP2, and the level of PFN1 in the control sample(s) indicates that the subject has active TB.

In one aspect the present invention provides methods for monitoring the effectiveness of a treatment in a subject having active tuberculosis (TB). The methods include determining the level of CD14, the level of PGLYRP2, and the level of PFN1 in a first sample(s) from the subject prior to the initiation of the treatment; determining the level of CD14, the level of PGLYRP2, and the level of PFN1 in a second sample(s) from the subject after at least a portion of the treatment has been administered; comparing the level of CD14, the level of PGLYRP2, and the level of PFN1 in the first sample(s) with a level of CD14, the level of PGLYRP2, and the level of PFN1 in the second sample(s), wherein a difference in the level of CD14, the level of PGLYRP2, and the level of PFN1 in the first sample(s) as compared to the level of CD14, the level of PGLYRP2, and the level of PFN1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of PGLYRP2, and the level and/or activity of PFN1 in each of the aliquots; and selecting a member of the library of compounds which modulates the level and/or the activity of CD14, the level and/or activity of PGLYRP2, and the level and/or activity of PFN1 in an aliquot as compared to the level and/or activity of CD14, the level and/or activity of PGLYRP2, and the level and/or activity of PFN1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of PGLYRP2, and the level and/or activity of PFN1, thereby treating the subject.

In one aspect the present invention provides methods for determining whether a subject has active tuberculosis (TB). The methods include determining the level of CD14, the level of CPN2, and the level of IGFBP6 in a sample(s) from the subject; comparing the level of CD14, the level of CPN2, and the level of IGFBP6 in the subject sample(s) with a level of CD14, a level of CPN2, and a level of IGFBP6 in a control sample(s), wherein a difference in the level of CD14, a difference in the level of CPN2, and a difference in the level of IGFBP6 in the subject sample(s) as compared to the level of CD14, the level of CPN2, and the level of IGFBP6 in the control sample(s) indicates that the subject has active TB.

In one aspect the present invention provides methods for monitoring the effectiveness of a treatment in a subject having active tuberculosis (TB). The methods include determining the level of CD14, the level of CPN2, and the level of IGFBP6 in a first sample(s) from the subject prior to the initiation of the treatment; determining the level of CD14, the level of CPN2, and the level of IGFBP6 in a second sample(s) from the subject after at least a portion of the treatment has been administered; comparing the level of CD14, the level of CPN2, and the level of IGFBP6 in the first sample(s) with a level of CD14, the level of CPN2, and the level of IGFBP6 in the second sample(s), wherein a difference in the level of CD14, the level of CPN2, and the level of IGFBP6 in the first sample(s) as compared to the level of CD14, the level of CPN2, and the level of IGFBP6 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of CPN2, and the level and/or activity of IGFBP6 in each of the aliquots; and selecting a member of the library of compounds which modulates the level and/or the activity of CD14, the level and/or activity of CPN2, and the level and/or activity of IGFBP6 in an aliquot as compared to the level and/or activity of CD14, the level and/or activity of CPN2, and the level and/or activity of IGFBP6 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, and the level and/or activity of IGFBP6, thereby treating the subject.

In one aspect the present invention provides methods for determining whether a subject has active tuberculosis (TB). The methods include determining the level of CD14, the level of PGLYRP2, and the level of TAGLN2 in a sample(s) from the subject; comparing the level of CD14, the level of PGLYRP2, and the level of TAGLN2 in the subject sample(s) with a level of CD14, a level of PGLYRP2, and a level of TAGLN2 in a control sample(s), wherein a difference in the level of CD14, a difference in the level of PGLYRP2, and a difference in the level of TAGLN2 in the subject sample(s) as compared to the level of CD14, the level of PGLYRP2, and the level of TAGLN2 in the control sample(s) indicates that the subject has active TB.

In one aspect the present invention provides methods for monitoring the effectiveness of a treatment in a subject having active tuberculosis (TB). The methods include determining the level of CD14, the level of PGLYRP2, and the level of TAGLN2 in a first sample(s) from the subject prior to the initiation of the treatment; determining the level of CD14, the level of PGLYRP2, and the level of TAGLN2 in a second sample(s) from the subject after at least a portion of the treatment has been administered; comparing the level of CD14, the level of PGLYRP2, and the level of TAGLN2 in the first sample(s) with a level of CD14, the level of PGLYRP2, and the level of TAGLN2 in the second sample(s), wherein a difference in the level of CD14, the level of PGLYRP2, and the level of TAGLN2 in the first sample(s) as compared to the level of CD14, the level of PGLYRP2, and the level of TAGLN2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of PGLYRP2, and the level and/or activity of TAGLN2 in each of the aliquots; and selecting a member of the library of compounds which modulates the level and/or the activity of CD14, the level and/or activity of PGLYRP2, and the level and/or activity of TAGLN2 in an aliquot as compared to the level and/or activity of CD14, the level and/or activity of PGLYRP2, and the level and/or activity of TAGLN2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of PGLYRP2, and the level and/or activity of TAGLN2, thereby treating the subject.

In one aspect the present invention provides methods for determining whether a subject has active tuberculosis (TB). The methods include determining the level of CD14, the level of VASN, and the level of TAGLN2 in a sample(s) from the subject; comparing the level of CD14, the level of VASN, and the level of TAGLN2 in the subject sample(s) with a level of CD14, a level of VASN, and a level of TAGLN2 in a control sample(s), wherein a difference in the level of CD14, a difference in the level of VASN, and a difference in the level of TAGLN2 in the subject sample(s) as compared to the level of CD14, the level of VASN, and the level of TAGLN2 in the control sample(s) indicates that the subject has active TB.

In one aspect the present invention provides methods for monitoring the effectiveness of a treatment in a subject having active tuberculosis (TB). The methods include determining the level of CD14, the level of VASN, and the level of TAGLN2 in a first sample(s) from the subject prior to the initiation of the treatment; determining the level of CD14, the level of VASN, and the level of TAGLN2 in a second sample(s) from the subject after at least a portion of the treatment has been administered; comparing the level of CD14, the level of VASN, and the level of TAGLN2 in the first sample(s) with a level of CD14, the level of VASN, and the level of TAGLN2 in the second sample(s), wherein a difference in the level of CD14, the level of VASN, and the level of TAGLN2 in the first sample(s) as compared to the level of CD14, the level of VASN, and the level of TAGLN2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level and/or activity of VASN, and the level and/or activity of TAGLN2 in each of the aliquots; and selecting a member of the library of compounds which modulates the level and/or the activity of CD14, the level and/or activity of VASN, and the level and/or activity of TAGLN2 in an aliquot as compared to the level and/or activity of CD14, the level and/or activity of VASN, and the level and/or activity of TAGLN2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of VASN, and the level and/or activity of TAGLN2, thereby treating the subject.

In one aspect the present invention provides methods for determining whether a subject has active tuberculosis (TB). The methods include determining the level of VASN, the level of PGLYRP2, and the level of TAGLN2 in a sample(s) from the subject; comparing the level of VASN, the level of PGLYRP2, and the level of TAGLN2 in the subject sample(s) with a level of VASN, a level of PGLYRP2, and a level of TAGLN2 in a control sample(s), wherein a difference in the level of VASN, a difference in the level of PGLYRP2, and a difference in the level of TAGLN2 in the subject sample(s) as compared to the level of VASN, the level of PGLYRP2, and the level of TAGLN2 in the control sample(s) indicates that the subject has active TB.

In one aspect the present invention provides methods for monitoring the effectiveness of a treatment in a subject having active tuberculosis (TB). The methods include determining the level of VASN, the level of PGLYRP2, and the level of TAGLN2 in a first sample(s) from the subject prior to the initiation of the treatment; determining the level of VASN, the level of PGLYRP2, and the level of TAGLN2 in a second sample(s) from the subject after at least a portion of the treatment has been administered; comparing the level of VASN, the level of PGLYRP2, and the level of TAGLN2 in the first sample(s) with a level of VASN, the level of PGLYRP2, and the level of TAGLN2 in the second sample(s), wherein a difference in the level of VASN, the level of PGLYRP2, and the level of TAGLN2 in the first sample(s) as compared to the level of VASN, the level of PGLYRP2, and the level of TAGLN2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of VASN, the level and/or activity of PGLYRP2, and the level and/or activity of TAGLN2 in each of the aliquots; and selecting a member of the library of compounds which modulates the level and/or the activity of VASN, the level and/or activity of PGLYRP2, and the level and/or activity of TAGLN2 in an aliquot as compared to the level and/or activity of VASN, the level and/or activity of PGLYRP2, and the level and/or activity of TAGLN2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of VASN, the level and/or activity of PGLYRP2, and the level and/or activity of TAGLN2, thereby treating the subject.

In one aspect the present invention provides methods for determining whether a subject has active tuberculosis (TB). The methods include determining the level of VASN, the level of PGLYRP2, and the level of PFN1 in a sample(s) from the subject; comparing the level of VASN, the level of PGLYRP2, and the level of PFN1 in the subject sample(s) with a level of VASN, a level of PGLYRP2, and a level of PFN1 in a control sample(s), wherein a difference in the level of VASN, a difference in the level of PGLYRP2, and a difference in the level of PFN1 in the subject sample(s) as compared to the level of VASN, the level of PGLYRP2, and the level of PFN1 in the control sample(s) indicates that the subject has active TB.

In one aspect the present invention provides methods for monitoring the effectiveness of a treatment in a subject having active tuberculosis (TB). The methods include determining the level of VASN, the level of PGLYRP2, and the level of PFN1 in a first sample(s) from the subject prior to the initiation of the treatment; determining the level of VASN, the level of PGLYRP2, and the level of PFN1 in a second sample(s) from the subject after at least a portion of the treatment has been administered; comparing the level of VASN, the level of PGLYRP2, and the level of PFN1 in the first sample(s) with a level of VASN, the level of PGLYRP2, and the level of PFN1 in the second sample(s), wherein a difference in the level of VASN, the level of PGLYRP2, and the level of PFN1 in the first sample(s) as compared to the level of VASN, the level of PGLYRP2, and the level of PFN1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of VASN, the level and/or activity of PGLYRP2, and the level and/or activity of PFN1 in each of the aliquots; and selecting a member of the library of compounds which modulates the level and/or the activity of VASN, the level and/or activity of PGLYRP2, and the level and/or activity of PFN1 in an aliquot as compared to the level and/or activity of VASN, the level and/or activity of PGLYRP2, and the level and/or activity of PFN1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of VASN, the level and/or activity of PGLYRP2, and the level and/or activity of PFN1, thereby treating the subject.

In one aspect the present invention provides methods for determining whether a subject has active tuberculosis (TB). The methods include determining the level of CD14, the level of CPN2, the level of PFN1, and the level of PGLYRP2 in a sample(s) from the subject; comparing the level of CD14, the level of CPN2, the level of PFN1, and the level of PGLYRP2 in the subject sample(s) with a level of CD14, a level of CPN2, a level of PFN1, and a level of PGLYRP2 in a control sample(s), wherein a difference in the level of CD14, a difference in the level of CPN2, a difference in the level of PFN1, and a difference in the level of PGLYRP2 in the subject sample(s) as compared to the level of CD14, the level of CPN2, the level of PFN1, and the level of PGLYRP2 in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of PFN1, and the level of PGLYRP2 in a first sample(s) from the subject prior to the initiation of the treatment; determining the level of CD14, the level of CPN2, the level of PFN1, and the level of PGLYRP2 in a second sample(s) from the subject after at least a portion of the treatment has been administered; comparing the level of CD14, the level of CPN2, the level of PFN1, and the level of PGLYRP2 in the first sample(s) with a level of CD14, the level of CPN2, the level of PFN1, and the level of PGLYRP2 in the second sample(s), wherein a difference in the level CD14, the level of CPN2, the level of PFN1, and the level of PGLYRP2 in the first sample(s) as compared to the level of CD14, the level of CPN2, the level of PFN1, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of PFN1, and the level of PGLYRP2 in each of the aliquots; and selecting a member of the library of compounds which modulates the level and/or the activity of the CD14, the level and/or activity of CPN2, the level and/or activity of PFN1, and the level and/or activity of PGLYRP2 in an aliquot as compared to the level and/or activity of CD14, the level and/or activity of CPN2, the level and/or activity of PFN1, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of PFN1, and the level and/or activity of PGLYRP2, thereby treating the subject.

In one aspect the present invention provides methods for determining whether a subject has active tuberculosis (TB). The methods include determining the level of CD14, the level of CPN2, the level of IGFBP6, and the level of TAGLN2 in a sample(s) from the subject; comparing the level of CD14, the level of CPN2, the level of IGFBP6, and the level of TAGLN2 in the subject sample(s) with a level of CD14, a level of CPN2, a level of IGFBP6, and a level of TAGLN2 in a control sample(s), wherein a difference in the level of CD14, a difference in the level of CPN2, a difference in the level of IGFBP6, and a difference in the level of TAGLN2 in the subject sample(s) as compared to the level of CD14, the level of CPN2, the level of IGFBP6, and the level of TAGLN2 in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of IGFBP6, and the level of TAGLN2 in a first sample(s) from the subject prior to the initiation of the treatment; determining the level of CD14, the level of CPN2, the level of IGFBP6, and the level of TAGLN2 in a second sample(s) from the subject after at least a portion of the treatment has been administered; comparing the level of CD14, the level of CPN2, the level of IGFBP6, and the level of TAGLN2 in the first sample(s) with a level of CD14, the level of CPN2, the level of IGFBP6, and the level of TAGLN2 in the second sample(s), wherein a difference in the level CD14, the level of CPN2, the level of IGFBP6, and the level of TAGLN2 in the first sample(s) as compared to the level of CD14, the level of CPN2, the level of IGFBP6, and the level of TAGLN2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of IGFBP6, and the level of TAGLN2 in each of the aliquots; and selecting a member of the library of compounds which modulates the level and/or the activity of the CD14, the level and/or activity of CPN2, the level and/or activity of IGFBP6, and the level and/or activity of TAGLN2 in an aliquot as compared to the level and/or activity of CD14, the level and/or activity of CPN2, the level and/or activity of IGFBP6, and the level and/or activity of TAGLN2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of IGFBP6, and the level and/or activity of TAGLN2, thereby treating the subject.

In one aspect the present invention provides methods for determining whether a subject has active tuberculosis (TB). The methods include determining the level of CD14, the level of CPN2, the level of PFN1, and the level of IGFBP6 in a sample(s) from the subject; comparing the level of CD14, the level of CPN2, the level of PFN1, and the level of IGFBP6 in the subject sample(s) with a level of CD14, a level of CPN2, a level of PFN1, and a level of IGFBP6 in a control sample(s), wherein a difference in the level of CD14, a difference in the level of CPN2, a difference in the level of PFN1, and a difference in the level of IGFBP6 in the subject sample(s) as compared to the level of CD14, the level of CPN2, the level of PFN1, and the level of IGFBP6 in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of PFN1, and the level of IGFBP6 in a first sample(s) from the subject prior to the initiation of the treatment; determining the level of CD14, the level of CPN2, the level of PFN1, and the level of IGFBP6 in a second sample(s) from the subject after at least a portion of the treatment has been administered; comparing the level of CD14, the level of CPN2, the level of PFN1, and the level of IGFBP6 in the first sample(s) with a level of CD14, the level of CPN2, the level of PFN1, and the level of IGFBP6 in the second sample(s), wherein a difference in the level CD14, the level of CPN2, the level of PFN1, and the level of IGFBP6 in the first sample(s) as compared to the level of CD14, the level of CPN2, the level of PFN1, and the level of IGFBP6 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of PFN1, and the level of IGFBP6 in each of the aliquots; and selecting a member of the library of compounds which modulates the level and/or the activity of the CD14, the level and/or activity of CPN2, the level and/or activity of PFN1, and the level and/or activity of IGFBP6 in an aliquot as compared to the level and/or activity of CD14, the level and/or activity of CPN2, the level and/or activity of PFN1, and the level and/or activity of IGFBP6 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of PFN1, and the level and/or activity of IGFBP6, thereby treating the subject.

In one aspect the present invention provides methods for determining whether a subject has active tuberculosis (TB). The methods include determining the level of CD14, the level of CPN2, the level of PFN1, and the level of TAGLN2 in a sample(s) from the subject; comparing the level of CD14, the level of CPN2, the level of PFN1, and the level of TAGLN2 in the subject sample(s) with a level of CD14, a level of CPN2, a level of PFN1, and a level of TAGLN2 in a control sample(s), wherein a difference in the level of CD14, a difference in the level of CPN2, a difference in the level of PFN1, and a difference in the level of TAGLN2 in the subject sample(s) as compared to the level of CD14, the level of CPN2, the level of PFN1, and the level of TAGLN2 in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of PFN1, and the level of TAGLN2 in a first sample(s) from the subject prior to the initiation of the treatment; determining the level of CD14, the level of CPN2, the level of PFN1, and the level of TAGLN2 in a second sample(s) from the subject after at least a portion of the treatment has been administered; comparing the level of CD14, the level of CPN2, the level of PFN1, and the level of TAGLN2 in the first sample(s) with a level of CD14, the level of CPN2, the level of PFN1, and the level of TAGLN2 in the second sample(s), wherein a difference in the level CD14, the level of CPN2, the level of PFN1, and the level of TAGLN2 in the first sample(s) as compared to the level of CD14, the level of CPN2, the level of PFN1, and the level of TAGLN2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of PFN1, and the level of TAGLN2 in each of the aliquots; and selecting a member of the library of compounds which modulates the level and/or the activity of the CD14, the level and/or activity of CPN2, the level and/or activity of PFN1, and the level and/or activity of TAGLN2 in an aliquot as compared to the level and/or activity of CD14, the level and/or activity of CPN2, the level and/or activity of PFN1, and the level and/or activity of TAGLN2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of PFN1, and the level and/or activity of TAGLN2, thereby treating the subject.

In one aspect the present invention provides methods for determining whether a subject has active tuberculosis (TB). The methods include determining the level of CD14, the level of CPN2, the level of TAGLN2, and the level of PGLYRP2 in a sample(s) from the subject; comparing the level of CD14, the level of CPN2, the level of TAGLN2, and the level of PGLYRP2 in the subject sample(s) with a level of CD14, a level of CPN2, a level of TAGLN2, and a level of PGLYRP2 in a control sample(s), wherein a difference in the level of CD14, a difference in the level of CPN2, a difference in the level of TAGLN2, and a difference in the level of PGLYRP2 in the subject sample(s) as compared to the level of CD14, the level of CPN2, the level of TAGLN2, and the level of PGLYRP2 in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of TAGLN2, and the level of PGLYRP2 in a first sample(s) from the subject prior to the initiation of the treatment; determining the level of CD14, the level of CPN2, the level of TAGLN2, and the level of PGLYRP2 in a second sample(s) from the subject after at least a portion of the treatment has been administered; comparing the level of CD14, the level of CPN2, the level of TAGLN2, and the level of PGLYRP2 in the first sample(s) with a level of CD14, the level of CPN2, the level of TAGLN2, and the level of PGLYRP2 in the second sample(s), wherein a difference in the level CD14, the level of CPN2, the level of TAGLN2, and the level of PGLYRP2 in the first sample(s) as compared to the level of CD14, the level of CPN2, the level of TAGLN2, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of TAGLN2, and the level of PGLYRP2 in each of the aliquots; and selecting a member of the library of compounds which modulates the level and/or the activity of the CD14, the level and/or activity of CPN2, the level and/or activity of TAGLN2, and the level and/or activity of PGLYRP2 in an aliquot as compared to the level and/or activity of CD14, the level and/or activity of CPN2, the level and/or activity of TAGLN2, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of TAGLN2, and the level and/or activity of PGLYRP2, thereby treating the subject.

In one aspect the present invention provides methods for determining whether a subject has active tuberculosis (TB). The methods include determining the level of CD14, the level of CPN2, the level of PFN1, and the level of SEPP1 in a sample(s) from the subject; comparing the level of CD14, the level of CPN2, the level of PFN1, and the level of SEPP1 in the subject sample(s) with a level of CD14, a level of CPN2, a level of PFN1, and a level of SEPP1 in a control sample(s), wherein a difference in the level of CD14, a difference in the level of CPN2, a difference in the level of PFN1, and a difference in the level of SEPP1 in the subject sample(s) as compared to the level of CD14, the level of CPN2, the level of PFN1, and the level of SEPP1 in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of PFN1, and the level of SEPP1 in a first sample(s) from the subject prior to the initiation of the treatment; determining the level of CD14, the level of CPN2, the level of PFN1, and the level of SEPP1 in a second sample(s) from the subject after at least a portion of the treatment has been administered; comparing the level of CD14, the level of CPN2, the level of PFN1, and the level of SEPP1 in the first sample(s) with a level of CD14, the level of CPN2, the level of PFN1, and the level of SEPP1 in the second sample(s), wherein a difference in the level CD14, the level of CPN2, the level of PFN1, and the level of SEPP1 in the first sample(s) as compared to the level of CD14, the level of CPN2, the level of PFN1, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of PFN1, and the level of SEPP1 in each of the aliquots; and selecting a member of the library of compounds which modulates the level and/or the activity of the CD14, the level and/or activity of CPN2, the level and/or activity of PFN1, and the level and/or activity of SEPP1 in an aliquot as compared to the level and/or activity of CD14, the level and/or activity of CPN2, the level and/or activity of PFN1, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of PFN1, and the level and/or activity of SEPP1, thereby treating the subject.

In one aspect the present invention provides methods for determining whether a subject has active tuberculosis (TB). The methods include determining the level of CD14, the level of CPN2, the level of PFN1, and the level of VASN in a sample(s) from the subject; comparing the level of CD14, the level of CPN2, the level of PFN1, and the level of VASN in the subject sample(s) with a level of CD14, a level of CPN2, a level of PFN1, and a level of VASN in a control sample(s), wherein a difference in the level of CD14, a difference in the level of CPN2, a difference in the level of PFN1, and a difference in the level of VASN in the subject sample(s) as compared to the level of CD14, the level of CPN2, the level of PFN1, and the level of VASN in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of PFN1, and the level of VASN in a first sample(s) from the subject prior to the initiation of the treatment; determining the level of CD14, the level of CPN2, the level of PFN1, and the level of VASN in a second sample(s) from the subject after at least a portion of the treatment has been administered; comparing the level of CD14, the level of CPN2, the level of PFN1, and the level of VASN in the first sample(s) with a level of CD14, the level of CPN2, the level of PFN1, and the level of VASN in the second sample(s), wherein a difference in the level CD14, the level of CPN2, the level of PFN1, and the level of VASN in the first sample(s) as compared to the level of CD14, the level of CPN2, the level of PFN1, and the level of VASN in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of PFN1, and the level of VASN in each of the aliquots; and selecting a member of the library of compounds which modulates the level and/or the activity of the CD14, the level and/or activity of CPN2, the level and/or activity of PFN1, and the level and/or activity of VASN in an aliquot as compared to the level and/or activity of CD14, the level and/or activity of CPN2, the level and/or activity of PFN1, and the level and/or activity of VASN in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of PFN1, and the level and/or activity of VASN, thereby treating the subject.

In one aspect the present invention provides methods for determining whether a subject has active tuberculosis (TB). The methods include determining the level of CD14, the level of VASN, the level of IGFBP6, and the level of TAGLN2 in a sample(s) from the subject; comparing the level of CD14, the level of VASN, the level of IGFBP6, and the level of TAGLN2 in the subject sample(s) with a level of CD14, a level of VASN, a level of IGFBP6, and a level of TAGLN2 in a control sample(s), wherein a difference in the level of CD14, a difference in the level of VASN, a difference in the level of IGFBP6, and a difference in the level of TAGLN2 in the subject sample(s) as compared to the level of CD14, the level of VASN, the level of IGFBP6, and the level of TAGLN2 in the control sample(s) indicates that the subject has active TB.

In one aspect the present invention provides methods for monitoring the effectiveness of a treatment in a subject having active tuberculosis (TB). The methods include determining the level of CD14, the level of VASN, the level of IGFBP6, and the level of TAGLN2 in a first sample(s) from the subject prior to the initiation of the treatment; determining the level of CD14, the level of VASN, the level of IGFBP6, and the level of TAGLN2 in a second sample(s) from the subject after at least a portion of the treatment has been administered; comparing the level of CD14, the level of VASN, the level of IGFBP6, and the level of TAGLN2 in the first sample(s) with a level of CD14, the level of VASN, the level of IGFBP6, and the level of TAGLN2 in the second sample(s), wherein a difference in the level CD14, the level of VASN, the level of IGFBP6, and the level of TAGLN2 in the first sample(s) as compared to the level of CD14, the level of VASN, the level of IGFBP6, and the level of TAGLN2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of VASN, the level of IGFBP6, and the level of TAGLN2 in each of the aliquots; and selecting a member of the library of compounds which modulates the level and/or the activity of the CD14, the level and/or activity of VASN, the level and/or activity of IGFBP6, and the level and/or activity of TAGLN2 in an aliquot as compared to the level and/or activity of CD14, the level and/or activity of VASN, the level and/or activity of IGFBP6, and the level and/or activity of TAGLN2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of VASN, the level and/or activity of IGFBP6, and the level and/or activity of TAGLN2, thereby treating the subject.

In one aspect the present invention provides methods for determining whether a subject has active tuberculosis (TB). The methods include determining the level of CD14, the level of CPN2, the level of SEPP1, and the level of TAGLN2 in a sample(s) from the subject; comparing the level of CD14, the level of CPN2, the level of SEPP1, and the level of TAGLN2 in the subject sample(s) with a level of CD14, a level of CPN2, a level of SEPP1, and a level of TAGLN2 in a control sample(s), wherein a difference in the level of CD14, a difference in the level of CPN2, a difference in the level of SEPP1, and a difference in the level of TAGLN2 in the subject sample(s) as compared to the level of CD14, the level of CPN2, the level of SEPP1, and the level of TAGLN2 in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of SEPP1, and the level of TAGLN2 in a first sample(s) from the subject prior to the initiation of the treatment; determining the level of CD14, the level of CPN2, the level of SEPP1, and the level of TAGLN2 in a second sample(s) from the subject after at least a portion of the treatment has been administered; comparing the level of CD14, the level of CPN2, the level of SEPP1, and the level of TAGLN2 in the first sample(s) with a level of CD14, the level of CPN2, the level of SEPP1, and the level of TAGLN2 in the second sample(s), wherein a difference in the level CD14, the level of CPN2, the level of SEPP1, and the level of TAGLN2 in the first sample(s) as compared to the level of CD14, the level of CPN2, the level of SEPP1, and the level of TAGLN2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of SEPP1, and the level of TAGLN2 in each of the aliquots; and selecting a member of the library of compounds which modulates the level and/or the activity of the CD14, the level and/or activity of CPN2, the level and/or activity of SEPP1, and the level and/or activity of TAGLN2 in an aliquot as compared to the level and/or activity of CD14, the level and/or activity of CPN2, the level and/or activity of SEPP1, and the level and/or activity of TAGLN2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of SEPP1, and the level and/or activity of TAGLN2, thereby treating the subject.

In one aspect the present invention provides methods for determining whether a subject has active tuberculosis (TB). The methods include determining the level of CD14, the level of CPN2, the level of TAGLN2, and the level of VASN in a sample(s) from the subject; comparing the level of CD14, the level of CPN2, the level of TAGLN2, and the level of VASN in the subject sample(s) with a level of CD14, a level of CPN2, a level of VASN, and a level of PGLYRP2 in a control sample(s), wherein a difference in the level of CD14, a difference in the level of CPN2, a difference in the level of TAGLN2, and a difference in the level of VASN in the subject sample(s) as compared to the level of CD14, the level of CPN2, the level of TAGLN2, and the level of VASN in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of TAGLN2, and the level of VASN in a first sample(s) from the subject prior to the initiation of the treatment; determining the level of CD14, the level of CPN2, the level of TAGLN2, and the level of VASN in a second sample(s) from the subject after at least a portion of the treatment has been administered; comparing the level of CD14, the level of CPN2, the level of TAGLN2, and the level of VASN in the first sample(s) with a level of CD14, the level of CPN2, the level of TAGLN2, and the level of VASN in the second sample(s), wherein a difference in the level CD14, the level of CPN2, the level of TAGLN2, and the level of VASN in the first sample(s) as compared to the level of CD14, the level of CPN2, the level of TAGLN2, and the level of VASN in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of TAGLN2, and the level of VASN in each of the aliquots; and selecting a member of the library of compounds which modulates the level and/or the activity of the CD14, the level and/or activity of CPN2, the level and/or activity of TAGLN2, and the level and/or activity of VASN in an aliquot as compared to the level and/or activity of CD14, the level and/or activity of CPN2, the level and/or activity of TAGLN2, and the level and/or activity of VASN in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of TAGLN2, and the level and/or activity of VASN, thereby treating the subject.

In one aspect the present invention provides methods for determining whether a subject has active tuberculosis (TB). The methods include determining the level of PGLYRP2, the level of CPN2, the level of TAGLN2, and the level of VASN in a sample(s) from the subject; comparing the level of PGLYRP2, the level of CPN2, the level of TAGLN2, and the level of VASN in the subject sample(s) with a level of PGLYRP2, a level of CPN2, a level of VASN, and a level of PGLYRP2 in a control sample(s), wherein a difference in the level of PGLYRP2, a difference in the level of CPN2, a difference in the level of TAGLN2, and a difference in the level of VASN in the subject sample(s) as compared to the level of PGLYRP2, the level of CPN2, the level of TAGLN2, and the level of VASN in the control sample(s) indicates that the subject has active TB.

In one aspect the present invention provides methods for monitoring the effectiveness of a treatment in a subject having active tuberculosis (TB). The methods include determining the level of PGLYRP2, the level of CPN2, the level of TAGLN2, and the level of VASN in a first sample(s) from the subject prior to the initiation of the treatment; determining the level of PGLYRP2, the level of CPN2, the level of TAGLN2, and the level of VASN in a second sample(s) from the subject after at least a portion of the treatment has been administered; comparing the level of PGLYRP2, the level of CPN2, the level of TAGLN2, and the level of VASN in the first sample(s) with a level of PGLYRP2, the level of CPN2, the level of TAGLN2, and the level of VASN in the second sample(s), wherein a difference in the level PGLYRP2, the level of CPN2, the level of TAGLN2, and the level of VASN in the first sample(s) as compared to the level of PGLYRP2, the level of CPN2, the level of TAGLN2, and the level of VASN in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PGLYRP2, the level of CPN2, the level of TAGLN2, and the level of VASN in each of the aliquots; and selecting a member of the library of compounds which modulates the level and/or the activity of the PGLYRP2, the level and/or activity of CPN2, the level and/or activity of TAGLN2, and the level and/or activity of VASN in an aliquot as compared to the level and/or activity of PGLYRP2, the level and/or activity of CPN2, the level and/or activity of TAGLN2, and the level and/or activity of VASN in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PGLYRP2, the level and/or activity of CPN2, the level and/or activity of TAGLN2, and the level and/or activity of VASN, thereby treating the subject.

In one aspect the present invention provides methods for determining whether a subject has active tuberculosis (TB). The methods include determining the level of CD14, the level of VASN, the level of IGFBP6, and the level of PFN1 in a sample(s) from the subject; comparing the level of CD14, the level of VASN, the level of IGFBP6, and the level of PFN1 in the subject sample(s) with a level of CD14, a level of VASN, a level of IGFBP6, and a level of PFN1 in a control sample(s), wherein a difference in the level of CD14, a difference in the level of VASN, a difference in the level of IGFBP6, and a difference in the level of PFN1 in the subject sample(s) as compared to the level of CD14, the level of VASN, the level of IGFBP6, and the level of PFN1 in the control sample(s) indicates that the subject has active TB.

In one aspect the present invention provides methods for monitoring the effectiveness of a treatment in a subject having active tuberculosis (TB). The methods include determining the level of CD14, the level of VASN, the level of IGFBP6, and the level of PFN1 in a first sample(s) from the subject prior to the initiation of the treatment; determining the level of CD14, the level of VASN, the level of IGFBP6, and the level of PFN1 in a second sample(s) from the subject after at least a portion of the treatment has been administered; comparing the level of CD14, the level of VASN, the level of IGFBP6, and the level of PFN1 in the first sample(s) with a level of CD14, the level of VASN, the level of IGFBP6, and the level of PFN1 in the second sample(s), wherein a difference in the level CD14, the level of VASN, the level of IGFBP6, and the level of PFN1 in the first sample(s) as compared to the level of CD14, the level of VASN, the level of IGFBP6, and the level of PFN1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of VASN, the level of IGFBP6, and the level of PFN1 in each of the aliquots; and selecting a member of the library of compounds which modulates the level and/or the activity of the CD14, the level and/or activity of VASN, the level and/or activity of IGFBP6, and the level and/or activity of PFN1 in an aliquot as compared to the level and/or activity of CD14, the level and/or activity of VASN, the level and/or activity of IGFBP6, and the level and/or activity of PFN1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of VASN, the level and/or activity of IGFBP6, and the level and/or activity of PFN1, thereby treating the subject.

In one aspect the present invention provides methods for determining whether a subject has active tuberculosis (TB). The methods include determining the level of CD14, the level of CPN2, the level of IGFBP6, and the level of PGLYRP2 in a sample(s) from the subject; comparing the level of CD14, the level of CPN2, the level of IGFBP6, and the level of PGLYRP2 in the subject sample(s) with a level of CD14, a level of CPN2, a level of IGFBP6, and a level of PGLYRP2 in a control sample(s), wherein a difference in the level of CD14, a difference in the level of CPN2, a difference in the level of IGFBP6, and a difference in the level of PGLYRP2 in the subject sample(s) as compared to the level of CD14, the level of CPN2, the level of IGFBP6, and the level of PGLYRP2 in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of IGFBP6, and the level of PGLYRP2 in a first sample(s) from the subject prior to the initiation of the treatment; determining the level of CD14, the level of CPN2, the level of IGFBP6, and the level of PGLYRP2 in a second sample(s) from the subject after at least a portion of the treatment has been administered; comparing the level of CD14, the level of CPN2, the level of IGFBP6, and the level of PGLYRP2 in the first sample(s) with a level of CD14, the level of CPN2, the level of IGFBP6, and the level of PGLYRP2 in the second sample(s), wherein a difference in the level CD14, the level of CPN2, the level of IGFBP6, and the level of PGLYRP2 in the first sample(s) as compared to the level of CD14, the level of CPN2, the level of IGFBP6, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of IGFBP6, and the level of PGLYRP2 in each of the aliquots; and selecting a member of the library of compounds which modulates the level and/or the activity of the CD14, the level and/or activity of CPN2, the level and/or activity of IGFBP6, and the level and/or activity of PGLYRP2 in an aliquot as compared to the level and/or activity of CD14, the level and/or activity of CPN2, the level and/or activity of IGFBP6, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of IGFBP6, and the level and/or activity of PGLYRP2, thereby treating the subject.

In one aspect the present invention provides methods for determining whether a subject has active tuberculosis (TB). The methods include determining the level of CD14, the level of PFN1, the level of IGFBP6, and the level of PGLYRP2 in a sample(s) from the subject; comparing the level of CD14, the level of PFN1, the level of IGFBP6, and the level of PGLYRP2 in the subject sample(s) with a level of CD14, a level of PFN1, a level of IGFBP6, and a level of PGLYRP2 in a control sample(s), wherein a difference in the level of CD14, a difference in the level of PFN1, a difference in the level of IGFBP6, and a difference in the level of PGLYRP2 in the subject sample(s) as compared to the level of CD14, the level of PFN1, the level of IGFBP6, and the level of PGLYRP2 in the control sample(s) indicates that the subject has active TB.

In one aspect the present invention provides methods for monitoring the effectiveness of a treatment in a subject having active tuberculosis (TB). The methods include determining the level of CD14, the level of PFN1, the level of IGFBP6, and the level of PGLYRP2 in a first sample(s) from the subject prior to the initiation of the treatment; determining the level of CD14, the level of PFN1, the level of IGFBP6, and the level of PGLYRP2 in a second sample(s) from the subject after at least a portion of the treatment has been administered; comparing the level of CD14, the level of PFN1, the level of IGFBP6, and the level of PGLYRP2 in the first sample(s) with a level of CD14, the level of PFN1, the level of IGFBP6, and the level of PGLYRP2 in the second sample(s), wherein a difference in the level CD14, the level of PFN1, the level of IGFBP6, and the level of PGLYRP2 in the first sample(s) as compared to the level of CD14, the level of PFN1, the level of IGFBP6, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of PFN1, the level of IGFBP6, and the level of PGLYRP2 in each of the aliquots; and selecting a member of the library of compounds which modulates the level and/or the activity of the CD14, the level and/or activity of PFN1, the level and/or activity of IGFBP6, and the level and/or activity of PGLYRP2 in an aliquot as compared to the level and/or activity of CD14, the level and/or activity of PFN1, the level and/or activity of IGFBP6, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of PFN1, the level and/or activity of IGFBP6, and the level and/or activity of PGLYRP2, thereby treating the subject.

In one aspect the present invention provides methods for determining whether a subject has active tuberculosis (TB). The methods include determining the level of CD14, the level of PFN1, the level of VASN, and the level of PGLYRP2 in a sample(s) from the subject; comparing the level of CD14, the level of PFN1, the level of VASN, and the level of PGLYRP2 in the subject sample(s) with a level of CD14, a level of PFN1, a level of VASN, and a level of PGLYRP2 in a control sample(s), wherein a difference in the level of CD14, a difference in the level of PFN1, a difference in the level of VASN, and a difference in the level of PGLYRP2 in the subject sample(s) as compared to the level of CD14, the level of PFN1, the level of VASN, and the level of PGLYRP2 in the control sample(s) indicates that the subject has active TB.

In one aspect the present invention provides methods for monitoring the effectiveness of a treatment in a subject having active tuberculosis (TB). The methods include determining the level of CD14, the level of PFN1, the level of VASN, and the level of PGLYRP2 in a first sample(s) from the subject prior to the initiation of the treatment; determining the level of CD14, the level of PFN1, the level of VASN, and the level of PGLYRP2 in a second sample(s) from the subject after at least a portion of the treatment has been administered; comparing the level of CD14, the level of PFN1, the level of VASN, and the level of PGLYRP2 in the first sample(s) with a level of CD14, the level of PFN1, the level of VASN, and the level of PGLYRP2 in the second sample(s), wherein a difference in the level CD14, the level of PFN1, the level of VASN, and the level of PGLYRP2 in the first sample(s) as compared to the level of CD14, the level of PFN1, the level of VASN, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of PFN1, the level of VASN, and the level of PGLYRP2 in each of the aliquots; and selecting a member of the library of compounds which modulates the level and/or the activity of the CD14, the level and/or activity of PFN1, the level and/or activity of VASN, and the level and/or activity of PGLYRP2 in an aliquot as compared to the level and/or activity of CD14, the level and/or activity of PFN1, the level and/or activity of VASN, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of PFN1, the level and/or activity of VASN, and the level and/or activity of PGLYRP2, thereby treating the subject.

In one aspect the present invention provides methods for determining whether a subject has active tuberculosis (TB). The methods include determining the level of CD14, the level of TAGLN2, the level of IGFBP6, and the level of PGLYRP2 in a sample(s) from the subject; comparing the level of CD14, the level of TAGLN2, the level of IGFBP6, and the level of PGLYRP2 in the subject sample(s) with a level of CD14, a level of TAGLN2, a level of IGFBP6, and a level of PGLYRP2 in a control sample(s), wherein a difference in the level of CD14, a difference in the level of TAGLN2, a difference in the level of IGFBP6, and a difference in the level of PGLYRP2 in the subject sample(s) as compared to the level of CD14, the level of TAGLN2, the level of IGFBP6, and the level of PGLYRP2 in the control sample(s) indicates that the subject has active TB.

In one aspect the present invention provides methods for monitoring the effectiveness of a treatment in a subject having active tuberculosis (TB). The methods include determining the level of CD14, the level of TAGLN2, the level of IGFBP6, and the level of PGLYRP2 in a first sample(s) from the subject prior to the initiation of the treatment; determining the level of CD14, the level of TAGLN2, the level of IGFBP6, and the level of PGLYRP2 in a second sample(s) from the subject after at least a portion of the treatment has been administered; comparing the level of CD14, the level of TAGLN2, the level of IGFBP6, and the level of PGLYRP2 in the first sample(s) with a level of CD14, the level of TAGLN2, the level of IGFBP6, and the level of PGLYRP2 in the second sample(s), wherein a difference in the level CD14, the level of TAGLN2, the level of IGFBP6, and the level of PGLYRP2 in the first sample(s) as compared to the level of CD14, the level of TAGLN2, the level of IGFBP6, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of TAGLN2, the level of IGFBP6, and the level of PGLYRP2 in each of the aliquots; and selecting a member of the library of compounds which modulates the level and/or the activity of the CD14, the level and/or activity of TAGLN2, the level and/or activity of IGFBP6, and the level and/or activity of PGLYRP2 in an aliquot as compared to the level and/or activity of CD14, the level and/or activity of TAGLN2, the level and/or activity of IGFBP6, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of TAGLN2, the level and/or activity of IGFBP6, and the level and/or activity of PGLYRP2, thereby treating the subject.

In one aspect the present invention provides methods for determining whether a subject has active tuberculosis (TB).

The methods include determining the level of CD14, the level of CPN2, the level of IGFBP6, and the level of SEPP1 in a sample(s) from the subject; comparing the level of CD14, the level of CPN2, the level of IGFBP6, and the level of SEPP1 in the subject sample(s) with a level of CD14, a level of CPN2, a level of IGFBP6, and a level of SEPP1 in a control sample(s), wherein a difference in the level of CD14, a difference in the level of CPN2, a difference in the level of IGFBP6, and a difference in the level of SEPP1 in the subject sample(s) as compared to the level of CD14, the level of CPN2, the level of IGFBP6, and the level of SEPP1 in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of IGFBP6, and the level of SEPP1 in a first sample(s) from the subject prior to the initiation of the treatment; determining the level of CD14, the level of CPN2, the level of IGFBP6, and the level of SEPP1 in a second sample(s) from the subject after at least a portion of the treatment has been administered; comparing the level of CD14, the level of CPN2, the level of IGFBP6, and the level of SEPP1 in the first sample(s) with a level of CD14, the level of CPN2, the level of IGFBP6, and the level of SEPP1 in the second sample(s), wherein a difference in the level CD14, the level of CPN2, the level of IGFBP6, and the level of SEPP1 in the first sample(s) as compared to the level of CD14, the level of CPN2, the level of IGFBP6, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of IGFBP6, and the level of SEPP1 in each of the aliquots; and selecting a member of the library of compounds which modulates the level and/or the activity of the CD14, the level and/or activity of CPN2, the level and/or activity of IGFBP6, and the level and/or activity of SEPP1 in an aliquot as compared to the level and/or activity of CD14, the level and/or activity of CPN2, the level and/or activity of IGFBP6, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of IGFBP6, and the level and/or activity of SEPP1, thereby treating the subject.

In one aspect the present invention provides methods for determining whether a subject has active tuberculosis (TB). The methods include determining the level of CD14, the level of PFN1, the level of IGFBP6, and the level of SEPP1 in a sample(s) from the subject; comparing the level of CD14, the level of PFN1, the level of IGFBP6, and the level of SEPP1 in the subject sample(s) with a level of CD14, a level of PFN1, a level of IGFBP6, and a level of SEPP1 in a control sample(s), wherein a difference in the level of CD14, a difference in the level of PFN1, a difference in the level of IGFBP6, and a difference in the level of SEPP1 in the subject sample(s) as compared to the level of CD14, the level of PFN1, the level of IGFBP6, and the level of SEPP1 in the control sample(s) indicates that the subject has active TB.

In one aspect the present invention provides methods for monitoring the effectiveness of a treatment in a subject having active tuberculosis (TB). The methods include determining the level of CD14, the level of PFN1, the level of IGFBP6, and the level of SEPP1 in a first sample(s) from the subject prior to the initiation of the treatment; determining the level of CD14, the level of PFN1, the level of IGFBP6, and the level of SEPP1 in a second sample(s) from the subject after at least a portion of the treatment has been administered; comparing the level of CD14, the level of PFN1, the level of IGFBP6, and the level of SEPP1 in the first sample(s) with a level of CD14, the level of PFN1, the level of IGFBP6, and the level of SEPP1 in the second sample(s), wherein a difference in the level CD14, the level of PFN1, the level of IGFBP6, and the level of SEPP1 in the first sample(s) as compared to the level of CD14, the level of PFN1, the level of IGFBP6, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of PFN1, the level of IGFBP6, and the level of SEPP1 in each of the aliquots; and selecting a member of the library of compounds which modulates the level and/or the activity of the CD14, the level and/or activity of PFN1, the level and/or activity of IGFBP6, and the level and/or activity of SEPP1 in an aliquot as compared to the level and/or activity of CD14, the level and/or activity of PFN1, the level and/or activity of IGFBP6, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of PFN1, the level and/or activity of IGFBP6, and the level and/or activity of SEPP1, thereby treating the subject.

In one aspect the present invention provides methods for determining whether a subject has active tuberculosis (TB). The methods include determining the level of CD14, the level of CPN2, the level of IGFBP6, and the level of VASN in a sample(s) from the subject; comparing the level of CD14, the level of CPN2, the level of IGFBP6, and the level of VASN in the subject sample(s) with a level of CD14, a level of CPN2, a level of IGFBP6, and a level of VASN in a control sample(s), wherein a difference in the level of CD14, a difference in the level of CPN2, a difference in the level of IGFBP6, and a difference in the level of VASN in the subject sample(s) as compared to the level of CD14, the level of CPN2, the level of IGFBP6, and the level of VASN in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of IGFBP6, and the level of VASN in a first sample(s) from the subject prior to the initiation of the treatment; determining the level of CD14, the level of CPN2, the level of IGFBP6, and the level of VASN in a second sample(s) from the subject after at least a portion of the treatment has been administered; comparing the level of CD14, the level of CPN2, the level of IGFBP6, and the level of VASN in the first sample(s) with a level of CD14, the level of CPN2, the level of IGFBP6, and the level of VASN in the second sample(s), wherein a difference in the level CD14, the level of CPN2, the level of IGFBP6, and the level of VASN in the first sample(s) as compared to the level of CD14, the level of CPN2, the level of IGFBP6, and the level of VASN in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of IGFBP6, and the level of VASN in each of the aliquots; and selecting a member of the library of compounds which modulates the level and/or the activity of the CD14, the level and/or activity of CPN2, the level and/or activity of IGFBP6, and the level and/or activity of VASN in an aliquot as compared to the level and/or activity of CD14, the level and/or activity of CPN2, the level and/or activity of IGFBP6, and the level and/or activity of VASN in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of IGFBP6, and the level and/or activity of VASN, thereby treating the subject.

In one aspect the present invention provides methods for determining whether a subject has active tuberculosis (TB). The methods include determining the level of CD14, the level of TAGLN2, the level of VASN, and the level of PGLYRP2 in a sample(s) from the subject; comparing the level of CD14, the level of TAGLN2, the level of VASN, and the level of PGLYRP2 in the subject sample(s) with a level of CD14, the level of TAGLN2, a level of VASN, and a level of PGLYRP2 in a control sample(s), wherein a difference in the level of CD14, a difference in the level of TAGLN2, a difference in the level of VASN, and a difference in the level of PGLYRP2 in the subject sample(s) as compared to the level of CD14, the level of TAGLN2, the level of VASN, and the level of PGLYRP2 in the control sample(s) indicates that the subject has active TB.

In one aspect the present invention provides methods for monitoring the effectiveness of a treatment in a subject having active tuberculosis (TB). The methods include determining the level of CD14, the level of TAGLN2, the level of VASN, and the level of PGLYRP2 in a first sample(s) from the subject prior to the initiation of the treatment; determining the level of CD14, the level of TAGLN2, the level of VASN, and the level of PGLYRP2 in a second sample(s) from the subject after at least a portion of the treatment has been administered; comparing the level of CD14, the level of TAGLN2, the level of VASN, and the level of PGLYRP2 in the first sample(s) with a level of CD14, the level of TAGLN2, the level of VASN, and the level of PGLYRP2 in the second sample(s), wherein a difference in the level CD14, the level of TAGLN2, the level of VASN, and the level of PGLYRP2 in the first sample(s) as compared to the level of CD14, the level of TAGLN2, the level of VASN, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of TAGLN2, the level of VASN, and the level of PGLYRP2 in each of the aliquots; and selecting a member of the library of compounds which modulates the level and/or the activity of the CD14, the level and/or activity of TAGLN2, the level and/or activity of VASN, and the level and/or activity of PGLYRP2 in an aliquot as compared to the level and/or activity of CD14, the level and/or activity of TAGLN2, the level and/or activity of VASN, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of TAGLN2, the level and/or activity of VASN, and the level and/or activity of PGLYRP2, thereby treating the subject.

In one aspect the present invention provides methods for determining whether a subject has active tuberculosis (TB). The methods include determining the level of CD14, the level of TAGLN2, the level of PFN1, and the level of PGLYRP2 in a sample(s) from the subject; comparing the level of CD14, the level of TAGLN2, the level of PFN1, and the level of PGLYRP2 in the subject sample(s) with a level of CD14, the level of TAGLN2, a level of PFN1, and a level of PGLYRP2 in a control sample(s), wherein a difference in the level of CD14, a difference in the level of TAGLN2, a difference in the level of PFN1, and a difference in the level of PGLYRP2 in the subject sample(s) as compared to the level of CD14, the level of TAGLN2, the level of PFN1, and the level of PGLYRP2 in the control sample(s) indicates that the subject has active TB.

In one aspect the present invention provides methods for monitoring the effectiveness of a treatment in a subject having active tuberculosis (TB). The methods include determining the level of CD14, the level of TAGLN2, the level of PFN1, and the level of PGLYRP2 in a first sample(s) from the subject prior to the initiation of the treatment; determining the level of CD14, the level of TAGLN2, the level of PFN1, and the level of PGLYRP2 in a second sample(s) from the subject after at least a portion of the treatment has been administered; comparing the level of CD14, the level of TAGLN2, the level of PFN1, and the level of PGLYRP2 in the first sample(s) with a level of CD14, the level of TAGLN2, the level of PFN1, and the level of PGLYRP2 in the second sample(s), wherein a difference in the level CD14, the level of TAGLN2, the level of PFN1, and the level of PGLYRP2 in the first sample(s) as compared to the level of CD14, the level of TAGLN2, the level of PFN1, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of TAGLN2, the level of PFN1, and the level of PGLYRP2 in each of the aliquots; and selecting a member of the library of compounds which modulates the level and/or the activity of the CD14, the level and/or activity of TAGLN2, the level and/or activity of PFN1, and the level and/or activity of PGLYRP2 in an aliquot as compared to the level and/or activity of CD14, the level and/or activity of TAGLN2, the level and/or activity of PFN1, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of TAGLN2, the level and/or activity of PFN1, and the level and/or activity of PGLYRP2, thereby treating the subject.

In one aspect the present invention provides methods for determining whether a subject has active tuberculosis (TB). The methods include determining the level of CD14, the level of PFN1, the level of IGFBP6, and the level of SEPP1 in a sample(s) from the subject; comparing the level of CD14, the level of PFN1, the level of IGFBP6, and the level of SEPP1 in the subject sample(s) with a level of CD14, a level of PFN1, a level of IGFBP6, and a level of SEPP1 in a control sample(s), wherein a difference in the level of CD14, a difference in the level of PFN1, a difference in the level of IGFBP6, and a difference in the level of SEPP1 in the subject sample(s) as compared to the level of CD14, the level of PFN1, the level of IGFBP6, and the level of SEPP1 in the control sample(s) indicates that the subject has active TB.

In one aspect the present invention provides methods for monitoring the effectiveness of a treatment in a subject having active tuberculosis (TB). The methods include determining the level of CD14, the level of PFN1, the level of IGFBP6, and the level of SEPP1 in a first sample(s) from the subject prior to the initiation of the treatment; determining the level of CD14, the level of PFN1, the level of IGFBP6, and the level of SEPP1 in a second sample(s) from the subject after at least a portion of the treatment has been administered; comparing the level of CD14, the level of PFN1, the level of IGFBP6, and the level of SEPP1 in the first sample(s) with a level of CD14, the level of PFN1, the level of IGFBP6, and the level of SEPP1 in the second sample(s), wherein a difference in the level CD14, the level of PFN1, the level of IGFBP6, and the level of SEPP1 in the first sample(s) as compared to the level of CD14, the level of PFN1, the level of IGFBP6, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of PFN1, the level of IGFBP6, and the level of SEPP1 in each of the aliquots; and selecting a member of the library of compounds which modulates the level and/or the activity of the CD14, the level and/or activity of PFN1, the level and/or activity of IGFBP6, and the level and/or activity of SEPP1 in an aliquot as compared to the level and/or activity of CD14, the level and/or activity of PFN1, the level and/or activity of IGFBP6, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of PFN1, the level and/or activity of IGFBP6, and the level and/or activity of SEPP1, thereby treating the subject.

In one aspect the present invention provides methods for determining whether a subject has active tuberculosis (TB). The methods include determining the level of CD14, the level of TAGLN2, the level of PFN1, and the level of VASN in a sample(s) from the subject; comparing the level of CD14, the level of TAGLN2, the level of PFN1, and the level of VASN in the subject sample(s) with a level of CD14, the level of TAGLN2, a level of PFN1, and a level of VASN in a control sample(s), wherein a difference in the level of CD14, a difference in the level of TAGLN2, a difference in the level of PFN1, and a difference in the level of VASN in the subject sample(s) as compared to the level of CD14, the level of TAGLN2, the level of PFN1, and the level of VASN in the control sample(s) indicates that the subject has active TB.

In one aspect the present invention provides methods for monitoring the effectiveness of a treatment in a subject having active tuberculosis (TB). The methods include determining the level of CD14, the level of TAGLN2, the level of PFN1, and the level of VASN in a first sample(s) from the subject prior to the initiation of the treatment; determining the level of CD14, the level of TAGLN2, the level of PFN1, and the level of VASN in a second sample(s) from the subject after at least a portion of the treatment has been administered; comparing the level of CD14, the level of TAGLN2, the level of PFN1, and the level of VASN in the first sample(s) with a level of CD14, the level of TAGLN2, the level of PFN1, and the level of VASN in the second sample(s), wherein a difference in the level CD14, the level of TAGLN2, the level of PFN1, and the level of VASN in the first sample(s) as compared to the level of CD14, the level of TAGLN2, the level of PFN1, and the level of VASN in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of TAGLN2, the level of PFN1, and the level of VASN in each of the aliquots; and selecting a member of the library of compounds which modulates the level and/or the activity of the CD14, the level and/or activity of TAGLN2, the level and/or activity of PFN1, and the level and/or activity of VASN in an aliquot as compared to the level and/or activity of CD14, the level and/or activity of TAGLN2, the level and/or activity of PFN1, and the level and/or activity of VASN in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of TAGLN2, the level and/or activity of PFN1, and the level and/or activity of VASN, thereby treating the subject.

In one aspect the present invention provides methods for determining whether a subject has active tuberculosis (TB). The methods include determining the level of CD14, the level of TAGLN2, the level of IGFBP6, and the level of SEPP1 in a sample(s) from the subject; comparing the level of CD14, the level of TAGLN2, the level of IGFBP6, and the level of SEPP1 in the subject sample(s) with a level of CD14, a level of TAGLN2, a level of IGFBP6, and a level of SEPP1 in a control sample(s), wherein a difference in the level of CD14, a difference in the level of TAGLN2, a difference in the level of IGFBP6, and a difference in the level of SEPP1 in the subject sample(s) as compared to the level of CD14, the level of TAGLN2, the level of IGFBP6, and the level of SEPP1 in the control sample(s) indicates that the subject has active TB.

In one aspect the present invention provides methods for monitoring the effectiveness of a treatment in a subject having active tuberculosis (TB). The methods include determining the level of CD14, the level of TAGLN2, the level of IGFBP6, and the level of SEPP1 in a first sample(s) from the subject prior to the initiation of the treatment; determining the level of CD14, the level of TAGLN2, the level of IGFBP6, and the level of SEPP1 in a second sample(s) from the subject after at least a portion of the treatment has been administered; comparing the level of CD14, the level of TAGLN2, the level of IGFBP6, and the level of SEPP1 in the first sample(s) with a level of CD14, the level of TAGLN2, the level of IGFBP6, and the level of SEPP1 in the second sample(s), wherein a difference in the level CD14, the level of TAGLN2, the level of IGFBP6, and the level of SEPP1 in the first sample(s) as compared to the level of CD14, the level of TAGLN2, the level of IGFBP6, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of TAGLN2, the level of IGFBP6, and the level of SEPP1 in each of the aliquots; and selecting a member of the library of compounds which modulates the level and/or the activity of the CD14, the level and/or activity of TAGLN2, the level and/or activity of IGFBP6, and the level and/or activity of SEPP1 in an aliquot as compared to the level and/or activity of CD14, the level and/or activity of TAGLN2, the level and/or activity of IGFBP6, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of TAGLN2, the level and/or activity of IGFBP6, and the level and/or activity of SEPP1, thereby treating the subject.

In one aspect the present invention provides methods for determining whether a subject has active tuberculosis (TB). The methods include determining the level of IGFBP6, the level of PFN1, the level of VASN, and the level of PGLYRP2 in a sample(s) from the subject; comparing the level of IGFBP6, the level of PFN1, the level of VASN, and the level of PGLYRP2 in the subject sample(s) with a level of IGFBP6, a level of PFN1, a level of VASN, and a level of PGLYRP2 in a control sample(s), wherein a difference in the level of IGFBP6, a difference in the level of PFN1, a difference in the level of VASN, and a difference in the level of PGLYRP2 in the subject sample(s) as compared to the level of IGFBP6, the level of PFN1, the level of VASN, and the level of PGLYRP2 in the control sample(s) indicates that the subject has active TB.

In one aspect the present invention provides methods for monitoring the effectiveness of a treatment in a subject having active tuberculosis (TB). The methods include determining the level of IGFBP6, the level of PFN1, the level of VASN, and the level of PGLYRP2 in a first sample(s) from the subject prior to the initiation of the treatment; determining the level of IGFBP6, the level of PFN1, the level of VASN, and the level of PGLYRP2 in a second sample(s) from the subject after at least a portion of the treatment has been administered; comparing the level of IGFBP6, the level of PFN1, the level of VASN, and the level of PGLYRP2 in the first sample(s) with a level of IGFBP6, the level of PFN1, the level of VASN, and the level of PGLYRP2 in the second sample(s), wherein a difference in the level IGFBP6, the level of PFN1, the level of VASN, and the level of PGLYRP2 in the first sample(s) as compared to the level of IGFBP6, the level of PFN1, the level of VASN, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of IGFBP6, the level of PFN1, the level of VASN, and the level of PGLYRP2 in each of the aliquots; and selecting a member of the library of compounds which modulates the level and/or the activity of the IGFBP6, the level and/or activity of PFN1, the level and/or activity of VASN, and the level and/or activity of PGLYRP2 in an aliquot as compared to the level and/or activity of IGFBP6, the level and/or activity of PFN1, the level and/or activity of VASN, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of IGFBP6, the level and/or activity of PFN1, the level and/or activity of VASN, and the level and/or activity of PGLYRP2, thereby treating the subject.

In one aspect the present invention provides methods for determining whether a subject has active tuberculosis (TB). The methods include determining the level of CPN2, the level of PFN1, the level of VASN, and the level of PGLYRP2 in a sample(s) from the subject; comparing the level of CPN2, the level of PFN1, the level of VASN, and the level of PGLYRP2 in the subject sample(s) with a level of CPN2, a level of PFN1, a level of VASN, and a level of PGLYRP2 in a control sample(s), wherein a difference in the level of CPN2, a difference in the level of PFN1, a difference in the level of VASN, and a difference in the level of PGLYRP2 in the subject sample(s) as compared to the level of CPN2, the level of PFN1, the level of VASN, and the level of PGLYRP2 in the control sample(s) indicates that the subject has active TB.

In one aspect the present invention provides methods for monitoring the effectiveness of a treatment in a subject having active tuberculosis (TB). The methods include determining the level of CPN2, the level of PFN1, the level of VASN, and the level of PGLYRP2 in a first sample(s) from the subject prior to the initiation of the treatment; determining the level of CPN2, the level of PFN1, the level of VASN, and the level of PGLYRP2 in a second sample(s) from the subject after at least a portion of the treatment has been administered; comparing the level of CPN2, the level of PFN1, the level of VASN, and the level of PGLYRP2 in the first sample(s) with a level of CPN2, the level of PFN1, the level of VASN, and the level of PGLYRP2 in the second sample(s), wherein a difference in the level CPN2, the level of PFN1, the level of VASN, and the level of PGLYRP2 in the first sample(s) as compared to the level of CPN2, the level of PFN1, the level of VASN, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CPN2, the level of PFN1, the level of VASN, and the level of PGLYRP2 in each of the aliquots; and selecting a member of the library of compounds which modulates the level and/or the activity of the CPN2, the level and/or activity of PFN1, the level and/or activity of VASN, and the level and/or activity of PGLYRP2 in an aliquot as compared to the level and/or activity of CPN2, the level and/or activity of PFN1, the level and/or activity of VASN, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CPN2, the level and/or activity of PFN1, the level and/or activity of VASN, and the level and/or activity of PGLYRP2, thereby treating the subject.

In one aspect the present invention provides methods for determining whether a subject has active tuberculosis (TB). The methods include determining the level of CD14, the level of TAGLN2, the level of PGLYBP2, and the level of SEPP1 in a sample(s) from the subject; comparing the level of CD14, the level of TAGLN2, the level of PGLYBP2, and the level of SEPP1 in the subject sample(s) with a level of CD14, a level of TAGLN2, a level of PGLYBP2, and a level of SEPP1 in a control sample(s), wherein a difference in the level of CD14, a difference in the level of TAGLN2, a difference in the level of PGLYBP2, and a difference in the level of SEPP1 in the subject sample(s) as compared to the level of CD14, the level of TAGLN2, the level of PGLYBP2, and the level of SEPP1 in the control sample(s) indicates that the subject has active TB.

In one aspect the present invention provides methods for monitoring the effectiveness of a treatment in a subject having active tuberculosis (TB). The methods include determining the level of CD14, the level of TAGLN2, the level of PGLYBP2, and the level of SEPP1 in a first sample(s) from the subject prior to the initiation of the treatment; determining the level of CD14, the level of TAGLN2, the level of PGLYBP2, and the level of SEPP1 in a second sample(s) from the subject after at least a portion of the treatment has been administered; comparing the level of CD14, the level of TAGLN2, the level of PGLYBP2, and the level of SEPP1 in the first sample(s) with a level of CD14, the level of TAGLN2, the level of PGLYBP2, and the level of SEPP1 in the second sample(s), wherein a difference in the level CD14, the level of TAGLN2, the level of PGLYBP2, and the level of SEPP1 in the first sample(s) as compared to the level of CD14, the level of TAGLN2, the level of PGLYBP2, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of TAGLN2, the level of PGLYBP2, and the level of SEPP1 in each of the aliquots; and selecting a member of the library of compounds which modulates the level and/or the activity of the CD14, the level and/or activity of TAGLN2, the level and/or activity of PGLYBP2, and the level and/or activity of SEPP1 in an aliquot as compared to the level and/or activity of CD14, the level and/or activity of TAGLN2, the level and/or activity of PGLYBP2, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of TAGLN2, the level and/or activity of PGLYBP2, and the level and/or activity of SEPP1, thereby treating the subject.

In one aspect the present invention provides methods for determining whether a subject has active tuberculosis (TB). The methods include determining the level of CPN2, the level of PFN1, the level of IGFBP6, and the level of PGLYRP2 in a sample(s) from the subject; comparing the level of CPN2, the level of PFN1, the level of IGFBP6, and the level of PGLYRP2 in the subject sample(s) with a level of CPN2, a level of PFN1, a level of IGFBP6, and a level of PGLYRP2 in a control sample(s), wherein a difference in the level of CPN2, a difference in the level of PFN1, a difference in the level of IGFBP6, and a difference in the level of PGLYRP2 in the subject sample(s) as compared to the level of CPN2, the level of PFN1, the level of IGFBP6, and the level of PGLYRP2 in the control sample(s) indicates that the subject has active TB.

In one aspect the present invention provides methods for monitoring the effectiveness of a treatment in a subject having active tuberculosis (TB). The methods include determining the level of CPN2, the level of PFN1, the level of IGFBP6, and the level of PGLYRP2 in a first sample(s) from the subject prior to the initiation of the treatment; determining the level of CPN2, the level of PFN1, the level of IGFBP6, and the level of PGLYRP2 in a second sample(s) from the subject after at least a portion of the treatment has been administered; comparing the level of CPN2, the level of PFN1, the level of IGFBP6, and the level of PGLYRP2 in the first sample(s) with a level of CPN2, the level of PFN1, the level of IGFBP6, and the level of PGLYRP2 in the second sample(s), wherein a difference in the level CPN2, the level of PFN1, the level of IGFBP6, and the level of PGLYRP2 in the first sample(s) as compared to the level of CPN2, the level of PFN1, the level of IGFBP6, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CPN2, the level of PFN1, the level of IGFBP6, and the level of PGLYRP2 in each of the aliquots; and selecting a member of the library of compounds which modulates the level and/or the activity of the CPN2, the level and/or activity of PFN1, the level and/or activity of IGFBP6, and the level and/or activity of PGLYRP2 in an aliquot as compared to the level and/or activity of CPN2, the level and/or activity of PFN1, the level and/or activity of IGFBP6, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CPN2, the level and/or activity of PFN1, the level and/or activity of IGFBP6, and the level and/or activity of PGLYRP2, thereby treating the subject.

In one aspect the present invention provides methods for determining whether a subject has active tuberculosis (TB). The methods include determining the level of CD14, the level of TAGLN2, the level of IGFBP6, and the level of PFN1 in a sample(s) from the subject; comparing the level of CD14, the level of TAGLN2, the level of IGFBP6, and the level of PFN1 in the subject sample(s) with a level of CD14, a level of TAGLN2, a level of IGFBP6, and a level of PFN1 in a control sample(s), wherein a difference in the level of CD14, a difference in the level of TAGLN2, a difference in the level of IGFBP6, and a difference in the level of PFN1 in the subject sample(s) as compared to the level of CD14, the level of TAGLN2, the level of IGFBP6, and the level of PFN1 in the control sample(s) indicates that the subject has active TB.

In one aspect the present invention provides methods for monitoring the effectiveness of a treatment in a subject having active tuberculosis (TB). The methods include determining the level of CD14, the level of TAGLN2, the level of IGFBP6, and the level of PFN1 in a first sample(s) from the subject prior to the initiation of the treatment; determining the level of CD14, the level of TAGLN2, the level of IGFBP6, and the level of PFN1 in a second sample(s) from the subject after at least a portion of the treatment has been administered; comparing the level of CD14, the level of TAGLN2, the level of IGFBP6, and the level of PFN1 in the first sample(s) with a level of CD14, the level of TAGLN2, the level of IGFBP6, and the level of PFN1 in the second sample(s), wherein a difference in the level CD14, the level of TAGLN2, the level of IGFBP6, and the level of PFN1 in the first sample(s) as compared to the level of CD14, the level of TAGLN2, the level of IGFBP6, and the level of PFN1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of TAGLN2, the level of IGFBP6, and the level of PFN1 in each of the aliquots; and selecting a member of the library of compounds which modulates the level and/or the activity of the CD14, the level and/or activity of TAGLN2, the level and/or activity of IGFBP6, and the level and/or activity of PFN1 in an aliquot as compared to the level and/or activity of CD14, the level and/or activity of TAGLN2, the level and/or activity of IGFBP6, and the level and/or activity of PFN1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of TAGLN2, the level and/or activity of IGFBP6, and the level and/or activity of PFN1, thereby treating the subject.

In one aspect the present invention provides methods for determining whether a subject has active tuberculosis (TB). The methods include determining the level of CPN2, the level of PFN1, the level of TAGLN2, and the level of PGLYRP2 in a sample(s) from the subject; comparing the level of CPN2, the level of PFN1, the level of TAGLN2, and the level of PGLYRP2 in the subject sample(s) with a level of CPN2, a level of PFN1, a level of TAGLN2, and a level of PGLYRP2 in a control sample(s), wherein a difference in the level of CPN2, a difference in the level of PFN1, a difference in the level of TAGLN2, and a difference in the level of PGLYRP2 in the subject sample(s) as compared to the level of CPN2, the level of PFN1, the level of TAGLN2, and the level of PGLYRP2 in the control sample(s) indicates that the subject has active TB.

In one aspect the present invention provides methods for monitoring the effectiveness of a treatment in a subject having active tuberculosis (TB). The methods include determining the level of CPN2, the level of PFN1, the level of TAGLN2, and the level of PGLYRP2 in a first sample(s) from the subject prior to the initiation of the treatment; determining the level of CPN2, the level of PFN1, the level of TAGLN2, and the level of PGLYRP2 in a second sample(s) from the subject after at least a portion of the treatment has been administered; comparing the level of CPN2, the level of PFN1, the level of TAGLN2, and the level of PGLYRP2 in the first sample(s) with a level of CPN2, the level of PFN1, the level of TAGLN2, and the level of PGLYRP2 in the second sample(s), wherein a difference in the level CPN2, the level of PFN1, the level of TAGLN2, and the level of PGLYRP2 in the first sample(s) as compared to the level of CPN2, the level of PFN1, the level of TAGLN2, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CPN2, the level of PFN1, the level of TAGLN2, and the level of PGLYRP2 in each of the aliquots; and selecting a member of the library of compounds which modulates the level and/or the activity of the CPN2, the level and/or activity of PFN1, the level and/or activity of TAGLN2, and the level and/or activity of PGLYRP2 in an aliquot as compared to the level and/or activity of CPN2, the level and/or activity of PFN1, the level and/or activity of TAGLN2, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CPN2, the level and/or activity of PFN1, the level and/or activity of TAGLN2, and the level and/or activity of PGLYRP2, thereby treating the subject.

In one aspect the present invention provides methods for determining whether a subject has active tuberculosis (TB). The methods include determining the level of CD14, the level of SEPP1, the level of PFN1, and the level of VASN in a sample(s) from the subject; comparing the level of CD14, the level of SEPP1, the level of PFN1, and the level of VASN in the subject sample(s) with a level of CD14, the level of SEPP1, a level of PFN1, and a level of VASN in a control sample(s), wherein a difference in the level of CD14, a difference in the level of SEPP1, a difference in the level of PFN1, and a difference in the level of VASN in the subject sample(s) as compared to the level of CD14, the level of SEPP1, the level of PFN1, and the level of VASN in the control sample(s) indicates that the subject has active TB.

In one aspect the present invention provides methods for monitoring the effectiveness of a treatment in a subject having active tuberculosis (TB). The methods include determining the level of CD14, the level of SEPP1, the level of PFN1, and the level of VASN in a first sample(s) from the subject prior to the initiation of the treatment; determining the level of CD14, the level of SEPP1, the level of PFN1, and the level of VASN in a second sample(s) from the subject after at least a portion of the treatment has been administered; comparing the level of CD14, the level of SEPP1, the level of PFN1, and the level of VASN in the first sample(s) with a level of CD14, the level of SEPP1, the level of PFN1, and the level of VASN in the second sample(s), wherein a difference in the level CD14, the level of SEPP1, the level of PFN1, and the level of VASN in the first sample(s) as compared to the level of CD14, the level of SEPP1, the level of PFN1, and the level of VASN in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of SEPP1, the level of PFN1, and the level of VASN in each of the aliquots; and selecting a member of the library of compounds which modulates the level and/or the activity of the CD14, the level and/or activity of SEPP1, the level and/or activity of PFN1, and the level and/or activity of VASN in an aliquot as compared to the level and/or activity of CD14, the level and/or activity of SEPP1, the level and/or activity of PFN1, and the level and/or activity of VASN in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of SEPP1, the level and/or activity of PFN1, and the level and/or activity of VASN, thereby treating the subject.

In one aspect the present invention provides methods for determining whether a subject has active tuberculosis (TB). The methods include determining the level of CD14, the level of SEPP1, the level of TAGLN2, and the level of VASN in a sample(s) from the subject; comparing the level of CD14, the level of SEPP1, the level of TAGLN2, and the level of VASN in the subject sample(s) with a level of CD14, the level of SEPP1, a level of TAGLN2, and a level of VASN in a control sample(s), wherein a difference in the level of CD14, a difference in the level of SEPP1, a difference in the level of TAGLN2, and a difference in the level of VASN in the subject sample(s) as compared to the level of CD14, the level of SEPP1, the level of TAGLN2, and the level of VASN in the control sample(s) indicates that the subject has active TB.

In one aspect the present invention provides methods for monitoring the effectiveness of a treatment in a subject having active tuberculosis (TB). The methods include determining the level of CD14, the level of SEPP1, the level of TAGLN2, and the level of VASN in a first sample(s) from the subject prior to the initiation of the treatment; determining the level of CD14, the level of SEPP1, the level of TAGLN2, and the level of VASN in a second sample(s) from the subject after at least a portion of the treatment has been administered; comparing the level of CD14, the level of SEPP1, the level of TAGLN2, and the level of VASN in the first sample(s) with a level of CD14, the level of SEPP1, the level of TAGLN2, and the level of VASN in the second sample(s), wherein a difference in the level CD14, the level of SEPP1, the level of TAGLN2, and the level of VASN in the first sample(s) as compared to the level of CD14, the level of SEPP1, the level of TAGLN2, and the level of VASN in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of SEPP1, the level of TAGLN2, and the level of VASN in each of the aliquots; and selecting a member of the library of compounds which modulates the level and/or the activity of the CD14, the level and/or activity of SEPP1, the level and/or activity of TAGLN2, and the level and/or activity of VASN in an aliquot as compared to the level and/or activity of CD14, the level and/or activity of SEPP1, the level and/or activity of TAGLN2, and the level and/or activity of VASN in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of SEPP1, the level and/or activity of TAGLN2, and the level and/or activity of VASN, thereby treating the subject.

In one aspect the present invention provides methods for determining whether a subject has active tuberculosis (TB). The methods include determining the level of CPN2, the level of TAGLN2, the level of IGFBP6, and the level of PGLYRP2 in a sample(s) from the subject; comparing the level of CPN2, the level of TAGLN2, the level of IGFBP6, and the level of PGLYRP2 in the subject sample(s) with a level of CPN2, a level of TAGLN2, a level of IGFBP6, and a level of PGLYRP2 in a control sample(s), wherein a difference in the level of CPN2, a difference in the level of TAGLN2, a difference in the level of IGFBP6, and a difference in the level of PGLYRP2 in the subject sample(s) as compared to the level of CPN2, the level of TAGLN2, the level of IGFBP6, and the level of PGLYRP2 in the control sample(s) indicates that the subject has active TB.

In one aspect the present invention provides methods for monitoring the effectiveness of a treatment in a subject having active tuberculosis (TB). The methods include determining the level of CPN2, the level of TAGLN2, the level of IGFBP6, and the level of PGLYRP2 in a first sample(s) from the subject prior to the initiation of the treatment; determining the level of CPN2, the level of TAGLN2, the level of IGFBP6, and the level of PGLYRP2 in a second sample(s) from the subject after at least a portion of the treatment has been administered; comparing the level of CPN2, the level of TAGLN2, the level of IGFBP6, and the level of PGLYRP2 in the first sample(s) with a level of CPN2, the level of TAGLN2, the level of IGFBP6, and the level of PGLYRP2 in the second sample(s), wherein a difference in the level CPN2, the level of TAGLN2, the level of IGFBP6, and the level of PGLYRP2 in the first sample(s) as compared to the level of CPN2, the level of TAGLN2, the level of IGFBP6, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CPN2, the level of TAGLN2, the level of IGFBP6, and the level of PGLYRP2 in each of the aliquots; and selecting a member of the library of compounds which modulates the level and/or the activity of the CPN2, the level and/or activity of TAGLN2, the level and/or activity of IGFBP6, and the level and/or activity of PGLYRP2 in an aliquot as compared to the level and/or activity of CPN2, the level and/or activity of TAGLN2, the level and/or activity of IGFBP6, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CPN2, the level and/or activity of TAGLN2, the level and/or activity of IGFBP6, and the level and/or activity of PGLYRP2, thereby treating the subject.

In one aspect the present invention provides methods for determining whether a subject has active tuberculosis (TB). The methods include determining the level of TAGLN2, the level of PFN1, the level of VASN, and the level of PGLYRP2 in a sample(s) from the subject; comparing the level of TAGLN2, the level of PFN1, the level of VASN, and the level of PGLYRP2 in the subject sample(s) with a level of TAGLN2, a level of PFN1, a level of VASN, and a level of PGLYRP2 in a control sample(s), wherein a difference in the level of TAGLN2, a difference in the level of PFN1, a difference in the level of VASN, and a difference in the level of PGLYRP2 in the subject sample(s) as compared to the level of TAGLN2, the level of PFN1, the level of VASN, and the level of PGLYRP2 in the control sample(s) indicates that the subject has active TB.

In one aspect the present invention provides methods for monitoring the effectiveness of a treatment in a subject having active tuberculosis (TB). The methods include determining the level of TAGLN2, the level of PFN1, the level of VASN, and the level of PGLYRP2 in a first sample(s) from the subject prior to the initiation of the treatment; determining the level of TAGLN2, the level of PFN1, the level of VASN, and the level of PGLYRP2 in a second sample(s) from the subject after at least a portion of the treatment has been administered; comparing the level of TAGLN2, the level of PFN1, the level of VASN, and the level of PGLYRP2 in the first sample(s) with a level of TAGLN2, the level of PFN1, the level of VASN, and the level of PGLYRP2 in the second sample(s), wherein a difference in the level TAGLN2, the level of PFN1, the level of VASN, and the level of PGLYRP2 in the first sample(s) as compared to the level of TAGLN2, the level of PFN1, the level of VASN, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of TAGLN2, the level of PFN1, the level of VASN, and the level of PGLYRP2 in each of the aliquots; and selecting a member of the library of compounds which modulates the level and/or the activity of the TAGLN2, the level and/or activity of PFN1, the level and/or activity of VASN, and the level and/or activity of PGLYRP2 in an aliquot as compared to the level and/or activity of TAGLN2, the level and/or activity of PFN1, the level and/or activity of VASN, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of TAGLN2, the level and/or activity of PFN1, the level and/or activity of VASN, and the level and/or activity of PGLYRP2, thereby treating the subject.

In one aspect the present invention provides methods for determining whether a subject has active tuberculosis (TB). The methods include determining the level of SEPP1, the level of PFN1, the level of VASN, and the level of PGLYRP2 in a sample(s) from the subject; comparing the level of SEPP1, the level of PFN1, the level of VASN, and the level of PGLYRP2 in the subject sample(s) with a level of SEPP1, a level of PFN1, a level of VASN, and a level of PGLYRP2 in a control sample(s), wherein a difference in the level of SEPP1, a difference in the level of PFN1, a difference in the level of VASN, and a difference in the level of PGLYRP2 in the subject sample(s) as compared to the level of SEPP1, the level of PFN1, the level of VASN, and the level of PGLYRP2 in the control sample(s) indicates that the subject has active TB.

In one aspect the present invention provides methods for monitoring the effectiveness of a treatment in a subject having active tuberculosis (TB). The methods include determining the level of SEPP1, the level of PFN1, the level of VASN, and the level of PGLYRP2 in a first sample(s) from the subject prior to the initiation of the treatment; determining the level of SEPP1, the level of PFN1, the level of VASN, and the level of PGLYRP2 in a second sample(s) from the subject after at least a portion of the treatment has been administered; comparing the level of SEPP1, the level of PFN1, the level of VASN, and the level of PGLYRP2 in the first sample(s) with a level of SEPP1, the level of PFN1, the level of VASN, and the level of PGLYRP2 in the second sample(s), wherein a difference in the level SEPP1, the level of PFN1, the level of VASN, and the level of PGLYRP2 in the first sample(s) as compared to the level of SEPP1, the level of PFN1, the level of VASN, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of SEPP1, the level of PFN1, the level of VASN, and the level of PGLYRP2 in each of the aliquots; and selecting a member of the library of compounds which modulates the level and/or the activity of the SEPP1, the level and/or activity of PFN1, the level and/or activity of VASN, and the level and/or activity of PGLYRP2 in an aliquot as compared to the level and/or activity of SEPP1, the level and/or activity of PFN1, the level and/or activity of VASN, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of SEPP1, the level and/or activity of PFN1, the level and/or activity of VASN, and the level and/or activity of PGLYRP2, thereby treating the subject.

In one aspect the present invention provides methods for determining whether a subject has active tuberculosis (TB). The methods include determining the level of CD14, the level of CPN2, the level of SEPP1, and the level of PGLYRP2 in a sample(s) from the subject; comparing the level of CD14, the level of CPN2, the level of SEPP1, and the level of PGLYRP2 in the subject sample(s) with a level of CD14, a level of CPN2, a level of SEPP1, and a level of PGLYRP2 in a control sample(s), wherein a difference in the level of CD14, a difference in the level of CPN2, a difference in the level of SEPP1, and a difference in the level of PGLYRP2 in the subject sample(s) as compared to the level of CD14, the level of CPN2, the level of SEPP1, and the level of PGLYRP2 in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of SEPP1, and the level of PGLYRP2 in a first sample(s) from the subject prior to the initiation of the treatment; determining the level of CD14, the level of CPN2, the level of SEPP1, and the level of PGLYRP2 in a second sample(s) from the subject after at least a portion of the treatment has been administered; comparing the level of CD14, the level of CPN2, the level of SEPP1, and the level of PGLYRP2 in the first sample(s) with a level of CD14, the level of CPN2, the level of SEPP1, and the level of PGLYRP2 in the second sample(s), wherein a difference in the level CD14, the level of CPN2, the level of SEPP1, and the level of PGLYRP2 in the first sample(s) as compared to the level of CD14, the level of CPN2, the level of SEPP1, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of SEPP1, and the level of PGLYRP2 in each of the aliquots; and selecting a member of the library of compounds which modulates the level and/or the activity of the CD14, the level and/or activity of CPN2, the level and/or activity of SEPP1, and the level and/or activity of PGLYRP2 in an aliquot as compared to the level and/or activity of CD14, the level and/or activity of CPN2, the level and/or activity of SEPP1, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of SEPP1, and the level and/or activity of PGLYRP2, thereby treating the subject.

In one aspect the present invention provides methods for determining whether a subject has active tuberculosis (TB). The methods include determining the level of CD14, the level of CPN2, the level of VASN, and the level of PGLYRP2 in a sample(s) from the subject; comparing the level of CD14, the level of CPN2, the level of VASN, and the level of PGLYRP2 in the subject sample(s) with a level of CD14, a level of CPN2, a level of VASN, and a level of PGLYRP2 in a control sample(s), wherein a difference in the level of CD14, a difference in the level of CPN2, a difference in the level of VASN, and a difference in the level of PGLYRP2 in the subject sample(s) as compared to the level of CD14, the level of CPN2, the level of VASN, and the level of PGLYRP2 in the control sample(s) indicates that the subject has active TB.

In one aspect the present invention provides methods for monitoring the effectiveness of a treatment in a subject having active tuberculosis (TB). The methods include determining the level of CD14, the level of CPN2, the level of VASN, and the level of PGLYRP2 in a first sample(s) from the subject prior to the initiation of the treatment; determining the level of CD14, the level of CPN2, the level of VASN, and the level of PGLYRP2 in a second sample(s) from the subject after at least a portion of the treatment has been administered; comparing the level of CD14, the level of CPN2, the level of VASN, and the level of PGLYRP2 in the first sample(s) with a level of CD14, the level of CPN2, the level of VASN, and the level of PGLYRP2 in the second sample(s), wherein a difference in the level CD14, the level of CPN2, the level of VASN, and the level of PGLYRP2 in the first sample(s) as compared to the level of CD14, the level of CPN2, the level of VASN, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of CD14, the level of CPN2, the level of VASN, and the level of PGLYRP2 in each of the aliquots; and selecting a member of the library of compounds which modulates the level and/or the activity of the CD14, the level and/or activity of CPN2, the level and/or activity of VASN, and the level and/or activity of PGLYRP2 in an aliquot as compared to the level and/or activity of CD14, the level and/or activity of CPN2, the level and/or activity of VASN, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of CD14, the level and/or activity of CPN2, the level and/or activity of VASN, and the level and/or activity of PGLYRP2, thereby treating the subject.

In one aspect the present invention provides methods for determining whether a subject has active tuberculosis (TB). The methods include determining the level of LCP1, the level of VASN, the level of PFN1, and the level of IGFBP6 in a sample(s) from the subject; comparing the level of LCP1, the level of VASN, the level of PFN1, and the level of IGFBP6 in the subject sample(s) with a level of LCP1, a level of VASN, a level of PFN1, and a level of IGFBP6 in a control sample(s), wherein a difference in the level of LCP1, a difference in the level of VASN, a difference in the level of PFN1, and a difference in the level of IGFBP6 in the subject sample(s) as compared to the level of LCP1, the level of VASN, the level of PFN1, and the level of IGFBP6 in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of PFN1, and the level of IGFBP6 in a first sample(s) from the subject prior to the initiation of the treatment; determining the level of LCP1, the level of VASN, the level of PFN1, and the level of IGFBP6 in a second sample(s) from the subject after at least a portion of the treatment has been administered; comparing the level of LCP1, the level of VASN, the level of PFN1, and the level of IGFBP6 in the first sample(s) with a level of LCP1, the level of VASN, the level of PFN1, and the level of IGFBP6 in the second sample(s), wherein a difference in the level LCP1, the level of VASN, the level of PFN1, and the level of IGFBP6 in the first sample(s) as compared to the level of LCP1, the level of VASN, the level of PFN1, and the level of IGFBP6 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level of VASN, the level of PFN1, and the level of IGFBP6 in each of the aliquots; and selecting a member of the library of compounds which modulates the level and/or the activity of the LCP1, the level and/or activity of VASN, the level and/or activity of PFN1, and the level and/or activity of IGFBP6 in an aliquot as compared to the level and/or activity of LCP1, the level and/or activity of VASN, the level and/or activity of PFN1, and the level and/or activity of IGFBP6 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, the level and/or activity of PFN1, and the level and/or activity of IGFBP6, thereby treating the subject.

In one aspect the present invention provides methods for determining whether a subject has active tuberculosis (TB). The methods include determining the level of LCP1, the level of VASN, the level of PFN1, and the level of LRG1 in a sample(s) from the subject; comparing the level of LCP1, the level of VASN, the level of PFN1, and the level of LRG1 in the subject sample(s) with a level of LCP1, a level of VASN, a level of PFN1, and a level of LRG1 in a control sample(s), wherein a difference in the level of LCP1, a difference in the level of VASN, a difference in the level of PFN1, and a difference in the level of LRG1 in the subject sample(s) as compared to the level of LCP1, the level of VASN, the level of PFN1, and the level of LRG1 in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of PFN1, and the level of LRG1 in a first sample(s) from the subject prior to the initiation of the treatment; determining the level of LCP1, the level of VASN, the level of PFN1, and the level of LRG1 in a second sample(s) from the subject after at least a portion of the treatment has been administered; comparing the level of LCP1, the level of VASN, the level of PFN1, and the level of LRG1 in the first sample(s) with a level of LCP1, the level of VASN, the level of PFN1, and the level of LRG1 in the second sample(s), wherein a difference in the level of LCP1, the level of VASN, the level of PFN1, and the level of LRG1 in the first sample(s) as compared to the level of LCP1, the level of VASN, the level of PFN1, and the level of LRG1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level of VASN, the level of PFN1, and the level of LRG1 of the invention in each of the aliquots; and selecting a member of the library of compounds which modulates the level and/or the activity of LCP1, the level of VASN, the level of PFN1, and the level of LRG1 in an aliquot as compared to the level and/or activity of LCP1, the level of VASN, the level of PFN1, and the level of LRG1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level of VASN, the level of PFN1, and the level of LRG1, thereby treating the subject.

In one aspect the present invention provides methods for determining whether a subject has active tuberculosis (TB). The methods include determining the level of LCP1, the level of VASN, the level of PFN1, and the level of PGLYRP2 in a sample(s) from the subject; comparing the level of LCP1, the level of VASN, the level of PFN1, and the level of PGLYRP2 in the subject sample(s) with a level of LCP1, a level of VASN, a level of PFN1, and a level of PGLYRP2 in a control sample(s), wherein a difference in the level of LCP1, a difference in the level of VASN, a difference in the level of PFN1, and a difference in the level of PGLYRP2 in the subject sample(s) as compared to the level of LCP1, the level of VASN, the level of PFN1, and the level of PGLYRP2 in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of PFN1, and the level of PGLYRP2 in a first sample(s) from the subject prior to the initiation of the treatment; determining the level of LCP1, the level of VASN, the level of PFN1, and the level of PGLYRP2 in a second sample(s) from the subject after at least a portion of the treatment has been administered; comparing the level of LCP1, the level of VASN, the level of PFN1, and the level of PGLYRP2 in the first sample(s) with a level of LCP1, the level of VASN, the level of PFN1, and the level of PGLYRP2 in the second sample(s), wherein a difference in the level of LCP1, the level of VASN, the level of PFN1, and the level of PGLYRP2 in the first sample(s) as compared to the level of LCP1, the level of VASN, the level of PFN1, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, the level and/or activity of PFN1, and the level and/or activity of PGLYRP2 in each of the aliquots; and selecting a member of the library of compounds which modulates the level and/or the activity of LCP1, the level and/or activity of VASN, the level and/or activity of PFN1, and the level and/or activity of PGLYRP2 in an aliquot as compared to the level and/or activity of LCP1, the level and/or activity of VASN, the level and/or activity of PFN1, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, the level and/or activity of PFN1, and the level and/or activity of PGLYRP2, thereby treating the subject.

In one aspect the present invention provides methods for determining whether a subject has active tuberculosis (TB). The methods include determining the level of LCP1, the level of VASN, the level of PFN1, and the level of APOA4 in a sample(s) from the subject; comparing the level of LCP1, the level of VASN, the level of PFN1, and the level of APOA4 in the subject sample(s) with a level of LCP1, a level of VASN, a level of PFN1, and a level of APOA4 in a control sample(s), wherein a difference in the level of LCP1, a difference in the level of VASN, a difference in the level of PFN1, and a difference in the level of APOA4 in the subject sample(s) as compared to the level of LCP1, the level of VASN, the level of PFN1, and the level of APOA4 in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of PFN1, and the level of APOA4 in a first sample(s) from the subject prior to the initiation of the treatment; determining the level of LCP1, the level of VASN, the level of PFN1, and the level of APOA4 in a second sample(s) from the subject after at least a portion of the treatment has been administered; comparing the level of LCP1, the level of VASN, the level of PFN1, and the level of APOA4 in the first sample(s) with a level of LCP1, the level of VASN, the level of PFN1, and the level of APOA4 in the second sample(s), wherein a difference in the level of LCP1, the level of VASN, the level of PFN1, and the level of APOA4 in the first sample(s) as compared to the level of LCP1, the level of VASN, the level of PFN1, and the level of APOA4 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, the level and/or activity of PFN1, and the level and/or activity of APOA4 in each of the aliquots; and selecting a member of the library of compounds which modulates the level and/or the activity of LCP1, the level and/or activity of VASN, the level and/or activity of PFN1, and the level and/or activity of APOA4 in an aliquot as compared to the level and/or activity of LCP1, the level and/or activity of VASN, the level and/or activity of PFN1, and the level and/or activity of APOA4 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, the level and/or activity of PFN1, and the level and/or activity of APOA4, thereby treating the subject.

In one aspect the present invention provides methods for determining whether a subject has active tuberculosis (TB). The methods include determining the level of LCP1, the level of VASN, the level of PFN1, and the level of BCHE in a sample(s) from the subject; comparing the level of LCP1, the level of VASN, the level of PFN1, and the level of BCHE in the subject sample(s) with a level of LCP1, a level of VASN, a level of PFN1, and a level of BCHE in a control sample(s), wherein a difference in the level of LCP1, a difference in the level of VASN, a difference in the level of PFN1, and a difference in the level of BCHE in the subject sample(s) as compared to the level of LCP1, the level of VASN, the level of PFN1, and the level of BCHE in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of PFN1, and the level of BCHE in a first sample(s) from the subject prior to the initiation of the treatment; determining the level of LCP1, the level of VASN, the level of PFN1, and the level of BCHE in a second sample(s) from the subject after at least a portion of the treatment has been administered; comparing the level of LCP1, the level of VASN, the level of PFN1, and the level of BCHE in the first sample(s) with a level of LCP1, the level of VASN, the level of PFN1, and the level of BCHE in the second sample(s), wherein a difference in the level of LCP1, the level of VASN, the level of PFN1, and the level of BCHE in the first sample(s) as compared to the level of LCP1, the level of VASN, the level of PFN1, and the level of BCHE in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, the level and/or activity of PFN1, and the level and/or activity of BCHE in each of the aliquots; and selecting a member of the library of compounds which modulates the level and/or the activity of LCP1, the level and/or activity of VASN, the level and/or activity of PFN1, and the level and/or activity of BCHE in an aliquot as compared to the level and/or activity of LCP1, the level and/or activity of VASN, the level and/or activity of PFN1, and the level and/or activity of BCHE of the invention in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, the level and/or activity of PFN1, and the level and/or activity of BCHE, thereby treating the subject.

In one aspect the present invention provides methods for determining whether a subject has active tuberculosis (TB). The methods include determining the level of LCP1, the level of VASN, the level of PFN1, and the level of PI16 in a sample(s) from the subject; comparing the level of LCP1, the level of VASN, the level of PFN1, and the level of PI16 in the subject sample(s) with a level of LCP1, a level of VASN, a level of PFN1, and a level of PI16 in a control sample(s), wherein a difference in the level of LCP1, a difference in the level of VASN, a difference in the level of PFN1, and a difference in the level of PI16 in the subject sample(s) as compared to the level of LCP1, the level of VASN, the level of PFN1, and the level of PI16 in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of PFN1, and the level of PI16 in a first sample(s) from the subject prior to the initiation of the treatment; determining the level of LCP1, the level of VASN, the level of PFN1, and the level of PI16 in a second sample(s) from the subject after at least a portion of the treatment has been administered; comparing the level of LCP1, the level of VASN, the level of PFN1, and the level of PI16 in the first sample(s) with a level of LCP1, the level of VASN, the level of PFN1, and the level of PI16 in the second sample(s), wherein a difference in the level of LCP1, the level of VASN, the level of PFN1, and the level of PI16 in the first sample(s) as compared to the level of LCP1, the level of VASN, the level of PFN1, and the level of PI16 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, the level and/or activity of PFN1, and the level and/or activity of PI16 in each of the aliquots; and selecting a member of the library of compounds which modulates the level and/or the activity of LCP1, the level and/or activity of VASN, the level and/or activity of PFN1, and the level and/or activity of PI16 in an aliquot as compared to the level and/or activity of LCP1, the level and/or activity of VASN, the level and/or activity of PFN1, and the level and/or activity of PI16 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, the level and/or activity of PFN1, and the level and/or activity of PI16, thereby treating the subject.

In one aspect the present invention provides methods for determining whether a subject has active tuberculosis (TB). The methods include determining the level of LCP1, the level of VASN, the level of PFN1, and the level of SEPP1 in a sample(s) from the subject; comparing the level of LCP1, the level of VASN, the level of PFN1, and the level of SEPP1 in the subject sample(s) with a level of LCP1, a level of VASN, a level of PFN1, and a level of SEPP1 in a control sample(s), wherein a difference in the level of LCP1, a difference in the level of VASN, a difference in the level of PFN1, and a difference in the level of SEPP1 in the subject sample(s) as compared to the level of LCP1, the level of VASN, the level of PFN1, and the level of SEPP1 in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of PFN1, and the level of SEPP1 in a first sample(s) from the subject prior to the initiation of the treatment; determining the level of LCP1, the level of VASN, the level of PFN1, and the level of SEPP1 in a second sample(s) from the subject after at least a portion of the treatment has been administered; comparing the level of LCP1, the level of VASN, the level of PFN1, and the level of SEPP1 in the first sample(s) with a level of LCP1, the level of VASN, the level of PFN1, and the level of SEPP1 in the second sample(s), wherein a difference in the level of LCP1, the level of VASN, the level of PFN1, and the level of SEPP1 in the first sample(s) as compared to the level of LCP1, the level of VASN, the level of PFN1, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, the level and/or activity of PFN1, and the level and/or activity of SEPP1 in each of the aliquots; and selecting a member of the library of compounds which modulates the level and/or the activity of LCP1, the level and/or activity of VASN, the level and/or activity of PFN1, and the level and/or activity of SEPP1 in an aliquot as compared to the level and/or activity of LCP1, the level and/or activity of VASN, the level and/or activity of PFN1, and the level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, the level and/or activity of PFN1, and the level and/or activity of SEPP1, thereby treating the subject.

In one aspect the present invention provides methods for determining whether a subject has active tuberculosis (TB). The methods include determining the level of LCP1, the level of VASN, the level of PFN1, and the level of APOA1 in a sample(s) from the subject; comparing the level of LCP1, the level of VASN, the level of PFN1, and the level of APOA1 in the subject sample(s) with a level of LCP1, a level of VASN, a level of PFN1, and a level of APOA1 in a control sample(s), wherein a difference in the level of LCP1, a difference in the level of VASN, a difference in the level of PFN1, and a difference in the level of APOA1 in the subject sample(s) as compared to the level of LCP1, the level of VASN, the level of PFN1, and the level of APOA1 in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of PFN1, and the level of APOA1 in a first sample(s) from the subject prior to the initiation of the treatment; determining the level of LCP1, the level of VASN, the level of PFN1, and the level of APOA1 in a second sample(s) from the subject after at least a portion of the treatment has been administered; comparing the level of LCP1, the level of VASN, the level of PFN1, and the level of APOA1 in the first sample(s) with a level of LCP1, the level of VASN, the level of PFN1, and the level of APOA1 in the second sample(s), wherein a difference in the level of LCP1, the level of VASN, the level of PFN1, and the level of APOA1 in the first sample(s) as compared to the level of LCP1, the level of VASN, the level of PFN1, and the level of APOA1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, the level and/or activity of PFN1, and the level and/or activity of APOA1 in each of the aliquots; and selecting a member of the library of compounds which modulates the level and/or the activity of LCP1, the level and/or activity of VASN, the level and/or activity of PFN1, and the level and/or activity of APOA1 in an aliquot as compared to the level and/or activity of LCP1, the level and/or activity of VASN, the level and/or activity of PFN1, and the level and/or activity of APOA1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, the level and/or activity of PFN1, and the level and/or activity of APOA1, thereby treating the subject.

In one aspect the present invention provides methods for determining whether a subject has active tuberculosis (TB). The methods include determining the level of LCP1, the level of VASN, the level of PFN1, and the level of IGFALS in a sample(s) from the subject; comparing the level of LCP1, the level of VASN, the level of PFN1, and the level of IGFALS in the subject sample(s) with a level of LCP1, a level of VASN, a level of PFN1, and a level of IGFALS in a control sample(s), wherein a difference in the level of LCP1, a difference in the level of VASN, a difference in the level of PFN1, and a difference in the level of IGFALS in the subject sample(s) as compared to the level of LCP1, the level of VASN, the level of PFN1, and the level of IGFALS in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of PFN1, and the level of IGFALS in a first sample(s) from the subject prior to the initiation of the treatment; determining the level of LCP1, the level of VASN, the level of PFN1, and the level of IGFALS in a second sample(s) from the subject after at least a portion of the treatment has been administered; comparing the level of LCP1, the level of VASN, the level of PFN1, and the level of IGFALS in the first sample(s) with a level of LCP1, the level of VASN, the level of PFN1, and the level of IGFALS in the second sample(s), wherein a difference in the level of LCP1, the level of VASN, the level of PFN1, and the level of IGFALS in the first sample(s) as compared to the level of LCP1, the level of VASN, the level of PFN1, and the level of IGFALS in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, the level and/or activity of PFN1, and the level and/or activity of IGFALS in each of the aliquots; and selecting a member of the library of compounds which modulates the level and/or the activity of LCP1, the level and/or activity of VASN, the level and/or activity of PFN1, and the level and/or activity of IGFALS in an aliquot as compared to the level and/or activity of LCP1, the level and/or activity of VASN, the level and/or activity of PFN1, and the level and/or activity of IGFALS in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, the level and/or activity of PFN1, and the level and/or activity of IGFALS, thereby treating the subject.

In one aspect the present invention provides methods for determining whether a subject has active tuberculosis (TB). The methods include determining the level of LCP1, the level of VASN, the level of PFN1, and the level of CD14 in a sample(s) from the subject; comparing the level of LCP1, the level of VASN, the level of PFN1, and the level of CD14 in the subject sample(s) with a level of LCP1, a level of VASN, a level of PFN1, and a level of CD14 in a control sample(s), wherein a difference in the level of LCP1, a difference in the level of VASN, a difference in the level of PFN1, and a difference in the level of CD14 in the subject sample(s) as compared to the level of LCP1, the level of VASN, the level of PFN1, and the level of CD14 in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of PFN1, and the level of CD14 in a first sample(s) from the subject prior to the initiation of the treatment; determining the level of LCP1, the level of VASN, the level of PFN1, and the level of CD14 in a second sample(s) from the subject after at least a portion of the treatment has been administered; comparing the level of LCP1, the level of VASN, the level of PFN1, and the level of CD14 in the first sample(s) with a level of LCP1, the level of VASN, the level of PFN1, and the level of CD14 in the second sample(s), wherein a difference in the level of LCP1, the level of VASN, the level of PFN1, and the level of CD14 in the first sample(s) as compared to the level of LCP1, the level of VASN, the level of PFN1, and the level of CD14 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, the level and/or activity of PFN1, and the level and/or activity of CD14 in each of the aliquots; and selecting a member of the library of compounds which modulates the level and/or the activity of LCP1, the level and/or activity of VASN, the level and/or activity of PFN1, and the level and/or activity of CD14 in an aliquot as compared to the level and/or activity of LCP1, the level and/or activity of VASN, the level and/or activity of PFN1, and the level and/or activity of CD14 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, the level and/or activity of PFN1, and the level and/or activity of CD14, thereby treating the subject.

In one aspect the present invention provides methods for determining whether a subject has active tuberculosis (TB). The methods include determining the level of LCP1, the level of VASN, the level of PFN1, and the level of TAGLN2 in a sample(s) from the subject; comparing the level of LCP1, the level of VASN, the level of PFN1, and the level of TAGLN2 in the subject sample(s) with a level of LCP1, a level of VASN, a level of PFN1, and a level of TAGLN2 in a control sample(s), wherein a difference in the level of LCP1, a difference in the level of VASN, a difference in the level of PFN1, and a difference in the level of TAGLN2 in the subject sample(s) as compared to the level of LCP1, the level of VASN, the level of PFN1, and the level of TAGLN2 in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of PFN1, and the level of TAGLN2 in a first sample(s) from the subject prior to the initiation of the treatment; determining the level of LCP1, the level of VASN, the level of PFN1, and the level of TAGLN2 in a second sample(s) from the subject after at least a portion of the treatment has been administered; comparing the level of LCP1, the level of VASN, the level of PFN1, and the level of TAGLN2 in the first sample(s) with a level of LCP1, the level of VASN, the level of PFN1, and the level of TAGLN2 in the second sample(s), wherein a difference in the level of LCP1, the level of VASN, the level of PFN1, and the level of TAGLN2 in the first sample(s) as compared to the level of the one or more markers in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, the level and/or activity of PFN1, and the level and/or activity of TAGLN2 in each of the aliquots; and selecting a member of the library of compounds which modulates the level and/or the activity of LCP1, the level and/or activity of VASN, the level and/or activity of PFN1, and the level and/or activity of TAGLN2 in an aliquot as compared to the level and/or activity of LCP1, the level and/or activity of VASN, the level and/or activity of PFN1, and the level and/or activity of TAGLN2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, the level and/or activity of PFN1, and the level and/or activity of TAGLN2, thereby treating the subject.

In one aspect the present invention provides methods for determining whether a subject has active tuberculosis (TB). The methods include determining the level of LCP1 and the level of TAGLN2 in a sample(s) from the subject; comparing the level of LCP1 and the level of TAGLN2 in the subject sample(s) with a level of LCP1 and a level of TAGLN2 in a control sample(s), wherein a difference in the level of LCP1 and a difference in the level of TAGLN2 in the subject sample(s) as compared to the level of LCP1 and the level of TAGLN2 in the control sample(s) indicates that the subject has active TB.

In one aspect the present invention provides methods for monitoring the effectiveness of a treatment in a subject having active tuberculosis (TB). The methods include determining the level of LCP1 and the level of TAGLN2 in a first sample(s) from the subject prior to the initiation of the treatment; determining the level of LCP1 and the level of TAGLN2 in a second sample(s) from the subject after at least a portion of the treatment has been administered; comparing the level of LCP1 and the level of TAGLN2 in the first sample(s) with a level of LCP1 and the level of TAGLN2 in the second sample(s), wherein a difference in the level of LCP1 and the level of TAGLN2 in the first sample(s) as compared to the level of LCP1 and the level of TAGLN2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1 and the level and/or activity of TAGLN2 in each of the aliquots; and selecting a member of the library of compounds which modulates the level and/or the activity of LCP1 and the level and/or activity of TAGLN2 in an aliquot as compared to the level and/or activity of LCP1 and the level and/or activity of TAGLN2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1 and the level and/or activity of TAGLN2, thereby treating the subject.

In one aspect the present invention provides methods for determining whether a subject has active tuberculosis (TB). The methods include determining the level of LCP1, the level of VASN, and the level of TAGLN2 in a sample(s) from the subject; comparing the level of LCP1, the level of VASN, and the level of TAGLN2 in the subject sample(s) with a level of LCP1, a level of VASN, and a level of TAGLN2 in a control sample(s), wherein a difference in the level of LCP1, a difference in the level of VASN, and a difference in the level of TAGLN2 in the subject sample(s) as compared to the level of LCP1, the level of VASN, and the level of TAGLN2 in the control sample(s) indicates that the subject has active TB.

In one aspect the present invention provides methods for monitoring the effectiveness of a treatment in a subject having active tuberculosis (TB). The methods include determining the level of LCP1, the level of VASN, and the level of TAGLN2 in a first sample(s) from the subject prior to the initiation of the treatment; determining the level of LCP1, the level of VASN, and the level of TAGLN2 in a second sample(s) from the subject after at least a portion of the treatment has been administered; comparing the level of LCP1, the level of VASN, and the level of TAGLN2 in the first sample(s) with a level of LCP1, the level of VASN, and the level of TAGLN2 in the second sample(s), wherein a difference in the level of LCP1, the level of VASN, and the level of TAGLN2 in the first sample(s) as compared to the level of LCP1, the level of VASN, and the level of TAGLN2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, and the level and/or activity of TAGLN2 in each of the aliquots; and selecting a member of the library of compounds which modulates the level and/or the activity of LCP1, the level and/or activity of VASN, and the level and/or activity of TAGLN2 in an aliquot as compared to the level and/or activity of LCP1, the level and/or activity of VASN, and the level and/or activity of TAGLN2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, and the level and/or activity of TAGLN2, thereby treating the subject.

In one aspect the present invention provides methods for determining whether a subject has active tuberculosis (TB). The methods include determining the level of LCP1, the level of VASN, the level of TAGLN2, and the level of IGFBP6 in a sample(s) from the subject; comparing the level of LCP1, the level of VASN, the level of TAGLN2, and the level of IGFBP6 in the subject sample(s) with a level of LCP1, a level of VASN, a level of TAGLN2, and a level of IGFBP6 in a control sample(s), wherein a difference in the level of LCP1, a difference in the level of VASN, a difference in the level of TAGLN2, and a difference in the level of IGFBP6 in the subject sample(s) as compared to the level of LCP1, the level of VASN, the level of TAGLN2, and the level of IGFBP6 in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of TAGLN2, and the level of IGFBP6 in a first sample(s) from the subject prior to the initiation of the treatment; determining the level of LCP1, the level of VASN, the level of TAGLN2, and the level of IGFBP6 in a second sample(s) from the subject after at least a portion of the treatment has been administered; comparing the level of LCP1, the level of VASN, the level of TAGLN2, and the level of IGFBP6 in the first sample(s) with a level of LCP1, the level of VASN, the level of TAGLN2, and the level of IGFBP6 in the second sample(s), wherein a difference in the level LCP1, the level of VASN, the level of TAGLN2, and the level of IGFBP6 in the first sample(s) as compared to the level of LCP1, the level of VASN, the level of TAGLN2, and the level of IGFBP6 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level of VASN, the level of TAGLN2, and the level of IGFBP6 in each of the aliquots; and selecting a member of the library of compounds which modulates the level and/or the activity of LCP1, the level and/or activity of VASN, the level and/or activity of TAGLN2, and the level and/or activity of IGFBP6 in an aliquot as compared to the level and/or activity of LCP1, the level and/or activity of VASN, the level and/or activity of TAGLN2, and the level and/or activity of IGFBP6 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, the level and/or activity of TAGLN2, and the level and/or activity of IGFBP6, thereby treating the subject.

In one aspect the present invention provides methods for determining whether a subject has active tuberculosis (TB). The methods include determining the level of LCP1, the level of VASN, the level of TAGLN2, and the level of LRG1 in a sample(s) from the subject; comparing the level of LCP1, the level of VASN, the level of TAGLN2, and the level of LRG1 in the subject sample(s) with a level of LCP1, a level of VASN, a level of TAGLN2, and a level of LRG1 in a control sample(s), wherein a difference in the level of LCP1, a difference in the level of VASN, a difference in the level of TAGLN2, and a difference in the level of LRG1 in the subject sample(s) as compared to the level of LCP1, the level of VASN, the level of TAGLN2, and the level of LRG1 in the control sample(s) indicates that the subject has active TB.

In one aspect the present invention provides methods for monitoring the effectiveness of a treatment in a subject having active tuberculosis (TB). The methods include determining the level of LCP1, a level of VASN, a level of TAGLN2, and a level of LRG1 in a first sample(s) from the subject prior to the initiation of the treatment; determining the level of LCP1, a level of VASN, a level of TAGLN2, and a level of LRG1 in a second sample(s) from the subject after at least a portion of the treatment has been administered; comparing the level of LCP1, a level of VASN, a level of TAGLN2, and a level of LRG1 in the first sample(s) with a level of LCP1, a level of VASN, a level of TAGLN2, and a level of LRG1 in the second sample(s), wherein a difference in the level of LCP1, a level of VASN, a level of TAGLN2, and a level of LRG1 in the first sample(s) as compared to the level of LCP1, a level of VASN, a level of TAGLN2, and a level of LRG1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, a level and/or activity of VASN, a level and/or activity of TAGLN2, and a level and/or activity of LRG1 in each of the aliquots; and selecting a member of the library of compounds which modulates the level and/or the activity of LCP1, a level and/or activity of VASN, a level and/or activity of TAGLN2, and a level and/or activity of LRG1 in an aliquot as compared to the level and/or activity of LCP1, a level and/or activity of VASN, a level and/or activity of TAGLN2, and a level and/or activity of LRG1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, a level and/or activity of VASN, a level and/or activity of TAGLN2, and a level and/or activity of LRG1, thereby treating the subject.

In one aspect the present invention provides methods for determining whether a subject has active tuberculosis (TB). The methods include determining the level of LCP1, the level of VASN, the level of TAGLN2, and the level of SEPP1 in a sample(s) from the subject; comparing the level of LCP1, the level of VASN, the level of TAGLN2, and the level of SEPP1 in the subject sample(s) with a level of LCP1, a level of VASN, a level of TAGLN2, and a level of SEPP1 in a control sample(s), wherein a difference in the level of LCP1, a difference in the level of VASN, a difference in the level of TAGLN2, and a difference in the level of SEPP1 in the subject sample(s) as compared to the level of LCP1, the level of VASN, the level of TAGLN2, and the level of SEPP1 in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of TAGLN2, and the level of SEPP1 in a first sample(s) from the subject prior to the initiation of the treatment; determining the level of LCP1, the level of VASN, the level of TAGLN2, and the level of SEPP1 in a second sample(s) from the subject after at least a portion of the treatment has been administered; comparing the level of LCP1, the level of VASN, the level of TAGLN2, and the level of SEPP1 in the first sample(s) with a level of LCP1, the level of VASN, the level of TAGLN2, and the level of SEPP1 in the second sample(s), wherein a difference in the level of LCP1, the level of VASN, the level of TAGLN2, and the level of SEPP1 in the first sample(s) as compared to the level of LCP1, the level of VASN, the level of TAGLN2, and the level of SEPP1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level level and/or activity of VASN, the level level and/or activity of TAGLN2, and the level level and/or activity of SEPP1 in each of the aliquots; and selecting a member of the library of compounds which modulates the level and/or the activity of LCP1, the level level and/or activity of VASN, the level level and/or activity of TAGLN2, and the level level and/or activity of SEPP1 in an aliquot as compared to the level and/or activity of LCP1, the level level and/or activity of VASN, the level level and/or activity of TAGLN2, and the level level and/or activity of SEPP1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level level and/or activity of VASN, the level level and/or activity of TAGLN2, and the level level and/or activity of SEPP1, thereby treating the subject.

In one aspect the present invention provides methods for determining whether a subject has active tuberculosis (TB). The methods include determining the level of LCP1 and the level of PGLYRP2 in a sample(s) from the subject; comparing the level of LCP1 and the level of PGLYRP2 in the subject sample(s) with a level of LCP1 and a level of PGLYRP2 in a control sample(s), wherein a difference in the level of LCP1 and a difference in the level of PGLYRP2 in the subject sample(s) as compared to the level of LCP1 and the level of PGLYRP2 in the control sample(s) indicates that the subject has active TB.

In one aspect the present invention provides methods for monitoring the effectiveness of a treatment in a subject having active tuberculosis (TB). The methods include determining the level of LCP1 and the level of PGLYRP2 in a first sample(s) from the subject prior to the initiation of the treatment; determining the level of LCP1 and the level of PGLYRP2 in a second sample(s) from the subject after at least a portion of the treatment has been administered; comparing the level of LCP1 and the level of PGLYRP2 in the first sample(s) with a level of LCP1 and the level of PGLYRP2 in the second sample(s), wherein a difference in the level of LCP1 and the level of PGLYRP2 in the first sample(s) as compared to the level of LCP1 and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1 and the level and/or activity of PGLYRP2 in each of the aliquots; and selecting a member of the library of compounds which modulates the level and/or the activity of LCP1 and the level and/or activity of PGLYRP2 in an aliquot as compared to the level and/or activity of LCP1 and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1 and the level and/or activity of PGLYRP2, thereby treating the subject.

In one aspect the present invention provides methods for determining whether a subject has active tuberculosis (TB). The methods include determining the level of LCP1, the level of VASN, and the level of PGLYRP2 in a sample(s) from the subject; comparing the level of LCP1, the level of VASN, and the level of PGLYRP2 in the subject sample(s) with a level of LCP1, a level of VASN, and a level of PGLYRP2 in a control sample(s), wherein a difference in the level of LCP1, a difference in the level of VASN, and a difference in the level of PGLYRP2 in the subject sample(s) as compared to the level of LCP1, the level of VASN, and the level of PGLYRP2 in the control sample(s) indicates that the subject has active TB.

In one aspect the present invention provides methods for monitoring the effectiveness of a treatment in a subject having active tuberculosis (TB). The methods include determining the level of LCP1, the level of VASN, and the level of PGLYRP2 in a first sample(s) from the subject prior to the initiation of the treatment; determining the level of LCP1, the level of VASN, and the level of PGLYRP2 in a second sample(s) from the subject after at least a portion of the treatment has been administered; comparing the level of LCP1, the level of VASN, and the level of PGLYRP2 in the first sample(s) with a level of LCP1, the level of VASN, and the level of PGLYRP2 in the second sample(s), wherein a difference in the level of LCP1, the level of VASN, and the level of PGLYRP2 in the first sample(s) as compared to the level of LCP1, the level of VASN, and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, and the level and/or activity of PGLYRP2 of the invention in each of the aliquots; and selecting a member of the library of compounds which modulates the level and/or the activity of LCP1, the level and/or activity of VASN, and the level and/or activity of PGLYRP2 in an aliquot as compared to the level and/or activity of LCP1, the level and/or activity of VASN, and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, and the level and/or activity of PGLYRP2, thereby treating the subject.

In one aspect the present invention provides methods for determining whether a subject has active tuberculosis (TB). The methods include determining the level of LCP1, the level of VASN, the level of PGLYRP2, and the level of PFN1 in a sample(s) from the subject; comparing the level of LCP1, the level of VASN, the level of PGLYRP2, and the level of PFN1 in the subject sample(s) with a level of LCP1, a level of VASN, a level of PGLYRP2, and a level of PFN1 in a control sample(s), wherein a difference in the level of LCP1, a difference in the level of VASN, a difference in the level of PGLYRP2, and a difference in the level of PFN1 in the subject sample(s) as compared to the level of LCP1, the level of VASN, the level of PGLYRP2, and the level of PFN1 in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of PGLYRP2, and the level of PFN1 in a first sample(s) from the subject prior to the initiation of the treatment; determining the level of LCP1, the level of VASN, the level of PGLYRP2, and the level of PFN1 in a second sample(s) from the subject after at least a portion of the treatment has been administered; comparing the level of LCP1, the level of VASN, the level of PGLYRP2, and the level of PFN1 in the first sample(s) with a level of LCP1, the level of VASN, the level of PGLYRP2, and the level of PFN1 in the second sample(s), wherein a difference in the level of LCP1, the level of VASN, the level of PGLYRP2, and the level of PFN1 in the first sample(s) as compared to the level of LCP1, the level of VASN, the level of PGLYRP2, and the level of PFN1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, the level and/or activity of PGLYRP2, and the level and/or activity of PFN1 in each of the aliquots; and selecting a member of the library of compounds which modulates the level and/or the activity of LCP1, the level and/or activity of VASN, the level and/or activity of PGLYRP2, and the level and/or activity of PFN1 in an aliquot as compared to the level and/or activity of LCP1, the level and/or activity of VASN, the level and/or activity of PGLYRP2, and the level and/or activity of PFN1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, the level and/or activity of PGLYRP2, and the level and/or activity of PFN1, thereby treating the subject.

In one aspect the present invention provides methods for determining whether a subject has active tuberculosis (TB). The methods include determining the level of LCP1, the level of VASN, the level of PGLYRP2, and the level of TAGLN2 in a sample(s) from the subject; comparing the level of LCP1, the level of VASN, the level of PGLYRP2, and the level of TAGLN2 in the subject sample(s) with a level of LCP1, a level of VASN, a level of PGLYRP2, and a level of TAGLN2 in a control sample(s), wherein a difference in the level of LCP1, a difference in the level of VASN, a difference in the level of PGLYRP2, and a difference in the level of TAGLN2 in the subject sample(s) as compared to the level of LCP1, the level of VASN, the level of PGLYRP2, and the level of TAGLN2 in the control sample(s) indicates that the subject has active TB.

In one aspect the present invention provides methods for monitoring the effectiveness of a treatment in a subject having active tuberculosis (TB). The methods include determining the level of LCP1, the level of VASN, the level of PGLYRP2, and the level of TAGLN2 in a first sample(s) from the subject prior to the initiation of the treatment; determining the level of LCP1, the level of VASN, the level of PGLYRP2, and the level of TAGLN2 in a second sample(s) from the subject after at least a portion of the treatment has been administered; comparing the level of LCP1, the level of VASN, the level of PGLYRP2, and the level of TAGLN2 in the first sample(s) with a level of LCP1, the level of VASN, the level of PGLYRP2, and the level of TAGLN2 in the second sample(s), wherein a difference in the level of LCP1, the level of VASN, the level of PGLYRP2, and the level of TAGLN2 in the first sample(s) as compared to the level of LCP1, the level of VASN, the level of PGLYRP2, and the level of TAGLN2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of LCP1, the level and/or activity of VASN, the level and/or activity of PGLYRP2, and the level and/or activity of TAGLN2 in each of the aliquots; and selecting a member of the library of compounds which modulates the level and/or the activity of LCP1, the level and/or activity of VASN, the level and/or activity of PGLYRP2, and the level and/or activity of TAGLN2 in an aliquot as compared to the level and/or activity of LCP1, the level and/or activity of VASN, the level and/or activity of PGLYRP2, and the level and/or activity of TAGLN2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of LCP1, the level and/or activity of VASN, the level and/or activity of PGLYRP2, and the level and/or activity of TAGLN2, thereby treating the subject.

In one aspect the present invention provides methods for determining whether a subject has active tuberculosis (TB). The methods include determining the level of PFN1 and the level of PI16 in a sample(s) from the subject; comparing the level of PFN1 and the level of PI16 in the subject sample(s) with a level of PFN1 and a level of PI16 in a control sample(s), wherein a difference in the level of PFN1 and a difference in the level of PI16 in the subject sample(s) as compared to the level of PFN1 and the level of PI16 in the control sample(s) indicates that the subject has active TB.

In one aspect the present invention provides methods for monitoring the effectiveness of a treatment in a subject having active tuberculosis (TB). The methods include determining the level of PFN1 and the level of PI16 in a first sample(s) from the subject prior to the initiation of the treatment; determining the level of PFN1 and the level of PI16 in a second sample(s) from the subject after at least a portion of the treatment has been administered; comparing the level of PFN1 and the level of PI16 in the first sample(s) with a level of PFN1 and the level of PI16 in the second sample(s), wherein a difference in the level of PFN1 and the level of PI16 in the first sample(s) as compared to the level of PFN1 and the level of PI16 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PFN1 and the level and/or activity of PI16 of the invention in each of the aliquots; and selecting a member of the library of compounds which modulates the level and/or the activity of PFN1 and the level and/or activity of PI16 in an aliquot as compared to the level and/or activity of PFN1 and the level and/or activity of PI16 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PFN1 and the level and/or activity of PI16, thereby treating the subject.

In one aspect the present invention provides methods for determining whether a subject has active tuberculosis (TB). The methods include determining the level of PFN1 and the level of PON1 in a sample(s) from the subject; comparing the level of PFN1 and the level of PON1 in the subject sample(s) with a level of PFN1 and a level of PON1 in a control sample(s), wherein a difference in the level of PFN1 and a difference in the level of PON1 in the subject sample(s) as compared to the level of PFN1 and the level of PON1 in the control sample(s) indicates that the subject has active TB.

In one aspect the present invention provides methods for monitoring the effectiveness of a treatment in a subject having active tuberculosis (TB). The methods include determining the level of PFN1 and the level of PON1 in a first sample(s) from the subject prior to the initiation of the treatment; determining the level of PFN1 and the level of PON1 in a second sample(s) from the subject after at least a portion of the treatment has been administered; comparing the level of PFN1 and the level of PON1 in the first sample(s) with a level of PFN1 and the level of PON1 in the second sample(s), wherein a difference in the level of PFN1 and the level of PON1 in the first sample(s) as compared to the level of PFN1 and the level of PON1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PFN1 and the level and/or activity of PON1 of the invention in each of the aliquots; and selecting a member of the library of compounds which modulates the level and/or the activity of PFN1 and the level and/or activity of PON1 in an aliquot as compared to the level and/or activity of PFN1 and the level and/or activity of PON1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PFN1 and the level and/or activity of PON1, thereby treating the subject.

In one aspect the present invention provides methods for determining whether a subject has active tuberculosis (TB). The methods include determining the level of PFN1 and the level of PTGDS in a sample(s) from the subject; comparing the level of PFN1 and the level of PTGDS in the subject sample(s) with a level of PFN1 and a level of PTGDS in a control sample(s), wherein a difference in the level of PFN1 and a difference in the level of PTGDS in the subject sample(s) as compared to the level of PFN1 and the level of PTGDS in the control sample(s) indicates that the subject has active TB.

In one aspect the present invention provides methods for monitoring the effectiveness of a treatment in a subject having active tuberculosis (TB). The methods include determining the level of PFN1 and the level of PTGDS in a first sample(s) from the subject prior to the initiation of the treatment; determining the level of PFN1 and the level of PTGDS in a second sample(s) from the subject after at least a portion of the treatment has been administered; comparing the level of PFN1 and the level of PTGDS in the first sample(s) with a level of PFN1 and the level of PTGDS in the second sample(s), wherein a difference in the level of PFN1 and the level of PTGDS in the first sample(s) as compared to the level of PFN1 and the level of PTGDS in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PFN1 and the level and/or activity of PTGDS in each of the aliquots; and selecting a member of the library of compounds which modulates the level and/or the activity of PFN1 and the level and/or activity of PTGDS in an aliquot as compared to the level and/or activity of PFN1 and the level and/or activity of PTGDS in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PFN1 and the level and/or activity of PTGDS, thereby treating the subject.

In one aspect the present invention provides methods for determining whether a subject has active tuberculosis (TB). The methods include determining the level of PI16 and the level of PON1 in a sample(s) from the subject; comparing the level of PI16 and the level of PON1 in the subject sample(s) with a level of PI16 and a level of PON1 in a control sample(s), wherein a difference in the level of PI16 and a difference in the level of PON1 in the subject sample(s) as compared to the level of PI16 and the level of PON1 in the control sample(s) indicates that the subject has active TB.

In one aspect the present invention provides methods for monitoring the effectiveness of a treatment in a subject having active tuberculosis (TB). The methods include determining the level of PI16 and the level of PON1 in a first sample(s) from the subject prior to the initiation of the treatment; determining the level of PI16 and the level of PON1 in a second sample(s) from the subject after at least a portion of the treatment has been administered; comparing the level of PI16 and the level of PON1 in the first sample(s) with a level of PI16 and the level of PON1 in the second sample(s), wherein a difference in the level of PI16 and the level of PON1 in the first sample(s) as compared to the level of PI16 and the level of PON1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PI16 and the level and/or activity of PON1 in each of the aliquots; and selecting a member of the library of compounds which modulates the level and/or the activity of PI16 and the level and/or activity of PON1 in an aliquot as compared to the level and/or activity of PI16 and the level and/or activity of PON1 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PI16 and the level and/or activity of PON1, thereby treating the subject.

In one aspect the present invention provides methods for determining whether a subject has active tuberculosis (TB). The methods include determining the level of PI16 and the level of PTGDS in a sample(s) from the subject; comparing the level of PI16 and the level of PTGDS in the subject sample(s) with a level of PI16 and a level of PTGDS in a control sample(s), wherein a difference in the level of PI16 and a difference in the level of PTGDS in the subject sample(s) as compared to the level of PI16 and the level of PTGDS in the control sample(s) indicates that the subject has active TB.

In one aspect the present invention provides methods for monitoring the effectiveness of a treatment in a subject having active tuberculosis (TB). The methods include determining the level of PI16 and the level of PTGDS in a first sample(s) from the subject prior to the initiation of the treatment; determining the level of PI16 and the level of PTGDS in a second sample(s) from the subject after at least a portion of the treatment has been administered; comparing the level of PI16 and the level of PTGDS in the first sample(s) with a level of PI16 and the level of PTGDS in the second sample(s), wherein a difference in the level of PI16 and the level of PTGDS in the first sample(s) as compared to the level of PI16 and the level of PTGDS in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PI16 and the level and/or activity of PTGDS in each of the aliquots; and selecting a member of the library of compounds which modulates the level and/or the activity of PI16 and the level and/or activity of PTGDS in an aliquot as compared to the level and/or activity of PI16 and the level and/or activity of PTGDS in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PI16 and the level and/or activity of PTGDS, thereby treating the subject.

In one aspect the present invention provides methods for determining whether a subject has active tuberculosis (TB). The methods include determining the level of PON1 and the level of PTGDS in a sample(s) from the subject; comparing the level of PON1 and the level of PTGDS in the subject sample(s) with a level of PON1 and a level of PTGDS in a control sample(s), wherein a difference in the level of PON1 and a difference in the level of PTGDS in the subject sample(s) as compared to the level of PON1 and the level of PTGDS in the control sample(s) indicates that the subject has active TB.

In one aspect the present invention provides methods for monitoring the effectiveness of a treatment in a subject having active tuberculosis (TB). The methods include determining the level of PON1 and the level of PTGDS in a first sample(s) from the subject prior to the initiation of the treatment; determining the level of PON1 and the level of PTGDS in a second sample(s) from the subject after at least a portion of the treatment has been administered; comparing the level of PON1 and the level of PTGDS in the first sample(s) with a level of PON1 and the level of PTGDS in the second sample(s), wherein a difference in the level of PON1 and the level of PTGDS in the first sample(s) as compared to the level of PON1 and the level of PTGDS in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PON1 and the level and/or activity of PTGDS in each of the aliquots; and selecting a member of the library of compounds which modulates the level and/or the activity of PON1 and the level and/or activity of PTGDS in an aliquot as compared to the level and/or activity PON1 and the level and/or activity of PTGDS in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PON1 and the level and/or activity of PTGDS, thereby treating the subject.

In one aspect the present invention provides methods for determining whether a subject has active tuberculosis (TB). The methods include determining the level of PFN1, the level of PI16, and the level of PON1 in a sample(s) from the subject; comparing the level of PFN1, the level of PI16, and the level of PON1 in the subject sample(s) with a level of PFN1, a level of PI16, and a level of PON1 in a control sample(s), wherein a difference in the level of PFN1, a difference in the level of PI16, and a difference in the level of PON1 in the subject sample(s) as compared to the level of PFN1, the level of PI16, and the level of PON1 in the control sample(s) indicates that the subject has active TB.

In one aspect the present invention provides methods for monitoring the effectiveness of a treatment in a subject having active tuberculosis (TB). The methods include determining the level of PFN1, the level of PI16, and the level of PON1 in a first sample(s) from the subject prior to the initiation of the treatment; determining the level of PFN1, the level of PI16, and the level of PON1 in a second sample(s) from the subject after at least a portion of the treatment has been administered; comparing the level of PFN1, the level of PI16, and the level of PON1 in the first sample(s) with a level of PFN1, the level of PI16, and the level of PON1 in the second sample(s), wherein a difference in the level of PFN1, the level of PI16, and the level of PON1 in the first sample(s) as compared to the level of PFN1, the level of PI16, and the level of PON1 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PFN1, the level and/or activity of PI16, and the level and/or activity of PON1 of the invention in each of the aliquots; and selecting a member of the library of compounds which modulates the level and/or the activity of PFN1, the level and/or activity of PI16, and the level and/or activity of PON1 in an aliquot as compared to the level and/or activity of PFN1, the level and/or activity of PI16, and the level and/or activity of PON1 in a control sample, thereby identifying a compound that is useful for treating a subject having active TB. In one aspect the present invention provides methods for treating a subject having active tuberculosis (TB). The methods include administering to the subject an effective amount of an agent that modulates the expression and/or activity of PFN1, the level and/or activity of PI16, and the level and/or activity of PON1, thereby treating the subject.

In one aspect the present invention provides methods for determining whether a subject has active tuberculosis (TB). The methods include determining the level of PFN1, the level of PI16, and the level of PTGDS in a sample(s) from the subject; comparing the level of PFN1, the level of PI16, and the level of PTGDS in the subject sample(s) with a level of PFN1, a level of PI16, and a level of PTGDS in a control sample(s), wherein a difference in the level of PFN1, a difference in the level of PI16, and a difference in the level of PTGDS in the subject sample(s) as compared to the level of PFN1, the level of PI16, and the level of PTGDS in the control sample(s) indicates that the subject has active TB.

In one aspect the present invention provides methods for monitoring the effectiveness of a treatment in a subject having active tuberculosis (TB). The methods include determining the level of PFN1, the level of PI16, and the level of PTGDS in a first sample(s) from the subject prior to the initiation of the treatment; determining the level of PFN1, the level of PI16, and the level of PTGDS in a second sample(s) from the subject after at least a portion of the treatment has been administered; comparing the level of PFN1, the level of PI16, and the level of PTGDS in the first sample(s) with a level of PFN1, the level of PI16, and the level of PTGDS in the second sample(s), wherein a difference in the level of PFN1, the level of PI16, and the level of PTGDS in the first sample(s) as compared to the level of PFN1, the level of PI16, and the level of PTGDS in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PFN1, the level and/or activity of PI16, and the level and/or activity of PTGDS in each of the aliquots; and selecting a member of the library of compounds which modulates the level and/or the activity of PFN1, the level and/or activity of PI16, and the level and/or activity of PTGDS in an aliquot as compared to the level and/or activity of PFN1, the level and/or activity of PI16, and the level and/or activity of PTGDS in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PFN1, the level and/or activity of PI16, and the level and/or activity of PTGDS, thereby treating the subject.

In one aspect the present invention provides methods for determining whether a subject has active tuberculosis (TB). The methods include determining the level of PON1, the level of PI16, and the level of PTGDS in a sample(s) from the subject; comparing the level of PON1, the level of PI16, and the level of PTGDS in the subject sample(s) with a level of PON1, a level of PI16, and a level of PTGDS in a control sample(s), wherein a difference in the level of PON1, a difference in the level of PI16, and a difference in the level of PTGDS in the subject sample(s) as compared to the level of PON1, the level of PI16, and the level of PTGDS in the control sample(s) indicates that the subject has active TB.

In one aspect the present invention provides methods for monitoring the effectiveness of a treatment in a subject having active tuberculosis (TB). The methods include determining the level of PON1, the level of PI16, and the level of PTGDS in a first sample(s) from the subject prior to the initiation of the treatment; determining the level of PON1, the level of PI16, and the level of PTGDS in a second sample(s) from the subject after at least a portion of the treatment has been administered; comparing the level of PON1, the level of PI16, and the level of PTGDS in the first sample(s) with a level of PON1, the level of PI16, and the level of PTGDS in the second sample(s), wherein a difference in the level of PON1, the level of PI16, and the level of PTGDS in the first sample(s) as compared to the level of PON1, the level of PI16, and the level of PTGDS in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PON1, the level and/or activity of PI16, and the level and/or activity of PTGDS in each of the aliquots; and selecting a member of the library of compounds which modulates the level and/or the activity of PON1, the level and/or activity of PI16, and the level and/or activity of PTGDS in an aliquot as compared to the level and/or activity of PON1, the level and/or activity of PI16, and the level and/or activity of PTGDS in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PON1, the level and/or activity of PI16, and the level and/or activity of PTGDS, thereby treating the subject.

In one aspect the present invention provides methods for determining whether a subject has active tuberculosis (TB). The methods include determining the level of PFN1, the level of PI16, the level of PON1, and the level of PTGDS in a sample(s) from the subject; comparing the level of PFN1, the level of PI16, the level of PON1, and the level of PTGDS in the subject sample(s) with a level of PFN1, a level of PI16, a level of PON1, and a level of PTGDS in a control sample(s), wherein a difference in the level of PFN1, a difference in the level of PI16, a difference in the level of PON1, and a difference in the level of PTGDS in the subject sample(s) as compared to the level of PFN1, the level of PI16, the level of PON1, and the level of PTGDS in the control sample(s) indicates that the subject has active TB.

In one aspect the present invention provides methods for monitoring the effectiveness of a treatment in a subject having active tuberculosis (TB). The methods include determining the level of PFN1, the level of PI16, the level of PON1 and a level of PTGDS in a first sample(s) from the subject prior to the initiation of the treatment; determining the level of PFN1, the level of PI16, the level of PON1 and the level of PTGDS in a second sample(s) from the subject after at least a portion of the treatment has been administered; comparing the level of PFN1, the level of PI16, the level of PON1 and the level of PTGDS in the first sample(s) with a level of PFN1, the level of PI16, the level of PON1 and the level of PTGDS in the second sample(s), wherein a difference in the level of PFN1, the level of PI16, the level of PON1 and the level of PTGDS in the first sample(s) as compared to the level of PFN1, the level of PI16, the level of PON1 and the level of PTGDS in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PFN1, the level and/or activity of PI16, the level and/or activity of PON1, and the level and/or activity of PTGDS in each of the aliquots; and selecting a member of the library of compounds which modulates the level and/or the activity of PFN1, the level and/or activity of PI16, the level and/or activity of PON1 and the level and/or activity of PTGDS in an aliquot as compared to the level and/or activity of PFN1, the level and/or activity of PI16, the level and/or activity of PON1 and the level and/or activity of PTGDS in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PFN1, the level and/or activity of PI16, the level and/or activity of PON1, and the level and/or activity of PTGDS thereby treating the subject.

In one aspect the present invention provides methods for determining whether a subject has active tuberculosis (TB).

The methods include determining the level of PFN1, the level of PON1, and the level of PTGDS in a sample(s) from the subject; comparing the level of PFN1, the level of PON1, and the level of PTGDS in the subject sample(s) with a level of PFN1, the level of PON1, and the level of PTGDS in a control sample(s), wherein a difference in the level of PFN1, a difference in the level of PON1, and a difference in the level of PTGDS, in the subject sample(s) as compared to the level of PFN1, the level of PON1, and the level of PTGDS in the control sample(s) indicates that the subject has active TB.

In one aspect the present invention provides methods for monitoring the effectiveness of a treatment in a subject having active tuberculosis (TB). The methods include determining the level of PFN1, the level of PON1, and the level of PTGDS in a first sample(s) from the subject prior to the initiation of the treatment; determining the level of PFN1, the level of PON1, and the level of PTGDS in a second sample(s) from the subject after at least a portion of the treatment has been administered; comparing the level of PFN1, the level of PON1, and the level of PTGDS in the first sample(s) with a level of PFN1, the level of PON1, and the level of PTGDS in the second sample(s), wherein a difference in the level of PFN1, the level of PON1, and the level of PTGDS in the first sample(s) as compared to the level of PFN1, the level of PON1, and the level of PTGDS in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of PFN1, the level and/or activity of PON1, the level and/or activity of PTGDS in each of the aliquots; and selecting a member of the library of compounds which modulates the level and/or the activity of PFN1, the level and/or activity of PON1, the level and/or activity of PTGDS in an aliquot as compared to the level and/or activity of PFN1, the level and/or activity of PON1, the level and/or activity of PTGDS in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of PFN1, the level and/or activity of PON1, the level and/or activity of PTGDS, thereby treating the subject.

In one aspect the present invention provides methods for determining whether a subject has active tuberculosis (TB). The methods include determining the level of VASN and the level of TAGLN2 in a sample(s) from the subject; comparing the level of VASN and the level of TAGLN2 in the subject sample(s) with a level of VASN and a level of TAGLN2 in a control sample(s), wherein a difference in the level of VASN and a difference in the level of TAGLN2 in the subject sample(s) as compared to the level of VASN and the level of TAGLN2 in the control sample(s) indicates that the subject has active TB.

In one aspect the present invention provides methods for monitoring the effectiveness of a treatment in a subject having active tuberculosis (TB). The methods include determining the level of VASN and the level of TAGLN2 in a first sample(s) from the subject prior to the initiation of the treatment; determining the level of VASN and the level of TAGLN2 in a second sample(s) from the subject after at least a portion of the treatment has been administered; comparing the level of VASN and the level of TAGLN2 in the first sample(s) with a level of VASN and the level of TAGLN2 in the second sample(s), wherein a difference in the level of VASN and the level of TAGLN2 in the first sample(s) as compared to the level of VASN and the level of TAGLN2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of VASN and the level and/or activity of TAGLN2 in each of the aliquots; and selecting a member of the library of compounds which modulates the level and/or the activity of VASN and the level and/or activity of TAGLN2 in an aliquot as compared to the level and/or activity of VASN and the level and/or activity of TAGLN2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of VASN and the level and/or activity of TAGLN2, thereby treating the subject.

In one aspect the present invention provides methods for determining whether a subject has active tuberculosis (TB). The methods include determining the level of VASN and the level of PGLYRP2 in a sample(s) from the subject; comparing the level of VASN and the level of PGLYRP2 in the subject sample(s) with a level of VASN and a level of PGLYRP2 in a control sample(s), wherein a difference in the level of VASN and a difference in the level of PGLYRP2 in the subject sample(s) as compared to the level of VASN and the level of PGLYRP2 in the control sample(s) indicates that the subject has active TB.

In one aspect the present invention provides methods for monitoring the effectiveness of a treatment in a subject having active tuberculosis (TB). The methods include determining the level of VASN and the level of PGLYRP2 in a first sample(s) from the subject prior to the initiation of the treatment; determining the level of VASN and the level of PGLYRP2 in a second sample(s) from the subject after at least a portion of the treatment has been administered; comparing the level of VASN and the level of PGLYRP2 in the first sample(s) with a level of VASN and the level of PGLYRP2 in the second sample(s), wherein a difference in the level of VASN and the level of PGLYRP2 in the first sample(s) as compared to the level of VASN and the level of PGLYRP2 in the second sample(s) indicates that the treatment is effective.

In one aspect the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of VASN and the level and/or activity of PGLYRP2 in each of the aliquots; and selecting a member of the library of compounds which modulates the level and/or the activity of VASN and the level and/or activity of PGLYRP2 in an aliquot as compared to the level and/or activity of VASN and the level and/or activity of PGLYRP2 in a control sample, thereby identifying a compound that is useful for treating a subject having active TB.

In one aspect the present invention provides methods for treating a subject having active tuberculosis (TB). The methods include administering to the subject an effective amount of an agent that modulates the expression and/or activity of VASN and the level and/or activity of PGLYRP2, thereby treating the subject.

In one embodiment, the subject is HIV positive (HIV+).

In one embodiment, the methods further comprise determining the level of one or more additional markers selected from the group consisting of APOE, SELL, TNXB, COMP, LUM, PGLYRP2, HABP2, LRG1, QSOX1, S100A8, APOC3, LCP1, VASN, PFN1, IGFBP6, LRG1, PGLYRP2, APOA4, BCHE, PI16, SEPP1, APOA1, IGFALS, CD14, TAGLN2, CPN2, APOC1, PEPD, GP1BA and PTGDS.

In another embodiment, the methods further comprise determining the level of one or more additional markers listed in Table 1.

In one embodiment, the level of the marker is an expression level and/or activity of the marker.

In one embodiment, the level in the subject sample(s) is determined by mass spectrometry. In one embodiment, the mass spectrometry is matrix assisted laser desorption/time of flight (MALDI/TOF) mass spectrometry, liquid chromatography quadruple ion trap electrospray (LCQ-MS), or surface enhanced laser desorption ionization/time of flight (SELDI/TOF) mass spectrometry. In another embodiment, the level in the subject sample(s) is determined by immunoassay.

In one embodiment, the sample(s) from the subject is a fluid sample(s). In another embodiment, the sample(s) from the subject is a tissue sample(s).

In one embodiment, the subject resides in North America or Europe.

In one aspect, the present invention provides kits for determining whether a subject has active tuberculosis (TB). The kits include reagents for determining the level of one or more markers listed in Table 1 in a subject sample(s) and instructions for use of the kit to determine whether the subject has active TB.

In one aspect, the present invention provides kits monitoring the effectiveness of a treatment in a subject having active TB. The kits include reagents for determining the level of one or more markers listed in Table 1 in a subject sample(s) and instructions for use of the kit to monitor the effectiveness of the treatment.

In one aspect, the present invention provides kits for determining whether a subject has active tuberculosis (TB). The kits include reagents for determining the level of CD14 and the level of APOE in a subject sample(s) and instructions for use of the kit to determine whether the subject has active TB.

In one aspect, the present invention provides kits monitoring the effectiveness of a treatment in a subject having active TB. The kits include reagents for determining the level of CD14 and the level of APOE in a subject sample(s) and instructions for use of the kit to monitor the effectiveness of the treatment.

In one aspect, the present invention provides kits for determining whether a subject has active tuberculosis (TB). The kits include reagents for determining the level of PEPD and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of PEPD and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of PEPD, the level of TNXB, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of PEPD, the level of TNXB, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of PEPD, the level of COMP, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of PEPD, the level of COMP, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of PEPD, the level of QSOX1, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of PEPD, the level of QSOX1, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of PEPD, the level of CD14, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of PEPD, the level of CD14, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of PEPD, the level of SEPP1, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of PEPD, the level of SEPP1, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of PEPD, the level of LUM, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of PEPD, the level of LUM, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of TNXB, the level of SEPP1, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of TNXB, the level of SEPP1, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of QSOX1, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of QSOX1, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of TNXB, the level of QSOX1, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of TNXB, the level of QSOX1, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of COMP, the level of SEPP1, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of COMP, the level of SEPP1, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of LUM, the level of SEPP1, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of LUM, the level of SEPP1, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of QSOX1, the level of SEPP1, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of QSOX1, the level of SEPP1, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, and the level of PEPD in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, and the level of PEPD in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of COMP, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of COMP, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of SELL, and the level of PEPD in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of SELL, and the level of PEPD in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of APOE, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of APOE, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of GP1BA, the level of PEPD, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of PEPD, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of COMP, the level of PEPD, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of COMP, the level of PEPD, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of COMP, the level of PEPD, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of COMP, the level of PEPD, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of COMP, the level of PEPD, the level of SELL, and the level of LUM in a subject sample(s) and instructions for use of the kit to determine whether the subject has active TB.

In one aspect, the present invention provides kits monitoring the effectiveness of a treatment in a subject having active TB. The kits include reagents for determining the level of COMP, the level of PEPD, the level of SELL, and the level of LUM in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PEPD, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PEPD, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PEPD, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PEPD, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PEPD, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PEPD, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of COMP, the level of PEPD, the level of SELL, and the level of GP1BA in a subject sample(s) and instructions for use of the kit to determine whether the subject has active TB.

In one aspect, the present invention provides kits monitoring the effectiveness of a treatment in a subject having active TB. The kits include reagents for determining the level of COMP, the level of PEPD, the level of SELL, and the level of GP1BA in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of PEPD, the level of SELL, and the level of COMP in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of PEPD, the level of SELL, and the level of COMP in a subject sample(s) and instructions for use of the kit to monitor the effectiveness of the treatment.

In one aspect, the present invention provides kits for determining whether a subject has active tuberculosis (TB). The kits include reagents for determining the level of LUM, the level of PEPD, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of LUM, the level of PEPD, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of PEPD, the level of SELL, and the level of CD14 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of PEPD, the level of SELL, and the level of CD14 in a subject sample(s) and instructions for use of the kit to monitor the effectiveness of the treatment.

In one aspect, the present invention provides kits for determining whether a subject has active tuberculosis (TB). The kits include reagents for determining the level of COMP, the level of PEPD, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of COMP, the level of PEPD, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of QSOX1, the level of PEPD, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of QSOX1, the level of PEPD, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of LUM, the level of PEPD, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of LUM, the level of PEPD, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PEPD, the level of SELL, and the level of COMP in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PEPD, the level of SELL, and the level of COMP in a subject sample(s) and instructions for use of the kit to monitor the effectiveness of the treatment.

In one aspect, the present invention provides kits for determining whether a subject has active tuberculosis (TB). The kits include reagents for determining the level of SEPP1, the level of PEPD, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of SEPP1, the level of PEPD, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of GP1BA, the level of PEPD, the level of SELL, and the level of CD14 in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of PEPD, the level of SELL, and the level of CD14 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of PEPD, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of PEPD, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of SEPP1, the level of PEPD, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of SEPP1, the level of PEPD, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PEPD, the level of SELL, and the level of LUM in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PEPD, the level of SELL, and the level of LUM in a subject sample(s) and instructions for use of the kit to monitor the effectiveness of the treatment.

In one aspect, the present invention provides kits for determining whether a subject has active tuberculosis (TB). The kits include reagents for determining the level of LUM, the level of PEPD, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of LUM, the level of PEPD, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of COMP, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of COMP, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of GP1BA, the level of PEPD, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of PEPD, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of PEPD, the level of SELL, and the level of LUM in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of PEPD, the level of SELL, and the level of LUM in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of PEPD, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of PEPD, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of PEPD, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of PEPD, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of COMP, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of COMP, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of QSOX1, the level of APOC1, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of QSOX1, the level of APOC1, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of LUM, the level of APOC1, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of LUM, the level of APOC1, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of GP1BA, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of GP1BA, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of GP1BA, the level of PEPD, the level of SELL, and the level of LUM in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of PEPD, the level of SELL, and the level of LUM in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of QSOX1, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of QSOX1, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of SEPP1, the level of PEPD, the level of SELL, and the level of GP1BA in a subject sample(s) and instructions for use of the kit to determine whether the subject has active TB.

In one aspect, the present invention provides kits monitoring the effectiveness of a treatment in a subject having active TB. The kits include reagents for determining the level of SEPP1, the level of PEPD, the level of SELL, and the level of GP1BA in a subject sample(s) and instructions for use of the kit to monitor the effectiveness of the treatment.

In one aspect, the present invention provides kits for determining whether a subject has active tuberculosis (TB). The kits include reagents for determining the level of QSOX1, the level of SEPP1, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of QSOX1, the level of SEPP1, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of LUM, the level of SEPP1, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of LUM, the level of SEPP1, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of GP1BA, the level of COMP, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of COMP, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of GP1BA, the level of PEPD, the level of SELL, and the level of APOC1 in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of PEPD, the level of SELL, and the level of APOC1 in a subject sample(s) and instructions for use of the kit to monitor the effectiveness of the treatment.

In one aspect, the present invention provides kits for determining whether a subject has active tuberculosis (TB). The kits include reagents for determining the level of COMP, the level of QSOX1, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of COMP, the level of QSOX1, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of COMP, the level of LUM, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of COMP, the level of LUM, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of QSOX1, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of QSOX1, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of SEPP1, the level of COMP, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of SEPP1, the level of COMP, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, the level of GP1BA, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, the level of GP1BA, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of QSOX1, the level of CD14, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of QSOX1, the level of CD14, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of TNXB, the level of APOC1, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of TNXB, the level of APOC1, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of GP1BA, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of GP1BA, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of GP1BA, the level of PEPD, the level of APOC1, and the level of CD14 in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of PEPD, the level of APOC1, and the level of CD14 in a subject sample(s) and instructions for use of the kit to monitor the effectiveness of the treatment.

In one aspect, the present invention provides kits for determining whether a subject has active tuberculosis (TB). The kits include reagents for determining the level of GP1BA, the level of CD14, the level of SELL, and the level of COMP in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of CD14, the level of SELL, and the level of COMP in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, the level of GP1BA, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, the level of GP1BA, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, the level of COMP, and the level of GP1BA in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, the level of COMP, and the level of GP1BA in a subject sample(s) and instructions for use of the kit to monitor the effectiveness of the treatment.

In one aspect, the present invention provides kits for determining whether a subject has active tuberculosis (TB). The kits include reagents for determining the level of QSOX1, the level of COMP, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of QSOX1, the level of COMP, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of QSOX1, the level of GP1BA, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of QSOX1, the level of GP1BA, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of QSOX1, the level of LUM, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of QSOX1, the level of LUM, the level of SELL, and the level of TNXB in a subject sample(s) and instructions for use of the kit to monitor the effectiveness of the treatment.

In one aspect, the present invention provides kits determining whether a subject has active tuberculosis (TB). The kits include reagents for determining the level of GP1BA, the level of SEPP1, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of SEPP1, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of LUM, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of LUM, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of GP1BA, the level of CD14, the level of LUM, and the level of APOC1 in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of CD14, the level of LUM, and the level of APOC1 in a subject sample(s) and instructions for use of the kit to monitor the effectiveness of the treatment.

In one aspect, the present invention provides kits for determining whether a subject has active tuberculosis (TB). The kits include reagents for determining the level of TNXB, the level of GP1BA, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of TNXB, the level of GP1BA, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of LUM, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of LUM, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of COMP, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of COMP, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of SEPP1, the level of CD14, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of SEPP1, the level of CD14, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of LUM, the level of SELL, the level of GP1BA, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of LUM, the level of SELL, the level of GP1BA, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of COMP, the level of CD14, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of COMP, the level of CD14, the level of SELL, and the level of SEPP1 in a subject sample(s) and instructions for use of the kit to monitor the effectiveness of the treatment.

In one aspect, the present invention provides kits determining whether a subject has active tuberculosis (TB). The kits include reagents for determining the level of TNXB, the level of LUM, the level of SELL, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of TNXB, the level of LUM, the level of SELL, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of GP1BA, the level of SELL, the level of TNXB, and the level of CD14 in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of SELL, the level of TNXB, and the level of CD14 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, the level of GP1BA, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, the level of GP1BA, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, the level of SELL, and the level of LUM in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, the level of SELL, and the level of LUM in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of SELL, the level of COMP, and the level of GP1BA in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of SELL, the level of COMP, and the level of GP1BA in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of COMP, the level of SELL, and the level of CD14 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of COMP, the level of SELL, and the level of CD14 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, the level of LUM, and the level of PEPD in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, the level of LUM, and the level of PEPD in a subject sample(s) and instructions for use of the kit to monitor the effectiveness of the treatment.

In one aspect, the present invention provides kits for determining whether a subject has active tuberculosis (TB). The kits include reagents for determining the level of COMP, the level of LUM, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of COMP, the level of LUM, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of GP1BA, the level of SEPP1, the level of SELL, and the level of CD14 in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of SEPP1, the level of SELL, and the level of CD14 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of LUM, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of LUM, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of GP1BA, the level of CD14, the level of LUM, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of CD14, the level of LUM, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of COMP, the level of SELL, and the level of LUM in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of COMP, the level of SELL, and the level of LUM in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of COMP, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of COMP, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of COMP, the level of GP1BA, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of COMP, the level of GP1BA, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of SEPP1, the level of CD14, the level of GP1BA, and the level of LUM in a subject sample(s) and instructions for use of the kit to determine whether the subject has active TB.

In one aspect, the present invention provides kits monitoring the effectiveness of a treatment in a subject having active TB. The kits include reagents for determining the level of SEPP1, the level of CD14, the level of GP1BA, and the level of LUM in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of TNXB, the level of GP1BA, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of TNXB, the level of GP1BA, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, the level of QSOX1, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, the level of QSOX1, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, the level of COMP, and the level of PEPD in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, the level of COMP, and the level of PEPD in a subject sample(s) and instructions for use of the kit to monitor the effectiveness of the treatment.

In one aspect, the present invention provides kits for determining whether a subject has active tuberculosis (TB). The kits include reagents for determining the level of GP1BA, the level of SELL, the level of TNXB, and the level of COMP in a subject sample(s) and instructions for use of the kit to determine whether the subject has active TB.

In one aspect, the present invention provides kits monitoring the effectiveness of a treatment in a subject having active TB. The kits include reagents for determining the level of GP1BA, the level of SELL, the level of TNXB, and the level of COMP in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, the level of LUM, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, the level of LUM, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of APOC1, the level of CD14, the level of PEPD, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of APOC1, the level of CD14, the level of PEPD, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of APOE, the level of SELL, and the level of TNXB in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of APOE, the level of SELL, and the level of TNXB in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of APOE, the level of SELL, and the level of COMP in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of APOE, the level of SELL, and the level of COMP in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of APOE, the level of SELL, and the level of LUM in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of APOE, the level of SELL, and the level of LUM in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of APOE, the level of SELL, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of APOE, the level of SELL, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of APOE, the level of SELL, and the level of HABP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of APOE, the level of SELL, and the level of HABP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of APOE, the level of SELL, and the level of LRG1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of APOE, the level of SELL, and the level of LRG1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of APOE, the level of SELL, and the level of QSOX1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of APOE, the level of SELL, and the level of QSOX1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of APOE, the level of SELL, and the level of S100A8 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of APOE, the level of SELL, and the level of S100A8 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of APOE, and the level of APOC3 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of APOE, and the level of APOC3 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of APOE, the level of APOC3, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of APOE, the level of APOC3, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level CD14, the level of APOE, the level of APOC3, and the level of SELL in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of APOE, the level of APOC3, and the level of SELL in a subject sample(s) and instructions for use of the kit to monitor the effectiveness of the treatment.

In one aspect, the present invention provides kits for determining whether a subject has active tuberculosis (TB). The kits include reagents for determining the level CD14, the level of APOE, the level of APOC3, and the level of HABP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of APOE, the level of APOC3, and the level of HABP2 in a subject sample(s) and instructions for use of the kit to monitor the effectiveness of the treatment.

In one aspect, the present invention provides kits for determining whether a subject has active tuberculosis (TB). The kits include reagents for determining the level LCP1 and the level of PFN1 in a subject sample(s) and instructions for use of the kit to determine whether the subject has active TB.

In one aspect, the present invention provides kits monitoring the effectiveness of a treatment in a subject having active TB. The kits include reagents for determining the level of LCP1 and the level of PFN1 in a subject sample(s) and instructions for use of the kit to monitor the effectiveness of the treatment.

In one aspect, the present invention provides kits for determining whether a subject has active tuberculosis (TB). The kits include reagents for determining the level LCP1 and the level of VASN in a subject sample(s) and instructions for use of the kit to determine whether the subject has active TB.

In one aspect, the present invention provides kits monitoring the effectiveness of a treatment in a subject having active TB. The kits include reagents for determining the level of LCP1 and the level of VASN in a subject sample(s) and instructions for use of the kit to monitor the effectiveness of the treatment.

In one aspect, the present invention provides kits for determining whether a subject has active tuberculosis (TB). The kits include reagents for determining the level of VASN and the level of PFN1 in a subject sample(s) and instructions for use of the kit to determine whether the subject has active TB.

In one aspect, the present invention provides kits monitoring the effectiveness of a treatment in a subject having active TB. The kits include reagents for determining the level of VASN and the level of PFN1 in a subject sample(s) and instructions for use of the kit to monitor the effectiveness of the treatment.

In one aspect, the present invention provides kits for determining whether a subject has active tuberculosis (TB). The kits include reagents for determining the level of LCP1, the level of VASN, and the level of PFN1 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, and the level of PFN1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, and the level of PFN1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, and the level of PFN1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, and the level of TAGLN2 a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PGLYRP2, and the level of PFN1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PGLYRP2, and the level of PFN1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, and the level of IGFBP6 a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, and the level of IGFBP6 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of TAGLN2, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of TAGLN2, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of VASN, and the level of TAGLN2 a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of VASN, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level of PGLYRP2, the level of VASN, and the level of TAGLN2 a subject sample(s) and instructions for use of the kit to determine whether the subject has active TB.

In one aspect, the present invention provides kits monitoring the effectiveness of a treatment in a subject having active TB. The kits include reagents for determining the level of PGLYRP2, the level of VASN, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level of PGLYRP2, the level of VASN, and the level of PFN1 a subject sample(s) and instructions for use of the kit to determine whether the subject has active TB.

In one aspect, the present invention provides kits monitoring the effectiveness of a treatment in a subject having active TB. The kits include reagents for determining the level of PGLYRP2, the level of VASN, and the level of PFN1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, the level of PFN1, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of PFN1, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, the level of IGFBP6, and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of IGFBP6, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, the level of PFN1, and the level of IGFBP6 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of PFN1, and the level of IGFBP6 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, the level of PFN1, and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of PFN1, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, the level of PGLYRP2, and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of PGLYRP2, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, the level of PFN1, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of PFN1, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, the level of PFN1, and the level of VASN in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of PFN1, and the level of VASN in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of IGFBP6, the level of TAGLN2, and the level of VASN in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of IGFBP6, the level of TAGLN2, and the level of VASN in a subject sample(s) and instructions for use of the kit to monitor the effectiveness of the treatment.

In one aspect, the present invention provides kits determining whether a subject has active tuberculosis (TB). The kits include reagents for determining the level of CD14, the level of CPN2, the level of SEPP1, and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of SEPP1, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, the level of VASN, and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of VASN, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level of PGLYRP2, the level of CPN2, the level of VASN, and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level of PGLYRP2, the level of CPN2, the level of VASN, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of IGFBP6, the level of VASN, and the level of PFN1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of IGFBP6, the level of VASN, and the level of PFN1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, the level of IGFBP6, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of IGFBP6, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PFN1, the level of IGFBP6, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PFN1, the level of IGFBP6, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PFN1, the level of VASN, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PFN1, the level of VASN, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of TAGLN2, the level of IGFBP6, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of TAGLN2, the level of IGFBP6, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, the level of IGFBP6, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of IGFBP6, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PFN1, the level of PGLYRP2, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PFN1, the level of PGLYRP2, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, the level of VASN, and the level of IGFBP6 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of VASN, and the level of IGFBP6 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of TAGLN2, the level of VASN, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of TAGLN2, the level of VASN, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PFN1, the level of TAGLN2, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PFN1, the level of TAGLN2, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PFN1, the level of IGFBP6, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PFN1, the level of IGFBP6, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PFN1, the level of TAGLN2, and the level of VASN in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PFN1, the level of TAGLN2, and the level of VASN in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of TAGLN2, the level of IGFBP6, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of TAGLN2, the level of IGFBP6, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of PFN1, the level of PGLYRP2, the level of VASN, and the level of IGFBP6 in a subject sample(s) and instructions for use of the kit to determine whether the subject has active TB.

In one aspect, the present invention provides kits monitoring the effectiveness of a treatment in a subject having active TB. The kits include reagents for determining the level of PFN1, the level of PGLYRP2, the level of VASN, and the level of IGFBP6 in a subject sample(s) and instructions for use of the kit to monitor the effectiveness of the treatment.

In one aspect, the present invention provides kits for determining whether a subject has active tuberculosis (TB). The kits include reagents for determining the level of CPN2, the level of PFN1, the level of VASN, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CPN2, the level of PFN1, the level of VASN, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of TAGLN2, the level of SEPP1, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of TAGLN2, the level of SEPP1, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CPN2, the level of PFN1, the level of IGFBP6, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CPN2, the level of PFN1, the level of IGFBP6, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PFN1, the level of IGFBP6, and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PFN1, the level of IGFBP6, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level of CPN2, the level of PFN1, the level of TAGLN2, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CPN2, the level of PFN1, the level of TAGLN2, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of PFN1, the level of VASN, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of PFN1, the level of VASN, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of SEPP1, the level of VASN, and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of SEPP1, the level of VASN, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level of CPN2, the level of IGFBP6, the level of TAGLN2, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CPN2, the level of IGFBP6, the level of TAGLN2, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of PGLYRP2, the level of PFN1, the level of VASN, and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level of PGLYRP2, the level of PFN1, the level of VASN, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level of PGLYRP2, the level of PFN1, the level of VASN, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of PGLYRP2, the level of PFN1, the level of VASN, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, the level of SEPP1, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of SEPP1, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of CD14, the level of CPN2, the level of VASN, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of CD14, the level of CPN2, the level of VASN, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of LCP1, the level of VASN, the level of PFN1, and the level of IGFBP6 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of PFN1, and the level of IGFBP6 in a subject sample(s) and instructions for use of the kit to monitor the effectiveness of the treatment.

In one aspect, the present invention provides kits for determining whether a subject has active tuberculosis (TB). The kits include reagents for determining the level of LCP1, the level of VASN, the level of PFN1, and the level of LRG1 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of PFN1, and the level of LRG1 in a subject sample(s) and instructions for use of the kit to monitor the effectiveness of the treatment.

In one aspect, the present invention provides kits for determining whether a subject has active tuberculosis (TB). The kits include reagents for determining the level of LCP1, the level of VASN, the level of PFN1, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of PFN1, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level of LCP1, the level of VASN, the level of PFN1, and the level of APOA4 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of PFN1, and the level of APOA4 in a subject sample(s) and instructions for use of the kit to monitor the effectiveness of the treatment.

In one aspect, the present invention provides kits for determining whether a subject has active tuberculosis (TB). The kits include reagents for determining the level LCP1, the level of VASN, the level of PFN1, and the level of BCHE in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of PFN1, and the level of BCHE in a subject sample(s) and instructions for use of the kit to monitor the effectiveness of the treatment.

In one aspect, the present invention provides kits for determining whether a subject has active tuberculosis (TB). The kits include reagents for determining the level LCP1, the level of VASN, the level of PFN1, and the level of PI16 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of PFN1, and the level of PI16 in a subject sample(s) and instructions for use of the kit to monitor the effectiveness of the treatment.

In one aspect, the present invention provides kits for determining whether a subject has active tuberculosis (TB). The kits include reagents for determining the level LCP1, the level of VASN, the level of PFN1, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of PFN1, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level LCP1, the level of VASN, the level of PFN1, and the level of APOA1 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of PFN1, and the level of APOA1 in a subject sample(s) and instructions for use of the kit to monitor the effectiveness of the treatment.

In one aspect, the present invention provides kits for determining whether a subject has active tuberculosis (TB). The kits include reagents for determining the level LCP1, the level of VASN, the level of PFN1, and the level of IGFALS in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of PFN1, and the level of IGFALS in a subject sample(s) and instructions for use of the kit to monitor the effectiveness of the treatment.

In one aspect, the present invention provides kits for determining whether a subject has active tuberculosis (TB). The kits include reagents for determining the level LCP1, the level of VASN, the level of PFN1, and the level of CD14 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of PFN1, and the level of CD14 in a subject sample(s) and instructions for use of the kit to monitor the effectiveness of the treatment.

In one aspect, the present invention provides kits for determining whether a subject has active tuberculosis (TB). The kits include reagents for determining the level LCP1, the level of VASN, the level of PFN1, and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of PFN1, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level LCP1 and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level of LCP1 and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level LCP1, the level of VASN, and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level LCP1, the level of VASN, the level of TAGLN2, and the level of IGFBP6 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of TAGLN2, and the level of IGFBP6 in a subject sample(s) and instructions for use of the kit to monitor the effectiveness of the treatment.

In one aspect, the present invention provides kits for determining whether a subject has active tuberculosis (TB). The kits include reagents for determining the level LCP1, a level of VASN, a level of TAGLN2, and a level of LRG1 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, a level of VASN, a level of TAGLN2, and a level of LRG1 in a subject sample(s) and instructions for use of the kit to monitor the effectiveness of the treatment.

In one aspect, the present invention provides kits for determining whether a subject has active tuberculosis (TB). The kits include reagents for determining the level LCP1, the level of VASN, the level of TAGLN2, and the level of SEPP1 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of TAGLN2, and the level of SEPP1 in a subject sample(s) and instructions for use of the kit to monitor the effectiveness of the treatment.

In one aspect, the present invention provides kits for determining whether a subject has active tuberculosis (TB). The kits include reagents for determining the level LCP1 and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of LCP1 and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level LCP1, the level of VASN, and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, and the level of PGLYRP2 in a subject sample(s) and instructions for use of the kit to monitor the effectiveness of the treatment.

In one aspect, the present invention provides kits for determining whether a subject has active tuberculosis (TB). The kits include reagents for determining the level LCP1, the level of VASN, the level of PGLYRP2, and the level of PFN1 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of PGLYRP2, and the level of PFN1 in a subject sample(s) and instructions for use of the kit to monitor the effectiveness of the treatment.

In one aspect, the present invention provides kits for determining whether a subject has active tuberculosis (TB). The kits include reagents for determining the level LCP1, the level of VASN, the level of PGLYRP2, and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level of LCP1, the level of VASN, the level of PGLYRP2, and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level PFN1 and the level of PI16 in a subject sample(s) and instructions for use of the kit to determine whether the subject has active TB.

In one aspect, the present invention provides kits monitoring the effectiveness of a treatment in a subject having active TB. The kits include reagents for determining the level of PFN1 and the level of PI16 in a subject sample(s) and instructions for use of the kit to monitor the effectiveness of the treatment.

In one aspect, the present invention provides kits for determining whether a subject has active tuberculosis (TB). The kits include reagents for determining the level PFN1 and the level of PON1 in a subject sample(s) and instructions for use of the kit to determine whether the subject has active TB.

In one aspect, the present invention provides kits monitoring the effectiveness of a treatment in a subject having active TB. The kits include reagents for determining the level of PFN1 and the level of PON1 in a subject sample(s) and instructions for use of the kit to monitor the effectiveness of the treatment.

In one aspect, the present invention provides kits for determining whether a subject has active tuberculosis (TB). The kits include reagents for determining the level PFN1 and the level of PTGDS in a subject sample(s) and instructions for use of the kit to determine whether the subject has active TB.

In one aspect, the present invention provides kits monitoring the effectiveness of a treatment in a subject having active TB. The kits include reagents for determining the level of PFN1 and the level of PTGDS in a subject sample(s) and instructions for use of the kit to monitor the effectiveness of the treatment.

In one aspect, the present invention provides kits for determining whether a subject has active tuberculosis (TB). The kits include reagents for determining the level PI16 and the level of PON1 in a subject sample(s) and instructions for use of the kit to determine whether the subject has active TB.

In one aspect, the present invention provides kits monitoring the effectiveness of a treatment in a subject having active TB. The kits include reagents for determining the level of PI16 and the level of PON1 in a subject sample(s) and instructions for use of the kit to monitor the effectiveness of the treatment.

In one aspect, the present invention provides kits for determining whether a subject has active tuberculosis (TB). The kits include reagents for determining the level PI16 and the level of PTGDS in a subject sample(s) and instructions for use of the kit to determine whether the subject has active TB.

In one aspect, the present invention provides kits monitoring the effectiveness of a treatment in a subject having active TB. The kits include reagents for determining the level of PI16 and the level of PTGDS in a subject sample(s) and instructions for use of the kit to monitor the effectiveness of the treatment.

In one aspect, the present invention provides kits for determining whether a subject has active tuberculosis (TB). The kits include reagents for determining the level PON1 and the level of PTGDS in a subject sample(s) and instructions for use of the kit to determine whether the subject has active TB.

In one aspect, the present invention provides kits monitoring the effectiveness of a treatment in a subject having active TB. The kits include reagents for determining the level of PON1 and the level of PTGDS in a subject sample(s) and instructions for use of the kit to monitor the effectiveness of the treatment.

In one aspect, the present invention provides kits for determining whether a subject has active tuberculosis (TB). The kits include reagents for determining the level PFN1, the level of PI16, and the level of PON1 in a subject sample(s) and instructions for use of the kit to determine whether the subject has active TB.

In one aspect, the present invention provides kits monitoring the effectiveness of a treatment in a subject having active TB. The kits include reagents for determining the level PFN1, the level of PI16, and the level of PON1 in a subject sample(s) and instructions for use of the kit to monitor the effectiveness of the treatment.

In one aspect, the present invention provides kits for determining whether a subject has active tuberculosis (TB). The kits include reagents for determining the level PFN1, the level of PI16, and the level of PTGDS in a subject sample(s) and instructions for use of the kit to determine whether the subject has active TB.

In one aspect, the present invention provides kits monitoring the effectiveness of a treatment in a subject having active TB. The kits include reagents for determining the level PFN1, the level of PI16, and the level of PTGDS in a subject sample(s) and instructions for use of the kit to monitor the effectiveness of the treatment.

In one aspect, the present invention provides kits for determining whether a subject has active tuberculosis (TB). The kits include reagents for determining the level PON1, the level of PI16, and the level of PTGDS in a subject sample(s) and instructions for use of the kit to determine whether the subject has active TB.

In one aspect, the present invention provides kits monitoring the effectiveness of a treatment in a subject having active TB. The kits include reagents for determining the level PON1, the level of PI16, and the level of PTGDS in a subject sample(s) and instructions for use of the kit to monitor the effectiveness of the treatment.

In one aspect, the present invention provides kits for determining whether a subject has active tuberculosis (TB). The kits include reagents for determining the level PFN1, the level of PON1, and the level of PTGDS in a subject sample(s) and instructions for use of the kit to determine whether the subject has active TB.

In one aspect, the present invention provides kits monitoring the effectiveness of a treatment in a subject having active TB. The kits include reagents for determining the level PFN1, the level of PON1, and the level of PTGDS in a subject sample(s) and instructions for use of the kit to monitor the effectiveness of the treatment.

In one aspect, the present invention provides kits for determining whether a subject has active tuberculosis (TB). The kits include reagents for determining the level PFN1, the level of PI16, the level of PON1, and the level of PTGDS in a subject sample(s) and instructions for use of the kit to determine whether the subject has active TB.

In one aspect, the present invention provides kits monitoring the effectiveness of a treatment in a subject having active TB. The kits include reagents for determining the level PFN1, the level of PI16, the level of PON1, and the level of PTGDS in a subject sample(s) and instructions for use of the kit to monitor the effectiveness of the treatment.

In one aspect, the present invention provides kits for determining whether a subject has active tuberculosis (TB). The kits include reagents for determining the level VASN and the level of TAGLN2 in a subject sample(s) and instructions for use of the kit to determine whether the subject has active TB.

In one aspect, the present invention provides kits monitoring the effectiveness of a treatment in a subject having active TB. The kits include reagents for determining the level VASN and the level of TAGLN2 in a subject sample(s) and instructions for use of the kit to monitor the effectiveness of the treatment.

In one aspect, the present invention provides kits for determining whether a subject has active tuberculosis (TB). The kits include reagents for determining the level VASN and the level of PGLYRP2 in a subject sample(s) and instructions for use of the kit to determine whether the subject has active TB.

In one aspect, the present invention provides kits monitoring the effectiveness of a treatment in a subject having active TB. The kits include reagents for determining the level VASN and the level of PGLYRP2 in a subject sample(s) and instructions for use of the kit to monitor the effectiveness of the treatment.

In one embodiment, the kits further comprise reagents for determining the level of any one or more of the markers listed in Table 1 in a sample(s) from the subject.

In one embodiment, the kits further comprise reagents for determining the level of one or more additional markers selected from the group consisting of APOE, SELL, TNXB, COMP, LUM, PGLYRP2, HABP2, LRG1, QSOX1, S100A8, APOC3, LCP1, VASN, PFN1, IGFBP6, LRG1, PGLYRP2, APOA4, BCHE, PI16, SEPP1, APOA1, IGFALS, CD14, TAGLN2, CPN2, APOC1, PEPD, GP1BA and PTGDS in a sample(s) from the subject.

In one embodiment, the sample is from an HIV− subject. In another embodiment, the sample is from an HIV+ subject.

In one embodiment, the subject resides in North America or Europe.

In one aspect, the present invention provides methods for identifying an active tuberculosis (TB) marker. The methods include identifying proteins differentially expressed in a sample(s) from an HIV+ subject having active TB and identifying proteins differentially expressed in a sample(s) from an HIV− subject having active TB, thereby generating a provisional list of active TB markers; determining the level of one or more of the provisional markers in a control sample; and determining the level of the one or more provisional markers in a test sample, wherein a difference in the level of a marker in the control sample as compared to the level in the test sample identifies the marker as an active TB marker.

In one aspect, the present invention provides methods for determining whether a subject has active tuberculosis (TB). The methods include determining the level of each marker in any one of the combination of markers set forth in any one of Tables 3, 4, 6, 7, 8, 10, 11, and 12 in a sample(s) from the subject; comparing the level of each of the markers of the combination in the subject sample(s) with a level of each of the markers of the combination in a control sample(s), wherein a difference in the level of all of the markers of the combination in the subject sample(s) as compared to the level of all of the markers of the combination in the control sample(s) indicates that the subject has active TB.

In one aspect, the present invention provides methods for monitoring the effectiveness of a treatment in a subject having active tuberculosis (TB). The methods include determining the level of any one of the combination of markers set forth in any one of Tables 3, 4, 6, 7, 8, 10, 11, and 12 in a first sample(s) from the subject prior to the initiation of the treatment; determining the level of each of the markers of the combination in a second sample(s) from the subject after at least a portion of the treatment has been administered; comparing the level of each of the markers of the combination in the first sample(s) with a level of each of the markers of the combination in the second sample(s), wherein a difference in the level of all of the markers of the combination in the first sample(s) as compared to the level of all of the markers of the combination in the second sample(s) indicates that the treatment is effective.

In one aspect, the present invention provides methods for identifying a compound that is useful for treating a subject having active tuberculosis (TB). The methods include contacting an aliquot of a sample(s) from the subject with each member of a library of compounds; determining the effect of a member of the library of compounds on the level and/or activity of each marker in any one of the combination of markers set forth in any one of Tables 3, 4, 6, 7, 8, 10, 11, and 12 in each of the aliquots; and selecting a member of the library of compounds which modulates the level and/or the activity of each of the markers of the combination in an aliquot as compared to the level and/or activity of each of the markers of the combination in a control sample, thereby identifying a compound that is useful for treating a subject having active TB.

In one aspect, the present invention provides methods for treating a subject having active tuberculosis (TB). The methods include administering to the subject an effective amount of an agent that modulates the expression and/or activity of each marker in any one of the combination of markers set forth in any one of Tables 3, 4, 6, 7, 8, 10, 11, and 12, thereby treating the subject.

In one embodiment, the combination of markers has an area under the curve (AUC) of about 0.85 to about 1.00.

In one aspect, the present invention provides kits for determining whether a subject has active tuberculosis (TB). The lits include reagents for determining the level of each marker in any one of the combination of markers set forth in any one of Tables 3, 4, 6, 7, 8, 10, 11, and 12 in a subject sample(s) and instructions for use of the kit to determine whether the subject has active TB.

In one aspect, the present invention provides kits for monitoring the effectiveness of a treatment in a subject having active TB. The kits include reagents for determining the level of each marker in any one of the combination of markers set forth in any one of Tables 3, 4, 6, 7, 8, 10, 11, and 12 in a subject sample(s) and instructions for use of the kit to monitor the effectiveness of the treatment.

In one embodiment, the combination of markers has an area under the curve (AUC) of about 0.85 to about 1.00.

BRIEF DESCRIPTION OF THE DRAWINGS

FIGS. 1A-1F depict the differentially expressed proteins in serum of HIV– subjects with TB relative to latent TB and non-infected controls. The differentially expressed proteins are indicated by dots arranged in the functional groups indicated. Intensity values per protein were normalized and the ratios derived were displayed in logarithmic scale (y-axis). Medians and standard deviations of the expression ratio of TB versus latent TB and non-infected is shown. Proteins were sorted by increasing differential expression.

FIG. 1A depicts the differentially expressed proteins in serum of HIV– subjects with TB relative to latent TB and non-infected controls associated with the functional group, coagulation.

FIG. 1B depicts the differentially expressed proteins in serum of HIV– subjects with TB relative to latent TB and non-infected controls associated with the functional group, immune cell trafficking.

FIG. 1C depicts the differentially expressed proteins in serum of HIV– subjects with TB relative to latent TB and non-infected controls associated with the functional group, inflammatory response.

FIG. 1D depicts the differentially expressed proteins in serum of HIV– subjects with TB relative to latent TB and non-infected controls associated with the functional group, lipid transport and regulation.

FIG. 1E depicts the differentially expressed proteins in serum of HIV– subjects with TB relative to latent TB and non-infected controls associated with the functional group, tissue development.

FIG. 1F depicts the differentially expressed proteins in serum of HIV– subjects with TB relative to latent TB and non-infected controls associated with other miscellaneous functional groups.

FIG. 2 depicts the differential expression of candidate biomarkers in serum of subjects with active TB relative to latent TB, non-infected controls, and subjects with other pulmonary infections. The comparisons were done in the context of HIV+ or HIV– co-infections. Shown are color-coded expression change ratios for each biomarker and comparison. Red represents up to an 8-fold increase in the numerator vs the denominator denoted per comparison, with the darker color representing the larger increases. Blue represents up to an 8-fold decrease in the numerator vs the denominator, with the darker color representing the larger decreases. White represents no change between numerator and denominator TB=active TB; NI=non-infected; LI=latent TB infection; ORD=other respiratory disease.

DETAILED DESCRIPTION OF THE INVENTION

Figure 1C:
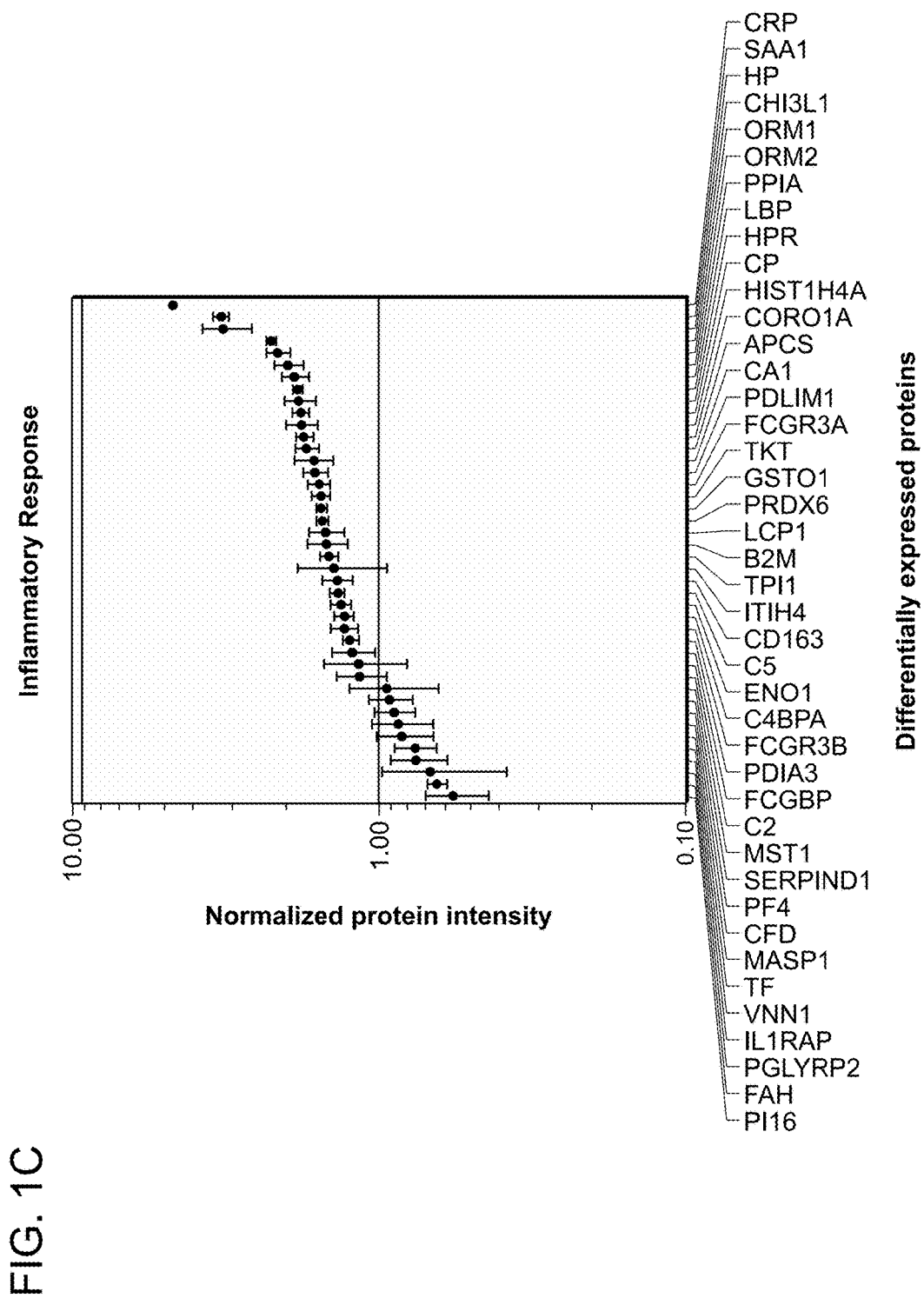

The present invention is based, at least in part, on the discovery of markers that are associated with active tuberculosis (TB). In particular, biomarkers associated with active TB have been discovered, prioritized, and validated in relevant in vitro experimental systems. The markers were identified as being expressed, e.g., essentially specifically expressed, in samples from subjects having active TB as compared to subjects having latent TB and/or other respiratory diseases (ORD) or pneumonias, such as community acquired pneumonia (viral or bacterial), non-tuberculous mycobacteria, pneumocysitis jiroveci pneumonia, methcillin resistant *Staphylococcus aureus* infection, viral pneumonia, and lung cancer.

Accordingly, the present invention provides sensitive and facile methods and kits for determining whether a subject has active TB, methods for identifying a compound that is useful for treating active TB, methods and kits for monitoring the effectiveness of a therapy for treating a subject having active TB, and methods for treating a subject having active TB by measuring and identifying particular markers, or particular combinations of markers.

Various aspects of the invention are described in further detail in the following subsections:

I. Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "marker" or "biomarker" is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median level, e.g., expression level, of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for, e.g., disease (prognostics and diagnostics), therapeutic effectiveness of a drug (theranostics) and of drug toxicity.

In some embodiments, the accuracy of a marker(s) useful in the compositions and methods of the present invention may be characterized by a Receiver Operating Characteristic curve ("ROC curve"). An ROC is a plot of the true positive rate against the false positive rate for the different possible cutpoints of a diagnostic marker(s). An ROC curve shows the relationship between sensitivity and specificity. That is, an increase in sensitivity will be accompanied by a decrease in specificity. The closer the curve follows the left axis and then the top edge of the ROC space, the more accurate the marker(s). Conversely, the closer the curve comes to the 45-degree diagonal of the ROC graph, the less accurate the marker(s). The area under the ROC is a measure of a marker(s) accuracy. The accuracy of the marker(s) depends on how well the marker(s) separates the group being tested into those with and without the disease in question. An area under the curve (referred to as "AUC") of 1 represents a perfect marker(s), while an area of 0.5 represents a less useful marker(s). Thus, in some embodiments, biomarker(s) and methods of the present invention have an AUC greater than about 0.50, an AUC greater than about 0.60, or an AUC greater than about 0.70.

"Tuberculosis" ("TB") is a multisystemic disease with myriad presentations and manifestations, and is the most common cause of infectious disease-related mortality worldwide. *Mycobacterium tuberculosis*, a tubercle *bacillus*, is the causative agent of TB. The lungs are the most common site for the development of TB (pulmonary TB), and about 85% of patients with TB present with pulmonary complaints. Nonetheless, "extrapulmonary TB", e.g., "disseminated TB", can occur as part of a primary or late, generalized infection. Extrapulmonary TB can affect bones and joints, bronchus, eye, intestines, larynx, peritoneum, meninges, pericardium, lymph node, organs of the male or female urinary and reproductive systems, skin, stomach, and/or urinary systems.

When a person is infected with *M tuberculosis*, the infection can take one of a variety of paths, most of which do not lead to actual TB. The infection may be cleared by the host immune system or suppressed into an inactive form called "latent tuberculosis infection", with resistant hosts controlling mycobacterial growth at distant foci before the development of active disease.

A subject has "latent tuberculosis ("LTB") (also referred to as "latent tuberculosis infection" ("LTBI")) when the subject is infected with *Mycobacterium tuberculosis* but does not have active tuberculosis disease. Subjects having latent tuberculosis are not infectious. The main risk is that approximately 10% of these patients (5% in the first two years after infection and 0.1% per year thereafter but higher risk if immunosuppressed) will go on to develop "active tuberculosis" ("active TB") and spread the disease at a later stage of their life if, for example, there is onset of a disease affecting the immune system (such as AIDS) or a disease whose treatment affects the immune system (e.g., chemotherapy in cancer or systemic steroids in asthma or Enbrel, Humira or Orencia in rheumatoid arthritis); malnutrition (which may be the result of illness or injury affecting the digestive system, or of a prolonged period of not eating, or disturbance in food availability such as famine, residence in refugee camp or concentration camp, or civil war; and/or degradation of the immune system due to aging.

"Miliary tuberculosis" (also known as "disseminated tuberculosis", "tuberculosis cutis acuta generalisata", and "Tuberculosis cutis disseminata") is a form of tuberculosis that is characterized by a wide dissemination into the human body and by the tiny size of the lesions (1-5 mm). Miliary tuberculosis is characterized by a chronic and contagious *Mycobacterium tuberculosis* infection that has spread to other organs of the body by the blood or lymph system. Its name comes from a distinctive pattern seen on a chest X-ray of many tiny spots distributed throughout the lung fields with the appearance similar to millet seeds—thus the term "military" tuberculosis. Miliary TB may infect any number of organs, including, for example, the lungs, liver, and spleen. Disseminated disease can occur within weeks of the primary infection, or may lie inactive for years before causing illness. Infants, the elderly, those infected with HIV, and those who take immune-suppressing medications are at higher risk for disseminated TB, because of their weaker immune systems.

The symptoms of a subject having TB are similar to the symptoms of a subject having an "other respiratory disease" or "ORD", such a pneumonia, and include, for example, cough (e.g., coughing that lasts three or more weeks, coughing up blood or sputum, chest pain, or pain with breathing or coughing), unintentional weight loss, fatigue, fever, night sweats, chills, and/or loss of appetite.

Methods to diagnose a subject as having active and/or latent TB are known in the art. The primary screening method for TB infection (active or latent) is the Mantoux tuberculin skin test with purified protein derivative (PPD). An in vitro blood test based on interferon-gamma release assay (IGRA) with antigens specific for *M. tuberculosis* can also be used to screen for latent TB infection. Chest X-rays and culturing of sputum samples may also be used.

A subject having latent TB usually has a skin test or blood test result indicating TB infection; has a normal chest x-ray and a negative sputum test; has TB bacteria in his/her body that are alive, but inactive; does not feel sick (e.g. does not have a cough and/or fever); and cannot spread TB bacteria to others. A subject having active TB usually has a positive skin test or tuberculosis blood test, may have an abnormal chest x-ray, or positive sputum smear or culture; has overt indications of illness (e.g., cough and/or fever), and can spread the disease to others.

Human immunodeficiency virus (HIV) is a lentivirus (slowly-replicating retrovirus) that causes acquired immunodeficiency syndrome (AIDS), an infectious disease in which progressive failure of the human immune system leads to life-threatening opportunistic infections and/or cancer.

HIV-1 testing is initially by an enzyme-linked immunosorbent assay (ELISA) to detect antibodies to HIV-1. Subjects are considered "HIV-negative" ("HIV−") if samples from the subject have a nonreactive result from the initial ELISA unless new exposure to an infected partner or partner of unknown HIV status has occurred. Subject samples with a reactive ELISA result are retested in duplicate. If the result of either duplicate test is reactive, the subject specimen is reported as repeatedly reactive and undergoes confirmatory testing with a more specific supplemental test (e.g., Western blot or an immunofluorescence assay (IFA)). Only subject samples that are repeatedly reactive by ELISA and positive by IFA or reactive by Western blot are considered "HIV-positive" ("HIV+") and indicative of HIV infection.

Specimens that are repeatedly ELISA-reactive occasionally provide an indeterminate Western blot result, which may be either an incomplete antibody response to HIV in an infected person or nonspecific reactions in an uninfected person.

Although IFA can be used to confirm infection in these ambiguous cases, this assay is not widely used. In general, a second specimen is collected more than a month later and retested for persons with indeterminate Western blot results. Although much less commonly available, nucleic acid testing (e.g., viral RNA or proviral DNA amplification method) can also help diagnosis in certain situations. In addition, a few tested specimens might provide inconclusive results because of a low quantity specimen. In these situations, a second specimen is collected and tested for HIV infection.

A "level of a marker" or "the level of a biomarker" refers to an amount of a marker present in a sample being tested. A level of a marker may be either in absolute level or amount (e.g., μg/ml) or a relative level or amount (e.g., relative intensity of signals).

A "higher level" or an "increase in the level" of marker refers to a level of a marker in a test sample that is greater than the standard error of the assay employed to assess the level of the marker, and is preferably at least twice, and more preferably three, four, five, six, seven, eight, nine, or ten or more times the level of marker in a control sample (e.g., a sample from a subject having latent TB, a subject having an ORD, an HIV− subject, an HIV+ subject, an HIV− subject having latent TB, and HIV+ subject having latent TB, an HIV− subject having an ORD, and HIV+ subject having an ORD, and/or, the average level of the marker in several control samples).

A "lower level" or a "decrease in the level" of a marker refers to a level of the marker in a test sample that is less than the standard error of the assay employed to assess the level of the marker, and preferably at least twice, and more preferably three, four, five, six, seven, eight, nine, or ten or more times less than the level of the marker in a control sample (e.g., a sample from a subject having latent TB, a subject having an ORD, an HIV− subject, an HIV+ subject, an HIV− subject having latent TB, and HIV+ subject having latent TB, an HIV− subject having an ORD, and HIV+ subject having an ORD, and/or, the average level of the marker in several control samples).

The term "known standard level" or "control level" refers to an accepted or pre-determined level of a marker which is used to compare the level of the marker in a sample derived from a subject. In one embodiment, the control level of a marker is based the level of the marker in a sample(s) from a subject(s) having latent TB. In another embodiment, the control level of a marker is based the level of the marker in a sample(s) from a subject(s) having an ORD. In another embodiment, the control level of a marker is based the level of the marker in a sample(s) from a subject(s) that is HIV−. In another embodiment, the control level of a marker is based the level of the marker in a sample(s) from a subject(s) that is HIV+. In another embodiment, the control level of a marker is based the level of the marker in a sample(s) from a subject(s) that is HIV− subject and has latent TB. In another embodiment, the control level of a marker is based the level of the marker in a sample(s) from a subject(s) that is HIV+ and has latent TB. In another embodiment, the control level of a marker is based the level of the marker in a sample(s) from a subject(s) that is HIV− subject and has an ORD. In another embodiment, the control level of a marker is based the level of the marker in a sample(s) from a subject(s) that is HIV+ subject and has an ORD, and/or, the average level of the marker in several control samples. In one embodiment, the control level of a marker in a sample from a subject is a level of the marker previously determined in a sample(s) from the subject. In yet another embodiment, the control level of a marker is based on the level of the marker in a sample from a subject(s) prior to the administration of a therapy for TB. In another embodiment, the control level of a marker is based on the level of the marker in a sample(s) from a subject(s) having active TB that is not contacted with a test compound. In another embodiment, the control level of a marker is based on the level of the marker in a sample(s) from a subject(s) having latent TB that is not contacted with a test compound. In another embodiment, the control level of a marker is based on the level of the marker in a sample(s) from a subject(s) having active TB that is contacted with a test compound. In another embodiment, the control level of a marker is based on the level of the marker in a sample(s) from a subject(s) having latent TB that is contacted with a test compound. In one embodiment, the control level of a marker is based on the expression level of the marker in a sample(s) from an animal model of TB, a cell, or a cell line derived from the animal model of TB.

Alternatively, and particularly as further information becomes available as a result of routine performance of the methods described herein, population-average values for "control" level of expression of a marker may be used. In other embodiments, the "control" level of a marker may be determined by determining the level of a marker in a subject sample obtained from a subject before the onset of active TB, from archived subject samples, and the like.

As used herein, the terms "patient" or "subject" refer to human and non-human animals, e.g., veterinary patients. The term "non-human animal" includes all vertebrates, e.g., mammals and non-mammals, such as non-human primates, mice, rabbits, sheep, dog, cat, horse, cow, chickens, amphibians, and reptiles. In one embodiment, the subject is a human, e.g., a pediatric and adult human. In one embodiment, a subject is HIV negative (HIV−). In another embodiment, the subject is HIV positive (HIV+). In another embodiment, the HIV status of the subject is unknown. In one embodiment, the subject resides in North America. In another embodiment, the subject resides in Europe. In another embodiment, the subject resides in Europe and is of European descent. In yet another embodiment, the subject resides in Europe and is not of European descent.

The term "sample" as used herein refers to a collection of similar cells or tissue isolated from a subject, as well as tissues, cells and fluids present within a subject. The term "sample" includes any body fluid (e.g., blood fluids, lymph, gynecological fluids, cystic fluid, urine, ocular fluids and fluids collected by bronchial lavage and/or peritoneal rinsing), or a cell from a subject. In one embodiment, the tissue or cell is removed from the subject. In another embodiment, the tissue or cell is present within the subject. Other subject samples include tear drops, serum, cerebrospinal fluid, feces, sputum and cell extracts. In one embodiment the sample is a blood sample. In another embodiment, the sample is a serum sample. In one embodiment, the biological sample contains protein molecules from the test subject. In another embodiment, the biological sample may contain mRNA molecules from the test subject or genomic DNA molecules from the test subject.

The term "determining" means methods which include detecting the presence or absence of marker(s) in the sample, quantifying the amount of marker(s) in the sample, and/or qualifying the type of biomarker. Measuring can be accomplished by methods known in the art and those further described herein.

As used herein, the various forms of the term "modulate" are intended to include stimulation (e.g., increasing or upregulating a particular response or activity) and inhibition (e.g., decreasing or downregulating a particular response or activity).

A kit is any manufacture (e.g. a package or container) comprising at least one reagent, e.g. a probe, a primer, or an antibody, for specifically detecting a marker of the invention, the manufacture being promoted, distributed, or sold as a unit for performing the methods of the present invention. In certain embodiments, a kit may include a substrate, e.g., a substrate comprising a capture reagent for one or more markers of the invention and/or a capture reagent bound to one or more markers of the invention. In some embodiments, such kits comprise instructions for determining the level of a marker(s) using mass spectrometry.

II. Markers of the Invention

The present invention is based upon the discovery of markers that are essentially specifically expressed in samples from subjects having active pulmonary tuberculosis (TB) (Table 1). These markers have been shown to be differentially present in samples of subjects (e.g., HIV− and HIV+ subjects) having active TB (i.e., active pulmonary TB) and control subjects.

Accordingly, the level of any one marker or any combination of markers listed in Tables 1 and found in a test sample compared to a control, or the presence or absence of one marker or combination of markers listed in Table 1 in the test sample may be used in the methods and kits of the present invention.

The markers of the invention are listed in Table 1 and are suitable for use in test samples from subjects in which the HIV status is unknown or in subjects in which the HIV status is known (i.e., subjects that are HIV+ or HIV−). The nucleotide and amino acid sequences of the markers are known in the art and may be found in, for example, the GenBank Accession numbers listed in Table 1, the entire contents of which are incorporated herein by reference.

TABLE 1

Markers of the Invention.

| Marker Name | Protein Description | UNIPROT_ID | UNIPROT ACCESSION | GENBANK ACCESSION |
|---|---|---|---|---|
| YWHAE | 14-3-3 protein epsilon | 1433E_HUMAN | P62258 | NP_006752.1 NM_006761.4 |
| YWHAZ | 14-3-3 protein zeta/delta | 1433Z_HUMAN | P63104 | NP_001129171.1 NP_001129172.1 NP_001129173.1 NP_001129174.1 NP_003397.1 NP_663723.1 NM_001135699.1 NM_001135700.1 NM_001135701.1 NM_001135702.1 NM_003406.3 NM_145690.2 |
| ORM1 | Alpha-1-acid glycoprotein 1 precursor | A1AG1_HUMAN | P02763 | NP_000598.2 NM_000607.2 |
| LRG1 | Leucine-rich alpha-2-glycoprotein precursor | A2GL_HUMAN | P02750 | NP_443204.1 NM_052972.2 |
| IGFALS | Insulin-like growth factor-binding protein complex acid labile subunit precursor | ALS_HUMAN | P35858 | NP_001139478.1 NP_004961.1 NM_001146006.1 NM_004970.2 |
| ANPEP | Aminopeptidase N | AMPN_HUMAN | P15144 | NP_001141.2 NM_001150.2 |
| LPA | Apolipoprotein(a) precursor | APOA_HUMAN | P08519 | NP_005568.2 NM_005577.2 |
| APOA1 | Apolipoprotein A-I precursor | APOA1_HUMAN | P02647 | NP_000030.1 NM_000039.1 |
| APOA4 | Apolipoprotein A-IV precursor | APOA4_HUMAN | P06727 | NP_000473.2 NM_000482.3 |
| APOC1 | Apolipoprotein C-I precursor | APOC1_HUMAN | P02654 | NP_001636.1 NM_001645.3 |
| APOC3 | Apolipoprotein C-III precursor | APOC3_HUMAN | P02656 | NP_000031.1 NM_000040.1 |
| APOE | Apolipoprotein E precursor | APOE_HUMAN | P02649 | NP_000032.1 NM_000041.2 |
| ATRN | Attractin precursor | ATRN_HUMAN | O75882 | NP_001193976.1 NP_647537.1 NP_647538.1 NM_001207047.1 NM_139321.2 NM_139322.2 |
| TGFBI | Transforming growth factor-beta-induced protein ig-h3 precursor | BGH3_HUMAN | Q15582 | NP_000349.1 NM_000358.2 |
| BTD | Biotinidase precursor | BTD_HUMAN | P43251 | NP_000051.1 NM_000060.2 |

TABLE 1-continued

Markers of the Invention.

| Marker Name | Protein Description | UNIPROT_ID | UNIPROT ACCESSION | GENBANK ACCESSION |
|---|---|---|---|---|
| CD163 | Scavenger receptor cysteine-rich type 1 protein M130 precursor | C163A_HUMAN | Q86VB7 | NP_004235.4 NP_981961.2 NM_004244.5 NM_203416.3 |
| CACNA2D1 | Voltage-dependent calcium channel subunit alpha-2/delta-1 precursor | CA2D1_HUMAN | P54289 | NP_000713.2 NM_000722.2 |
| CDH5 | Cadherin-5 precursor | CADH5_HUMAN | P33151 | NP_001786.2 NM_001795.3 |
| CA1 | Carbonic anhydrase 1 | CAH1_HUMAN | P00915 | NP_001122301.1 NP_001122302.1 NP_001122303.1 NP_001158302.1 NP_001729.1 NM_001128829.2 NM_001128830.2 NM_001128831.2 NM_001164830.1 NM_001738.3 |
| CA2 | Carbonic anhydrase 2 | CAH2_HUMAN | P00918 | NP_000058.1 NM_000067.2 |
| CPB2 | Carboxypeptidase B2 precursor | CBPB2_HUMAN | Q96IY4 | NP_001863.2 NM_001872.3 |
| CPN1 | Carboxypeptidase N catalytic chain precursor | CBPN_HUMAN | P15169 | NP_001299.1 NM_001308.2 |
| CD14 | Monocyte differentiation antigen CD14 precursor | CD14_HUMAN | P08571 | NP_000582.1 NP_001035110.1 NP_001167575.1 NP_001167576.1 NM_000591.3 NM_001040021.2 NM_001174104.1 NM_001174105.1 |
| BCHE | Cholinesterase precursor | CHLE_HUMAN | P06276 | NP_000046.1 NM_000055.2 |
| CLU | Clusterin precursor | CLUS_HUMAN | P10909 | NP_001822.3 NM_001831.3 |
| CNDP1 | Beta-Ala-His dipeptidase precursor | CNDP1_HUMAN | Q96KN2 | NP_116038.4 NM_032649.5 |
| CNTN1 | Contactin-1 precursor | CNTN1_HUMAN | Q12860 | NP_001242992.1 NP_001242993.1 NP_001834.2 NP_778203.1 NM_001256063.1 NM_001256064.1 NM_001843.3 NM_175038.2 |
| COMP | Cartilage oligomeric matrix protein precursor | COMP_HUMAN | P49747 | NP_000086.2 NM_000095.2 |
| CPN2 | Carboxypeptidase N subunit 2 precursor | CPN2_HUMAN | P22792 | NP_001073982.2 NM_001080513.2 |
| DBH | Dopamine beta-hydroxylase | DOPO_HUMAN | P09172 | NP_000778.3 NM_000787.3 |
| ECM1 | Extracellular matrix protein 1 precursor | ECM1_HUMAN | Q16610 | NP_001189787.1 NP_004416.2 NP_073155.2 NM_001202858.1 NM_004425.3 NM_022664.2 |
| PROCR | Endothelial protein C receptor precursor | EPCR_HUMAN | Q9UNN8 | NP_006395.2 NM_006404.3 |
| FCN3 | Ficolin-3 precursor | FCN3_HUMAN | O75636 | NP_003656.2 NP_775628.1 NM_003665.2 NM_173452.1 |
| GP1BA | Platelet glycoprotein Ib alpha chain precursor | GP1BA_HUMAN | P07359 | NP_000164.5 NM_000173.5 |
| GP5 | Platelet glycoprotein V precursor | GPV_HUMAN | P40197 | NP_004479.1 NM_004488.2 |
| GPX3 | Glutathione peroxidase 3 precursor | GPX3_HUMAN | P22352 | NP_002075.2 NM_002084.3 |

TABLE 1-continued

Markers of the Invention.

| Marker Name | Protein Description | UNIPROT_ID | UNIPROT ACCESSION | GENBANK ACCESSION |
|---|---|---|---|---|
| HIST2H2BE | Histone H2B type 2-E | H2B2E_HUMAN | Q16778 | NP_003519.1<br>NM_003528.2 |
| HABP2 | Hyaluronan-binding protein 2 precursor | HABP2_HUMAN | Q14520 | NP_001171131.1<br>NP_004123.1<br>NM_001177660.1<br>NM_004132.3 |
| HGFAC | Hepatocyte growth factor activator precursor | HGFA_HUMAN | Q04756 | NP_001519.1<br>NM_001528.2 |
| MST1 | Hepatocyte growth factor-like protein precursor | HGFL_HUMAN | P26927 | NP_066278.3<br>NM_020998.3 |
| HYOU1 | Hypoxia up-regulated protein 1 precursor | HYOU1_HUMAN | Q9Y4L1 | NP_001124463.1<br>NP_006380.1<br>NM_001130991.1<br>NM_006389.3 |
| IGFBP3 | Insulin-like growth factor-binding protein 3 precursor | IBP3_HUMAN | P17936 | NP_000589.2<br>NP_001013416.1<br>NM_000598.4<br>NM_001013398.1 |
| IGFBP6 | Insulin-like growth factor-binding protein 6 precursor | IBP6_HUMAN | P24592 | NP_002169.1<br>NM_002178.2 |
| IGF2 | Insulin-like growth factor II precursor | IGF2_HUMAN | P01344 | NP_000603.1<br>NP_001007140.2<br>NM_000612.4<br>NM_001007139.4 |
| CKM | Creatine kinase M-type | KCRM_HUMAN | P06732 | NP_001815.2<br>NM_001824.4 |
| KNG1 | Kininogen-1 precursor | KNG1_HUMAN | P01042 | NP_000884.1<br>NP_001095886.1<br>NM_000893.3<br>NM_001102416.2 |
| LCAT | Phosphatidylcholine-sterol acyltransferase precursor | LCAT_HUMAN | P04180 | NP_000220.1<br>NM_000229.1 |
| LGALS3BP | Galectin-3-binding protein precursor | LG3BP_HUMAN | Q08380 | NP_005558.1<br>NM_005567.3 |
| LUM | Lumican precursor | LUM_HUMAN | P51884 | NP_002336.1<br>NM_002345.3 |
| SELL | L-selectin precursor | LYAM1_HUMAN | P14151 | NP_000646.2<br>NM_000655.4 |
| MAN1A1 | Mannosyl-oligosaccharide 1,2-alpha-mannosidase IA | MA1A1_HUMAN | P33908 | NP_005898.2<br>NM_005907.3 |
| MASP1 | Mannan-binding lectin serine protease 1 precursor | MASP1_HUMAN | P48740 | NP_001027019.1<br>NP_001870.3<br>NP_624302.1<br>NM_001031849.2<br>NM_001879.5<br>NM_139125.3 |
| MASP2 | Mannan-binding lectin serine protease 2 precursor | MASP2_HUMAN | O00187 | NP_006601.2<br>NP_631947.1<br>NM_006610.3<br>NM_139208.2 |
| Mtb81 | Malate synthase G | MASZ_MYCTU | P0A5J4 | NP_216353.1<br>NP_336342.1<br>NC_000962.2<br>NC_002755.2<br>NC_018143.1 |
| MINPP1 | Multiple inositol polyphosphate phosphatase 1 precursor | MINP1_HUMAN | Q9UNW1 | NP_001171588.1<br>NP_001171589.1<br>NP_004888.2<br>NM_001178117.1<br>NM_001178118.1<br>NM_004897.4 |
| MTP51 | MPT51/MPB51 antigen | MPT51_MYCTU | P0A4V6 | NP_338462.1<br>NC_002755.2<br>NC_018143.1<br>NC_000962.2 |
| NCAM1 | Neural cell adhesion molecule 1 precursor | NCAM1_HUMAN | P13591 | NP_000606.3<br>NP_001070150.1<br>NP_001229537.1<br>NP_851996.2<br>NM_000615.6<br>NM_001076682.3<br>NM_001242608.1<br>NM_181351.4 |

TABLE 1-continued

Markers of the Invention.

| Marker Name | Protein Description | UNIPROT_ID | UNIPROT ACCESSION | GENBANK ACCESSION |
|---|---|---|---|---|
| NID1 | Nidogen-1 precursor | NID1_HUMAN | P14543 | NP_002499.2 NM_002508.2 |
| PCSK9 | Proprotein convertase subtilisin/kexin type 9 precursor | PCSK9_HUMAN | Q8NBP7 | NP_777596.2 NM_174936.3 |
| PDLIM1 | PDZ and LIM domain protein 1 | PDLI1_HUMAN | O00151 | NP_066272.1 NM_020992.3 |
| PEPD | Xaa-Pro dipeptidase | PEPD_HUMAN | P12955 | NP_000276.2 NP_001159528.1 NP_001159529.1 NM_000285.3 NM_001166056.1 NM_001166057.1 |
| PGLYRP2 | N-acetylmuramoyl-L-alanine amidase precursor | PGRP2_HUMAN | Q96PD5 | NP_443122.3 NM_052890.3 |
| GPLD1 | Phosphatidylinositol-glycan-specific phospholipase D precursor | PHLD_HUMAN | P80108 | NP_001494.2 NM_001503.3 |
| PI16 | Peptidase inhibitor 16 precursor | PI16_HUMAN | Q6UXB8 | NP_001186088.1 NP_699201.2 NM_001199159.1 NM_153370.2 |
| LCP1 | Plastin-2 | PLSL_HUMAN | P13796 | NP_002289.2 NM_002298.4 |
| PON1 | Serum paraoxonase/arylesterase 1 | PON1_HUMAN | P27169 | NP_000437.3 NM_000446.5 |
| PRDX2 | Peroxiredoxin-2 | PRDX2_HUMAN | P32119 | NP_005800.3 NP_859428.1 NM_005809.4 NM_181738.1 |
| PRG4 | Proteoglycan 4 precursor | PRG4_HUMAN | Q92954 | NP_001121180.1 NP_001121181.1 NP_001121182.1 NP_005798.2 NM_001127708.1 NM_001127709.1 NM_001127710.1 NM_005807.3 |
| PFN1 | Profilin-1 | PROF1_HUMAN | P07737 | NP_005013.1 NM_005022.3 |
| PROS1 | Vitamin K-dependent protein S precursor | PROS_HUMAN | P07225 | NP_000304.2 NM_000313.3 |
| PTGDS | Prostaglandin-H2 D-isomerase precursor | PTGDS_HUMAN | P41222 | NP_000945.3 NM_000954.5 |
| PTPRG | Receptor-type tyrosine protein phosphatase gamma precursor | PTPRG_HUMAN | P23470 | NP_002832.3 NM_002841.3 |
| QSOX1 | Sulfhydryl oxidase 1 precursor | QSOX1_HUMAN | O00391 | NP_001004128.1 NP_002817.2 NM_001004128.2 NM_002826.4 |
| S100A8 | Protein S100-A8 | S10A8_HUMAN | P05109 | NP_002955.2 NM_002964.4 |
| S100A9 | Protein S100-A9 | S10A9_HUMAN | P06702 | NP_002956.1 NM_002965.3 |
| SEPP1 | Selenoprotein P precursor | SEPP1_HUMAN | P49908 | NP_001078955.1 NP_005401.3 NM_001085486.1 NM_005410.2 |
| SHBG | Sex hormone-binding globulin precursor | SHBG_HUMAN | P04278 | NP_001031.2 NP_001139752.1 NP_001139753.1 NM_001040.3 NM_001146280.1 NM_001146281.1 |
| SPP2 | Secreted phosphoprotein 24 precursor | SPP24_HUMAN | Q13103 | NP_008875.1 NM_006944.2 |
| SPARC | SPARC precursor | SPRC_HUMAN | P09486 | NP_003109.1 NM_003118.3 |
| TAGLN2 | Transgelin-2 | TAGL2_HUMAN | P37802 | NP_003555.1 NM_003564.1 |
| TNXB | Tenascin-X precursor | TENX_HUMAN | P22105 | NP_061978.6 NP_115859.2 NM_019105.6 NM_032470.3 |

TABLE 1-continued

Markers of the Invention.

| Marker Name | Protein Description | UNIPROT_ID | UNIPROT ACCESSION | GENBANK ACCESSION |
|---|---|---|---|---|
| CLEC3B | Tetranectin precursor | TETN_HUMAN | P05452 | NP_003269.2<br>NM_003278.2 |
| TLN1 | Talin-1 | TLN1_HUMAN | Q9Y490 | NP_006280.3<br>NM_006289.3 |
| THBS1 | Thrombospondin-1 precursor | TSP1_HUMAN | P07996 | NP_003237.2<br>NM_003246.2 |
| VASN | Vasorin precursor | VASN_HUMAN | Q6EMK4 | NP_612449.2<br>NM_138440.2 |
| VCAM1 | Vascular cell adhesion protein 1 precursor | VCAM1_HUMAN | P19320 | NP_001069.1<br>NP_001186763.1<br>NP_542413.1<br>NM_001078.3<br>NM_001199834.1<br>NM_080682.2 |
| VTN | Vitronectin precursor | VTNC_HUMAN | P04004 | NP_000629.3<br>NM_000638.3 |
| VWF | von Willebrand factor precursor | VWF_HUMAN | P04275 | NP_000543.2<br>NM_000552.3 |
| ZYX | Zyxin | ZYX_HUMAN | Q15942 | NP_001010972.1<br>NP_003452.1<br>NM_001010972.1<br>NM_003461.4 |

In one embodiment, the one or more additional markers is selected from the group consisting of APOE, SELL, TNXB, COMP, LUM, PGLYRP2, HABP2, LRG1, QSOX1, S100A8, APOC3, LCP1, VASN, PFN1, IGFBP6, LRG1, PGLYRP2, APOA4, BCHE, PI16, SEPP1, APOA1, IGFALS, CD14, TAGLN2, CPN2, APOC1, PEPD, GP1BA and PTGDS.

In certain aspects of the invention, a single marker (e.g., any one of the markers listed in Table 1) may be used in the methods and compositions of the invention. In one embodiment, the one or more markers is selected from the group consisting of CPB2, GP1BA, GP5, GPX3, PROCR, VWF, ATRN, CD14, DBH, SELL, VCAM1, S100A8, S100A9, CD163, CPN1, FCN3, HIST2H2BE, KNG1, MASP1, MASP2, PROS1, YWHAZ, CA1, ORM1, PDLIM1, PGLYRP2, LCAT, LPA, PCSK9, PON1, PTGDS, APOA1, APOA4, APOC1, APOC3, APOE, ANPEP, BCHE, BTD, CDH5, CLEC3B, CLU, CNTN1, ECM1, GPLD1, HABP2, HGFAC, HYOU1, IGFALS, IGFBP3, IGFBP6, LCP1, LGALS3BP, LUM, MINPP1, MST1, NCAM1, NID1, PEPD, PFN1, PRG4, QSOX1, SEPP1, SHBG, SPARC, TGFBI, THBS1, TLN1, TNXB, VASN, VTN, YWHAE, CA2, CKM, CNDP1, COMP, IGF2, LRG1, PI16, PRDX2, PTPRG, SPP2, TAGLN2, ZYX, MTB81, MTB51, CACNA2D1, CPN2, and MAN1A1.

In one embodiment, the markers is selected from the group consisting of APOE, SELL, TNXB, COMP, LUM, PGLYRP2, HABP2, LRG1, QSOX1, S100A8, APOC3, LCP1, VASN, PFN1, IGFBP6, LRG1, PGLYRP2, APOA4, BCHE, PI16, SEPP1, APOA1, IGFALS, CD14, TAGLN2, CPN2, APOC1, PEPD, GP1BA and PTGDS.

In one embodiment, the subject is HIV− and the marker for use in the methods and compositions of the invention is APOE. In one embodiment, the subject is HIV− and the marker is SELL. In one embodiment, the subject is HIV− and the marker is TNXB. In one embodiment, the subject is HIV− and the marker is COMP. In one embodiment, the subject is HIV− and the marker is LUM. In one embodiment, the subject is HIV− and the marker is PGLYRP2. In one embodiment, the subject is HIV− and the marker is HABP2. In one embodiment, the subject is HIV− and the marker is LRG1. In one embodiment, the subject is HIV− and the marker is QSOX1. In one embodiment, the subject is HIV− and the marker is S100A8. In one embodiment, the subject is HIV− and the marker is APOC3. In one embodiment, the subject is HIV− and the marker is CD14. In one embodiment, the subject is HIV− and the marker is SEPP1. In one embodiment, the subject is HIV− and the marker is APOC1. In one embodiment, the subject is HIV− and the marker is PEPD. In one embodiment, the subject is HIV− and the marker is GP1BA. In one embodiment, the subject is HIV+ and the marker is LCP1. In one embodiment, the subject is HIV+ and the marker is VASN. In one embodiment, the subject is HIV+ and the marker is PFN1. In one embodiment, the subject is HIV+ and the marker is IGFBP6. In one embodiment, the subject is HIV+ and the marker is LRG1. In one embodiment, the subject is HIV+ and the marker is PGLYRP2. In one embodiment, the subject is HIV+ and the marker is APOA4. In one embodiment, the subject is HIV+ and the marker is BCHE. In one embodiment, the subject is HIV+ and the marker is PI16. In one embodiment, the subject is HIV+ and the marker is SEPP1. In one embodiment, the subject is HIV+ and the marker is APOA1. In one embodiment, the subject is HIV+ and the marker is IGFALS. In one embodiment, the subject is HIV+ and the marker is CD14. In one embodiment, the subject is HIV+ and the marker is TAGLN2. In one embodiment, the subject is HIV+ and the marker is PTGDS. In one embodiment, the subject is HIV+ and the marker is CPN2.

In some embodiments, the methods may further comprise determining the level of a marker selected from the group consisting of the markers listed in Table 1. In other embodiments, the methods may further comprise determining the level of one or more markers selected from the group consisting of CPB2, GP1BA, GP5, GPX3, PROCR, VWF, ATRN, CD14, DBH, SELL, VCAM1, S100A8, S100A9, CD163, CPN1, FCN3, HIST2H2BE, KNG1, MASP1, MASP2, PROS1, YWHAZ, CA1, ORM1, PDLIM1, PGLYRP2, LCAT, LPA, PCSK9, PON1, PTGDS, APOA1, APOA4, APOC1, APOC3, APOE, ANPEP, BCHE, BTD, CDH5, CLEC3B, CLU, CNTN1, ECM1, GPLD1, HABP2, HGFAC, HYOU1, IGFALS, IGFBP3, IGFBP6, LCP1, LGALS3BP, LUM, MINPP1, MST1, NCAM1, NID1, PEPD, PFN1, PRG4, QSOX1, SEPP1, SHBG, SPARC, TGFBI, THBS1, TLN1, TNXB, VASN, VTN, YWHAE, CA2, CKM, CNDP1, COMP, IGF2, LRG1, PI16, PRDX2, PTPRG, SPP2, TAGLN2, ZYX, MTB81, MTB51, CACNA2D1, CPN2, and MAN1A1.

In other aspects of the invention, more than one marker, e.g., a plurality of markers, e.g., two, three, four, five, six, seven, eight, nine, ten, eleven, or more markers, may be used in the methods and compositions of the invention. For example, in one embodiment, the combination of markers suitable for use in the methods and compositions of the invention include one of the combination of markers set forth in Table 3. In one embodiment, the subject is HIV−. In another embodiment, the combination of markers suitable for use in the methods and compositions of the invention include one of the combination of markers set forth in Table 4. In one embodiment, the subject is HIV+. In another embodiment, the combination of markers suitable for use in the methods and compositions of the invention include one of the combination of markers set forth in Table 6. In one embodiment, the subject is HIV−. In another embodiment, the combination of markers suitable for use in the methods and compositions of the invention include one of the combination of markers set forth in Table 7. In one embodiment, the subject is HIV−. In another embodiment, the combination of markers suitable for use in the methods and compositions of the invention include one of the combination of markers set forth in Table 8. In one embodiment, the subject is HIV−. In another embodiment, the combination of markers suitable for use in the methods and compositions of the invention include one of the combination of markers set forth in Table 10. In one embodiment, the subject is HIV+. In another embodiment, the combination of markers suitable for use in the methods and compositions of the invention include one of the combination of markers set forth in Table 11. In one embodiment, the subject is HIV+. In another embodiment, the combination of markers suitable for use in the methods and compositions of the invention include one of the combination of markers set forth in Table 12. In one embodiment, the subject is HIV+.

In one embodiment, the subject is HIV− and the markers for use in the methods and compositions of the invention include CD14 and APOE. In one embodiment, the subject is HIV− and the markers include PEPD and SELL. In one embodiment, the subject is HIV− and the markers include CD14, APOE, and SELL. In one embodiment, the subject is HIV− and the markers include PEPD, TNXB, and SELL. In one embodiment, the subject is HIV− and the markers include PEPD, COMP, and SELL. In one embodiment, the subject is HIV− and the markers include PEPD, QSOX1, and SELL. In one embodiment, the subject is HIV− and the markers include PEPD, CD14, and SELL. In one embodiment, the subject is HIV− and the markers include PEPD, SEPP1, and SELL. In one embodiment, the subject is HIV− and the markers include PEPD, LUM, and SELL. In one embodiment, the subject is HIV− and the markers include SELL, SEPP1, and TNXB. In one embodiment, the subject is HIV− and the markers include APOC1, QSOX1, and SELL. In one embodiment, the subject is HIV− and the markers include TNXB, QSOX1, and SELL. In one embodiment, the subject is HIV− and the markers include COMP, SEPP1, and SELL. In one embodiment, the subject is HIV− and the markers include LUM, SEPP1, and SELL. In one embodiment, the subject is HIV− and the markers include SEPP1, QSOX1, and SELL. In one embodiment, the subject is HIV− and the markers include APOC1, CD14, and PEPD.

In one embodiment, the subject is HIV− and the markers include APOC1, COMP, and SELL. In one embodiment, the subject is HIV− and the markers include APOC1, QSOX1, and CD14. In one embodiment, the subject is HIV− and the markers include APOC1, PEPD, and SELL. In one embodiment, the subject is HIV− and the markers include CD14, APOE, SELL, and TNXB. In one embodiment, the subject is HIV− and the markers include CD14, APOE, SELL, and COMP. In one embodiment, the subject is HIV− and the markers include CD14, APOE, SELL, and LUM. In one embodiment, the subject is HIV− and the markers include CD14, APOE, SELL, and PGLYRP2. In one embodiment, the subject is HIV− and the markers include CD14, APOE, SELL, and HABP2. In one embodiment, the subject is HIV− and the markers include CD14, APOE, SELL, and LRG1. In one embodiment, the subject is HIV− and the markers include CD14, APOE, SELL, and QSOX1. In one embodiment, the subject is HIV− and the markers include CD14, APOE, SELL, and S100A8. In one embodiment, the subject is HIV− and the markers include CD14, APOE, and APOC3. In one embodiment, the subject is HIV− and the markers include CD14, APOE, APOC3, and PGLYRP2. In one embodiment, the subject is HIV− and the markers include CD14, APOE, APOC3, and SELL. In one embodiment, the subject is HIV− and the markers include CD14, APOE, APOC3, and HABP2. In one embodiment, the subject is HIV− and the markers include GP1BA, PEPD, SELL, and TNXB. In one embodiment, the subject is HIV− and the markers include COMP, PEPD, SELL, and TNXB. In one embodiment, the subject is HIV− and the markers include COMP, PEPD, SELL, and QSOX1. In one embodiment, the subject is HIV− and the markers include COMP, PEPD, SELL, and LUM. In one embodiment, the subject is HIV− and the markers include CD14, PEPD, SELL, and TNXB. In one embodiment, the subject is HIV- and the markers include CD14, PEPD, SELL, and SEPP1. In one embodiment, the subject is HIV- and the markers include CD14, PEPD, SELL, and QSOX1. In one embodiment, the subject is HIV− and the markers include COMP, PEPD, SELL, and GP1BA. In one embodiment, the subject is HIV− and the markers include APOC1, PEPD, SELL, and COMP. In one embodiment, the subject is HIV− and the markers include LUM, PEPD, SELL, and TNXB. In one embodiment, the subject is HIV− and the markers include APOC1, PEPD, SELL, and CD14. In one embodiment, the subject is HIV− and the markers include COMP, PEPD, SELL, and SEPP1. In one embodiment, the subject is HIV− and the markers include QSOX1, PEPD, SELL, and TNXB. In one embodiment, the subject is HIV− and the markers include LUM, PEPD, SELL, and SEPP1. In one embodiment, the subject is HIV− and the markers include CD14, PEPD, SELL, and COMP. In one embodiment, the subject is HIV− and the markers include TNXB, PEPD, SELL, and SEPP1. In one embodiment, the subject is HIV− and the markers include CD14, PEPD, SELL, and GP1BA. In one embodiment, the subject is HIV− and the markers include APOC1, PEPD, SELL, and TNXB. In one embodiment, the subject is HIV− and the markers include QSOX1, PEPD, SELL, and SEPP1. In one embodiment, the subject is HIV− and the markers include CD14, PEPD, SELL, and LUM. In one embodiment, the subject is HIV− and the markers include LUM, PEPD, SELL, and QSOX1. In one embodiment, the subject is HIV− and the markers include APOC1, COMP, SELL, and SEPP1. In one embodiment, the subject is HIV− and the markers include GP1BA, PEPD, SELL, and QSOX1. In one embodiment, the subject is HIV− and the markers include APOC1, PEPD, SELL, and LUM. In one embodiment, the subject is HIV− and the markers include APOC1, PEPD, SELL, and QSOX1. In one embodiment, the subject is HIV− and the markers include APOC1, PEPD, SELL, and SEPP1. In one embodiment, the subject is HIV− and the markers include APOC1, COMP, SELL, and QSOX1. In one embodiment, the subject is HIV− and the markers include APOC1, CD14, SELL, and QSOX1. In one embodiment, the subject is HIV− and the markers include APOC1, QSOX1, SELL, and SEPP1. In one embodiment, the subject is HIV− and the markers include APOC1, LUM, SELL, and QSOX1. In one embodiment, the subject is HIV− and the markers include CD14, GP1BA, SELL, and QSOX1. In one embodiment, the subject is HIV− and the markers include GP1BA, PEPD, SELL, and LUM. In one embodiment, the subject is HIV− and the markers include APOC1, QSOX1, SELL, and TNXB. In one embodiment, the subject is HIV− and the markers include GP1BA, PEPD, SELL, and SEPP1. In one embodiment, the subject is HIV− and the markers include QSOX1, TNXB, SELL, and SEPP1. In one embodiment, the subject is HIV− and the markers include LUM, QSOX1, SELL, and SEPP1. In one embodiment, the subject is HIV− and the markers include COMP, GP1BA, SELL, and SEPP1. In one embodiment, the subject is HIV− and the markers include APOC1, PEPD, SELL, and GP1BA. In one embodiment, the subject is HIV− and the markers include COMP, QSOX1, SELL, and SEPP1. In one embodiment, the subject is HIV− and the markers include COMP, LUM, SELL, and SEPP1. In one embodiment, the subject is HIV− and the markers include CD14, QSOX1, SELL, and SEPP1. In one embodiment, the subject is HIV− and the markers include COMP, TNXB, SELL, and SEPP1. In one embodiment, the subject is HIV− and the markers include CD14, APOC1, GP1BA, and QSOX1. In one embodiment, the subject is HIV− and the markers include CD14, QSOX1, SELL, and TNXB. In one embodiment, the subject is HIV- and the markers include APOC1, TNXB, SELL, and SEPP1. In one embodiment, the subject is HIV− and the markers include APOC1, GP1BA, SELL, and QSOX1. In one embodiment, the subject is HIV− and the markers include APOC1, PEPD, CD14, and GP1BA. In one embodiment, the subject is HIV− and the markers include CD14, COMP, SELL, and GP1BA. In one embodiment, the subject is HIV− and the markers include CD14, APOC1, GP1BA, and TNXB. In one embodiment, the subject is HIV− and the markers include CD14, APOC1, COMP, and GP1BA. In one embodiment, the subject is HIV− and the markers include COMP, QSOX1, SELL, and TNXB. In one embodiment, the subject is HIV− and the markers include GP1BA, QSOX1, SELL, and TNXB. In one embodiment, the subject is HIV− and the markers include LUM, QSOX1, SELL, and TNXB. In one embodiment, the subject is HIV− and the markers include GP1BA, QSOX1, SELL, and SEPP1. In one embodiment, the subject is HIV- and the markers include APOC1, LUM, SELL, and SEPP1. In one embodiment, the subject is HIV− and the markers include APOC1, CD14, GP1BA, and LUM. In one embodiment, the subject is HIV− and the markers include GP1BA, SEPP1, SELL, and TNXB. In one embodiment, the subject is HIV− and the markers include CD14, LUM, SELL, and SEPP1. In one embodiment, the subject is HIV− and the markers include COMP, CD14, SELL, and TNXB. In one embodiment, the subject is HIV− and the markers include CD14, SEPP1, SELL, and TNXB. In one embodiment, the subject is HIV− and the markers include GP1BA, LUM, SELL, and SEPP1. In one embodiment, the subject is HIV− and the markers include CD14, COMP, SELL, and SEPP1. In one embodiment, the subject is HIV− and the markers include LUM, SEPP1, SELL, and TNXB.

In one embodiment, the subject is HIV− and the markers include APOC1, CD14, SELL, and TNXB. In one embodiment, the subject is HIV− and the markers include CD14, GP1BA, SELL, and TNXB. In one embodiment, the subject is HIV− and the markers include APOC1, CD14, GP1BA, and SEPP1. In one embodiment, the subject is HIV− and the markers include APOC1, CD14, SELL, and LUM. In one embodiment, the subject is HIV- and the markers include APOC1, COMP, SELL, and GP1BA. In one embodiment, the subject is HIV− and the markers include APOC1, CD14, SELL, and COMP. In one embodiment, the subject is HIV− and the markers include APOC1, CD14, PEPD, and LUM. In one embodiment, the subject is HIV− and the markers include COMP, TNXB, SELL, and LUM. In one embodiment, the subject is HIV− and the markers include GP1BA, CD14, SELL, and SEPP1. In one embodiment, the subject is HIV− and the markers include TNXB, CD14, SELL, and LUM. In one embodiment, the subject is HIV− and the markers include GP1BA, CD14, SELL, and LUM. In one embodiment, the subject is HIV− and the markers include APOC1, COMP, SELL, and LUM. In one embodiment, the subject is HIV− and the markers include APOC1, COMP, SELL, and TNXB. In one embodiment, the subject is HIV− and the markers include COMP, CD14, GP1BA, and SEPP1. In one embodiment, the subject is HIV− and the markers include GP1BA, CD14, SEPP1, and LUM. In one embodiment, the subject is HIV− and the markers include GP1BA, CD14, SEPP1, and TNXB. In one embodiment, the subject is HIV− and the markers include APOC1, CD14, QSOX1, and SEPP1. In one embodiment, the subject is HIV− and the markers include APOC1, CD14, COMP, and PEPD. In one embodiment, the subject is HIV− and the markers include COMP, GP1BA, SELL, and TNXB. In one embodiment, the subject is HIV− and the markers include APOC1, CD14, QSOX1, and LUM. In one embodiment, the subject is HIV− and the markers include APOC1, CD14, PEPD, and TNXB. In one embodiment, the subject is HIV+ and the markers include LCP1 and VASN. In one embodiment, the subject is HIV+ and the markers include LCP1 and PFN1. In one embodiment, the subject is HIV+ and the markers include VASN and PFN1. In one embodiment, the subject is HIV+ and the markers include CD14, CPN2, and PFN1. In one embodiment, the subject is HIV+ and the markers include CD14, CPN2, and TAGLN2. In one embodiment, the subject is HIV+ and the markers include CD14, PGLYRP2, and PFN1. In one embodiment, the subject is HIV+ and the markers include CD14, CPN2, and IGFBP6. In one embodiment, the subject is HIV+ and the markers include CD14, PGLYRP2, and TAGLN2. In one embodiment, the subject is HIV+ and the markers include CD14, VASN, and TAGLN2. In one embodiment, the subject is HIV+ and the markers include VASN, PGLYRP2, and TAGLN2. In one embodiment, the subject is HIV+ and the markers include VASN, PGLYRP2, and PFN1. In one embodiment, the subject is HIV+ and the markers include LCP1, VASN, and PFN1. In one embodiment, the subject is HIV+ and the markers include CD14, CPN2, PFN1, and PGLYRP2. In one embodiment, the subject is HIV+ and the markers include CD14, CPN2, IGFBP6, and TAGLN2. In one embodiment, the subject is HIV+ and the markers include CD14, CPN2, PFN1, and IGFBP6. In one embodiment, the subject is HIV+ and the markers include CD14, CPN2, PFN1, and TAGLN2. In one embodiment, the subject is HIV+ and the markers include CD14, CPN2, PGLYRP2, and TAGLN2. In one embodiment, the subject is HIV+ and the markers include CD14, CPN2, PFN1, and SEPP1. In one embodiment, the subject is HIV+ and the markers include CD14, CPN2, PFN1, and VASN. In one embodiment, the subject is HIV+ and the markers include CD14, VASN, IGFBP6, and TAGLN2. In one embodiment, the subject is HIV+ and the markers include CD14, CPN2, SEPP1, and TAGLN2. In one embodiment, the subject is HIV+ and the markers include CD14, CPN2, VASN, and TAGLN2. In one embodiment, the subject is HIV+ and the markers include CPN2, PGLYRP2, VASN, and TAGLN2. In one embodiment, the subject is HIV+ and the markers include CD14, PFN1, IGFBP6, and VASN. In one embodiment, the subject is HIV+ and the markers include CD14, CPN2, IGFBP6, and PGLYRP2. In one embodiment, the subject is HIV+ and the markers include CD14, PFN1, IGFBP6, and PGLYRP2. In one embodiment, the subject is HIV+ and the markers include CD14, PFN1, PGLYRP2, and VASN. In one embodiment, the subject is HIV+ and the markers include CD14, PGLYRP2, IGFBP6, and TAGLN2. In one embodiment, the subject is HIV+ and the markers include CD14, CPN2, IGFBP6, and SEPP1. In one embodiment, the subject is HIV+ and the markers include CD14, PFN1, PGLYRP2, and SEPP1. In one embodiment, the subject is HIV+ and the markers include CD14, CPN2, IGFBP6, and VASN. In one embodiment, the subject is HIV+ and the markers include CD14, PGLYRP2, TAGLN2, and VASN. In one embodiment, the subject is HIV+ and the markers include CD14, PFN1, PGLYRP2, and TAGLN2. In one embodiment, the subject is HIV+ and the markers include CD14, PFN1, IGFBP6, and SEPP1. In one embodiment, the subject is HIV+ and the markers include CD14, PFN1, TAGLN2, and VASN. In one embodiment, the subject is HIV+ and the markers include CD14, SEPP1, IGFBP6, and TAGLN2. In one embodiment, the subject is HIV+ and the markers include PGLYRP2, PFN1, IGFBP6, and VASN. In one embodiment, the subject is HIV+ and the markers include CPN2, PFN1, PGLYRP2, and VASN. In one embodiment, the subject is HIV+ and the markers include CD14, PGLYRP2, SEPP1, and TAGLN2. In one embodiment, the subject is HIV+ and the markers include CPN2, PFN1, IGFBP6, and PGLYRP2. In one embodiment, the subject is HIV+ and the markers include CD14, PFN1, IGFBP6, and TAGLN2. In one embodiment, the subject is HIV+ and the markers include CPN2, PFN1, PGLYRP2, and TAGLN2. In one embodiment, the subject is HIV+ and the markers include CD14, PFN1, SEPP1, and VASN. In one embodiment, the subject is HIV+ and the markers include CD14, SEPP1, TAGLN2, and VASN. In one embodiment, the subject is HIV+ and the markers include CPN2, PGLYRP2, IGFBP6, and TAGLN2. In one embodiment, the subject is HIV+ and the markers include PGLYRP2, PFN1, TAGLN2, and VASN. In one embodiment, the subject is HIV+ and the markers include PGLYRP2, PFN1, SEPP1, and VASN. In one embodiment, the subject is HIV+ and the markers include CD14, CPN2, PGLYRP2, and SEPP1. In one embodiment, the subject is HIV+ and the markers include CD14, CPN2, PGLYRP2, and VASN. In one embodiment, the subject is HIV+ and the markers include LCP1, VASN, PFN1, and IGFBP6. In one embodiment, the subject is HIV+ and the markers include LCP1, VASN, PFN1, and LRG1. In one embodiment, the subject is HIV+ and the markers include LCP1, VASN, PFN1, and PGLYRP2. In one embodiment, the subject is HIV+ and the markers include LCP1, VASN, PFN1, and APOA4. In one embodiment, the subject is HIV+ and the markers include LCP1, VASN, PFN1, and BCHE. In one embodiment, the subject is HIV+ and the markers include LCP1, VASN, PFN1, and PI16. In one embodiment, the subject is HIV+ and the markers include LCP1, VASN, PFN1, and SEPP1. In one embodiment, the subject is HIV+ and the markers include LCP1, VASN, PFN1, and APOA1. In one embodiment, the subject is HIV+ and the markers include LCP1, VASN, PFN1, and IGFALS. In one embodiment, the subject is HIV+ and the markers include LCP1, VASN, PFN1, and CD14. In one embodiment, the subject is HIV+ and the markers include LCP1, VASN, PFN1, and TAGLN2. In one embodiment, the subject is HIV+ and the markers include LCP1 and TAGLN2. In one embodiment, the subject is HIV+ and the markers include LCP1, VASN, and TAGLN2. In one embodiment, the subject is HIV+ and the markers include LCP1, VASN, TAGLN2, and IGFBP6. In one embodiment, the subject is HIV+ and the markers include LCP1, VASN, TAGLN2, and LRG1. In one embodiment, the subject is HIV+ and the markers include LCP1, VASN, TAGLN2, and SEPP1. In one embodiment, the subject is HIV+ and the markers include LCP1 and PGLYRP2. In one embodiment, the subject is HIV+ and the markers include LCP1, VASN, and PGLYRP2. In one embodiment, the subject is HIV+ and the markers include LCP1, VASN, PGLYRP2, and PFN1. In one embodiment, the subject is HIV+ and the markers include LCP1, VASN, PGLYRP2, and TAGLN2. In one embodiment, the subject is HIV+ and the markers include PFN1 and PI16. In one embodiment, the subject is HIV+ and the markers include PFN1 and PON1. In one embodiment, the subject is HIV+ and the markers include PFN1 and PTGDS. In one embodiment, the subject is HIV+ and the markers include PI16 and PON1. In one embodiment, the subject is HIV+ and the markers include PI16 and PTGDS. In one embodiment, the subject is HIV+ and the markers include PON1 and PTGDS. In one embodiment, the subject is HIV+ and the markers include PFN1, PI16, and PON1. In one embodiment, the subject is HIV+ and the markers include PFN1, PI16, and PTGDS. In one embodiment, the subject is HIV+ and the markers include PI16, PON1, and PTGDS. In one embodiment, the subject is HIV+ and the markers include PFN1, PI16, PON1, and PTGDS.

In some embodiments, the methods may further comprise determining the level of a marker selected from the group consisting of the markers listed in Table 1. In other embodiments, the methods may further comprise determining the level of a further comprise determining the level of one or more markers selected from the group consisting of CPB2, GP1BA, GP5, GPX3, PROCR, VWF, ATRN, CD14, DBH, SELL, VCAM1, S100A8, S100A9, CD163, CPN1, FCN3, HIST2H2BE, KNG1, MASP1, MASP2, PROS1, YWHAZ, CA1, ORM1, PDLIM1, PGLYRP2, LCAT, LPA, PCSK9, PON1, PTGDS, APOA1, APOA4, APOC1, APOC3, APOE, ANPEP, BCHE, BTD, CDH5, CLEC3B, CLU, CNTN1, ECM1, GPLD1, HABP2, HGFAC, HYOU1, IGFALS, IGFBP3, IGFBP6, LCP1, LGALS3BP, LUM, MINPP1, MST1, NCAM1, NID1, PEPD, PFN1, PRG4, QSOX1, SEPP1, SHBG, SPARC, TGFBI, THBS1, TLN1, TNXB, VASN, VTN, YWHAE, CA2, CKM, CNDP1, COMP, IGF2, LRG1, PI16, PRDX2, PTPRG, SPP2, TAGLN2, ZYX, MTB81, MTB51, CACNA2D1, CPN2, and MAN1A1.

III. Methods of the Invention

A. Diagnostic Methods

In certain aspects, the present invention provides diagnostic methods. For example, in one aspect, the present invention provides methods for determining whether a subject has active tuberculosis (TB). The methods include determining the level of one or more markers of the invention in a sample(s) from the subject with a level of the one or more markers in a control sample(s). A difference in the level (e.g., higher or lower) of the one or more markers in the sample(s) from the subject as compared to the level of the one or more markers in the control sample indicates that the subject has active TB.

The methods of the present invention can be practiced in conjunction with any other method(s) used by the skilled practitioner to diagnose, prognose, and/or monitor TB. For example, the methods of the invention may be performed in conjunction with any clinical measurement of TB known in the art including serological, cytological and/or detection (and quantification, if appropriate) of other molecular markers. In one embodiment, the methods of the invention are practiced in conjunction with an HIV test.

In any of the methods (and kits) of the invention, the level of a marker(s) of the invention in a sample obtained from a subject may be determined by any of a wide variety of well-known techniques and methods, which transform a marker of the invention within the sample into a moiety that can be detected and quantified. Non-limiting examples of such methods include analyzing the sample using immunological methods for detection of proteins, protein purification methods, protein function or activity assays, nucleic acid hybridization methods, nucleic acid reverse transcription methods, and nucleic acid amplification methods, immunoblotting, Western blotting, Northern blotting, electron microscopy, mass spectrometry, e.g., MALDI-TOF and SELDI-TOF, immunoprecipitations, immunofluorescence, immunohistochemistry, enzyme linked immunosorbent assays (ELISAs), e.g., amplified ELISA, quantitative blood based assays, e.g., serum ELISA, quantitative urine based assays, flow cytometry, Southern hybridizations, array analysis, and the like, and combinations or sub-combinations thereof.

For example, an mRNA sample may be obtained from the sample from the subject (e.g., blood, serum, bronchial lavage, mouth swab, biopsy, or peripheral blood mononuclear cells, by standard methods) and expression of mRNA(s) encoding a marker of the invention in the sample may be detected and/or determined using standard molecular biology techniques, such as PCR analysis. A preferred method of PCR analysis is reverse transcriptase-polymerase chain reaction (RT-PCR). Other suitable systems for mRNA sample analysis include microarray analysis (e.g., using Affymetrix's microarray system or Illumina's BeadArray Technology).

It will be readily understood by the ordinarily skilled artisan that essentially any technical means established in the art for detecting the level a marker of the invention at either the nucleic acid or protein level, can be used to determine the level a marker of the invention as discussed herein.

In one embodiment, the level of a marker of the invention in a sample is determined by detecting a transcribed polynucleotide, or portion thereof, e.g., mRNA, or cDNA, of a marker of the invention gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., (1984) *Nuc. Acids Res.* 12:7035-56), Northern blotting, in situ hybridization, and microarray analysis.

In one embodiment, the level of a marker of the invention is determined using a nucleic acid probe. The term "probe", as used herein, refers to any molecule that is capable of selectively binding to a specific marker of the invention. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction (PCR) analyses and probe arrays. One method for the determination of mRNA levels involves contacting the isolated mRNA with a nucleic acid molecule (probe) that can hybridize to a marker mRNA. The nucleic acid probe can be, for example, a full-length cDNA, or a portion thereof, such as an oligonucleotide of at least about 7, 10, 15, 20, 25, 30, 35, 40, 45, 50, 100, 250 or about 500 nucleotides in length and sufficient to specifically hybridize under stringent conditions to marker genomic DNA.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of a marker of the invention mRNA.

An alternative method for determining the level of a marker of the invention in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self-sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of a marker of the invention is determined by quantitative fluorogenic RT-PCR (i.e., the TaqMan™ System). Such methods typically utilize pairs of oligonucleotide primers that are specific for a marker of the invention. Methods for designing oligonucleotide primers specific for a known sequence are well known in the art.

The level of a marker of the invention mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of a level of a marker of the invention may also comprise using nucleic acid probes in solution.

In one embodiment of the invention, microarrays are used to detect the level of a marker of the invention. Microarrays are particularly well suited for this purpose because of the reproducibility between different experiments. DNA microarrays provide one method for the simultaneous measurement of the levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, e.g., U.S. Pat. Nos. 6,040,138, 5,800,992 and 6,020,135, 6,033, 860, and 6,344,316, which are incorporated herein by reference. High-density oligonucleotide arrays are particularly useful for determining the gene expression profile for a large number of RNA's in a sample.

In certain situations it may be possible to assay for the level of a marker of the invention at the protein level, using a detection reagent that detects the protein product encoded by the mRNA of a marker of the invention. For example, if an antibody reagent is available that binds specifically to a marker of the invention protein product to be detected, and not to other proteins, then such an antibody reagent can be used to detect the expression of a marker of the invention in a cellular sample from the subject, or a preparation derived from the cellular sample, using standard antibody-based techniques known in the art, such as FACS analysis, and the like.

Other known methods for detecting a marker of the invention at the protein level include methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoas say (RIA), enzyme-linked immunosorbent assays (ELISAs), immunofluorescent assays, and Western blotting.

Proteins from samples can be isolated using techniques that are well known to those of skill in the art. The protein isolation methods employed can, for example, be those described in Harlow and Lane (Harlow and Lane, 1988, Antibodies: A Laboratory Manual, Cold Spring Harbor Laboratory Press, Cold Spring Harbor, N.Y.).

In one embodiment, antibodies, or antibody fragments, are used in methods such as Western blots or immunofluorescence techniques to detect the expressed proteins. Antibodies for determining the expression of a marker of the invention are commercially available and one of ordinary skill in the art can readily identify appropriate antibodies for use in the methods of the invention.

It is generally preferable to immobilize either the antibody or proteins on a solid support for Western blots and immunofluorescence techniques. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means. Means of detecting proteins using electrophoretic techniques are well known to those of skill in the art (see generally, R. Scopes (1982) *Protein Purification*, Springer-Verlag, N.Y.; Deutscher, (1990) *Methods in Enzymology* Vol. 182: *Guide to Protein Purification*, Academic Press, Inc., N.Y.).

Other standard methods include immunoassay techniques which are well known to one of ordinary skill in the art and may be found in Principles And Practice Of Immunoassay, 2nd Edition, Price and Newman, eds., MacMillan (1997) and Antibodies, A Laboratory Manual, Harlow and Lane, eds., Cold Spring Harbor Laboratory, Ch. 9 (1988), each of which is incorporated herein by reference in its entirety.

Antibodies used in immunoassays to determine the level of a marker of the invention, may be labeled with a detectable label. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In one embodiment, the antibody is labeled, e.g. a radio-labeled, chromophore-labeled, fluorophore-labeled, or enzyme-labeled antibody. In another embodiment, an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a marker of the invention.

In one embodiment of the invention, proteomic methods, e.g., mass spectrometry, are used to determine the level of a marker of the invention. Mass spectrometry is an analytical technique that consists of ionizing chemical compounds to generate charged molecules (or fragments thereof) and measuring their mass-to-charge ratios. In a typical mass spectrometry procedure, a sample is obtained from a subject, loaded onto the mass spectrometry, and its components (e.g., a marker of the invention) are ionized by different methods (e.g., by impacting them with an electron beam), resulting in the formation of charged particles (ions). The mass-to-charge ratio of the particles is then calculated from the motion of the ions as they transit through electromagnetic fields.

For example, matrix-associated laser desorption/ionization time-of-flight mass spectrometry (MALDI-TOF MS) or surface-enhanced laser desorption/ionization time-of-flight mass spectrometry (SELDI-TOF MS) which involves the application of a biological sample, such as serum, to a protein-binding chip (Wright, G. L., Jr., et al. (2002) *Expert Rev Mol Diagn* 2:549; Li, J., et al. (2002) *Clin Chem* 48:1296; Laronga, C., et al. (2003) *Dis Markers* 19:229; Petricoin, E. F., et al. (2002) 359:572; Adam, B. L., et al. (2002) *Cancer Res* 62:3609; Tolson, J., et al. (2004) *Lab Invest* 84:845; Xiao, Z., et al. (2001) *Cancer Res* 61:6029) can be used to determine the level of a marker of the invention.

Furthermore, in vivo techniques for determination of the level of a marker of the invention include introducing into a subject a labeled antibody directed against a marker of the invention, which binds to and transforms a marker of the invention into a detectable molecule. As discussed above, the presence, level, or even location of the detectable marker of the invention in a subject may be detected determined by standard imaging techniques.

In general, it is preferable that the difference between the level of a marker of the invention in a sample from a subject and the amount of a marker of the invention in a control sample, is as great as possible. Although this difference can be as small as the limit of detection of the method for determining the level of a marker it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater than the standard error of the assessment method.

B. Methods for Monitoring the Effectiveness of a Treatment

The present invention also provides methods for monitoring the effectiveness of a therapy or treatment regimen or any other therapeutic approach useful for treating a subject having active TB and/or inhibiting the progression of TB to disseminated TB (or a complication associated with disseminated TB (e.g., spinal and kidney meningitis, peritonitis, pericarditis, bone and joint complications, fallopian tube infection, bowel infection, Adult respiratory distress syndrome (ARDS), liver inflammation, lung failure, and/or relapse of the disease) in a subject having TB.

In these methods the level of one or more markers of the invention in a pair of samples (a first sample not subjected to the treatment regimen and a second sample subjected to at least a portion of the treatment regimen) is assessed. A modulation in the level of expression of the one or more markers in the first sample, relative to the second sample, is an indication that the therapy is effective for treating a subject having active TB and/or inhibiting the progression of TB to disseminated TB (or a complication associated with disseminated TB (e.g., spinal and kidney meningitis, peritonitis, pericarditis, bone and joint complications, fallopian tube infection, bowel infection, Adult respiratory distress syndrome (ARDS), liver inflammation, lung failure, and/or relapse of the disease) in a subject having TB.

C. Screening Methods

Using the methods described herein, a variety of molecules, particularly molecules sufficiently small to be able to cross the cell membrane, may be screened in order to identify molecules which modulate, e.g., decrease or increase, the level and/or activity of a marker(s) of the invention. Compounds so identified can be administered to a subject in order to for treating a subject having active TB and/or inhibiting the progression of TB to disseminated TB (or a complication associated with disseminated TB (e.g., spinal and kidney meningitis, peritonitis, pericarditis, bone and joint complications, fallopian tube infection, bowel infection, Adult respiratory distress syndrome (ARDS), liver inflammation, lung failure, and/or relapse of the disease) in a subject having TB.

Accordingly, in one embodiment, the invention provides methods for identifying modulators, i.e., candidate or test compounds or agents (e.g., enzymes, peptides, peptidomimetics, small molecules, ribozymes, or marker antisense molecules) which bind to a marker polypeptide; have a stimulatory or inhibitory effect on a marker expression; marker processing; marker post-translational modification (e.g., glycosylation, ubiquitinization, or phosphorylation); marker activity; and/or have a stimulatory or inhibitory effect on the expression, processing or activity of a marker target molecule.

Methods for identifying a compound that can modulate the level and/or activity of a marker in a cell (in vitro and/or in vivo), for treating a subject having active TB and/or inhibiting the progression of TB to disseminated TB (or a complication associated with disseminated TB) (also referred to herein as screening assays) include separately contacting an aliquot of a sample (e.g., a sample from the subject) with each member of a library of compounds; determining the effect of a member of the library of compounds on the level of one or more marker(s) of the invention (and/or the activity of one or more marker(s) of the invention) in each of the aliquots; and selecting a member of the library of compounds which modulates the level of and/or the activity of the one or more marker(s) of the invention in an aliquot as compared to the level and/or activity of the one or more marker(s) of the invention in a control sample, thereby identifying a compound that can modulate the level and/or activity of a marker in a cell, for treating a subject having active TB and/or inhibiting the progression of pulmonary TB to disseminated TB (or a complication associated with disseminated TB).

As used interchangeably herein, the terms "marker activity" and "biological activity of a marker" include activities exerted by a marker(s) protein on marker responsive cell or tissue, or on marker(s) nucleic acid molecule or protein target molecule, as determined in vivo, and/or in vitro, according to standard techniques. A marker(s) activity can be a direct activity, such as an association with a marker-target molecule. Alternatively, a marker(s) activity is an indirect activity, such as a downstream biological event mediated by interaction of the marker(s) protein with a marker-target molecule or other molecule in a signal-transduction pathway involving the marker(s). The biological activities of the markers of the invention are known in the art and can be found at, for example, www.uniprot.org. The Uniprot Accession Numbers for each of the markers of the invention are provided in Table 1. The entire contents of each of these Uniprot records are hereby incorporated by reference. Methods for determining the effect of a compound on the level and/or activity of marker are known in the art and/or described herein.

A variety of test compounds can be evaluated using the screening assays described herein. The term "test compound" includes any reagent or test agent which is employed in the assays of the invention and assayed for its ability to influence the expression and/or activity of a marker. More than one compound, e.g., a plurality of compounds, can be tested at the same time for their ability to modulate the expression and/or activity of a marker in a screening assay. The term "screening assay" preferably refers to assays which test the ability of a plurality of compounds to influence the readout of choice rather than to tests which test the ability of one compound to influence a readout. Preferably, the subject assays identify compounds not previously known to have the effect that is being screened for. In one embodiment, high throughput screening can be used to assay for the activity of a compound.

Candidate/test compounds include, for example, 1) peptides such as soluble peptides, including Ig-tailed fusion peptides and members of random peptide libraries (see, e.g., Lam, K. S. et al. (1991) *Nature* 354:82-84; Houghten, R. et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), 6) mutant forms of marker(s) molecules, e.g., dominant negative mutant forms of the molecules, 7) nucleic acids, 8) carbohydrates, and 9) natural product extract compounds.

Test compounds can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc Natl Acad Sci USA* 89:1865-1869) or phage (Scott and Smith (1990) *Science* 249:386-390; Devlin (1990) *Science* 249: 404-406; Cwirla et al. (1990) *Proc. Natl. Acad. Sci.* 87:6378-6382; Felici (1991) *J. Mol. Biol.* 222:301-310; Ladner supra.).

Compounds identified in the screening assays can be used in methods of modulating one or more of the biological responses regulated by a marker. It will be understood that it may be desirable to formulate such compound(s) as pharmaceutical compositions prior to contacting them with cells.

Once a test compound is identified by one of the variety of methods described hereinbefore, the selected test compound (or "compound of interest") can then be further evaluated for its effect on cells, for example by contacting the compound of interest with cells either in vivo (e.g., by administering the compound of interest to a subject or animal model) or ex vivo (e.g., by isolating cells from the subject or animal model and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response).

Computer-based analysis of a marker with a known structure can also be used to identify molecules which will bind to a marker of the invention. Such methods rank molecules based on their shape complementary to a receptor site. For example, using a 3-D database, a program such as DOCK can be used to identify molecules which will bind. See DesJarlias et al. (1988) *J. Med. Chem.* 31:722; Meng et al. (1992) *J. Computer Chem.* 13:505; Meng et al. (1993) *Proteins* 17:266; Shoichet et al. (1993) *Science* 259:1445. In addition, the electronic complementarity of a molecule to a marker can be analyzed to identify molecules which bind to the marker. This can be determined using, for example, a molecular mechanics force field as described in Meng et al. (1992) *J. Computer Chem.* 13:505 and Meng et al. (1993) *Proteins* 17:266. Other programs which can be used include CLIX which uses a GRID force field in docking of putative ligands. See Lawrence et al. (1992) *Proteins* 12:31; Goodford et al. (1985) *J. Med. Chem.* 28:849; Boobbyer et al. (1989) *J. Med. Chem.* 32:1083.

The instant invention also pertains to compounds identified using the foregoing screening assays.

D. Methods for Modulating the Expression and/or Activity of a Biomarker of the Invention Yet another aspect of the invention pertains to methods of modulating expression and/or activity of a marker in a cell. The modulatory methods of the invention involve contacting the cell with an agent that modulates the expression and/or activity of a marker such that the expression and/or activity of a marker in the cell is modulated. In order for the expression and/or activity of a marker to be modulated in a cell, the cell is contacted with a modulatory agent in an amount sufficient to modulate the expression and/or activity of a marker.

A "modulator" or "modulatory agent" is a compound or molecule that modulates, and may be, e.g., an agonist, antagonist, activator, stimulator, suppressor, or inhibitor. As used herein, the term "modulator" refers to any moiety which modulates activity of a marker(s), including moieties which modulates marker(s) expression or modulates marker(s) function. The modulator may act by modulating the activity of a marker polypeptide in the cell, (e.g., by contacting a cell with an agent that, e.g., interferes with the binding of a marker(s) to a molecule with which it interacts, changes the binding specificity of a marker(s), or post-translationally modifies a marker(s) or the expression of a marker(s), (e.g., by modulating transcription of the marker gene or translation of the marker mRNA). Accordingly, the invention features methods for modulating one or more biological responses regulated by a marker(s) by contacting the cells with a modulator of the expression and/or activity the marker(s) such that the biological response is modulated.

Representative modulators are described below and include, but are not limited to, proteins, nucleic acid molecules, antibodies, nucleic acids (e.g., antisense molecules, such as ribozymes and RNA interfering agents), immuno-conjugates (e.g., an antibody conjugated to a therapeutic agent), small molecules, fusion proteins, adnectins, aptamers, anticalins, lipocalins, and marker-derived peptidic compounds.

As used herein, the term "contacting" (e.g., contacting a cell with a modulator) is intended to include incubating the modulator and the cell together in vitro (e.g., adding the modulator to cells in culture) or administering the modulator to a subject such that the modulator and cells of the subject are contacted in vivo. The term "contacting" is not intended to include exposure of cells to an agent that may occur naturally in a subject (i.e., exposure that may occur as a result of a natural physiological process).

In one embodiment, the modulatory methods of the invention are performed in vitro. In another embodiment, the modulatory methods of the invention are performed in vivo, e.g., in a subject, e.g., having active TB, that would benefit from modulation of the expression and/or activity of a marker of the invention.

Accordingly, the present invention also provides methods for treating a subject having active TB and methods for reducing or inhibiting the development of complications associated with the disease in a subject The methods of "inhibiting", "slowing", and/or "treating" include administration of a marker modulator to a subject in order to cure or to prolong the health or survival of a subject beyond that expected in the absence of such treatment.

The terms "patient" or "subject" as used herein is intended to include human and veterinary patients. In a particular embodiment, the subject is a human. The term "non-human animal" includes all vertebrates, e.g., mammals and non-mammals, such as non-human primates, mice, rabbits, sheep, dog, cow, chickens, amphibians, and reptiles.

The methods of the invention also contemplate the use of marker(s) modulators in combination with other therapies, including life-style changes. Thus, in addition to the use of marker(s) modulators, the methods of the invention may also include administering to the subject one or more "standard" therapies. For example, the modulators can be administered in combination with (i.e., together with or linked to (i.e., an immunoconjugate)) cytotoxins, immunosuppressive agents, radiotoxic agents, and/or therapeutic antibodies. Particular co-therapeutics contemplated by the present invention include, but are not limited to, Isoniazid, Rifampin (Rifadin, Rimactane), Ethambutol (Myambutol), Pyrazinamide, streptomycin, vitamin D, Clarithromycin, Dapsone, Ofloxacin, Rifabutin, Non-nucleoside reverse transcriptase inhibitors (NNRTIs; e.g., efavirenz (Sustiva), etravirine (Intelence) and nevirapine (Viramune, Nucleoside reverse transcriptase inhibitors (NRTIs; e.g., Abacavir (Ziagen), and the combination drugs emtricitabine and tenofovir (Truvada), and lamivudine and zidovudine (Combivir), Protease inhibitors (PIs; e.g., atazanavir (Reyataz), darunavir (Prezista), fosamprenavir (Lexiva) and ritonavir (Norvir), Entry or fusion inhibitors, e.g., enfuvirtide (Fuzeon) and maraviroc (Selzentry), and Integrase inhibitors, e.g., Raltegravir (Isentress), or combinations thereof.

Marker(s) modulators and the co-therapeutic agent or co-therapy can be administered in the same formulation or separately. In the case of separate administration, the marker(s) modulators can be administered before, after or concurrently with the co-therapeutic or co-therapy. One agent may precede or follow administration of the other agent by intervals ranging from minutes to weeks. In embodiments where two or more different kinds of therapeutic agents are applied separately to a subject, one would generally ensure that a significant period of time did not expire between the time of each delivery, such that these different kinds of agents would still be able to exert an advantageously combined effect on the target tissues or cells.

In one embodiment, the marker(s) modulators (e.g., an anti-marker(s) antibody) may be linked to a second binding molecule, such as an antibody (i.e., thereby forming a bispecific molecule) or other binding agent that, for example, binds to a different target or a different epitope on the marker(s).

The term "effective amount" as used herein, refers to that amount of marker(s) modulators, which is sufficient to treat and/or inhibit the progression of active TB and/or a complication of TB in a subject when administered to a subject. An effective amount will vary depending upon the subject and the severity of the disease and age of the subject, the manner of administration and the like, which can readily be determined by one of ordinary skill in the art. Marker(s) modulators dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of a marker(s) modulator. Dosage regimens may be adjusted to provide the optimum therapeutic response. An effective amount is also one in which any toxic or detrimental effects (i.e., side effects) of a marker(s) modulator are minimized and/or outweighed by the beneficial effects.

Actual dosage levels of the marker(s) modulators used in the methods of the present invention may be varied so as to obtain an amount of the active ingredient which is effective to achieve the desired response, e.g., inhibiting the progression of diabetes, for a particular patient, composition, and mode of administration, without being toxic to the patient. The selected dosage level will depend upon a variety of pharmacokinetic factors including the activity of the particular marker(s) modulator employed, or the ester, salt or amide thereof, the route of administration, the time of administration, the rate of excretion of the particular modulator being employed, the duration of the treatment, other drugs, compounds and/or materials used in combination with the particular modulator employed, the age, sex, weight, condition, general health and prior medical history of the patient being treated, and like factors well known in the medical arts. A physician or veterinarian having ordinary skill in the art can readily determine and prescribe the effective amount of the modulator required. For example, the physician or veterinarian could start doses of the modulator at levels lower than that required in order to achieve the desired therapeutic effect and gradually increase the dosage until the desired effect is achieved. In general, a suitable daily dose of a marker(s) modulator will be that amount which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a marker(s) modulator may be administered as two, three, four, five, six or more sub-doses administered separately at appropriate intervals throughout the day, optionally, in unit dosage forms. While it is possible for a marker(s) modulator of the present invention to be administered alone, it is preferable to administer the modulator as a pharmaceutical formulation (composition).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the marker(s) modulators used in the methods of the present invention may be administered once or twice weekly by subcutaneous injection or once or twice monthly by subcutaneous injection.

To administer a marker(s) modulator used in the methods of the present invention by certain routes of administration, it may be necessary to include the modulator in a formulation suitable for preventing its inactivation. For example, the marker(s) modulator may be administered to a subject in an appropriate carrier, for example, liposomes, or a diluent. Pharmaceutically acceptable diluents include saline and aqueous buffer solutions. Liposomes include water-in-oil-in-water CGF emulsions, as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active marker(s) modulator, use thereof in pharmaceutical compositions is contemplated. Supplementary active compounds can also be incorporated with the marker(s) modulator.

Marker(s) modulators used in the methods of the invention typically must be sterile and stable under the conditions of manufacture and storage. The modulator can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including an agent that delays absorption, for example, monostearate salts and gelatin.

Sterile injectable solutions can be prepared by incorporating the active modulator in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Marker(s) modulators that can be used in the methods of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the modulator which produces a therapeutic effect. Generally, out of one hundred percent, this amount will range from about 0.001% to about 90% of active ingredient, preferably from about 0.005% to about 70%, most preferably from about 0.01% to about 30%.

The phrases "parenteral administration" and "administered parenterally", as used herein, means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and non-aqueous carriers which may be employed along with the marker(s) modulators utilized in the methods of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Marker(s) modulators may also be administered with adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When marker(s) modulators used in the methods of the present invention are administered to humans and animals, they can be given alone or as a pharmaceutical modulator containing, for example, 0.001 to 90% (more preferably, 0.005 to 70%, such as 0.01 to 30%) of active ingredient in combination with a pharmaceutically acceptable carrier.

Marker(s) modulators can be administered with medical devices known in the art. For example, in a preferred embodiment, a modulator can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

1. Inhibitory Agents

According to a modulatory method of the invention, the expression and/or activity of a marker(s) is inhibited in a cell or subject by contacting the cell with (or administering to a subject) an inhibitory agent. Inhibitory agents of the invention can be, for example, molecules that act to decrease or inhibit the expression and/or activity of the marker(s).

In one embodiment of the invention, the modulatory, e.g., therapeutic, and diagnostic methods described herein employ an antibody that binds, e.g., directly to or indirectly to, and inhibits marker(s) activity and/or down-modulates marker(s) expression.

The term "antibody" or "immunoglobulin," as used interchangeably herein, includes whole antibodies and any antigen binding fragment (i.e., "antigen-binding portion") or single chains thereof. An "antibody" comprises at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., a marker). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including VH and VL domains; (vi) a dAb fragment (Ward et al. (1989) Nature 341, 544-546), which consists of a $V_H$ domain; (vii) a dAb which consists of a VH or a VL domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242, 423-426; and Huston et al. (1988) Proc. Natl. Acad. Sci. USA 85, 5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "antibody", as used herein, includes polyclonal antibodies, monoclonal antibodies, chimeric antibodies, humanized antibodies, and human antibodies, and those that occur naturally or are recombinantly produced according to methods well known in the art.

In one embodiment, an antibody for use in the methods of the invention is a bispecific antibody. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) Clin. Exp. Immunol. 79, 315-321; Kostelny et al. (1992) J. Immunol. 148, 1547-1553.

In another embodiment, an antibody for use in the methods of the invention is a camelid antibody as described in, for example, PCT Publication WO 94/04678, the entire contents of which are incorporated herein by reference.

A region of the camelid antibody that is the small, single variable domain identified as $V_{HH}$ can be obtained by genetic engineering to yield a small protein having high affinity for a target, resulting in a low molecular weight, antibody-derived protein known as a "camelid nanobody". See U.S. Pat. No. 5,759,808; see also Stijlemans et al., 2004 J. Biol. Chem. 279: 1256-1261; Dumoulin et al., 2003 Nature 424: 783-788; Pleschberger et al., 2003 Bioconjugate Chem. 14: 440-448; Cortez-Retamozo et al., 2002 Int. J. Cancer 89: 456-62; and Lauwereys, et al., 1998 EMBO J. 17: 3512-3520. Engineered libraries of camelid antibodies and antibody fragments are commercially available, for example, from Ablynx, Ghent, Belgium. Accordingly, a feature of the present invention is a camelid nanobody having high affinity for a marker.

In other embodiments of the invention, an antibody for use in the methods of the invention is a diabody, a single chain diabody, or a di-diabody.

Diabodies are bivalent, bispecific molecules in which $V_H$ and $V_L$ domains are expressed on a single polypeptide chain, connected by a linker that is too short to allow for pairing between the two domains on the same chain. The $V_H$ and $V_L$ domains pair with complementary domains of another chain, thereby creating two antigen binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure $V_{HA}$—$V_{LB}$ and $V_{HB}$—$V_{LA}$ ($V_H$—$V_L$ configuration), or $V_{LA}$—$V_{HB}$ and $V_{LB}$—$V_{HA}$ ($V_L$—$V_H$ configuration) within the same cell. Most of them can be expressed in soluble form in bacteria.

Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21).

A diabody can be fused to Fc to generate a "di-diabody" (see Lu et al., 2004 J. Biol. Chem., 279(4):2856-65).

Marker binding molecules that exhibit functional properties of antibodies but derive their framework and antigen binding portions from other polypeptides (e.g., polypeptides other than those encoded by antibody genes or generated by the recombination of antibody genes in vivo) may also be used in the methods of the present invention. The antigen binding domains (e.g., marker binding domains) of these binding molecules are generated through a directed evolution process. See U.S. Pat. No. 7,115,396. Molecules that have an overall fold similar to that of a variable domain of an antibody (an "immunoglobulin-like" fold) are appropriate scaffold proteins. Scaffold proteins suitable for deriving antigen binding molecules include fibronectin or a fibronectin dimer, tenascin, N-cadherin, E-cadherin, ICAM, titin, GCSF-receptor, cytokine receptor, glycosidase inhibitor, antibiotic chromoprotein, myelin membrane adhesion molecule P0, CD8, CD4, CD2, class I MHC, T-cell antigen receptor, CD1, C2 and I-set domains of VCAM-1, I-set immunoglobulin domain of myosin-binding protein C, I-set immunoglobulin domain of myosin-binding protein H, I-set immunoglobulin domain of telokin, NCAM, twitchin, neuroglian, growth hormone receptor, erythropoietin receptor, prolactin receptor, interferon-gamma receptor, β-galactosidase/glucuronidase, β-glucuronidase, transglutaminase, T-cell antigen receptor, superoxide dismutase, tissue factor domain, cytochrome F, green fluorescent protein, GroEL, and thaumatin.

To generate non-antibody binding molecules, a library of clones is created in which sequences in regions of the scaffold protein that form antigen binding surfaces (e.g., regions analogous in position and structure to CDRs of an antibody variable domain immunoglobulin fold) are randomized. Library clones are tested for specific binding to the antigen of interest (e.g., a marker(s) of the invention) and for other functions (e.g., inhibition of biological activity of a marker(s) of the invention). Selected clones can be used as the basis for further randomization and selection to produce derivatives of higher affinity for the antigen.

High affinity binding molecules are generated, for example, using the tenth module of fibronectin III ($^{10}$Fn3) as the scaffold, described in U.S. Pat. Nos. 6,818,418 and 7,115,396; Roberts and Szostak, 1997 Proc. Natl. Acad. Sci USA 94:12297; U.S. Pat. No. 6,261,804; U.S. Pat. No. 6,258,558; and Szostak et al. WO98/31700, the entire contents of each of which are incorporated herein by reference.

Non-antibody binding molecules can be produced as dimers or multimers to increase avidity for the target antigen. For example, the antigen binding domain is expressed as a fusion with a constant region (Fc) of an antibody that forms Fc-Fc dimers. See, e.g., U.S. Pat. No. 7,115,396, the entire contents of which are incorporated herein by reference.

The therapeutic methods of the invention also may be practiced through the use of antibody fragments and antibody mimetics. As detailed below, a wide variety of antibody fragment and antibody mimetic technologies have now been developed and are widely known in the art. While a number of these technologies, such as domain antibodies, Nanobodies, and UniBodies make use of fragments of, or other modifications to, traditional antibody structures, there are also alternative technologies, such as Adnectins, Affibodies, DARPins, Anticalins, Avimers, and Versabodies that employ binding structures that, while they mimic traditional antibody binding, are generated from and function via distinct mechanisms. Some of these alternative structures are reviewed in Gill and Damle (2006) 17: 653-658.

Domain Antibodies (dAbs) are the smallest functional binding units of antibodies, corresponding to the variable regions of either the heavy (VH) or light (VL) chains of human antibodies. Domantis has developed a series of large and highly functional libraries of fully human VH and VL dAbs (more than ten billion different sequences in each library), and uses these libraries to select dAbs that are specific to therapeutic targets. In contrast to many conventional antibodies, domain antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; U.S. Serial No. 2004/0110941; European patent application No. 1433846 and European Patents 0368684 & 0616640; WO05/035572, WO04/101790, WO04/081026, WO04/058821, WO04/003019 and WO03/002609, the contents of each of which is herein incorporated by reference in its entirety.

Nanobodies are antibody-derived therapeutic proteins that contain the unique structural and functional properties of naturally-occurring heavy-chain antibodies. These heavy-chain antibodies contain a single variable domain (VHH) and two constant domains (CH2 and CH3). Importantly, the cloned and isolated VHH domain is a perfectly stable polypeptide harboring the full antigen-binding capacity of the original heavy-chain antibody. Nanobodies have a high homology with the VH domains of human antibodies and can be further humanized without any loss of activity.

Nanobodies are encoded by single genes and are efficiently produced in almost all prokaryotic and eukaryotic hosts, e.g., E. coli (see, e.g., U.S. Pat. No. 6,765,087, which is herein incorporated by reference in its entirety), molds (for example Aspergillus or Trichoderma) and yeast (for example Saccharomyces, Kluyveromyces, Hansenula or Pichia) (see, e.g., U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see, e.g., WO 06/079372, which is herein incorporated by reference in its entirety) is a proprietary method for generating Nanobodies against a desired target, based on automated high-throughput selection of B-cells and could be used in the context of the instant invention.

UniBodies are another antibody fragment technology, however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. Further details of UniBodies may be obtained by reference to patent application WO2007/059782, which is herein incorporated by reference in its entirety.

Adnectin molecules are engineered binding proteins derived from one or more domains of the fibronectin protein. In one embodiment, adnectin molecules are derived from the fibronectin type 2I domain by altering the native protein which is composed of multiple beta strands distributed between two beta sheets. Depending on the originating tissue, fibronectin may contain multiple type 2I domains which may be denoted, e.g., $^1$Fn3, $^2$Fn3, $^3$Fn3, etc. Adnectin molecules may also be derived from polymers of $^{10}$Fn3 related molecules rather than a simple monomeric $^{10}$Fn3 structure.

Although the native $^{10}$Fn3 domain typically binds to integrin, $^{10}$Fn3 proteins adapted to become adnectin molecules are altered so to bind antigens of interest, e.g., a marker(s). In one embodiment, the alteration to the $^{10}$Fn3 molecule comprises at least one mutation to a beta strand. In a preferred embodiment, the loop regions which connect the beta strands of the $^{10}$Fn3 molecule are altered to bind to an antigen of interest, e.g., a marker(s).

The alterations in the $^{10}$Fn3 may be made by any method known in the art including, but not limited to, error prone PCR, site-directed mutagenesis, DNA shuffling, or other types of recombinational mutagenesis which have been referenced herein. In one example, variants of the DNA encoding the $^{10}$Fn3 sequence may be directly synthesized in vitro, and later transcribed and translated in vitro or in vivo. Alternatively, a natural $^{10}$Fn3 sequence may be isolated or cloned from the genome using standard methods (as performed, e.g., in U.S. Pat. Application No. 20070082365), and then mutated using mutagenesis methods known in the art.

An aptamer is another type of antibody-mimetic which may be used in the methods of the present invention. Aptamers are typically small nucleotide polymers that bind to specific molecular targets. Aptamers may be single or double stranded nucleic acid molecules (DNA or RNA), although DNA based aptamers are most commonly double stranded. There is no defined length for an aptamer nucleic acid; however, aptamer molecules are most commonly between 15 and 40 nucleotides long.

Aptamers may be generated using a variety of techniques, but were originally developed using in vitro selection (Ellington and Szostak. (1990) *Nature.* 346(6287):818-22) and the SELEX method (systematic evolution of ligands by exponential enrichment) (Schneider et al. 1992. *J Mol Biol.* 228(3):862-9) the contents of which are incorporated herein by reference. Other methods to make and uses of aptamers have been published including Klussmann. The Aptamer Handbook: Functional Oligonucleotides and Their Applications. ISBN: 978-3-527-31059-3; Ulrich et al. 2006. *Comb Chem High Throughput Screen* 9(8):619-32; Cerchia and de Franciscis. 2007. *Methods Mol Biol.* 361:187-200; Ireson and Kelland. 2006. *Mol Cancer Ther.* 2006 5(12):2957-62; U.S. Pat. Nos. 5,582,981; 5,840,867; 5,756,291; 6,261,783; 6,458,559; 5,792,613; 6,111,095 and 7,960,102; and U.S. Patent Publication Nos. 2007/0009476, 20050260164, and 2004/0110235 which are all incorporated herein by reference.

Aptamer molecules made from peptides instead of nucleotides may also be used in the methods of the invention. Peptide aptamers share many properties with nucleotide aptamers (e.g., small size and ability to bind target molecules with high affinity) and they may be generated by selection methods that have similar principles to those used to generate nucleotide aptamers, for example Baines and Colas. 2006. *Drug Discov Today.* 11(7-8):334-41; and Bickle et al. 2006. *Nat Protoc.* 1(3):1066-91 which are incorporated herein by reference.

Affibody molecules represent a class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, et al. *Nat Biotechnol* 1997; 15:772-7. Ronmark J, et al., *Eur J Biochem* 2002; 269:2647-55). Further details of Affibodies and methods of production thereof may be obtained by reference to U.S. Pat. No. 5,831,012 which is herein incorporated by reference in its entirety.

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

Additional information regarding DARPins and other DRP technologies can be found in U.S. Patent Application Publication No. 2004/0132028 and International Patent Application Publication No. WO 02/20565, both of which are hereby incorporated by reference in their entirety.

Anticalins are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved β-barrel which supports four loops at one terminus of the protein. These loops form the entrance to a binding pocket and conformational differences in this part of the molecule account for the variation in binding specificity between individual lipocalins.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have successfully demonstrated that Anticalins can be developed that are specific for virtually any human target protein can be isolated and binding affinities in the nanomolar or higher range can be obtained.

Anticalins can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains.

Additional information regarding Anticalins can be found in U.S. Pat. No. 7,250,297 and International Patent Application Publication No. WO 99/16873, both of which are hereby incorporated by reference in their entirety.

Another antibody mimetic technology useful in the context of the instant invention are Avimers. Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets.

Additional information regarding Avimers can be found in U.S. Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Versabodies are another antibody mimetic technology that could be used in the context of the instant invention. Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

Additional information regarding Versabodies can be found in U.S. Patent Application Publication No. 2007/0191272 which is hereby incorporated by reference in its entirety.

SMIPs™ (Small Modular ImmunoPharmaceuticals—Trubion Pharmaceuticals) engineered to maintain and optimize target binding, effector functions, in vivo half-life, and expression levels. SMIPS consist of three distinct modular domains. First they contain a binding domain which may consist of any protein which confers specificity (e.g., cell surface receptors, single chain antibodies, soluble proteins, etc). Secondly, they contain a hinge domain which serves as a flexible linker between the binding domain and the effector domain, and also helps control multimerization of the SMIP drug. Finally, SMIPS contain an effector domain which may be derived from a variety of molecules including Fc domains or other specially designed proteins. The modularity of the design, which allows the simple construction of SMIPs with a variety of different binding, hinge, and effector domains, provides for rapid and customizable drug design.

More information on SMIPs, including examples of how to design them, may be found in Zhao et al. (2007) Blood 110:2569-77 and the following U.S. Patent Publication Nos. 20050238646; 20050202534; 20050202028; 20050202023; 20050202012; 20050186216; 20050180970; and 20050175614.

In another aspect, the methods of the present invention employ immunoconjugate agents that target a marker(s) and which inhibit or down-modulate the marker(s). Agents that can be targeted to a marker(s) include, but are not limited to, cytotoxic agents, anti-inflammatory agents, e.g., a steroidal or nonsteroidal inflammatory agent, or a cytotoxin antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In another embodiment, marker(s) modulators employed in the methods of the invention are small molecules. As used herein, the term "small molecule" is a term of the art and includes molecules that are less than about 7500, less than about 5000, less than about 1000 molecular weight or less than about 500 molecular weight, and inhibit marker(s) activity. Exemplary small molecules include, but are not limited to, small organic molecules (e.g., Cane et al. 1998. Science 282:63), and natural product extract libraries. In another embodiment, the compounds are small, organic non-peptidic compounds Like antibodies, these small molecule inhibitors indirectly or directly inhibit the activity of a marker(s).

In another embodiment, the marker(s) modulators employed in the methods of the present invention is an antisense nucleic acid molecule that is complementary to a gene encoding a marker(s) or to a portion of that gene, or a recombinant expression vector encoding the antisense nucleic acid molecule. As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can form a hydrogen bond to a sense nucleic acid.

The use of antisense nucleic acids to down-modulate the expression of a particular protein in a cell is well known in the art (see e.g., Weintraub, H. et al., Antisense RNA as a molecular tool for genetic analysis, *Reviews—Trends in Genetics*, Vol. 1(1) 1986; Askari, F. K. and McDonnell, W. M. (1996) *N. Eng. J. Med.* 334:316-318; Bennett, M. R. and Schwartz, S. M. (1995) *Circulation* 92:1981-1993; Mercola, D. and Cohen, J. S. (1995) *Cancer Gene Ther.* 2:47-59; Rossi, J. J. (1995) *Br. Med. Bull.* 51:217-225; Wagner, R. W. (1994) *Nature* 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Antisense nucleic acids can be designed according to the rules of Watson and Crick base pairing. The antisense nucleic acid molecule can be complementary to the entire coding region of marker(s) mRNA, but more preferably is an oligonucleotide which is antisense to only a portion of the coding or noncoding region of marker(s) mRNA. For example, the antisense oligonucleotide can be complementary to the region surrounding the translation start site of marker(s) mRNA. An antisense oligonucleotide can be, for example, about 5, 10, 15, 20, 25, 30, 35, 40, 45 or 50 nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules that can be utilized in the methods of the present invention are typically administered to a subject or generated in situ such that they hybridize with or bind to cellular mRNA and/or genomic DNA encoding a marker(s) to thereby inhibit expression by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using vectors well known in the art and described in, for example, US20070111230 the entire contents of which are incorporated herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule employed by the methods of the present invention can include an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In another embodiment, an antisense nucleic acid used in the methods of the present invention is a compound that mediates RNAi. RNA interfering agents include, but are not limited to, nucleic acid molecules including RNA molecules which are homologous to a marker(s) or a fragment thereof, "short interfering RNA" (siRNA), "short hairpin" or "small hairpin RNA" (shRNA), and small molecules which interfere with or inhibit expression of a target gene by RNA interference (RNAi). RNA interference is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. Kits for synthesis of RNAi are commercially available from, e.g., New England Biolabs and Ambion. In one embodiment one or more of the chemistries described above for use in antisense RNA can be employed.

In still another embodiment, an antisense nucleic acid is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988, *Nature* 334:585-591) can be used to catalytically cleave marker(s) mRNA transcripts to thereby inhibit translation of the marker(s) mRNA.

Alternatively, gene expression can be inhibited by targeting nucleotide sequences complementary to the regulatory region of a marker(s) (e.g., the promoter and/or enhancers) to form triple helical structures that prevent transcription of the marker(s) gene. See generally, Helene, C., 1991, *Anticancer Drug Des.* 6(6):569-84; Helene, C. et al., 1992, *Ann. N.Y. Acad. Sci.* 660:27-36; and Maher, L. J., 1992, *Bioassays* 14(12):807-15.

In another embodiment, the marker(s) modulator used in the methods of the present invention is a fusion protein or peptidic compound derived from the marker(s) amino acid sequence. In particular, the inhibitory compound comprises a fusion protein or a portion of a marker(s) (or a mimetic thereof) that mediates interaction of the marker(s) with a target molecule such that contact of the marker(s) with this fusion protein or peptidic compound competitively inhibits the interaction of the marker(s) with the target molecule. Such fusion proteins and peptidic compounds can be made using standard techniques known in the art. For example, peptidic compounds can be made by chemical synthesis using standard peptide synthesis techniques and then introduced into cells by a variety of means known in the art for introducing peptides into cells (e.g., liposome and the like).

The in vivo half-life of the fusion protein or peptidic compounds of the invention can be improved by making peptide modifications, such as the addition of N-linked glycosylation sites into the marker(s) or conjugating the marker(s) to poly(ethylene glycol) (PEG; pegylation), e.g., via lysine-monopegylation. Such techniques have proven to be beneficial in prolonging the half-life of therapeutic protein drugs. It is expected that pegylation of marker(s) polypeptides of the invention may result in similar pharmaceutical advantages.

In addition, pegylation can be achieved in any part of a polypeptide of the invention by the introduction of a nonnatural amino acid. Certain nonnatural amino acids can be introduced by the technology described in Deiters et al., *J Am Chem Soc* 125:11782-11783, 2003; Wang and Schultz, *Science* 301:964-967, 2003; Wang et al., *Science* 292:498-500, 2001; Zhang et al., *Science* 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the nonnatural amino acid of choice. Particular nonnatural amino acids that are beneficial for purpose of conjugating moieties to the polypeptides of the invention include those with acetylene and azido side chains. Marker(s) polypeptides containing these novel amino acids can then be pegylated at these chosen sites in the protein.

2. Stimulatory Agents

According to a modulatory method of the invention, the expression and/or activity of a marker(s) is stimulated in a cell or subject by contacting the cell with (or administering to a subject) a stimulatory agent. Stimulatory agents of the invention can be, for example, molecules that act to stimulate or increase the expression and/or activity of the marker(s).

Examples of such stimulatory agents include active marker(s) polypeptide and nucleic acid molecules encoding the marker(s) that are introduced into the cell to increase expression and/or activity of the marker in the cell. A preferred stimulatory agent is a nucleic acid molecule encoding a marker(s) polypeptide, wherein the nucleic acid molecule is introduced into the cell in a form suitable for expression of the active marker(s) polypeptide in the cell. To express a marker(s) polypeptide in a cell, typically a marker(s)-encoding cDNA (full length or partial cDNA sequence) is first introduced into a recombinant expression vector using standard molecular biology techniques, and the vector may be transfected into cells using standard molecular biology techniques. A cDNA can be obtained, for example, by amplification using the polymerase chain reaction (PCR), using primers based on the marker(s) nucleotide sequence or by screening an appropriate cDNA library.

The nucleic acids for use in the methods of the invention can also be prepared, e.g., by standard recombinant DNA techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

In one embodiment, a nucleic acid molecule encoding a marker(s) may be present in an inducible construct. In another embodiment, a nucleic acid molecule encoding marker(s) may be present in a construct which leads to constitutive expression. In one embodiment, a nucleic acid molecule encoding marker(s) may be delivered to cells, or to subjects, in the absence of a vector.

A nucleic acid molecule encoding marker(s) may be delivered to cells or to subjects using a viral vector, preferably one whose use for gene therapy is well known in the art. Techniques for the formation of vectors or virions are generally described in "Working Toward Human Gene Therapy," Chapter 28 in Recombinant DNA, 2nd Ed., Watson, J. D. et al., eds., New York: Scientific American Books, pp. 567-581 (1992). An overview of suitable viral vectors or virions is provided in Wilson, J. M., Clin. Exp. Immunol. 107(Suppl. 1):31-32 (1997), as well as Nakanishi, M., Crit. Rev. Therapeu. Drug Carrier Systems 12:263-310 (1995); Robbins, P. D., et al., Trends Biotechnol. 16:35-40 (1998); Zhang, J., et al., Cancer Metastasis Rev. 15:385-401(1996); and Kramm, C. M., et al., Brain Pathology 5:345-381 (1995). Such vectors may be derived from viruses that contain RNA (Vile, R. G., et al., Br. Med Bull. 51:12-30 (1995)) or DNA (Ali M., et al., Gene Ther. 1:367-384 (1994)).

Examples of viral vector systems utilized in the gene therapy art and, thus, suitable for use in the present invention, include the following: retroviruses (Vile, R. G., supra; U.S. Pat. Nos. 5,741,486 and 5,763,242); adenoviruses (Brody, S. L., et al., Ann. N.Y. Acad. Sci. 716: 90-101 (1994); Heise, C. et al., Nat. Med. 3:639-645 (1997)); adenoviral/retroviral chimeras (Bilbao, G., et al., FASEB J. 11:624-634 (1997); Feng, M., et al., Nat. Biotechnol. 15:866-870 (1997)); adeno-associated viruses (Flotte, T. R. and Carter, B. J., Gene Ther. 2:357-362 (1995); U.S. Pat. No. 5,756,283); herpes simplex virus I or II (Latchman, D. S., Mol. Biotechnol. 2:179-195 (1994); U.S. Pat. No. 5,763,217; Chase, M., et al., Nature Biotechnol. 16:444-448 (1998)); parvovirus (Shaughnessy, E., et al., Semin Oncol. 23:159-171 (1996)); reticuloendotheliosis virus (Donburg, R., Gene Therap. 2:301-310 (1995)). Extrachromosomal replicating vectors may also be used in the gene therapy methods of the present invention. Such vectors are described in, for example, Calos, M. P. (1996) Trends Genet. 12:463-466, the entire contents of which are incorporated herein by reference. Other viruses that can be used as vectors for gene delivery include poliovirus, papillomavirus, vaccinia virus, lentivirus, as well as hybrid or chimeric vectors incorporating favorable aspects of two or more viruses (Nakanishi, M. (1995) Crit. Rev. Therapeu. Drug Carrier Systems 12:263-310; Zhang, J., et al. (1996) Cancer Metastasis Rev. 15:385-401; Jacoby, D. R., et al. (1997) Gene Therapy 4:1281-1283).

The term "AAV vector" refers to a vector derived from an adeno-associated virus serotype, including without limitation, AAV-1, AAV-2, AAV-3, AAV-4, AAV-5, or AAVX7. "rAAV vector" refers to a vector that includes AAV nucleotide sequences as well as heterologous nucleotide sequences. rAAV vectors require only the 145 base terminal repeats in cis to generate virus. All other viral sequences are dispensable and may be supplied in trans (Muzyczka (1992) Curr. Topics Microbiol. Immunol. 158:97). Typically, the rAAV vector genome will only retain the inverted terminal repeat (ITR) sequences so as to maximize the size of the transgene that can be efficiently packaged by the vector. The ITRs need not be the wild-type nucleotide sequences, and may be altered, e.g., by the insertion, deletion or substitution of nucleotides, as long as the sequences provide for functional rescue, replication and packaging. In particular embodiments, the AAV vector is an AAV2/5 or AAV2/8 vector. Suitable AAV vectors are described in, for example, U.S. Pat. No. 7,056,502 and Yan et al. (2002) J. Virology 76(5): 2043-2053, the entire contents of which are incorporated herein by reference.

As used herein, the term "lentivirus" refers to a group (or genus) of retroviruses that give rise to slowly developing disease. Viruses included within this group include HIV (human immunodeficiency virus; including but not limited to HIV type 1 and HIV type 2), the etiologic agent of the human acquired immunodeficiency syndrome (AIDS); visna-maedi, which causes encephalitis (visna) or pneumonia (maedi) in sheep; the caprine arthritis-encephalitis virus, which causes immune deficiency, arthritis, and encephalopathy in goats; equine infectious anemia virus (EIAV), which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells). In one embodiment of the invention, the lentivirus is not HIV.

As used herein, the term "adenovirus" ("Ad") refers to a group of double-stranded DNA viruses with a linear genome of about 36 kb. See, e.g., Berkner et al., Curr. Top. Microbiol. Immunol., 158: 39-61 (1992). In some embodiments, the adenovirus-based vector is an Ad-2 or Ad-5 based vector. See, e.g., Muzyczka, Curr. Top. Microbiol. Immunol., 158: 97-123, 1992; Ali et al., 1994 Gene Therapy 1: 367-384; U.S. Pat. Nos. 4,797,368, and 5,399,346. Suitable adenovirus vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types. Additionally, introduced adenovirus DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenovirus genome for foreign DNA is large (up to 8 kilobases) relative to other gene delivery vectors (Haj-Ahmand et al. J. Virol. 57, 267-273 [1986]).

In one embodiment, an adenovirus is a replication defective adenovirus. Most replication-defective adenoviral vectors currently in use have all or parts of the viral E1 and E3 genes deleted but retain as much as 80% of the adenovirus genetic material. Adenovirus vectors deleted for all viral coding regions are also described by Kochanek et al. and Chamberlain et al. (U.S. Pat. No. 5,985,846 and U.S. Pat. No. 6,083,750). Such viruses are unable to replicate as viruses in the absence of viral products provided by a second virus, referred to as a "helper" virus.

In one embodiment, an adenoviral vector is a "gutless" vector. Such vectors contain a minimal amount of adenovirus DNA and are incapable of expressing any adenovirus antigens (hence the term "gutless"). The gutless replication defective Ad vectors provide the significant advantage of accommodating large inserts of foreign DNA while completely eliminating the problem of expressing adenoviral genes that result in an immunological response to viral proteins when a gutless replication defective Ad vector is used in gene therapy. Methods for producing gutless replication defective Ad vectors have been described, for example, in U.S. Pat. No. 5,981,225 to Kochanek et al., and U.S. Pat. Nos. 6,063,622 and 6,451,596 to Chamberlain et al; Parks et al., PNAS 93:13565 (1996) and Lieber et al., J. Virol. 70:8944-8960 (1996).

In another embodiment, an adenoviral vector is a "conditionally replicative adenovirus" ("CRAds"). CRAds are genetically modified to preferentially replicate in specific cells by either (i) replacing viral promoters with tissue specific promoters or (ii) deletion of viral genes important for replication that are compensated for by the target cells only. The skilled artisan would be able to identify epithelial cell specific promoters.

Other art known adenoviral vectors may be used in the methods of the invention. Examples include Ad vectors with recombinant fiber proteins for modified tropism (as described in, e.g., van Beusechem et al., 2000 Gene Ther. 7: 1940-1946), protease pre-treated viral vectors (as described in, e.g., Kuriyama et al., 2000 Hum. Gene Ther. 11: 2219-2230), E2a temperature sensitive mutant Ad vectors (as described in, e.g., Engelhardt et al., 1994 Hum. Gene Ther. 5: 1217-1229), and "gutless" Ad vectors (as described in, e.g., Armentano et al., 1997 J. Virol. 71: 2408-2416; Chen et al., 1997 Proc. Nat. Acad. Sci. USA 94: 1645-1650; Schieder et al., 1998 Nature Genetics 18: 180-183).

The vector will include one or more promoters or enhancers, the selection of which will be known to those skilled in the art. Suitable promoters include, but are not limited to, the retroviral long terminal repeat (LTR), the SV40 promoter, the human cytomegalovirus (CMV) promoter, and other viral and eukaryotic cellular promoters known to the skilled artisan.

Guidance in the construction of gene therapy vectors and the introduction thereof into affected subjects for therapeutic purposes may be obtained in the above-referenced publications, as well as in U.S. Pat. Nos. 5,631,236, 5,688,773, 5,691,177, 5,670,488, 5,529,774, 5,601,818, and PCT Publication No. WO 95/06486, the entire contents of which are incorporated herein by reference.

Generally, methods are known in the art for viral infection of the cells of interest. Gene therapy vectors comprising a nucleic acid molecule encoding a marker(s) can be delivered to a subject or a cell by any suitable method in the art, for example, intravenous injection, local administration, e.g., application of the nucleic acid in a gel, oil, or cream, (see, e.g., U.S. Pat. No. 5,328,470), stereotactic injection (see, e.g., Chen et al. (1994) Proc. Natl. Acad. Sci. U.S.A. 91:3054), gene gun, or by electroporation (see, e.g., Matsuda and Cepko (2007) Proc. Natl. Acad. Sci. U.S.A. 104:1027), using lipid-based transfection reagents, or by any other suitable transfection method.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAMFECT™ (OZ Biosciences, France) and the like), or electroporation (e.g., in vivo electroporation). Suitable methods for transforming or transfecting host cells can be found in Sambrook, et al. (Molecular Cloning: A Laboratory Manual.

2nd, ed., Cold Spring harbor Laboratory, Cold Spring Harbor Laboratory Press, Cold Spring Harbor, N.Y., 1989), and other laboratory manuals.

In one embodiment, a marker(s) is delivered to a subject or cells in the form of a peptide or protein. In order to produce such peptides or proteins, recombinant expression vectors of the invention can be designed for expression of one or more marker(s) proteins, and/or portion(s) thereof in prokaryotic or eukaryotic cells. For example, one or more marker proteins and/or portion(s) thereof can be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

In one embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include retinal cell-type-specific promoters (e.g., rhodopsin regulatory sequences, Cabp5, Cralbp, Nrl, Crx, Ndrg4, clusterin, Rax, Hes1 and the like (Matsuda and Cepko, supra)), the albumin promoter (liver-specific, Pinkert et al. (1987) Genes Dev. 1:268), neuron-specific promoters (e.g., the neurofilament promoter; Byrne and Ruddle (1989) Proc. Natl. Acad. Sci. U.S.A. 86:5473). Developmentally-regulated promoters are also encompassed, for example the α-fetoprotein promoter (Campes and Tilghman (1989) Genes Dev. 3:537).

Application of the methods of the invention for the treatment and/or prevention of a active TB can result in curing the disorder, decreasing at least one symptom associated with the disorder, either in the long term or short term or simply a transient beneficial effect to the subject. Accordingly, as used herein, the terms "treat," "treatment" and "treating" include the application or administration of agents, as described herein, to a subject who is suffering from a active TB, or who is susceptible to such conditions with the purpose of curing, healing, alleviating, relieving, altering, remedying, ameliorating, improving or affecting such conditions or at least one symptom of such conditions. As used herein, the condition is also "treated" if recurrence of the condition is reduced, slowed, delayed or prevented.

A modulatory agent, such as a chemical compound, can be administered to a subject as a pharmaceutical composition. Such compositions typically comprise the modulatory agent and a pharmaceutically acceptable carrier, discussed supra. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described above.

E. Methods of Identifying Active TB Biomarkers

The present invention further provides methods for identifying active biomarkers useful as markers for, e.g., disease (prognostics and diagnostics), therapeutic effectiveness of a drug (theranostics) and of drug toxicity. For example, as described above, the markers described herein and the markers identified using the methods for biomarker discovery are useful for, e.g., determining whether a subject has active TB; monitoring the effectiveness of a therapy for treating TB, reducing or slowing down the progression of TB, and/or reducing or inhibiting the development of complications associated with the disease in a subject; in screening assays to identify molecules which modulate, e.g., decrease or increase, the expression and/or activity of a marker(s) of the invention for e.g., use as therapeutics.

Methods for identifying an active TB marker are described in the working examples and include identifying proteins differentially expressed in the serum of HIV+ subjects having TB, identifying proteins differentially expressed in the serum of HIV− subjects having TB thereby generating a provisional list of active TB markers, determining the level of a marker in a sample form a control subject, e.g., an HIV+ subject having latent TB, an HIV− subject having latent TB, an HIV+ subject having ORD, and an HIV− subject having ORD, and determining the level of the marker in a test sample from a subject, e.g., an HIV+ subject having active TB and an HIV− subject having active TB. A difference in the level of a marker in the control sample as compared to the level in the test sample, e.g., a statistically significant level, identifies the marker as an active TB marker.

IV. Kits of the Invention

The invention also provides kits for determining whether a subject has active TB. Kits for monitoring the effectiveness of a treatment for active TB are also provided.

These kits include means for determining the level of one or more markers of the invention and instructions for use of the kit.

The kits of the invention may optionally comprise additional components useful for performing the methods of the invention. By way of example, the kits may comprise reagents for obtaining a biological sample from a subject, a control sample, one or more sample compartments, a diabetic therapeutic, an instructional material which describes performance of a method of the invention and tissue specific controls/standards.

The reagents for determining the level of one or more marker(s) can include, for example, buffers or other reagents for use in an assay for evaluating the level of one or more markers, e.g., expression level (e.g., at either the mRNA or protein level). The instructions can be, for example, printed instructions for performing the assay for evaluating the level of one or more marker(s) of the invention.

The reagents for isolating a biological sample from a subject can comprise one or more reagents that can be used to obtain a fluid or tissue from a subject, such as means for obtaining a saliva or blood.

The kits of the invention may further comprise reagents for culturing a sample obtained from a subject.

Preferably, the kits are designed for use with a human subject.

The present invention is further illustrated by the following examples which should not be construed as further limiting. The contents of all references, patents and published patent applications cited throughout this application, as well as the Figures, are expressly incorporated herein by reference in their entirety.

EXAMPLES

Example I. Biomarker Identification

Materials and Methods
Study Design and Subjects

The studies described below entailed two parts, a discovery and a verification phase. For both parts, independent serum samples from HIV uninfected (HIV−) and HIV-infected (HIV+) subjects were evaluated. Within both the HIV− and the HIV+ subjects, TB cases were compared to various controls groups in a case-control design. Subjects were 21-80 years old and enrolled at 4 public hospitals in New York City from 2007-2011. TB cases were confirmed by a positive respiratory or other body fluid culture for *M. tuberculosis* or, if culture-negative, by a positive response to antituberculous treatment (ATT). They were further categorized by sputum smear microscopy results and considered smear-positive if one of the initial three sputum smears were positive regardless of number of acid-fast bacilli (AFB) detected. All TB patients were enrolled prior to or within the first 7 days of ATT. Control groups consisted of either asymptomatic healthy volunteers without abnormalities on chest X-ray who were categorized by Tuberculin skin-test (TST) or of symptomatic patients with signs and symptoms of TB who were ultimately diagnosed with an other respiratory disease (ORD). TST negative controls were considered TB uninfected. All TST+ controls had a history of *M. bovis Bacillus* Calmette-Guerin (BCG) vaccine and were further categorized by an interferon-gamma release assay result (IGRA; QuantiFERON®-TB Gold, Celestis, Australia). Asymptomatic controls with a positive IGRA were considered to have latent tuberulosis infection (LTBI). All subjects provided written informed consent prior to enrollment. Approval for human subjects' research was obtained from the Internal Review Boards at the New York University School of Medicine, NY, N.Y., and the Albert Einstein College of Medicine, Bronx, N.Y. For the discovery phase sera from TB patients (n=24) and asymptomatic controls (n=40), and for the verification phase sera from a different set of TB patients (n=46), ORD patients (n=6) and asymptomatic controls (n=97) were evaluated and compared. Subjects were bled at the time of enrolment, and sera were stored at −80° C. until tested. Written informed consent was obtained from all subjects prior to enrollment. Approval for human subjects' research was obtained from the Institutional Review Board of the Albert Einstein College of Medicine.

Sample Processing.

To avoid introducing bias in the sample preparation, the samples were grouped into blocks containing one of each of the groups (if possible). The order of the groups within each block was then randomized. For the discovery samples, all samples were depleted of abundant proteins with an antibody column (IgY14 and Supermix, Sigma). After the depletion step for all samples, the remaining lower abundance proteins were digested with trypsin (Promega). Following freeze-drying of the digested samples, they were resolubilized and treated with TCEP (tris(2-carboxyethyl) phosphine) to reduce disulfide bonds. The samples were then desalted by solid phase extraction using a 3M Empore C18 desalting plate and distributed into 96-well plates and vacuum evaporated. Peptides were stored at −20° C. until use. For the verification samples, most abundant proteins were depleted from all samples by tandem immunodepletion using an HSA/IgG column (Agilent Technologies) due to the unusually high levels of immunoglobulins in the blood of the HIV+ patients and with an IgY14 and Supermix (Sigma) column. After the depletion step for all samples, the remaining lower abundance proteins were digested with trypsin overnight (Promega) at a trypsin to protein ratio of 1:10, and desalted by solid phase extraction using a 3M Empore C18 desalting plate. Peptides were freeze-dried and stored at −20° C. until use.

Tandem Mass Spectrometry Analysis

Freeze dried peptides were resuspended in 92.5/7.5 water/acn+0.2% formic acid and analyzed using a nanoAcquity pump (Waters) coupled to a Q-TOF mass spectrometer (Waters). Peptide separation was achieved using a Waters nanoAcquity Symmetry UPLC Trap column (180 μm×20 mm, 5 μm particle size) and a Waters nanoAcquity UPLC BEH300 analytical column (150 μm×100 mm, 1.7 μm particle size). Each sample was loaded on the trapping column for 3 min at a flow rate of 10 μL/min, and then the gradient was started at a flow rate at 1.8 μL/min. The total run time per sample was 105 min. Components were detected and matched across all samples using the Elucidator software (Rosetta Biosoftware) and compared for relative peak intensity. All intensity values were log (base e) transformed with values <0 replaced by 0. Peak intensity was normalized to account for small differences in protein concentration between samples: a subset of the samples was used to create an average sample (i.e. the Reference sample) against which all samples were then normalized. The normalization factors were chosen so that the median of log ratios between each sample and the Reference sample over all the peptides was adjusted to zero. For batch-effect correction, a one-way ANOVA model $I_{ij}=M+D_i+\epsilon_{ij}$ (I: intensity, M: overall interception, and D: batch-factor) was solved and parameters $D_i$ (i=1,2) under the constraint of $\Sigma_{i=1}^{2}(N_i*D_i)=0$ were obtained; the $D_i$'s were then subtracted from the normalized intensities to form the "batch-effect corrected" intensities. Intensities below the limit of detection (LOD=30) were transformed to avoid spurious large fold changes: intensities in the range of (0, LOD) were linearly mapped to the range of (LOD/2, LOD). A one-way ANOVA analysis was then applied to identify peptides that were differentially expressed between the groups of interest. High stringency thresholds were used to ensure the statistical significance of the identified peptides. Each group was analyzed using the same one-way ANOVA model [=(Montgomery, D.C., *Design and Analysis of Experiments*, Wiley, 2001; Keeping, E. S., *Introduction to Statistical Inference*, Dover Publication, Inc. 1995): $I_{ij}=M+C_i+\epsilon_{ij}$ where I is the peptide intensity, M is the overall average intensity, C is the 'clinical group' factor, and $\epsilon$ is random error. FDR (false detection rate) and q-value were calculated, based on the p-values obtained from the ANOVA, using Storey's method (Storey, J. D. (2002) *Journal of the Royal Statistical Society* 64(3):479-498) to make multiple testing adjustments (implemented in MATLAB) (mathworks.com/access/helpdesk/help/helpdesk.html; MATLAB for Math Works Inc.). 'Post hoc' contrast analyses were conducted using Tukey's hsd (Hochberg, Y., and A. C. Tamhane. *Multiple Comparison Procedures*. John Wiley & Sons, 1987) method to calculate p-values associated with each pair wise comparison. Protein identification was done by analysis of replicate samples by tandem mass spectrometry (LC-MS/MS). Differentially expressed peptides were targeted for sequencing, and the resulting fragmentation patterns were matched to the corresponding peptide sequences found in a custom protein database using Mascot (Matrix Science) software. A protein level analysis was then applied using an extension of the one-way ANOVA used above in the peptide level analysis, which takes into consideration that one protein may have several peptides, by introducing a 'peptide factor' in the model: $I_{ijk}=M+C_i+P_j+\epsilon_{ijk}$ where I is the protein intensity, M an overall constant, C the 'clinical group', and P the peptide factor. The number of the levels for P is protein-dependent, equal to the number of children peptides for the protein. These calculations were implemented in MATLAB (math-works.com/access/helpdesk/help/helpdesk.html; MATLAB for Math Works Inc.). Proteins were considered to be differentially expressed if they met the following thresholds: p- and q-values<0.05, and Differential Intensity (DI) superior at 1.1-fold change.

Multiple Reaction Monitoring Mass Spectrometry

A multiplex MRM assay was developed for the selected biomarker candidates. The assay contained 244 peptides representing 89 host proteins and 2 *M. tuberculosis* proteins. Peptides were synthesized by JPT Peptide Technologies (Berlin, Germany). The synthesized peptides were resolubilized in 72/25 water/DMSO, pooled and diluted with water+0.2% formic acid to a final concentration of 2 nmol/mL. Five µL of this solution was analyzed on a QTRAP 5500 mass spectrometer (ABSciex, Canada) using a 320 µm×150 mm, 5 µm particle size, Thermo Biobasic C18 column. A linear gradient of 10-40% acetonitrile (0.2% formic acid) in 30 minutes was used for peptide separation. MS/MS spectra of the synthetic peptides were acquired using selected reaction monitoring (SRM)-triggered MS/MS allowing the identification of peptide and peptide fragments (transitions). The two most intense fragment ions (b or y fragment ions only) in the MS/MS spectrum and its elution time were determined for each acquired peptide. The collision energy (CE) was then optimized for each of the chosen transitions. The CE values evaluated were the empirical calculated CE value and the empirical CE value −6, +3 and +6. Independent plasma samples from those used for the discovery study by tandem mass spectrometry were processed as described and the resulting peptides were analyzed by the MRM assay.

Expression analysis of MRM data was performed using R version 2.14.0, platform x86_64-pc-mingw32/x64 (64-bit). The calculation of q-values was done using function "qvalue" from Storey's package "qvalue" version 1.24.0. A limit of quantification (LOQ), defined as an intensity value below which the measure is deemed unreliable, was determined empirically according to the QTRAP 5500 and was set to 10000, pre-normalization. The detection rate (DR), defined for each group that needed to be compared, was defined as the proportion of samples with a raw intensity (i.e. pre normalization) value greater or equal to the LOQ. Transitions for which the DR was below 50% for one of the two groups were excluded from expression analysis. Prior to expression analysis, an outlier and pattern detection analysis was performed. The distribution of sample detection was investigated and a sample was rejected from analysis because of a poor detection rate. The sample intensity average distribution by depletion day was also investigated and three samples were rejected for being too weak. A standard Principal Component Analysis (PCA) was applied to the ln intensities in order to visually assess any pattern in the data that are likely to be unrelated to sample condition. Differential intensity ratios (DI) were then calculated for each transition, for two-group comparisons (e.g. Active TB vs Latent TB), as the ratio of the median normalized intensities of each group. Prior to calculating the differential intensity ratios, all intensity values that were below the LOQ quantity in the raw data prior to normalization were replaced by the half-LOQ value. Student's t-test were applied for the expression analysis Protein-level statistics were also computed by first linearly combining the transitions of a given protein into a single variable and then applying a t-test on it.

IPA Analysis

Data were analyzed through the use of IPA (Ingenuity® Systems, ingenuity.com). Expression analysis results were combined by cell type. Differential expression results (DI cut-off of 1.1 and p<0.05 and q<0.05) were analyzed independently for HIV− and HIV+ backgrounds. The Functional Analysis identified the biological functions and/or diseases that were most significant to each dataset. Proteins from the dataset that were associated with biological functions and/or diseases in the Ingenuity Knowledge Base were considered for the analysis. Right-tailed Fisher's exact test was used to calculate a p-value determining the probability that each biological function and/or disease assigned to that data set is due to chance alone. Each protein was assigned to a functional category mainly based on IPA analysis, combined with additional literature search.

Panel Definition

Area Under the Curve (AUC) values were computed from bootstrap. Select n samples with replacement (i.e. take a sample at random, then a second—with the first selected sample being possibly selected again, and so on). By design, some samples are left out, called out-of-bag. The selected samples (some more than once) are called the bootstrap samples. Build panel on the bootstrap samples and evaluate on the out-of-bag sample by calculating AUC. This was done 100 times. Reported AUC is the average of the 100 AUC. Each protein was represented by a single transition. Transitions with a DR lower than 80% were filtered-out. Among the remaining transitions, proteins for which the transitions were not trending the same way, based on DI, were filtered-out. The selected transition of a protein was the one with the highest DR. In situation of ties, this transition was selected randomly. Logistic Regression models were built with the proteins (i.e. represented by its selected transition) as explanatory variables. All combinations of proteins from 1 to 4 were systematically fitted into such logistic models. Proteins were then ranked by their propensity to be a good team player. For k from 1 to 4, combinations were ranked by their AUC and for each protein, the mean rank of the combinations they appear in, for a given k, was calculated. Within each k, the protein rank was calculated as the rank of the average rank. The final rank was taken as the weighted average over k of the ranks.

Results

Identification of Plasma Protein Changes Associated with Active Pulmonary TB

Figure 1D:
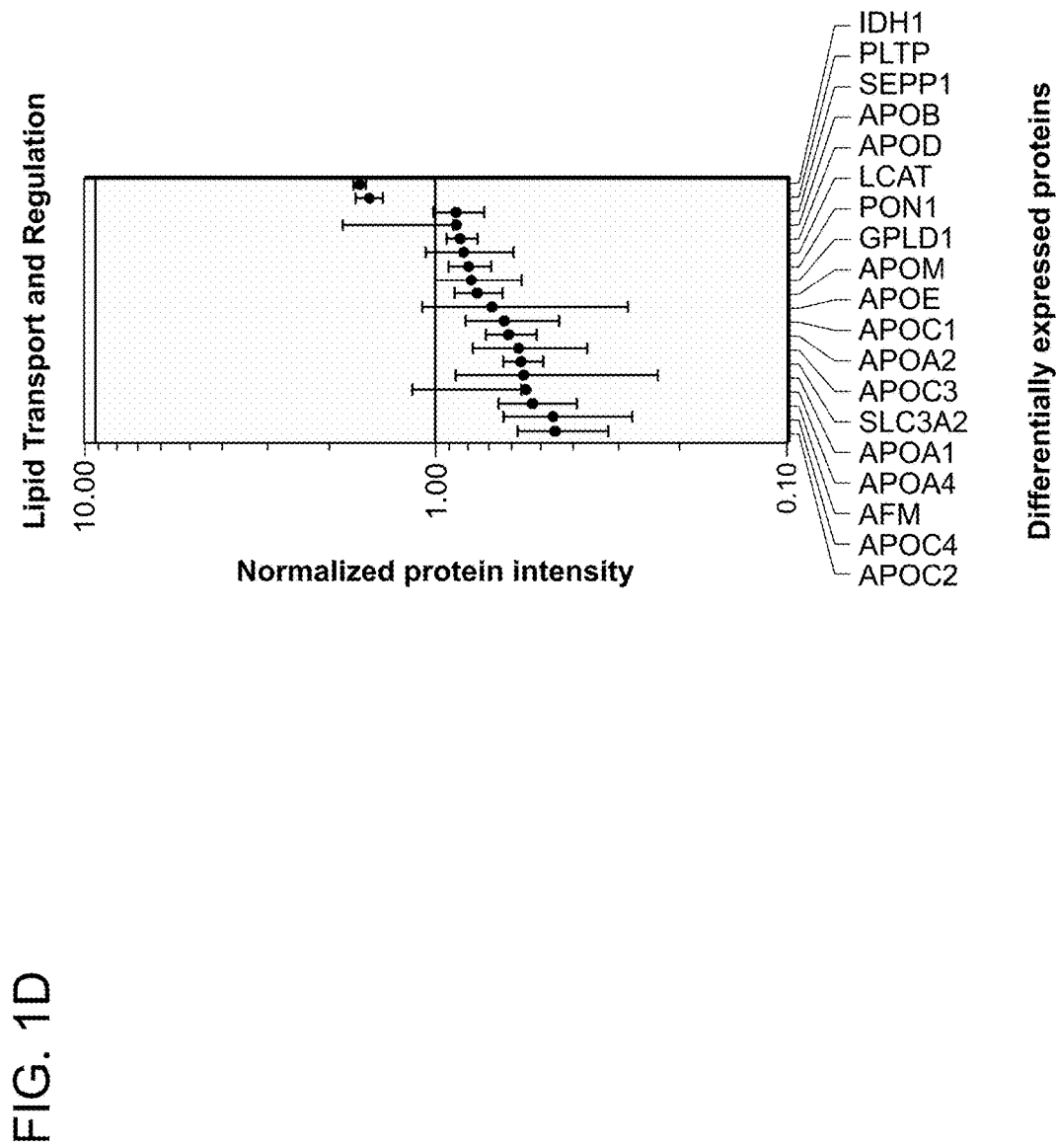
Figure 1E:
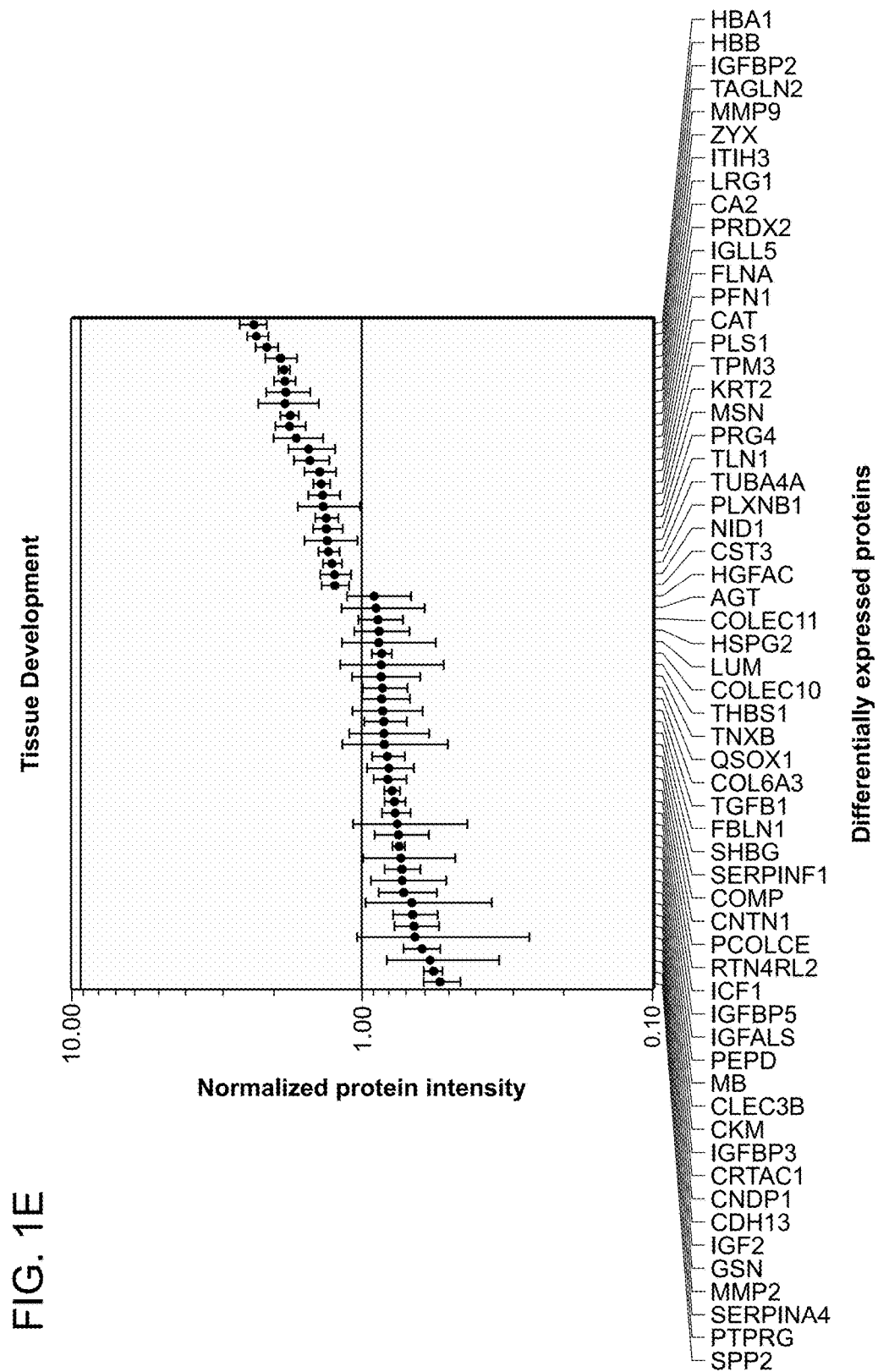
Figure 1F:
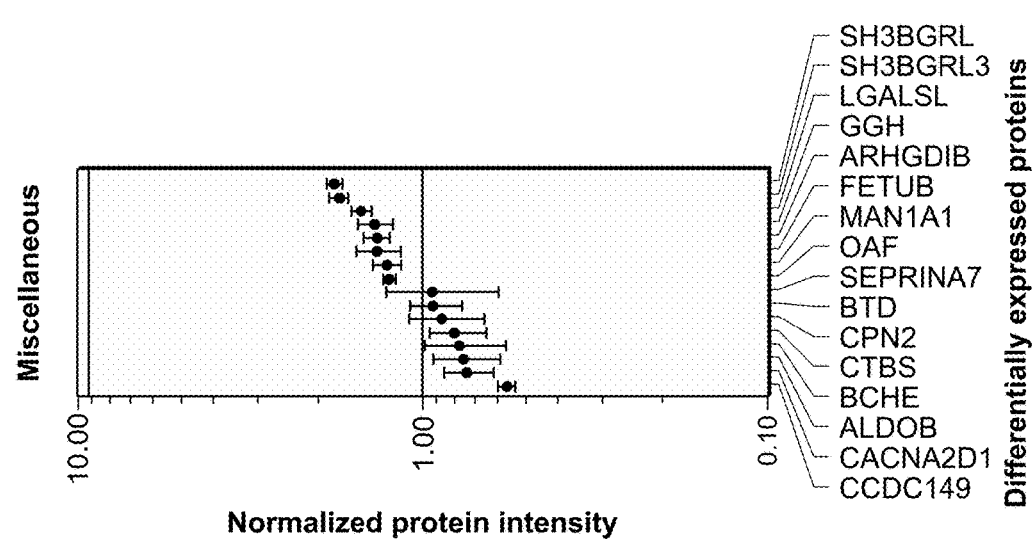

One hundred forty plasma proteins were identified to be significantly differentially expressed in the serum of HIV− subjects with active TB in comparison to controls (uninfected and LTBI) ((p<0.05); FIG. 1, Tables 2A-2E). Tables 2A-2E provide the DI (Differential Intensity) value for each protein. If the DI value is above 1 the level of the protein is upregulated. If the DI value is less than 1, the level of the marker is downregulated. The differentially expressed proteins segregated into a small number of biological processes. The 3 most populated groups were associated with the immune response, lipid transport and regulation, and tissue development and repair (FIG. 1).

Figure 2:
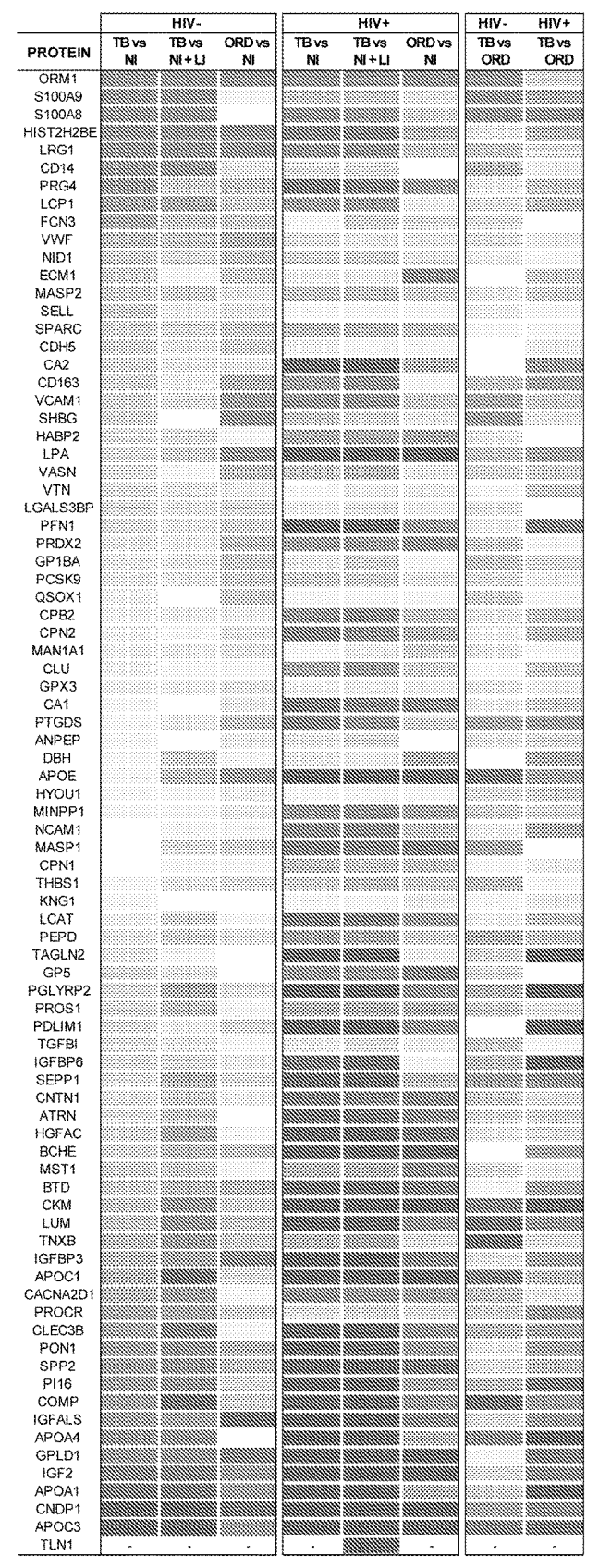

One hundred and twenty six plasma proteins were identified to be significantly (p<0.05) differentially expressed in serum from HIV+ subjects with active TB in comparison to HIV+ controls (uninfected and LTBI) (FIG. 2, Tables 2A-2E). The differentially expressed proteins segregated into the same main biological function categories defined by the HIV− groups.

These results indicate that the host physiological changes associated with TB can be sufficiently reflected in the blood and that a relatively detailed assessment of the host response to TB can be made. Furthermore, effects of HIV co-infection also appear to be sufficiently reflected in the blood. This demonstrates that host biomarkers for TB can be identified in body fluids, such as blood, independent from the site of *M. tuberculosis* infection.

Candidate Serum Protein Biomarkers of Active TB

All the significantly differentially expressed proteins in the HIV− or HIV+ subjects were individually evaluated for inclusion into a multiplex MRM-MS assay which would be used to assay an independent set of clinical samples. The differentially expressed proteins were ranked by whether they had a known or novel association with infectious disease, whether they belonged to the acute phase response, and how frequently they were observed to be differentially expressed in the Caprion plasma study database which contained studies from a wide range of disease indications. This ranking was done to assess the likelihood of the significantly differentially proteins as potentially specific host response biomarkers of active TB. Proteins that were components of the acute phase response or had been repeatedly observed to be differentially expressed in multiple studies were assessed most likely to be non-specific and were not selected for inclusion in the multiplex MRM-MS assay.

Eighty nine of the differentially proteins were selected for inclusion in the multiplex assay (Table 1) as well as two *M. tuberculosis* proteins and 17 other host proteins. The *M. tuberculosis* proteins included were not detected in the verification samples. This result was not surprising, given the comparatively early stage of TB all the subjects used in the study. The differential expression measured for each of the host biomarker candidates identified in the discovery sample set, however, was comparable to their corresponding expression in the verification sample set. The directionality of the expression change of each candidate biomarker was reproduced in both sample sets, though the magnitude of the changes observed were greater in the verification set, owing to the better resolution of the QTRAP mass spectrometer used for the MRM-MS data acquisition compared to the QTOF instrument used in the initial biomarker discovery experiments. These results demonstrated that the differential expression observed in the initial sample groups could be reproduced using an independent set of samples, and that the effects on the host physiology observed were reproducible.

The biomarker verification sample set contained an additional group than the discovery sample set, one comprised of samples from subjects with diverse other respiratory disease than TB (ORD), such as pneumonias. These subjects displayed a similar clinical presentation as active TB, and represented the diseases that a TB diagnostic test would need to distinguish from. Thus, these samples were used to assess the clinically relevant specificity of the candidate biomarkers in the multiplex MRM-MS assay. The HIV+ and HIV− groups were analyzed separately. Classification analysis demonstrated that individually, the vast majority of the biomarker candidates were not able to accurately distinguish between TB and ORDs, independent of HIV status. The performance of the individual biomarker candidates ranged between 0.636 to 0.746 AUC for the HIV− groups, and 0.561 to 0.804 AUC for the HIV+ groups. The only exception was CD14, which was able to distinguish between TB and the other pneumonias with an AUC of 0.950, but only in the HIV− groups. Its performance in the HIV+ groups was a much less effective 0.612.

Combining the biomarker candidates into panels was a more effective strategy to derive high performing discriminators (Tables 3 and 4). Even so, most of the candidate biomarkers did not appear to have utility in panel combinations. Only 13 of the 89 (15%) candidate biomarker proteins assayed were able to improve the performance of a panel combination in the HIV− groups, and 23 of the 89 (26%) of the candidates assayed did the same in the HIV+ groups. Furthermore, the performance gained with each additional biomarker candidate became progressively smaller (Tables 3 and 4). These results indicated that it was possible to increase the overall test performance by using small combinations of individual biomarkers, and that large biomarker panels were not necessary to achieve this performance.

TABLE 3

HIV− panels

| Active TB vs pneumonia, HIV− | | | | | | accuracy | auc |
|---|---|---|---|---|---|---|---|
| CD14 | APOE | + | none | + | none = | 0.95 | 0.977 |
|  |  | + | SELL | + | none = | 0.95 | 0.984 |
|  |  |  |  | + | TNXB = | 0.95 | 1.000 |
|  |  |  |  | + | COMP = | 0.93 | 0.989 |
|  |  |  |  | + | LUM = | 0.93 | 0.989 |
|  |  |  |  | + | PGLYRP2 = | 0.95 | 0.989 |
|  |  |  |  | + | HABP2 = | 0.93 | 0.986 |
|  |  |  |  | + | LRG1 = | 0.95 | 0.986 |
|  |  |  |  | + | QSOX1 = | 0.93 | 0.986 |
|  |  |  |  | + | S100A8 = | 0.95 | 0.986 |
| CD14 | APOE | + | APOC3 | + | none = | 0.93 | 0.979 |
|  |  |  |  | + | PGLYRP2 = | 0.93 | 0.991 |
|  |  |  |  | + | SELL = | 0.93 | 0.989 |
|  |  |  |  | + | HABP2 = | 0.93 | 0.986 |

TABLE 4

HIV+ panels

| Active TB vs pneumonia, HIV+ | | | | | accuracy | auc |
|---|---|---|---|---|---|---|
| LCP1 | VASN | PFN1 | + | none = | 0.94 | 0.980 |
|  |  |  | + | IGFBP6 = | 0.94 | 1.000 |
|  |  |  | + | LRG1 = | 0.94 | 1.000 |
|  |  |  | + | PGLYRP2 = | 0.91 | 0.996 |
|  |  |  | + | APOA4 = | 0.94 | 0.992 |
|  |  |  | + | BCHE = | 0.94 | 0.992 |
|  |  |  | + | PI16 = | 0.94 | 0.988 |
|  |  |  | + | SEPP1 = | 0.94 | 0.988 |
|  |  |  | + | APOA1 = | 0.94 | 0.984 |
|  |  |  | + | IGFALS = | 0.91 | 0.984 |
|  |  |  | + | CD14 = |  | 0.980 |
|  |  |  | + | TAGLN2 = | 0.94 | 0.984 |
| LCP1 | VASN | TAGLN2 | + | none = | 0.94 | 0.965 |
|  |  |  | + | IGFBP6 = | 0.97 | 1.000 |
|  |  |  | + | LRG1 = | 0.94 | 1.000 |
|  |  |  | + | SEPP1 = | 0.97 | 0.984 |
| LCP1 | VASN | PGLYRP2 | + | none = | 0.94 | 0.925 |
|  |  |  | + | PFN1 = | 0.94 | 0.984 |
|  |  |  | + | TAGLN2 = | 0.94 | 0.984 |
| PFN1 PI16 PON1 | | PTGDS | + | none = | 0.91 | 0.992 |

The panel combinations able to distinguish TB from ORDs differed dependent on the HIV co-infection background. The composition of the panels in HIV+ subjects differed from that of the panels in HIV− subjects. Although the sizes of the panels were similar independent of HIV background, two combinations of 4 proteins were able to perfectly separate the HIV+TB group from the HIV+ORDs (Table 4). None of the biomarkers in these panels, however, had individual performances comparable to the strong individual performance of CD14 in the HIV-samples, indicating that these particular panels benefitted substantially more from biomarker complementarity.

This data demonstrated that modestly sized panels of protein biomarkers that reflect the physiological changes in the host during an active TB infection can be used to identify active TB, and to distinguish the disease from similarly presenting pneumonias in the presence or absence of an HIV co-infection.

TABLE 2A

Marker Discovery

| PROTEIN | #PEPTIDES | q-value | Active TB vs LTBI (HIV−) | | | Active TB vs LTBI (HIV+) | | | Active TB vs LTBI (HIV− and HIV+) | | |
|---|---|---|---|---|---|---|---|---|---|---|---|
| | | | DE | ANOVA DI | p-value | DE | ANOVA DI | p-value | DE | ANOVA DI | p-value |
| A1BG | 3 | 0.031 | | 0.85 | 0.208 | | 1.09 | 0.495 | | 0.96 | 0.658 |
| A2M | 119 | 0.000 | | 1.22 | 0.000 | | 0.84 | 0.000 | | 1.02 | 0.286 |
| ABI3BP | 7 | 0.062 | | 0.96 | 0.650 | | 0.90 | 0.220 | | 0.94 | 0.246 |
| ACTN1 | 0 | — | | — | — | | — | — | | — | — |
| ADAMTS13 | 5 | 0.000 | | 0.71 | 0.000 | | 0.91 | 0.313 | | 0.80 | 0.001 |
| ADAMTSL4 | 1 | 0.041 | | 0.84 | 0.342 | | 0.97 | 0.892 | | 0.90 | 0.448 |
| AFM | 6 | 0.000 | X | 0.42 | 0.000 | | 0.56 | 0.000 | X | 0.48 | 0.000 |
| AGT | 25 | 0.000 | | 0.86 | 0.002 | | 0.96 | 0.471 | | 0.91 | 0.007 |
| AHSG | 2 | 0.062 | | 1.23 | 0.214 | | 1.22 | 0.238 | | 1.22 | 0.087 |
| ALB | 12 | 0.020 | | 0.98 | 0.840 | | 1.10 | 0.240 | | 1.04 | 0.517 |
| ALCAM | 5 | 0.140 | | 1.03 | 0.731 | | 1.05 | 0.643 | | 1.04 | 0.573 |
| ALDOA | 6 | 0.016 | | 1.06 | 0.582 | | 1.02 | 0.891 | | 1.04 | 0.625 |
| ALDOB | 6 | 0.000 | | 0.61 | 0.000 | | 0.73 | 0.020 | | 0.66 | 0.000 |
| AMBP | 12 | 0.096 | | 0.95 | 0.528 | | 0.95 | 0.558 | | 0.95 | 0.394 |
| ANGPTL3 | 3 | 0.007 | | 1.19 | 0.135 | | 0.90 | 0.405 | | 1.05 | 0.614 |
| ANPEP | 9 | 0.005 | | 1.04 | 0.640 | | 0.90 | 0.167 | | 0.97 | 0.552 |
| AOC3 | 3 | 0.087 | | 1.22 | 0.126 | | 1.10 | 0.499 | | 1.16 | 0.117 |
| APCS | 5 | 0.000 | | 1.46 | 0.002 | | 1.22 | 0.118 | | 1.34 | 0.001 |
| APOA1 | 42 | 0.000 | | 0.60 | 0.000 | | 0.63 | 0.000 | | 0.62 | 0.000 |
| APOA2 | 6 | 0.000 | | 0.62 | 0.000 | | 0.63 | 0.000 | | 0.63 | 0.000 |
| APOA4 | 149 | 0.000 | X | 0.50 | 0.000 | | 0.51 | 0.000 | | 0.50 | 0.000 |
| APOB | 262 | 0.000 | | 0.75 | 0.000 | | 0.78 | 0.000 | | 0.76 | 0.000 |
| APOC1 | 7 | 0.000 | | 0.50 | 0.000 | X | 0.48 | 0.000 | X | 0.49 | 0.000 |
| APOC2 | 6 | 0.000 | X | 0.33 | 0.000 | X | 0.31 | 0.000 | X | 0.32 | 0.000 |
| APOC3 | 12 | 0.000 | X | 0.38 | 0.000 | X | 0.34 | 0.000 | X | 0.36 | 0.000 |
| APOC4 | 8 | 0.000 | X | 0.33 | 0.000 | X | 0.28 | 0.000 | X | 0.30 | 0.000 |
| APOD | 3 | 0.011 | | 0.85 | 0.164 | | 0.79 | 0.048 | | 0.83 | 0.018 |
| APOE | 47 | 0.000 | | 0.56 | 0.000 | X | 0.42 | 0.000 | X | 0.49 | 0.000 |
| APOF | 3 | 0.032 | | 0.89 | 0.380 | | 1.06 | 0.666 | | 0.97 | 0.733 |
| APOL1 | 9 | 0.066 | | 1.14 | 0.188 | | 1.09 | 0.375 | | 1.12 | 0.120 |
| APOM | 3 | 0.000 | | 0.58 | 0.000 | | 0.65 | 0.008 | | 0.61 | 0.000 |
| APP | 6 | 0.021 | | 0.97 | 0.764 | | 1.16 | 0.101 | | 1.06 | 0.375 |
| ARHGDIB | 3 | 0.000 | | 1.30 | 0.071 | | 1.26 | 0.124 | | 1.28 | 0.024 |
| ARPC5 | 0 | — | | — | — | | — | — | | — | — |
| ATP6AP1L | 0 | — | | — | — | | — | — | | — | — |
| ATRN | 26 | 0.000 | | 0.78 | 0.000 | | 0.81 | 0.000 | | 0.79 | 0.000 |
| AXL | 1 | 0.084 | | 0.74 | 0.282 | | 0.70 | 0.229 | | 0.72 | 0.105 |
| AZGP1 | 40 | 0.000 | | 1.11 | 0.002 | | 1.24 | 0.000 | | 1.17 | 0.000 |
| B2M | 16 | 0.000 | | 1.36 | 0.000 | | 1.17 | 0.009 | | 1.27 | 0.000 |
| B4GALT1 | 1 | 0.161 | | 1.25 | 0.331 | | 1.15 | 0.569 | | 1.20 | 0.265 |
| BCHE | 12 | 0.000 | | 0.76 | 0.000 | | 0.76 | 0.000 | | 0.76 | 0.000 |
| BLVRB | 1 | 0.096 | | 1.13 | 0.703 | | 1.06 | 0.861 | | 1.09 | 0.687 |
| BST1 | 4 | 0.023 | | 1.11 | 0.341 | | 1.20 | 0.101 | | 1.15 | 0.073 |
| BTD | 7 | 0.028 | | 0.78 | 0.050 | | 0.86 | 0.246 | | 0.82 | 0.027 |
| C1R | 66 | 0.020 | | 1.00 | 0.938 | | 1.03 | 0.428 | | 1.01 | 0.554 |
| C1RL | 21 | 0.047 | | 1.06 | 0.317 | | 1.01 | 0.890 | | 1.04 | 0.414 |
| C1S | 57 | 0.003 | | 0.93 | 0.011 | | 0.97 | 0.376 | | 0.95 | 0.015 |
| C2 | 44 | 0.000 | | 1.08 | 0.029 | | 0.98 | 0.598 | | 1.03 | 0.223 |
| C3 | 3 | 0.054 | | 1.16 | 0.367 | | 1.05 | 0.775 | | 1.11 | 0.397 |
| C4BPA | 3 | 0.003 | | 1.28 | 0.036 | | 1.24 | 0.076 | | 1.26 | 0.007 |
| C5 | 2 | 0.003 | | 1.26 | 0.111 | | 0.98 | 0.871 | | 1.11 | 0.314 |
| C6 | 0 | — | | — | — | | — | — | | — | — |
| C9 | 0 | — | | — | — | | — | — | | — | — |
| CA1 | 7 | 0.000 | | 1.35 | 0.071 | | 1.00 | 0.998 | | 1.17 | 0.195 |
| CA2 | 3 | 0.000 | | 1.46 | 0.093 | | 1.33 | 0.217 | | 1.40 | 0.043 |
| CACNA2D1 | 5 | 0.000 | | 0.74 | 0.001 | | 0.90 | 0.242 | | 0.81 | 0.002 |
| CALM1 | 0 | — | | — | — | | — | — | | — | — |
| CALU | 2 | 0.074 | | 1.06 | 0.744 | | 1.29 | 0.168 | | 1.16 | 0.240 |
| CAT | 5 | 0.000 | | 1.10 | 0.439 | | 1.11 | 0.401 | | 1.11 | 0.270 |
| CCDC149 | 1 | 0.000 | | 0.54 | 0.007 | | 0.58 | 0.021 | | 0.56 | 0.000 |
| CD14 | 19 | 0.000 | | 1.21 | 0.000 | | 1.09 | 0.096 | | 1.15 | 0.000 |
| CD163 | 6 | 0.000 | | 1.27 | 0.019 | | 1.20 | 0.079 | | 1.24 | 0.004 |
| CD44 | 4 | 0.055 | | 0.94 | 0.637 | | 0.89 | 0.395 | | 0.92 | 0.358 |
| CD59 | 1 | 0.074 | | 1.17 | 0.264 | | 1.21 | 0.194 | | 1.19 | 0.084 |
| CD5L | 14 | 0.000 | | 1.36 | 0.000 | | 1.96 | 0.000 | | 1.62 | 0.000 |
| CD84 | 1 | 0.006 | | 1.18 | 0.524 | | 1.18 | 0.537 | | 1.18 | 0.411 |
| CD93 | 3 | 0.074 | | 0.92 | 0.514 | | 0.90 | 0.401 | | 0.91 | 0.296 |
| CDH1 | 4 | 0.024 | | 1.05 | 0.683 | | 1.01 | 0.942 | | 1.03 | 0.730 |

TABLE 2A-continued

Marker Discovery

| | | | | | | Active TB vs LTBI (HIV−) | | | Active TB vs LTBI (HIV+) | | | Active TB vs LTBI (HIV− and HIV+) | | |
|---|---|---|---|---|---|---|---|---|---|---|---|---|---|---|
| PROTEIN | #PEPTIDES | q-value | DE | ANOVA DI | p-value | DE | ANOVA DI | p-value | DE | ANOVA DI | p-value |
| CDH13 | 4 | 0.000 | | 0.67 | 0.001 | | 0.79 | 0.051 | | 0.72 | 0.000 |
| CDH2 | 1 | 0.046 | | 0.74 | 0.193 | | 0.69 | 0.132 | | 0.72 | 0.047 |
| CDH5 | 9 | 0.003 | | 1.03 | 0.687 | | 0.97 | 0.620 | | 1.00 | 0.965 |
| CETP | 1 | 0.085 | | 0.77 | 0.347 | | 0.70 | 0.213 | | 0.74 | 0.121 |
| CFB | 0 | — | | — | — | | — | — | | — | — |
| CFD | 10 | 0.000 | | 0.81 | 0.001 | | 0.86 | 0.014 | | 0.83 | 0.000 |
| CFL1 | 0 | — | | — | — | | — | — | | — | — |
| CFP | 1 | 0.179 | | 0.92 | 0.660 | | 0.87 | 0.448 | | 0.90 | 0.394 |
| CHI3L1 | 1 | 0.000 | X | 2.07 | 0.003 | X | 2.16 | 0.003 | X | 2.11 | 0.000 |
| CHL1 | 15 | 0.001 | | 0.97 | 0.608 | | 0.93 | 0.261 | | 0.95 | 0.261 |
| CKM | 3 | 0.000 | | 0.63 | 0.004 | | 0.62 | 0.004 | | 0.62 | 0.000 |
| CLC | 1 | 0.113 | | 1.09 | 0.742 | | 1.33 | 0.263 | | 1.20 | 0.313 |
| CLEC3B | 25 | 0.000 | | 0.70 | 0.000 | | 0.71 | 0.000 | | 0.70 | 0.000 |
| CLIC1 | 0 | — | | — | — | | — | — | | — | — |
| CLU | 50 | 0.001 | | 0.98 | 0.612 | | 0.94 | 0.083 | | 0.96 | 0.124 |
| CNDP1 | 32 | 0.000 | | 0.62 | 0.000 | | 0.95 | 0.349 | | 0.76 | 0.000 |
| CNN2 | 1 | 0.000 | | 1.28 | 0.434 | | 1.29 | 0.427 | | 1.29 | 0.328 |
| CNTN1 | 7 | 0.000 | | 0.79 | 0.002 | | 1.01 | 0.867 | | 0.89 | 0.062 |
| COL18A1 | 2 | 0.134 | | 0.80 | 0.254 | | 0.87 | 0.495 | | 0.83 | 0.194 |
| COL6A1 | 3 | 0.089 | | 0.85 | 0.197 | | 0.95 | 0.710 | | 0.90 | 0.237 |
| COL6A3 | 10 | 0.000 | | 0.82 | 0.000 | | 0.94 | 0.307 | | 0.87 | 0.001 |
| COLEC10 | 2 | 0.007 | | 0.87 | 0.217 | | 0.84 | 0.137 | | 0.85 | 0.055 |
| COLEC11 | 6 | 0.001 | | 0.87 | 0.064 | | 0.82 | 0.010 | | 0.85 | 0.002 |
| COMP | 5 | 0.000 | | 0.77 | 0.002 | | 0.64 | 0.000 | | 0.70 | 0.000 |
| CORO1A | 2 | 0.000 | | 1.62 | 0.010 | | 1.42 | 0.067 | | 1.52 | 0.004 |
| CORO1B | 1 | 0.206 | | 1.14 | 0.671 | | 1.11 | 0.744 | | 1.12 | 0.588 |
| COTL1 | 1 | 0.007 | | 1.19 | 0.553 | | 1.39 | 0.284 | | 1.28 | 0.281 |
| CP | 3 | 0.000 | | 1.77 | 0.000 | | 1.07 | 0.670 | | 1.39 | 0.007 |
| CPB2 | 20 | 0.205 | | 1.00 | 0.960 | | 1.02 | 0.637 | | 1.01 | 0.722 |
| CPN1 | 21 | 0.140 | | 1.03 | 0.547 | | 1.02 | 0.713 | | 1.02 | 0.493 |
| CPN2 | 17 | 0.000 | | 0.85 | 0.021 | | 0.85 | 0.027 | | 0.85 | 0.002 |
| CPQ | 1 | 0.005 | | 0.95 | 0.822 | | 0.61 | 0.026 | | 0.77 | 0.109 |
| CRP | 3 | 0.000 | X | 4.45 | 0.000 | X | 2.22 | 0.003 | X | 3.20 | 0.000 |
| CRTAC1 | 8 | 0.000 | | 0.62 | 0.000 | | 0.62 | 0.000 | | 0.62 | 0.000 |
| CSF1R | 3 | 0.048 | | 0.85 | 0.244 | | 0.87 | 0.321 | | 0.86 | 0.130 |
| CST3 | 6 | 0.005 | | 1.10 | 0.344 | | 1.15 | 0.183 | | 1.12 | 0.113 |
| CTBS | 9 | 0.000 | | 0.74 | 0.000 | | 0.65 | 0.000 | | 0.70 | 0.000 |
| CTSD | 1 | 0.042 | | 1.09 | 0.738 | | 0.85 | 0.539 | | 0.97 | 0.866 |
| DAG1 | 3 | 0.057 | | 0.98 | 0.821 | | 0.97 | 0.740 | | 0.97 | 0.698 |
| DBH | 7 | 0.020 | | 0.83 | 0.181 | | 0.94 | 0.660 | | 0.88 | 0.208 |
| DPEP2 | 1 | 0.113 | | 0.86 | 0.533 | | 1.00 | 0.989 | | 0.93 | 0.657 |
| DPP4 | 1 | 0.041 | | 0.89 | 0.429 | | 1.15 | 0.382 | | 1.00 | 0.985 |
| DSG2 | 1 | 0.066 | | 0.92 | 0.559 | | 1.00 | 0.985 | | 0.95 | 0.666 |
| ECM1 | 12 | 0.000 | | 1.04 | 0.606 | | 1.15 | 0.053 | | 1.09 | 0.095 |
| ENDOD1 | 1 | 0.147 | | 0.77 | 0.263 | | 0.89 | 0.643 | | 0.83 | 0.253 |
| ENG | 1 | 0.085 | | 1.34 | 0.329 | | 0.99 | 0.981 | | 1.16 | 0.487 |
| ENO1 | 3 | 0.000 | | 1.20 | 0.164 | | 1.27 | 0.073 | | 1.23 | 0.034 |
| ENPP2 | 7 | 0.000 | | 1.18 | 0.112 | | 0.80 | 0.043 | | 0.98 | 0.829 |
| ERAP1 | 1 | 0.192 | | 1.02 | 0.888 | | 1.02 | 0.887 | | 1.02 | 0.839 |
| F10 | 19 | 0.000 | | 0.99 | 0.802 | | 1.01 | 0.900 | | 1.00 | 0.923 |
| F11 | 12 | 0.001 | | 0.91 | 0.089 | | 0.93 | 0.207 | | 0.92 | 0.038 |
| F12 | 23 | 0.000 | | 0.63 | 0.000 | | 0.63 | 0.000 | | 0.63 | 0.000 |
| F13A1 | 6 | 0.000 | | 0.81 | 0.060 | | 0.56 | 0.000 | | 0.68 | 0.000 |
| F13B | 13 | 0.000 | | 0.99 | 0.848 | | 0.86 | 0.019 | | 0.92 | 0.086 |
| F2 | 16 | 0.089 | | 1.02 | 0.714 | | 1.06 | 0.369 | | 1.04 | 0.383 |
| F5 | 24 | 0.006 | | 1.04 | 0.450 | | 1.11 | 0.051 | | 1.07 | 0.062 |
| F7 | 5 | 0.000 | | 0.75 | 0.003 | | 0.68 | 0.000 | | 0.72 | 0.000 |
| F9 | 16 | 0.000 | | 0.80 | 0.001 | | 0.72 | 0.000 | | 0.76 | 0.000 |
| FAH | 1 | 0.003 | | 0.80 | 0.472 | | 0.51 | 0.031 | | 0.64 | 0.050 |
| FAM3C | 1 | 0.144 | | 0.98 | 0.903 | | 1.10 | 0.546 | | 1.04 | 0.744 |
| FBLN1 | 8 | 0.000 | | 0.84 | 0.012 | | 0.86 | 0.048 | | 0.85 | 0.002 |
| FBXO33 | 0 | — | | — | — | | — | — | | — | — |
| FCGBP | 12 | 0.000 | | 1.19 | 0.004 | | 1.08 | 0.240 | | 1.14 | 0.005 |
| FCGR3A | 5 | 0.000 | | 1.41 | 0.006 | | 1.47 | 0.003 | | 1.44 | 0.000 |
| FCGR3B | 4 | 0.000 | | 1.46 | 0.008 | | 0.95 | 0.736 | | 1.19 | 0.103 |
| FCN2 | 11 | 0.000 | | 1.05 | 0.452 | | 0.96 | 0.524 | | 1.01 | 0.911 |
| FCN3 | 13 | 0.172 | | 0.94 | 0.410 | | 1.00 | 0.992 | | 0.97 | 0.556 |
| FETUB | 13 | 0.000 | | 1.32 | 0.000 | | 0.82 | 0.004 | | 1.05 | 0.311 |
| FGA | 19 | 0.000 | | 1.42 | 0.000 | | 1.84 | 0.000 | | 1.60 | 0.000 |
| FGB | 0 | — | | — | — | | — | — | | — | — |
| FGFR1 | 1 | 0.132 | | 0.87 | 0.571 | | 1.00 | 0.984 | | 0.93 | 0.687 |
| FGG | 0 | — | | — | — | | — | — | | — | — |
| FKBP1A | 1 | 0.039 | | 1.20 | 0.432 | | 1.24 | 0.364 | | 1.22 | 0.248 |
| FLNA | 10 | 0.000 | | 1.42 | 0.003 | | 1.28 | 0.046 | | 1.35 | 0.001 |

TABLE 2A-continued

Marker Discovery

| PROTEIN | #PEPTIDES | q-value | Active TB vs LTBI (HIV−) | | | | Active TB vs LTBI (HIV+) | | | Active TB vs LTBI (HIV− and HIV+) | | |
|---|---|---|---|---|---|---|---|---|---|---|---|---|
| | | | DE | ANOVA DI | p-value | DE | ANOVA DI | p-value | | DE | ANOVA DI | p-value |
| FLT4 | 1 | 0.203 | | 1.07 | 0.728 | | 0.93 | 0.694 | | | 1.00 | 0.988 |
| FN1 | 3 | 0.022 | | 1.21 | 0.204 | | 0.89 | 0.454 | | | 1.05 | 0.683 |
| FTL | 2 | 0.002 | | 1.00 | 0.991 | | 1.30 | 0.317 | | | 1.13 | 0.502 |
| FUCA1 | 1 | 0.138 | | 1.21 | 0.591 | | 0.90 | 0.776 | | | 1.05 | 0.843 |
| FUCA2 | 1 | 0.015 | | 1.19 | 0.411 | | 0.91 | 0.669 | | | 1.05 | 0.774 |
| GALNT2 | 1 | 0.089 | | 1.02 | 0.939 | | 1.25 | 0.326 | | | 1.12 | 0.467 |
| GAPDH | 2 | 0.003 | | 0.93 | 0.690 | | 0.93 | 0.699 | | | 0.93 | 0.595 |
| GC | 1 | 0.096 | | 0.76 | 0.168 | | 0.87 | 0.482 | | | 0.81 | 0.133 |
| GGH | 9 | 0.000 | | 1.31 | 0.000 | | 0.86 | 0.025 | | | 1.07 | 0.150 |
| GK | 0 | — | | — | — | | — | — | | | — | — |
| GNPTG | 2 | 0.100 | | 0.92 | 0.505 | | 1.01 | 0.921 | | | 0.96 | 0.676 |
| GOSR1 | 0 | — | | — | — | | — | — | | | — | — |
| GP1BA | 9 | 0.000 | | 1.02 | 0.795 | | 1.35 | 0.000 | | | 1.16 | 0.002 |
| GP5 | 6 | 0.006 | | 0.90 | 0.266 | | 1.17 | 0.105 | | | 1.02 | 0.772 |
| GPLD1 | 18 | 0.000 | | 0.73 | 0.000 | | 0.71 | 0.000 | | | 0.72 | 0.000 |
| GPR126 | 1 | 0.148 | | 0.88 | 0.395 | | 0.91 | 0.574 | | | 0.89 | 0.311 |
| GPX3 | 16 | 0.000 | | 0.94 | 0.290 | | 1.14 | 0.024 | | | 1.03 | 0.451 |
| GSN | 58 | 0.000 | | 0.63 | 0.000 | | 0.66 | 0.000 | | | 0.64 | 0.000 |
| GSTO1 | 1 | 0.001 | | 1.46 | 0.032 | | 1.08 | 0.689 | | | 1.26 | 0.084 |
| GSTP1 | 0 | — | | — | — | | — | — | | | — | — |
| HABP2 | 7 | 0.042 | | 0.98 | 0.803 | | 0.85 | 0.068 | | | 0.92 | 0.157 |
| HBA1 | 11 | 0.000 | X | 2.11 | 0.000 | | 1.79 | 0.000 | | | 1.95 | 0.000 |
| HBB | 6 | 0.000 | X | 2.03 | 0.000 | | 1.80 | 0.001 | | | 1.91 | 0.000 |
| HEG1 | 1 | 0.208 | | 0.91 | 0.559 | | 0.99 | 0.962 | | | 0.95 | 0.643 |
| HGFAC | 16 | 0.004 | | 0.84 | 0.024 | | 0.97 | 0.698 | | | 0.90 | 0.058 |
| HIST1H4A | 5 | 0.000 | | 1.73 | 0.000 | | 1.25 | 0.132 | | | 1.48 | 0.000 |
| HP | 39 | 0.000 | X | 3.01 | 0.000 | X | 2.97 | 0.000 | | X | 2.99 | 0.000 |
| HPR | 10 | 0.000 | | 1.76 | 0.000 | | 1.56 | 0.000 | | | 1.66 | 0.000 |
| HPX | 2 | 0.207 | | 0.94 | 0.695 | | 1.05 | 0.773 | | | 0.99 | 0.929 |
| HRNR | 7 | 0.000 | | 1.20 | 0.203 | | 1.36 | 0.037 | | | 1.28 | 0.022 |
| HSP90B1 | 4 | 0.021 | | 0.87 | 0.252 | | 0.77 | 0.039 | | | 0.82 | 0.026 |
| HSPA5 | 10 | 0.052 | | 1.02 | 0.774 | | 1.00 | 0.976 | | | 1.01 | 0.852 |
| HSPA8 | 0 | — | | — | — | | — | — | | | — | — |
| HSPB1 | 0 | — | | — | — | | — | — | | | — | — |
| HSPG2 | 9 | 0.000 | | 0.89 | 0.108 | | 1.01 | 0.902 | | | 0.95 | 0.284 |
| HYOU1 | 3 | 0.060 | | 0.85 | 0.214 | | 0.97 | 0.825 | | | 0.91 | 0.296 |
| ICAM1 | 5 | 0.000 | | 1.45 | 0.000 | | 1.16 | 0.109 | | | 1.31 | 0.000 |
| ICAM2 | 1 | 0.206 | | 1.06 | 0.740 | | 1.06 | 0.736 | | | 1.06 | 0.632 |
| ICOSLG | 1 | 0.050 | | 0.80 | 0.103 | | 0.98 | 0.892 | | | 0.88 | 0.210 |
| IDH1 | 1 | 0.003 | | 1.58 | 0.030 | | 1.20 | 0.392 | | | 1.39 | 0.034 |
| IGF1 | 2 | 0.002 | | 0.80 | 0.171 | | 0.95 | 0.759 | | | 0.86 | 0.245 |
| IGF2 | 5 | 0.000 | | 0.66 | 0.000 | | 0.81 | 0.040 | | | 0.73 | 0.000 |
| IGF2R | 1 | 0.062 | | 1.05 | 0.758 | | 1.09 | 0.610 | | | 1.07 | 0.565 |
| IGFALS | 37 | 0.000 | | 0.75 | 0.000 | | 0.95 | 0.207 | | | 0.84 | 0.000 |
| IGFBP1 | 1 | 0.154 | | 0.74 | 0.373 | | 0.75 | 0.399 | | | 0.75 | 0.213 |
| IGFBP2 | 6 | 0.000 | X | 2.49 | 0.000 | | 1.99 | 0.000 | | X | 2.23 | 0.000 |
| IGFBP3 | 13 | 0.000 | | 0.73 | 0.000 | | 0.98 | 0.795 | | | 0.84 | 0.001 |
| IGFBP4 | 1 | 0.124 | | 1.22 | 0.479 | | 0.91 | 0.734 | | | 1.06 | 0.777 |
| IGFBP5 | 3 | 0.000 | | 0.78 | 0.021 | | 0.99 | 0.959 | | | 0.88 | 0.104 |
| IGFBP6 | 2 | 0.006 | | 0.81 | 0.061 | | 1.07 | 0.564 | | | 0.92 | 0.349 |
| IGFBP7 | 1 | 0.181 | | 0.89 | 0.467 | | 1.04 | 0.811 | | | 0.96 | 0.712 |
| IGLL5 | 19 | 0.000 | | 1.94 | 0.000 | | 1.87 | 0.000 | | | 1.91 | 0.000 |
| IL1R2 | 1 | 0.030 | | 0.87 | 0.323 | | 0.75 | 0.060 | | | 0.81 | 0.045 |
| IL1RAP | 7 | 0.000 | | 0.77 | 0.004 | | 1.08 | 0.420 | | | 0.90 | 0.136 |
| IL6ST | 3 | 0.134 | | 1.26 | 0.256 | | 1.08 | 0.697 | | | 1.17 | 0.276 |
| ISLR | 3 | 0.013 | | 0.79 | 0.024 | | 0.92 | 0.428 | | | 0.85 | 0.031 |
| ITGB1 | 1 | 0.083 | | 0.82 | 0.335 | | 0.75 | 0.174 | | | 0.79 | 0.098 |
| ITIH1 | 2 | 0.161 | | 1.17 | 0.344 | | 1.16 | 0.390 | | | 1.16 | 0.200 |
| ITIH2 | 3 | 0.079 | | 0.85 | 0.185 | | 0.91 | 0.467 | | | 0.88 | 0.147 |
| ITIH3 | 17 | 0.000 | | 1.71 | 0.000 | | 1.48 | 0.000 | | | 1.60 | 0.000 |
| ITIH4 | 59 | 0.000 | | 1.34 | 0.000 | | 1.35 | 0.000 | | | 1.34 | 0.000 |
| KIT | 2 | 0.000 | | 0.72 | 0.059 | | 0.67 | 0.025 | | | 0.70 | 0.004 |
| KLKB1 | 14 | 0.000 | | 0.84 | 0.004 | | 0.89 | 0.062 | | | 0.86 | 0.001 |
| KNG1 | 7 | 0.019 | | 1.16 | 0.405 | | 1.39 | 0.074 | | | 1.26 | 0.071 |
| KRT1 | 30 | 0.000 | | 1.11 | 0.166 | | 1.08 | 0.348 | | | 1.10 | 0.104 |
| KRT10 | 8 | 0.018 | | 1.22 | 0.175 | | 1.30 | 0.074 | | | 1.26 | 0.028 |
| KRT14 | 3 | 0.198 | | 0.95 | 0.730 | | 1.01 | 0.931 | | | 0.98 | 0.848 |
| KRT2 | 11 | 0.000 | | 1.41 | 0.009 | | 1.30 | 0.051 | | | 1.36 | 0.001 |
| KRT5 | 1 | 0.088 | | 1.47 | 0.263 | | 1.39 | 0.358 | | | 1.43 | 0.144 |
| KRT9 | 16 | 0.000 | | 1.24 | 0.055 | | 1.18 | 0.160 | | | 1.21 | 0.021 |
| LAMB1 | 1 | 0.116 | | 0.88 | 0.388 | | 0.84 | 0.253 | | | 0.86 | 0.153 |
| LAMP1 | 2 | 0.089 | | 0.90 | 0.411 | | 0.93 | 0.582 | | | 0.92 | 0.333 |
| LAMP2 | 2 | 0.198 | | 0.92 | 0.623 | | 0.92 | 0.625 | | | 0.92 | 0.487 |
| LASP1 | 1 | 0.034 | | 0.97 | 0.912 | | 1.12 | 0.674 | | | 1.04 | 0.844 |

TABLE 2A-continued

Marker Discovery

| | | | | Active TB vs LTBI (HIV−) | | | Active TB vs LTBI (HIV+) | | | Active TB vs LTBI (HIV− and HIV+) | | |
|---|---|---|---|---|---|---|---|---|---|---|---|---|
| PROTEIN | #PEPTIDES | q-value | DE | ANOVA DI | p-value | DE | ANOVA DI | p-value | DE | ANOVA DI | p-value |
| LBP | 1 | 0.000 | | 1.69 | 0.010 | | 1.61 | 0.023 | | 1.65 | 0.001 |
| LCAT | 18 | 0.000 | | 0.77 | 0.000 | | 0.75 | 0.000 | | 0.76 | 0.000 |
| LCN2 | 2 | 0.082 | | 1.24 | 0.269 | | 1.18 | 0.395 | | 1.21 | 0.166 |
| LCP1 | 12 | 0.000 | | 1.43 | 0.000 | | 1.27 | 0.000 | | 1.35 | 0.000 |
| LDHB | 3 | 0.126 | | 1.00 | 0.995 | | 1.04 | 0.773 | | 1.02 | 0.841 |
| LGALS3BP | 28 | 0.000 | | 0.95 | 0.331 | | 0.79 | 0.000 | | 0.87 | 0.001 |
| LGALSL | 2 | 0.000 | | 1.43 | 0.037 | | 1.29 | 0.155 | | 1.36 | 0.031 |
| LILRA1 | 1 | 0.062 | | 0.81 | 0.611 | | 0.60 | 0.229 | | 0.70 | 0.242 |
| LILRA3 | 1 | 0.039 | | 1.21 | 0.548 | | 0.89 | 0.739 | | 1.05 | 0.841 |
| LPA | 16 | 0.000 | | 1.02 | 0.803 | | 1.33 | 0.005 | | 1.16 | 0.036 |
| LRG1 | 45 | 0.000 | | 1.73 | 0.000 | | 1.49 | 0.000 | | 1.61 | 0.000 |
| LRP1 | 4 | 0.192 | | 1.00 | 0.980 | | 1.04 | 0.710 | | 1.02 | 0.786 |
| LSAMP | 1 | 0.074 | | 0.87 | 0.398 | | 1.08 | 0.651 | | 0.97 | 0.766 |
| LUM | 34 | 0.000 | | 0.78 | 0.000 | | 0.83 | 0.000 | | 0.80 | 0.000 |
| LYVE1 | 4 | 0.054 | | 0.92 | 0.410 | | 0.99 | 0.947 | | 0.95 | 0.522 |
| LYZ | 2 | 0.003 | | 1.51 | 0.015 | | 1.01 | 0.948 | | 1.25 | 0.079 |
| MAN1A1 | 5 | 0.001 | | 1.28 | 0.008 | | 1.01 | 0.938 | | 1.14 | 0.051 |
| MAN2A2 | 1 | 0.179 | | 0.96 | 0.806 | | 1.03 | 0.867 | | 0.99 | 0.948 |
| MASP1 | 17 | 0.000 | | 0.84 | 0.000 | | 0.84 | 0.000 | | 0.84 | 0.000 |
| MASP2 | 8 | 0.135 | | 0.95 | 0.496 | | 0.99 | 0.912 | | 0.97 | 0.571 |
| MB | 1 | 0.005 | | 0.63 | 0.015 | | 0.73 | 0.100 | | 0.67 | 0.004 |
| MBL2 | 4 | 0.008 | | 1.01 | 0.928 | | 1.08 | 0.574 | | 1.04 | 0.658 |
| MCAM | 1 | 0.013 | | 0.63 | 0.031 | | 0.82 | 0.354 | | 0.71 | 0.028 |
| MEGF8 | 2 | 0.217 | | 0.94 | 0.678 | | 1.02 | 0.918 | | 0.97 | 0.816 |
| MIF | 0 | — | | — | — | | — | — | | — | — |
| MINPP1 | 2 | 0.149 | | 0.89 | 0.440 | | 0.96 | 0.797 | | 0.93 | 0.462 |
| MMP2 | 3 | 0.000 | | 0.60 | 0.000 | | 0.65 | 0.000 | | 0.62 | 0.000 |
| MMP9 | 2 | 0.000 | | 1.98 | 0.000 | | 1.75 | 0.003 | | 1.87 | 0.000 |
| MMRN2 | 1 | 0.075 | | 0.80 | 0.266 | | 1.02 | 0.919 | | 0.90 | 0.465 |
| MRPS26 | 1 | 0.055 | | 0.88 | 0.642 | | 0.63 | 0.091 | | 0.75 | 0.139 |
| MSN | 3 | 0.000 | | 1.17 | 0.260 | | 1.07 | 0.621 | | 1.12 | 0.287 |
| MST1 | 15 | 0.000 | | 1.01 | 0.873 | | 0.86 | 0.032 | | 0.94 | 0.189 |
| MTPN | 1 | 0.005 | | 0.97 | 0.933 | | 0.96 | 0.915 | | 0.96 | 0.903 |
| NAGLU | 3 | 0.005 | | 1.05 | 0.681 | | 0.84 | 0.147 | | 0.94 | 0.506 |
| NCAM1 | 2 | 0.096 | | 0.84 | 0.239 | | 0.99 | 0.924 | | 0.91 | 0.360 |
| NEO1 | 1 | 0.024 | | 0.74 | 0.081 | | 0.78 | 0.164 | | 0.76 | 0.025 |
| NID1 | 7 | 0.000 | | 1.15 | 0.064 | | 1.24 | 0.004 | | 1.19 | 0.001 |
| NRGN | 1 | 0.013 | | 1.02 | 0.952 | | 0.94 | 0.833 | | 0.98 | 0.924 |
| NRP1 | 3 | 0.013 | | 1.13 | 0.245 | | 1.20 | 0.096 | | 1.17 | 0.051 |
| NUCB1 | 1 | 0.060 | | 1.36 | 0.256 | | 1.53 | 0.123 | | 1.44 | 0.058 |
| NUP210L | 1 | 0.011 | | 1.64 | 0.153 | X | 2.09 | 0.038 | | 1.84 | 0.015 |
| OAF | 2 | 0.000 | | 1.16 | 0.134 | | 1.27 | 0.022 | | 1.21 | 0.008 |
| OLFM1 | 2 | 0.093 | | 0.92 | 0.587 | | 1.01 | 0.955 | | 0.96 | 0.722 |
| ORM1 | 10 | 0.000 | X | 2.21 | 0.000 | | 1.59 | 0.000 | | 1.89 | 0.000 |
| ORM2 | 10 | 0.000 | | 1.95 | 0.000 | | 1.29 | 0.013 | | 1.61 | 0.000 |
| PAM | 1 | 0.158 | | 1.17 | 0.376 | | 1.09 | 0.637 | | 1.13 | 0.329 |
| PCOLCE | 4 | 0.000 | | 0.74 | 0.001 | | 0.84 | 0.061 | | 0.78 | 0.000 |
| PCSK9 | 3 | 0.011 | | 0.77 | 0.050 | | 0.78 | 0.064 | | 0.77 | 0.007 |
| PDIA3 | 2 | 0.021 | | 1.19 | 0.155 | | 1.21 | 0.128 | | 1.20 | 0.039 |
| PDLIM1 | 3 | 0.000 | | 1.37 | 0.178 | | 1.54 | 0.075 | | 1.45 | 0.048 |
| PEPD | 9 | 0.000 | | 0.73 | 0.000 | | 0.74 | 0.000 | | 0.73 | 0.000 |
| PF4 | 11 | 0.000 | | 0.87 | 0.028 | | 1.14 | 0.043 | | 0.99 | 0.831 |
| PFN1 | 7 | 0.000 | | 1.32 | 0.012 | | 1.33 | 0.013 | | 1.33 | 0.002 |
| PGLYRP2 | 28 | 0.000 | | 0.68 | 0.000 | | 0.69 | 0.000 | | 0.68 | 0.000 |
| PI16 | 6 | 0.000 | | 0.50 | 0.000 | | 0.66 | 0.003 | | 0.57 | 0.000 |
| PIGR | 1 | 0.047 | | 1.39 | 0.159 | | 0.98 | 0.934 | | 1.18 | 0.342 |
| PLEK | 1 | 0.005 | | 0.91 | 0.808 | | 0.94 | 0.871 | | 0.92 | 0.791 |
| PLS1 | 1 | 0.031 | | 1.39 | 0.079 | | 1.25 | 0.242 | | 1.32 | 0.036 |
| PLTP | 3 | 0.001 | | 1.58 | 0.005 | | 1.26 | 0.160 | | 1.42 | 0.003 |
| PLXNB1 | 2 | 0.011 | | 1.12 | 0.352 | | 1.23 | 0.109 | | 1.17 | 0.078 |
| PODXL | 1 | 0.218 | | 0.96 | 0.816 | | 0.93 | 0.657 | | 0.94 | 0.631 |
| PON1 | 5 | 0.003 | | 0.77 | 0.012 | | 0.89 | 0.286 | | 0.82 | 0.011 |
| PON3 | 0 | — | | — | — | | — | — | | — | — |
| POR | 0 | — | | — | — | | — | — | | — | — |
| POSTN | 2 | 0.074 | | 1.00 | 0.985 | | 1.15 | 0.359 | | 1.07 | 0.527 |
| PPBP | 23 | 0.000 | | 1.04 | 0.470 | | 1.20 | 0.001 | | 1.11 | 0.007 |
| PPIA | 5 | 0.000 | | 1.65 | 0.000 | | 1.78 | 0.000 | | 1.71 | 0.000 |
| PPIB | 1 | 0.027 | | 1.31 | 0.175 | | 1.38 | 0.119 | | 1.34 | 0.041 |
| PRAP1 | 1 | 0.017 | | 0.70 | 0.158 | | 0.67 | 0.129 | | 0.69 | 0.037 |
| PRDX2 | 6 | 0.000 | | 1.47 | 0.009 | | 1.16 | 0.331 | | 1.31 | 0.012 |
| PRDX6 | 1 | 0.018 | | 1.35 | 0.251 | | 1.28 | 0.350 | | 1.32 | 0.139 |
| PRG4 | 5 | 0.000 | | 1.16 | 0.180 | | 1.08 | 0.502 | | 1.12 | 0.162 |
| PROC | 9 | 0.014 | | 0.88 | 0.079 | | 0.90 | 0.136 | | 0.89 | 0.022 |
| PROCR | 4 | 0.071 | | 0.87 | 0.240 | | 0.91 | 0.457 | | 0.89 | 0.177 |

TABLE 2A-continued

Marker Discovery

| | | | Active TB vs LTBI (HIV−) | | | Active TB vs LTBI (HIV+) | | | Active TB vs LTBI (HIV− and HIV+) | | |
|---|---|---|---|---|---|---|---|---|---|---|---|
| PROTEIN | #PEPTIDES | q-value | DE | ANOVA DI | p-value | DE | ANOVA DI | p-value | DE | ANOVA DI | p-value |
| PROS1 | 14 | 0.000 | | 0.76 | 0.000 | | 0.89 | 0.076 | | 0.82 | 0.000 |
| PROZ | 12 | 0.000 | | 0.87 | 0.121 | | 0.78 | 0.008 | | 0.83 | 0.004 |
| PRSS1 | 1 | 0.203 | | 1.07 | 0.763 | | 1.19 | 0.456 | | 1.13 | 0.459 |
| PRSS3 | 1 | 0.202 | | 1.02 | 0.920 | | 1.11 | 0.662 | | 1.06 | 0.707 |
| PTGDS | 2 | 0.189 | | 1.05 | 0.784 | | 1.15 | 0.439 | | 1.10 | 0.466 |
| PTPRG | 1 | 0.000 | | 0.59 | 0.015 | | 0.63 | 0.038 | | 0.61 | 0.001 |
| PTPRJ | 4 | 0.003 | | 0.84 | 0.033 | | 0.84 | 0.049 | | 0.84 | 0.004 |
| PTPRS | 1 | 0.203 | | 0.94 | 0.736 | | 0.99 | 0.955 | | 0.96 | 0.774 |
| PVR | 6 | 0.021 | | 0.96 | 0.662 | | 1.00 | 0.965 | | 0.98 | 0.776 |
| PVRL1 | 1 | 0.221 | | 0.95 | 0.757 | | 0.97 | 0.880 | | 0.96 | 0.738 |
| PZP | 8 | 0.000 | | 1.36 | 0.032 | | 1.01 | 0.955 | | 1.18 | 0.117 |
| QSOX1 | 11 | 0.000 | | 0.86 | 0.009 | | 0.78 | 0.000 | | 0.82 | 0.000 |
| RBBP8 | 1 | 0.027 | | 2.05 | 0.114 | | 2.31 | 0.075 | X | 2.17 | 0.016 |
| RNASE1 | 1 | 0.207 | | 1.13 | 0.637 | | 1.16 | 0.597 | | 1.15 | 0.473 |
| RTN4RL2 | 1 | 0.006 | | 0.71 | 0.015 | | 0.84 | 0.247 | | 0.77 | 0.011 |
| S100A12 | 2 | 0.002 | | 1.21 | 0.404 | | 0.96 | 0.867 | | 1.08 | 0.640 |
| S100A8 | 9 | 0.000 | | 1.43 | 0.001 | | 1.51 | 0.000 | | 1.47 | 0.000 |
| S100A9 | 18 | 0.000 | | 1.85 | 0.000 | | 1.83 | 0.000 | | 1.84 | 0.000 |
| SAA1 | 4 | 0.000 | X | 2.49 | 0.000 | X | 2.19 | 0.001 | X | 2.34 | 0.000 |
| SAA4 | 14 | 0.000 | | 0.83 | 0.014 | | 0.71 | 0.000 | | 0.77 | 0.000 |
| SDPR | 1 | 0.006 | | 1.39 | 0.322 | | 1.46 | 0.270 | | 1.42 | 0.166 |
| SELL | 8 | 0.000 | | 1.13 | 0.107 | | 1.14 | 0.106 | | 1.13 | 0.025 |
| SEMA4B | 1 | 0.014 | | 0.75 | 0.157 | | 0.68 | 0.067 | | 0.72 | 0.024 |
| SEPP1 | 8 | 0.001 | | 0.80 | 0.006 | | 0.83 | 0.033 | | 0.81 | 0.001 |
| SERPINA1 | 78 | 0.000 | | 1.94 | 0.000 | | 1.37 | 0.000 | | 1.65 | 0.000 |
| SERPINA10 | 16 | 0.000 | | 0.95 | 0.390 | | 0.76 | 0.000 | | 0.85 | 0.000 |
| SERPINA3 | 6 | 0.000 | | 1.66 | 0.000 | | 1.56 | 0.000 | | 1.61 | 0.000 |
| SERPINA4 | 22 | 0.000 | | 0.56 | 0.000 | | 0.59 | 0.000 | | 0.57 | 0.000 |
| SERPINA6 | 14 | 0.004 | | 1.03 | 0.708 | | 0.91 | 0.192 | | 0.97 | 0.542 |
| SERPINA7 | 37 | 0.000 | | 0.95 | 0.207 | | 0.77 | 0.000 | | 0.86 | 0.000 |
| SERPINB1 | 1 | 0.000 | | 1.51 | 0.057 | | 1.41 | 0.119 | | 1.46 | 0.026 |
| SERPINC1 | 1 | 0.007 | | 1.79 | 0.025 | | 1.51 | 0.126 | | 1.65 | 0.007 |
| SERPIND1 | 25 | 0.000 | | 0.90 | 0.060 | | 0.82 | 0.000 | | 0.86 | 0.000 |
| SERPINF1 | 41 | 0.000 | | 0.73 | 0.000 | | 0.78 | 0.000 | | 0.76 | 0.000 |
| SERPINF2 | 1 | 0.039 | | 1.48 | 0.082 | | 1.28 | 0.282 | | 1.38 | 0.044 |
| SERPING1 | 15 | 0.005 | | 0.85 | 0.016 | | 0.94 | 0.389 | | 0.90 | 0.021 |
| SH3BGRL | 1 | 0.000 | | 1.70 | 0.021 | | 1.65 | 0.033 | | 1.68 | 0.003 |
| SH3BGRL3 | 3 | 0.000 | | 1.59 | 0.014 | | 1.67 | 0.008 | | 1.62 | 0.001 |
| SHBG | 16 | 0.000 | | 1.09 | 0.314 | | 0.71 | 0.000 | | 0.89 | 0.073 |
| SLC3A2 | 2 | 0.000 | | 0.57 | 0.000 | | 0.60 | 0.001 | | 0.58 | 0.000 |
| SNCA | 0 | — | | — | — | | — | — | | — | — |
| SNED1 | 1 | 0.119 | | 1.13 | 0.489 | | 0.99 | 0.963 | | 1.06 | 0.640 |
| SOD3 | 5 | 0.004 | | 0.94 | 0.538 | | 0.76 | 0.011 | | 0.85 | 0.031 |
| SORL1 | 2 | 0.089 | | 1.07 | 0.813 | | 1.16 | 0.590 | | 1.11 | 0.594 |
| SOWAHC | 0 | — | | — | — | | — | — | | — | — |
| SPARC | 11 | 0.000 | | 1.02 | 0.739 | | 1.36 | 0.000 | | 1.17 | 0.002 |
| SPARCL1 | 2 | 0.042 | | 0.91 | 0.533 | | 1.11 | 0.498 | | 1.00 | 0.994 |
| SPP2 | 2 | 0.000 | | 0.61 | 0.004 | | 0.55 | 0.001 | | 0.58 | 0.000 |
| SRGN | 3 | 0.017 | | 1.01 | 0.942 | | 1.24 | 0.071 | | 1.11 | 0.208 |
| SSC5D | 2 | 0.049 | | 0.99 | 0.950 | | 0.84 | 0.363 | | 0.91 | 0.513 |
| STXBP3 | 0 | — | | — | — | | — | — | | — | — |
| TAGLN2 | 7 | 0.000 | | 1.65 | 0.000 | | 1.76 | 0.000 | | 1.70 | 0.000 |
| TF | 8 | 0.001 | | 0.84 | 0.080 | | 0.96 | 0.702 | | 0.89 | 0.128 |
| TGFBI | 14 | 0.000 | | 0.87 | 0.046 | | 0.95 | 0.493 | | 0.91 | 0.059 |
| THBS1 | 30 | 0.000 | | 0.76 | 0.000 | | 0.96 | 0.458 | | 0.85 | 0.000 |
| TIMP1 | 1 | 0.181 | | 0.98 | 0.917 | | 1.20 | 0.419 | | 1.08 | 0.632 |
| TKT | 3 | 0.000 | | 1.43 | 0.016 | | 1.35 | 0.050 | | 1.39 | 0.002 |
| TLN1 | 11 | 0.000 | | 1.18 | 0.048 | | 1.22 | 0.026 | | 1.20 | 0.005 |
| TMSB4X | 6 | 0.000 | | 1.51 | 0.006 | | 1.45 | 0.017 | | 1.48 | 0.001 |
| TNC | 5 | 0.205 | | 1.01 | 0.957 | | 1.05 | 0.667 | | 1.03 | 0.741 |
| TNXB | 19 | 0.000 | | 0.83 | 0.000 | | 0.84 | 0.000 | | 0.83 | 0.000 |
| TPI1 | 2 | 0.001 | | 1.38 | 0.055 | | 1.22 | 0.250 | | 1.30 | 0.036 |
| TPM3 | 3 | 0.000 | | 1.25 | 0.156 | | 1.27 | 0.139 | | 1.26 | 0.062 |
| TPM4 | 1 | 0.072 | | 1.00 | 0.994 | | 1.11 | 0.760 | | 1.05 | 0.844 |
| TREML1 | 3 | 0.000 | | 1.40 | 0.043 | | 1.79 | 0.001 | | 1.57 | 0.000 |
| TTR | 4 | 0.208 | | 0.92 | 0.551 | | 1.00 | 0.987 | | 0.96 | 0.673 |
| TUBA4A | 2 | 0.003 | | 1.30 | 0.075 | | 1.31 | 0.075 | | 1.30 | 0.014 |
| UMOD | 1 | 0.066 | | 1.17 | 0.298 | | 1.16 | 0.328 | | 1.16 | 0.147 |
| VASN | 7 | 0.072 | | 0.90 | 0.108 | | 0.95 | 0.435 | | 0.92 | 0.090 |
| VASP | 1 | 0.003 | | 1.16 | 0.522 | | 1.21 | 0.428 | | 1.18 | 0.348 |
| VCAM1 | 12 | 0.007 | | 1.10 | 0.161 | | 1.02 | 0.816 | | 1.06 | 0.241 |
| VCL | 5 | 0.008 | | 1.10 | 0.364 | | 1.21 | 0.079 | | 1.15 | 0.067 |
| VIM | 2 | 0.219 | | 0.94 | 0.804 | | 0.95 | 0.842 | | 0.94 | 0.750 |
| VNN1 | 4 | 0.001 | | 0.63 | 0.006 | | 0.86 | 0.368 | | 0.73 | 0.010 |

TABLE 2A-continued

Marker Discovery

| PROTEIN | #PEPTIDES | Active TB vs LTBI (HIV−) | | | | Active TB vs LTBI (HIV+) | | | Active TB vs LTBI (HIV− and HIV+) | | |
|---|---|---|---|---|---|---|---|---|---|---|---|
| | | q-value | DE | ANOVA DI | p-value | DE | ANOVA DI | p-value | DE | ANOVA DI | p-value |
| VTN | 4 | 0.027 | | 0.86 | 0.159 | | 0.82 | 0.061 | | 0.84 | 0.022 |
| VWF | 60 | 0.000 | | 1.05 | 0.192 | | 0.93 | 0.057 | | 0.99 | 0.729 |
| YWHAE | 0 | — | | — | — | | — | — | | — | — |
| YWHAG | 0 | — | | — | — | | — | — | | — | — |
| YWHAZ | 0 | — | | — | — | | — | — | | — | — |
| ZYX | 3 | 0.000 | | 1.58 | 0.093 | | 1.71 | 0.054 | | 1.64 | 0.021 |

*Differential expression (DE) thresholds: p-value < 0.05 | q-value < 0.05 | ANOVA DI > 2

TABLE 2B

Marker Discovery

| PROTEIN | #PEPTIDES | Active TB vs Asymptomatic (HIV−) | | | | Active TB vs Asymptomatic (HIV+) | | | Asymptomatic (HIV− and HIV+) | | |
|---|---|---|---|---|---|---|---|---|---|---|---|
| | | q-value | DE | ANOVA DI | p-value | DE | ANOVA DI | p-value | DE | ANOVA DI | p-value |
| A1BG | 3 | 0.031 | | 0.96 | 0.750 | | 1.09 | 0.518 | | 1.02 | 0.821 |
| A2M | 119 | 0.000 | | 0.74 | 0.000 | | 0.87 | 0.000 | | 0.80 | 0.000 |
| ABI3BP | 7 | 0.062 | | 1.04 | 0.639 | | 1.03 | 0.753 | | 1.03 | 0.581 |
| ACTN1 | 0 | — | | — | — | | — | — | | — | — |
| ADAMTS13 | 5 | 0.000 | | 0.80 | 0.013 | | 0.90 | 0.239 | | 0.85 | 0.012 |
| ADAMTSL4 | 1 | 0.041 | | 0.75 | 0.118 | | 1.02 | 0.898 | | 0.87 | 0.326 |
| AFM | 6 | 0.000 | | 0.62 | 0.000 | | 0.50 | 0.000 | | 0.56 | 0.000 |
| AGT | 25 | 0.000 | | 0.86 | 0.003 | | 0.82 | 0.000 | | 0.84 | 0.000 |
| AHSG | 2 | 0.062 | | 1.28 | 0.142 | | 1.15 | 0.413 | | 1.21 | 0.104 |
| ALB | 12 | 0.020 | | 1.16 | 0.078 | | 1.06 | 0.485 | | 1.11 | 0.084 |
| ALCAM | 5 | 0.140 | | 1.12 | 0.249 | | 1.08 | 0.437 | | 1.10 | 0.173 |
| ALDOA | 6 | 0.016 | | 1.27 | 0.034 | | 1.04 | 0.733 | | 1.15 | 0.085 |
| ALDOB | 6 | 0.000 | | 0.94 | 0.625 | | 0.64 | 0.001 | | 0.78 | 0.009 |
| AMBP | 12 | 0.096 | | 1.07 | 0.442 | | 0.96 | 0.659 | | 1.01 | 0.818 |
| ANGPTL3 | 3 | 0.007 | | 1.16 | 0.232 | | 0.97 | 0.818 | | 1.06 | 0.510 |
| ANPEP | 9 | 0.005 | | 0.89 | 0.117 | | 0.89 | 0.112 | | 0.89 | 0.027 |
| AOC3 | 3 | 0.087 | | 1.06 | 0.671 | | 1.10 | 0.475 | | 1.08 | 0.422 |
| APCS | 5 | 0.000 | | 1.85 | 0.000 | | 1.32 | 0.031 | | 1.56 | 0.000 |
| APOA1 | 42 | 0.000 | X | 0.47 | 0.000 | | 0.69 | 0.000 | | 0.57 | 0.000 |
| APOA2 | 6 | 0.000 | | 0.59 | 0.000 | | 0.70 | 0.000 | | 0.64 | 0.000 |
| APOA4 | 149 | 0.000 | | 0.55 | 0.000 | | 0.66 | 0.000 | | 0.60 | 0.000 |
| APOB | 262 | 0.000 | | 0.92 | 0.000 | | 0.76 | 0.000 | | 0.83 | 0.000 |
| APOC1 | 7 | 0.000 | | 0.69 | 0.010 | X | 0.50 | 0.000 | | 0.59 | 0.000 |
| APOC2 | 6 | 0.000 | | 0.62 | 0.002 | X | 0.33 | 0.000 | X | 0.45 | 0.000 |
| APOC3 | 12 | 0.000 | | 0.63 | 0.000 | X | 0.33 | 0.000 | X | 0.45 | 0.000 |
| APOC4 | 8 | 0.000 | | 0.55 | 0.000 | X | 0.31 | 0.000 | X | 0.41 | 0.000 |
| APOD | 3 | 0.011 | | 0.82 | 0.084 | | 0.82 | 0.086 | | 0.82 | 0.015 |
| APOE | 47 | 0.000 | | 0.78 | 0.000 | X | 0.44 | 0.000 | | 0.59 | 0.000 |
| APOF | 3 | 0.032 | | 1.19 | 0.192 | | 1.04 | 0.770 | | 1.11 | 0.264 |
| APOL1 | 9 | 0.066 | | 1.10 | 0.338 | | 1.16 | 0.142 | | 1.13 | 0.087 |
| APOM | 3 | 0.000 | | 0.89 | 0.465 | | 0.63 | 0.003 | | 0.75 | 0.012 |
| APP | 6 | 0.021 | | 1.07 | 0.434 | | 0.97 | 0.758 | | 1.02 | 0.741 |
| ARHGDIB | 3 | 0.000 | | 1.35 | 0.044 | | 0.84 | 0.261 | | 1.07 | 0.548 |
| ARPC5 | 0 | — | | — | — | | — | — | | — | — |
| ATP6AP1L | 0 | — | | — | — | | — | — | | — | — |
| ATRN | 26 | 0.000 | | 0.84 | 0.000 | | 0.76 | 0.000 | | 0.80 | 0.000 |
| AXL | 1 | 0.084 | | 0.71 | 0.241 | | 0.87 | 0.633 | | 0.79 | 0.237 |
| AZGP1 | 40 | 0.000 | | 1.06 | 0.076 | | 1.20 | 0.000 | | 1.13 | 0.000 |
| B2M | 16 | 0.000 | | 1.53 | 0.000 | | 1.27 | 0.000 | | 1.40 | 0.000 |
| B4GALT1 | 1 | 0.161 | | 1.20 | 0.445 | | 1.14 | 0.572 | | 1.17 | 0.339 |
| BCHE | 12 | 0.000 | | 0.75 | 0.000 | | 0.68 | 0.000 | | 0.71 | 0.000 |
| BLVRB | 1 | 0.096 | | 1.50 | 0.209 | | 1.36 | 0.342 | | 1.43 | 0.112 |
| BST1 | 4 | 0.023 | | 0.96 | 0.700 | | 1.11 | 0.344 | | 1.03 | 0.694 |
| BTD | 7 | 0.028 | | 0.85 | 0.212 | | 0.87 | 0.280 | | 0.86 | 0.101 |
| C1R | 66 | 0.020 | | 1.00 | 0.914 | | 1.06 | 0.061 | | 1.03 | 0.214 |
| C1RL | 21 | 0.047 | | 0.98 | 0.677 | | 1.08 | 0.193 | | 1.03 | 0.534 |
| C1S | 57 | 0.003 | | 0.96 | 0.197 | | 0.99 | 0.831 | | 0.98 | 0.291 |
| C2 | 44 | 0.000 | | 1.16 | 0.000 | | 1.04 | 0.227 | | 1.10 | 0.000 |
| C3 | 3 | 0.054 | | 1.33 | 0.095 | | 1.18 | 0.327 | | 1.25 | 0.062 |
| C4BPA | 3 | 0.003 | | 1.26 | 0.051 | | 1.03 | 0.797 | | 1.14 | 0.123 |
| C5 | 2 | 0.003 | | 1.38 | 0.028 | | 1.03 | 0.824 | | 1.20 | 0.102 |
| C6 | 0 | — | | — | — | | — | — | | — | — |

TABLE 2B-continued

| | | Marker Discovery | | | | | | | | |
|---|---|---|---|---|---|---|---|---|---|---|
| | | | Active TB vs Asymptomatic (HIV−) | | | Active TB vs Asymptomatic (HIV+) | | | Asymptomatic (HIV− and HIV+) | |
| PROTEIN | #PEPTIDES | q-value | DE | ANOVA DI | p-value | DE | ANOVA DI | p-value | DE | ANOVA DI | p-value |
| C9 | 0 | — | | — | — | | — | — | | — | — |
| CA1 | 7 | 0.000 | | 1.91 | 0.000 | | 1.51 | 0.015 | | 1.70 | 0.000 |
| CA2 | 3 | 0.000 | X | 2.13 | 0.001 | | 1.37 | 0.178 | | 1.71 | 0.001 |
| CACNA2D1 | 5 | 0.000 | | 0.71 | 0.000 | | 0.95 | 0.551 | | 0.82 | 0.004 |
| CALM1 | 0 | — | | — | — | | — | — | | — | — |
| CALU | 2 | 0.074 | | 1.19 | 0.353 | | 1.23 | 0.264 | | 1.21 | 0.149 |
| CAT | 5 | 0.000 | | 1.71 | 0.000 | | 1.15 | 0.270 | | 1.40 | 0.000 |
| CCDC149 | 1 | 0.000 | | 0.59 | 0.027 | | 0.60 | 0.033 | | 0.60 | 0.002 |
| CD14 | 19 | 0.000 | | 1.12 | 0.028 | | 1.23 | 0.000 | | 1.17 | 0.000 |
| CD163 | 6 | 0.000 | | 1.38 | 0.002 | | 1.13 | 0.248 | | 1.25 | 0.003 |
| CD44 | 4 | 0.055 | | 1.14 | 0.323 | | 1.04 | 0.758 | | 1.09 | 0.361 |
| CD59 | 1 | 0.074 | | 1.20 | 0.212 | | 1.14 | 0.362 | | 1.17 | 0.120 |
| CD5L | 14 | 0.000 | | 0.98 | 0.852 | | 1.82 | 0.000 | | 1.34 | 0.000 |
| CD84 | 1 | 0.006 | | 1.32 | 0.304 | | 0.67 | 0.128 | | 0.94 | 0.746 |
| CD93 | 3 | 0.074 | | 0.82 | 0.111 | | 0.89 | 0.357 | | 0.85 | 0.076 |
| CDH1 | 4 | 0.024 | | 1.21 | 0.100 | | 1.19 | 0.132 | | 1.20 | 0.026 |
| CDH13 | 4 | 0.000 | | 0.63 | 0.000 | | 0.86 | 0.230 | | 0.73 | 0.001 |
| CDH2 | 1 | 0.046 | | 0.92 | 0.725 | | 0.76 | 0.248 | | 0.83 | 0.282 |
| CDH5 | 9 | 0.003 | | 0.94 | 0.312 | | 1.13 | 0.068 | | 1.03 | 0.572 |
| CETP | 1 | 0.085 | | 0.70 | 0.217 | | 0.84 | 0.544 | | 0.77 | 0.188 |
| CFB | 0 | — | | — | — | | — | — | | — | — |
| CFD | 10 | 0.000 | | 0.93 | 0.242 | | 0.84 | 0.004 | | 0.88 | 0.005 |
| CFL1 | 0 | — | | — | — | | — | — | | — | — |
| CFP | 1 | 0.179 | | 1.01 | 0.966 | | 1.02 | 0.927 | | 1.01 | 0.923 |
| CHI3L1 | 1 | 0.000 | X | 2.36 | 0.001 | | 1.53 | 0.096 | | 1.90 | 0.001 |
| CHL1 | 15 | 0.001 | | 1.00 | 0.974 | | 0.85 | 0.007 | | 0.92 | 0.063 |
| CKM | 3 | 0.000 | | 0.82 | 0.222 | | 0.64 | 0.008 | | 0.72 | 0.007 |
| CLC | 1 | 0.113 | | 1.31 | 0.302 | | 1.20 | 0.474 | | 1.25 | 0.213 |
| CLEC3B | 25 | 0.000 | | 0.70 | 0.000 | | 0.76 | 0.000 | | 0.73 | 0.000 |
| CLIC1 | 0 | — | | — | — | | — | — | | — | — |
| CLU | 50 | 0.001 | | 1.03 | 0.371 | | 1.04 | 0.231 | | 1.04 | 0.142 |
| CNDP1 | 32 | 0.000 | | 0.64 | 0.000 | | 0.65 | 0.000 | | 0.64 | 0.000 |
| CNN2 | 1 | 0.000 | | 1.43 | 0.268 | X | 0.49 | 0.028 | | 0.84 | 0.495 |
| CNTN1 | 7 | 0.000 | | 0.75 | 0.001 | | 0.90 | 0.207 | | 0.82 | 0.002 |
| COL18A1 | 2 | 0.134 | | 0.94 | 0.755 | | 0.85 | 0.423 | | 0.89 | 0.429 |
| COL6A1 | 3 | 0.089 | | 0.99 | 0.909 | | 0.87 | 0.303 | | 0.93 | 0.421 |
| COL6A3 | 10 | 0.000 | | 0.82 | 0.001 | | 0.91 | 0.116 | | 0.86 | 0.001 |
| COLEC10 | 2 | 0.007 | | 0.78 | 0.045 | | 0.78 | 0.040 | | 0.78 | 0.004 |
| COLEC11 | 6 | 0.001 | | 0.83 | 0.017 | | 0.90 | 0.173 | | 0.87 | 0.008 |
| COMP | 5 | 0.000 | | 0.81 | 0.017 | | 0.68 | 0.000 | | 0.74 | 0.000 |
| CORO1A | 2 | 0.000 | | 1.84 | 0.002 | | 0.89 | 0.550 | | 1.28 | 0.096 |
| CORO1B | 1 | 0.206 | | 0.96 | 0.895 | | 0.94 | 0.854 | | 0.95 | 0.820 |
| COTL1 | 1 | 0.007 | | 1.59 | 0.133 | | 0.73 | 0.305 | | 1.08 | 0.754 |
| CP | 3 | 0.000 | | 1.74 | 0.001 | | 1.24 | 0.199 | | 1.47 | 0.002 |
| CPB2 | 20 | 0.205 | | 1.01 | 0.829 | | 0.98 | 0.727 | | 1.00 | 0.925 |
| CPN1 | 21 | 0.140 | | 0.98 | 0.683 | | 0.98 | 0.597 | | 0.98 | 0.510 |
| CPN2 | 17 | 0.000 | | 0.82 | 0.007 | | 0.82 | 0.007 | | 0.82 | 0.000 |
| CPQ | 1 | 0.005 | | 0.77 | 0.252 | | 0.68 | 0.088 | | 0.72 | 0.054 |
| CRP | 3 | 0.000 | X | 4.41 | 0.000 | X | 3.18 | 0.000 | X | 3.74 | 0.000 |
| CRTAC1 | 8 | 0.000 | | 0.79 | 0.002 | | 0.68 | 0.000 | | 0.73 | 0.000 |
| CSF1R | 3 | 0.048 | | 1.08 | 0.575 | | 0.92 | 0.547 | | 1.00 | 0.977 |
| CST3 | 6 | 0.005 | | 1.30 | 0.011 | | 1.13 | 0.252 | | 1.21 | 0.010 |
| CTBS | 9 | 0.000 | | 0.81 | 0.001 | | 0.75 | 0.000 | | 0.78 | 0.000 |
| CTSD | 1 | 0.042 | | 1.37 | 0.230 | | 0.86 | 0.578 | | 1.09 | 0.662 |
| DAG1 | 3 | 0.057 | | 1.02 | 0.847 | | 1.16 | 0.160 | | 1.09 | 0.262 |
| DBH | 7 | 0.020 | | 0.76 | 0.054 | | 0.96 | 0.780 | | 0.85 | 0.123 |
| DPEP2 | 1 | 0.113 | | 0.95 | 0.840 | | 1.23 | 0.401 | | 1.08 | 0.652 |
| DPP4 | 1 | 0.041 | | 0.89 | 0.476 | | 0.87 | 0.382 | | 0.88 | 0.273 |
| DSG2 | 1 | 0.066 | | 0.80 | 0.138 | | 0.99 | 0.971 | | 0.89 | 0.291 |
| ECM1 | 12 | 0.000 | | 1.07 | 0.323 | | 1.24 | 0.002 | | 1.16 | 0.005 |
| ENDOD1 | 1 | 0.147 | | 0.87 | 0.550 | | 0.94 | 0.787 | | 0.90 | 0.534 |
| ENG | 1 | 0.085 | | 1.45 | 0.231 | | 1.27 | 0.448 | | 1.36 | 0.166 |
| ENO1 | 3 | 0.000 | | 1.43 | 0.007 | | 0.90 | 0.422 | | 1.13 | 0.204 |
| ENPP2 | 7 | 0.000 | | 1.00 | 0.984 | | 1.12 | 0.298 | | 1.06 | 0.467 |
| ERAP1 | 1 | 0.192 | | 1.11 | 0.477 | | 1.10 | 0.535 | | 1.10 | 0.337 |
| F10 | 19 | 0.000 | | 1.07 | 0.089 | | 1.12 | 0.006 | | 1.10 | 0.002 |
| F11 | 12 | 0.001 | | 0.85 | 0.006 | | 0.95 | 0.381 | | 0.90 | 0.011 |
| F12 | 23 | 0.000 | | 0.59 | 0.000 | | 0.77 | 0.000 | | 0.67 | 0.000 |
| F13A1 | 6 | 0.000 | | 0.72 | 0.005 | | 0.88 | 0.276 | | 0.79 | 0.007 |
| F13B | 13 | 0.000 | | 0.82 | 0.002 | | 0.86 | 0.018 | | 0.84 | 0.000 |
| F2 | 16 | 0.089 | | 1.10 | 0.153 | | 1.02 | 0.736 | | 1.06 | 0.214 |

TABLE 2B-continued

Marker Discovery

| PROTEIN | #PEPTIDES | Active TB vs Asymptomatic (HIV−) | | | | Active TB vs Asymptomatic (HIV+) | | | | Asymptomatic (HIV− and HIV+) | | |
|---|---|---|---|---|---|---|---|---|---|---|---|---|
| | | q-value | DE | ANOVA DI | p-value | DE | ANOVA DI | p-value | DE | ANOVA DI | p-value |
| F5 | 24 | 0.006 | | 1.12 | 0.032 | | 1.07 | 0.186 | | 1.10 | 0.015 |
| F7 | 5 | 0.000 | | 0.84 | 0.083 | | 0.80 | 0.022 | | 0.82 | 0.005 |
| F9 | 16 | 0.000 | | 0.83 | 0.005 | | 0.79 | 0.001 | | 0.81 | 0.000 |
| FAH | 1 | 0.003 | X | 0.50 | 0.028 | | 0.59 | 0.096 | | 0.54 | 0.007 |
| FAM3C | 1 | 0.144 | | 1.11 | 0.498 | | 1.14 | 0.398 | | 1.12 | 0.276 |
| FBLN1 | 8 | 0.000 | | 0.79 | 0.002 | | 0.88 | 0.077 | | 0.83 | 0.001 |
| FBXO33 | 0 | — | | — | — | | — | — | | — | — |
| FCGBP | 12 | 0.000 | | 1.19 | 0.007 | | 0.93 | 0.291 | | 1.05 | 0.263 |
| FCGR3A | 5 | 0.000 | | 1.69 | 0.000 | | 1.39 | 0.010 | | 1.53 | 0.000 |
| FCGR3B | 4 | 0.000 | | 1.06 | 0.684 | | 1.45 | 0.011 | | 1.24 | 0.046 |
| FCN2 | 11 | 0.000 | | 1.10 | 0.174 | | 1.28 | 0.000 | | 1.19 | 0.001 |
| FCN3 | 13 | 0.172 | | 0.95 | 0.489 | | 0.98 | 0.827 | | 0.96 | 0.522 |
| FETUB | 13 | 0.000 | | 1.32 | 0.000 | | 1.09 | 0.203 | | 1.20 | 0.000 |
| FGA | 19 | 0.000 | | 1.57 | 0.000 | | 1.40 | 0.000 | | 1.48 | 0.000 |
| FGB | 0 | — | | — | — | | — | — | | — | — |
| FGFR1 | 1 | 0.132 | | 0.76 | 0.276 | | 0.87 | 0.562 | | 0.81 | 0.233 |
| FGG | 0 | — | | — | — | | — | — | | — | — |
| FKBP1A | 1 | 0.039 | | 1.34 | 0.221 | | 0.87 | 0.559 | | 1.08 | 0.660 |
| FLNA | 10 | 0.000 | | 1.50 | 0.001 | | 0.69 | 0.003 | | 1.02 | 0.841 |
| FLT4 | 1 | 0.203 | | 1.05 | 0.810 | | 1.05 | 0.797 | | 1.05 | 0.722 |
| FN1 | 3 | 0.022 | | 1.16 | 0.345 | | 1.15 | 0.358 | | 1.15 | 0.196 |
| FTL | 2 | 0.002 | | 1.85 | 0.018 | | 1.59 | 0.073 | | 1.71 | 0.003 |
| FUCA1 | 1 | 0.138 | | 1.38 | 0.373 | | 1.18 | 0.647 | | 1.28 | 0.337 |
| FUCA2 | 1 | 0.015 | | 1.40 | 0.119 | | 0.89 | 0.584 | | 1.12 | 0.502 |
| GALNT2 | 1 | 0.089 | | 1.21 | 0.402 | | 1.30 | 0.243 | | 1.25 | 0.154 |
| GAPDH | 2 | 0.003 | | 1.04 | 0.830 | | 0.62 | 0.016 | | 0.80 | 0.135 |
| GC | 1 | 0.096 | | 0.94 | 0.747 | | 0.95 | 0.800 | | 0.94 | 0.680 |
| GGH | 9 | 0.000 | | 1.40 | 0.000 | | 1.03 | 0.686 | | 1.20 | 0.000 |
| GK | 0 | — | | — | — | | — | — | | — | — |
| GNPTG | 2 | 0.100 | | 1.11 | 0.401 | | 1.06 | 0.636 | | 1.08 | 0.352 |
| GOSR1 | 0 | — | | — | — | | — | — | | — | — |
| GP1BA | 9 | 0.000 | | 1.18 | 0.014 | | 0.94 | 0.339 | | 1.05 | 0.313 |
| GP5 | 6 | 0.006 | | 0.99 | 0.887 | | 0.97 | 0.744 | | 0.98 | 0.745 |
| GPLD1 | 18 | 0.000 | | 0.78 | 0.000 | | 0.67 | 0.000 | | 0.72 | 0.000 |
| GPR126 | 1 | 0.148 | | 1.04 | 0.829 | | 0.92 | 0.622 | | 0.98 | 0.843 |
| GPX3 | 16 | 0.000 | | 1.12 | 0.046 | | 1.18 | 0.004 | | 1.15 | 0.001 |
| GSN | 58 | 0.000 | | 0.62 | 0.000 | | 0.65 | 0.000 | | 0.63 | 0.000 |
| GSTO1 | 1 | 0.001 | | 1.58 | 0.011 | | 1.20 | 0.319 | | 1.38 | 0.018 |
| GSTP1 | 0 | — | | — | — | | — | — | | — | — |
| HABP2 | 7 | 0.042 | | 0.97 | 0.716 | | 0.96 | 0.652 | | 0.97 | 0.568 |
| HBA1 | 11 | 0.000 | X | 2.49 | 0.000 | | 1.78 | 0.000 | X | 2.10 | 0.000 |
| HBB | 6 | 0.000 | X | 2.47 | 0.000 | | 1.69 | 0.002 | X | 2.04 | 0.000 |
| HEG1 | 1 | 0.208 | | 0.95 | 0.772 | | 1.00 | 0.993 | | 0.97 | 0.830 |
| HGFAC | 16 | 0.004 | | 0.88 | 0.090 | | 0.90 | 0.156 | | 0.89 | 0.029 |
| HIST1H4A | 5 | 0.000 | | 1.74 | 0.000 | | 0.98 | 0.890 | | 1.31 | 0.015 |
| HP | 39 | 0.000 | X | 2.94 | 0.000 | X | 2.19 | 0.000 | X | 2.53 | 0.000 |
| HPR | 10 | 0.000 | | 1.61 | 0.000 | | 1.54 | 0.000 | | 1.58 | 0.000 |
| HPX | 2 | 0.207 | | 0.98 | 0.919 | | 1.04 | 0.824 | | 1.01 | 0.932 |
| HRNR | 7 | 0.000 | | 0.89 | 0.430 | | 1.38 | 0.030 | | 1.11 | 0.337 |
| HSP90B1 | 4 | 0.021 | | 0.87 | 0.262 | | 0.84 | 0.177 | | 0.85 | 0.082 |
| HSPA5 | 10 | 0.052 | | 1.07 | 0.236 | | 0.95 | 0.417 | | 1.01 | 0.794 |
| HSPA8 | 0 | — | | — | — | | — | — | | — | — |
| HSPB1 | 0 | — | | — | — | | — | — | | — | — |
| HSPG2 | 9 | 0.000 | | 0.82 | 0.006 | | 0.92 | 0.280 | | 0.87 | 0.007 |
| HYOU1 | 3 | 0.060 | | 0.82 | 0.144 | | 0.95 | 0.685 | | 0.88 | 0.191 |
| ICAM1 | 5 | 0.000 | | 1.67 | 0.000 | | 1.38 | 0.001 | | 1.52 | 0.000 |
| ICAM2 | 1 | 0.206 | | 1.04 | 0.843 | | 1.13 | 0.493 | | 1.08 | 0.525 |
| ICOSLG | 1 | 0.050 | | 0.99 | 0.964 | | 0.91 | 0.518 | | 0.95 | 0.631 |
| IDH1 | 1 | 0.003 | | 1.68 | 0.018 | | 1.36 | 0.155 | | 1.51 | 0.008 |
| IGF1 | 2 | 0.002 | | 0.63 | 0.008 | | 0.92 | 0.639 | | 0.76 | 0.032 |
| IGF2 | 5 | 0.000 | | 0.63 | 0.000 | | 0.85 | 0.103 | | 0.73 | 0.000 |
| IGF2R | 1 | 0.062 | | 1.31 | 0.099 | | 1.13 | 0.463 | | 1.21 | 0.090 |
| IGFALS | 37 | 0.000 | | 0.69 | 0.000 | | 0.89 | 0.005 | | 0.79 | 0.000 |
| IGFBP1 | 1 | 0.154 | | 0.76 | 0.428 | | 0.87 | 0.674 | | 0.81 | 0.382 |
| IGFBP2 | 6 | 0.000 | | 1.72 | 0.000 | X | 2.12 | 0.000 | | 1.91 | 0.000 |
| IGFBP3 | 13 | 0.000 | | 0.67 | 0.000 | | 0.98 | 0.778 | | 0.81 | 0.000 |
| IGFBP4 | 1 | 0.124 | | 0.83 | 0.515 | | 1.01 | 0.980 | | 0.91 | 0.659 |
| IGFBP5 | 3 | 0.000 | | 0.73 | 0.003 | | 0.98 | 0.885 | | 0.84 | 0.039 |
| IGFBP6 | 2 | 0.006 | | 1.05 | 0.696 | | 1.02 | 0.864 | | 1.03 | 0.701 |
| IGFBP7 | 1 | 0.181 | | 0.95 | 0.757 | | 0.99 | 0.960 | | 0.97 | 0.798 |
| IGLL5 | 19 | 0.000 | | 1.33 | 0.001 | | 1.65 | 0.000 | | 1.48 | 0.000 |

TABLE 2B-continued

Marker Discovery

| PROTEIN | #PEPTIDES | q-value | Active TB vs Asymptomatic (HIV−) | | | Active TB vs Asymptomatic (HIV+) | | | Asymptomatic (HIV− and HIV+) | | |
|---|---|---|---|---|---|---|---|---|---|---|---|
| | | | DE | ANOVA DI | p-value | DE | ANOVA DI | p-value | DE | ANOVA DI | p-value |
| IL1R2 | 1 | 0.030 | | 0.93 | 0.630 | | 0.97 | 0.835 | | 0.95 | 0.624 |
| IL1RAP | 7 | 0.000 | | 0.68 | 0.000 | | 0.83 | 0.051 | | 0.75 | 0.000 |
| IL6ST | 3 | 0.134 | | 1.22 | 0.350 | | 1.12 | 0.582 | | 1.17 | 0.295 |
| ISLR | 3 | 0.013 | | 0.95 | 0.641 | | 0.89 | 0.259 | | 0.92 | 0.264 |
| ITGB1 | 1 | 0.083 | | 0.83 | 0.385 | | 0.79 | 0.268 | | 0.81 | 0.156 |
| ITIH1 | 2 | 0.161 | | 1.08 | 0.644 | | 1.08 | 0.634 | | 1.08 | 0.504 |
| ITIH2 | 3 | 0.079 | | 0.86 | 0.237 | | 0.97 | 0.834 | | 0.92 | 0.328 |
| ITIH3 | 17 | 0.000 | | 1.86 | 0.000 | | 1.52 | 0.000 | | 1.68 | 0.000 |
| ITIH4 | 59 | 0.000 | | 1.32 | 0.000 | | 1.25 | 0.000 | | 1.29 | 0.000 |
| KIT | 2 | 0.000 | | 0.54 | 0.001 | | 0.72 | 0.061 | | 0.62 | 0.000 |
| KLKB1 | 14 | 0.000 | | 0.87 | 0.027 | | 0.81 | 0.001 | | 0.84 | 0.000 |
| KNG1 | 7 | 0.019 | | 1.06 | 0.731 | | 1.36 | 0.092 | | 1.20 | 0.155 |
| KRT1 | 30 | 0.000 | | 0.81 | 0.009 | | 1.09 | 0.304 | | 0.94 | 0.269 |
| KRT10 | 8 | 0.018 | | 1.13 | 0.420 | | 1.30 | 0.074 | | 1.21 | 0.068 |
| KRT14 | 3 | 0.198 | | 0.91 | 0.503 | | 0.93 | 0.647 | | 0.92 | 0.426 |
| KRT2 | 11 | 0.000 | | 1.19 | 0.210 | | 1.39 | 0.015 | | 1.29 | 0.010 |
| KRT5 | 1 | 0.088 | | 1.29 | 0.469 | | 1.60 | 0.185 | | 1.44 | 0.142 |
| KRT9 | 16 | 0.000 | | 0.84 | 0.124 | | 1.27 | 0.036 | | 1.03 | 0.695 |
| LAMB1 | 1 | 0.116 | | 0.98 | 0.907 | | 0.91 | 0.533 | | 0.95 | 0.596 |
| LAMP1 | 2 | 0.089 | | 0.98 | 0.861 | | 0.83 | 0.159 | | 0.90 | 0.265 |
| LAMP2 | 2 | 0.198 | | 0.88 | 0.459 | | 0.90 | 0.560 | | 0.89 | 0.346 |
| LASP1 | 1 | 0.034 | | 1.32 | 0.315 | | 0.73 | 0.265 | | 0.98 | 0.941 |
| LBP | 1 | 0.000 | | 1.96 | 0.001 | | 1.61 | 0.022 | | 1.78 | 0.000 |
| LCAT | 18 | 0.000 | | 0.83 | 0.001 | | 0.73 | 0.000 | | 0.78 | 0.000 |
| LCN2 | 2 | 0.082 | | 1.06 | 0.750 | | 0.93 | 0.713 | | 1.00 | 0.972 |
| LCP1 | 12 | 0.000 | | 1.46 | 0.000 | | 1.27 | 0.000 | | 1.36 | 0.000 |
| LDHB | 3 | 0.126 | | 1.18 | 0.221 | | 1.05 | 0.716 | | 1.11 | 0.263 |
| LGALS3BP | 28 | 0.000 | | 1.25 | 0.000 | | 0.77 | 0.000 | | 0.98 | 0.677 |
| LGALSL | 2 | 0.000 | | 1.53 | 0.016 | | 0.65 | 0.017 | | 1.00 | 0.989 |
| LILRA1 | 1 | 0.062 | | 1.07 | 0.876 | | 0.60 | 0.236 | | 0.80 | 0.474 |
| LILRA3 | 1 | 0.039 | | 1.32 | 0.400 | | 0.70 | 0.289 | | 0.96 | 0.883 |
| LPA | 16 | 0.000 | | 0.83 | 0.071 | | 0.80 | 0.025 | | 0.82 | 0.005 |
| LRG1 | 45 | 0.000 | | 1.78 | 0.000 | | 1.65 | 0.000 | | 1.72 | 0.000 |
| LRP1 | 4 | 0.192 | | 1.08 | 0.421 | | 1.01 | 0.908 | | 1.05 | 0.516 |
| LSAMP | 1 | 0.074 | | 0.90 | 0.528 | | 1.10 | 0.565 | | 1.00 | 0.970 |
| LUM | 34 | 0.000 | | 0.91 | 0.023 | | 0.79 | 0.000 | | 0.85 | 0.000 |
| LYVE1 | 4 | 0.054 | | 0.85 | 0.110 | | 0.91 | 0.342 | | 0.88 | 0.073 |
| LYZ | 2 | 0.003 | | 1.06 | 0.731 | | 1.00 | 0.991 | | 1.03 | 0.808 |
| MAN1A1 | 5 | 0.001 | | 1.18 | 0.083 | | 1.07 | 0.485 | | 1.12 | 0.093 |
| MAN2A2 | 1 | 0.179 | | 1.13 | 0.445 | | 1.04 | 0.831 | | 1.08 | 0.484 |
| MASP1 | 17 | 0.000 | | 0.83 | 0.000 | | 0.87 | 0.002 | | 0.85 | 0.000 |
| MASP2 | 8 | 0.135 | | 1.00 | 0.987 | | 0.93 | 0.283 | | 0.96 | 0.444 |
| MB | 1 | 0.005 | | 0.87 | 0.465 | | 0.78 | 0.210 | | 0.82 | 0.157 |
| MBL2 | 4 | 0.008 | | 1.06 | 0.642 | | 1.37 | 0.020 | | 1.21 | 0.052 |
| MCAM | 1 | 0.013 | | 0.70 | 0.109 | | 0.77 | 0.231 | | 0.73 | 0.049 |
| MEGF8 | 2 | 0.217 | | 1.01 | 0.955 | | 1.00 | 0.995 | | 1.00 | 0.965 |
| MIF | 0 | — | | — | — | | — | — | | — | — |
| MINPP1 | 2 | 0.149 | | 0.99 | 0.929 | | 0.87 | 0.329 | | 0.92 | 0.452 |
| MMP2 | 3 | 0.000 | | 0.62 | 0.000 | | 0.67 | 0.000 | | 0.64 | 0.000 |
| MMP9 | 2 | 0.000 | | 1.68 | 0.005 | | 1.15 | 0.441 | | 1.39 | 0.014 |
| MMRN2 | 1 | 0.075 | | 1.13 | 0.546 | | 0.96 | 0.858 | | 1.04 | 0.766 |
| MRPS26 | 1 | 0.055 | | 0.90 | 0.699 | | 0.95 | 0.860 | | 0.93 | 0.692 |
| MSN | 3 | 0.000 | | 1.37 | 0.027 | | 0.74 | 0.030 | | 1.00 | 0.981 |
| MST1 | 15 | 0.000 | | 1.21 | 0.005 | | 0.91 | 0.177 | | 1.05 | 0.322 |
| MTPN | 1 | 0.005 | | 1.58 | 0.285 | | 0.46 | 0.067 | | 0.85 | 0.625 |
| NAGLU | 3 | 0.005 | | 1.12 | 0.358 | | 0.86 | 0.217 | | 0.98 | 0.829 |
| NCAM1 | 2 | 0.096 | | 0.87 | 0.341 | | 0.98 | 0.911 | | 0.92 | 0.455 |
| NEO1 | 1 | 0.024 | | 0.88 | 0.452 | | 0.76 | 0.117 | | 0.82 | 0.098 |
| NID1 | 7 | 0.000 | | 1.24 | 0.005 | | 1.25 | 0.004 | | 1.24 | 0.000 |
| NRGN | 1 | 0.013 | | 1.02 | 0.954 | | 0.56 | 0.042 | | 0.75 | 0.181 |
| NRP1 | 3 | 0.013 | | 0.96 | 0.729 | | 1.16 | 0.191 | | 1.06 | 0.503 |
| NUCB1 | 1 | 0.060 | | 1.18 | 0.556 | | 1.35 | 0.277 | | 1.26 | 0.230 |
| NUP210L | 1 | 0.011 | | 1.20 | 0.613 | | 1.72 | 0.128 | | 1.44 | 0.153 |
| OAF | 2 | 0.000 | | 1.30 | 0.013 | | 1.30 | 0.013 | | 1.30 | 0.000 |
| OLFM1 | 2 | 0.093 | | 1.01 | 0.934 | | 1.18 | 0.282 | | 1.10 | 0.414 |
| ORM1 | 10 | 0.000 | | 1.95 | 0.000 | | 1.75 | 0.000 | | 1.85 | 0.000 |
| ORM2 | 10 | 0.000 | | 1.88 | 0.000 | | 1.57 | 0.000 | | 1.72 | 0.000 |
| PAM | 1 | 0.158 | | 0.99 | 0.952 | | 1.12 | 0.538 | | 1.05 | 0.691 |
| PCOLCE | 4 | 0.000 | | 0.87 | 0.152 | | 0.83 | 0.051 | | 0.85 | 0.018 |
| PCSK9 | 3 | 0.011 | | 0.93 | 0.613 | | 0.90 | 0.426 | | 0.91 | 0.357 |
| PDIA3 | 2 | 0.021 | | 1.26 | 0.061 | | 1.12 | 0.372 | | 1.19 | 0.050 |

TABLE 2B-continued

Marker Discovery

| PROTEIN | #PEPTIDES | q-value | Active TB vs Asymptomatic (HIV−) | | | Active TB vs Asymptomatic (HIV+) | | | Asymptomatic (HIV− and HIV+) | | |
|---|---|---|---|---|---|---|---|---|---|---|---|
| | | | DE | ANOVA DI | p-value | DE | ANOVA DI | p-value | DE | ANOVA DI | p-value |
| PDLIM1 | 3 | 0.000 | | 1.88 | 0.009 | | 0.57 | 0.019 | | 1.03 | 0.865 |
| PEPD | 9 | 0.000 | | 0.71 | 0.000 | | 0.65 | 0.000 | | 0.68 | 0.000 |
| PF4 | 11 | 0.000 | | 0.92 | 0.235 | | 0.95 | 0.408 | | 0.94 | 0.165 |
| PFN1 | 7 | 0.000 | | 1.68 | 0.000 | | 0.59 | 0.000 | | 0.99 | 0.955 |
| PGLYRP2 | 28 | 0.000 | | 0.64 | 0.000 | | 0.71 | 0.000 | | 0.67 | 0.000 |
| PI16 | 6 | 0.000 | | 0.63 | 0.001 | | 0.78 | 0.079 | | 0.70 | 0.000 |
| PIGR | 1 | 0.047 | | 1.35 | 0.220 | | 1.18 | 0.507 | | 1.26 | 0.189 |
| PLEK | 1 | 0.005 | | 1.23 | 0.614 | X | 0.41 | 0.029 | | 0.71 | 0.273 |
| PLS1 | 1 | 0.031 | | 1.34 | 0.130 | | 1.19 | 0.364 | | 1.26 | 0.084 |
| PLTP | 3 | 0.001 | | 1.32 | 0.097 | | 1.38 | 0.053 | | 1.35 | 0.012 |
| PLXNB1 | 2 | 0.011 | | 1.33 | 0.028 | | 1.16 | 0.242 | | 1.24 | 0.018 |
| PODXL | 1 | 0.218 | | 1.00 | 0.992 | | 0.97 | 0.859 | | 0.98 | 0.892 |
| PON1 | 5 | 0.003 | | 0.80 | 0.047 | | 0.85 | 0.135 | | 0.83 | 0.015 |
| PON3 | 0 | — | | — | — | | — | — | | — | — |
| POR | 0 | — | | — | — | | — | — | | — | — |
| POSTN | 2 | 0.074 | | 1.04 | 0.776 | | 1.24 | 0.166 | | 1.14 | 0.242 |
| PPBP | 23 | 0.000 | | 1.11 | 0.073 | | 1.25 | 0.000 | | 1.17 | 0.000 |
| PPIA | 5 | 0.000 | X | 2.07 | 0.000 | | 0.86 | 0.304 | | 1.33 | 0.011 |
| PPIB | 1 | 0.027 | | 1.34 | 0.157 | | 1.05 | 0.815 | | 1.18 | 0.244 |
| PRAP1 | 1 | 0.017 | | 1.11 | 0.694 | | 0.93 | 0.780 | | 1.01 | 0.935 |
| PRDX2 | 6 | 0.000 | X | 2.04 | 0.000 | | 1.47 | 0.011 | | 1.73 | 0.000 |
| PRDX6 | 1 | 0.028 | | 1.69 | 0.048 | | 1.32 | 0.293 | | 1.50 | 0.031 |
| PRG4 | 5 | 0.000 | | 1.43 | 0.002 | | 1.05 | 0.667 | | 1.23 | 0.014 |
| PROC | 9 | 0.014 | | 0.87 | 0.056 | | 0.92 | 0.248 | | 0.89 | 0.031 |
| PROCR | 4 | 0.071 | | 1.05 | 0.678 | | 0.92 | 0.473 | | 0.98 | 0.831 |
| PROS1 | 14 | 0.000 | | 0.88 | 0.048 | | 0.95 | 0.426 | | 0.92 | 0.053 |
| PROZ | 12 | 0.000 | | 0.78 | 0.006 | | 0.96 | 0.662 | | 0.86 | 0.026 |
| PRSS1 | 1 | 0.203 | | 1.04 | 0.882 | | 1.08 | 0.741 | | 1.06 | 0.731 |
| PRSS3 | 1 | 0.202 | | 0.98 | 0.939 | | 1.15 | 0.544 | | 1.06 | 0.705 |
| PTGDS | 2 | 0.189 | | 1.01 | 0.964 | | 1.11 | 0.570 | | 1.06 | 0.664 |
| PTPRG | 1 | 0.000 | | 0.52 | 0.003 | | 0.57 | 0.013 | | 0.55 | 0.000 |
| PTPRJ | 4 | 0.003 | | 0.98 | 0.831 | | 0.96 | 0.656 | | 0.97 | 0.641 |
| PTPRS | 1 | 0.203 | | 0.93 | 0.698 | | 1.07 | 0.730 | | 1.00 | 0.975 |
| PVR | 6 | 0.021 | | 0.98 | 0.865 | | 1.20 | 0.085 | | 1.09 | 0.278 |
| PVRL1 | 1 | 0.221 | | 0.97 | 0.882 | | 0.99 | 0.975 | | 0.98 | 0.896 |
| PZP | 8 | 0.000 | | 0.82 | 0.179 | | 1.13 | 0.404 | | 0.96 | 0.723 |
| QSOX1 | 11 | 0.000 | | 0.80 | 0.000 | | 0.88 | 0.045 | | 0.84 | 0.000 |
| RBBP8 | 1 | 0.027 | | 1.35 | 0.518 | | 1.42 | 0.456 | | 1.39 | 0.316 |
| RNASE1 | 1 | 0.207 | | 1.06 | 0.828 | | 1.00 | 0.987 | | 1.03 | 0.885 |
| RTN4RL2 | 1 | 0.006 | | 0.87 | 0.323 | | 0.79 | 0.112 | | 0.83 | 0.071 |
| S100A12 | 2 | 0.002 | | 1.19 | 0.451 | | 0.63 | 0.046 | | 0.87 | 0.405 |
| S100A8 | 9 | 0.000 | | 1.73 | 0.000 | | 0.87 | 0.201 | | 1.22 | 0.016 |
| S100A9 | 18 | 0.000 | X | 2.01 | 0.000 | | 1.05 | 0.534 | | 1.45 | 0.000 |
| SAA1 | 4 | 0.000 | X | 2.74 | 0.000 | X | 2.16 | 0.001 | X | 2.43 | 0.000 |
| SAA4 | 14 | 0.000 | | 1.11 | 0.163 | | 0.75 | 0.000 | | 0.91 | 0.105 |
| SDPR | 1 | 0.006 | | 1.53 | 0.211 | | 0.68 | 0.264 | | 1.02 | 0.930 |
| SELL | 8 | 0.000 | | 0.95 | 0.517 | | 1.18 | 0.037 | | 1.06 | 0.316 |
| SEMA4B | 1 | 0.014 | | 0.99 | 0.952 | | 0.76 | 0.196 | | 0.87 | 0.341 |
| SEPP1 | 8 | 0.001 | | 0.89 | 0.178 | | 0.89 | 0.174 | | 0.89 | 0.057 |
| SERPINA1 | 78 | 0.000 | | 1.55 | 0.000 | | 1.79 | 0.000 | | 1.67 | 0.000 |
| SERPINA10 | 16 | 0.000 | | 1.01 | 0.910 | | 0.99 | 0.865 | | 1.00 | 0.969 |
| SERPINA3 | 6 | 0.000 | | 1.46 | 0.003 | | 1.64 | 0.000 | | 1.55 | 0.000 |
| SERPINA4 | 22 | 0.000 | X | 0.49 | 0.000 | | 0.62 | 0.000 | | 0.55 | 0.000 |
| SERPINA6 | 14 | 0.004 | | 0.86 | 0.044 | | 1.00 | 0.963 | | 0.93 | 0.169 |
| SERPINA7 | 37 | 0.000 | | 0.87 | 0.001 | | 0.94 | 0.168 | | 0.90 | 0.001 |
| SERPINB1 | 1 | 0.000 | | 1.64 | 0.026 | | 0.87 | 0.529 | | 1.19 | 0.304 |
| SERPINC1 | 1 | 0.007 | | 1.50 | 0.127 | | 1.56 | 0.095 | | 1.53 | 0.022 |
| SERPIND1 | 25 | 0.000 | | 0.91 | 0.081 | | 0.71 | 0.000 | | 0.81 | 0.000 |
| SERPINF1 | 41 | 0.000 | | 0.92 | 0.027 | | 0.87 | 0.000 | | 0.90 | 0.000 |
| SERPINF2 | 1 | 0.039 | | 1.18 | 0.476 | | 1.37 | 0.177 | | 1.27 | 0.142 |
| SERPING1 | 15 | 0.005 | | 0.91 | 0.144 | | 0.97 | 0.675 | | 0.94 | 0.187 |
| SH3BGRL | 1 | 0.000 | | 1.87 | 0.008 | | 1.09 | 0.717 | | 1.43 | 0.044 |
| SH3BGRL3 | 3 | 0.000 | | 1.86 | 0.001 | | 0.85 | 0.414 | | 1.26 | 0.113 |
| SHBG | 16 | 0.000 | | 0.58 | 0.000 | | 0.83 | 0.035 | | 0.69 | 0.000 |
| SLC3A2 | 2 | 0.000 | | 0.55 | 0.000 | | 0.73 | 0.047 | | 0.63 | 0.000 |
| SNCA | 0 | — | | — | — | | — | — | | — | — |
| SNED1 | 1 | 0.119 | | 1.22 | 0.286 | | 1.00 | 0.997 | | 1.10 | 0.452 |
| SOD3 | 5 | 0.004 | | 0.93 | 0.507 | | 0.86 | 0.154 | | 0.89 | 0.146 |
| SORL1 | 2 | 0.089 | | 1.44 | 0.195 | | 0.95 | 0.848 | | 1.17 | 0.439 |
| SOWAHC | 0 | — | | — | — | | — | — | | — | — |
| SPARC | 11 | 0.000 | | 1.12 | 0.139 | | 1.15 | 0.055 | | 1.13 | 0.019 |

TABLE 2B-continued

Marker Discovery

| PROTEIN | #PEPTIDES | Active TB vs Asymptomatic (HIV−) | | | | Active TB vs Asymptomatic (HIV+) | | | | Asymptomatic (HIV− and HIV+) | | | |
|---|---|---|---|---|---|---|---|---|---|---|---|---|---|
| | | q-value | DE | ANOVA DI | p-value | | DE | ANOVA DI | p-value | | DE | ANOVA DI | p-value |
| SPARCL1 | 2 | 0.042 | | 1.01 | 0.933 | | | 1.22 | 0.189 | | | 1.11 | 0.331 |
| SPP2 | 2 | 0.000 | X | 0.45 | 0.000 | | X | 0.48 | 0.000 | | X | 0.47 | 0.000 |
| SRGN | 3 | 0.017 | | 1.06 | 0.633 | | | 1.20 | 0.133 | | | 1.13 | 0.170 |
| SSC5D | 2 | 0.049 | | 1.20 | 0.355 | | | 0.87 | 0.475 | | | 1.02 | 0.883 |
| STXBP3 | 0 | — | | — | — | | | — | — | | | — | — |
| TAGLN2 | 7 | 0.000 | X | 2.15 | 0.000 | | | 0.60 | 0.000 | | | 1.14 | 0.263 |
| TF | 8 | 0.001 | | 0.80 | 0.030 | | | 0.79 | 0.025 | | | 0.79 | 0.002 |
| TGFBI | 14 | 0.000 | | 0.75 | 0.000 | | | 0.96 | 0.593 | | | 0.85 | 0.002 |
| THBS1 | 30 | 0.000 | | 0.91 | 0.050 | | | 0.86 | 0.001 | | | 0.88 | 0.000 |
| TIMP1 | 1 | 0.181 | | 1.05 | 0.809 | | | 1.01 | 0.958 | | | 1.03 | 0.835 |
| TKT | 3 | 0.000 | | 1.63 | 0.001 | | | 1.26 | 0.125 | | | 1.44 | 0.001 |
| TLN1 | 11 | 0.000 | | 1.34 | 0.001 | | | 0.79 | 0.006 | | | 1.02 | 0.707 |
| TMSB4X | 6 | 0.000 | | 1.70 | 0.001 | | | 0.63 | 0.003 | | | 1.04 | 0.761 |
| TNC | 5 | 0.205 | | 1.08 | 0.509 | | | 1.02 | 0.878 | | | 1.05 | 0.566 |
| TNXB | 19 | 0.000 | | 0.82 | 0.000 | | | 0.94 | 0.185 | | | 0.88 | 0.000 |
| TPI1 | 2 | 0.001 | | 1.47 | 0.027 | | | 0.96 | 0.807 | | | 1.19 | 0.180 |
| TPM3 | 3 | 0.000 | | 1.43 | 0.025 | | | 0.69 | 0.019 | | | 0.99 | 0.942 |
| TPM4 | 1 | 0.072 | | 1.29 | 0.457 | | | 0.71 | 0.313 | | | 0.96 | 0.854 |
| TREML1 | 3 | 0.000 | | 1.98 | 0.000 | | | 1.12 | 0.491 | | | 1.49 | 0.002 |
| TTR | 4 | 0.208 | | 1.00 | 0.977 | | | 0.97 | 0.816 | | | 0.98 | 0.854 |
| TUBA4A | 2 | 0.003 | | 1.26 | 0.125 | | | 0.95 | 0.721 | | | 1.09 | 0.413 |
| UMOD | 1 | 0.066 | | 1.24 | 0.151 | | | 1.21 | 0.215 | | | 1.22 | 0.054 |
| VASN | 7 | 0.072 | | 0.98 | 0.723 | | | 0.97 | 0.640 | | | 0.97 | 0.562 |
| VASP | 1 | 0.003 | | 1.19 | 0.472 | | | 0.66 | 0.077 | | | 0.88 | 0.488 |
| VCAM1 | 12 | 0.007 | | 1.12 | 0.111 | | | 1.15 | 0.040 | | | 1.13 | 0.010 |
| VCL | 5 | 0.008 | | 1.19 | 0.111 | | | 0.97 | 0.740 | | | 1.07 | 0.378 |
| VIM | 2 | 0.219 | | 1.04 | 0.879 | | | 1.02 | 0.928 | | | 1.03 | 0.863 |
| VNN1 | 4 | 0.001 | | 0.83 | 0.275 | | | 0.72 | 0.054 | | | 0.77 | 0.036 |
| VTN | 4 | 0.027 | | 0.89 | 0.297 | | | 0.87 | 0.192 | | | 0.88 | 0.098 |
| VWF | 60 | 0.000 | | 1.09 | 0.023 | | | 1.02 | 0.626 | | | 1.05 | 0.052 |
| YWHAE | 0 | — | | — | — | | | — | — | | | — | — |
| YWHAG | 0 | — | | — | — | | | — | — | | | — | — |
| YWHAZ | 0 | — | | — | — | | | — | — | | | — | — |
| ZYX | 3 | 0.000 | X | 2.16 | 0.006 | | | 0.59 | 0.061 | | | 1.13 | 0.569 |

*Differential expression (DE) thresholds: p-value <0.05|q-value <0.05|ANOVA DI >2

TABLE 2C

Marker Discovery

| PROTEIN | #PEPTIDES | Asymptomatic (HIV−) and LTBI (HIV−) | | | | Active TB vs Asymptomatic (HIV+) and LTBI (HIV+) | | | | Active TB vs Asymptomatic and LTBI|HIV+/− | | | |
|---|---|---|---|---|---|---|---|---|---|---|---|---|---|
| | | q-value | DE | ANOVA DI | p-value | | DE | ANOVA DI | p-value | | DE | ANOVA DI | p-value |
| A1BG | 3 | 0.031 | | 0.90 | 0.259 | | | 1.09 | 0.349 | | | 0.99 | 0.877 |
| A2M | 119 | 0.000 | | 0.96 | 0.062 | | | 0.85 | 0.000 | | | 0.91 | 0.000 |
| ABI3BP | 7 | 0.062 | | 1.00 | 0.992 | | | 0.96 | 0.523 | | | 0.98 | 0.665 |
| ACTN1 | 0 | — | | — | — | | | — | — | | | — | — |
| ADAMTS13 | 5 | 0.000 | | 0.75 | 0.000 | | | 0.91 | 0.125 | | | 0.82 | 0.000 |
| ADAMTSL4 | 1 | 0.041 | | 0.79 | 0.076 | | | 1.00 | 0.995 | | | 0.89 | 0.226 |
| AFM | 6 | 0.000 | | 0.51 | 0.000 | | | 0.53 | 0.000 | | | 0.52 | 0.000 |
| AGT | 25 | 0.000 | | 0.86 | 0.000 | | | 0.89 | 0.001 | | | 0.87 | 0.000 |
| AHSG | 2 | 0.062 | | 1.25 | 0.056 | | | 1.19 | 0.155 | | | 1.22 | 0.023 |
| ALB | 12 | 0.020 | | 1.06 | 0.297 | | | 1.08 | 0.189 | | | 1.07 | 0.110 |
| ALCAM | 5 | 0.140 | | 1.07 | 0.302 | | | 1.06 | 0.382 | | | 1.07 | 0.195 |
| ALDOA | 6 | 0.016 | | 1.15 | 0.068 | | | 1.03 | 0.738 | | | 1.09 | 0.139 |
| ALDOB | 6 | 0.000 | | 0.75 | 0.003 | | | 0.69 | 0.000 | | | 0.72 | 0.000 |
| AMBP | 12 | 0.096 | | 1.00 | 0.949 | | | 0.96 | 0.471 | | | 0.98 | 0.662 |
| ANGPTL3 | 3 | 0.007 | | 1.17 | 0.058 | | | 0.94 | 0.453 | | | 1.05 | 0.430 |
| ANPEP | 9 | 0.005 | | 0.96 | 0.471 | | | 0.89 | 0.038 | | | 0.93 | 0.060 |
| AOC3 | 3 | 0.087 | | 1.14 | 0.163 | | | 1.10 | 0.328 | | | 1.12 | 0.106 |
| APCS | 5 | 0.000 | | 1.64 | 0.000 | | | 1.27 | 0.009 | | | 1.45 | 0.000 |
| APOA1 | 42 | 0.000 | | 0.54 | 0.000 | | | 0.66 | 0.000 | | | 0.59 | 0.000 |
| APOA2 | 6 | 0.000 | | 0.61 | 0.000 | | | 0.66 | 0.000 | | | 0.63 | 0.000 |
| APOA4 | 149 | 0.000 | | 0.52 | 0.000 | | | 0.58 | 0.000 | | | 0.55 | 0.000 |

TABLE 2C-continued

| | | | | Marker Discovery | | | | | | |
|---|---|---|---|---|---|---|---|---|---|---|
| | | | | Asymptomatic (HIV−) and LTBI (HIV−) | | | Active TB vs Asymptomatic (HIV+) and LTBI (HIV+) | | Active TB vs Asymptomatic and LTBI\|HIV+/− | |
| PROTEIN | #PEPTIDES | q-value | DE | ANOVA DI | p-value | DE | ANOVA DI | p-value | DE | ANOVA DI | p-value |
| APOB | 262 | 0.000 | | 0.83 | 0.000 | | 0.77 | 0.000 | | 0.80 | 0.000 |
| APOC1 | 7 | 0.000 | | 0.58 | 0.000 | X | 0.49 | 0.000 | | 0.53 | 0.000 |
| APOC2 | 6 | 0.000 | X | 0.45 | 0.000 | X | 0.32 | 0.000 | X | 0.38 | 0.000 |
| APOC3 | 12 | 0.000 | X | 0.48 | 0.000 | X | 0.34 | 0.000 | X | 0.40 | 0.000 |
| APOC4 | 8 | 0.000 | X | 0.42 | 0.000 | X | 0.29 | 0.000 | X | 0.35 | 0.000 |
| APOD | 3 | 0.011 | | 0.84 | 0.029 | | 0.81 | 0.009 | | 0.82 | 0.001 |
| APOE | 47 | 0.000 | | 0.65 | 0.000 | X | 0.43 | 0.000 | | 0.53 | 0.000 |
| APOF | 3 | 0.032 | | 1.02 | 0.806 | | 1.05 | 0.616 | | 1.04 | 0.614 |
| APOL1 | 9 | 0.066 | | 1.12 | 0.109 | | 1.13 | 0.097 | | 1.12 | 0.027 |
| APOM | 3 | 0.000 | | 0.71 | 0.003 | | 0.64 | 0.000 | | 0.68 | 0.000 |
| APP | 6 | 0.021 | | 1.02 | 0.757 | | 1.06 | 0.353 | | 1.04 | 0.404 |
| ARHGDIB | 3 | 0.000 | | 1.33 | 0.009 | | 1.03 | 0.777 | | 1.17 | 0.053 |
| ARPC5 | 0 | — | | — | — | | — | — | | — | — |
| ATP6AP1L | 0 | — | | — | — | | — | — | | — | — |
| ATRN | 26 | 0.000 | | 0.81 | 0.000 | | 0.78 | 0.000 | | 0.80 | 0.000 |
| AXL | 1 | 0.084 | | 0.72 | 0.110 | | 0.78 | 0.229 | | 0.75 | 0.053 |
| AZGP1 | 40 | 0.000 | | 1.09 | 0.001 | | 1.22 | 0.000 | | 1.15 | 0.000 |
| B2M | 16 | 0.000 | | 1.44 | 0.000 | | 1.22 | 0.000 | | 1.33 | 0.000 |
| B4GALT1 | 1 | 0.161 | | 1.23 | 0.211 | | 1.15 | 0.413 | | 1.19 | 0.149 |
| BCHE | 12 | 0.000 | | 0.76 | 0.000 | | 0.72 | 0.000 | | 0.74 | 0.000 |
| BLVRB | 1 | 0.096 | | 1.29 | 0.258 | | 1.20 | 0.427 | | 1.25 | 0.179 |
| BST1 | 4 | 0.023 | | 1.03 | 0.670 | | 1.15 | 0.070 | | 1.09 | 0.136 |
| BTD | 7 | 0.028 | | 0.81 | 0.023 | | 0.86 | 0.114 | | 0.84 | 0.009 |
| C1R | 66 | 0.020 | | 1.00 | 0.986 | | 1.04 | 0.061 | | 1.02 | 0.215 |
| C1RL | 21 | 0.047 | | 1.02 | 0.659 | | 1.04 | 0.312 | | 1.03 | 0.327 |
| C1S | 57 | 0.003 | | 0.95 | 0.007 | | 0.98 | 0.440 | | 0.96 | 0.017 |
| C2 | 44 | 0.000 | | 1.12 | 0.000 | | 1.01 | 0.632 | | 1.06 | 0.001 |
| C3 | 3 | 0.054 | | 1.24 | 0.075 | | 1.11 | 0.373 | | 1.17 | 0.069 |
| C4BPA | 3 | 0.003 | | 1.27 | 0.005 | | 1.13 | 0.155 | | 1.20 | 0.004 |
| C5 | 2 | 0.003 | | 1.32 | 0.008 | | 1.00 | 0.966 | | 1.15 | 0.072 |
| C6 | 0 | — | | — | — | | — | — | | — | — |
| C9 | 0 | — | | — | — | | — | — | | — | — |
| CA1 | 7 | 0.000 | | 1.59 | 0.000 | | 1.23 | 0.092 | | 1.40 | 0.000 |
| CA2 | 3 | 0.000 | | 1.75 | 0.001 | | 1.35 | 0.071 | | 1.54 | 0.001 |
| CACNA2D1 | 5 | 0.000 | | 0.72 | 0.000 | | 0.92 | 0.214 | | 0.81 | 0.000 |
| CALM1 | 0 | — | | — | — | | — | — | | — | — |
| CALU | 2 | 0.074 | | 1.12 | 0.383 | | 1.26 | 0.076 | | 1.18 | 0.073 |
| CAT | 5 | 0.000 | | 1.36 | 0.001 | | 1.13 | 0.185 | | 1.24 | 0.002 |
| CCDC149 | 1 | 0.000 | | 0.57 | 0.000 | | 0.59 | 0.001 | | 0.58 | 0.000 |
| CD14 | 19 | 0.000 | | 1.17 | 0.000 | | 1.16 | 0.000 | | 1.16 | 0.000 |
| CD163 | 6 | 0.000 | | 1.32 | 0.000 | | 1.17 | 0.041 | | 1.24 | 0.000 |
| CD44 | 4 | 0.055 | | 1.03 | 0.745 | | 0.96 | 0.705 | | 1.00 | 0.978 |
| CD59 | 1 | 0.074 | | 1.19 | 0.091 | | 1.18 | 0.112 | | 1.18 | 0.024 |
| CD5L | 14 | 0.000 | | 1.17 | 0.017 | | 1.89 | 0.000 | | 1.48 | 0.000 |
| CD84 | 1 | 0.006 | | 1.24 | 0.268 | | 0.89 | 0.543 | | 1.05 | 0.721 |
| CD93 | 3 | 0.074 | | 0.87 | 0.120 | | 0.90 | 0.215 | | 0.88 | 0.058 |
| CDH1 | 4 | 0.024 | | 1.12 | 0.162 | | 1.10 | 0.270 | | 1.11 | 0.089 |
| CDH13 | 4 | 0.000 | | 0.65 | 0.000 | | 0.82 | 0.026 | | 0.73 | 0.000 |
| CDH2 | 1 | 0.046 | | 0.82 | 0.234 | | 0.72 | 0.059 | | 0.77 | 0.036 |
| CDH5 | 9 | 0.003 | | 0.98 | 0.697 | | 1.04 | 0.355 | | 1.01 | 0.729 |
| CETP | 1 | 0.085 | | 0.74 | 0.123 | | 0.77 | 0.185 | | 0.75 | 0.048 |
| CFB | 0 | — | | — | — | | — | — | | — | — |
| CFD | 10 | 0.000 | | 0.87 | 0.001 | | 0.85 | 0.000 | | 0.86 | 0.000 |
| CFL1 | 0 | — | | — | — | | — | — | | — | — |
| CFP | 1 | 0.179 | | 0.96 | 0.770 | | 0.94 | 0.635 | | 0.95 | 0.593 |
| CHI3L1 | 1 | 0.000 | X | 2.21 | 0.000 | | 1.82 | 0.001 | X | 2.01 | 0.000 |
| CHL1 | 15 | 0.001 | | 0.99 | 0.727 | | 0.89 | 0.007 | | 0.94 | 0.044 |
| CKM | 3 | 0.000 | | 0.71 | 0.004 | | 0.63 | 0.000 | | 0.67 | 0.000 |
| CLC | 1 | 0.113 | | 1.19 | 0.342 | | 1.27 | 0.190 | | 1.22 | 0.119 |
| CLEC3B | 25 | 0.000 | | 0.70 | 0.000 | | 0.73 | 0.000 | | 0.72 | 0.000 |
| CLIC1 | 0 | — | | — | — | | — | — | | — | — |
| CLU | 50 | 0.001 | | 1.01 | 0.812 | | 0.99 | 0.707 | | 1.00 | 0.932 |
| CNDP1 | 32 | 0.000 | | 0.63 | 0.000 | | 0.79 | 0.000 | | 0.70 | 0.000 |
| CNN2 | 1 | 0.000 | | 1.35 | 0.234 | | 0.80 | 0.369 | | 1.04 | 0.826 |
| CNTN1 | 7 | 0.000 | | 0.77 | 0.000 | | 0.95 | 0.443 | | 0.86 | 0.001 |
| COL18A1 | 2 | 0.134 | | 0.86 | 0.297 | | 0.86 | 0.293 | | 0.86 | 0.150 |
| COL6A1 | 3 | 0.089 | | 0.91 | 0.313 | | 0.91 | 0.325 | | 0.91 | 0.176 |
| COL6A3 | 10 | 0.000 | | 0.82 | 0.000 | | 0.93 | 0.068 | | 0.87 | 0.000 |
| COLEC10 | 2 | 0.007 | | 0.83 | 0.024 | | 0.81 | 0.012 | | 0.82 | 0.001 |
| COLEC11 | 6 | 0.001 | | 0.85 | 0.003 | | 0.86 | 0.006 | | 0.86 | 0.000 |
| COMP | 5 | 0.000 | | 0.79 | 0.000 | | 0.66 | 0.000 | | 0.72 | 0.000 |

TABLE 2C-continued

| | | | | Marker Discovery | | | | | | |
|---|---|---|---|---|---|---|---|---|---|---|
| | | | | Asymptomatic (HIV−) and LTBI (HIV−) | | | Active TB vs Asymptomatic (HIV+) and LTBI (HIV+) | | Active TB vs Asymptomatic and LTBI\|HIV+/− | |
| PROTEIN | #PEPTIDES | q-value | DE | ANOVA DI | p-value | DE | ANOVA DI | p-value | DE | ANOVA DI | p-value |
| CORO1A | 2 | 0.000 | | 1.72 | 0.000 | | 1.13 | 0.401 | | 1.40 | 0.002 |
| CORO1B | 1 | 0.206 | | 1.05 | 0.825 | | 1.02 | 0.919 | | 1.04 | 0.819 |
| COTL1 | 1 | 0.007 | | 1.37 | 0.169 | | 1.01 | 0.975 | | 1.18 | 0.330 |
| CP | 3 | 0.000 | | 1.75 | 0.000 | | 1.15 | 0.228 | | 1.43 | 0.000 |
| CPB2 | 20 | 0.205 | | 1.01 | 0.855 | | 1.00 | 0.931 | | 1.00 | 0.854 |
| CPN1 | 21 | 0.140 | | 1.01 | 0.874 | | 1.00 | 0.911 | | 1.00 | 0.972 |
| CPN2 | 17 | 0.000 | | 0.84 | 0.000 | | 0.84 | 0.001 | | 0.84 | 0.000 |
| CPQ | 1 | 0.005 | | 0.86 | 0.344 | | 0.64 | 0.005 | | 0.75 | 0.016 |
| CRP | 3 | 0.000 | X | 4.43 | 0.000 | X | 2.66 | 0.000 | X | 3.45 | 0.000 |
| CRTAC1 | 8 | 0.000 | | 0.70 | 0.000 | | 0.65 | 0.000 | | 0.67 | 0.000 |
| CSF1R | 3 | 0.048 | | 0.96 | 0.647 | | 0.90 | 0.266 | | 0.93 | 0.291 |
| CST3 | 6 | 0.005 | | 1.19 | 0.017 | | 1.14 | 0.083 | | 1.16 | 0.005 |
| CTBS | 9 | 0.000 | | 0.77 | 0.000 | | 0.70 | 0.000 | | 0.74 | 0.000 |
| CTSD | 1 | 0.042 | | 1.22 | 0.286 | | 0.86 | 0.404 | | 1.03 | 0.857 |
| DAG1 | 3 | 0.057 | | 1.00 | 0.974 | | 1.06 | 0.454 | | 1.03 | 0.634 |
| DBH | 7 | 0.020 | | 0.80 | 0.023 | | 0.95 | 0.613 | | 0.87 | 0.058 |
| DPEP2 | 1 | 0.113 | | 0.90 | 0.552 | | 1.11 | 0.543 | | 1.00 | 0.995 |
| DPP4 | 1 | 0.041 | | 0.89 | 0.301 | | 1.00 | 0.999 | | 0.94 | 0.468 |
| DSG2 | 1 | 0.066 | | 0.86 | 0.149 | | 1.00 | 0.969 | | 0.92 | 0.305 |
| ECM1 | 12 | 0.000 | | 1.05 | 0.298 | | 1.20 | 0.000 | | 1.12 | 0.002 |
| ENDOD1 | 1 | 0.147 | | 0.81 | 0.215 | | 0.92 | 0.598 | | 0.86 | 0.218 |
| ENG | 1 | 0.085 | | 1.39 | 0.124 | | 1.12 | 0.600 | | 1.25 | 0.153 |
| ENO1 | 3 | 0.000 | | 1.30 | 0.006 | | 1.07 | 0.501 | | 1.18 | 0.022 |
| ENPP2 | 7 | 0.000 | | 1.09 | 0.254 | | 0.95 | 0.498 | | 1.02 | 0.737 |
| ERAP1 | 1 | 0.192 | | 1.06 | 0.553 | | 1.06 | 0.585 | | 1.06 | 0.425 |
| F10 | 19 | 0.000 | | 1.03 | 0.336 | | 1.06 | 0.044 | | 1.04 | 0.045 |
| F11 | 12 | 0.001 | | 0.88 | 0.002 | | 0.94 | 0.133 | | 0.91 | 0.002 |
| F12 | 23 | 0.000 | | 0.61 | 0.000 | | 0.70 | 0.000 | | 0.65 | 0.000 |
| F13A1 | 6 | 0.000 | | 0.76 | 0.001 | | 0.70 | 0.000 | | 0.73 | 0.000 |
| F13B | 13 | 0.000 | | 0.90 | 0.027 | | 0.86 | 0.001 | | 0.88 | 0.000 |
| F2 | 16 | 0.089 | | 1.06 | 0.218 | | 1.04 | 0.385 | | 1.05 | 0.152 |
| F5 | 24 | 0.006 | | 1.08 | 0.046 | | 1.09 | 0.022 | | 1.09 | 0.004 |
| F7 | 5 | 0.000 | | 0.79 | 0.001 | | 0.73 | 0.000 | | 0.76 | 0.000 |
| F9 | 16 | 0.000 | | 0.81 | 0.000 | | 0.75 | 0.000 | | 0.78 | 0.000 |
| FAH | 1 | 0.003 | | 0.64 | 0.047 | | 0.55 | 0.008 | | 0.59 | 0.002 |
| FAM3C | 1 | 0.144 | | 1.04 | 0.707 | | 1.12 | 0.301 | | 1.08 | 0.332 |
| FBLN1 | 8 | 0.000 | | 0.81 | 0.000 | | 0.87 | 0.008 | | 0.84 | 0.000 |
| FBXO33 | 0 | — | | — | — | | — | — | | — | — |
| FCGBP | 12 | 0.000 | | 1.19 | 0.000 | | 1.00 | 0.934 | | 1.10 | 0.007 |
| FCGR3A | 5 | 0.000 | | 1.54 | 0.000 | | 1.43 | 0.000 | | 1.49 | 0.000 |
| FCGR3B | 4 | 0.000 | | 1.25 | 0.034 | | 1.17 | 0.135 | | 1.21 | 0.014 |
| FCN2 | 11 | 0.000 | | 1.07 | 0.151 | | 1.11 | 0.047 | | 1.09 | 0.021 |
| FCN3 | 13 | 0.172 | | 0.94 | 0.287 | | 0.99 | 0.884 | | 0.97 | 0.404 |
| FETUB | 13 | 0.000 | | 1.32 | 0.000 | | 0.95 | 0.265 | | 1.12 | 0.003 |
| FGA | 19 | 0.000 | | 1.49 | 0.000 | | 1.60 | 0.000 | | 1.54 | 0.000 |
| FGB | 0 | — | | — | — | | — | — | | — | — |
| FGFR1 | 1 | 0.132 | | 0.82 | 0.244 | | 0.93 | 0.689 | | 0.87 | 0.274 |
| FGG | 0 | — | | — | — | | — | — | | — | — |
| FKBP1A | 1 | 0.039 | | 1.26 | 0.167 | | 1.04 | 0.822 | | 1.15 | 0.265 |
| FLNA | 10 | 0.000 | | 1.45 | 0.000 | | 0.94 | 0.499 | | 1.18 | 0.017 |
| FLT4 | 1 | 0.203 | | 1.06 | 0.673 | | 0.99 | 0.922 | | 1.02 | 0.815 |
| FN1 | 3 | 0.022 | | 1.18 | 0.122 | | 1.01 | 0.904 | | 1.10 | 0.254 |
| FTL | 2 | 0.002 | | 1.34 | 0.122 | | 1.43 | 0.057 | | 1.38 | 0.019 |
| FUCA1 | 1 | 0.138 | | 1.29 | 0.314 | | 1.03 | 0.901 | | 1.16 | 0.427 |
| FUCA2 | 1 | 0.015 | | 1.29 | 0.093 | | 0.90 | 0.486 | | 1.08 | 0.506 |
| GALNT2 | 1 | 0.089 | | 1.10 | 0.527 | | 1.27 | 0.125 | | 1.18 | 0.140 |
| GAPDH | 2 | 0.003 | | 0.98 | 0.888 | | 0.76 | 0.053 | | 0.86 | 0.170 |
| GC | 1 | 0.096 | | 0.84 | 0.222 | | 0.91 | 0.498 | | 0.87 | 0.186 |
| GGH | 9 | 0.000 | | 1.35 | 0.000 | | 0.94 | 0.200 | | 1.13 | 0.001 |
| GK | 0 | — | | — | — | | — | — | | — | — |
| GNPTG | 2 | 0.100 | | 1.01 | 0.931 | | 1.04 | 0.689 | | 1.02 | 0.740 |
| GOSR1 | 0 | — | | — | — | | — | — | | — | — |
| GP1BA | 9 | 0.000 | | 1.09 | 0.078 | | 1.12 | 0.021 | | 1.11 | 0.006 |
| GP5 | 6 | 0.006 | | 0.94 | 0.372 | | 1.06 | 0.367 | | 1.00 | 0.987 |
| GPLD1 | 18 | 0.000 | | 0.75 | 0.000 | | 0.69 | 0.000 | | 0.72 | 0.000 |
| GPR126 | 1 | 0.148 | | 0.95 | 0.636 | | 0.92 | 0.454 | | 0.93 | 0.395 |
| GPX3 | 16 | 0.000 | | 1.02 | 0.563 | | 1.16 | 0.000 | | 1.09 | 0.006 |
| GSN | 58 | 0.000 | | 0.62 | 0.000 | | 0.66 | 0.000 | | 0.64 | 0.000 |
| GSTO1 | 1 | 0.001 | | 1.52 | 0.001 | | 1.14 | 0.318 | | 1.32 | 0.006 |
| GSTP1 | 0 | — | | — | — | | — | — | | — | — |
| HABP2 | 7 | 0.042 | | 0.97 | 0.670 | | 0.91 | 0.110 | | 0.94 | 0.174 |

TABLE 2C-continued

| | | Marker Discovery | | | | | | | | |
|---|---|---|---|---|---|---|---|---|---|---|
| | | | Asymptomatic (HIV−) and LTBI (HIV−) | | | Active TB vs Asymptomatic (HIV+) and LTBI (HIV+) | | | Active TB vs Asymptomatic and LTBI\|HIV+/− | | |
| PROTEIN | #PEPTIDES | q-value | DE | ANOVA DI | p-value | DE | ANOVA DI | p-value | DE | ANOVA DI | p-value |
| HBA1 | 11 | 0.000 | X | 2.28 | 0.000 | | 1.78 | 0.000 | X | 2.02 | 0.000 |
| HBB | 6 | 0.000 | X | 2.23 | 0.000 | | 1.74 | 0.000 | | 1.98 | 0.000 |
| HEG1 | 1 | 0.208 | | 0.93 | 0.527 | | 1.00 | 0.968 | | 0.96 | 0.633 |
| HGFAC | 16 | 0.004 | | 0.86 | 0.005 | | 0.93 | 0.204 | | 0.89 | 0.006 |
| HIST1H4A | 5 | 0.000 | | 1.74 | 0.000 | | 1.10 | 0.338 | | 1.39 | 0.000 |
| HP | 39 | 0.000 | X | 2.98 | 0.000 | X | 2.55 | 0.000 | X | 2.76 | 0.000 |
| HPR | 10 | 0.000 | | 1.68 | 0.000 | | 1.55 | 0.000 | | 1.62 | 0.000 |
| HPX | 2 | 0.207 | | 0.96 | 0.721 | | 1.04 | 0.716 | | 1.00 | 0.996 |
| HRNR | 7 | 0.000 | | 1.04 | 0.700 | | 1.37 | 0.003 | | 1.19 | 0.026 |
| HSP90B1 | 4 | 0.021 | | 0.87 | 0.111 | | 0.80 | 0.016 | | 0.83 | 0.007 |
| HSPA5 | 10 | 0.052 | | 1.04 | 0.313 | | 0.98 | 0.553 | | 1.01 | 0.762 |
| HSPA8 | 0 | — | | — | — | | — | — | | — | — |
| HSPB1 | 0 | — | | — | — | | — | — | | — | — |
| HSPG2 | 9 | 0.000 | | 0.86 | 0.003 | | 0.97 | 0.502 | | 0.91 | 0.012 |
| HYOU1 | 3 | 0.060 | | 0.84 | 0.058 | | 0.96 | 0.657 | | 0.90 | 0.111 |
| ICAM1 | 5 | 0.000 | | 1.55 | 0.000 | | 1.27 | 0.001 | | 1.41 | 0.000 |
| ICAM2 | 1 | 0.206 | | 1.05 | 0.702 | | 1.09 | 0.461 | | 1.07 | 0.437 |
| ICOSLG | 1 | 0.050 | | 0.89 | 0.234 | | 0.95 | 0.588 | | 0.91 | 0.226 |
| IDH1 | 1 | 0.003 | | 1.62 | 0.001 | | 1.28 | 0.103 | | 1.45 | 0.002 |
| IGF1 | 2 | 0.002 | | 0.71 | 0.005 | | 0.94 | 0.586 | | 0.81 | 0.026 |
| IGF2 | 5 | 0.000 | | 0.64 | 0.000 | | 0.83 | 0.009 | | 0.73 | 0.000 |
| IGF2R | 1 | 0.062 | | 1.16 | 0.182 | | 1.11 | 0.384 | | 1.14 | 0.125 |
| IGFALS | 37 | 0.000 | | 0.72 | 0.000 | | 0.92 | 0.004 | | 0.81 | 0.000 |
| IGFBP1 | 1 | 0.154 | | 0.75 | 0.227 | | 0.81 | 0.364 | | 0.78 | 0.140 |
| IGFBP2 | 6 | 0.000 | X | 2.08 | 0.000 | X | 2.05 | 0.000 | X | 2.07 | 0.000 |
| IGFBP3 | 13 | 0.000 | | 0.70 | 0.000 | | 0.98 | 0.703 | | 0.82 | 0.000 |
| IGFBP4 | 1 | 0.124 | | 1.01 | 0.944 | | 0.96 | 0.826 | | 0.99 | 0.919 |
| IGFBP5 | 3 | 0.000 | | 0.75 | 0.000 | | 0.99 | 0.890 | | 0.86 | 0.013 |
| IGFBP6 | 2 | 0.006 | | 0.92 | 0.287 | | 1.04 | 0.607 | | 0.98 | 0.694 |
| IGFBP7 | 1 | 0.181 | | 0.92 | 0.452 | | 1.02 | 0.892 | | 0.96 | 0.660 |
| IGLL5 | 19 | 0.000 | | 1.62 | 0.000 | | 1.76 | 0.000 | | 1.69 | 0.000 |
| IL1R2 | 1 | 0.030 | | 0.90 | 0.307 | | 0.86 | 0.150 | | 0.88 | 0.090 |
| IL1RAP | 7 | 0.000 | | 0.72 | 0.000 | | 0.95 | 0.428 | | 0.83 | 0.000 |
| IL6ST | 3 | 0.134 | | 1.24 | 0.144 | | 1.10 | 0.506 | | 1.17 | 0.147 |
| ISLR | 3 | 0.013 | | 0.86 | 0.054 | | 0.90 | 0.180 | | 0.88 | 0.027 |
| ITGB1 | 1 | 0.083 | | 0.83 | 0.188 | | 0.77 | 0.075 | | 0.80 | 0.034 |
| ITIH1 | 2 | 0.161 | | 1.13 | 0.314 | | 1.12 | 0.343 | | 1.12 | 0.178 |
| ITIH2 | 3 | 0.079 | | 0.85 | 0.077 | | 0.94 | 0.508 | | 0.90 | 0.099 |
| ITIH3 | 17 | 0.000 | | 1.78 | 0.000 | | 1.50 | 0.000 | | 1.64 | 0.000 |
| ITIH4 | 59 | 0.000 | | 1.33 | 0.000 | | 1.30 | 0.000 | | 1.31 | 0.000 |
| KIT | 2 | 0.000 | | 0.63 | 0.000 | | 0.69 | 0.004 | | 0.66 | 0.000 |
| KLKB1 | 14 | 0.000 | | 0.85 | 0.000 | | 0.85 | 0.000 | | 0.85 | 0.000 |
| KNG1 | 7 | 0.019 | | 1.11 | 0.402 | | 1.37 | 0.014 | | 1.23 | 0.028 |
| KRT1 | 30 | 0.000 | | 0.96 | 0.447 | | 1.08 | 0.170 | | 1.02 | 0.698 |
| KRT10 | 8 | 0.018 | | 1.17 | 0.126 | | 1.30 | 0.012 | | 1.23 | 0.006 |
| KRT14 | 3 | 0.198 | | 0.93 | 0.481 | | 0.97 | 0.793 | | 0.95 | 0.507 |
| KRT2 | 11 | 0.000 | | 1.30 | 0.006 | | 1.35 | 0.002 | | 1.32 | 0.000 |
| KRT5 | 1 | 0.088 | | 1.39 | 0.184 | | 1.49 | 0.107 | | 1.44 | 0.043 |
| KRT9 | 16 | 0.000 | | 1.03 | 0.732 | | 1.22 | 0.015 | | 1.12 | 0.063 |
| LAMB1 | 1 | 0.116 | | 0.93 | 0.476 | | 0.88 | 0.208 | | 0.90 | 0.174 |
| LAMP1 | 2 | 0.089 | | 0.94 | 0.474 | | 0.88 | 0.167 | | 0.91 | 0.153 |
| LAMP2 | 2 | 0.198 | | 0.90 | 0.386 | | 0.91 | 0.446 | | 0.90 | 0.261 |
| LASP1 | 1 | 0.034 | | 1.13 | 0.559 | | 0.91 | 0.635 | | 1.01 | 0.929 |
| LBP | 1 | 0.000 | | 1.81 | 0.000 | | 1.61 | 0.001 | | 1.71 | 0.000 |
| LCAT | 18 | 0.000 | | 0.80 | 0.000 | | 0.74 | 0.000 | | 0.77 | 0.000 |
| LCN2 | 2 | 0.082 | | 1.15 | 0.311 | | 1.05 | 0.735 | | 1.10 | 0.349 |
| LCP1 | 12 | 0.000 | | 1.45 | 0.000 | | 1.27 | 0.000 | | 1.36 | 0.000 |
| LDHB | 3 | 0.126 | | 1.08 | 0.405 | | 1.04 | 0.646 | | 1.06 | 0.378 |
| LGALS3BP | 28 | 0.000 | | 1.08 | 0.066 | | 0.78 | 0.000 | | 0.92 | 0.011 |
| LGALSL | 2 | 0.000 | | 1.48 | 0.004 | | 0.92 | 0.530 | | 1.17 | 0.140 |
| LILRA1 | 1 | 0.062 | | 0.92 | 0.790 | | 0.60 | 0.087 | | 0.75 | 0.188 |
| LILRA3 | 1 | 0.039 | | 1.27 | 0.307 | | 0.79 | 0.319 | | 1.01 | 0.967 |
| LPA | 16 | 0.000 | | 0.93 | 0.309 | | 1.03 | 0.681 | | 0.98 | 0.668 |
| LRG1 | 45 | 0.000 | | 1.75 | 0.000 | | 1.57 | 0.000 | | 1.66 | 0.000 |
| LRP1 | 4 | 0.192 | | 1.04 | 0.572 | | 1.02 | 0.731 | | 1.03 | 0.535 |
| LSAMP | 1 | 0.074 | | 0.89 | 0.287 | | 1.09 | 0.458 | | 0.98 | 0.811 |
| LUM | 34 | 0.000 | | 0.84 | 0.000 | | 0.81 | 0.000 | | 0.83 | 0.000 |
| LYVE1 | 4 | 0.054 | | 0.89 | 0.094 | | 0.95 | 0.475 | | 0.92 | 0.103 |
| LYZ | 2 | 0.003 | | 1.28 | 0.050 | | 1.01 | 0.958 | | 1.14 | 0.170 |
| MAN1A1 | 5 | 0.001 | | 1.23 | 0.002 | | 1.04 | 0.585 | | 1.13 | 0.014 |
| MAN2A2 | 1 | 0.179 | | 1.04 | 0.732 | | 1.03 | 0.786 | | 1.04 | 0.666 |

TABLE 2C-continued

Marker Discovery

| PROTEIN | #PEPTIDES | Asymptomatic (HIV−) and LTBI (HIV−) | | | | Active TB vs Asymptomatic (HIV+) and LTBI (HIV+) | | | | Active TB vs Asymptomatic and LTBI|HIV+/− | | |
|---|---|---|---|---|---|---|---|---|---|---|---|---|
| | | q-value | DE | ANOVA DI | p-value | DE | ANOVA DI | | p-value | DE | ANOVA DI | p-value |
| MASP1 | 17 | 0.000 | | 0.83 | 0.000 | | 0.85 | | 0.000 | | 0.84 | 0.000 |
| MASP2 | 8 | 0.135 | | 0.98 | 0.615 | | 0.96 | | 0.405 | | 0.97 | 0.366 |
| MB | 1 | 0.005 | | 0.73 | 0.027 | | 0.75 | | 0.045 | | 0.74 | 0.004 |
| MBL2 | 4 | 0.008 | | 1.04 | 0.705 | | 1.21 | | 0.044 | | 1.12 | 0.112 |
| MCAM | 1 | 0.013 | | 0.66 | 0.007 | | 0.79 | | 0.127 | | 0.72 | 0.005 |
| MEGF8 | 2 | 0.217 | | 0.97 | 0.791 | | 1.01 | | 0.938 | | 0.99 | 0.893 |
| MIF | 0 | — | | — | — | | — | | — | | — | — |
| MINPP1 | 2 | 0.149 | | 0.94 | 0.534 | | 0.91 | | 0.383 | | 0.93 | 0.305 |
| MMP2 | 3 | 0.000 | | 0.61 | 0.000 | | 0.66 | | 0.000 | | 0.63 | 0.000 |
| MMP9 | 2 | 0.000 | | 1.83 | 0.000 | | 1.42 | | 0.010 | | 1.62 | 0.000 |
| MMRN2 | 1 | 0.075 | | 0.94 | 0.698 | | 0.99 | | 0.958 | | 0.97 | 0.755 |
| MRPS26 | 1 | 0.055 | | 0.89 | 0.554 | | 0.77 | | 0.194 | | 0.83 | 0.194 |
| MSN | 3 | 0.000 | | 1.26 | 0.025 | | 0.89 | | 0.253 | | 1.06 | 0.453 |
| MST1 | 15 | 0.000 | | 1.10 | 0.047 | | 0.89 | | 0.014 | | 0.99 | 0.803 |
| MTPN | 1 | 0.005 | | 1.22 | 0.523 | | 0.66 | | 0.190 | | 0.90 | 0.673 |
| NAGLU | 3 | 0.005 | | 1.08 | 0.356 | | 0.85 | | 0.058 | | 0.96 | 0.545 |
| NCAM1 | 2 | 0.096 | | 0.85 | 0.130 | | 0.98 | | 0.883 | | 0.91 | 0.252 |
| NEO1 | 1 | 0.024 | | 0.80 | 0.073 | | 0.77 | | 0.035 | | 0.79 | 0.008 |
| NID1 | 7 | 0.000 | | 1.19 | 0.001 | | 1.24 | | 0.000 | | 1.22 | 0.000 |
| NRGN | 1 | 0.013 | | 1.02 | 0.936 | | 0.72 | | 0.123 | | 0.86 | 0.336 |
| NRP1 | 3 | 0.013 | | 1.05 | 0.546 | | 1.18 | | 0.038 | | 1.11 | 0.075 |
| NUCB1 | 1 | 0.060 | | 1.27 | 0.214 | | 1.44 | | 0.060 | | 1.35 | 0.034 |
| NUP210L | 1 | 0.011 | | 1.41 | 0.165 | | 1.90 | | 0.011 | | 1.63 | 0.009 |
| OAF | 2 | 0.000 | | 1.23 | 0.006 | | 1.28 | | 0.001 | | 1.25 | 0.000 |
| OLFM1 | 2 | 0.093 | | 0.96 | 0.736 | | 1.09 | | 0.425 | | 1.02 | 0.764 |
| ORM1 | 10 | 0.000 | X | 2.08 | 0.000 | | 1.67 | | 0.000 | | 1.87 | 0.000 |
| ORM2 | 10 | 0.000 | | 1.92 | 0.000 | | 1.43 | | 0.000 | | 1.66 | 0.000 |
| PAM | 1 | 0.158 | | 1.08 | 0.545 | | 1.10 | | 0.439 | | 1.09 | 0.336 |
| PCOLCE | 4 | 0.000 | | 0.80 | 0.001 | | 0.83 | | 0.008 | | 0.81 | 0.000 |
| PCSK9 | 3 | 0.011 | | 0.84 | 0.081 | | 0.83 | | 0.065 | | 0.84 | 0.016 |
| PDIA3 | 2 | 0.021 | | 1.22 | 0.021 | | 1.16 | | 0.087 | | 1.19 | 0.006 |
| PDLIM1 | 3 | 0.000 | | 1.60 | 0.011 | | 0.93 | | 0.717 | | 1.23 | 0.144 |
| PEPD | 9 | 0.000 | | 0.72 | 0.000 | | 0.69 | | 0.000 | | 0.71 | 0.000 |
| PF4 | 11 | 0.000 | | 0.89 | 0.018 | | 1.04 | | 0.405 | | 0.96 | 0.284 |
| PFN1 | 7 | 0.000 | | 1.48 | 0.000 | | 0.89 | | 0.173 | | 1.15 | 0.042 |
| PGLYRP2 | 28 | 0.000 | | 0.66 | 0.000 | | 0.70 | | 0.000 | | 0.68 | 0.000 |
| PI16 | 6 | 0.000 | | 0.56 | 0.000 | | 0.72 | | 0.001 | | 0.63 | 0.000 |
| PIGR | 1 | 0.047 | | 1.37 | 0.060 | | 1.07 | | 0.678 | | 1.22 | 0.118 |
| PLEK | 1 | 0.005 | | 1.05 | 0.874 | | 0.62 | | 0.113 | | 0.81 | 0.352 |
| PLS1 | 1 | 0.031 | | 1.36 | 0.019 | | 1.22 | | 0.135 | | 1.29 | 0.009 |
| PLTP | 3 | 0.001 | | 1.45 | 0.002 | | 1.32 | | 0.019 | | 1.38 | 0.000 |
| PLXNB1 | 2 | 0.011 | | 1.22 | 0.031 | | 1.20 | | 0.052 | | 1.21 | 0.005 |
| PODXL | 1 | 0.218 | | 0.98 | 0.858 | | 0.95 | | 0.654 | | 0.96 | 0.663 |
| PON1 | 5 | 0.003 | | 0.78 | 0.002 | | 0.87 | | 0.071 | | 0.82 | 0.001 |
| PON3 | 0 | — | | — | — | | — | | — | | — | — |
| POR | 0 | — | | — | — | | — | | — | | — | — |
| POSTN | 2 | 0.074 | | 1.02 | 0.835 | | 1.19 | | 0.102 | | 1.10 | 0.218 |
| PPBP | 23 | 0.000 | | 1.07 | 0.083 | | 1.22 | | 0.000 | | 1.14 | 0.000 |
| PPIA | 5 | 0.000 | | 1.84 | 0.000 | | 1.24 | | 0.055 | | 1.52 | 0.000 |
| PPIB | 1 | 0.027 | | 1.32 | 0.053 | | 1.20 | | 0.208 | | 1.26 | 0.029 |
| PRAP1 | 1 | 0.017 | | 0.87 | 0.470 | | 0.79 | | 0.227 | | 0.83 | 0.182 |
| PRDX2 | 6 | 0.000 | | 1.72 | 0.000 | | 1.31 | | 0.014 | | 1.50 | 0.000 |
| PRDX6 | 1 | 0.028 | | 1.50 | 0.028 | | 1.30 | | 0.157 | | 1.40 | 0.014 |
| PRG4 | 5 | 0.000 | | 1.28 | 0.002 | | 1.07 | | 0.442 | | 1.17 | 0.010 |
| PROC | 9 | 0.014 | | 0.87 | 0.010 | | 0.91 | | 0.062 | | 0.89 | 0.003 |
| PROCR | 4 | 0.071 | | 0.95 | 0.571 | | 0.92 | | 0.306 | | 0.93 | 0.283 |
| PROS1 | 14 | 0.000 | | 0.82 | 0.000 | | 0.92 | | 0.072 | | 0.87 | 0.000 |
| PROZ | 12 | 0.000 | | 0.83 | 0.003 | | 0.87 | | 0.030 | | 0.85 | 0.000 |
| PRSS1 | 1 | 0.203 | | 1.05 | 0.744 | | 1.13 | | 0.439 | | 1.09 | 0.446 |
| PRSS3 | 1 | 0.202 | | 1.00 | 0.982 | | 1.13 | | 0.452 | | 1.06 | 0.597 |
| PTGDS | 2 | 0.189 | | 1.03 | 0.817 | | 1.13 | | 0.340 | | 1.08 | 0.421 |
| PTPRG | 1 | 0.000 | | 0.56 | 0.000 | | 0.60 | | 0.001 | | 0.58 | 0.000 |
| PTPRJ | 4 | 0.003 | | 0.90 | 0.097 | | 0.90 | | 0.095 | | 0.90 | 0.024 |
| PTPRS | 1 | 0.203 | | 0.93 | 0.604 | | 1.03 | | 0.836 | | 0.98 | 0.821 |
| PVR | 6 | 0.021 | | 0.97 | 0.668 | | 1.10 | | 0.216 | | 1.03 | 0.600 |
| PVRL1 | 1 | 0.221 | | 0.96 | 0.739 | | 0.98 | | 0.895 | | 0.97 | 0.743 |
| PZP | 8 | 0.000 | | 1.07 | 0.530 | | 1.07 | | 0.539 | | 1.07 | 0.398 |
| QSOX1 | 11 | 0.000 | | 0.83 | 0.000 | | 0.83 | | 0.000 | | 0.83 | 0.000 |
| RBBP8 | 1 | 0.027 | | 1.68 | 0.115 | | 1.81 | | 0.076 | | 1.74 | 0.022 |
| RNASE1 | 1 | 0.207 | | 1.10 | 0.618 | | 1.07 | | 0.713 | | 1.09 | 0.543 |
| RTN4RL2 | 1 | 0.006 | | 0.78 | 0.016 | | 0.82 | | 0.055 | | 0.80 | 0.003 |

TABLE 2C-continued

Marker Discovery

| PROTEIN | #PEPTIDES | Asymptomatic (HIV−) and LTBI (HIV−) | | | | Active TB vs Asymptomatic (HIV+) and LTBI (HIV+) | | | | Active TB vs Asymptomatic and LTBI\|HIV+/− | | | |
|---|---|---|---|---|---|---|---|---|---|---|---|---|---|
| | | q-value | DE | ANOVA DI | p-value | DE | ANOVA DI | p-value | DE | | ANOVA DI | p-value | |
| S100A12 | 2 | 0.002 | | 1.20 | 0.271 | | 0.78 | 0.133 | | | 0.97 | 0.817 | |
| S100A8 | 9 | 0.000 | | 1.57 | 0.000 | | 1.14 | 0.109 | | | 1.34 | 0.000 | |
| S100A9 | 18 | 0.000 | | 1.93 | 0.000 | | 1.39 | 0.000 | | | 1.64 | 0.000 | |
| SAA1 | 4 | 0.000 | X | 2.61 | 0.000 | X | 2.18 | 0.000 | X | | 2.39 | 0.000 | |
| SAA4 | 14 | 0.000 | | 0.96 | 0.408 | | 0.73 | 0.000 | | | 0.84 | 0.000 | |
| SDPR | 1 | 0.006 | | 1.46 | 0.136 | | 1.00 | 0.991 | | | 1.21 | 0.308 | |
| SELL | 8 | 0.000 | | 1.04 | 0.470 | | 1.16 | 0.010 | | | 1.10 | 0.027 | |
| SEMA4B | 1 | 0.014 | | 0.86 | 0.290 | | 0.72 | 0.029 | | | 0.79 | 0.030 | |
| SEPP1 | 8 | 0.001 | | 0.84 | 0.004 | | 0.86 | 0.014 | | | 0.85 | 0.000 | |
| SERPINA1 | 78 | 0.000 | | 1.75 | 0.000 | | 1.57 | 0.000 | | | 1.66 | 0.000 | |
| SERPINA10 | 16 | 0.000 | | 0.98 | 0.591 | | 0.87 | 0.002 | | | 0.92 | 0.016 | |
| SERPINA3 | 6 | 0.000 | | 1.56 | 0.000 | | 1.60 | 0.000 | | | 1.58 | 0.000 | |
| SERPINA4 | 22 | 0.000 | | 0.52 | 0.000 | | 0.60 | 0.000 | | | 0.56 | 0.000 | |
| SERPINA6 | 14 | 0.004 | | 0.94 | 0.277 | | 0.95 | 0.379 | | | 0.95 | 0.180 | |
| SERPINA7 | 37 | 0.000 | | 0.91 | 0.002 | | 0.85 | 0.000 | | | 0.88 | 0.000 | |
| SERPINB1 | 1 | 0.000 | | 1.57 | 0.006 | | 1.11 | 0.532 | | | 1.32 | 0.028 | |
| SERPINC1 | 1 | 0.007 | | 1.65 | 0.007 | | 1.53 | 0.022 | | | 1.59 | 0.001 | |
| SERPIND1 | 25 | 0.000 | | 0.91 | 0.011 | | 0.76 | 0.000 | | | 0.83 | 0.000 | |
| SERPINF1 | 41 | 0.000 | | 0.82 | 0.000 | | 0.83 | 0.000 | | | 0.82 | 0.000 | |
| SERPINF2 | 1 | 0.039 | | 1.33 | 0.079 | | 1.32 | 0.085 | | | 1.33 | 0.017 | |
| SERPING1 | 15 | 0.005 | | 0.88 | 0.006 | | 0.96 | 0.368 | | | 0.92 | 0.013 | |
| SH3BGRL | 1 | 0.000 | | 1.78 | 0.001 | | 1.34 | 0.087 | | | 1.55 | 0.001 | |
| SH3BGRL3 | 3 | 0.000 | | 1.71 | 0.000 | | 1.19 | 0.221 | | | 1.44 | 0.001 | |
| SHBG | 16 | 0.000 | | 0.81 | 0.001 | | 0.77 | 0.000 | | | 0.79 | 0.000 | |
| SLC3A2 | 2 | 0.000 | | 0.56 | 0.000 | | 0.66 | 0.000 | | | 0.61 | 0.000 | |
| SNCA | 0 | — | | — | — | | — | — | | | — | — | |
| SNED1 | 1 | 0.119 | | 1.17 | 0.211 | | 1.00 | 0.975 | | | 1.08 | 0.396 | |
| SOD3 | 5 | 0.004 | | 0.93 | 0.371 | | 0.81 | 0.005 | | | 0.87 | 0.014 | |
| SORL1 | 2 | 0.089 | | 1.23 | 0.294 | | 1.05 | 0.807 | | | 1.14 | 0.369 | |
| SOWAHC | 0 | — | | — | — | | — | — | | | — | — | |
| SPARC | 11 | 0.000 | | 1.07 | 0.217 | | 1.25 | 0.000 | | | 1.15 | 0.000 | |
| SPARCL1 | 2 | 0.042 | | 0.96 | 0.692 | | 1.17 | 0.160 | | | 1.05 | 0.510 | |
| SPP2 | 2 | 0.000 | | 0.53 | 0.000 | | 0.51 | 0.000 | | | 0.52 | 0.000 | |
| SRGN | 3 | 0.017 | | 1.03 | 0.706 | | 1.22 | 0.019 | | | 1.12 | 0.075 | |
| SSC5D | 2 | 0.049 | | 1.08 | 0.559 | | 0.85 | 0.252 | | | 0.96 | 0.720 | |
| STXBP3 | 0 | — | | — | — | | — | — | | | — | — | |
| TAGLN2 | 7 | 0.000 | | 1.87 | 0.000 | | 1.03 | 0.790 | | | 1.40 | 0.000 | |
| TF | 8 | 0.001 | | 0.82 | 0.006 | | 0.87 | 0.066 | | | 0.84 | 0.002 | |
| TGFBI | 14 | 0.000 | | 0.81 | 0.000 | | 0.96 | 0.392 | | | 0.88 | 0.001 | |
| THBS1 | 30 | 0.000 | | 0.83 | 0.000 | | 0.91 | 0.006 | | | 0.87 | 0.000 | |
| TIMP1 | 1 | 0.181 | | 1.01 | 0.929 | | 1.10 | 0.539 | | | 1.06 | 0.628 | |
| TKT | 3 | 0.000 | | 1.52 | 0.000 | | 1.30 | 0.014 | | | 1.41 | 0.000 | |
| TLN1 | 11 | 0.000 | | 1.25 | 0.000 | | 0.98 | 0.728 | | | 1.11 | 0.029 | |
| TMSB4X | 6 | 0.000 | | 1.60 | 0.000 | | 0.96 | 0.700 | | | 1.24 | 0.015 | |
| TNC | 5 | 0.205 | | 1.04 | 0.626 | | 1.03 | 0.681 | | | 1.04 | 0.541 | |
| TNXB | 19 | 0.000 | | 0.82 | 0.000 | | 0.89 | 0.001 | | | 0.85 | 0.000 | |
| TPI1 | 2 | 0.001 | | 1.42 | 0.004 | | 1.08 | 0.525 | | | 1.24 | 0.019 | |
| TPM3 | 3 | 0.000 | | 1.33 | 0.017 | | 0.93 | 0.563 | | | 1.12 | 0.222 | |
| TPM4 | 1 | 0.072 | | 1.13 | 0.622 | | 0.89 | 0.623 | | | 1.00 | 0.988 | |
| TREML1 | 3 | 0.000 | | 1.65 | 0.000 | | 1.42 | 0.006 | | | 1.53 | 0.000 | |
| TTR | 4 | 0.208 | | 0.96 | 0.651 | | 0.99 | 0.879 | | | 0.97 | 0.678 | |
| TUBA4A | 2 | 0.003 | | 1.28 | 0.023 | | 1.11 | 0.327 | | | 1.19 | 0.027 | |
| UMOD | 1 | 0.066 | | 1.20 | 0.078 | | 1.18 | 0.111 | | | 1.19 | 0.021 | |
| VASN | 7 | 0.072 | | 0.93 | 0.161 | | 0.96 | 0.380 | | | 0.95 | 0.120 | |
| VASP | 1 | 0.003 | | 1.17 | 0.374 | | 0.89 | 0.520 | | | 1.03 | 0.852 | |
| VCAM1 | 12 | 0.007 | | 1.11 | 0.037 | | 1.08 | 0.108 | | | 1.09 | 0.012 | |
| VCL | 5 | 0.008 | | 1.14 | 0.085 | | 1.08 | 0.322 | | | 1.11 | 0.065 | |
| VIM | 2 | 0.219 | | 0.99 | 0.938 | | 0.99 | 0.939 | | | 0.99 | 0.915 | |
| VNN1 | 4 | 0.001 | | 0.72 | 0.007 | | 0.79 | 0.049 | | | 0.75 | 0.002 | |
| VTN | 4 | 0.027 | | 0.88 | 0.083 | | 0.84 | 0.025 | | | 0.86 | 0.007 | |
| VWF | 60 | 0.000 | | 1.07 | 0.013 | | 0.97 | 0.320 | | | 1.02 | 0.292 | |
| YWHAE | 0 | — | | — | — | | — | — | | | — | — | |
| YWHAG | 0 | — | | — | — | | — | — | | | — | — | |
| YWHAZ | 0 | — | | — | — | | — | — | | | — | — | |
| ZYX | 3 | 0.000 | | 1.83 | 0.004 | | 1.01 | 0.971 | | | 1.37 | 0.051 | |

*Differential expression (DE) thresholds: p-value <0.05|q-value <0.05|ANOVA DI >2

TABLE 2D

| | | Marker Discovery | | | | | | |
|---|---|---|---|---|---|---|---|---|
| | | | Active TB vs Asymptomatic | | | | Active TB vs LTBI | |
| PROTEIN | #PEPTIDES | DE | ANOVA DI | p-value | q-value | DE | ANOVA DI | p-value | q-value |
|---|---|---|---|---|---|---|---|---|---|
| A1BG | 4 | X | 0.46 | 0.000 | 0.000 | | 0.55 | 0.000 | 0.000 |
| A2M | 33 | | 1.96 | 0.000 | 0.000 | | 1.75 | 0.000 | 0.000 |
| ABI3BP | 3 | | 1.54 | 0.000 | 0.000 | | 1.24 | 0.007 | 0.000 |
| ACTN1 | 0 | | — | — | — | | — | — | — |
| ADAMTS13 | 0 | | — | — | — | | — | — | — |
| ADAMTSL4 | 0 | | — | — | — | | — | — | — |
| AFM | 0 | | — | — | — | | — | — | — |
| AGT | 18 | X | 2.59 | 0.000 | 0.000 | X | 2.28 | 0.000 | 0.000 |
| AHSG | 0 | | — | — | — | | — | — | — |
| ALB | 4 | X | 0.45 | 0.000 | 0.000 | | 0.62 | 0.000 | 0.000 |
| ALCAM | 0 | | — | — | — | | — | — | — |
| ALDOA | 0 | | — | — | — | | — | — | — |
| ALDOB | 0 | | — | — | — | | — | — | — |
| AMBP | 1 | X | 3.98 | 0.000 | 0.000 | X | 2.74 | 0.000 | 0.000 |
| ANGPTL3 | 0 | | — | — | — | | — | — | — |
| ANPEP | 2 | | 1.74 | 0.000 | 0.000 | | 1.59 | 0.002 | 0.000 |
| AOC3 | 0 | | — | — | — | | — | — | — |
| APCS | 2 | X | 3.34 | 0.000 | 0.000 | X | 2.80 | 0.000 | 0.000 |
| APOA1 | 38 | X | 0.50 | 0.000 | 0.000 | | 0.60 | 0.000 | 0.000 |
| APOA2 | 10 | | 0.51 | 0.000 | 0.000 | | 0.59 | 0.000 | 0.000 |
| APOA4 | 58 | | 1.80 | 0.000 | 0.000 | | 1.78 | 0.000 | 0.000 |
| APOB | 90 | | 1.32 | 0.000 | 0.000 | | 1.21 | 0.000 | 0.000 |
| APOC1 | 6 | X | 0.23 | 0.000 | 0.000 | X | 0.34 | 0.000 | 0.000 |
| APOC2 | 11 | | 0.55 | 0.000 | 0.000 | | 0.69 | 0.000 | 0.000 |
| APOC3 | 4 | | 0.75 | 0.006 | 0.000 | | 1.02 | 0.846 | 0.000 |
| APOC4 | 0 | | — | — | — | | — | — | — |
| APOD | 0 | | — | — | — | | — | — | — |
| APOE | 22 | X | 0.47 | 0.000 | 0.000 | | 0.57 | 0.000 | 0.000 |
| APOF | 4 | | 0.71 | 0.006 | 0.000 | | 0.69 | 0.003 | 0.000 |
| APOL1 | 3 | | 0.89 | 0.345 | 0.001 | | 0.93 | 0.554 | 0.001 |
| APOM | 0 | | — | — | — | | — | — | — |
| APP | 1 | | 1.26 | 0.264 | 0.001 | | 1.31 | 0.194 | 0.001 |
| ARHGDIB | 0 | | — | — | — | | — | — | — |
| ARPC5 | 0 | | — | — | — | | — | — | — |
| ATP6AP1L | 1 | | 1.47 | 0.022 | 0.000 | | 1.37 | 0.056 | 0.000 |
| ATRN | 4 | X | 2.46 | 0.000 | 0.000 | | 1.98 | 0.000 | 0.000 |
| AXL | 0 | | — | — | — | | — | — | — |
| AZGP1 | 17 | | 1.67 | 0.000 | 0.000 | | 1.38 | 0.000 | 0.000 |
| B2M | 4 | | 1.58 | 0.001 | 0.000 | | 1.51 | 0.003 | 0.000 |
| B4GALT1 | 0 | | — | — | — | | — | — | — |
| BCHE | 0 | | — | — | — | | — | — | — |
| BLVRB | 0 | | — | — | — | | — | — | — |
| BST1 | 0 | | — | — | — | | — | — | — |
| BTD | 2 | X | 2.42 | 0.000 | 0.000 | | 1.88 | 0.000 | 0.000 |
| C1R | 16 | | 1.92 | 0.000 | 0.000 | | 1.90 | 0.000 | 0.000 |
| C1RL | 5 | X | 2.37 | 0.000 | 0.000 | X | 2.01 | 0.000 | 0.000 |
| C1S | 21 | | 1.58 | 0.000 | 0.000 | | 1.64 | 0.000 | 0.000 |
| C2 | 21 | X | 2.61 | 0.000 | 0.000 | X | 2.25 | 0.000 | 0.000 |
| C3 | 8 | | 0.70 | 0.000 | 0.000 | | 0.77 | 0.008 | 0.000 |
| C4BPA | 0 | | — | — | — | | — | — | — |
| C5 | 4 | X | 0.41 | 0.000 | 0.000 | X | 0.46 | 0.000 | 0.000 |
| C6 | 3 | X | 0.36 | 0.000 | 0.000 | X | 0.43 | 0.000 | 0.000 |
| C9 | 3 | | 0.80 | 0.036 | 0.000 | | 0.76 | 0.009 | 0.000 |
| CA1 | 8 | X | 3.28 | 0.000 | 0.000 | X | 2.67 | 0.000 | 0.000 |
| CA2 | 4 | X | 2.15 | 0.000 | 0.000 | | 1.89 | 0.000 | 0.000 |
| CACNA2D1 | 1 | | 1.80 | 0.001 | 0.000 | | 1.46 | 0.036 | 0.000 |
| CALM1 | 0 | | — | — | — | | — | — | — |
| CALU | 0 | | — | — | — | | — | — | — |
| CAT | 1 | X | 2.96 | 0.000 | 0.000 | X | 2.65 | 0.000 | 0.000 |
| CCDC149 | 1 | X | 5.40 | 0.000 | 0.000 | X | 4.59 | 0.000 | 0.000 |
| CD14 | 3 | X | 4.47 | 0.000 | 0.000 | X | 3.34 | 0.000 | 0.000 |
| CD163 | 0 | | — | — | — | | — | — | — |
| CD44 | 0 | | — | — | — | | — | — | — |
| CD59 | 0 | | — | — | — | | — | — | — |
| CD5L | 1 | X | 2.17 | 0.000 | 0.000 | | 1.54 | 0.040 | 0.000 |
| CD84 | 0 | | — | — | — | | — | — | — |
| CD93 | 0 | | — | — | — | | — | — | — |
| CDH1 | 0 | | — | — | — | | — | — | — |
| CDH13 | 3 | | 1.35 | 0.003 | 0.000 | | 1.33 | 0.005 | 0.000 |
| CDH2 | 0 | | — | — | — | | — | — | — |
| CDH5 | 4 | | 1.29 | 0.005 | 0.000 | | 1.27 | 0.009 | 0.000 |
| CETP | 0 | | — | — | — | | — | — | — |
| CFB | 6 | | 0.61 | 0.000 | 0.000 | | 0.69 | 0.000 | 0.000 |
| CFD | 3 | | 1.77 | 0.000 | 0.000 | | 1.49 | 0.000 | 0.000 |

TABLE 2D-continued

| | | Marker Discovery | | | | | | |
|---|---|---|---|---|---|---|---|---|
| | | Active TB vs Asymptomatic | | | | Active TB vs LTBI | | |
| PROTEIN | #PEPTIDES | DE | ANOVA DI | p-value | q-value | DE | ANOVA DI | p-value | q-value |
| CFL1 | 0 | | — | — | — | | — | — | — |
| CFP | 0 | | — | — | — | | — | — | — |
| CHI3L1 | 0 | | — | — | — | | — | — | — |
| CHL1 | 4 | | 1.68 | 0.000 | 0.000 | | 1.55 | 0.000 | 0.000 |
| CKM | 0 | | — | — | — | | — | — | — |
| CLC | 0 | | — | — | — | | — | — | — |
| CLEC3B | 7 | | 1.58 | 0.000 | 0.000 | | 1.10 | 0.395 | 0.000 |
| CLIC1 | 0 | | — | — | — | | — | — | — |
| CLU | 36 | | 1.03 | 0.433 | 0.000 | | 1.00 | 0.905 | 0.000 |
| CNDP1 | 4 | | 1.57 | 0.000 | 0.000 | | 1.37 | 0.002 | 0.000 |
| CNN2 | 0 | | — | — | — | | — | — | — |
| CNTN1 | 0 | | — | — | — | | — | — | — |
| COL18A1 | 0 | | — | — | — | | — | — | — |
| COL6A1 | 0 | | — | — | — | | — | — | — |
| COL6A3 | 1 | | 1.94 | 0.000 | 0.000 | | 1.51 | 0.017 | 0.000 |
| COLEC10 | 0 | | — | — | — | | — | — | — |
| COLEC11 | 1 | | 1.61 | 0.003 | 0.000 | | 1.22 | 0.202 | 0.000 |
| COMP | 0 | | — | — | — | | — | — | — |
| CORO1A | 0 | | — | — | — | | — | — | — |
| CORO1B | 0 | | — | — | — | | — | — | — |
| COTL1 | 0 | | — | — | — | | — | — | — |
| CP | 12 | X | 0.48 | 0.000 | 0.000 | | 0.54 | 0.000 | 0.000 |
| CPB2 | 9 | X | 2.61 | 0.000 | 0.000 | X | 2.17 | 0.000 | 0.000 |
| CPN1 | 7 | | 1.89 | 0.000 | 0.000 | | 1.69 | 0.000 | 0.000 |
| CPN2 | 8 | X | 3.02 | 0.000 | 0.000 | X | 2.27 | 0.000 | 0.000 |
| CPQ | 0 | | — | — | — | | — | — | — |
| CRP | 1 | X | 4.24 | 0.000 | 0.000 | X | 3.68 | 0.000 | 0.000 |
| CRTAC1 | 0 | | — | — | — | | — | — | — |
| CSF1R | 0 | | — | — | — | | — | — | — |
| CST3 | 2 | | 1.00 | 0.991 | 0.000 | | 0.89 | 0.433 | 0.000 |
| CTBS | 0 | | — | — | — | | — | — | — |
| CTSD | 0 | | — | — | — | | — | — | — |
| DAG1 | 2 | | 0.60 | 0.003 | 0.000 | | 0.69 | 0.026 | 0.000 |
| DBH | 2 | X | 2.39 | 0.000 | 0.000 | | 1.69 | 0.005 | 0.000 |
| DPEP2 | 0 | | — | — | — | | — | — | — |
| DPP4 | 0 | | — | — | — | | — | — | — |
| DSG2 | 0 | | — | — | — | | — | — | — |
| ECM1 | 0 | | — | — | — | | — | — | — |
| ENDOD1 | 0 | | — | — | — | | — | — | — |
| ENG | 0 | | — | — | — | | — | — | — |
| ENO1 | 0 | | — | — | — | | — | — | — |
| ENPP2 | 0 | | — | — | — | | — | — | — |
| ERAP1 | 0 | | — | — | — | | — | — | — |
| F10 | 8 | | 1.83 | 0.000 | 0.000 | | 1.79 | 0.000 | 0.000 |
| F11 | 2 | | 1.33 | 0.025 | 0.000 | | 1.25 | 0.076 | 0.000 |
| F12 | 3 | X | 2.08 | 0.000 | 0.000 | | 1.66 | 0.000 | 0.000 |
| F13A1 | 0 | | — | — | — | | — | — | — |
| F13B | 1 | X | 2.08 | 0.000 | 0.000 | | 1.78 | 0.000 | 0.000 |
| F2 | 5 | | 0.95 | 0.589 | 0.000 | | 1.12 | 0.250 | 0.000 |
| F5 | 9 | | 1.89 | 0.000 | 0.000 | | 1.64 | 0.000 | 0.000 |
| F7 | 1 | X | 2.28 | 0.000 | 0.000 | | 1.90 | 0.000 | 0.000 |
| F9 | 5 | X | 2.86 | 0.000 | 0.000 | X | 2.48 | 0.000 | 0.000 |
| FAH | 0 | | — | — | — | | — | — | — |
| FAM3C | 0 | | — | — | — | | — | — | — |
| FBLN1 | 2 | | 1.83 | 0.000 | 0.000 | | 1.51 | 0.000 | 0.000 |
| FBXO33 | 0 | | — | — | — | | — | — | — |
| FCGBP | 0 | | — | — | — | | — | — | — |
| FCGR3A | 1 | X | 2.16 | 0.000 | 0.000 | | 1.94 | 0.000 | 0.000 |
| FCGR3B | 1 | | 1.01 | 0.872 | 0.017 | | 0.99 | 0.950 | 0.017 |
| FCN2 | 0 | | — | — | — | | — | — | — |
| FCN3 | 2 | X | 3.03 | 0.000 | 0.000 | X | 2.12 | 0.000 | 0.000 |
| FETUB | 5 | | 1.27 | 0.009 | 0.000 | | 1.26 | 0.012 | 0.000 |
| FGA | 5 | X | 2.66 | 0.000 | 0.000 | X | 2.07 | 0.000 | 0.000 |
| FGB | 0 | | — | — | — | | — | — | — |
| FGFR1 | 0 | | — | — | — | | — | — | — |
| FGG | 0 | | — | — | — | | — | — | — |
| FKBP1A | 1 | X | 2.36 | 0.000 | 0.000 | X | 2.29 | 0.000 | 0.000 |
| FLNA | 1 | | 1.83 | 0.000 | 0.000 | | 1.75 | 0.000 | 0.000 |
| FLT4 | 0 | | — | — | — | | — | — | — |
| FN1 | 0 | | — | — | — | | — | — | — |
| FTL | 2 | X | 2.98 | 0.000 | 0.000 | X | 2.45 | 0.000 | 0.000 |
| FUCA1 | 0 | | — | — | — | | — | — | — |
| FUCA2 | 0 | | — | — | — | | — | — | — |
| GALNT2 | 0 | | — | — | — | | — | — | — |

TABLE 2D-continued

| | | | Marker Discovery | | | | | | |
| --- | --- | --- | --- | --- | --- | --- | --- | --- | --- |
| | | | Active TB vs Asymptomatic | | | | Active TB vs LTBI | | |
| PROTEIN | #PEPTIDES | DE | ANOVA DI | p-value | q-value | DE | ANOVA DI | p-value | q-value |
| GAPDH | 0 | | — | — | — | | — | — | — |
| GC | 1 | X | 0.36 | 0.000 | 0.000 | | 0.52 | 0.001 | 0.000 |
| GGH | 1 | X | 3.40 | 0.000 | 0.000 | X | 2.85 | 0.000 | 0.000 |
| GK | 0 | | — | — | — | | — | — | — |
| GNPTG | 0 | | — | — | — | | — | — | — |
| GOSR1 | 1 | | 0.98 | 0.914 | 0.001 | | 0.91 | 0.618 | 0.001 |
| GP1BA | 4 | X | 3.61 | 0.000 | 0.000 | X | 2.81 | 0.000 | 0.000 |
| GP5 | 0 | | — | — | — | | — | — | — |
| GPLD1 | 6 | X | 2.34 | 0.000 | 0.000 | | 1.87 | 0.000 | 0.000 |
| GPR126 | 0 | | — | — | — | | — | — | — |
| GPX3 | 5 | | 1.57 | 0.000 | 0.000 | | 1.22 | 0.026 | 0.000 |
| GSN | 36 | | 1.06 | 0.123 | 0.000 | | 0.94 | 0.070 | 0.000 |
| GSTO1 | 0 | | — | — | — | | — | — | — |
| GSTP1 | 1 | | 1.92 | 0.000 | 0.000 | | 1.85 | 0.000 | 0.000 |
| HABP2 | 0 | | — | — | — | | — | — | — |
| HBA1 | 4 | X | 2.27 | 0.000 | 0.000 | X | 2.26 | 0.000 | 0.000 |
| HBB | 5 | X | 3.97 | 0.000 | 0.000 | X | 3.12 | 0.000 | 0.000 |
| HEG1 | 0 | | — | — | — | | — | — | — |
| HGFAC | 2 | X | 2.53 | 0.000 | 0.000 | | 1.82 | 0.000 | 0.000 |
| HIST1H4A | 1 | | 1.27 | 0.279 | 0.000 | | 1.13 | 0.575 | 0.000 |
| HP | 10 | | 1.82 | 0.000 | 0.000 | | 1.58 | 0.000 | 0.000 |
| HPR | 1 | X | 2.85 | 0.000 | 0.000 | | 1.97 | 0.001 | 0.000 |
| HPX | 1 | X | 4.66 | 0.000 | 0.000 | X | 2.63 | 0.000 | 0.000 |
| HRNR | 0 | | — | — | — | | — | — | — |
| HSP90B1 | 0 | | — | — | — | | — | — | — |
| HSPA5 | 1 | | 1.05 | 0.624 | 0.005 | | 1.01 | 0.921 | 0.005 |
| HSPA8 | 0 | | — | — | — | | — | — | — |
| HSPB1 | 0 | | — | — | — | | — | — | — |
| HSPG2 | 1 | | 1.24 | 0.308 | 0.008 | | 1.20 | 0.378 | 0.008 |
| HYOU1 | 0 | | — | — | — | | — | — | — |
| ICAM1 | 1 | X | 2.36 | 0.000 | 0.000 | | 1.98 | 0.000 | 0.000 |
| ICAM2 | 1 | | 1.87 | 0.000 | 0.000 | | 1.55 | 0.005 | 0.000 |
| ICOSLG | 0 | | — | — | — | | — | — | — |
| IDH1 | 0 | | — | — | — | | — | — | — |
| IGF1 | 0 | | — | — | — | | — | — | — |
| IGF2 | 0 | | — | — | — | | — | — | — |
| IGF2R | 0 | | — | — | — | | — | — | — |
| IGFALS | 15 | | 1.92 | 0.000 | 0.000 | | 1.66 | 0.000 | 0.000 |
| IGFBP1 | 0 | | — | — | — | | — | — | — |
| IGFBP2 | 0 | | — | — | — | | — | — | — |
| IGFBP3 | 3 | | 0.95 | 0.618 | 0.005 | | 0.91 | 0.391 | 0.005 |
| IGFBP4 | 0 | | — | — | — | | — | — | — |
| IGFBP5 | 0 | | — | — | — | | — | — | — |
| IGFBP6 | 0 | | — | — | — | | — | — | — |
| IGFBP7 | 0 | | — | — | — | | — | — | — |
| IGLL5 | 1 | X | 3.82 | 0.000 | 0.000 | X | 2.27 | 0.000 | 0.000 |
| IL1R2 | 0 | | — | — | — | | — | — | — |
| 1L1RAP | 0 | | — | — | — | | — | — | — |
| IL6ST | 0 | | — | — | — | | — | — | — |
| ISLR | 0 | | — | — | — | | — | — | — |
| ITGB1 | 0 | | — | — | — | | — | — | — |
| ITIH1 | 7 | | 0.55 | 0.000 | 0.000 | | 0.59 | 0.000 | 0.000 |
| ITIH2 | 22 | | 0.54 | 0.000 | 0.000 | | 0.59 | 0.000 | 0.000 |
| ITIH3 | 20 | | 1.09 | 0.050 | 0.000 | | 1.06 | 0.170 | 0.000 |
| ITIH4 | 18 | X | 3.74 | 0.000 | 0.000 | X | 2.91 | 0.000 | 0.000 |
| KIT | 0 | | — | — | — | | — | — | — |
| KLKB1 | 2 | | 0.70 | 0.003 | 0.000 | | 0.66 | 0.000 | 0.000 |
| KNG1 | 7 | | 0.66 | 0.000 | 0.000 | | 0.67 | 0.000 | 0.000 |
| KRT1 | 2 | X | 2.48 | 0.000 | 0.000 | X | 2.35 | 0.000 | 0.000 |
| KRT10 | 2 | X | 2.26 | 0.000 | 0.000 | X | 2.17 | 0.000 | 0.000 |
| KRT14 | 0 | | — | — | — | | — | — | — |
| KRT2 | 1 | X | 2.31 | 0.000 | 0.000 | X | 2.20 | 0.000 | 0.000 |
| KRT5 | 0 | | — | — | — | | — | — | — |
| KRT9 | 2 | | 1.32 | 0.037 | 0.000 | | 1.36 | 0.021 | 0.000 |
| LAMB1 | 0 | | — | — | — | | — | — | — |
| LAMP1 | 1 | | 0.55 | 0.012 | 0.000 | | 0.60 | 0.029 | 0.000 |
| LAMP2 | 0 | | — | — | — | | — | — | — |
| LASP1 | 0 | | — | — | — | | — | — | — |
| LBP | 0 | | — | — | — | | — | — | — |
| LCAT | 6 | | 1.84 | 0.000 | 0.000 | | 1.65 | 0.000 | 0.000 |
| LCN2 | 0 | | — | — | — | | — | — | — |
| LCP1 | 2 | | 1.49 | 0.001 | 0.000 | | 1.36 | 0.007 | 0.000 |
| LDHB | 0 | | — | — | — | | — | — | — |
| LGALS3BP | 10 | X | 2.05 | 0.000 | 0.000 | | 1.72 | 0.000 | 0.000 |

TABLE 2D-continued

| | | | Marker Discovery | | | | | | |
|---|---|---|---|---|---|---|---|---|---|
| | | | Active TB vs Asymptomatic | | | | Active TB vs LTBI | | |
| PROTEIN | #PEPTIDES | DE | ANOVA DI | p-value | q-value | DE | ANOVA DI | p-value | q-value |
| LGALSL | 0 | | — | — | — | | — | — | — |
| LILRA1 | 0 | | — | — | — | | — | — | — |
| LILRA3 | 0 | | — | — | — | | — | — | — |
| LPA | 0 | | — | — | — | | — | — | — |
| LRG1 | 31 | X | 3.04 | 0.000 | 0.000 | X | 2.68 | 0.000 | 0.000 |
| LRP1 | 0 | | — | — | — | | — | — | — |
| LSAMP | 0 | | — | — | — | | — | — | — |
| LUM | 24 | X | 2.08 | 0.000 | 0.000 | | 1.79 | 0.000 | 0.000 |
| LYVE1 | 1 | X | 2.12 | 0.000 | 0.000 | | 1.73 | 0.001 | 0.000 |
| LYZ | 0 | | — | — | — | | — | — | — |
| MAN1A1 | 0 | | — | — | — | | — | — | — |
| MAN2A2 | 0 | | — | — | — | | — | — | — |
| MASP1 | 1 | X | 2.33 | 0.000 | 0.000 | | 1.94 | 0.000 | 0.000 |
| MASP2 | 2 | | 1.58 | 0.000 | 0.000 | | 1.47 | 0.000 | 0.000 |
| MB | 0 | | — | — | — | | — | — | — |
| MBL2 | 1 | X | 3.41 | 0.000 | 0.000 | X | 2.68 | 0.000 | 0.000 |
| MCAM | 3 | | 1.11 | 0.277 | 0.000 | | 1.05 | 0.635 | 0.000 |
| MEGF8 | 0 | | — | — | — | | — | — | — |
| MIF | 0 | | — | — | — | | — | — | — |
| MINPP1 | 0 | | — | — | — | | — | — | — |
| MMP2 | 1 | | 1.79 | 0.000 | 0.000 | | 1.49 | 0.006 | 0.000 |
| MMP9 | 0 | | — | — | — | | — | — | — |
| MMRN2 | 0 | | — | — | — | | — | — | — |
| MRPS26 | 0 | | — | — | — | | — | — | — |
| MSN | 0 | | — | — | — | | — | — | — |
| MST1 | 1 | X | 3.46 | 0.000 | 0.000 | X | 2.64 | 0.000 | 0.000 |
| MTPN | 0 | | — | — | — | | — | — | — |
| NAGLU | 0 | | — | — | — | | — | — | — |
| NCAM1 | 0 | | — | — | — | | — | — | — |
| NEO1 | 0 | | — | — | — | | — | — | — |
| NID1 | 0 | | — | — | — | | — | — | — |
| NRGN | 0 | | — | — | — | | — | — | — |
| NRP1 | 1 | X | 2.12 | 0.000 | 0.000 | | 1.96 | 0.000 | 0.000 |
| NUCB1 | 0 | | — | — | — | | — | — | — |
| NUP210L | 0 | | — | — | — | | — | — | — |
| OAF | 0 | | — | — | — | | — | — | — |
| OLFM1 | 0 | | — | — | — | | — | — | — |
| ORM1 | 1 | | 1.55 | 0.031 | 0.000 | | 1.55 | 0.030 | 0.000 |
| ORM2 | 1 | | 1.27 | 0.156 | 0.000 | | 1.25 | 0.182 | 0.000 |
| PAM | 0 | | — | — | — | | — | — | — |
| PCOLCE | 1 | | 1.87 | 0.000 | 0.000 | | 1.43 | 0.024 | 0.000 |
| PCSK9 | 0 | | — | — | — | | — | — | — |
| PDIA3 | 0 | | — | — | — | | — | — | — |
| PDLIM1 | 1 | X | 3.90 | 0.000 | 0.000 | X | 4.46 | 0.000 | 0.000 |
| PEPD | 0 | | — | — | — | | — | — | — |
| PF4 | 0 | | — | — | — | | — | — | — |
| PFN1 | 3 | X | 2.98 | 0.000 | 0.000 | X | 2.88 | 0.000 | 0.000 |
| PGLYRP2 | 4 | | 1.43 | 0.001 | 0.000 | | 1.19 | 0.108 | 0.000 |
| PI16 | 5 | | 1.65 | 0.000 | 0.000 | | 1.34 | 0.001 | 0.000 |
| PIGR | 0 | | — | — | — | | — | — | — |
| PLEK | 0 | | — | — | — | | — | — | — |
| PLS1 | 0 | | — | — | — | | — | — | — |
| PLTP | 0 | | — | — | — | | — | — | — |
| PLXNB1 | 0 | | — | — | — | | — | — | — |
| PODXL | 0 | | — | — | — | | — | — | — |
| PON1 | 10 | | 0.54 | 0.000 | 0.000 | | 0.56 | 0.000 | 0.000 |
| PON3 | 1 | X | 0.28 | 0.000 | 0.000 | X | 0.29 | 0.000 | 0.000 |
| POR | 1 | | 0.96 | 0.901 | 0.021 | | 1.05 | 0.875 | 0.021 |
| POSTN | 1 | | 1.95 | 0.011 | 0.000 | | 1.54 | 0.097 | 0.000 |
| PPBP | 6 | | 1.98 | 0.000 | 0.000 | | 1.59 | 0.000 | 0.000 |
| PPIA | 2 | X | 2.41 | 0.000 | 0.000 | X | 2.43 | 0.000 | 0.000 |
| PPIB | 0 | | — | — | — | | — | — | — |
| PRAP1 | 0 | | — | — | — | | — | — | — |
| PRDX2 | 4 | X | 3.13 | 0.000 | 0.000 | X | 2.65 | 0.000 | 0.000 |
| PRDX6 | 1 | X | 2.41 | 0.000 | 0.000 | X | 2.12 | 0.000 | 0.000 |
| PRG4 | 1 | | 1.30 | 0.061 | 0.000 | | 1.13 | 0.368 | 0.000 |
| PROC | 4 | | 1.72 | 0.000 | 0.000 | | 1.51 | 0.001 | 0.000 |
| PROCR | 1 | X | 2.58 | 0.000 | 0.000 | X | 2.01 | 0.003 | 0.000 |
| PROS1 | 4 | X | 2.06 | 0.000 | 0.000 | | 1.93 | 0.000 | 0.000 |
| PROZ | 3 | X | 2.11 | 0.000 | 0.000 | | 1.63 | 0.000 | 0.000 |
| PRSS1 | 0 | | — | — | — | | — | — | — |
| PRSS3 | 1 | X | 2.21 | 0.000 | 0.000 | | 1.73 | 0.000 | 0.000 |
| PTGDS | 1 | | 1.63 | 0.005 | 0.000 | | 1.32 | 0.111 | 0.000 |
| PTPRG | 0 | | — | — | — | | — | — | — |

TABLE 2D-continued

| | | | Marker Discovery | | | | | | |
|---|---|---|---|---|---|---|---|---|---|
| | | | Active TB vs Asymptomatic | | | | Active TB vs LTBI | | |
| PROTEIN | #PEPTIDES | DE | ANOVA DI | p-value | q-value | DE | ANOVA DI | p-value | q-value |
| PTPRJ | 1 | | 1.29 | 0.096 | 0.000 | | 1.18 | 0.288 | 0.000 |
| PTPRS | 0 | | — | — | — | | — | — | — |
| PVR | 2 | X | 2.42 | 0.000 | 0.000 | | 1.97 | 0.000 | 0.000 |
| PVRL1 | 0 | | — | — | — | | — | — | — |
| PZP | 5 | | 1.93 | 0.000 | 0.000 | | 1.73 | 0.000 | 0.000 |
| QSOX1 | 2 | X | 4.42 | 0.000 | 0.000 | X | 3.54 | 0.000 | 0.000 |
| RBBP8 | 0 | | — | — | — | | — | — | — |
| RNASE1 | 0 | | — | — | — | | — | — | — |
| RTN4RL2 | 0 | | — | — | — | | — | — | — |
| S100A12 | 0 | | — | — | — | | — | — | — |
| S100A8 | 5 | | 1.27 | 0.116 | 0.000 | | 1.24 | 0.151 | 0.000 |
| S100A9 | 8 | X | 4.00 | 0.000 | 0.000 | X | 3.40 | 0.000 | 0.000 |
| SAA1 | 1 | X | 3.25 | 0.000 | 0.000 | X | 3.46 | 0.000 | 0.000 |
| SAA4 | 3 | | 0.58 | 0.001 | 0.000 | | 0.62 | 0.002 | 0.000 |
| SDPR | 0 | | — | — | — | | — | — | — |
| SELL | 2 | X | 2.26 | 0.000 | 0.000 | | 1.81 | 0.000 | 0.000 |
| SEMA4B | 0 | | — | — | — | | — | — | — |
| SEPP1 | 3 | | 1.36 | 0.011 | 0.000 | | 1.14 | 0.256 | 0.000 |
| SERPINA1 | 43 | | 1.24 | 0.000 | 0.000 | | 1.35 | 0.000 | 0.000 |
| SERPINA10 | 1 | | 1.80 | 0.000 | 0.000 | | 1.61 | 0.000 | 0.000 |
| SERPINA3 | 3 | | 0.87 | 0.386 | 0.012 | | 0.94 | 0.715 | 0.012 |
| SERPINA4 | 7 | X | 2.45 | 0.000 | 0.000 | | 1.87 | 0.000 | 0.000 |
| SERPINA6 | 7 | X | 2.58 | 0.000 | 0.000 | | 1.96 | 0.000 | 0.000 |
| SERPINA7 | 17 | X | 2.72 | 0.000 | 0.000 | X | 2.18 | 0.000 | 0.000 |
| SERPINB1 | 0 | | — | — | — | | — | — | — |
| SERPINC1 | 2 | | 0.66 | 0.000 | 0.000 | | 0.76 | 0.011 | 0.000 |
| SERPIND1 | 11 | X | 2.18 | 0.000 | 0.000 | | 1.76 | 0.000 | 0.000 |
| SERPINF1 | 25 | X | 2.26 | 0.000 | 0.000 | | 1.84 | 0.000 | 0.000 |
| SERPINF2 | 0 | | — | — | — | | — | — | — |
| SERPING1 | 3 | X | 3.44 | 0.000 | 0.000 | X | 2.66 | 0.000 | 0.000 |
| SH3BGRL | 0 | | — | — | — | | — | — | — |
| SH3BGRL3 | 3 | X | 2.53 | 0.000 | 0.000 | X | 2.50 | 0.000 | 0.000 |
| SHBG | 2 | | 1.86 | 0.001 | 0.000 | | 1.62 | 0.011 | 0.000 |
| SLC3A2 | 0 | | — | — | — | | — | — | — |
| SNCA | 0 | | — | — | — | | — | — | — |
| SNED1 | 0 | | — | — | — | | — | — | — |
| SOD3 | 1 | | 1.52 | 0.013 | 0.000 | | 1.47 | 0.021 | 0.000 |
| SORL1 | 0 | | — | — | — | | — | — | — |
| SOWAHC | 1 | | 1.87 | 0.060 | 0.000 | | 1.89 | 0.054 | 0.000 |
| SPARC | 3 | | 1.89 | 0.000 | 0.000 | | 1.68 | 0.000 | 0.000 |
| SPARCL1 | 0 | | — | — | — | | — | — | — |
| SPP2 | 0 | | — | — | — | | — | — | — |
| SRGN | 0 | | — | — | — | | — | — | — |
| SSC5D | 0 | | — | — | — | | — | — | — |
| STXBP3 | 0 | | — | — | — | | — | — | — |
| TAGLN2 | 1 | X | 2.40 | 0.001 | 0.000 | X | 2.76 | 0.000 | 0.000 |
| TF | 0 | | — | — | — | | — | — | — |
| TGFBI | 6 | X | 2.18 | 0.000 | 0.000 | | 1.83 | 0.000 | 0.000 |
| THBS1 | 7 | | 1.67 | 0.000 | 0.000 | | 1.58 | 0.000 | 0.000 |
| TIMP1 | 0 | | — | — | — | | — | — | — |
| TKT | 1 | | 0.64 | 0.003 | 0.000 | | 0.68 | 0.011 | 0.000 |
| TLN1 | 0 | | — | — | — | | — | — | — |
| TMSB4X | 1 | | 1.38 | 0.001 | 0.000 | | 1.29 | 0.011 | 0.000 |
| TNC | 2 | X | 2.25 | 0.000 | 0.000 | | 1.93 | 0.000 | 0.000 |
| TNXB | 7 | | 1.09 | 0.305 | 0.001 | | 1.01 | 0.905 | 0.001 |
| TPI1 | 1 | X | 2.31 | 0.000 | 0.000 | | 1.98 | 0.000 | 0.000 |
| TPM3 | 0 | | — | — | — | | — | — | — |
| TPM4 | 0 | | — | — | — | | — | — | — |
| TREML1 | 0 | | — | — | — | | — | — | — |
| TTR | 19 | X | 0.43 | 0.000 | 0.000 | X | 0.49 | 0.000 | 0.000 |
| TUBA4A | 0 | | — | — | — | | — | — | — |
| UMOD | 1 | | 0.76 | 0.062 | 0.000 | | 0.79 | 0.101 | 0.000 |
| VASN | 5 | X | 2.54 | 0.000 | 0.000 | X | 2.03 | 0.000 | 0.000 |
| VASP | 0 | | — | — | — | | — | — | — |
| VCAM1 | 1 | X | 4.22 | 0.000 | 0.000 | X | 2.72 | 0.000 | 0.000 |
| VCL | 1 | X | 2.04 | 0.000 | 0.000 | X | 2.07 | 0.000 | 0.000 |
| VIM | 0 | | — | — | — | | — | — | — |
| VNN1 | 0 | | — | — | — | | — | — | — |
| VTN | 0 | | — | — | — | | — | — | — |
| VWF | 8 | X | 2.85 | 0.000 | 0.000 | X | 2.35 | 0.000 | 0.000 |
| YWHAE | 0 | | — | — | — | | — | — | — |

TABLE 2D-continued

Marker Discovery

| PROTEIN | #PEPTIDES | Active TB vs Asymptomatic | | | | Active TB vs LTBI | | | |
|---|---|---|---|---|---|---|---|---|---|
| | | DE | ANOVA DI | p-value | q-value | DE | ANOVA DI | p-value | q-value |
| YWHAG | 0 | | — | — | — | | — | — | — |
| YWHAZ | 0 | | — | — | — | | — | — | — |
| ZYX | 0 | | — | — | — | | — | — | — |

*Differential expression (DE) thresholds: p-value < 0.05 | q-value < 0.05 | ANOVA DI > 2

TABLE 2E

Marker Discovery

| PROTEIN | #PEPTIDES | Active TB vs (Asymptomatic and LTBI) | | | | Active TB vs Extrapulmonary | | | |
|---|---|---|---|---|---|---|---|---|---|
| | | DE | ANOVA DI | p-value | q-value | DE | ANOVA DI | p-value | q-value |
| A1BG | 4 | | 0.50 | 0.000 | 0.000 | | 0.81 | 0.036 | 0.000 |
| A2M | 33 | | 1.85 | 0.000 | 0.000 | | 1.70 | 0.000 | 0.000 |
| ABI3BP | 3 | | 1.38 | 0.000 | 0.000 | | 0.88 | 0.122 | 0.000 |
| ACTN1 | 0 | | — | — | — | | — | — | — |
| ADAMTS13 | 0 | | — | — | — | | — | — | — |
| ADAMTSL4 | 0 | | — | — | — | | — | — | — |
| AFM | 0 | | — | — | — | | — | — | — |
| AGT | 18 | X | 2.43 | 0.000 | 0.000 | X | 2.02 | 0.000 | 0.000 |
| AHSG | 0 | | — | — | — | | — | — | — |
| ALB | 4 | | 0.53 | 0.000 | 0.000 | | 0.73 | 0.002 | 0.000 |
| ALCAM | 0 | | — | — | — | | — | — | — |
| ALDOA | 0 | | — | — | — | | — | — | — |
| ALDOB | 0 | | — | — | — | | — | — | — |
| AMBP | 1 | X | 3.29 | 0.000 | 0.000 | | 1.70 | 0.025 | 0.000 |
| ANGPTL3 | 0 | | — | — | — | | — | — | — |
| ANPEP | 2 | | 1.66 | 0.000 | 0.000 | | 1.21 | 0.216 | 0.000 |
| AOC3 | 0 | | — | — | — | | — | — | — |
| APCS | 2 | X | 3.05 | 0.000 | 0.000 | | 1.34 | 0.015 | 0.000 |
| APOA1 | 38 | | 0.55 | 0.000 | 0.000 | | 0.79 | 0.000 | 0.000 |
| APOA2 | 10 | | 0.55 | 0.000 | 0.000 | | 0.91 | 0.290 | 0.000 |
| APOA4 | 58 | | 1.79 | 0.000 | 0.000 | X | 2.15 | 0.000 | 0.000 |
| APOB | 90 | | 1.26 | 0.000 | 0.000 | X | 2.89 | 0.000 | 0.000 |
| APOC1 | 6 | X | 0.28 | 0.000 | 0.000 | X | 0.31 | 0.000 | 0.000 |
| APOC2 | 11 | | 0.62 | 0.000 | 0.000 | | 0.54 | 0.000 | 0.000 |
| APOC3 | 4 | | 0.88 | 0.119 | 0.000 | | 1.57 | 0.000 | 0.000 |
| APOC4 | 0 | | — | — | — | | — | — | — |
| APOD | 0 | | — | — | — | | — | — | — |
| APOE | 22 | | 0.51 | 0.000 | 0.000 | | 0.81 | 0.000 | 0.000 |
| APOF | 4 | | 0.70 | 0.000 | 0.000 | X | 0.25 | 0.000 | 0.000 |
| APOL1 | 3 | | 0.91 | 0.341 | 0.000 | | 0.76 | 0.026 | 0.001 |
| APOM | 0 | | — | — | — | | — | — | — |
| APP | 1 | | 1.28 | 0.131 | 0.001 | | 0.91 | 0.649 | 0.001 |
| ARHGDIB | 0 | | — | — | — | | — | — | — |
| ARPC5 | 0 | | — | — | — | | — | — | — |
| ATP6AP1L | 1 | | 1.42 | 0.009 | 0.000 | | 1.01 | 0.938 | 0.000 |
| ATRN | 4 | X | 2.20 | 0.000 | 0.000 | | 1.72 | 0.000 | 0.000 |
| AXL | 0 | | — | — | — | | — | — | — |
| AZGP1 | 17 | | 1.51 | 0.000 | 0.000 | | 0.85 | 0.003 | 0.000 |
| B2M | 4 | | 1.54 | 0.000 | 0.000 | | 1.23 | 0.149 | 0.000 |
| B4GALT1 | 0 | | — | — | — | | — | — | — |
| BCHE | 0 | | — | — | — | | — | — | — |
| BLVRB | 0 | | — | — | — | | — | — | — |
| BST1 | 0 | | — | — | — | | — | — | — |
| BTD | 2 | X | 2.13 | 0.000 | 0.000 | | 1.69 | 0.000 | 0.000 |
| C1R | 16 | | 1.91 | 0.000 | 0.000 | X | 3.17 | 0.000 | 0.000 |
| C1RL | 5 | X | 2.18 | 0.000 | 0.000 | X | 2.06 | 0.000 | 0.000 |
| C1S | 21 | | 1.61 | 0.000 | 0.000 | X | 2.09 | 0.000 | 0.000 |
| C2 | 21 | X | 2.42 | 0.000 | 0.000 | | 1.29 | 0.000 | 0.000 |
| C3 | 8 | | 0.73 | 0.000 | 0.000 | | 1.08 | 0.427 | 0.000 |
| C4BPA | 0 | | — | — | — | | — | — | — |
| C5 | 4 | X | 0.44 | 0.000 | 0.000 | | 1.05 | 0.652 | 0.000 |
| C6 | 3 | X | 0.39 | 0.000 | 0.000 | | 0.94 | 0.567 | 0.000 |
| C9 | 3 | | 0.78 | 0.003 | 0.000 | | 1.19 | 0.105 | 0.000 |
| CA1 | 8 | X | 2.95 | 0.000 | 0.000 | | 1.09 | 0.383 | 0.000 |
| CA2 | 4 | X | 2.01 | 0.000 | 0.000 | | 0.91 | 0.444 | 0.000 |
| CACNA2D1 | 1 | | 1.62 | 0.001 | 0.000 | | 1.41 | 0.068 | 0.000 |
| CALM1 | 0 | | — | — | — | | — | — | — |
| CALU | 0 | | — | — | — | | — | — | — |

TABLE 2E-continued

| | | Marker Discovery | | | | | | | |
|---|---|---|---|---|---|---|---|---|---|
| | | | Active TB vs (Asymptomatic and LTBI) | | | | Active TB vs Extrapulmonary | | |
| PROTEIN | #PEPTIDES | DE | ANOVA DI | p-value | q-value | DE | ANOVA DI | p-value | q-value |
| CAT | 1 | X | 2.80 | 0.000 | 0.000 | | 1.40 | 0.103 | 0.000 |
| CCDC149 | 1 | X | 4.97 | 0.000 | 0.000 | X | 4.81 | 0.000 | 0.000 |
| CD14 | 3 | X | 3.85 | 0.000 | 0.000 | | 1.43 | 0.003 | 0.000 |
| CD163 | 0 | | — | — | — | | — | — | — |
| CD44 | 0 | | — | — | — | | — | — | — |
| CD59 | 0 | | — | — | — | | — | — | — |
| CD5L | 1 | | 1.82 | 0.000 | 0.000 | | 1.89 | 0.003 | 0.000 |
| CD84 | 0 | | — | — | — | | — | — | — |
| CD93 | 0 | | — | — | — | | — | — | — |
| CDH1 | 0 | | — | — | — | | — | — | — |
| CDH13 | 3 | | 1.34 | 0.000 | 0.000 | | 1.18 | 0.119 | 0.000 |
| CDH2 | 0 | | — | — | — | | — | — | — |
| CDH5 | 4 | | 1.28 | 0.001 | 0.000 | | 1.03 | 0.765 | 0.000 |
| CETP | 0 | | — | — | — | | — | — | — |
| CFB | 6 | | 0.65 | 0.000 | 0.000 | | 0.96 | 0.611 | 0.000 |
| CFD | 3 | | 1.62 | 0.000 | 0.000 | | 0.82 | 0.068 | 0.000 |
| CFL1 | 0 | | — | — | — | | — | — | — |
| CFP | 0 | | — | — | — | | — | — | — |
| CHI3L1 | 0 | | — | — | — | | — | — | — |
| CHL1 | 4 | | 1.62 | 0.000 | 0.000 | | 1.55 | 0.000 | 0.000 |
| CKM | 0 | | — | — | — | | — | — | — |
| CLC | 0 | | — | — | — | | — | — | — |
| CLEC3B | 7 | | 1.31 | 0.003 | 0.000 | | 1.28 | 0.031 | 0.000 |
| CLIC1 | 0 | | — | — | — | | — | — | — |
| CLU | 36 | | 1.01 | 0.686 | 0.000 | | 1.66 | 0.000 | 0.000 |
| CNDP1 | 4 | | 1.46 | 0.000 | 0.000 | X | 2.45 | 0.000 | 0.000 |
| CNN2 | 0 | | — | — | — | | — | — | — |
| CNTN1 | 0 | | — | — | — | | — | — | — |
| COL18A1 | 0 | | — | — | — | | — | — | — |
| COL6A1 | 0 | | — | — | — | | — | — | — |
| COL6A3 | 1 | | 1.71 | 0.000 | 0.000 | | 0.84 | 0.326 | 0.000 |
| COLEC10 | 0 | | — | — | — | | — | — | — |
| COLEC11 | 1 | | 1.40 | 0.009 | 0.000 | | 1.56 | 0.007 | 0.000 |
| COMP | 0 | | — | — | — | | — | — | — |
| CORO1A | 0 | | — | — | — | | — | — | — |
| CORO1B | 0 | | — | — | — | | — | — | — |
| COTL1 | 0 | | — | — | — | | — | — | — |
| CP | 12 | | 0.51 | 0.000 | 0.000 | | 0.82 | 0.005 | 0.000 |
| CPB2 | 9 | X | 2.38 | 0.000 | 0.000 | | 1.62 | 0.000 | 0.000 |
| CPN1 | 7 | | 1.78 | 0.000 | 0.000 | | 1.23 | 0.019 | 0.000 |
| CPN2 | 8 | X | 2.61 | 0.000 | 0.000 | | 1.73 | 0.000 | 0.000 |
| CPQ | 0 | | — | — | — | | — | — | — |
| CRP | 1 | X | 3.94 | 0.000 | 0.000 | | 1.00 | 0.997 | 0.000 |
| CRTAC1 | 0 | | — | — | — | | — | — | — |
| CSF1R | 0 | | — | — | — | | — | — | — |
| CST3 | 2 | | 0.94 | 0.625 | 0.000 | X | 0.48 | 0.000 | 0.000 |
| CTBS | 0 | | — | — | — | | — | — | — |
| CTSD | 0 | | — | — | — | | — | — | — |
| DAG1 | 2 | | 0.65 | 0.001 | 0.000 | | 0.86 | 0.398 | 0.000 |
| DBH | 2 | | 2.00 | 0.000 | 0.000 | | 1.32 | 0.146 | 0.000 |
| DPEP2 | 0 | | — | — | — | | — | — | — |
| DPP4 | 0 | | — | — | — | | — | — | — |
| DSG2 | 0 | | — | — | — | | — | — | — |
| ECM1 | 0 | | — | — | — | | — | — | — |
| ENDOD1 | 0 | | — | — | — | | — | — | — |
| ENG | 0 | | — | — | — | | — | — | — |
| ENO1 | 0 | | — | — | — | | — | — | — |
| ENPP2 | 0 | | — | — | — | | — | — | — |
| ERAP1 | 0 | | — | — | — | | — | — | — |
| F10 | 8 | | 1.81 | 0.000 | 0.000 | | 1.16 | 0.033 | 0.000 |
| F11 | 2 | | 1.28 | 0.012 | 0.000 | | 1.11 | 0.433 | 0.000 |
| F12 | 3 | | 1.85 | 0.000 | 0.000 | | 1.46 | 0.008 | 0.000 |
| F13A1 | 0 | | — | — | — | | — | — | — |
| F13B | 1 | | 1.92 | 0.000 | 0.000 | | 1.64 | 0.001 | 0.000 |
| F2 | 5 | | 1.03 | 0.693 | 0.000 | X | 2.59 | 0.000 | 0.000 |
| F5 | 9 | | 1.76 | 0.000 | 0.000 | | 1.58 | 0.000 | 0.000 |
| F7 | 1 | X | 2.08 | 0.000 | 0.000 | X | 2.68 | 0.000 | 0.000 |
| F9 | 5 | X | 2.66 | 0.000 | 0.000 | X | 2.15 | 0.000 | 0.000 |
| FAH | 0 | | — | — | — | | — | — | — |
| FAM3C | 0 | | — | — | — | | — | — | — |
| FBLN1 | 2 | | 1.66 | 0.000 | 0.000 | | 1.22 | 0.100 | 0.000 |
| FBXO33 | 0 | | — | — | — | | — | — | — |
| FCGBP | 0 | | — | — | — | | — | — | — |
| FCGR3A | 1 | X | 2.05 | 0.000 | 0.000 | | 0.71 | 0.054 | 0.000 |

TABLE 2E-continued

| | | Marker Discovery | | | | | | | |
|---|---|---|---|---|---|---|---|---|---|
| | | Active TB vs (Asymptomatic and LTBI) | | | | Active TB vs Extrapulmonary | | | |
| PROTEIN | #PEPTIDES | DE | ANOVA DI | p-value | q-value | DE | ANOVA DI | p-value | q-value |
| FCGR3B | 1 | | 1.00 | 0.953 | 0.019 | | 0.94 | 0.507 | 0.017 |
| FCN2 | 0 | | — | — | — | | — | — | — |
| FCN3 | 2 | X | 2.53 | 0.000 | 0.000 | | 1.93 | 0.000 | 0.000 |
| FETUB | 5 | | 1.27 | 0.001 | 0.000 | | 1.19 | 0.070 | 0.000 |
| FGA | 5 | X | 2.34 | 0.000 | 0.000 | | 0.86 | 0.327 | 0.000 |
| FGB | 0 | | — | — | — | | — | — | — |
| FGFR1 | 0 | | — | — | — | | — | — | — |
| FGG | 0 | | — | — | — | | — | — | — |
| FKBP1A | 1 | X | 2.33 | 0.000 | 0.000 | | 1.36 | 0.106 | 0.000 |
| FLNA | 1 | | 1.79 | 0.000 | 0.000 | | 1.78 | 0.000 | 0.000 |
| FLT4 | 0 | | — | — | — | | — | — | — |
| FN1 | 0 | | — | — | — | | — | — | — |
| FTL | 2 | X | 2.70 | 0.000 | 0.000 | X | 0.39 | 0.000 | 0.000 |
| FUCA1 | 0 | | — | — | — | | — | — | — |
| FUCA2 | 0 | | — | — | — | | — | — | — |
| GALNT2 | 0 | | — | — | — | | — | — | — |
| GAPDH | 0 | | — | — | — | | — | — | — |
| GC | 1 | X | 0.43 | 0.000 | 0.000 | | 1.09 | 0.673 | 0.000 |
| GGH | 1 | X | 3.11 | 0.000 | 0.000 | | 0.95 | 0.776 | 0.000 |
| GK | 0 | | — | — | — | | — | — | — |
| GNPTG | 0 | | — | — | — | | — | — | — |
| GOSR1 | 1 | | 0.94 | 0.703 | 0.000 | | 1.38 | 0.102 | 0.001 |
| GP1BA | 4 | X | 3.17 | 0.000 | 0.000 | | 1.50 | 0.000 | 0.000 |
| GP5 | 0 | | — | — | — | | — | — | — |
| GPLD1 | 6 | X | 2.09 | 0.000 | 0.000 | X | 2.35 | 0.000 | 0.000 |
| GPR126 | 0 | | — | — | — | | — | — | — |
| GPX3 | 5 | | 1.38 | 0.000 | 0.000 | | 0.91 | 0.298 | 0.000 |
| GSN | 36 | | 0.99 | 0.840 | 0.000 | | 1.28 | 0.000 | 0.000 |
| GSTO1 | 0 | | — | — | — | | — | — | — |
| GSTP1 | 1 | | 1.89 | 0.000 | 0.000 | | 1.12 | 0.519 | 0.000 |
| HABP2 | 0 | | — | — | — | | — | — | — |
| HBA1 | 4 | X | 2.27 | 0.000 | 0.000 | | 1.24 | 0.172 | 0.000 |
| HBB | 5 | X | 3.51 | 0.000 | 0.000 | | 1.29 | 0.062 | 0.000 |
| HEG1 | 0 | | — | — | — | | — | — | — |
| HGFAC | 2 | X | 2.14 | 0.000 | 0.000 | X | 2.54 | 0.000 | 0.000 |
| HIST1H4A | 1 | | 1.20 | 0.309 | 0.000 | | 0.51 | 0.003 | 0.000 |
| HP | 10 | | 1.69 | 0.000 | 0.000 | | 0.74 | 0.001 | 0.000 |
| HPR | 1 | X | 2.36 | 0.000 | 0.000 | | 1.41 | 0.100 | 0.000 |
| HPX | 1 | X | 3.48 | 0.000 | 0.000 | | 1.16 | 0.504 | 0.000 |
| HRNR | 0 | | — | — | — | | — | — | — |
| HSP90B1 | 0 | | — | — | — | | — | — | — |
| HSPA5 | 1 | | 1.03 | 0.716 | 0.005 | | 0.89 | 0.311 | 0.005 |
| HSPA8 | 0 | | — | — | — | | — | — | — |
| HSPB1 | 0 | | — | — | — | | — | — | — |
| HSPG2 | 1 | | 1.22 | 0.236 | 0.006 | | 0.98 | 0.911 | 0.008 |
| HYOU1 | 0 | | — | — | — | | — | — | — |
| ICAM1 | 1 | X | 2.16 | 0.000 | 0.000 | | 1.05 | 0.736 | 0.000 |
| ICAM2 | 1 | | 1.70 | 0.000 | 0.000 | | 0.89 | 0.450 | 0.000 |
| ICOSLG | 0 | | — | — | — | | — | — | — |
| IDH1 | 0 | | — | — | — | | — | — | — |
| IGF1 | 0 | | — | — | — | | — | — | — |
| IGF2 | 0 | | — | — | — | | — | — | — |
| IGF2R | 0 | | — | — | — | | — | — | — |
| IGFALS | 15 | | 1.78 | 0.000 | 0.000 | | 1.51 | 0.000 | 0.000 |
| IGFBP1 | 0 | | — | — | — | | — | — | — |
| IGFBP2 | 0 | | — | — | — | | — | — | — |
| IGFBP3 | 3 | | 0.93 | 0.396 | 0.004 | | 1.07 | 0.535 | 0.005 |
| IGFBP4 | 0 | | — | — | — | | — | — | — |
| IGFBP5 | 0 | | — | — | — | | — | — | — |
| IGFBP6 | 0 | | — | — | — | | — | — | — |
| IGFBP7 | 0 | | — | — | — | | — | — | — |
| IGLL5 | 1 | X | 2.93 | 0.000 | 0.000 | | 1.50 | 0.087 | 0.000 |
| IL1R2 | 0 | | — | — | — | | — | — | — |
| IL1RAP | 0 | | — | — | — | | — | — | — |
| IL6ST | 0 | | — | — | — | | — | — | — |
| ISLR | 0 | | — | — | — | | — | — | — |
| ITGB1 | 0 | | — | — | — | | — | — | — |
| ITIH1 | 7 | | 0.57 | 0.000 | 0.000 | | 0.67 | 0.000 | 0.000 |
| ITIH2 | 22 | | 0.56 | 0.000 | 0.000 | | 0.79 | 0.000 | 0.000 |
| ITIH3 | 20 | | 1.08 | 0.039 | 0.000 | | 0.54 | 0.000 | 0.000 |
| ITIH4 | 18 | X | 3.29 | 0.000 | 0.000 | X | 2.48 | 0.000 | 0.000 |
| KIT | 0 | | — | — | — | | — | — | — |
| KLKB1 | 2 | | 0.68 | 0.000 | 0.000 | | 0.95 | 0.687 | 0.000 |
| KNG1 | 7 | | 0.66 | 0.000 | 0.000 | | 1.08 | 0.451 | 0.000 |

TABLE 2E-continued

| | | Marker Discovery | | | | | | | |
|---|---|---|---|---|---|---|---|---|---|
| | | Active TB vs (Asymptomatic and LTBI) | | | | Active TB vs Extrapulmonary | | | |
| PROTEIN | #PEPTIDES | DE | ANOVA DI | p-value | q-value | DE | ANOVA DI | p-value | q-value |
| KRT1 | 2 | X | 2.41 | 0.000 | 0.000 | | 1.40 | 0.073 | 0.000 |
| KRT10 | 2 | X | 2.21 | 0.000 | 0.000 | | 1.14 | 0.432 | 0.000 |
| KRT14 | 0 | | — | — | — | | — | — | — |
| KRT2 | 1 | X | 2.25 | 0.000 | 0.000 | | 1.46 | 0.085 | 0.000 |
| KRT5 | 0 | | — | — | — | | — | — | — |
| KRT9 | 2 | | 1.34 | 0.006 | 0.000 | | 1.13 | 0.386 | 0.000 |
| LAMB1 | 0 | | — | — | — | | — | — | — |
| LAMP1 | 1 | | 0.58 | 0.004 | 0.000 | X | 0.28 | 0.000 | 0.000 |
| LAMP2 | 0 | | — | — | — | | — | — | — |
| LASP1 | 0 | | — | — | — | | — | — | — |
| LBP | 0 | | — | — | — | | — | — | — |
| LCAT | 6 | | 1.74 | 0.000 | 0.000 | | 1.20 | 0.019 | 0.000 |
| LCN2 | 0 | | — | — | — | | — | — | — |
| LCP1 | 2 | | 1.42 | 0.000 | 0.000 | | 0.77 | 0.028 | 0.000 |
| LDHB | 0 | | — | — | — | | — | — | — |
| LGALS3BP | 10 | | 1.87 | 0.000 | 0.000 | | 1.13 | 0.075 | 0.000 |
| LGALSL | 0 | | — | — | — | | — | — | — |
| LILRA1 | 0 | | — | — | — | | — | — | — |
| LILRA3 | 0 | | — | — | — | | — | — | — |
| LPA | 0 | | — | — | — | | — | — | — |
| LRG1 | 31 | X | 2.85 | 0.000 | 0.000 | | 0.81 | 0.000 | 0.000 |
| LRP1 | 0 | | — | — | — | | — | — | — |
| LSAMP | 0 | | — | — | — | | — | — | — |
| LUM | 24 | | 1.92 | 0.000 | 0.000 | | 1.38 | 0.000 | 0.000 |
| LYVE1 | 1 | | 1.91 | 0.000 | 0.000 | | 1.49 | 0.018 | 0.000 |
| LYZ | 0 | | — | — | — | | — | — | — |
| MAN1A1 | 0 | | — | — | — | | — | — | — |
| MAN2A2 | 0 | | — | — | — | | — | — | — |
| MASP1 | 1 | X | 2.12 | 0.000 | 0.000 | | 1.81 | 0.000 | 0.000 |
| MASP2 | 2 | | 1.52 | 0.000 | 0.000 | | 1.33 | 0.005 | 0.000 |
| MB | 0 | | — | — | — | | — | — | — |
| MBL2 | 1 | X | 3.02 | 0.000 | 0.000 | X | 2.60 | 0.000 | 0.000 |
| MCAM | 3 | | 1.08 | 0.335 | 0.000 | | 1.27 | 0.018 | 0.000 |
| MEGF8 | 0 | | — | — | — | | — | — | — |
| MIF | 0 | | — | — | — | | — | — | — |
| MINPP1 | 0 | | — | — | — | | — | — | — |
| MMP2 | 1 | | 1.63 | 0.000 | 0.000 | | 0.95 | 0.749 | 0.000 |
| MMP9 | 0 | | — | — | — | | — | — | — |
| MMRN2 | 0 | | — | — | — | | — | — | — |
| MRPS26 | 0 | | — | — | — | | — | — | — |
| MSN | 0 | | — | — | — | | — | — | — |
| MST1 | 1 | X | 3.01 | 0.000 | 0.000 | X | 2.64 | 0.000 | 0.000 |
| MTPN | 0 | | — | — | — | | — | — | — |
| NAGLU | 0 | | — | — | — | | — | — | — |
| NCAM1 | 0 | | — | — | — | | — | — | — |
| NEO1 | 0 | | — | — | — | | — | — | — |
| NID1 | 0 | | — | — | — | | — | — | — |
| NRGN | 0 | | — | — | — | | — | — | — |
| NRP1 | 1 | X | 2.04 | 0.000 | 0.000 | | 1.10 | 0.517 | 0.000 |
| NUCB1 | 0 | | — | — | — | | — | — | — |
| NUP210L | 0 | | — | — | — | | — | — | — |
| OAF | 0 | | — | — | — | | — | — | — |
| OLFM1 | 0 | | — | — | — | | — | — | — |
| ORM1 | 1 | | 1.55 | 0.007 | 0.000 | | 0.60 | 0.016 | 0.000 |
| ORM2 | 1 | | 1.26 | 0.086 | 0.000 | | 0.85 | 0.367 | 0.000 |
| PAM | 0 | | — | — | — | | — | — | — |
| PCOLCE | 1 | | 1.63 | 0.000 | 0.000 | | 0.78 | 0.127 | 0.000 |
| PCSK9 | 0 | | — | — | — | | — | — | — |
| PDIA3 | 0 | | — | — | — | | — | — | — |
| PDLIM1 | 1 | X | 4.18 | 0.000 | 0.000 | X | 4.55 | 0.000 | 0.000 |
| PEPD | 0 | | — | — | — | | — | — | — |
| PF4 | 0 | | — | — | — | | — | — | — |
| PFN1 | 3 | X | 2.93 | 0.000 | 0.000 | X | 2.19 | 0.000 | 0.000 |
| PGLYRP2 | 4 | | 1.30 | 0.002 | 0.000 | | 1.96 | 0.000 | 0.000 |
| PI16 | 5 | | 1.48 | 0.000 | 0.000 | | 1.68 | 0.000 | 0.000 |
| PIGR | 0 | | — | — | — | | — | — | — |
| PLEK | 0 | | — | — | — | | — | — | — |
| PLS1 | 0 | | — | — | — | | — | — | — |
| PLTP | 0 | | — | — | — | | — | — | — |
| PLXNB1 | 0 | | — | — | — | | — | — | — |
| PODXL | 0 | | — | — | — | | — | — | — |
| PON1 | 10 | | 0.55 | 0.000 | 0.000 | | 0.78 | 0.001 | 0.000 |
| PON3 | 1 | X | 0.29 | 0.000 | 0.000 | | 0.71 | 0.115 | 0.000 |
| POR | 1 | | 1.01 | 0.981 | 0.027 | | 1.17 | 0.634 | 0.021 |

TABLE 2E-continued

| | | Marker Discovery | | | | | | | |
|---|---|---|---|---|---|---|---|---|---|
| | | | Active TB vs (Asymptomatic and LTBI) | | | | Active TB vs Extrapulmonary | | |
| PROTEIN | #PEPTIDES | DE | ANOVA DI | p-value | q-value | DE | ANOVA DI | p-value | q-value |
| POSTN | 1 | | 1.73 | 0.009 | 0.000 | X | 0.45 | 0.003 | 0.000 |
| PPBP | 6 | | 1.77 | 0.000 | 0.000 | | 1.17 | 0.085 | 0.000 |
| PPIA | 2 | X | 2.42 | 0.000 | 0.000 | | 1.57 | 0.004 | 0.000 |
| PPIB | 0 | | — | — | — | | — | — | — |
| PRAP1 | 0 | | — | — | — | | — | — | — |
| PRDX2 | 4 | X | 2.88 | 0.000 | 0.000 | | 0.84 | 0.173 | 0.000 |
| PRDX6 | 1 | X | 2.26 | 0.000 | 0.000 | | 1.38 | 0.104 | 0.000 |
| PRG4 | 1 | | 1.21 | 0.087 | 0.000 | | 0.90 | 0.474 | 0.000 |
| PROC | 4 | | 1.61 | 0.000 | 0.000 | | 1.92 | 0.000 | 0.000 |
| PROCR | 1 | X | 2.27 | 0.000 | 0.000 | | 1.12 | 0.643 | 0.000 |
| PROS1 | 4 | | 1.99 | 0.000 | 0.000 | | 1.47 | 0.000 | 0.000 |
| PROZ | 3 | | 1.85 | 0.000 | 0.000 | | 1.54 | 0.001 | 0.000 |
| PRSS1 | 0 | | — | — | — | | — | — | — |
| PRSS3 | 1 | | 1.95 | 0.000 | 0.000 | | 1.27 | 0.075 | 0.000 |
| PTGDS | 1 | | 1.46 | 0.007 | 0.000 | | 0.66 | 0.021 | 0.000 |
| PTPRG | 0 | | — | — | — | | — | — | — |
| PTPRJ | 1 | | 1.23 | 0.091 | 0.000 | | 0.88 | 0.416 | 0.000 |
| PTPRS | 0 | | — | — | — | | — | — | — |
| PVR | 2 | X | 2.18 | 0.000 | 0.000 | | 1.27 | 0.034 | 0.000 |
| PVRL1 | 0 | | — | — | — | | — | — | — |
| PZP | 5 | | 1.83 | 0.000 | 0.000 | | 1.61 | 0.000 | 0.000 |
| QSOX1 | 2 | X | 3.94 | 0.000 | 0.000 | | 1.55 | 0.006 | 0.000 |
| RBBP8 | 0 | | — | — | — | | — | — | — |
| RNASE1 | 0 | | — | — | — | | — | — | — |
| RTN4RL2 | 0 | | — | — | — | | — | — | — |
| S100A12 | 0 | | — | — | — | | — | — | — |
| S100A8 | 5 | | 1.25 | 0.061 | 0.000 | | 0.94 | 0.687 | 0.000 |
| S100A9 | 8 | X | 3.68 | 0.000 | 0.000 | | 1.37 | 0.002 | 0.000 |
| SAA1 | 1 | X | 3.35 | 0.000 | 0.000 | X | 0.19 | 0.000 | 0.000 |
| SAA4 | 3 | | 0.60 | 0.000 | 0.000 | | 0.65 | 0.009 | 0.000 |
| SDPR | 0 | | — | — | — | | — | — | — |
| SELL | 2 | X | 2.01 | 0.000 | 0.000 | | 1.18 | 0.283 | 0.000 |
| SEMA4B | 0 | | — | — | — | | — | — | — |
| SEPP1 | 3 | | 1.24 | 0.023 | 0.000 | | 1.89 | 0.000 | 0.000 |
| SERPINA1 | 43 | | 1.30 | 0.000 | 0.000 | | 0.91 | 0.029 | 0.000 |
| SERPINA10 | 1 | | 1.70 | 0.000 | 0.000 | | 1.61 | 0.001 | 0.000 |
| SERPINA3 | 3 | | 0.91 | 0.446 | 0.013 | | 0.84 | 0.283 | 0.012 |
| SERPINA4 | 7 | X | 2.13 | 0.000 | 0.000 | X | 2.19 | 0.000 | 0.000 |
| SERPINA6 | 7 | X | 2.24 | 0.000 | 0.000 | | 1.41 | 0.000 | 0.000 |
| SERPINA7 | 17 | X | 2.43 | 0.000 | 0.000 | | 1.56 | 0.000 | 0.000 |
| SERPINB1 | 0 | | — | — | — | | — | — | — |
| SERPINC1 | 2 | | 0.71 | 0.000 | 0.000 | | 1.29 | 0.025 | 0.000 |
| SERPIND1 | 11 | | 1.95 | 0.000 | 0.000 | | 1.51 | 0.000 | 0.000 |
| SERPINF1 | 25 | X | 2.03 | 0.000 | 0.000 | | 1.29 | 0.000 | 0.000 |
| SERPINF2 | 0 | | — | — | — | | — | — | — |
| SERPING1 | 3 | X | 3.02 | 0.000 | 0.000 | X | 2.19 | 0.000 | 0.000 |
| SH3BGRL | 0 | | — | — | — | | — | — | — |
| SH3BGRL3 | 3 | X | 2.52 | 0.000 | 0.000 | | 1.73 | 0.000 | 0.000 |
| SHBG | 2 | | 1.73 | 0.000 | 0.000 | X | 2.15 | 0.000 | 0.000 |
| SLC3A2 | 0 | | — | — | — | | — | — | — |
| SNCA | 0 | | — | — | — | | — | — | — |
| SNED1 | 0 | | — | — | — | | — | — | — |
| SOD3 | 1 | | 1.49 | 0.003 | 0.000 | | 1.15 | 0.412 | 0.000 |
| SORL1 | 0 | | — | — | — | | — | — | — |
| SOWAHC | 1 | | 1.88 | 0.017 | 0.000 | X | 3.45 | 0.000 | 0.000 |
| SPARC | 3 | | 1.78 | 0.000 | 0.000 | | 0.67 | 0.000 | 0.000 |
| SPARCL1 | 0 | | — | — | — | | — | — | — |
| SPP2 | 0 | | — | — | — | | — | — | — |
| SRGN | 0 | | — | — | — | | — | — | — |
| SSC5D | 0 | | — | — | — | | — | — | — |
| STXBP3 | 0 | | — | — | — | | — | — | — |
| TAGLN2 | 1 | X | 2.58 | 0.000 | 0.000 | X | 3.31 | 0.000 | 0.000 |
| TF | 0 | | — | — | — | | — | — | — |
| TGFBI | 6 | | 1.99 | 0.000 | 0.000 | | 0.86 | 0.065 | 0.000 |
| THBS1 | 7 | | 1.62 | 0.000 | 0.000 | | 1.88 | 0.000 | 0.000 |
| TIMP1 | 0 | | — | — | — | | — | — | — |
| TKT | 1 | | 0.66 | 0.001 | 0.000 | | 1.09 | 0.592 | 0.000 |
| TLN1 | 0 | | — | — | — | | — | — | — |
| TMSB4X | 1 | | 1.33 | 0.000 | 0.000 | | 1.14 | 0.202 | 0.000 |
| TNC | 2 | X | 2.08 | 0.000 | 0.000 | | 0.68 | 0.003 | 0.000 |
| TNXB | 7 | | 1.05 | 0.482 | 0.001 | | 1.19 | 0.040 | 0.001 |
| TPI1 | 1 | X | 2.14 | 0.000 | 0.000 | | 0.78 | 0.210 | 0.000 |
| TPM3 | 0 | | — | — | — | | — | — | — |
| TPM4 | 0 | | — | — | — | | — | — | — |

TABLE 2E-continued

Marker Discovery

| | | Active TB vs (Asymptomatic and LTBI) | | | | Active TB vs Extrapulmonary | | | |
|---|---|---|---|---|---|---|---|---|---|
| PROTEIN | #PEPTIDES | DE | ANOVA DI | p-value | q-value | DE | ANOVA DI | p-value | q-value |
| TREML1 | 0 | | — | — | — | | — | — | — |
| TTR | 19 | X | 0.46 | 0.000 | 0.000 | | 1.04 | 0.495 | 0.000 |
| TUBA4A | 0 | | — | — | — | | — | — | — |
| UMOD | 1 | | 0.78 | 0.029 | 0.000 | | 1.01 | 0.944 | 0.000 |
| VASN | 5 | X | 2.27 | 0.000 | 0.000 | | 1.28 | 0.003 | 0.000 |
| VASP | 0 | | — | — | — | | — | — | — |
| VCAM1 | 1 | X | 3.37 | 0.000 | 0.000 | | 1.57 | 0.071 | 0.000 |
| VCL | 1 | X | 2.05 | 0.000 | 0.000 | X | 2.09 | 0.000 | 0.000 |
| VIM | 0 | | — | — | — | | — | — | — |
| VNN1 | 0 | | — | — | — | | — | — | — |
| VTN | 0 | | — | — | — | | — | — | — |
| VWF | 8 | X | 2.58 | 0.000 | 0.000 | X | 2.26 | 0.000 | 0.000 |
| YWHAE | 0 | | — | — | — | | — | — | — |
| YWHAG | 0 | | — | — | — | | — | — | — |
| YWHAZ | 0 | | — | — | — | | — | — | — |
| ZYX | 0 | | — | — | — | | — | — | — |

*Differential expression (DE) thresholds: p-value < 0.05 | q-value < 0.05 | ANOVA DI > 2

Example II. Biomarker Identification

As described in Example 1, plasma samples from subjects with active TB were compared to samples from subjects with latent TB or healthy controls, and proteins that were significantly differentially expressed in a condition-specific manner were identified (Table 1). A subset of these proteins was selected to include in a multiplex MRM assay. A second, independent set of samples was then analyzed with the MRM assay. The second set included samples from subjects with active TB, latent TB, healthy controls, as well as from subjects that had other respiratory diseases of similar clinical presentation as TB. This sample set also included subjects belonging to the 4 clinical groups indicated but which also had an HIV co-infection.

The data collected from the second set of clinical samples was used to define combinations of up to 4 biomarker proteins able to distinguish active TB from the other clinical groups, with and without HIV co-infection (see, e.g., Tables 3 and 4).

In order to confirm the utility of these markers and combinations of markers, additional statistical analyses were performed to characterize individual biomarkers and combinations of biomarkers (up to 4 candidates) that can be used to distinguish active TB from latent TB and other respiratory diseases in the presence or absence of HIV infection.

The statistical analysis was initiated using all of the candidate biomarkers in Table 1. The method split the data into five test sets, each with a proportion of Active TB samples to other respiratory disease samples as close as possible to that of the full data set. For each test set, four fifths of the data were defined to be that test set's corresponding training set. Each training set was again split at random by stratified sampling into two halves. One half was used to fit a logistic regression model, which was then used to calculate out-of-sample predictive scores for the other half. This random half-and-half split procedure was repeated a number of times equal to three times the sample size of the training set; out-of-sample predictive scores and the corresponding true outcomes were aggregated over all random splits and AUCs were estimated from these. Since there are five training sets, five such AUC estimates were generated for each panel, which were then averaged. Panel selection was carried out by examining various summaries of protein performance and also direct examination of the panels with the best AUC estimates. To compute the final AUC estimates of the selected panels, each test set was scored by a logistic regression model fit to the corresponding training set; the resulting out-of-sample predictive scores and true outcomes aggregated over all five test sets, forming the final set from which AUCs were estimated. This nested cross-validation approach reduced the risk of data overfitting, averaged out sampling artifacts, and provided independent performance testing.

The candidate biomarkers were then ranked by their ability to distinguish active TB from the other respiratory diseases individually and in combinations of up to 4 candidates, by the change in relative rank when the candidate biomarkers were used in panels, and by the frequency with which each biomarker appeared in the best performing panels. The HIV+ and HIV− groups were analyzed separately. Analysis of the ranking identified the best performing biomarkers for the HIV− (Tables 5-8) and HIV+ groups (Tables 9-12) which were able to accurately distinguish active TB from other respiratory diseases.

The performance of the individual biomarker candidates ranged between 0.428 to 0.804 AUC for the HIV− groups, and 0.625 to 0.770 AUC for the HIV+ groups (Tables 5 and 9).

Combining the biomarker candidates into panels was a more effective strategy to derive high performing discriminators (Tables 6-8 and 10-12). One of the 45 combinations of two candidate biomarker proteins (2%) assayed were able to improve the performance in the HIV− groups, but none of the combinations of two proteins assayed were able to improve the performance in the HIV+ groups. Sixteen of the 120 combinations of three candidate biomarker proteins (13%) assayed were able to improve the performance in the HIV− groups, and 8 of the 56 (14%) of the candidates assayed did the same in the HIV+ groups. Eighty-four of the 210 combinations of four candidate biomarker proteins (40%) assayed were able to improve the performance in the HIV− groups, and 37 of the 70 (53%) of the candidates assayed did the same in the HIV+ groups.

These results indicated it was possible to derive high performing panels from combinations of three or four candidates.

TABLE 5

HIV− panels
Individual Candidate Biomarkers

| | |
|---|---|
| COMP | 0.804 |
| TNXB | 0.795 |
| LUM | 0.794 |
| CD14 | 0.756 |
| SEPP1 | 0.721 |
| QSOX1 | 0.716 |
| APOC1 | 0.701 |
| PEPD | 0.673 |
| APOE | 0.629 |
| SELL | 0.596 |
| MASP1 | 0.475 |
| HIST2H2BE | 0.447 |
| GP1BA | 0.428 |

TABLE 6

HIV− panels
Combination of Two Candidate Biomarkers

| protein.1 | protein.2 | AUC |
|---|---|---|
| PEPD | SELL | 0.847 |
| SELL | SEPP1 | 0.825 |
| QSOX1 | SELL | 0.825 |
| COMP | SELL | 0.823 |
| CD14 | LUM | 0.822 |
| APOC1 | CD14 | 0.820 |
| CD14 | PEPD | 0.818 |
| CD14 | SEPP1 | 0.816 |
| APOE | CD14 | 0.816 |
| SELL | TNXB | 0.813 |
| CD14 | GP1BA | 0.810 |
| APOC1 | COMP | 0.809 |
| CD14 | TNXB | 0.808 |
| CD14 | QSOX1 | 0.803 |
| CD14 | COMP | 0.802 |
| LUM | SELL | 0.796 |
| APOE | COMP | 0.789 |
| COMP | TNXB | 0.788 |
| COMP | SEPP1 | 0.782 |
| LUM | TNXB | 0.778 |
| LUM | SEPP1 | 0.775 |
| APOC1 | LUM | 0.772 |
| COMP | HIST2H2BE | 0.769 |
| CD14 | MASP1 | 0.768 |
| APOE | LUM | 0.765 |
| LUM | PEPD | 0.761 |
| COMP | QSOX1 | 0.761 |
| LUM | QSOX1 | 0.761 |
| COMP | MASP1 | 0.760 |
| COMP | PEPD | 0.759 |
| COMP | LUM | 0.754 |
| HIST2H2BE | LUM | 0.753 |
| COMP | GP1BA | 0.750 |
| QSOX1 | TNXB | 0.748 |
| LUM | MASP1 | 0.742 |
| APOC1 | TNXB | 0.742 |
| MASP1 | TNXB | 0.740 |
| PEPD | TNXB | 0.739 |
| GP1BA | LUM | 0.738 |
| SEPP1 | TNXB | 0.738 |
| GP1BA | TNXB | 0.738 |
| HIST2H2BE | TNXB | 0.737 |
| APOE | TNXB | 0.735 |
| APOC1 | QSOX1 | 0.731 |
| APOC1 | SELL | 0.729 |
| CD14 | HIST2H2BE | 0.722 |
| CD14 | SELL | 0.720 |
| QSOX1 | SEPP1 | 0.717 |
| MASP1 | SEPP1 | 0.717 |
| MASP1 | SELL | 0.702 |
| GP1BA | SEPP1 | 0.688 |
| APOC1 | PEPD | 0.687 |
| APOE | QSOX1 | 0.684 |

TABLE 6-continued

HIV− panels
Combination of Two Candidate Biomarkers

| protein.1 | protein.2 | AUC |
|---|---|---|
| PEPD | SEPP1 | 0.679 |
| APOC1 | SEPP1 | 0.679 |
| HIST2H2BE | SEPP1 | 0.675 |
| APOE | SELL | 0.670 |
| APOE | SEPP1 | 0.669 |
| PEPD | QSOX1 | 0.668 |
| APOC1 | APOE | 0.662 |
| HIST2H2BE | QSOX1 | 0.658 |
| MASP1 | QSOX1 | 0.656 |
| GP1BA | QSOX1 | 0.655 |
| GP1BA | PEPD | 0.647 |
| APOC1 | GP1BA | 0.646 |
| APOC1 | MASP1 | 0.641 |
| APOC1 | HIST2H2BE | 0.633 |
| APOE | PEPD | 0.627 |
| MASP1 | PEPD | 0.624 |
| HIST2H2BE | PEPD | 0.612 |
| APOE | MASP1 | 0.573 |
| APOE | HIST2H2BE | 0.573 |
| GP1BA | SELL | 0.566 |
| APOE | GP1BA | 0.563 |
| HIST2H2BE | SELL | 0.554 |
| HIST2H2BE | MASP1 | 0.453 |
| GP1BA | MASP1 | 0.445 |
| GP1BA | HIST2H2BE | 0.434 |

TABLE 7

HIV− panels
Combination of Three Candidate Biomarkers

| protein.1 | protein.2 | protein.3 | AUC |
|---|---|---|---|
| PEPD | SELL | TNXB | 0.999 |
| COMP | PEPD | SELL | 0.999 |
| PEPD | QSOX1 | SELL | 0.966 |
| CD14 | PEPD | SELL | 0.956 |
| PEPD | SELL | SEPP1 | 0.946 |
| LUM | PEPD | SELL | 0.931 |
| SELL | SEPP1 | TNXB | 0.912 |
| APOC1 | QSOX1 | SELL | 0.906 |
| CD14 | HIST2H2BE | SEPP1 | 0.902 |
| QSOX1 | SELL | TNXB | 0.901 |
| COMP | SELL | SEPP1 | 0.901 |
| LUM | SELL | SEPP1 | 0.896 |
| QSOX1 | SELL | SEPP1 | 0.891 |
| APOE | CD14 | GP1BA | 0.876 |
| APOC1 | CD14 | PEPD | 0.870 |
| CD14 | HIST2H2BE | LUM | 0.863 |
| MASP1 | QSOX1 | SELL | 0.860 |
| APOC1 | COMP | SELL | 0.854 |
| APOC1 | CD14 | QSOX1 | 0.853 |
| COMP | MASP1 | SELL | 0.850 |
| CD14 | HIST2H2BE | PEPD | 0.849 |
| APOC1 | PEPD | SELL | 0.848 |
| APOC1 | CD14 | COMP | 0.842 |
| MASP1 | PEPD | SELL | 0.841 |
| APOC1 | LUM | SELL | 0.841 |
| COMP | SELL | TNXB | 0.840 |
| APOC1 | CD14 | GP1BA | 0.839 |
| CD14 | GP1BA | TNXB | 0.838 |
| CD14 | GP1BA | SEPP1 | 0.837 |
| COMP | QSOX1 | SELL | 0.837 |
| GP1BA | PEPD | SELL | 0.834 |
| APOC1 | CD14 | LUM | 0.833 |
| APOC1 | APOE | CD14 | 0.831 |
| CD14 | COMP | GP1BA | 0.829 |
| CD14 | GP1BA | LUM | 0.829 |
| APOE | CD14 | PEPD | 0.829 |
| CD14 | SELL | TNXB | 0.827 |
| CD14 | GP1BA | QSOX1 | 0.823 |
| CD14 | LUM | TNXB | 0.823 |

TABLE 7-continued

HIV− panels
Combination of Three Candidate Biomarkers

| protein.1 | protein.2 | protein.3 | AUC |
|---|---|---|---|
| APOE | COMP | SELL | 0.823 |
| COMP | GP1BA | SELL | 0.822 |
| MASP1 | SELL | TNXB | 0.822 |
| APOE | SELL | TNXB | 0.822 |
| APOC1 | CD14 | TNXB | 0.821 |
| APOE | SELL | SEPP1 | 0.820 |
| CD14 | SELL | SEPP1 | 0.819 |
| CD14 | LUM | SEPP1 | 0.818 |
| APOE | CD14 | LUM | 0.818 |
| HIST2H2BE | PEPD | SELL | 0.817 |
| APOE | CD14 | TNXB | 0.817 |
| LUM | QSOX1 | SELL | 0.813 |
| APOC1 | CD14 | HIST2H2BE | 0.812 |
| APOE | QSOX1 | SELL | 0.809 |
| COMP | HIST2H2BE | SELL | 0.807 |
| APOE | PEPD | SELL | 0.807 |
| CD14 | HIST2H2BE | TNXB | 0.804 |
| CD14 | COMP | HIST2H2BE | 0.803 |
| APOE | CD14 | MASP1 | 0.803 |
| CD14 | GP1BA | PEPD | 0.803 |
| CD14 | COMP | TNXB | 0.803 |
| LUM | SELL | TNXB | 0.802 |
| GP1BA | QSOX1 | SELL | 0.800 |
| CD14 | PEPD | TNXB | 0.800 |
| CD14 | LUM | PEPD | 0.800 |
| CD14 | QSOX1 | SELL | 0.799 |
| CD14 | SEPP1 | TNXB | 0.797 |
| APOE | CD14 | COMP | 0.797 |
| CD14 | QSOX1 | TNXB | 0.796 |
| APOC1 | SELL | TNXB | 0.795 |
| APOE | CD14 | QSOX1 | 0.794 |
| CD14 | COMP | SELL | 0.793 |
| CD14 | PEPD | SEPP1 | 0.792 |
| CD14 | LUM | SELL | 0.792 |
| APOE | CD14 | SELL | 0.792 |
| APOC1 | CD14 | SEPP1 | 0.791 |
| HIST2H2BE | SELL | SEPP1 | 0.791 |
| APOE | CD14 | HIST2H2BE | 0.791 |
| CD14 | QSOX1 | SEPP1 | 0.790 |
| MASP1 | SELL | SEPP1 | 0.790 |
| CD14 | LUM | MASP1 | 0.789 |
| GP1BA | SELL | SEPP1 | 0.788 |
| HIST2H2BE | SELL | TNXB | 0.787 |
| CD14 | COMP | SEPP1 | 0.786 |
| APOC1 | SELL | SEPP1 | 0.786 |
| CD14 | MASP1 | SELL | 0.785 |
| GP1BA | SELL | TNXB | 0.784 |
| CD14 | GP1BA | MASP1 | 0.784 |
| APOE | CD14 | SEPP1 | 0.784 |
| HIST2H2BE | QSOX1 | SELL | 0.783 |
| CD14 | GP1BA | SELL | 0.783 |
| APOC1 | CD14 | SELL | 0.782 |
| APOC1 | CD14 | MASP1 | 0.780 |
| CD14 | LUM | QSOX1 | 0.778 |
| CD14 | HIST2H2BE | QSOX1 | 0.778 |
| APOE | LUM | SELL | 0.776 |
| COMP | LUM | SELL | 0.776 |
| GP1BA | LUM | SELL | 0.773 |
| CD14 | MASP1 | TNXB | 0.773 |
| CD14 | COMP | PEPD | 0.772 |
| APOC1 | COMP | MASP1 | 0.770 |
| LUM | MASP1 | SELL | 0.770 |
| CD14 | PEPD | QSOX1 | 0.769 |
| CD14 | COMP | MASP1 | 0.768 |
| CD14 | COMP | LUM | 0.767 |
| CD14 | MASP1 | QSOX1 | 0.766 |
| CD14 | MASP1 | SEPP1 | 0.764 |
| APOC1 | COMP | PEPD | 0.763 |
| APOC1 | COMP | TNXB | 0.762 |
| CD14 | GP1BA | HIST2H2BE | 0.761 |
| HIST2H2BE | LUM | SELL | 0.761 |
| APOC1 | APOE | COMP | 0.759 |
| CD14 | MASP1 | PEPD | 0.757 |
| APOC1 | COMP | QSOX1 | 0.756 |
| APOC1 | COMP | SEPP1 | 0.755 |
| APOC1 | COMP | GP1BA | 0.754 |
| APOE | COMP | MASP1 | 0.754 |
| APOC1 | COMP | HIST2H2BE | 0.752 |
| APOC1 | COMP | LUM | 0.752 |
| COMP | MASP1 | TNXB | 0.752 |
| COMP | HIST2H2BE | TNXB | 0.750 |
| CD14 | COMP | QSOX1 | 0.749 |
| COMP | PEPD | TNXB | 0.746 |
| APOE | COMP | TNXB | 0.745 |
| LUM | MASP1 | TNXB | 0.744 |
| CD14 | HIST2H2BE | MASP1 | 0.744 |
| COMP | SEPP1 | TNXB | 0.743 |
| COMP | GP1BA | TNXB | 0.743 |
| HIST2H2BE | LUM | TNXB | 0.742 |
| COMP | MASP1 | SEPP1 | 0.740 |
| LUM | MASP1 | SEPP1 | 0.740 |
| LUM | SEPP1 | TNXB | 0.740 |
| APOE | COMP | GP1BA | 0.738 |
| COMP | QSOX1 | SEPP1 | 0.737 |
| LUM | QSOX1 | TNXB | 0.737 |
| APOE | COMP | PEPD | 0.736 |
| COMP | QSOX1 | TNXB | 0.736 |
| COMP | LUM | TNXB | 0.736 |
| COMP | HIST2H2BE | SEPP1 | 0.736 |
| APOE | COMP | SEPP1 | 0.736 |
| GP1BA | LUM | TNXB | 0.736 |
| APOC1 | LUM | QSOX1 | 0.736 |
| APOE | LUM | TNXB | 0.735 |
| LUM | PEPD | TNXB | 0.735 |
| APOC1 | LUM | TNXB | 0.734 |
| APOC1 | LUM | PEPD | 0.733 |
| LUM | QSOX1 | SEPP1 | 0.733 |
| COMP | GP1BA | SEPP1 | 0.730 |
| APOE | COMP | HIST2H2BE | 0.730 |
| COMP | LUM | SEPP1 | 0.729 |
| APOC1 | HIST2H2BE | LUM | 0.728 |
| APOE | COMP | QSOX1 | 0.728 |
| COMP | PEPD | SEPP1 | 0.728 |
| HIST2H2BE | LUM | SEPP1 | 0.728 |
| APOE | COMP | LUM | 0.727 |
| COMP | HIST2H2BE | MASP1 | 0.727 |
| APOC1 | LUM | MASP1 | 0.726 |
| LUM | PEPD | SEPP1 | 0.726 |
| APOE | LUM | PEPD | 0.725 |
| COMP | HIST2H2BE | PEPD | 0.725 |
| APOE | LUM | QSOX1 | 0.725 |
| APOE | LUM | SEPP1 | 0.724 |
| MASP1 | SEPP1 | TNXB | 0.724 |
| APOE | LUM | MASP1 | 0.724 |
| COMP | HIST2H2BE | LUM | 0.724 |
| APOE | GP1BA | LUM | 0.724 |
| COMP | HIST2H2BE | QSOX1 | 0.723 |
| APOC1 | LUM | SEPP1 | 0.723 |
| APOC1 | GP1BA | LUM | 0.723 |
| APOC1 | APOE | LUM | 0.721 |
| GP1BA | LUM | SEPP1 | 0.720 |
| COMP | GP1BA | HIST2H2BE | 0.718 |
| APOE | HIST2H2BE | LUM | 0.718 |
| COMP | MASP1 | QSOX1 | 0.717 |
| COMP | GP1BA | PEPD | 0.714 |
| APOC1 | MASP1 | QSOX1 | 0.714 |
| COMP | LUM | PEPD | 0.714 |
| APOC1 | MASP1 | SELL | 0.714 |
| HIST2H2BE | LUM | QSOX1 | 0.714 |
| COMP | LUM | MASP1 | 0.713 |
| COMP | GP1BA | MASP1 | 0.713 |
| HIST2H2BE | LUM | PEPD | 0.712 |
| GP1BA | LUM | PEPD | 0.712 |
| LUM | MASP1 | PEPD | 0.711 |
| COMP | LUM | QSOX1 | 0.711 |
| APOC1 | QSOX1 | TNXB | 0.711 |
| LUM | PEPD | QSOX1 | 0.711 |
| COMP | GP1BA | LUM | 0.710 |
| LUM | MASP1 | QSOX1 | 0.710 |
| MASP1 | QSOX1 | TNXB | 0.709 |

TABLE 7-continued

HIV- panels
Combination of Three Candidate Biomarkers

| protein.1 | protein.2 | protein.3 | AUC |
|---|---|---|---|
| APOC1 | APOE | SELL | 0.709 |
| COMP | MASP1 | PEPD | 0.709 |
| MASP1 | QSOX1 | SEPP1 | 0.708 |
| GP1BA | LUM | QSOX1 | 0.707 |
| QSOX1 | SEPP1 | TNXB | 0.706 |
| GP1BA | PEPD | TNXB | 0.706 |
| MASP1 | PEPD | TNXB | 0.706 |
| GP1BA | QSOX1 | TNXB | 0.706 |
| GP1BA | HIST2H2BE | LUM | 0.703 |
| APOC1 | MASP1 | TNXB | 0.703 |
| COMP | PEPD | QSOX1 | 0.702 |
| HIST2H2BE | QSOX1 | TNXB | 0.701 |
| APOC1 | PEPD | TNXB | 0.701 |
| COMP | GP1BA | QSOX1 | 0.701 |
| APOC1 | GP1BA | TNXB | 0.700 |
| GP1BA | SEPP1 | TNXB | 0.700 |
| PEPD | QSOX1 | TNXB | 0.699 |
| APOE | QSOX1 | TNXB | 0.698 |
| HIST2H2BE | SEPP1 | TNXB | 0.697 |
| APOE | GP1BA | TNXB | 0.697 |
| APOE | MASP1 | SELL | 0.696 |
| HIST2H2BE | LUM | MASP1 | 0.694 |
| APOE | MASP1 | TNXB | 0.694 |
| APOC1 | HIST2H2BE | TNXB | 0.693 |
| PEPD | SEPP1 | TNXB | 0.690 |
| GP1BA | LUM | MASP1 | 0.690 |
| GP1BA | HIST2H2BE | TNXB | 0.689 |
| APOC1 | GP1BA | QSOX1 | 0.688 |
| HIST2H2BE | PEPD | TNXB | 0.688 |
| APOC1 | APOE | TNXB | 0.687 |
| APOE | PEPD | TNXB | 0.687 |
| HIST2H2BE | MASP1 | TNXB | 0.686 |
| APOC1 | APOE | QSOX1 | 0.686 |
| APOC1 | HIST2H2BE | QSOX1 | 0.684 |
| APOC1 | QSOX1 | SEPP1 | 0.683 |
| APOE | HIST2H2BE | TNXB | 0.683 |
| APOC1 | HIST2H2BE | SELL | 0.683 |
| APOC1 | SEPP1 | TNXB | 0.682 |
| APOE | SEPP1 | TNXB | 0.681 |
| MASP1 | PEPD | SEPP1 | 0.681 |
| APOC1 | PEPD | QSOX1 | 0.679 |
| APOC1 | MASP1 | SEPP1 | 0.678 |
| GP1BA | MASP1 | TNXB | 0.676 |
| APOC1 | GP1BA | SELL | 0.676 |
| GP1BA | QSOX1 | SEPP1 | 0.676 |
| GP1BA | MASP1 | SEPP1 | 0.674 |
| CD14 | HIST2H2BE | SELL | 0.674 |
| APOC1 | GP1BA | PEPD | 0.672 |
| HIST2H2BE | QSOX1 | SEPP1 | 0.672 |
| HIST2H2BE | MASP1 | SEPP1 | 0.672 |
| GP1BA | PEPD | SEPP1 | 0.668 |
| HIST2H2BE | MASP1 | SELL | 0.666 |
| APOE | MASP1 | SEPP1 | 0.660 |
| PEPD | QSOX1 | SEPP1 | 0.659 |
| APOE | QSOX1 | SEPP1 | 0.657 |
| APOC1 | MASP1 | PEPD | 0.657 |
| GP1BA | MASP1 | SELL | 0.657 |
| APOC1 | PEPD | SEPP1 | 0.649 |
| APOC1 | GP1BA | SEPP1 | 0.649 |
| APOE | HIST2H2BE | SELL | 0.647 |
| GP1BA | HIST2H2BE | SEPP1 | 0.647 |
| APOE | MASP1 | QSOX1 | 0.643 |
| HIST2H2BE | PEPD | SEPP1 | 0.636 |
| APOE | GP1BA | SEPP1 | 0.636 |
| GP1BA | PEPD | QSOX1 | 0.636 |
| APOC1 | HIST2H2BE | SEPP1 | 0.636 |
| APOE | HIST2H2BE | QSOX1 | 0.635 |
| APOE | GP1BA | QSOX1 | 0.635 |
| APOE | PEPD | QSOX1 | 0.633 |
| APOC1 | APOE | PEPD | 0.632 |
| APOC1 | HIST2H2BE | PEPD | 0.629 |
| MASP1 | PEPD | QSOX1 | 0.629 |
| APOC1 | APOE | SEPP1 | 0.628 |
| APOC1 | APOE | MASP1 | 0.624 |
| APOC1 | APOE | GP1BA | 0.624 |
| APOE | HIST2H2BE | SEPP1 | 0.623 |
| HIST2H2BE | PEPD | QSOX1 | 0.622 |
| APOE | GP1BA | SELL | 0.621 |
| GP1BA | MASP1 | PEPD | 0.620 |
| APOE | GP1BA | PEPD | 0.620 |
| GP1BA | MASP1 | QSOX1 | 0.617 |
| APOE | PEPD | SEPP1 | 0.616 |
| GP1BA | HIST2H2BE | QSOX1 | 0.613 |
| HIST2H2BE | MASP1 | QSOX1 | 0.609 |
| GP1BA | HIST2H2BE | PEPD | 0.606 |
| APOC1 | APOE | HIST2H2BE | 0.605 |
| APOE | MASP1 | PEPD | 0.600 |
| APOC1 | GP1BA | HIST2H2BE | 0.598 |
| APOC1 | GP1BA | MASP1 | 0.587 |
| APOC1 | HIST2H2BE | MASP1 | 0.587 |
| HIST2H2BE | MASP1 | PEPD | 0.578 |
| APOE | HIST2H2BE | PEPD | 0.576 |
| GP1BA | HIST2H2BE | SELL | 0.573 |
| APOE | HIST2H2BE | MASP1 | 0.536 |
| APOE | GP1BA | HIST2H2BE | 0.534 |
| APOE | GP1BA | MASP1 | 0.527 |
| GP1BA | HIST2H2BE | MASP1 | 0.435 |

TABLE 8

HIV- panels
Combination of Four Candidate Biomarkers

| protein.1 | protein.2 | protein.3 | protein.4 | AUC |
|---|---|---|---|---|
| MASP1 | PEPD | QSOX1 | SELL | 1.000 |
| GP1BA | PEPD | SELL | TNXB | 1.000 |
| COMP | PEPD | SELL | TNXB | 1.000 |
| COMP | PEPD | QSOX1 | SELL | 1.000 |
| COMP | LUM | PEPD | SELL | 1.000 |
| COMP | HIST2H2BE | PEPD | SELL | 1.000 |
| CD14 | PEPD | SELL | TNXB | 1.000 |
| CD14 | PEPD | SELL | SEPP1 | 1.000 |
| CD14 | PEPD | QSOX1 | SELL | 1.000 |
| CD14 | HIST2H2BE | PEPD | SELL | 1.000 |
| APOE | COMP | PEPD | SELL | 1.000 |
| COMP | GP1BA | PEPD | SELL | 1.000 |
| APOC1 | COMP | PEPD | SELL | 1.000 |
| LUM | PEPD | SELL | TNXB | 1.000 |
| HIST2H2BE | LUM | PEPD | SELL | 1.000 |
| COMP | MASP1 | PEPD | SELL | 1.000 |
| APOC1 | CD14 | PEPD | SELL | 1.000 |
| APOC1 | CD14 | HIST2H2BE | LUM | 1.000 |
| COMP | PEPD | SELL | SEPP1 | 1.000 |
| PEPD | QSOX1 | SELL | TNXB | 1.000 |
| APOE | LUM | PEPD | SELL | 1.000 |
| CD14 | MASP1 | PEPD | SELL | 1.000 |
| LUM | PEPD | SELL | SEPP1 | 1.000 |
| CD14 | COMP | PEPD | SELL | 1.000 |
| PEPD | SELL | SEPP1 | TNXB | 1.000 |
| CD14 | HIST2H2BE | SEPP1 | TNXB | 1.000 |
| CD14 | GP1BA | PEPD | SELL | 1.000 |
| MASP1 | PEPD | SELL | TNXB | 1.000 |
| APOC1 | PEPD | SELL | TNXB | 0.999 |
| APOC1 | APOE | CD14 | GP1BA | 0.999 |
| PEPD | QSOX1 | SELL | SEPP1 | 0.999 |
| CD14 | LUM | PEPD | SELL | 0.999 |
| LUM | PEPD | QSOX1 | SELL | 0.999 |
| APOC1 | MASP1 | QSOX1 | SELL | 0.999 |
| APOE | PEPD | QSOX1 | SELL | 0.999 |
| MASP1 | PEPD | SELL | SEPP1 | 0.999 |
| APOC1 | COMP | SELL | SEPP1 | 0.999 |
| CD14 | GP1BA | HIST2H2BE | SEPP1 | 0.999 |
| CD14 | HIST2H2BE | PEPD | TNXB | 0.998 |
| HIST2H2BE | PEPD | SELL | TNXB | 0.998 |
| APOC1 | CD14 | COMP | HIST2H2BE | 0.998 |
| GP1BA | PEPD | QSOX1 | SELL | 0.998 |

TABLE 8-continued

HIV- panels
Combination of Four Candidate Biomarkers

| protein.1 | protein.2 | protein.3 | protein.4 | AUC |
|---|---|---|---|---|
| APOC1 | CD14 | HIST2H2BE | SEPP1 | 0.998 |
| APOE | PEPD | SELL | TNXB | 0.997 |
| COMP | HIST2H2BE | SELL | SEPP1 | 0.997 |
| APOC1 | LUM | PEPD | SELL | 0.996 |
| LUM | MASP1 | PEPD | SELL | 0.995 |
| APOC1 | PEPD | QSOX1 | SELL | 0.981 |
| MASP1 | QSOX1 | SELL | TNXB | 0.981 |
| APOC1 | PEPD | SELL | SEPP1 | 0.980 |
| APOC1 | COMP | MASP1 | SELL | 0.979 |
| APOC1 | COMP | QSOX1 | SELL | 0.977 |
| APOC1 | CD14 | QSOX1 | SELL | 0.976 |
| APOC1 | QSOX1 | SELL | SEPP1 | 0.976 |
| MASP1 | QSOX1 | SELL | SEPP1 | 0.969 |
| APOE | CD14 | PEPD | SELL | 0.967 |
| HIST2H2BE | PEPD | QSOX1 | SELL | 0.964 |
| CD14 | MASP1 | QSOX1 | SELL | 0.963 |
| APOC1 | LUM | QSOX1 | SELL | 0.961 |
| CD14 | HIST2H2BE | LUM | SEPP1 | 0.960 |
| CD14 | HIST2H2BE | PEPD | SEPP1 | 0.956 |
| CD14 | GP1BA | QSOX1 | SELL | 0.956 |
| APOE | CD14 | GP1BA | LUM | 0.956 |
| GP1BA | LUM | PEPD | SELL | 0.955 |
| APOE | CD14 | GP1BA | SEPP1 | 0.951 |
| APOE | COMP | SELL | SEPP1 | 0.950 |
| APOC1 | QSOX1 | SELL | TNXB | 0.949 |
| APOE | SELL | SEPP1 | TNXB | 0.946 |
| HIST2H2BE | PEPD | SELL | SEPP1 | 0.946 |
| HIST2H2BE | SELL | SEPP1 | TNXB | 0.945 |
| GP1BA | PEPD | SELL | SEPP1 | 0.944 |
| APOE | PEPD | SELL | SEPP1 | 0.942 |
| APOE | CD14 | HIST2H2BE | TNXB | 0.942 |
| HIST2H2BE | QSOX1 | SELL | SEPP1 | 0.940 |
| MASP1 | SELL | SEPP1 | TNXB | 0.938 |
| QSOX1 | SELL | SEPP1 | TNXB | 0.937 |
| APOE | CD14 | HIST2H2BE | SEPP1 | 0.936 |
| LUM | QSOX1 | SELL | SEPP1 | 0.934 |
| APOE | MASP1 | QSOX1 | SELL | 0.934 |
| APOC1 | HIST2H2BE | QSOX1 | SELL | 0.933 |
| APOC1 | CD14 | HIST2H2BE | TNXB | 0.933 |
| APOE | COMP | MASP1 | SELL | 0.932 |
| APOE | CD14 | GP1BA | TNXB | 0.932 |
| CD14 | HIST2H2BE | QSOX1 | SEPP1 | 0.931 |
| COMP | GP1BA | SELL | SEPP1 | 0.931 |
| APOE | CD14 | COMP | HIST2H2BE | 0.928 |
| CD14 | COMP | HIST2H2BE | SEPP1 | 0.927 |
| APOC1 | GP1BA | PEPD | SELL | 0.927 |
| COMP | QSOX1 | SELL | SEPP1 | 0.927 |
| APOE | CD14 | COMP | GP1BA | 0.927 |
| APOE | CD14 | GP1BA | SELL | 0.926 |
| APOE | CD14 | GP1BA | MASP1 | 0.926 |
| APOE | CD14 | GP1BA | PEPD | 0.925 |
| APOC1 | CD14 | HIST2H2BE | QSOX1 | 0.925 |
| APOE | CD14 | GP1BA | QSOX1 | 0.924 |
| COMP | LUM | SELL | SEPP1 | 0.922 |
| CD14 | HIST2H2BE | LUM | PEPD | 0.921 |
| CD14 | MASP1 | SELL | TNXB | 0.920 |
| CD14 | QSOX1 | SELL | SEPP1 | 0.919 |
| APOE | LUM | SELL | SEPP1 | 0.919 |
| HIST2H2BE | LUM | SELL | SEPP1 | 0.916 |
| APOE | CD14 | HIST2H2BE | PEPD | 0.916 |
| APOE | CD14 | HIST2H2BE | LUM | 0.916 |
| APOE | QSOX1 | SELL | TNXB | 0.916 |
| COMP | MASP1 | SELL | SEPP1 | 0.914 |
| APOE | QSOX1 | SELL | SEPP1 | 0.914 |
| COMP | SELL | SEPP1 | TNXB | 0.913 |
| APOC1 | CD14 | GP1BA | QSOX1 | 0.912 |
| CD14 | QSOX1 | SELL | TNXB | 0.911 |
| APOC1 | CD14 | HIST2H2BE | PEPD | 0.911 |
| CD14 | HIST2H2BE | MASP1 | SEPP1 | 0.909 |
| APOC1 | SELL | SEPP1 | TNXB | 0.908 |
| CD14 | HIST2H2BE | SELL | SEPP1 | 0.907 |
| COMP | HIST2H2BE | MASP1 | SELL | 0.906 |
| LUM | MASP1 | SELL | SEPP1 | 0.905 |
| APOC1 | GP1BA | QSOX1 | SELL | 0.902 |
| APOE | CD14 | SELL | TNXB | 0.901 |
| APOC1 | CD14 | GP1BA | PEPD | 0.901 |
| CD14 | COMP | GP1BA | SELL | 0.901 |
| APOC1 | CD14 | GP1BA | TNXB | 0.900 |
| COMP | MASP1 | QSOX1 | SELL | 0.900 |
| APOC1 | CD14 | COMP | GP1BA | 0.900 |
| COMP | QSOX1 | SELL | TNXB | 0.900 |
| HIST2H2BE | QSOX1 | SELL | TNXB | 0.900 |
| GP1BA | QSOX1 | SELL | TNXB | 0.898 |
| COMP | MASP1 | SELL | TNXB | 0.898 |
| LUM | QSOX1 | SELL | TNXB | 0.897 |
| CD14 | HIST2H2BE | PEPD | QSOX1 | 0.897 |
| GP1BA | QSOX1 | SELL | SEPP1 | 0.897 |
| APOC1 | LUM | SELL | SEPP1 | 0.897 |
| CD14 | GP1BA | HIST2H2BE | LUM | 0.896 |
| GP1BA | MASP1 | PEPD | SELL | 0.895 |
| APOC1 | CD14 | GP1BA | LUM | 0.895 |
| APOE | MASP1 | PEPD | SELL | 0.894 |
| GP1BA | SELL | SEPP1 | TNXB | 0.891 |
| CD14 | LUM | SELL | SEPP1 | 0.889 |
| CD14 | COMP | SELL | TNXB | 0.888 |
| APOE | CD14 | GP1BA | HIST2H2BE | 0.888 |
| CD14 | SELL | SEPP1 | TNXB | 0.887 |
| LUM | MASP1 | QSOX1 | SELL | 0.886 |
| COMP | HIST2H2BE | QSOX1 | SELL | 0.885 |
| GP1BA | LUM | SELL | SEPP1 | 0.884 |
| CD14 | COMP | GP1BA | HIST2H2BE | 0.884 |
| CD14 | COMP | SELL | SEPP1 | 0.883 |
| CD14 | COMP | MASP1 | SELL | 0.883 |
| HIST2H2BE | MASP1 | QSOX1 | SELL | 0.883 |
| APOC1 | LUM | MASP1 | SELL | 0.883 |
| APOC1 | COMP | HIST2H2BE | SELL | 0.882 |
| LUM | SELL | SEPP1 | TNXB | 0.882 |
| APOC1 | APOE | COMP | SELL | 0.879 |
| GP1BA | MASP1 | QSOX1 | SELL | 0.877 |
| CD14 | HIST2H2BE | LUM | MASP1 | 0.877 |
| APOC1 | CD14 | SELL | TNXB | 0.876 |
| CD14 | GP1BA | SELL | TNXB | 0.876 |
| APOC1 | CD14 | GP1BA | SEPP1 | 0.876 |
| CD14 | COMP | HIST2H2BE | SELL | 0.874 |
| APOC1 | CD14 | LUM | SELL | 0.874 |
| APOC1 | CD14 | MASP1 | PEPD | 0.872 |
| CD14 | HIST2H2BE | LUM | SELL | 0.872 |
| APOC1 | COMP | GP1BA | SELL | 0.871 |
| APOC1 | CD14 | COMP | SELL | 0.870 |
| HIST2H2BE | MASP1 | PEPD | SELL | 0.870 |
| APOE | CD14 | QSOX1 | SELL | 0.869 |
| APOC1 | MASP1 | PEPD | SELL | 0.869 |
| CD14 | HIST2H2BE | LUM | TNXB | 0.869 |
| APOE | CD14 | COMP | SELL | 0.868 |
| APOC1 | APOE | CD14 | LUM | 0.868 |
| APOE | CD14 | MASP1 | SELL | 0.867 |
| CD14 | LUM | MASP1 | SELL | 0.867 |
| APOE | CD14 | LUM | PEPD | 0.867 |
| APOE | CD14 | LUM | SELL | 0.867 |
| APOC1 | CD14 | LUM | PEPD | 0.865 |
| COMP | LUM | SELL | TNXB | 0.865 |
| COMP | GP1BA | MASP1 | SELL | 0.864 |
| CD14 | GP1BA | SELL | SEPP1 | 0.864 |
| CD14 | LUM | SELL | TNXB | 0.864 |
| CD14 | GP1BA | HIST2H2BE | PEPD | 0.863 |
| CD14 | GP1BA | LUM | SELL | 0.863 |
| APOC1 | CD14 | GP1BA | HIST2H2BE | 0.863 |
| CD14 | COMP | HIST2H2BE | TNXB | 0.862 |
| APOC1 | COMP | LUM | SELL | 0.861 |
| APOE | COMP | SELL | TNXB | 0.861 |
| CD14 | HIST2H2BE | LUM | QSOX1 | 0.860 |
| APOC1 | COMP | SELL | TNXB | 0.860 |
| CD14 | COMP | GP1BA | SEPP1 | 0.859 |
| CD14 | GP1BA | LUM | SEPP1 | 0.859 |
| CD14 | GP1BA | SEPP1 | TNXB | 0.858 |
| APOE | CD14 | LUM | MASP1 | 0.858 |
| APOC1 | HIST2H2BE | PEPD | SELL | 0.858 |
| APOC1 | APOE | CD14 | PEPD | 0.856 |
| CD14 | HIST2H2BE | QSOX1 | TNXB | 0.855 |
| APOC1 | CD14 | QSOX1 | SEPP1 | 0.855 |

TABLE 8-continued

HIV– panels
Combination of Four Candidate Biomarkers

| protein.1 | protein.2 | protein.3 | protein.4 | AUC |
|---|---|---|---|---|
| CD14 | HIST2H2BE | SELL | TNXB | 0.855 |
| CD14 | GP1BA | HIST2H2BE | TNXB | 0.854 |
| APOE | CD14 | SELL | SEPP1 | 0.853 |
| APOC1 | CD14 | COMP | PEPD | 0.850 |
| APOE | CD14 | HIST2H2BE | MASP1 | 0.849 |
| COMP | GP1BA | SELL | TNXB | 0.849 |
| APOE | CD14 | MASP1 | TNXB | 0.849 |
| COMP | GP1BA | HIST2H2BE | SELL | 0.848 |
| APOC1 | CD14 | LUM | QSOX1 | 0.848 |
| APOC1 | APOE | CD14 | HIST2H2BE | 0.848 |
| APOC1 | CD14 | PEPD | TNXB | 0.848 |
| COMP | LUM | MASP1 | SELL | 0.848 |
| APOC1 | CD14 | MASP1 | QSOX1 | 0.846 |
| APOC1 | APOE | CD14 | TNXB | 0.845 |
| APOE | COMP | QSOX1 | SELL | 0.844 |
| COMP | HIST2H2BE | SELL | TNXB | 0.843 |
| CD14 | COMP | HIST2H2BE | LUM | 0.843 |
| APOC1 | APOE | LUM | SELL | 0.843 |
| CD14 | GP1BA | LUM | TNXB | 0.843 |
| CD14 | COMP | GP1BA | TNXB | 0.843 |
| CD14 | GP1BA | QSOX1 | TNXB | 0.841 |
| CD14 | GP1BA | PEPD | TNXB | 0.841 |
| APOC1 | APOE | CD14 | SELL | 0.841 |
| APOE | MASP1 | SELL | TNXB | 0.841 |
| APOC1 | CD14 | PEPD | SEPP1 | 0.841 |
| CD14 | COMP | LUM | SEPP1 | 0.840 |
| CD14 | GP1BA | QSOX1 | SEPP1 | 0.837 |
| APOC1 | CD14 | LUM | TNXB | 0.837 |
| APOC1 | GP1BA | HIST2H2BE | QSOX1 | 0.836 |
| APOC1 | CD14 | QSOX1 | TNXB | 0.836 |
| APOC1 | CD14 | GP1BA | SELL | 0.836 |
| APOC1 | CD14 | COMP | QSOX1 | 0.836 |
| CD14 | MASP1 | PEPD | TNXB | 0.836 |
| APOC1 | CD14 | PEPD | QSOX1 | 0.835 |
| CD14 | LUM | MASP1 | TNXB | 0.835 |
| CD14 | GP1BA | PEPD | SEPP1 | 0.834 |
| APOE | COMP | LUM | SELL | 0.834 |
| COMP | GP1BA | QSOX1 | SELL | 0.833 |
| LUM | MASP1 | SELL | TNXB | 0.833 |
| APOE | CD14 | PEPD | TNXB | 0.833 |
| APOC1 | APOE | CD14 | QSOX1 | 0.832 |
| CD14 | HIST2H2BE | MASP1 | PEPD | 0.830 |
| APOC1 | CD14 | COMP | LUM | 0.830 |
| APOE | LUM | QSOX1 | SELL | 0.828 |
| APOE | CD14 | COMP | PEPD | 0.827 |
| CD14 | GP1BA | MASP1 | SELL | 0.827 |
| CD14 | GP1BA | MASP1 | TNXB | 0.827 |
| GP1BA | HIST2H2BE | PEPD | SELL | 0.827 |
| CD14 | COMP | LUM | TNXB | 0.826 |
| CD14 | LUM | SEPP1 | TNXB | 0.826 |
| APOC1 | CD14 | COMP | SEPP1 | 0.825 |
| HIST2H2BE | LUM | QSOX1 | SELL | 0.825 |
| APOE | LUM | SELL | TNXB | 0.824 |
| APOC1 | APOE | CD14 | COMP | 0.823 |
| CD14 | GP1BA | MASP1 | SEPP1 | 0.823 |
| APOE | GP1BA | PEPD | SELL | 0.823 |
| CD14 | GP1BA | MASP1 | QSOX1 | 0.823 |
| APOE | CD14 | HIST2H2BE | QSOX1 | 0.823 |
| APOC1 | CD14 | COMP | MASP1 | 0.822 |
| APOC1 | APOE | PEPD | SELL | 0.822 |
| APOC1 | LUM | SELL | TNXB | 0.822 |
| APOC1 | CD14 | LUM | MASP1 | 0.822 |
| APOE | CD14 | LUM | QSOX1 | 0.820 |
| HIST2H2BE | MASP1 | SELL | TNXB | 0.820 |
| APOE | COMP | GP1BA | SELL | 0.820 |
| APOE | CD14 | PEPD | SEPP1 | 0.820 |
| CD14 | LUM | QSOX1 | SELL | 0.819 |
| CD14 | COMP | GP1BA | MASP1 | 0.819 |
| CD14 | COMP | GP1BA | PEPD | 0.819 |
| CD14 | COMP | QSOX1 | SELL | 0.818 |
| APOC1 | CD14 | MASP1 | TNXB | 0.817 |
| APOE | CD14 | LUM | SEPP1 | 0.817 |
| CD14 | LUM | PEPD | SEPP1 | 0.817 |
| APOE | COMP | HIST2H2BE | SELL | 0.817 |
| APOC1 | HIST2H2BE | LUM | SELL | 0.817 |
| APOC1 | CD14 | COMP | TNXB | 0.816 |
| APOC1 | CD14 | SEPP1 | TNXB | 0.816 |
| GP1BA | LUM | QSOX1 | SELL | 0.816 |
| APOE | MASP1 | SELL | SEPP1 | 0.816 |
| CD14 | GP1BA | LUM | PEPD | 0.816 |
| CD14 | GP1BA | LUM | MASP1 | 0.815 |
| APOE | CD14 | MASP1 | PEPD | 0.815 |
| APOC1 | CD14 | LUM | SEPP1 | 0.814 |
| CD14 | GP1BA | LUM | QSOX1 | 0.811 |
| CD14 | LUM | QSOX1 | TNXB | 0.811 |
| CD14 | GP1BA | HIST2H2BE | MASP1 | 0.810 |
| APOE | CD14 | COMP | LUM | 0.809 |
| APOE | CD14 | LUM | TNXB | 0.808 |
| APOC1 | APOE | CD14 | SEPP1 | 0.808 |
| CD14 | COMP | GP1BA | LUM | 0.808 |
| CD14 | LUM | QSOX1 | SEPP1 | 0.808 |
| APOC1 | GP1BA | LUM | SELL | 0.807 |
| APOC1 | CD14 | HIST2H2BE | MASP1 | 0.806 |
| APOC1 | APOE | SELL | TNXB | 0.806 |
| CD14 | GP1BA | PEPD | QSOX1 | 0.806 |
| HIST2H2BE | LUM | SELL | TNXB | 0.806 |
| GP1BA | LUM | SELL | TNXB | 0.804 |
| COMP | GP1BA | LUM | SELL | 0.804 |
| APOC1 | MASP1 | SELL | TNXB | 0.804 |
| APOE | GP1BA | QSOX1 | SELL | 0.804 |
| CD14 | LUM | PEPD | TNXB | 0.804 |
| CD14 | MASP1 | SELL | SEPP1 | 0.804 |
| CD14 | COMP | GP1BA | QSOX1 | 0.803 |
| APOC1 | CD14 | GP1BA | MASP1 | 0.803 |
| APOC1 | APOE | CD14 | MASP1 | 0.801 |
| APOC1 | CD14 | SELL | SEPP1 | 0.800 |
| APOE | LUM | MASP1 | SELL | 0.800 |
| APOE | CD14 | SEPP1 | TNXB | 0.800 |
| CD14 | COMP | MASP1 | TNXB | 0.799 |
| CD14 | MASP1 | QSOX1 | TNXB | 0.797 |
| COMP | LUM | QSOX1 | SELL | 0.797 |
| CD14 | COMP | HIST2H2BE | MASP1 | 0.796 |
| CD14 | HIST2H2BE | QSOX1 | SELL | 0.796 |
| APOE | HIST2H2BE | SELL | SEPP1 | 0.795 |
| HIST2H2BE | MASP1 | SELL | SEPP1 | 0.795 |
| CD14 | LUM | MASP1 | PEPD | 0.795 |
| APOE | CD14 | PEPD | QSOX1 | 0.794 |
| APOE | HIST2H2BE | SELL | TNXB | 0.794 |
| GP1BA | MASP1 | SELL | TNXB | 0.794 |
| CD14 | HIST2H2BE | MASP1 | QSOX1 | 0.794 |
| APOC1 | CD14 | HIST2H2BE | SELL | 0.793 |
| APOE | CD14 | QSOX1 | TNXB | 0.793 |
| APOE | GP1BA | SELL | TNXB | 0.792 |
| CD14 | COMP | PEPD | SEPP1 | 0.792 |
| CD14 | HIST2H2BE | MASP1 | TNXB | 0.792 |
| APOE | CD14 | COMP | MASP1 | 0.792 |
| CD14 | COMP | HIST2H2BE | QSOX1 | 0.792 |
| APOC1 | APOE | SELL | SEPP1 | 0.791 |
| CD14 | MASP1 | SEPP1 | TNXB | 0.791 |
| CD14 | LUM | MASP1 | SEPP1 | 0.791 |
| APOE | GP1BA | SELL | SEPP1 | 0.790 |
| CD14 | PEPD | SEPP1 | TNXB | 0.790 |
| CD14 | COMP | LUM | PEPD | 0.789 |
| GP1BA | HIST2H2BE | QSOX1 | SELL | 0.789 |
| APOE | HIST2H2BE | PEPD | SELL | 0.787 |
| APOE | CD14 | COMP | TNXB | 0.785 |
| COMP | HIST2H2BE | LUM | SELL | 0.785 |
| APOE | HIST2H2BE | QSOX1 | SELL | 0.781 |
| CD14 | COMP | SEPP1 | TNXB | 0.781 |
| CD14 | GP1BA | MASP1 | PEPD | 0.779 |
| APOE | CD14 | HIST2H2BE | SELL | 0.779 |
| APOE | CD14 | MASP1 | QSOX1 | 0.778 |
| CD14 | COMP | LUM | SELL | 0.777 |
| APOE | CD14 | QSOX1 | SEPP1 | 0.776 |
| APOC1 | CD14 | MASP1 | SELL | 0.775 |
| APOC1 | CD14 | MASP1 | SEPP1 | 0.774 |
| APOE | CD14 | COMP | SEPP1 | 0.772 |
| GP1BA | MASP1 | SELL | SEPP1 | 0.772 |
| APOC1 | HIST2H2BE | SELL | SEPP1 | 0.771 |
| APOE | GP1BA | LUM | SELL | 0.770 |

TABLE 8-continued

HIV– panels
Combination of Four Candidate Biomarkers

| protein.1 | protein.2 | protein.3 | protein.4 | AUC |
|---|---|---|---|---|
| APOE | CD14 | COMP | QSOX1 | 0.770 |
| APOE | CD14 | MASP1 | SEPP1 | 0.769 |
| APOC1 | HIST2H2BE | SELL | TNXB | 0.768 |
| CD14 | COMP | PEPD | TNXB | 0.768 |
| CD14 | QSOX1 | SEPP1 | TNXB | 0.764 |
| APOC1 | GP1BA | SELL | TNXB | 0.764 |
| CD14 | LUM | PEPD | QSOX1 | 0.764 |
| CD14 | HIST2H2BE | MASP1 | SELL | 0.763 |
| CD14 | COMP | QSOX1 | TNXB | 0.763 |
| CD14 | MASP1 | PEPD | SEPP1 | 0.763 |
| APOC1 | MASP1 | SELL | SEPP1 | 0.762 |
| CD14 | PEPD | QSOX1 | TNXB | 0.761 |
| GP1BA | HIST2H2BE | SELL | TNXB | 0.760 |
| APOC1 | GP1BA | SELL | SEPP1 | 0.759 |
| CD14 | LUM | MASP1 | QSOX1 | 0.759 |
| GP1BA | HIST2H2BE | SELL | SEPP1 | 0.751 |
| CD14 | COMP | LUM | MASP1 | 0.750 |
| GP1BA | LUM | MASP1 | SELL | 0.750 |
| CD14 | GP1BA | HIST2H2BE | SELL | 0.749 |
| CD14 | PEPD | QSOX1 | SEPP1 | 0.749 |
| CD14 | COMP | MASP1 | PEPD | 0.748 |
| CD14 | COMP | QSOX1 | SEPP1 | 0.748 |
| CD14 | COMP | MASP1 | SEPP1 | 0.747 |
| HIST2H2BE | LUM | MASP1 | SELL | 0.746 |
| APOC1 | APOE | COMP | MASP1 | 0.746 |
| APOE | HIST2H2BE | LUM | SELL | 0.746 |
| APOC1 | COMP | MASP1 | TNXB | 0.744 |
| CD14 | MASP1 | QSOX1 | SEPP1 | 0.743 |
| APOC1 | COMP | HIST2H2BE | MASP1 | 0.742 |
| CD14 | COMP | PEPD | QSOX1 | 0.738 |
| APOC1 | COMP | MASP1 | SEPP1 | 0.737 |
| GP1BA | HIST2H2BE | LUM | SELL | 0.737 |
| CD14 | COMP | LUM | QSOX1 | 0.735 |
| CD14 | COMP | MASP1 | QSOX1 | 0.734 |
| APOC1 | COMP | LUM | MASP1 | 0.734 |
| APOC1 | COMP | MASP1 | QSOX1 | 0.733 |
| APOC1 | COMP | GP1BA | MASP1 | 0.732 |
| APOE | COMP | MASP1 | TNXB | 0.728 |
| APOC1 | COMP | HIST2H2BE | TNXB | 0.727 |
| CD14 | MASP1 | PEPD | QSOX1 | 0.726 |
| COMP | HIST2H2BE | MASP1 | TNXB | 0.726 |
| APOC1 | COMP | HIST2H2BE | PEPD | 0.725 |
| APOC1 | COMP | GP1BA | TNXB | 0.723 |
| APOC1 | COMP | HIST2H2BE | QSOX1 | 0.723 |
| APOC1 | COMP | MASP1 | PEPD | 0.722 |
| APOC1 | APOE | COMP | PEPD | 0.722 |
| APOC1 | COMP | GP1BA | HIST2H2BE | 0.720 |
| COMP | MASP1 | SEPP1 | TNXB | 0.720 |
| APOC1 | COMP | PEPD | TNXB | 0.720 |
| APOC1 | COMP | QSOX1 | TNXB | 0.720 |
| LUM | MASP1 | SEPP1 | TNXB | 0.719 |
| APOC1 | COMP | HIST2H2BE | LUM | 0.719 |
| APOC1 | COMP | PEPD | SEPP1 | 0.718 |
| APOC1 | APOE | COMP | GP1BA | 0.716 |
| APOC1 | COMP | SEPP1 | TNXB | 0.716 |
| APOE | LUM | MASP1 | TNXB | 0.715 |
| COMP | HIST2H2BE | PEPD | TNXB | 0.714 |
| HIST2H2BE | LUM | MASP1 | TNXB | 0.714 |
| APOC1 | COMP | PEPD | QSOX1 | 0.713 |
| APOC1 | COMP | QSOX1 | SEPP1 | 0.712 |
| COMP | MASP1 | PEPD | TNXB | 0.711 |
| APOC1 | COMP | GP1BA | QSOX1 | 0.710 |
| COMP | LUM | MASP1 | TNXB | 0.710 |
| APOC1 | COMP | GP1BA | SEPP1 | 0.709 |
| APOC1 | COMP | GP1BA | PEPD | 0.708 |
| APOC1 | APOE | COMP | TNXB | 0.708 |
| APOE | COMP | PEPD | TNXB | 0.708 |
| COMP | MASP1 | QSOX1 | TNXB | 0.708 |
| APOE | COMP | GP1BA | MASP1 | 0.707 |
| APOE | COMP | GP1BA | TNXB | 0.707 |
| APOC1 | COMP | HIST2H2BE | SEPP1 | 0.707 |
| COMP | GP1BA | MASP1 | SEPP1 | 0.706 |
| APOC1 | APOE | COMP | QSOX1 | 0.706 |
| COMP | GP1BA | PEPD | TNXB | 0.705 |
| COMP | GP1BA | HIST2H2BE | TNXB | 0.705 |
| APOC1 | COMP | GP1BA | LUM | 0.705 |
| APOE | GP1BA | LUM | TNXB | 0.705 |
| APOC1 | APOE | COMP | SEPP1 | 0.704 |
| COMP | HIST2H2BE | LUM | TNXB | 0.702 |
| COMP | HIST2H2BE | SEPP1 | TNXB | 0.702 |
| COMP | HIST2H2BE | MASP1 | SEPP1 | 0.702 |
| APOC1 | COMP | LUM | PEPD | 0.702 |
| APOC1 | APOE | COMP | HIST2H2BE | 0.702 |
| APOC1 | COMP | LUM | TNXB | 0.702 |
| APOC1 | COMP | LUM | SEPP1 | 0.701 |
| LUM | MASP1 | QSOX1 | SEPP1 | 0.701 |
| LUM | MASP1 | PEPD | TNXB | 0.701 |
| COMP | GP1BA | SEPP1 | TNXB | 0.701 |
| APOE | COMP | HIST2H2BE | TNXB | 0.700 |
| COMP | LUM | MASP1 | SEPP1 | 0.699 |
| APOC1 | COMP | LUM | QSOX1 | 0.699 |
| COMP | PEPD | SEPP1 | TNXB | 0.699 |
| APOE | COMP | MASP1 | SEPP1 | 0.699 |
| COMP | HIST2H2BE | QSOX1 | SEPP1 | 0.699 |
| APOE | COMP | HIST2H2BE | LUM | 0.698 |
| COMP | HIST2H2BE | LUM | SEPP1 | 0.698 |
| LUM | MASP1 | QSOX1 | TNXB | 0.698 |
| COMP | GP1BA | MASP1 | TNXB | 0.698 |
| GP1BA | LUM | PEPD | TNXB | 0.698 |
| APOE | COMP | HIST2H2BE | MASP1 | 0.697 |
| GP1BA | HIST2H2BE | LUM | TNXB | 0.697 |
| GP1BA | LUM | MASP1 | SEPP1 | 0.697 |
| APOC1 | LUM | MASP1 | TNXB | 0.697 |
| LUM | MASP1 | PEPD | SEPP1 | 0.697 |
| APOC1 | APOE | LUM | MASP1 | 0.696 |
| APOC1 | MASP1 | QSOX1 | TNXB | 0.696 |
| COMP | MASP1 | PEPD | SEPP1 | 0.696 |
| APOC1 | LUM | MASP1 | QSOX1 | 0.696 |
| COMP | GP1BA | HIST2H2BE | SEPP1 | 0.696 |
| APOE | LUM | MASP1 | SEPP1 | 0.695 |
| GP1BA | LUM | QSOX1 | TNXB | 0.695 |
| APOC1 | APOE | MASP1 | SELL | 0.695 |
| GP1BA | LUM | MASP1 | TNXB | 0.694 |
| HIST2H2BE | LUM | MASP1 | SEPP1 | 0.694 |
| APOC1 | LUM | MASP1 | PEPD | 0.693 |
| GP1BA | LUM | SEPP1 | TNXB | 0.693 |
| APOE | COMP | SEPP1 | TNXB | 0.692 |
| APOC1 | LUM | PEPD | TNXB | 0.692 |
| APOE | COMP | MASP1 | QSOX1 | 0.692 |
| COMP | GP1BA | LUM | TNXB | 0.692 |
| APOC1 | HIST2H2BE | LUM | MASP1 | 0.692 |
| APOC1 | HIST2H2BE | LUM | TNXB | 0.691 |
| APOE | COMP | MASP1 | PEPD | 0.691 |
| COMP | HIST2H2BE | MASP1 | QSOX1 | 0.691 |
| COMP | MASP1 | QSOX1 | SEPP1 | 0.691 |
| APOC1 | LUM | MASP1 | SEPP1 | 0.691 |
| APOE | COMP | LUM | MASP1 | 0.690 |
| LUM | PEPD | QSOX1 | TNXB | 0.690 |
| LUM | QSOX1 | SEPP1 | TNXB | 0.690 |
| APOE | LUM | PEPD | TNXB | 0.690 |
| APOE | COMP | GP1BA | HIST2H2BE | 0.689 |
| LUM | PEPD | SEPP1 | TNXB | 0.689 |
| APOE | COMP | HIST2H2BE | PEPD | 0.688 |
| APOC1 | GP1BA | HIST2H2BE | LUM | 0.688 |
| APOC1 | LUM | QSOX1 | TNXB | 0.688 |
| COMP | QSOX1 | SEPP1 | TNXB | 0.688 |
| APOC1 | GP1BA | LUM | TNXB | 0.688 |
| APOE | COMP | HIST2H2BE | LUM | 0.688 |
| APOC1 | LUM | QSOX1 | SEPP1 | 0.688 |
| COMP | HIST2H2BE | PEPD | SEPP1 | 0.687 |
| APOE | COMP | QSOX1 | TNXB | 0.687 |
| APOE | COMP | LUM | TNXB | 0.687 |
| APOC1 | GP1BA | LUM | QSOX1 | 0.687 |
| APOE | COMP | GP1BA | SEPP1 | 0.687 |
| APOE | COMP | GP1BA | PEPD | 0.687 |
| COMP | HIST2H2BE | QSOX1 | TNXB | 0.686 |
| HIST2H2BE | LUM | QSOX1 | TNXB | 0.686 |
| HIST2H2BE | LUM | PEPD | TNXB | 0.686 |
| COMP | GP1BA | PEPD | SEPP1 | 0.686 |
| APOC1 | HIST2H2BE | LUM | QSOX1 | 0.686 |

TABLE 8-continued

HIV− panels
Combination of Four Candidate Biomarkers

| protein.1 | protein.2 | protein.3 | protein.4 | AUC |
|---|---|---|---|---|
| APOE | LUM | MASP1 | PEPD | 0.686 |
| APOE | GP1BA | LUM | PEPD | 0.686 |
| APOE | GP1BA | LUM | MASP1 | 0.686 |
| APOE | COMP | HIST2H2BE | SEPP1 | 0.686 |
| APOC1 | GP1BA | LUM | PEPD | 0.686 |
| MASP1 | QSOX1 | SEPP1 | TNXB | 0.686 |
| APOE | HIST2H2BE | LUM | TNXB | 0.686 |
| COMP | LUM | SEPP1 | TNXB | 0.685 |
| COMP | LUM | PEPD | TNXB | 0.685 |
| HIST2H2BE | LUM | SEPP1 | TNXB | 0.685 |
| APOC1 | HIST2H2BE | LUM | PEPD | 0.684 |
| COMP | HIST2H2BE | MASP1 | PEPD | 0.684 |
| APOE | COMP | PEPD | SEPP1 | 0.684 |
| COMP | GP1BA | QSOX1 | TNXB | 0.684 |
| APOE | COMP | GP1BA | LUM | 0.683 |
| APOC1 | MASP1 | QSOX1 | SEPP1 | 0.683 |
| APOC1 | LUM | PEPD | QSOX1 | 0.683 |
| APOC1 | LUM | PEPD | SEPP1 | 0.683 |
| APOE | HIST2H2BE | MASP1 | SELL | 0.683 |
| APOC1 | LUM | SEPP1 | TNXB | 0.683 |
| COMP | HIST2H2BE | LUM | QSOX1 | 0.683 |
| APOE | COMP | GP1BA | QSOX1 | 0.682 |
| GP1BA | LUM | PEPD | SEPP1 | 0.682 |
| COMP | LUM | QSOX1 | TNXB | 0.682 |
| COMP | LUM | QSOX1 | SEPP1 | 0.682 |
| APOE | HIST2H2BE | LUM | MASP1 | 0.682 |
| APOE | COMP | QSOX1 | SEPP1 | 0.682 |
| COMP | HIST2H2BE | LUM | MASP1 | 0.682 |
| APOE | LUM | QSOX1 | TNXB | 0.681 |
| APOC1 | APOE | GP1BA | LUM | 0.681 |
| COMP | GP1BA | QSOX1 | SEPP1 | 0.681 |
| COMP | HIST2H2BE | LUM | PEPD | 0.681 |
| APOC1 | APOE | LUM | QSOX1 | 0.680 |
| APOC1 | APOE | LUM | SEPP1 | 0.680 |
| APOC1 | HIST2H2BE | LUM | SEPP1 | 0.680 |
| COMP | GP1BA | HIST2H2BE | PEPD | 0.680 |
| COMP | GP1BA | HIST2H2BE | QSOX1 | 0.679 |
| APOE | COMP | LUM | PEPD | 0.679 |
| COMP | GP1BA | LUM | SEPP1 | 0.679 |
| APOC1 | APOE | LUM | TNXB | 0.679 |
| GP1BA | LUM | QSOX1 | SEPP1 | 0.678 |
| HIST2H2BE | LUM | QSOX1 | SEPP1 | 0.678 |
| COMP | PEPD | QSOX1 | TNXB | 0.678 |
| APOC1 | HIST2H2BE | QSOX1 | TNXB | 0.678 |
| MASP1 | PEPD | SEPP1 | TNXB | 0.678 |
| GP1BA | HIST2H2BE | LUM | SEPP1 | 0.678 |
| APOC1 | APOE | HIST2H2BE | LUM | 0.677 |
| HIST2H2BE | LUM | PEPD | SEPP1 | 0.677 |
| GP1BA | MASP1 | PEPD | TNXB | 0.677 |
| COMP | HIST2H2BE | PEPD | QSOX1 | 0.677 |
| APOE | LUM | SEPP1 | TNXB | 0.676 |
| APOE | LUM | MASP1 | QSOX1 | 0.676 |
| APOC1 | MASP1 | SEPP1 | TNXB | 0.676 |
| COMP | GP1BA | HIST2H2BE | MASP1 | 0.676 |
| COMP | GP1BA | LUM | MASP1 | 0.676 |
| COMP | GP1BA | LUM | PEPD | 0.675 |
| LUM | PEPD | QSOX1 | SEPP1 | 0.675 |
| APOE | COMP | PEPD | QSOX1 | 0.675 |
| COMP | GP1BA | MASP1 | PEPD | 0.675 |
| APOC1 | GP1BA | LUM | SEPP1 | 0.674 |
| APOC1 | GP1BA | QSOX1 | TNXB | 0.674 |
| COMP | LUM | MASP1 | PEPD | 0.674 |
| APOE | COMP | HIST2H2BE | QSOX1 | 0.674 |
| COMP | GP1BA | HIST2H2BE | LUM | 0.673 |
| APOE | COMP | LUM | SEPP1 | 0.673 |
| COMP | LUM | PEPD | SEPP1 | 0.673 |
| APOC1 | APOE | MASP1 | QSOX1 | 0.673 |
| GP1BA | HIST2H2BE | LUM | PEPD | 0.673 |
| APOE | GP1BA | LUM | SEPP1 | 0.672 |
| APOE | GP1BA | LUM | QSOX1 | 0.672 |
| APOC1 | GP1BA | LUM | MASP1 | 0.672 |
| HIST2H2BE | MASP1 | SEPP1 | TNXB | 0.671 |
| APOE | LUM | PEPD | QSOX1 | 0.671 |
| APOE | COMP | LUM | QSOX1 | 0.671 |
| GP1BA | LUM | MASP1 | PEPD | 0.671 |
| GP1BA | HIST2H2BE | PEPD | TNXB | 0.671 |
| APOC1 | MASP1 | PEPD | TNXB | 0.671 |
| APOC1 | HIST2H2BE | MASP1 | SELL | 0.670 |
| GP1BA | PEPD | SEPP1 | TNXB | 0.670 |
| GP1BA | MASP1 | SEPP1 | TNXB | 0.670 |
| APOE | HIST2H2BE | LUM | SEPP1 | 0.670 |
| COMP | PEPD | QSOX1 | SEPP1 | 0.670 |
| APOC1 | APOE | LUM | SEPP1 | 0.669 |
| APOE | HIST2H2BE | LUM | PEPD | 0.669 |
| APOE | MASP1 | QSOX1 | TNXB | 0.669 |
| GP1BA | LUM | PEPD | QSOX1 | 0.669 |
| APOE | GP1BA | HIST2H2BE | LUM | 0.668 |
| GP1BA | PEPD | QSOX1 | TNXB | 0.668 |
| APOE | MASP1 | SEPP1 | TNXB | 0.668 |
| GP1BA | MASP1 | QSOX1 | TNXB | 0.668 |
| APOE | LUM | PEPD | SEPP1 | 0.668 |
| MASP1 | PEPD | QSOX1 | TNXB | 0.668 |
| GP1BA | MASP1 | QSOX1 | SEPP1 | 0.668 |
| APOE | HIST2H2BE | LUM | QSOX1 | 0.667 |
| APOC1 | HIST2H2BE | MASP1 | QSOX1 | 0.667 |
| GP1BA | HIST2H2BE | QSOX1 | TNXB | 0.667 |
| APOC1 | GP1BA | PEPD | TNXB | 0.666 |
| COMP | GP1BA | MASP1 | QSOX1 | 0.666 |
| APOE | MASP1 | PEPD | TNXB | 0.666 |
| HIST2H2BE | QSOX1 | SEPP1 | TNXB | 0.666 |
| APOC1 | PEPD | QSOX1 | TNXB | 0.665 |
| HIST2H2BE | MASP1 | QSOX1 | TNXB | 0.665 |
| APOC1 | GP1BA | HIST2H2BE | QSOX1 | 0.665 |
| GP1BA | QSOX1 | SEPP1 | TNXB | 0.665 |
| APOC1 | APOE | MASP1 | TNXB | 0.664 |
| LUM | MASP1 | PEPD | QSOX1 | 0.664 |
| HIST2H2BE | LUM | MASP1 | PEPD | 0.664 |
| APOC1 | APOE | HIST2H2BE | SELL | 0.664 |
| HIST2H2BE | MASP1 | QSOX1 | SEPP1 | 0.664 |
| APOC1 | QSOX1 | SEPP1 | TNXB | 0.663 |
| APOE | LUM | QSOX1 | SEPP1 | 0.663 |
| APOC1 | MASP1 | PEPD | QSOX1 | 0.663 |
| COMP | GP1BA | PEPD | QSOX1 | 0.663 |
| HIST2H2BE | LUM | PEPD | QSOX1 | 0.663 |
| APOC1 | HIST2H2BE | MASP1 | TNXB | 0.663 |
| APOC1 | GP1BA | MASP1 | QSOX1 | 0.663 |
| COMP | GP1BA | LUM | QSOX1 | 0.662 |
| GP1BA | HIST2H2BE | SEPP1 | TNXB | 0.662 |
| GP1BA | HIST2H2BE | LUM | QSOX1 | 0.662 |
| APOE | GP1BA | MASP1 | SELL | 0.661 |
| COMP | LUM | PEPD | QSOX1 | 0.661 |
| COMP | LUM | MASP1 | QSOX1 | 0.661 |
| APOC1 | APOE | QSOX1 | TNXB | 0.661 |
| APOE | GP1BA | QSOX1 | TNXB | 0.660 |
| APOE | GP1BA | PEPD | TNXB | 0.659 |
| HIST2H2BE | LUM | MASP1 | QSOX1 | 0.659 |
| APOC1 | MASP1 | PEPD | SEPP1 | 0.659 |
| APOC1 | GP1BA | MASP1 | SELL | 0.659 |
| HIST2H2BE | MASP1 | PEPD | TNXB | 0.658 |
| GP1BA | MASP1 | PEPD | SEPP1 | 0.658 |
| GP1BA | LUM | MASP1 | QSOX1 | 0.658 |
| APOC1 | APOE | GP1BA | QSOX1 | 0.657 |
| HIST2H2BE | PEPD | QSOX1 | SEPP1 | 0.656 |
| COMP | MASP1 | PEPD | QSOX1 | 0.656 |
| APOC1 | APOE | GP1BA | SELL | 0.656 |
| PEPD | QSOX1 | SEPP1 | TNXB | 0.654 |
| APOC1 | GP1BA | HIST2H2BE | TNXB | 0.654 |
| APOC1 | APOE | GP1BA | TNXB | 0.653 |
| APOE | HIST2H2BE | MASP1 | TNXB | 0.652 |
| APOC1 | PEPD | SEPP1 | TNXB | 0.651 |
| APOE | HIST2H2BE | QSOX1 | TNXB | 0.649 |
| APOC1 | GP1BA | QSOX1 | SEPP1 | 0.649 |
| APOC1 | APOE | PEPD | TNXB | 0.648 |
| APOC1 | HIST2H2BE | PEPD | TNXB | 0.648 |
| GP1BA | HIST2H2BE | LUM | MASP1 | 0.648 |
| APOC1 | GP1BA | MASP1 | TNXB | 0.648 |
| HIST2H2BE | PEPD | SEPP1 | TNXB | 0.647 |
| APOC1 | GP1BA | PEPD | QSOX1 | 0.646 |
| APOE | GP1BA | HIST2H2BE | TNXB | 0.646 |
| MASP1 | PEPD | QSOX1 | SEPP1 | 0.645 |

TABLE 8-continued

HIV− panels
Combination of Four Candidate Biomarkers

| protein.1 | protein.2 | protein.3 | protein.4 | AUC |
|---|---|---|---|---|
| APOC1 | GP1BA | SEPP1 | TNXB | 0.645 |
| APOC1 | GP1BA | HIST2H2BE | PEPD | 0.644 |
| GP1BA | HIST2H2BE | QSOX1 | SEPP1 | 0.643 |
| APOE | MASP1 | PEPD | SEPP1 | 0.643 |
| APOE | GP1BA | MASP1 | TNXB | 0.643 |
| APOC1 | PEPD | QSOX1 | SEPP1 | 0.643 |
| APOC1 | APOE | HIST2H2BE | TNXB | 0.643 |
| APOC1 | GP1BA | MASP1 | PEPD | 0.643 |
| APOE | PEPD | QSOX1 | TNXB | 0.643 |
| APOE | MASP1 | QSOX1 | SEPP1 | 0.643 |
| APOE | GP1BA | SEPP1 | TNXB | 0.641 |
| APOC1 | HIST2H2BE | QSOX1 | SEPP1 | 0.640 |
| APOC1 | HIST2H2BE | SEPP1 | TNXB | 0.638 |
| HIST2H2BE | MASP1 | PEPD | SEPP1 | 0.638 |
| APOC1 | GP1BA | PEPD | SEPP1 | 0.638 |
| APOC1 | HIST2H2BE | MASP1 | SEPP1 | 0.637 |
| APOC1 | APOE | PEPD | QSOX1 | 0.637 |
| GP1BA | HIST2H2BE | MASP1 | SEPP1 | 0.636 |
| APOC1 | HIST2H2BE | PEPD | QSOX1 | 0.635 |
| APOC1 | APOE | SEPP1 | TNXB | 0.634 |
| APOC1 | APOE | HIST2H2BE | QSOX1 | 0.634 |
| APOC1 | GP1BA | MASP1 | SEPP1 | 0.634 |
| APOE | QSOX1 | SEPP1 | TNXB | 0.633 |
| GP1BA | HIST2H2BE | MASP1 | SELL | 0.633 |
| APOC1 | APOE | QSOX1 | SEPP1 | 0.633 |
| GP1BA | PEPD | QSOX1 | SEPP1 | 0.632 |
| APOE | HIST2H2BE | PEPD | TNXB | 0.632 |
| APOC1 | GP1BA | HIST2H2BE | SELL | 0.632 |
| APOE | HIST2H2BE | SEPP1 | TNXB | 0.631 |
| APOC1 | APOE | GP1BA | PEPD | 0.631 |
| GP1BA | HIST2H2BE | MASP1 | TNXB | 0.629 |
| APOC1 | APOE | MASP1 | SEPP1 | 0.628 |
| GP1BA | HIST2H2BE | PEPD | SEPP1 | 0.627 |
| APOE | GP1BA | QSOX1 | SEPP1 | 0.627 |
| APOE | HIST2H2BE | MASP1 | SEPP1 | 0.626 |
| APOE | PEPD | SEPP1 | TNXB | 0.625 |
| APOE | GP1BA | MASP1 | SEPP1 | 0.624 |
| APOC1 | APOE | MASP1 | PEPD | 0.619 |
| APOE | GP1BA | HIST2H2BE | SELL | 0.618 |
| APOC1 | GP1BA | HIST2H2BE | SEPP1 | 0.617 |
| HIST2H2BE | PEPD | QSOX1 | SEPP1 | 0.616 |
| APOC1 | HIST2H2BE | MASP1 | PEPD | 0.614 |
| GP1BA | MASP1 | PEPD | QSOX1 | 0.613 |
| APOE | HIST2H2BE | QSOX1 | SEPP1 | 0.611 |
| APOE | GP1BA | PEPD | SEPP1 | 0.611 |
| APOC1 | HIST2H2BE | PEPD | SEPP1 | 0.609 |
| GP1BA | HIST2H2BE | PEPD | QSOX1 | 0.604 |
| APOE | GP1BA | MASP1 | QSOX1 | 0.603 |
| APOC1 | APOE | GP1BA | SEPP1 | 0.603 |
| APOE | MASP1 | PEPD | QSOX1 | 0.603 |
| APOE | PEPD | QSOX1 | SEPP1 | 0.599 |
| APOE | GP1BA | HIST2H2BE | SEPP1 | 0.598 |
| APOE | GP1BA | MASP1 | PEPD | 0.597 |
| APOC1 | APOE | PEPD | SEPP1 | 0.596 |
| APOE | HIST2H2BE | MASP1 | QSOX1 | 0.595 |
| HIST2H2BE | MASP1 | PEPD | QSOX1 | 0.592 |
| APOC1 | APOE | HIST2H2BE | SEPP1 | 0.588 |
| APOE | GP1BA | HIST2H2BE | QSOX1 | 0.588 |
| GP1BA | HIST2H2BE | MASP1 | PEPD | 0.584 |
| APOC1 | APOE | HIST2H2BE | PEPD | 0.584 |
| APOC1 | APOE | GP1BA | HIST2H2BE | 0.582 |
| APOE | GP1BA | HIST2H2BE | PEPD | 0.581 |
| GP1BA | HIST2H2BE | MASP1 | QSOX1 | 0.581 |
| APOE | HIST2H2BE | PEPD | QSOX1 | 0.581 |
| APOC1 | APOE | GP1BA | MASP1 | 0.579 |
| APOC1 | APOE | HIST2H2BE | MASP1 | 0.576 |
| APOE | HIST2H2BE | PEPD | SEPP1 | 0.574 |
| APOE | HIST2H2BE | MASP1 | PEPD | 0.559 |

TABLE 9

HIV+ panels
Individual Candidate Biomarkers

| protein.1 | AUC |
|---|---|
| PGLYRP2 | 0.770 |
| IGFBP6 | 0.766 |
| SEPP1 | 0.704 |
| TAGLN2 | 0.692 |
| APOA1 | 0.681 |
| CPN2 | 0.678 |
| PFN1 | 0.672 |
| APOA4 | 0.671 |
| VASN | 0.656 |
| CD14 | 0.625 |
| CD163 | 0.604 |
| TLN1 | 0.599 |
| VCAM1 | 0.595 |
| CLU | 0.592 |
| S100A8 | 0.531 |
| MST1 | 0.505 |
| S100A9 | 0.463 |

TABLE 10

HIV+ panels
Combination of Two Candidate Biomarkers

| protein.1 | protein.2 | AUC |
|---|---|---|
| CPN2 | MST1 | 0.860 |
| VASN | VCAM1 | 0.817 |
| IGFBP6 | PGLYRP2 | 0.816 |
| PFN1 | S100A8 | 0.803 |
| PGLYRP2 | TAGLN2 | 0.791 |
| PFN1 | PGLYRP2 | 0.790 |
| CD14 | CPN2 | 0.786 |
| PGLYRP2 | VASN | 0.775 |
| MST1 | PGLYRP2 | 0.772 |
| S100A8 | S100A9 | 0.771 |
| IGFBP6 | TAGLN2 | 0.768 |
| PFN1 | S100A9 | 0.767 |
| CD163 | VASN | 0.762 |
| CD14 | PFN1 | 0.760 |
| CD14 | PGLYRP2 | 0.758 |
| IGFBP6 | PFN1 | 0.752 |
| CPN2 | PGLYRP2 | 0.750 |
| PGLYRP2 | VCAM1 | 0.746 |
| S100A8 | TAGLN2 | 0.745 |
| CPN2 | IGFBP6 | 0.745 |
| APOA1 | PGLYRP2 | 0.743 |
| PGLYRP2 | SEPP1 | 0.742 |
| CD163 | PGLYRP2 | 0.742 |
| PFN1 | SEPP1 | 0.738 |
| CD14 | TAGLN2 | 0.738 |
| SEPP1 | TAGLN2 | 0.736 |
| PGLYRP2 | TLN1 | 0.735 |
| APOA4 | TAGLN2 | 0.735 |
| APOA4 | PGLYRP2 | 0.733 |
| CD14 | VASN | 0.730 |
| S100A9 | TAGLN2 | 0.730 |
| CD14 | CLU | 0.729 |
| IGFBP6 | MST1 | 0.729 |
| IGFBP6 | S100A8 | 0.728 |
| CPN2 | TLN1 | 0.725 |
| CLU | MST1 | 0.721 |
| CD14 | IGFBP6 | 0.720 |
| SEPP1 | TLN1 | 0.717 |
| IGFBP6 | S100A9 | 0.713 |
| APOA4 | PFN1 | 0.713 |
| APOA1 | MST1 | 0.709 |
| IGFBP6 | VASN | 0.709 |
| CD163 | SEPP1 | 0.709 |
| APOA1 | PFN1 | 0.708 |
| PGLYRP2 | S100A9 | 0.703 |
| APOA1 | IGFBP6 | 0.703 |
| APOA1 | TAGLN2 | 0.702 |

TABLE 10-continued

HIV+ panels
Combination of Two Candidate Biomarkers

| protein.1 | protein.2 | AUC |
|---|---|---|
| CD163 | IGFBP6 | 0.702 |
| CD163 | CPN2 | 0.699 |
| APOA4 | TLN1 | 0.699 |
| APOA4 | MST1 | 0.699 |
| IGFBP6 | SEPP1 | 0.698 |
| MST1 | SEPP1 | 0.697 |
| MST1 | VASN | 0.696 |
| CLU | PGLYRP2 | 0.695 |
| APOA4 | CD14 | 0.692 |
| IGFBP6 | VCAM1 | 0.691 |
| PGLYRP2 | S100A8 | 0.688 |
| CPN2 | VCAM1 | 0.688 |
| IGFBP6 | TLN1 | 0.688 |
| APOA1 | CD163 | 0.687 |
| APOA4 | IGFBP6 | 0.685 |
| CLU | IGFBP6 | 0.684 |
| MST1 | TAGLN2 | 0.678 |
| CD14 | SEPP1 | 0.677 |
| SEPP1 | VCAM1 | 0.676 |
| TAGLN2 | VASN | 0.674 |
| APOA4 | CD163 | 0.673 |
| MST1 | PFN1 | 0.673 |
| APOA1 | CD14 | 0.672 |
| CPN2 | PFN1 | 0.670 |
| PFN1 | VASN | 0.670 |
| APOA4 | VCAM1 | 0.667 |
| CPN2 | SEPP1 | 0.666 |
| CPN2 | TAGLN2 | 0.666 |
| TAGLN2 | VCAM1 | 0.663 |
| CLU | PFN1 | 0.661 |
| CD163 | TAGLN2 | 0.657 |
| TLN1 | VASN | 0.656 |
| CD163 | PFN1 | 0.655 |
| PFN1 | VCAM1 | 0.655 |
| CLU | TAGLN2 | 0.655 |
| APOA1 | TLN1 | 0.653 |
| CD163 | TLN1 | 0.653 |
| CLU | TLN1 | 0.650 |
| APOA1 | CPN2 | 0.649 |
| CPN2 | S100A8 | 0.649 |
| APOA1 | SEPP1 | 0.647 |
| CLU | VCAM1 | 0.646 |
| S100A8 | TLN1 | 0.645 |
| SEPP1 | VASN | 0.644 |
| CD163 | CLU | 0.644 |
| APOA4 | CPN2 | 0.641 |
| APOA1 | VASN | 0.637 |
| CLU | SEPP1 | 0.632 |
| APOA1 | VCAM1 | 0.631 |
| CPN2 | S100A9 | 0.630 |
| S100A8 | VASN | 0.629 |
| APOA4 | SEPP1 | 0.629 |
| CPN2 | VASN | 0.624 |
| CD14 | TLN1 | 0.623 |
| APOA4 | VASN | 0.618 |
| TLN1 | VCAM1 | 0.617 |
| S100A8 | SEPP1 | 0.616 |
| S100A9 | VASN | 0.615 |
| S100A9 | SEPP1 | 0.613 |
| APOA4 | S100A8 | 0.608 |
| APOA1 | S100A8 | 0.607 |
| S100A9 | TLN1 | 0.606 |
| PFN1 | TAGLN2 | 0.602 |
| APOA1 | S100A9 | 0.598 |
| CD14 | VCAM1 | 0.597 |
| APOA4 | CLU | 0.596 |
| APOA4 | S100A9 | 0.596 |
| CD14 | CD163 | 0.592 |
| APOA1 | APOA4 | 0.583 |
| APOA1 | CLU | 0.581 |
| TAGLN2 | TLN1 | 0.580 |
| CLU | VASN | 0.579 |
| PFN1 | TLN1 | 0.565 |
| S100A8 | VCAM1 | 0.563 |
| CLU | S100A8 | 0.562 |
| CLU | CPN2 | 0.552 |
| CD14 | S100A8 | 0.550 |
| CD163 | S100A8 | 0.549 |
| CD163 | MST1 | 0.547 |
| CD14 | S100A9 | 0.545 |
| CD14 | MST1 | 0.541 |
| MST1 | VCAM1 | 0.538 |
| MST1 | S100A8 | 0.538 |
| MST1 | TLN1 | 0.538 |
| CD163 | VCAM1 | 0.533 |
| CLU | S100A9 | 0.530 |
| S100A9 | VCAM1 | 0.527 |
| CD163 | S100A9 | 0.517 |
| MST1 | S100A9 | 0.489 |

TABLE 11

HIV+ panels
Combination of Three Candidate Biomarkers

| protein.1 | protein.2 | protein.3 | AUC |
|---|---|---|---|
| APOA1 | CPN2 | MST1 | 1.000 |
| CD163 | S100A8 | S100A9 | 1.000 |
| CD163 | TAGLN2 | VASN | 1.000 |
| S100A8 | S100A9 | VCAM1 | 1.000 |
| CPN2 | MST1 | SEPP1 | 1.000 |
| CD163 | TLN1 | VASN | 1.000 |
| CD14 | CPN2 | PFN1 | 1.000 |
| CD163 | PFN1 | VASN | 1.000 |
| CD14 | CLU | PFN1 | 1.000 |
| PFN1 | S100A8 | SEPP1 | 1.000 |
| CPN2 | IGFBP6 | MST1 | 1.000 |
| CD14 | CPN2 | MST1 | 0.999 |
| CPN2 | MST1 | PGLYRP2 | 0.999 |
| CD14 | CLU | TAGLN2 | 0.999 |
| CPN2 | MST1 | PFN1 | 0.999 |
| CD14 | CPN2 | TAGLN2 | 0.999 |
| PFN1 | S100A9 | SEPP1 | 0.999 |
| CD14 | PFN1 | S100A8 | 0.996 |
| CPN2 | MST1 | TLN1 | 0.972 |
| IGFBP6 | PFN1 | S100A8 | 0.938 |
| CPN2 | MST1 | VCAM1 | 0.920 |
| CPN2 | MST1 | S100A8 | 0.919 |
| PFN1 | S100A8 | VCAM1 | 0.912 |
| PGLYRP2 | TAGLN2 | VCAM1 | 0.909 |
| CD14 | PFN1 | PGLYRP2 | 0.906 |
| CPN2 | MST1 | S100A9 | 0.903 |
| CD14 | CPN2 | IGFBP6 | 0.899 |
| CD14 | PGLYRP2 | TAGLN2 | 0.899 |
| CPN2 | IGFBP6 | TLN1 | 0.899 |
| IGFBP6 | PFN1 | S100A9 | 0.896 |
| PFN1 | PGLYRP2 | S100A8 | 0.894 |
| CD14 | CPN2 | TLN1 | 0.894 |
| CD163 | MST1 | VASN | 0.892 |
| PFN1 | PGLYRP2 | VCAM1 | 0.889 |
| APOA4 | CPN2 | MST1 | 0.889 |
| APOA1 | CD163 | PFN1 | 0.887 |
| CPN2 | MST1 | TAGLN2 | 0.886 |
| PFN1 | S100A8 | S100A9 | 0.878 |
| MST1 | PFN1 | S100A8 | 0.871 |
| CD14 | CLU | TLN1 | 0.870 |
| CD14 | CPN2 | S100A9 | 0.869 |
| CD163 | CPN2 | TLN1 | 0.865 |
| CD163 | PFN1 | S100A8 | 0.863 |
| PFN1 | S100A8 | TAGLN2 | 0.862 |
| MST1 | PFN1 | PGLYRP2 | 0.858 |
| MST1 | PGLYRP2 | TAGLN2 | 0.858 |
| CD163 | IGFBP6 | VASN | 0.856 |
| CD163 | CPN2 | MST1 | 0.856 |
| CD14 | TAGLN2 | VASN | 0.854 |
| PGLYRP2 | TAGLN2 | VASN | 0.852 |

TABLE 11-continued

HIV+ panels
Combination of Three Candidate Biomarkers

| protein.1 | protein.2 | protein.3 | AUC |
|---|---|---|---|
| TAGLN2 | VASN | VCAM1 | 0.849 |
| PFN1 | PGLYRP2 | VASN | 0.848 |
| APOA1 | CD14 | PFN1 | 0.843 |
| S100A8 | S100A9 | TAGLN2 | 0.842 |
| APOA1 | PFN1 | S100A8 | 0.839 |
| IGFBP6 | PFN1 | PGLYRP2 | 0.838 |
| CPN2 | PGLYRP2 | TLN1 | 0.837 |
| APOA4 | CD14 | PFN1 | 0.837 |
| CD163 | CLU | TLN1 | 0.837 |
| PFN1 | VASN | VCAM1 | 0.836 |
| IGFBP6 | PGLYRP2 | TAGLN2 | 0.836 |
| CD163 | PFN1 | PGLYRP2 | 0.836 |
| CD14 | CD163 | CPN2 | 0.835 |
| MST1 | VASN | VCAM1 | 0.833 |
| CD14 | PFN1 | S100A9 | 0.833 |
| CD14 | CD163 | VASN | 0.833 |
| CPN2 | MST1 | VASN | 0.832 |
| APOA1 | PFN1 | S100A9 | 0.831 |
| CD14 | IGFBP6 | TAGLN2 | 0.830 |
| APOA1 | CD163 | TAGLN2 | 0.829 |
| CD14 | CPN2 | VASN | 0.827 |
| APOA4 | PFN1 | S100A8 | 0.826 |
| CD163 | PGLYRP2 | VASN | 0.826 |
| CD163 | CPN2 | IGFBP6 | 0.825 |
| CLU | CPN2 | MST1 | 0.823 |
| IGFBP6 | S100A8 | TAGLN2 | 0.823 |
| PFN1 | S100A8 | VASN | 0.822 |
| IGFBP6 | VASN | VCAM1 | 0.822 |
| PFN1 | S100A9 | VCAM1 | 0.822 |
| CPN2 | PFN1 | PGLYRP2 | 0.821 |
| APOA1 | CD14 | TAGLN2 | 0.820 |
| MST1 | PFN1 | S100A9 | 0.817 |
| CD14 | IGFBP6 | PFN1 | 0.817 |
| PGLYRP2 | VASN | VCAM1 | 0.817 |
| PFN1 | PGLYRP2 | S100A9 | 0.816 |
| CD14 | CPN2 | PGLYRP2 | 0.815 |
| PFN1 | S100A9 | VASN | 0.813 |
| S100A8 | TAGLN2 | VCAM1 | 0.812 |
| IGFBP6 | S100A9 | TAGLN2 | 0.812 |
| PGLYRP2 | S100A8 | S100A9 | 0.811 |
| CD163 | SEPP1 | TAGLN2 | 0.811 |
| MST1 | S100A8 | TAGLN2 | 0.810 |
| S100A8 | SEPP1 | TAGLN2 | 0.810 |
| APOA1 | S100A8 | S100A9 | 0.809 |
| CD14 | CPN2 | VCAM1 | 0.809 |
| APOA4 | CD14 | TAGLN2 | 0.809 |
| APOA4 | PFN1 | S100A9 | 0.809 |
| IGFBP6 | S100A8 | S100A9 | 0.808 |
| CPN2 | PGLYRP2 | TAGLN2 | 0.808 |
| S100A9 | SEPP1 | TAGLN2 | 0.808 |
| CPN2 | IGFBP6 | PGLYRP2 | 0.806 |
| CPN2 | PFN1 | S100A8 | 0.805 |
| CD163 | PGLYRP2 | TAGLN2 | 0.804 |
| CPN2 | PFN1 | S100A9 | 0.803 |
| CD14 | S100A8 | TAGLN2 | 0.797 |
| PFN1 | S100A9 | TAGLN2 | 0.794 |
| CD14 | PFN1 | SEPP1 | 0.793 |
| CD163 | CLU | MST1 | 0.793 |
| APOA4 | CD14 | CPN2 | 0.792 |
| MST1 | PFN1 | SEPP1 | 0.792 |
| CPN2 | IGFBP6 | VCAM1 | 0.791 |
| CLU | IGFBP6 | MST1 | 0.790 |
| CLU | PFN1 | S100A8 | 0.790 |
| IGFBP6 | PGLYRP2 | VCAM1 | 0.790 |
| PFN1 | PGLYRP2 | TAGLN2 | 0.790 |
| CD163 | PFN1 | S100A9 | 0.789 |
| CD14 | VASN | VCAM1 | 0.789 |
| CD14 | PFN1 | VASN | 0.789 |
| APOA4 | TAGLN2 | VCAM1 | 0.788 |
| CLU | MST1 | PGLYRP2 | 0.787 |
| CPN2 | IGFBP6 | S100A9 | 0.787 |
| CPN2 | IGFBP6 | S100A8 | 0.786 |
| MST1 | S100A8 | S100A9 | 0.782 |
| CD14 | CPN2 | S100A8 | 0.782 |
| CD163 | PFN1 | SEPP1 | 0.781 |
| CLU | MST1 | VCAM1 | 0.780 |
| MST1 | S100A9 | TAGLN2 | 0.779 |
| S100A9 | TAGLN2 | VCAM1 | 0.779 |
| PFN1 | PGLYRP2 | SEPP1 | 0.778 |
| CD14 | SEPP1 | TAGLN2 | 0.777 |
| PGLYRP2 | TLN1 | VCAM1 | 0.774 |
| APOA4 | CD163 | PFN1 | 0.774 |
| CD163 | IGFBP6 | PGLYRP2 | 0.772 |
| APOA1 | IGFBP6 | PGLYRP2 | 0.772 |
| CD14 | IGFBP6 | PGLYRP2 | 0.772 |
| S100A8 | S100A9 | TLN1 | 0.772 |
| CPN2 | PFN1 | VCAM1 | 0.772 |
| CD14 | CLU | MST1 | 0.771 |
| CPN2 | PGLYRP2 | VASN | 0.771 |
| CD14 | PGLYRP2 | TLN1 | 0.771 |
| IGFBP6 | MST1 | PGLYRP2 | 0.771 |
| APOA1 | PFN1 | PGLYRP2 | 0.771 |
| PFN1 | PGLYRP2 | TLN1 | 0.771 |
| IGFBP6 | PGLYRP2 | TLN1 | 0.769 |
| CPN2 | S100A8 | TAGLN2 | 0.769 |
| PGLYRP2 | SEPP1 | TAGLN2 | 0.769 |
| APOA4 | CD163 | TAGLN2 | 0.768 |
| APOA4 | PGLYRP2 | TAGLN2 | 0.768 |
| IGFBP6 | PGLYRP2 | SEPP1 | 0.767 |
| IGFBP6 | PGLYRP2 | VASN | 0.767 |
| CD14 | CLU | IGFBP6 | 0.767 |
| CD14 | PGLYRP2 | VASN | 0.766 |
| S100A8 | S100A9 | SEPP1 | 0.766 |
| APOA4 | CD163 | TLN1 | 0.766 |
| CD163 | CPN2 | PGLYRP2 | 0.766 |
| APOA4 | S100A8 | S100A9 | 0.765 |
| MST1 | PGLYRP2 | VASN | 0.765 |
| CLU | CPN2 | PGLYRP2 | 0.765 |
| CD163 | MST1 | PGLYRP2 | 0.765 |
| CD163 | VASN | VCAM1 | 0.764 |
| APOA4 | PFN1 | PGLYRP2 | 0.764 |
| APOA4 | CD14 | TLN1 | 0.764 |
| APOA4 | IGFBP6 | PGLYRP2 | 0.764 |
| CD14 | S100A8 | S100A9 | 0.763 |
| TLN1 | VASN | VCAM1 | 0.763 |
| CLU | PFN1 | S100A9 | 0.763 |
| CPN2 | IGFBP6 | TAGLN2 | 0.763 |
| MST1 | PFN1 | VASN | 0.763 |
| CPN2 | IGFBP6 | PFN1 | 0.762 |
| CLU | MST1 | TAGLN2 | 0.761 |
| IGFBP6 | MST1 | VASN | 0.760 |
| CD163 | S100A8 | TAGLN2 | 0.759 |
| CPN2 | S100A8 | S100A9 | 0.759 |
| CD14 | CPN2 | SEPP1 | 0.759 |
| PGLYRP2 | TLN1 | VASN | 0.759 |
| CLU | PGLYRP2 | TLN1 | 0.759 |
| MST1 | PGLYRP2 | SEPP1 | 0.758 |
| APOA1 | MST1 | PGLYRP2 | 0.758 |
| APOA1 | CD163 | VASN | 0.755 |
| CPN2 | PGLYRP2 | VCAM1 | 0.754 |
| IGFBP6 | TAGLN2 | VCAM1 | 0.754 |
| IGFBP6 | PGLYRP2 | S100A9 | 0.754 |
| CD14 | CD163 | CLU | 0.753 |
| APOA4 | CPN2 | TLN1 | 0.753 |
| S100A8 | VASN | VCAM1 | 0.753 |
| APOA4 | IGFBP6 | MST1 | 0.751 |
| APOA1 | CD14 | PGLYRP2 | 0.751 |
| CD14 | S100A9 | TAGLN2 | 0.751 |
| CD14 | CLU | VASN | 0.751 |
| APOA1 | PGLYRP2 | TAGLN2 | 0.750 |
| CLU | PFN1 | PGLYRP2 | 0.750 |
| APOA4 | PGLYRP2 | TLN1 | 0.749 |
| CD14 | MST1 | PGLYRP2 | 0.748 |
| CD14 | PGLYRP2 | VCAM1 | 0.747 |
| CPN2 | PGLYRP2 | SEPP1 | 0.746 |
| CD163 | SEPP1 | TLN1 | 0.745 |
| PGLYRP2 | SEPP1 | VASN | 0.745 |
| CD14 | IGFBP6 | VASN | 0.745 |
| APOA4 | CPN2 | PGLYRP2 | 0.744 |
| MST1 | SEPP1 | TAGLN2 | 0.744 |

TABLE 11-continued

HIV+ panels
Combination of Three Candidate Biomarkers

| protein.1 | protein.2 | protein.3 | AUC |
|---|---|---|---|
| CLU | MST1 | PFN1 | 0.744 |
| IGFBP6 | PFN1 | VCAM1 | 0.744 |
| APOA4 | MST1 | PGLYRP2 | 0.743 |
| MST1 | TAGLN2 | VASN | 0.743 |
| CD163 | PGLYRP2 | TLN1 | 0.743 |
| PFN1 | S100A8 | TLN1 | 0.743 |
| CD14 | CD163 | PGLYRP2 | 0.742 |
| CD163 | IGFBP6 | TAGLN2 | 0.742 |
| PGLYRP2 | S100A9 | TAGLN2 | 0.740 |
| IGFBP6 | TAGLN2 | VASN | 0.740 |
| MST1 | PGLYRP2 | TLN1 | 0.740 |
| CD14 | PGLYRP2 | SEPP1 | 0.740 |
| S100A9 | VASN | VCAM1 | 0.740 |
| APOA4 | MST1 | PFN1 | 0.739 |
| APOA4 | PFN1 | VCAM1 | 0.739 |
| CLU | IGFBP6 | PGLYRP2 | 0.739 |
| IGFBP6 | MST1 | PFN1 | 0.739 |
| CPN2 | S100A9 | TAGLN2 | 0.739 |
| CLU | PGLYRP2 | TAGLN2 | 0.739 |
| PGLYRP2 | SEPP1 | TLN1 | 0.738 |
| IGFBP6 | S100A8 | TLN1 | 0.738 |
| APOA1 | PGLYRP2 | VASN | 0.737 |
| CPN2 | S100A8 | TLN1 | 0.737 |
| CD163 | IGFBP6 | PFN1 | 0.737 |
| CLU | MST1 | TLN1 | 0.737 |
| APOA1 | CD14 | CPN2 | 0.737 |
| APOA4 | VASN | VCAM1 | 0.737 |
| APOA4 | MST1 | TAGLN2 | 0.736 |
| MST1 | PGLYRP2 | VCAM1 | 0.736 |
| APOA4 | S100A8 | TAGLN2 | 0.736 |
| CD14 | CLU | CPN2 | 0.736 |
| APOA4 | CD14 | PGLYRP2 | 0.736 |
| PGLYRP2 | S100A8 | TAGLN2 | 0.735 |
| IGFBP6 | MST1 | TAGLN2 | 0.735 |
| CPN2 | TAGLN2 | VCAM1 | 0.734 |
| IGFBP6 | PGLYRP2 | S100A8 | 0.733 |
| CD163 | MST1 | SEPP1 | 0.733 |
| CLU | MST1 | VASN | 0.732 |
| APOA1 | S100A8 | TAGLN2 | 0.732 |
| S100A8 | TAGLN2 | VASN | 0.731 |
| S100A8 | S100A9 | VASN | 0.730 |
| CPN2 | IGFBP6 | VASN | 0.730 |
| SEPP1 | TAGLN2 | VCAM1 | 0.730 |
| CPN2 | PGLYRP2 | S100A8 | 0.729 |
| CD163 | SEPP1 | VASN | 0.729 |
| S100A9 | TAGLN2 | VASN | 0.729 |
| CPN2 | VASN | VCAM1 | 0.729 |
| APOA1 | IGFBP6 | MST1 | 0.728 |
| CLU | S100A8 | S100A9 | 0.728 |
| CD163 | CPN2 | VASN | 0.728 |
| MST1 | PGLYRP2 | S100A9 | 0.727 |
| APOA4 | CD14 | IGFBP6 | 0.727 |
| CD14 | CD163 | TAGLN2 | 0.727 |
| PFN1 | SEPP1 | VCAM1 | 0.727 |
| CPN2 | TLN1 | VCAM1 | 0.727 |
| APOA1 | CPN2 | PGLYRP2 | 0.726 |
| CD163 | PGLYRP2 | S100A9 | 0.726 |
| APOA1 | CPN2 | IGFBP6 | 0.726 |
| CD163 | S100A9 | TAGLN2 | 0.726 |
| CLU | VASN | VCAM1 | 0.726 |
| APOA1 | CD14 | TLN1 | 0.726 |
| CD14 | CLU | VCAM1 | 0.726 |
| APOA4 | TLN1 | VCAM1 | 0.725 |
| CD14 | CLU | SEPP1 | 0.725 |
| APOA4 | S100A8 | TLN1 | 0.725 |
| CD163 | S100A8 | VASN | 0.724 |
| PGLYRP2 | TAGLN2 | TLN1 | 0.724 |
| CD14 | CLU | PGLYRP2 | 0.724 |
| CPN2 | PGLYRP2 | S100A9 | 0.724 |
| CLU | CPN2 | IGFBP6 | 0.723 |
| CD14 | S100A9 | VASN | 0.722 |
| CD163 | PGLYRP2 | SEPP1 | 0.722 |
| CLU | MST1 | SEPP1 | 0.722 |
| CLU | IGFBP6 | S100A8 | 0.721 |
| CD163 | CLU | VASN | 0.721 |
| CLU | PGLYRP2 | VASN | 0.721 |
| APOA1 | PGLYRP2 | S100A8 | 0.721 |
| APOA4 | S100A9 | TAGLN2 | 0.721 |
| CD14 | CD163 | PFN1 | 0.720 |
| IGFBP6 | PFN1 | TAGLN2 | 0.720 |
| IGFBP6 | SEPP1 | TAGLN2 | 0.719 |
| CLU | IGFBP6 | S100A9 | 0.719 |
| CD14 | SEPP1 | VASN | 0.719 |
| APOA4 | PGLYRP2 | VASN | 0.717 |
| CPN2 | IGFBP6 | SEPP1 | 0.717 |
| APOA4 | IGFBP6 | TLN1 | 0.717 |
| APOA1 | IGFBP6 | TAGLN2 | 0.717 |
| APOA1 | PGLYRP2 | S100A9 | 0.717 |
| PGLYRP2 | S100A9 | VASN | 0.717 |
| CLU | MST1 | S100A8 | 0.716 |
| APOA1 | TAGLN2 | VCAM1 | 0.716 |
| PGLYRP2 | S100A8 | VASN | 0.715 |
| CD163 | S100A9 | VASN | 0.715 |
| SEPP1 | VASN | VCAM1 | 0.715 |
| APOA4 | CD163 | VASN | 0.715 |
| APOA4 | CD14 | VASN | 0.715 |
| CLU | IGFBP6 | TAGLN2 | 0.714 |
| CD14 | SEPP1 | TLN1 | 0.713 |
| MST1 | PGLYRP2 | S100A8 | 0.713 |
| IGFBP6 | PFN1 | SEPP1 | 0.713 |
| CLU | IGFBP6 | VCAM1 | 0.713 |
| PGLYRP2 | SEPP1 | VCAM1 | 0.713 |
| APOA1 | VASN | VCAM1 | 0.712 |
| APOA4 | CPN2 | IGFBP6 | 0.712 |
| APOA1 | IGFBP6 | PFN1 | 0.712 |
| APOA1 | CD163 | MST1 | 0.712 |
| APOA1 | CD163 | TLN1 | 0.711 |
| APOA4 | CD163 | PGLYRP2 | 0.710 |
| APOA4 | S100A9 | TLN1 | 0.710 |
| PFN1 | S100A9 | TLN1 | 0.710 |
| APOA1 | CD163 | IGFBP6 | 0.710 |
| IGFBP6 | S100A8 | VCAM1 | 0.709 |
| CLU | IGFBP6 | TLN1 | 0.709 |
| CLU | S100A9 | TAGLN2 | 0.709 |
| APOA1 | CD163 | PGLYRP2 | 0.709 |
| CPN2 | SEPP1 | TLN1 | 0.709 |
| APOA1 | IGFBP6 | S100A9 | 0.709 |
| IGFBP6 | MST1 | S100A8 | 0.709 |
| CD163 | CLU | IGFBP6 | 0.709 |
| APOA1 | S100A9 | TAGLN2 | 0.708 |
| CLU | PGLYRP2 | VCAM1 | 0.708 |
| CD14 | S100A8 | VASN | 0.708 |
| CLU | S100A8 | TAGLN2 | 0.708 |
| CD163 | IGFBP6 | S100A8 | 0.707 |
| IGFBP6 | S100A8 | VASN | 0.707 |
| APOA1 | IGFBP6 | S100A8 | 0.706 |
| IGFBP6 | S100A8 | SEPP1 | 0.706 |
| CD14 | MST1 | TAGLN2 | 0.705 |
| CLU | TLN1 | VCAM1 | 0.705 |
| IGFBP6 | PFN1 | VASN | 0.705 |
| CD14 | TLN1 | VASN | 0.705 |
| CD14 | PFN1 | TAGLN2 | 0.705 |
| IGFBP6 | S100A9 | VASN | 0.705 |
| APOA4 | MST1 | TLN1 | 0.704 |
| IGFBP6 | MST1 | SEPP1 | 0.704 |
| APOA4 | SEPP1 | TLN1 | 0.704 |
| APOA1 | CD14 | IGFBP6 | 0.704 |
| CLU | PFN1 | VCAM1 | 0.704 |
| APOA4 | CLU | TLN1 | 0.704 |
| CLU | IGFBP6 | PFN1 | 0.703 |
| APOA1 | CLU | MST1 | 0.703 |
| APOA4 | PGLYRP2 | VCAM1 | 0.703 |
| CD14 | MST1 | PFN1 | 0.703 |
| PFN1 | SEPP1 | TLN1 | 0.703 |
| APOA1 | MST1 | TAGLN2 | 0.703 |
| APOA1 | PFN1 | VCAM1 | 0.702 |
| APOA1 | PGLYRP2 | SEPP1 | 0.702 |
| APOA1 | APOA4 | PGLYRP2 | 0.702 |
| APOA4 | CD163 | PGLYRP2 | 0.702 |
| CD14 | CLU | S100A9 | 0.702 |
| CD163 | CLU | PGLYRP2 | 0.702 |

TABLE 11-continued

HIV+ panels
Combination of Three Candidate Biomarkers

| protein.1 | protein.2 | protein.3 | AUC |
|---|---|---|---|
| APOA4 | IGFBP6 | TAGLN2 | 0.702 |
| APOA4 | CD14 | CLU | 0.701 |
| APOA4 | IGFBP6 | PFN1 | 0.701 |
| APOA1 | MST1 | PFN1 | 0.701 |
| MST1 | SEPP1 | TLN1 | 0.700 |
| CD14 | TAGLN2 | VCAM1 | 0.700 |
| MST1 | SEPP1 | VASN | 0.699 |
| CD14 | PGLYRP2 | S100A9 | 0.699 |
| IGFBP6 | TLN1 | VASN | 0.699 |
| APOA1 | PGLYRP2 | TLN1 | 0.699 |
| CD14 | IGFBP6 | S100A8 | 0.699 |
| CD163 | IGFBP6 | SEPP1 | 0.698 |
| CLU | MST1 | S100A9 | 0.697 |
| CLU | TAGLN2 | VCAM1 | 0.697 |
| APOA4 | IGFBP6 | S100A8 | 0.696 |
| PGLYRP2 | S100A9 | TLN1 | 0.696 |
| PGLYRP2 | S100A8 | VCAM1 | 0.696 |
| CD14 | IGFBP6 | SEPP1 | 0.696 |
| APOA4 | PGLYRP2 | S100A8 | 0.696 |
| APOA1 | MST1 | S100A8 | 0.695 |
| APOA4 | PGLYRP2 | S100A9 | 0.695 |
| SEPP1 | TAGLN2 | TLN1 | 0.695 |
| PGLYRP2 | S100A9 | VCAM1 | 0.695 |
| S100A8 | SEPP1 | TLN1 | 0.694 |
| APOA4 | TAGLN2 | TLN1 | 0.694 |
| CD14 | MST1 | VASN | 0.694 |
| CD163 | CPN2 | SEPP1 | 0.694 |
| IGFBP6 | SEPP1 | VCAM1 | 0.694 |
| CD163 | PGLYRP2 | S100A8 | 0.693 |
| CPN2 | S100A9 | TLN1 | 0.693 |
| CD14 | PFN1 | VCAM1 | 0.693 |
| CD163 | PGLYRP2 | VCAM1 | 0.693 |
| IGFBP6 | MST1 | S100A9 | 0.693 |
| MST1 | S100A8 | VASN | 0.692 |
| APOA4 | PFN1 | TLN1 | 0.692 |
| IGFBP6 | TAGLN2 | TLN1 | 0.691 |
| PGLYRP2 | S100A8 | TLN1 | 0.691 |
| APOA1 | CD163 | CPN2 | 0.690 |
| APOA1 | CD14 | CLU | 0.689 |
| APOA4 | PGLYRP2 | SEPP1 | 0.688 |
| APOA4 | IGFBP6 | S100A9 | 0.687 |
| SEPP1 | TLN1 | VCAM1 | 0.686 |
| CD163 | CPN2 | PFN1 | 0.685 |
| APOA4 | IGFBP6 | VCAM1 | 0.685 |
| APOA1 | PGLYRP2 | VCAM1 | 0.684 |
| CD14 | IGFBP6 | MST1 | 0.684 |
| APOA4 | MST1 | SEPP1 | 0.683 |
| CD14 | PGLYRP2 | S100A8 | 0.683 |
| IGFBP6 | SEPP1 | TLN1 | 0.682 |
| CD163 | IGFBP6 | MST1 | 0.682 |
| CLU | PGLYRP2 | SEPP1 | 0.682 |
| S100A9 | SEPP1 | TLN1 | 0.681 |
| APOA1 | CD14 | VASN | 0.681 |
| PGLYRP2 | S100A9 | SEPP1 | 0.680 |
| CD163 | IGFBP6 | TLN1 | 0.680 |
| IGFBP6 | S100A9 | TLN1 | 0.680 |
| APOA4 | CD163 | IGFBP6 | 0.680 |
| IGFBP6 | PFN1 | TLN1 | 0.679 |
| CD14 | IGFBP6 | TLN1 | 0.679 |
| APOA4 | CD163 | CPN2 | 0.679 |
| IGFBP6 | S100A9 | VCAM1 | 0.678 |
| MST1 | SEPP1 | VCAM1 | 0.678 |
| APOA1 | MST1 | VASN | 0.678 |
| MST1 | S100A9 | VASN | 0.678 |
| APOA4 | CLU | MST1 | 0.677 |
| CD163 | CPN2 | TAGLN2 | 0.677 |
| IGFBP6 | TLN1 | VCAM1 | 0.677 |
| APOA4 | TLN1 | VASN | 0.676 |
| APOA4 | MST1 | VASN | 0.676 |
| CD14 | CD163 | SEPP1 | 0.676 |
| CLU | IGFBP6 | VASN | 0.675 |
| CLU | S100A8 | TLN1 | 0.674 |
| CD163 | CLU | PFN1 | 0.674 |
| IGFBP6 | MST1 | VCAM1 | 0.674 |
| S100A8 | TAGLN2 | TLN1 | 0.674 |
| CPN2 | S100A8 | VCAM1 | 0.673 |
| MST1 | TLN1 | VASN | 0.673 |
| APOA1 | IGFBP6 | VASN | 0.673 |
| CD14 | CLU | S100A8 | 0.673 |
| APOA1 | IGFBP6 | VCAM1 | 0.672 |
| CD14 | PFN1 | TLN1 | 0.672 |
| S100A8 | TLN1 | VASN | 0.672 |
| MST1 | S100A8 | SEPP1 | 0.671 |
| APOA1 | MST1 | SEPP1 | 0.671 |
| APOA1 | CD163 | SEPP1 | 0.670 |
| PGLYRP2 | S100A8 | SEPP1 | 0.670 |
| CD14 | IGFBP6 | VCAM1 | 0.670 |
| CD14 | CD163 | IGFBP6 | 0.669 |
| CPN2 | PFN1 | TLN1 | 0.669 |
| APOA4 | CD163 | MST1 | 0.668 |
| APOA1 | CPN2 | TLN1 | 0.667 |
| APOA4 | CLU | PGLYRP2 | 0.667 |
| CLU | PFN1 | SEPP1 | 0.667 |
| CD163 | CPN2 | S100A8 | 0.666 |
| CD163 | IGFBP6 | S100A9 | 0.666 |
| CPN2 | SEPP1 | TAGLN2 | 0.666 |
| APOA4 | MST1 | VCAM1 | 0.665 |
| APOA1 | CLU | PGLYRP2 | 0.665 |
| APOA4 | PFN1 | SEPP1 | 0.665 |
| CPN2 | PFN1 | SEPP1 | 0.664 |
| CPN2 | TAGLN2 | TLN1 | 0.664 |
| APOA4 | CPN2 | VCAM1 | 0.663 |
| APOA4 | CLU | PFN1 | 0.663 |
| APOA1 | IGFBP6 | TLN1 | 0.662 |
| APOA4 | CLU | TAGLN2 | 0.662 |
| APOA4 | CD14 | MST1 | 0.662 |
| SEPP1 | TLN1 | VASN | 0.661 |
| CPN2 | SEPP1 | VCAM1 | 0.661 |
| APOA1 | APOA4 | TLN1 | 0.661 |
| IGFBP6 | S100A9 | SEPP1 | 0.661 |
| APOA1 | MST1 | TLN1 | 0.661 |
| CD163 | CLU | TAGLN2 | 0.660 |
| APOA1 | CLU | IGFBP6 | 0.660 |
| APOA1 | PFN1 | SEPP1 | 0.660 |
| PFN1 | SEPP1 | TAGLN2 | 0.659 |
| IGFBP6 | MST1 | TLN1 | 0.659 |
| APOA1 | CPN2 | VCAM1 | 0.658 |
| APOA4 | SEPP1 | TAGLN2 | 0.657 |
| APOA1 | CPN2 | PFN1 | 0.657 |
| CLU | S100A9 | TLN1 | 0.655 |
| IGFBP6 | SEPP1 | VASN | 0.655 |
| CLU | SEPP1 | TLN1 | 0.655 |
| CD14 | TAGLN2 | TLN1 | 0.654 |
| CLU | IGFBP6 | SEPP1 | 0.654 |
| APOA4 | CD163 | SEPP1 | 0.654 |
| CLU | PGLYRP2 | S100A8 | 0.654 |
| APOA1 | PFN1 | VASN | 0.654 |
| S100A8 | TLN1 | VCAM1 | 0.654 |
| CLU | SEPP1 | TAGLN2 | 0.653 |
| APOA4 | CPN2 | PFN1 | 0.652 |
| CD163 | S100A8 | TLN1 | 0.652 |
| MST1 | S100A9 | SEPP1 | 0.652 |
| CD163 | MST1 | TAGLN2 | 0.651 |
| APOA4 | CLU | IGFBP6 | 0.651 |
| APOA1 | SEPP1 | VCAM1 | 0.651 |
| CLU | PGLYRP2 | S100A9 | 0.651 |
| CPN2 | TLN1 | VASN | 0.651 |
| SEPP1 | TAGLN2 | VASN | 0.651 |
| APOA1 | SEPP1 | TAGLN2 | 0.650 |
| PFN1 | SEPP1 | VASN | 0.650 |
| APOA1 | SEPP1 | TLN1 | 0.650 |
| CD163 | CLU | SEPP1 | 0.649 |
| APOA1 | MST1 | S100A9 | 0.649 |
| CD163 | CPN2 | S100A9 | 0.648 |
| CD14 | IGFBP6 | S100A9 | 0.648 |
| APOA4 | TAGLN2 | VASN | 0.648 |
| CPN2 | S100A9 | VCAM1 | 0.647 |
| S100A9 | TLN1 | VASN | 0.647 |
| APOA1 | CD14 | MST1 | 0.646 |
| APOA4 | CPN2 | TAGLN2 | 0.646 |

TABLE 11-continued

HIV+ panels
Combination of Three Candidate Biomarkers

| protein.1 | protein.2 | protein.3 | AUC |
|---|---|---|---|
| APOA1 | PFN1 | TAGLN2 | 0.646 |
| APOA4 | CD14 | S100A9 | 0.645 |
| CPN2 | PFN1 | TAGLN2 | 0.645 |
| CD163 | CPN2 | VCAM1 | 0.644 |
| CD163 | MST1 | PFN1 | 0.643 |
| APOA1 | IGFBP6 | SEPP1 | 0.643 |
| CD163 | IGFBP6 | VCAM1 | 0.642 |
| APOA1 | CD14 | S100A8 | 0.642 |
| APOA1 | TLN1 | VCAM1 | 0.642 |
| APOA1 | CD163 | S100A9 | 0.641 |
| APOA4 | PFN1 | VASN | 0.640 |
| APOA1 | CPN2 | TAGLN2 | 0.639 |
| CD14 | SEPP1 | VCAM1 | 0.639 |
| APOA1 | CD14 | CD163 | 0.638 |
| CLU | TAGLN2 | TLN1 | 0.638 |
| APOA4 | CD14 | S100A8 | 0.638 |
| APOA1 | APOA4 | PFN1 | 0.638 |
| MST1 | PFN1 | TAGLN2 | 0.638 |
| APOA1 | TAGLN2 | VASN | 0.637 |
| APOA1 | S100A8 | TLN1 | 0.637 |
| APOA4 | IGFBP6 | VASN | 0.637 |
| S100A9 | TAGLN2 | TLN1 | 0.636 |
| APOA1 | APOA4 | MST1 | 0.636 |
| CLU | SEPP1 | VCAM1 | 0.635 |
| APOA4 | CD163 | CLU | 0.635 |
| APOA4 | MST1 | S100A8 | 0.633 |
| APOA1 | CD163 | CLU | 0.633 |
| APOA1 | CLU | PFN1 | 0.633 |
| APOA4 | CD14 | SEPP1 | 0.633 |
| APOA1 | PFN1 | TLN1 | 0.632 |
| APOA1 | APOA4 | IGFBP6 | 0.632 |
| APOA1 | TAGLN2 | TLN1 | 0.632 |
| APOA1 | CD14 | S100A9 | 0.632 |
| APOA4 | SEPP1 | VCAM1 | 0.631 |
| APOA4 | PFN1 | TAGLN2 | 0.631 |
| MST1 | TAGLN2 | VCAM1 | 0.630 |
| APOA4 | CD163 | S100A9 | 0.630 |
| CLU | TLN1 | VASN | 0.630 |
| APOA1 | CD14 | SEPP1 | 0.629 |
| APOA1 | APOA4 | TAGLN2 | 0.629 |
| APOA4 | CD14 | VCAM1 | 0.627 |
| APOA1 | TLN1 | VASN | 0.627 |
| APOA4 | CD14 | CD163 | 0.627 |
| CD163 | S100A8 | SEPP1 | 0.626 |
| APOA1 | S100A9 | TLN1 | 0.626 |
| CD14 | CD163 | TLN1 | 0.625 |
| APOA4 | CD163 | S100A8 | 0.625 |
| CLU | PFN1 | VASN | 0.624 |
| CD163 | SEPP1 | VCAM1 | 0.624 |
| CD14 | S100A8 | TLN1 | 0.623 |
| CPN2 | PFN1 | VASN | 0.622 |
| CD163 | S100A9 | SEPP1 | 0.622 |
| CD163 | TAGLN2 | TLN1 | 0.621 |
| CD163 | S100A9 | TLN1 | 0.621 |
| CLU | S100A8 | VCAM1 | 0.621 |
| CPN2 | S100A8 | SEPP1 | 0.621 |
| MST1 | S100A8 | TLN1 | 0.620 |
| APOA4 | CLU | VCAM1 | 0.620 |
| APOA4 | MST1 | S100A9 | 0.619 |
| S100A9 | TLN1 | VCAM1 | 0.619 |
| CPN2 | TAGLN2 | VASN | 0.619 |
| APOA4 | IGFBP6 | SEPP1 | 0.619 |
| TAGLN2 | TLN1 | VASN | 0.618 |
| APOA1 | CLU | TAGLN2 | 0.618 |
| CD14 | MST1 | SEPP1 | 0.618 |
| APOA4 | S100A9 | VCAM1 | 0.618 |
| CLU | CPN2 | VCAM1 | 0.617 |
| CLU | PFN1 | TLN1 | 0.617 |
| CPN2 | S100A8 | VASN | 0.617 |
| APOA1 | APOA4 | CD163 | 0.617 |
| APOA4 | S100A8 | VCAM1 | 0.616 |
| PFN1 | TAGLN2 | VASN | 0.615 |
| CLU | CPN2 | TLN1 | 0.614 |
| APOA1 | MST1 | VCAM1 | 0.614 |
| CD163 | PFN1 | TLN1 | 0.614 |
| APOA1 | CD14 | S100A8 | 0.613 |
| CPN2 | S100A9 | SEPP1 | 0.613 |
| APOA1 | SEPP1 | VASN | 0.612 |
| CLU | CPN2 | PFN1 | 0.612 |
| CLU | TAGLN2 | VASN | 0.612 |
| PFN1 | TAGLN2 | VCAM1 | 0.611 |
| APOA1 | CLU | VCAM1 | 0.610 |
| CD163 | CLU | CPN2 | 0.610 |
| APOA1 | CPN2 | S100A8 | 0.610 |
| CPN2 | SEPP1 | VASN | 0.609 |
| CD163 | CLU | VCAM1 | 0.608 |
| PFN1 | TLN1 | VASN | 0.608 |
| APOA1 | APOA4 | CD14 | 0.608 |
| MST1 | PFN1 | VCAM1 | 0.607 |
| CPN2 | S100A9 | VASN | 0.607 |
| CD163 | PFN1 | TAGLN2 | 0.607 |
| CD14 | TLN1 | VCAM1 | 0.605 |
| S100A8 | SEPP1 | VASN | 0.605 |
| APOA4 | CPN2 | S100A8 | 0.604 |
| CLU | CPN2 | TAGLN2 | 0.604 |
| APOA1 | CD14 | VCAM1 | 0.604 |
| APOA1 | CD163 | VCAM1 | 0.602 |
| CD163 | TAGLN2 | VCAM1 | 0.602 |
| APOA1 | CLU | TLN1 | 0.602 |
| APOA1 | S100A8 | VASN | 0.600 |
| CLU | PFN1 | TAGLN2 | 0.600 |
| CLU | S100A9 | VCAM1 | 0.599 |
| APOA1 | CPN2 | VASN | 0.599 |
| APOA4 | CD163 | VCAM1 | 0.599 |
| APOA4 | CPN2 | VASN | 0.599 |
| CD14 | S100A9 | SEPP1 | 0.598 |
| APOA1 | CPN2 | S100A9 | 0.598 |
| APOA4 | CPN2 | SEPP1 | 0.598 |
| CD163 | TLN1 | VCAM1 | 0.598 |
| CD163 | CLU | S100A8 | 0.598 |
| CD14 | S100A8 | SEPP1 | 0.597 |
| MST1 | PFN1 | TLN1 | 0.595 |
| S100A8 | SEPP1 | VCAM1 | 0.594 |
| APOA4 | S100A8 | SEPP1 | 0.594 |
| S100A9 | SEPP1 | VASN | 0.594 |
| CD163 | PFN1 | VCAM1 | 0.592 |
| CLU | CPN2 | SEPP1 | 0.591 |
| S100A9 | SEPP1 | VCAM1 | 0.590 |
| APOA1 | APOA4 | VCAM1 | 0.588 |
| TAGLN2 | TLN1 | VCAM1 | 0.588 |
| APOA1 | CPN2 | SEPP1 | 0.588 |
| APOA4 | S100A8 | VASN | 0.587 |
| APOA1 | S100A9 | VASN | 0.586 |
| PFN1 | TLN1 | VCAM1 | 0.586 |
| APOA4 | CPN2 | S100A9 | 0.585 |
| CD14 | S100A9 | TLN1 | 0.585 |
| APOA1 | S100A8 | VCAM1 | 0.584 |
| APOA1 | CLU | CPN2 | 0.583 |
| CD163 | CLU | S100A9 | 0.579 |
| APOA4 | S100A9 | SEPP1 | 0.579 |
| APOA1 | S100A8 | SEPP1 | 0.577 |
| APOA4 | S100A9 | VASN | 0.576 |
| APOA4 | SEPP1 | VASN | 0.576 |
| MST1 | TAGLN2 | TLN1 | 0.575 |
| CLU | SEPP1 | VASN | 0.575 |
| CLU | S100A8 | VASN | 0.575 |
| CD163 | MST1 | TLN1 | 0.574 |
| CLU | S100A8 | SEPP1 | 0.574 |
| MST1 | S100A9 | TLN1 | 0.572 |
| APOA4 | CLU | SEPP1 | 0.569 |
| APOA1 | S100A9 | VCAM1 | 0.569 |
| APOA1 | APOA4 | SEPP1 | 0.568 |
| CLU | S100A9 | VASN | 0.567 |
| APOA1 | S100A9 | SEPP1 | 0.567 |
| PFN1 | TAGLN2 | TLN1 | 0.565 |
| APOA1 | APOA4 | CPN2 | 0.565 |
| APOA1 | APOA4 | S100A8 | 0.564 |
| APOA4 | CLU | S100A8 | 0.562 |
| CLU | S100A9 | SEPP1 | 0.559 |
| APOA1 | APOA4 | S100A9 | 0.557 |

TABLE 11-continued

HIV+ panels
Combination of Three Candidate Biomarkers

| protein.1 | protein.2 | protein.3 | AUC |
|---|---|---|---|
| CLU | CPN2 | S100A8 | 0.555 |
| APOA1 | CLU | SEPP1 | 0.552 |
| APOA1 | APOA4 | VASN | 0.551 |
| APOA4 | CLU | CPN2 | 0.551 |
| APOA4 | CLU | S100A9 | 0.551 |
| APOA4 | CLU | VASN | 0.551 |
| CD14 | MST1 | VCAM1 | 0.551 |
| CD14 | CD163 | VCAM1 | 0.550 |
| CLU | CPN2 | VASN | 0.549 |
| CD14 | S100A8 | VCAM1 | 0.547 |
| CD14 | S100A9 | VCAM1 | 0.545 |
| APOA1 | CLU | S100A8 | 0.542 |
| APOA1 | CLU | VASN | 0.542 |
| CD14 | CD163 | MST1 | 0.540 |
| CD14 | MST1 | TLN1 | 0.540 |
| MST1 | S100A8 | VCAM1 | 0.539 |
| CLU | CPN2 | S100A9 | 0.533 |
| MST1 | TLN1 | VCAM1 | 0.531 |
| CD14 | CD163 | S100A8 | 0.530 |
| APOA1 | CLU | S100A9 | 0.530 |
| CD163 | MST1 | S100A8 | 0.530 |
| APOA1 | APOA4 | CLU | 0.529 |
| CD14 | CD163 | S100A9 | 0.524 |
| CD163 | S100A8 | VCAM1 | 0.518 |
| CD14 | MST1 | S100A8 | 0.517 |
| MST1 | S100A9 | VCAM1 | 0.507 |
| CD14 | MST1 | S100A9 | 0.502 |
| CD163 | MST1 | S100A9 | 0.499 |
| CD163 | MST1 | VCAM1 | 0.493 |
| CD163 | S100A9 | VCAM1 | 0.491 |

TABLE 12

HIV+ panels
Combination of Four Candidate Biomarkers

| protein.1 | protein.2 | protein.3 | protein.4 | AUC |
|---|---|---|---|---|
| APOA1 | APOA4 | CPN2 | MST1 | 1.000 |
| APOA1 | CD14 | CLU | PFN1 | 1.000 |
| APOA1 | CD14 | CPN2 | MST1 | 1.000 |
| APOA1 | CD163 | CPN2 | MST1 | 1.000 |
| APOA1 | CD163 | PFN1 | S100A8 | 1.000 |
| APOA1 | CD163 | PFN1 | VASN | 1.000 |
| APOA1 | CD163 | S100A8 | S100A9 | 1.000 |
| APOA1 | CD163 | TAGLN2 | VASN | 1.000 |
| APOA1 | CD163 | TLN1 | VASN | 1.000 |
| APOA1 | CPN2 | IGFBP6 | MST1 | 1.000 |
| APOA1 | CPN2 | MST1 | PGLYRP2 | 1.000 |
| APOA1 | CPN2 | MST1 | S100A8 | 1.000 |
| APOA1 | CPN2 | MST1 | S100A9 | 1.000 |
| APOA1 | CPN2 | MST1 | VASN | 1.000 |
| APOA1 | CPN2 | MST1 | VCAM1 | 1.000 |
| APOA1 | PFN1 | S100A8 | VCAM1 | 1.000 |
| APOA1 | S100A8 | S100A9 | VCAM1 | 1.000 |
| APOA4 | CD163 | S100A8 | S100A9 | 1.000 |
| APOA4 | CD163 | TAGLN2 | VASN | 1.000 |
| APOA4 | CD163 | TLN1 | VASN | 1.000 |
| APOA4 | CPN2 | MST1 | SEPP1 | 1.000 |
| APOA4 | PFN1 | S100A8 | SEPP1 | 1.000 |
| APOA4 | PFN1 | S100A8 | VCAM1 | 1.000 |
| APOA4 | S100A8 | S100A9 | VCAM1 | 1.000 |
| CD14 | CD163 | CLU | PFN1 | 1.000 |
| CD14 | CD163 | CLU | TAGLN2 | 1.000 |
| CD14 | CD163 | CPN2 | MST1 | 1.000 |
| CD14 | CD163 | CPN2 | PFN1 | 1.000 |
| CD14 | CD163 | CPN2 | TAGLN2 | 1.000 |
| CD14 | CD163 | PFN1 | VASN | 1.000 |
| CD14 | CD163 | S100A8 | S100A9 | 1.000 |
| CD14 | CD163 | TAGLN2 | VASN | 1.000 |
| CD14 | CD163 | TLN1 | VASN | 1.000 |
| CD14 | CLU | CPN2 | MST1 | 1.000 |
| CD14 | CLU | IGFBP6 | PFN1 | 1.000 |
| CD14 | CLU | MST1 | PFN1 | 1.000 |
| CD14 | CLU | PFN1 | PGLYRP2 | 1.000 |
| CD14 | CLU | PFN1 | SEPP1 | 1.000 |
| CD14 | CLU | PFN1 | VCAM1 | 1.000 |
| CD14 | CLU | TAGLN2 | VCAM1 | 1.000 |
| CD14 | CPN2 | IGFBP6 | MST1 | 1.000 |
| CD14 | CPN2 | IGFBP6 | PFN1 | 1.000 |
| CD14 | CPN2 | IGFBP6 | S100A8 | 1.000 |
| CD14 | CPN2 | IGFBP6 | TAGLN2 | 1.000 |
| CD14 | CPN2 | MST1 | PFN1 | 1.000 |
| CD14 | CPN2 | MST1 | PGLYRP2 | 1.000 |
| CD14 | CPN2 | MST1 | TLN1 | 1.000 |
| CD14 | CPN2 | PFN1 | PGLYRP2 | 1.000 |
| CD14 | CPN2 | PFN1 | VCAM1 | 1.000 |
| CD14 | CPN2 | TAGLN2 | VCAM1 | 1.000 |
| CD14 | PFN1 | S100A8 | S100A9 | 1.000 |
| CD14 | PFN1 | S100A8 | TAGLN2 | 1.000 |
| CD14 | S100A8 | S100A9 | VCAM1 | 1.000 |
| CD163 | CLU | MST1 | VASN | 1.000 |
| CD163 | CLU | S100A8 | S100A9 | 1.000 |
| CD163 | CLU | TAGLN2 | VASN | 1.000 |
| CD163 | CLU | TLN1 | VASN | 1.000 |
| CD163 | CPN2 | IGFBP6 | MST1 | 1.000 |
| CD163 | CPN2 | IGFBP6 | TLN1 | 1.000 |
| CD163 | CPN2 | MST1 | SEPP1 | 1.000 |
| CD163 | CPN2 | MST1 | TLN1 | 1.000 |
| CD163 | CPN2 | MST1 | VASN | 1.000 |
| CD163 | CPN2 | TAGLN2 | VASN | 1.000 |
| CD163 | CPN2 | TLN1 | VASN | 1.000 |
| CD163 | IGFBP6 | S100A8 | S100A9 | 1.000 |
| CD163 | IGFBP6 | TAGLN2 | VASN | 1.000 |
| CD163 | IGFBP6 | TLN1 | VASN | 1.000 |
| CD163 | MST1 | TAGLN2 | VASN | 1.000 |
| CD163 | MST1 | TLN1 | VASN | 1.000 |
| CD163 | PFN1 | S100A8 | S100A9 | 1.000 |
| CD163 | PFN1 | S100A8 | SEPP1 | 1.000 |
| CD163 | PFN1 | S100A8 | VASN | 1.000 |
| CD163 | PFN1 | S100A9 | SEPP1 | 1.000 |
| CD163 | PFN1 | S100A9 | VASN | 1.000 |
| CD163 | PFN1 | TAGLN2 | VASN | 1.000 |
| CD163 | PGLYRP2 | S100A8 | S100A9 | 1.000 |
| CD163 | PGLYRP2 | TAGLN2 | VASN | 1.000 |
| CD163 | PGLYRP2 | TLN1 | VASN | 1.000 |
| CD163 | S100A8 | S100A9 | SEPP1 | 1.000 |
| CD163 | S100A8 | S100A9 | TAGLN2 | 1.000 |
| CD163 | S100A8 | S100A9 | TLN1 | 1.000 |
| CD163 | S100A8 | S100A9 | VASN | 1.000 |
| CD163 | S100A8 | S100A9 | VCAM1 | 1.000 |
| CD163 | S100A9 | TAGLN2 | VASN | 1.000 |
| CD163 | S100A9 | TLN1 | VASN | 1.000 |
| CD163 | SEPP1 | TAGLN2 | VASN | 1.000 |
| CD163 | SEPP1 | TLN1 | VASN | 1.000 |
| CD163 | TAGLN2 | TLN1 | VASN | 1.000 |
| CD163 | TAGLN2 | VASN | VCAM1 | 1.000 |
| CLU | CPN2 | MST1 | SEPP1 | 1.000 |
| CLU | PFN1 | S100A8 | VCAM1 | 1.000 |
| CLU | S100A8 | S100A9 | VCAM1 | 1.000 |
| CPN2 | IGFBP6 | MST1 | PFN1 | 1.000 |
| CPN2 | IGFBP6 | MST1 | PGLYRP2 | 1.000 |
| CPN2 | IGFBP6 | MST1 | S100A9 | 1.000 |
| CPN2 | IGFBP6 | MST1 | VCAM1 | 1.000 |
| CPN2 | IGFBP6 | PFN1 | S100A8 | 1.000 |
| CPN2 | MST1 | PFN1 | SEPP1 | 1.000 |
| CPN2 | MST1 | PGLYRP2 | SEPP1 | 1.000 |
| CPN2 | MST1 | PGLYRP2 | VASN | 1.000 |
| CPN2 | MST1 | PGLYRP2 | VCAM1 | 1.000 |
| CPN2 | MST1 | S100A8 | VCAM1 | 1.000 |
| CPN2 | MST1 | S100A9 | SEPP1 | 1.000 |
| CPN2 | MST1 | SEPP1 | TAGLN2 | 1.000 |
| CPN2 | MST1 | SEPP1 | VASN | 1.000 |
| CPN2 | MST1 | SEPP1 | VCAM1 | 1.000 |
| CPN2 | MST1 | TAGLN2 | VCAM1 | 1.000 |
| CPN2 | MST1 | TLN1 | VCAM1 | 1.000 |
| CPN2 | MST1 | VASN | VCAM1 | 1.000 |

TABLE 12-continued

HIV+ panels
Combination of Four Candidate Biomarkers

| protein.1 | protein.2 | protein.3 | protein.4 | AUC |
|---|---|---|---|---|
| CPN2 | PFN1 | S100A8 | VCAM1 | 1.000 |
| CPN2 | S100A8 | S100A9 | VCAM1 | 1.000 |
| IGFBP6 | PFN1 | S100A8 | VCAM1 | 1.000 |
| IGFBP6 | S100A8 | S100A9 | VCAM1 | 1.000 |
| IGFBP6 | TAGLN2 | VASN | VCAM1 | 1.000 |
| MST1 | S100A8 | S100A9 | TAGLN2 | 1.000 |
| MST1 | S100A8 | S100A9 | VCAM1 | 1.000 |
| PFN1 | S100A8 | S100A9 | VCAM1 | 1.000 |
| PFN1 | S100A8 | SEPP1 | VCAM1 | 1.000 |
| PFN1 | S100A8 | TAGLN2 | VCAM1 | 1.000 |
| PFN1 | S100A8 | VASN | VCAM1 | 1.000 |
| PFN1 | S100A9 | SEPP1 | VCAM1 | 1.000 |
| PFN1 | S100A9 | VASN | VCAM1 | 1.000 |
| PGLYRP2 | S100A8 | S100A9 | VCAM1 | 1.000 |
| PGLYRP2 | TAGLN2 | VASN | VCAM1 | 1.000 |
| S100A8 | S100A9 | SEPP1 | VCAM1 | 1.000 |
| S100A8 | S100A9 | TAGLN2 | VCAM1 | 1.000 |
| S100A8 | S100A9 | TLN1 | VCAM1 | 1.000 |
| S100A8 | S100A9 | VASN | VCAM1 | 1.000 |
| S100A8 | SEPP1 | TAGLN2 | VCAM1 | 1.000 |
| S100A8 | TAGLN2 | VASN | VCAM1 | 1.000 |
| S100A9 | TAGLN2 | VASN | VCAM1 | 1.000 |
| APOA1 | CD163 | PFN1 | S100A9 | 1.000 |
| APOA1 | CPN2 | MST1 | PFN1 | 1.000 |
| APOA1 | CPN2 | MST1 | TAGLN2 | 1.000 |
| APOA4 | CPN2 | MST1 | VCAM1 | 1.000 |
| CD163 | TLN1 | VASN | VCAM1 | 1.000 |
| CLU | CPN2 | MST1 | PGLYRP2 | 1.000 |
| CPN2 | IGFBP6 | MST1 | TAGLN2 | 1.000 |
| APOA1 | CLU | CPN2 | MST1 | 1.000 |
| CD163 | S100A8 | SEPP1 | TAGLN2 | 1.000 |
| CD163 | IGFBP6 | PFN1 | S100A8 | 1.000 |
| CPN2 | TAGLN2 | VASN | VCAM1 | 1.000 |
| CD163 | CPN2 | MST1 | PGLYRP2 | 1.000 |
| CD163 | S100A8 | TLN1 | VASN | 1.000 |
| CPN2 | IGFBP6 | MST1 | S100A8 | 1.000 |
| CD14 | CPN2 | MST1 | VASN | 1.000 |
| APOA1 | CPN2 | MST1 | SEPP1 | 1.000 |
| PFN1 | PGLYRP2 | S100A8 | S100A9 | 1.000 |
| CD163 | MST1 | PFN1 | VASN | 1.000 |
| CD163 | PFN1 | PGLYRP2 | VASN | 1.000 |
| PFN1 | PGLYRP2 | VASN | VCAM1 | 1.000 |
| CD14 | IGFBP6 | PFN1 | S100A8 | 1.000 |
| CPN2 | PFN1 | S100A8 | SEPP1 | 1.000 |
| CD163 | IGFBP6 | PFN1 | VASN | 1.000 |
| APOA1 | CPN2 | MST1 | TLN1 | 1.000 |
| CPN2 | MST1 | S100A9 | VCAM1 | 1.000 |
| APOA1 | CD14 | PFN1 | TLN1 | 1.000 |
| CPN2 | IGFBP6 | MST1 | TLN1 | 1.000 |
| CD14 | CPN2 | IGFBP6 | S100A9 | 1.000 |
| CPN2 | IGFBP6 | PFN1 | S100A9 | 1.000 |
| CD14 | CPN2 | PFN1 | S100A8 | 1.000 |
| APOA4 | CD163 | PFN1 | S100A8 | 1.000 |
| APOA4 | CD14 | CPN2 | PFN1 | 1.000 |
| CD163 | S100A8 | TAGLN2 | VASN | 1.000 |
| CD14 | CLU | CPN2 | PFN1 | 1.000 |
| CD14 | CPN2 | PFN1 | TAGLN2 | 1.000 |
| CD163 | PFN1 | TLN1 | VASN | 1.000 |
| CD14 | CPN2 | MST1 | VCAM1 | 1.000 |
| CD14 | CPN2 | PGLYRP2 | TAGLN2 | 1.000 |
| APOA1 | CD14 | CPN2 | PFN1 | 1.000 |
| CD14 | CPN2 | PFN1 | SEPP1 | 1.000 |
| CD163 | PFN1 | SEPP1 | VASN | 1.000 |
| CPN2 | MST1 | S100A8 | S100A9 | 1.000 |
| CPN2 | S100A8 | TAGLN2 | VCAM1 | 1.000 |
| CD14 | CPN2 | PFN1 | VASN | 1.000 |
| CD14 | CLU | PFN1 | S100A8 | 1.000 |
| CD14 | CLU | PFN1 | TAGLN2 | 1.000 |
| CD163 | CPN2 | MST1 | PFN1 | 1.000 |
| PFN1 | S100A8 | S100A9 | SEPP1 | 1.000 |
| CD163 | CPN2 | S100A8 | S100A9 | 1.000 |
| APOA1 | CD14 | PFN1 | S100A8 | 1.000 |
| CD14 | CLU | PGLYRP2 | TAGLN2 | 1.000 |
| CD14 | CLU | PFN1 | S100A9 | 1.000 |
| CD163 | CLU | PFN1 | VASN | 1.000 |
| CD163 | CPN2 | PFN1 | VASN | 1.000 |
| APOA1 | CD14 | CLU | TAGLN2 | 1.000 |
| CPN2 | MST1 | PFN1 | VCAM1 | 1.000 |
| CD163 | PFN1 | S100A8 | TAGLN2 | 1.000 |
| CD14 | CPN2 | PFN1 | S100A9 | 1.000 |
| CPN2 | PFN1 | S100A9 | VCAM1 | 1.000 |
| APOA1 | CD163 | S100A8 | TAGLN2 | 1.000 |
| CPN2 | MST1 | SEPP1 | TLN1 | 1.000 |
| CLU | PFN1 | S100A9 | VCAM1 | 1.000 |
| CPN2 | IGFBP6 | MST1 | SEPP1 | 1.000 |
| CD14 | CPN2 | MST1 | SEPP1 | 1.000 |
| CD14 | CPN2 | MST1 | TAGLN2 | 1.000 |
| CPN2 | MST1 | S100A8 | SEPP1 | 1.000 |
| APOA4 | CD163 | CPN2 | MST1 | 1.000 |
| CPN2 | IGFBP6 | S100A8 | S100A9 | 1.000 |
| CD14 | CLU | IGFBP6 | TAGLN2 | 1.000 |
| CD14 | CLU | PFN1 | VASN | 1.000 |
| APOA4 | PFN1 | S100A9 | SEPP1 | 1.000 |
| CPN2 | IGFBP6 | S100A8 | TAGLN2 | 1.000 |
| S100A9 | SEPP1 | TAGLN2 | VCAM1 | 1.000 |
| CD14 | CPN2 | IGFBP6 | TLN1 | 1.000 |
| IGFBP6 | PFN1 | S100A9 | VASN | 1.000 |
| PFN1 | PGLYRP2 | S100A8 | TAGLN2 | 1.000 |
| CPN2 | IGFBP6 | S100A9 | TAGLN2 | 1.000 |
| IGFBP6 | PFN1 | S100A8 | TAGLN2 | 1.000 |
| CLU | PFN1 | S100A8 | SEPP1 | 1.000 |
| MST1 | PFN1 | S100A8 | S100A9 | 1.000 |
| CD163 | PFN1 | VASN | VCAM1 | 1.000 |
| APOA1 | CD163 | S100A9 | TAGLN2 | 1.000 |
| PFN1 | S100A8 | SEPP1 | VASN | 1.000 |
| APOA4 | CD14 | CLU | PFN1 | 1.000 |
| IGFBP6 | PFN1 | S100A8 | VASN | 1.000 |
| PGLYRP2 | SEPP1 | TAGLN2 | VCAM1 | 1.000 |
| CD14 | IGFBP6 | TAGLN2 | VASN | 1.000 |
| IGFBP6 | PFN1 | S100A9 | TAGLN2 | 1.000 |
| APOA4 | CD163 | PFN1 | VASN | 1.000 |
| CD14 | CLU | MST1 | TAGLN2 | 1.000 |
| PFN1 | PGLYRP2 | S100A9 | VASN | 1.000 |
| CD163 | MST1 | S100A8 | S100A9 | 1.000 |
| CPN2 | MST1 | PFN1 | TAGLN2 | 1.000 |
| CD14 | IGFBP6 | PFN1 | S100A9 | 1.000 |
| PFN1 | PGLYRP2 | S100A8 | VASN | 1.000 |
| APOA4 | TAGLN2 | VASN | VCAM1 | 0.999 |
| APOA1 | PFN1 | S100A8 | SEPP1 | 0.999 |
| CPN2 | MST1 | PGLYRP2 | TLN1 | 0.999 |
| CD14 | PFN1 | S100A8 | SEPP1 | 0.999 |
| PFN1 | PGLYRP2 | S100A8 | VCAM1 | 0.999 |
| IGFBP6 | PFN1 | S100A8 | SEPP1 | 0.999 |
| MST1 | PFN1 | S100A8 | VASN | 0.999 |
| MST1 | S100A8 | TAGLN2 | VASN | 0.999 |
| APOA1 | CD14 | CD163 | TAGLN2 | 0.999 |
| PFN1 | PGLYRP2 | S100A9 | SEPP1 | 0.999 |
| PFN1 | S100A9 | SEPP1 | TAGLN2 | 0.999 |
| MST1 | S100A9 | TAGLN2 | VASN | 0.999 |
| PFN1 | PGLYRP2 | S100A8 | SEPP1 | 0.999 |
| CPN2 | MST1 | PGLYRP2 | S100A9 | 0.999 |
| CLU | CPN2 | MST1 | PFN1 | 0.999 |
| CD14 | PFN1 | S100A8 | VASN | 0.999 |
| APOA4 | CD14 | CPN2 | MST1 | 0.999 |
| CD163 | CPN2 | MST1 | S100A8 | 0.999 |
| APOA4 | CD163 | PFN1 | S100A9 | 0.999 |
| CD14 | CLU | CPN2 | IGFBP6 | 0.999 |
| APOA4 | CD14 | CPN2 | IGFBP6 | 0.999 |
| APOA1 | S100A8 | TAGLN2 | VCAM1 | 0.999 |
| CPN2 | MST1 | S100A8 | TLN1 | 0.999 |
| MST1 | PFN1 | S100A9 | SEPP1 | 0.999 |
| APOA4 | CD14 | CLU | TAGLN2 | 0.999 |
| IGFBP6 | PFN1 | VASN | VCAM1 | 0.999 |
| MST1 | PFN1 | S100A8 | SEPP1 | 0.999 |
| APOA1 | CD163 | PGLYRP2 | TAGLN2 | 0.999 |
| CD14 | CPN2 | SEPP1 | TAGLN2 | 0.999 |
| CD14 | CPN2 | MST1 | S100A8 | 0.999 |
| CLU | PFN1 | S100A9 | SEPP1 | 0.999 |
| PFN1 | PGLYRP2 | S100A9 | VCAM1 | 0.999 |
| CD14 | CPN2 | TAGLN2 | VASN | 0.999 |

TABLE 12-continued

HIV+ panels
Combination of Four Candidate Biomarkers

| protein.1 | protein.2 | protein.3 | protein.4 | AUC |
|---|---|---|---|---|
| CD14 | CPN2 | S100A8 | TAGLN2 | 0.999 |
| CD14 | CLU | CPN2 | TAGLN2 | 0.999 |
| MST1 | PFN1 | S100A9 | VASN | 0.999 |
| CD163 | S100A9 | SEPP1 | TAGLN2 | 0.999 |
| APOA1 | MST1 | PFN1 | S100A8 | 0.999 |
| APOA1 | CD14 | CPN2 | TAGLN2 | 0.999 |
| CLU | S100A8 | TAGLN2 | VCAM1 | 0.999 |
| IGFBP6 | PFN1 | S100A9 | VCAM1 | 0.999 |
| CPN2 | PGLYRP2 | TAGLN2 | VCAM1 | 0.999 |
| IGFBP6 | PFN1 | S100A9 | SEPP1 | 0.999 |
| APOA4 | CPN2 | MST1 | PFN1 | 0.999 |
| APOA1 | PFN1 | S100A9 | VCAM1 | 0.999 |
| CPN2 | MST1 | S100A8 | TAGLN2 | 0.999 |
| CD14 | PFN1 | S100A9 | SEPP1 | 0.999 |
| CPN2 | MST1 | PGLYRP2 | S100A8 | 0.999 |
| CPN2 | IGFBP6 | MST1 | VASN | 0.999 |
| APOA1 | CD163 | MST1 | PFN1 | 0.999 |
| CD14 | CLU | SEPP1 | TAGLN2 | 0.999 |
| CD14 | CLU | TAGLN2 | VASN | 0.999 |
| CD14 | CPN2 | S100A9 | TAGLN2 | 0.999 |
| APOA4 | CPN2 | MST1 | TAGLN2 | 0.999 |
| CPN2 | PFN1 | S100A9 | SEPP1 | 0.999 |
| CD14 | CLU | S100A8 | TAGLN2 | 0.999 |
| APOA4 | CPN2 | MST1 | PGLYRP2 | 0.999 |
| CPN2 | IGFBP6 | TLN1 | VCAM1 | 0.998 |
| CD14 | CD163 | PFN1 | PGLYRP2 | 0.998 |
| CPN2 | MST1 | PGLYRP2 | TAGLN2 | 0.998 |
| IGFBP6 | PFN1 | PGLYRP2 | S100A8 | 0.998 |
| CD14 | CPN2 | MST1 | S100A9 | 0.998 |
| CD14 | CLU | S100A9 | TAGLN2 | 0.998 |
| CD14 | CD163 | CPN2 | TLN1 | 0.998 |
| IGFBP6 | PFN1 | S100A8 | S100A9 | 0.998 |
| CD163 | CPN2 | MST1 | TAGLN2 | 0.998 |
| CD163 | CPN2 | PFN1 | TLN1 | 0.998 |
| CD14 | CPN2 | PFN1 | TLN1 | 0.998 |
| APOA1 | PFN1 | PGLYRP2 | VASN | 0.998 |
| APOA4 | CPN2 | IGFBP6 | MST1 | 0.998 |
| SEPP1 | TAGLN2 | VASN | VCAM1 | 0.998 |
| APOA1 | PFN1 | S100A9 | SEPP1 | 0.998 |
| CLU | TAGLN2 | VASN | VCAM1 | 0.998 |
| APOA4 | CD14 | CPN2 | TAGLN2 | 0.998 |
| CD14 | CPN2 | TAGLN2 | TLN1 | 0.998 |
| PFN1 | S100A8 | SEPP1 | TAGLN2 | 0.998 |
| PFN1 | TAGLN2 | VASN | VCAM1 | 0.998 |
| APOA4 | CD163 | S100A8 | TAGLN2 | 0.998 |
| CPN2 | MST1 | S100A9 | TLN1 | 0.998 |
| CPN2 | MST1 | PFN1 | PGLYRP2 | 0.998 |
| CPN2 | MST1 | S100A9 | TAGLN2 | 0.998 |
| CPN2 | MST1 | PFN1 | VASN | 0.998 |
| CD14 | PFN1 | PGLYRP2 | TLN1 | 0.998 |
| APOA4 | CD14 | PFN1 | S100A8 | 0.998 |
| PFN1 | S100A9 | SEPP1 | VASN | 0.998 |
| CD163 | CLU | MST1 | PFN1 | 0.998 |
| APOA1 | CD163 | MST1 | TAGLN2 | 0.998 |
| CPN2 | MST1 | PFN1 | TLN1 | 0.998 |
| CD14 | S100A8 | S100A9 | TAGLN2 | 0.998 |
| CLU | MST1 | VASN | VCAM1 | 0.997 |
| CPN2 | MST1 | PFN1 | S100A9 | 0.997 |
| CD14 | PFN1 | S100A8 | TLN1 | 0.997 |
| CD14 | CPN2 | PGLYRP2 | S100A9 | 0.997 |
| CD14 | CLU | TAGLN2 | TLN1 | 0.997 |
| CPN2 | MST1 | PFN1 | S100A8 | 0.997 |
| CD14 | PFN1 | S100A8 | VCAM1 | 0.997 |
| CD14 | CD163 | S100A9 | VASN | 0.997 |
| CD163 | CPN2 | TLN1 | VCAM1 | 0.997 |
| CD14 | TAGLN2 | TLN1 | VASN | 0.997 |
| APOA4 | CPN2 | MST1 | TLN1 | 0.997 |
| CD14 | MST1 | PFN1 | S100A8 | 0.997 |
| APOA1 | CD14 | CD163 | PFN1 | 0.997 |
| CPN2 | PGLYRP2 | S100A8 | S100A9 | 0.997 |
| APOA1 | CD14 | TAGLN2 | TLN1 | 0.997 |
| CLU | IGFBP6 | PFN1 | S100A8 | 0.997 |
| CPN2 | MST1 | TLN1 | VASN | 0.997 |
| CLU | MST1 | PFN1 | S100A8 | 0.996 |
| PFN1 | S100A8 | SEPP1 | TLN1 | 0.996 |
| CD163 | PGLYRP2 | SEPP1 | VASN | 0.996 |
| CD163 | CPN2 | PFN1 | S100A8 | 0.996 |
| PFN1 | S100A9 | SEPP1 | VCAM1 | 0.996 |
| CD163 | PFN1 | PGLYRP2 | VCAM1 | 0.996 |
| PFN1 | PGLYRP2 | S100A9 | TAGLN2 | 0.996 |
| CD14 | PFN1 | S100A9 | VASN | 0.996 |
| CD14 | CLU | PFN1 | TLN1 | 0.995 |
| PGLYRP2 | S100A8 | S100A9 | TAGLN2 | 0.995 |
| IGFBP6 | MST1 | PFN1 | S100A8 | 0.995 |
| CLU | PFN1 | S100A8 | TAGLN2 | 0.994 |
| CD163 | CLU | PFN1 | S100A8 | 0.994 |
| CPN2 | PGLYRP2 | TAGLN2 | VASN | 0.994 |
| APOA4 | PFN1 | PGLYRP2 | VCAM1 | 0.994 |
| CD14 | CD163 | S100A8 | VASN | 0.993 |
| APOA1 | CPN2 | IGFBP6 | TLN1 | 0.993 |
| CLU | CPN2 | MST1 | TLN1 | 0.991 |
| CD14 | CD163 | PFN1 | S100A8 | 0.991 |
| CD14 | CPN2 | S100A8 | S100A9 | 0.989 |
| CD14 | CD163 | CPN2 | IGFBP6 | 0.986 |
| CLU | CPN2 | IGFBP6 | MST1 | 0.982 |
| CLU | CPN2 | MST1 | VCAM1 | 0.972 |
| CPN2 | MST1 | TAGLN2 | TLN1 | 0.969 |
| CLU | IGFBP6 | PFN1 | S100A9 | 0.969 |
| APOA1 | IGFBP6 | PFN1 | S100A9 | 0.967 |
| CD163 | CPN2 | PGLYRP2 | TLN1 | 0.967 |
| APOA4 | IGFBP6 | PFN1 | S100A8 | 0.967 |
| MST1 | PFN1 | S100A8 | TAGLN2 | 0.967 |
| APOA4 | CPN2 | IGFBP6 | TLN1 | 0.966 |
| CD163 | PFN1 | PGLYRP2 | TLN1 | 0.966 |
| CD14 | CD163 | CLU | TLN1 | 0.966 |
| APOA1 | IGFBP6 | PFN1 | S100A8 | 0.965 |
| CLU | PGLYRP2 | TAGLN2 | VCAM1 | 0.964 |
| CD14 | IGFBP6 | PFN1 | VASN | 0.959 |
| CD163 | IGFBP6 | PFN1 | S100A9 | 0.959 |
| CD163 | CLU | CPN2 | MST1 | 0.958 |
| CPN2 | IGFBP6 | SEPP1 | TLN1 | 0.957 |
| APOA4 | CD163 | PGLYRP2 | TAGLN2 | 0.956 |
| APOA1 | CD163 | PFN1 | TAGLN2 | 0.956 |
| IGFBP6 | PFN1 | S100A8 | TLN1 | 0.955 |
| CD163 | CLU | PGLYRP2 | TLN1 | 0.955 |
| CLU | S100A9 | TAGLN2 | VCAM1 | 0.955 |
| CD163 | PGLYRP2 | SEPP1 | TAGLN2 | 0.952 |
| PFN1 | PGLYRP2 | TLN1 | VCAM1 | 0.951 |
| CPN2 | IGFBP6 | S100A8 | TLN1 | 0.951 |
| CD163 | MST1 | PFN1 | PGLYRP2 | 0.950 |
| APOA4 | PFN1 | VASN | VCAM1 | 0.947 |
| IGFBP6 | PFN1 | PGLYRP2 | VCAM1 | 0.946 |
| CLU | PFN1 | PGLYRP2 | VCAM1 | 0.945 |
| CD14 | PFN1 | PGLYRP2 | S100A8 | 0.942 |
| CD163 | IGFBP6 | PGLYRP2 | TAGLN2 | 0.939 |
| CD14 | CPN2 | IGFBP6 | PGLYRP2 | 0.937 |
| CD14 | TAGLN2 | VASN | VCAM1 | 0.934 |
| CD14 | IGFBP6 | PFN1 | PGLYRP2 | 0.934 |
| APOA1 | PFN1 | PGLYRP2 | VCAM1 | 0.934 |
| IGFBP6 | PGLYRP2 | TAGLN2 | VCAM1 | 0.933 |
| CD14 | CPN2 | PGLYRP2 | S100A8 | 0.933 |
| CD14 | CPN2 | IGFBP6 | VCAM1 | 0.932 |
| MST1 | PFN1 | S100A8 | VCAM1 | 0.932 |
| CD163 | CPN2 | MST1 | S100A9 | 0.931 |
| CD163 | PFN1 | S100A8 | VCAM1 | 0.931 |
| CD163 | MST1 | PFN1 | S100A8 | 0.930 |
| CD163 | CPN2 | S100A8 | TLN1 | 0.929 |
| IGFBP6 | MST1 | PFN1 | S100A9 | 0.928 |
| CLU | MST1 | PFN1 | S100A9 | 0.928 |
| CD14 | PFN1 | PGLYRP2 | VASN | 0.928 |
| CD163 | CLU | MST1 | TLN1 | 0.927 |
| CLU | PFN1 | S100A9 | TAGLN2 | 0.927 |
| CD14 | PFN1 | VASN | VCAM1 | 0.927 |
| CD163 | PFN1 | PGLYRP2 | S100A9 | 0.927 |
| CLU | CPN2 | MST1 | S100A8 | 0.925 |
| CD163 | PFN1 | S100A9 | TAGLN2 | 0.925 |
| CD163 | CLU | MST1 | TAGLN2 | 0.925 |
| CD14 | IGFBP6 | PGLYRP2 | TAGLN2 | 0.924 |
| APOA4 | CPN2 | MST1 | S100A9 | 0.924 |
| CPN2 | PFN1 | PGLYRP2 | VCAM1 | 0.924 |

TABLE 12-continued

HIV+ panels
Combination of Four Candidate Biomarkers

| protein.1 | protein.2 | protein.3 | protein.4 | AUC |
|---|---|---|---|---|
| APOA4 | IGFBP6 | PFN1 | S100A9 | 0.924 |
| CPN2 | IGFBP6 | TAGLN2 | TLN1 | 0.923 |
| IGFBP6 | PFN1 | PGLYRP2 | S100A9 | 0.923 |
| APOA1 | CD14 | IGFBP6 | PFN1 | 0.923 |
| CD14 | CPN2 | IGFBP6 | SEPP1 | 0.923 |
| CPN2 | MST1 | S100A8 | VASN | 0.922 |
| APOA4 | CPN2 | MST1 | S100A8 | 0.922 |
| APOA4 | CLU | CPN2 | MST1 | 0.922 |
| APOA1 | CD163 | IGFBP6 | TAGLN2 | 0.922 |
| CPN2 | PFN1 | VASN | VCAM1 | 0.922 |
| PFN1 | PGLYRP2 | TAGLN2 | VCAM1 | 0.922 |
| MST1 | S100A8 | SEPP1 | TAGLN2 | 0.921 |
| CD163 | IGFBP6 | PFN1 | PGLYRP2 | 0.920 |
| APOA4 | CD14 | IGFBP6 | PFN1 | 0.920 |
| PFN1 | S100A9 | TAGLN2 | VCAM1 | 0.920 |
| CPN2 | MST1 | TAGLN2 | VASN | 0.920 |
| APOA1 | CD163 | PFN1 | PGLYRP2 | 0.920 |
| CPN2 | MST1 | S100A9 | VASN | 0.919 |
| IGFBP6 | S100A8 | S100A9 | TAGLN2 | 0.919 |
| CPN2 | IGFBP6 | PGLYRP2 | TLN1 | 0.919 |
| CD163 | MST1 | VASN | VCAM1 | 0.918 |
| CLU | MST1 | TLN1 | VCAM1 | 0.918 |
| APOA1 | CD14 | CPN2 | IGFBP6 | 0.917 |
| IGFBP6 | PFN1 | S100A9 | TLN1 | 0.917 |
| APOA4 | CPN2 | IGFBP6 | PGLYRP2 | 0.917 |
| CD14 | PFN1 | PGLYRP2 | SEPP1 | 0.917 |
| CLU | CPN2 | MST1 | S100A9 | 0.916 |
| PFN1 | S100A8 | TLN1 | VCAM1 | 0.916 |
| CPN2 | PFN1 | S100A9 | TAGLN2 | 0.916 |
| CD14 | PFN1 | PGLYRP2 | VCAM1 | 0.915 |
| CD163 | CPN2 | PFN1 | PGLYRP2 | 0.915 |
| CPN2 | PFN1 | PGLYRP2 | S100A8 | 0.914 |
| MST1 | PFN1 | PGLYRP2 | VCAM1 | 0.913 |
| APOA4 | MST1 | PFN1 | S100A8 | 0.913 |
| APOA1 | CD14 | IGFBP6 | TAGLN2 | 0.913 |
| PFN1 | PGLYRP2 | SEPP1 | VCAM1 | 0.913 |
| CD163 | CLU | PFN1 | PGLYRP2 | 0.912 |
| CD163 | CPN2 | SEPP1 | TLN1 | 0.912 |
| CPN2 | IGFBP6 | S100A9 | TLN1 | 0.912 |
| IGFBP6 | S100A8 | TAGLN2 | VCAM1 | 0.911 |
| CD163 | CLU | S100A8 | TLN1 | 0.911 |
| CD163 | MST1 | S100A9 | VASN | 0.910 |
| APOA4 | CD163 | CPN2 | TLN1 | 0.909 |
| CD163 | IGFBP6 | S100A8 | TAGLN2 | 0.909 |
| PFN1 | PGLYRP2 | TLN1 | VASN | 0.909 |
| CPN2 | PFN1 | PGLYRP2 | S100A9 | 0.909 |
| APOA1 | CD14 | CPN2 | PGLYRP2 | 0.908 |
| APOA4 | CD14 | PFN1 | VASN | 0.907 |
| S100A8 | S100A9 | SEPP1 | TAGLN2 | 0.906 |
| CD14 | CPN2 | IGFBP6 | VASN | 0.906 |
| CD163 | CPN2 | PGLYRP2 | TAGLN2 | 0.906 |
| CD163 | CLU | CPN2 | TLN1 | 0.905 |
| CD14 | PGLYRP2 | TAGLN2 | VASN | 0.904 |
| APOA1 | CD163 | CLU | PFN1 | 0.903 |
| APOA1 | CD14 | PFN1 | PGLYRP2 | 0.903 |
| APOA4 | CPN2 | PGLYRP2 | TLN1 | 0.903 |
| CLU | CPN2 | MST1 | TAGLN2 | 0.902 |
| APOA1 | CD163 | MST1 | VASN | 0.902 |
| APOA4 | CD14 | PFN1 | PGLYRP2 | 0.901 |
| APOA4 | PGLYRP2 | TAGLN2 | VCAM1 | 0.900 |
| CD14 | CLU | MST1 | TLN1 | 0.900 |
| APOA4 | PFN1 | S100A8 | S100A9 | 0.899 |
| CD163 | PGLYRP2 | TAGLN2 | VCAM1 | 0.898 |
| APOA4 | CD163 | CLU | TLN1 | 0.898 |
| CD14 | CD163 | CPN2 | VASN | 0.898 |
| CD14 | CD163 | SEPP1 | TAGLN2 | 0.897 |
| CD14 | IGFBP6 | S100A8 | TAGLN2 | 0.897 |
| APOA1 | APOA4 | CD163 | TAGLN2 | 0.896 |
| APOA4 | CD14 | IGFBP6 | TAGLN2 | 0.896 |
| CD163 | IGFBP6 | S100A9 | TAGLN2 | 0.896 |
| CD14 | PFN1 | PGLYRP2 | TAGLN2 | 0.896 |
| PFN1 | S100A8 | S100A9 | TLN1 | 0.895 |
| PFN1 | S100A8 | S100A9 | TAGLN2 | 0.895 |
| PGLYRP2 | S100A8 | TAGLN2 | VCAM1 | 0.894 |
| CPN2 | IGFBP6 | PFN1 | TLN1 | 0.894 |
| CD14 | S100A8 | TAGLN2 | VASN | 0.894 |
| CD163 | CLU | IGFBP6 | TLN1 | 0.892 |
| APOA1 | CD163 | PFN1 | TLN1 | 0.892 |
| APOA4 | PFN1 | S100A8 | TAGLN2 | 0.892 |
| CD14 | S100A9 | TAGLN2 | VASN | 0.892 |
| APOA4 | CD14 | CPN2 | TLN1 | 0.891 |
| CPN2 | S100A8 | S100A9 | SEPP1 | 0.891 |
| CD14 | IGFBP6 | PFN1 | SEPP1 | 0.891 |
| CLU | MST1 | TAGLN2 | VCAM1 | 0.891 |
| CPN2 | PFN1 | PGLYRP2 | TLN1 | 0.890 |
| CD14 | CD163 | PGLYRP2 | TAGLN2 | 0.890 |
| APOA1 | PGLYRP2 | TAGLN2 | VCAM1 | 0.890 |
| APOA4 | CD163 | PFN1 | PGLYRP2 | 0.890 |
| CD163 | CLU | S100A9 | TLN1 | 0.890 |
| CD14 | PFN1 | PGLYRP2 | S100A9 | 0.890 |
| APOA4 | S100A8 | TAGLN2 | VCAM1 | 0.889 |
| CD14 | PGLYRP2 | TAGLN2 | VCAM1 | 0.889 |
| CD163 | MST1 | PGLYRP2 | VASN | 0.889 |
| CD163 | MST1 | PGLYRP2 | TAGLN2 | 0.888 |
| CLU | MST1 | S100A8 | TAGLN2 | 0.888 |
| CPN2 | S100A9 | TAGLN2 | VCAM1 | 0.888 |
| CD14 | IGFBP6 | S100A9 | TAGLN2 | 0.887 |
| APOA1 | CD14 | PGLYRP2 | TAGLN2 | 0.887 |
| CPN2 | PFN1 | S100A8 | TAGLN2 | 0.887 |
| APOA1 | PFN1 | S100A8 | TAGLN2 | 0.887 |
| CD14 | PFN1 | S100A9 | TAGLN2 | 0.887 |
| CD14 | PFN1 | TAGLN2 | VASN | 0.887 |
| CPN2 | IGFBP6 | TAGLN2 | VCAM1 | 0.887 |
| CD14 | PFN1 | SEPP1 | TLN1 | 0.886 |
| CD14 | PGLYRP2 | TAGLN2 | TLN1 | 0.886 |
| CD163 | CPN2 | MST1 | VCAM1 | 0.886 |
| CD14 | IGFBP6 | SEPP1 | TAGLN2 | 0.886 |
| CPN2 | IGFBP6 | TLN1 | VASN | 0.886 |
| CD163 | IGFBP6 | MST1 | VASN | 0.884 |
| CD163 | PFN1 | PGLYRP2 | S100A8 | 0.884 |
| CD14 | MST1 | PFN1 | PGLYRP2 | 0.884 |
| MST1 | PFN1 | S100A9 | TAGLN2 | 0.884 |
| APOA4 | CD14 | PGLYRP2 | TAGLN2 | 0.883 |
| CD163 | MST1 | S100A8 | VASN | 0.883 |
| CPN2 | PGLYRP2 | S100A8 | TAGLN2 | 0.883 |
| CLU | PFN1 | VASN | VCAM1 | 0.882 |
| MST1 | PFN1 | PGLYRP2 | S100A9 | 0.882 |
| CD163 | MST1 | SEPP1 | VASN | 0.882 |
| CLU | PFN1 | S100A8 | S100A9 | 0.882 |
| CD163 | PFN1 | PGLYRP2 | SEPP1 | 0.882 |
| PGLYRP2 | S100A9 | TAGLN2 | VCAM1 | 0.881 |
| CD14 | CPN2 | S100A8 | TLN1 | 0.881 |
| MST1 | PFN1 | PGLYRP2 | S100A8 | 0.880 |
| CPN2 | IGFBP6 | PFN1 | VCAM1 | 0.880 |
| CD14 | MST1 | TAGLN2 | VASN | 0.879 |
| APOA1 | PFN1 | S100A9 | TAGLN2 | 0.879 |
| APOA1 | CD14 | PFN1 | VASN | 0.879 |
| APOA1 | PFN1 | S100A8 | S100A9 | 0.878 |
| PFN1 | S100A8 | TAGLN2 | VASN | 0.878 |
| CD14 | SEPP1 | TAGLN2 | TLN1 | 0.878 |
| MST1 | PFN1 | PGLYRP2 | TAGLN2 | 0.878 |
| APOA1 | CD163 | IGFBP6 | PFN1 | 0.878 |
| CD14 | CPN2 | TLN1 | VASN | 0.877 |
| CPN2 | S100A8 | S100A9 | TAGLN2 | 0.877 |
| APOA1 | TAGLN2 | VASN | VCAM1 | 0.877 |
| MST1 | S100A9 | SEPP1 | TAGLN2 | 0.877 |
| CLU | MST1 | S100A9 | TAGLN2 | 0.877 |
| CPN2 | IGFBP6 | SEPP1 | VCAM1 | 0.876 |
| CLU | MST1 | PFN1 | PGLYRP2 | 0.876 |
| APOA4 | S100A8 | SEPP1 | TAGLN2 | 0.876 |
| CLU | MST1 | PFN1 | VCAM1 | 0.876 |
| MST1 | PGLYRP2 | TAGLN2 | VASN | 0.876 |
| CLU | MST1 | PGLYRP2 | TAGLN2 | 0.876 |
| MST1 | TAGLN2 | VASN | VCAM1 | 0.875 |
| CLU | CPN2 | IGFBP6 | TLN1 | 0.875 |
| MST1 | PFN1 | S100A8 | TLN1 | 0.875 |
| MST1 | S100A9 | VASN | VCAM1 | 0.875 |
| APOA1 | CD14 | TAGLN2 | VASN | 0.875 |
| MST1 | PFN1 | VASN | VCAM1 | 0.874 |
| IGFBP6 | PFN1 | PGLYRP2 | VASN | 0.874 |

TABLE 12-continued

HIV+ panels
Combination of Four Candidate Biomarkers

| protein.1 | protein.2 | protein.3 | protein.4 | AUC |
|---|---|---|---|---|
| CPN2 | PFN1 | PGLYRP2 | VASN | 0.874 |
| MST1 | PFN1 | PGLYRP2 | TLN1 | 0.874 |
| CLU | CPN2 | IGFBP6 | VCAM1 | 0.874 |
| APOA1 | CD14 | CPN2 | TLN1 | 0.874 |
| MST1 | PFN1 | PGLYRP2 | VASN | 0.874 |
| CD14 | CLU | S100A8 | TLN1 | 0.874 |
| PGLYRP2 | TAGLN2 | TLN1 | VCAM1 | 0.874 |
| CD163 | CPN2 | IGFBP6 | PGLYRP2 | 0.873 |
| APOA1 | CD14 | CLU | TLN1 | 0.873 |
| CPN2 | IGFBP6 | VASN | VCAM1 | 0.873 |
| APOA4 | CD14 | PFN1 | SEPP1 | 0.873 |
| CD14 | CLU | SEPP1 | TLN1 | 0.872 |
| CPN2 | PFN1 | S100A8 | S100A9 | 0.872 |
| MST1 | PGLYRP2 | TAGLN2 | VCAM1 | 0.872 |
| CD14 | PGLYRP2 | SEPP1 | TAGLN2 | 0.872 |
| CD14 | CD163 | CLU | VASN | 0.872 |
| PGLYRP2 | S100A8 | S100A9 | TLN1 | 0.872 |
| CD14 | CPN2 | SEPP1 | TLN1 | 0.872 |
| IGFBP6 | MST1 | PGLYRP2 | TAGLN2 | 0.872 |
| CD163 | CLU | PFN1 | TLN1 | 0.871 |
| PFN1 | S100A8 | TAGLN2 | TLN1 | 0.871 |
| CD163 | CPN2 | S100A9 | TLN1 | 0.871 |
| CPN2 | IGFBP6 | PFN1 | PGLYRP2 | 0.871 |
| CD163 | CPN2 | TAGLN2 | TLN1 | 0.871 |
| APOA4 | CD14 | TAGLN2 | VASN | 0.871 |
| CD14 | IGFBP6 | PFN1 | TAGLN2 | 0.871 |
| CD14 | MST1 | PGLYRP2 | TAGLN2 | 0.871 |
| CD14 | CPN2 | S100A9 | TLN1 | 0.870 |
| APOA4 | CLU | MST1 | TAGLN2 | 0.870 |
| CD14 | PGLYRP2 | S100A9 | TAGLN2 | 0.870 |
| APOA1 | MST1 | PFN1 | S100A9 | 0.869 |
| CD14 | PGLYRP2 | S100A8 | TAGLN2 | 0.869 |
| APOA1 | CD163 | CLU | TAGLN2 | 0.869 |
| APOA4 | PFN1 | S100A9 | TAGLN2 | 0.869 |
| APOA4 | CD14 | PFN1 | S100A9 | 0.869 |
| APOA1 | MST1 | PFN1 | PGLYRP2 | 0.869 |
| APOA1 | S100A8 | S100A9 | TAGLN2 | 0.869 |
| PFN1 | SEPP1 | VASN | VCAM1 | 0.868 |
| IGFBP6 | MST1 | S100A8 | TAGLN2 | 0.868 |
| CPN2 | PFN1 | PGLYRP2 | TAGLN2 | 0.868 |
| CLU | PFN1 | PGLYRP2 | S100A8 | 0.868 |
| APOA4 | PFN1 | PGLYRP2 | VASN | 0.868 |
| IGFBP6 | MST1 | PFN1 | PGLYRP2 | 0.868 |
| MST1 | PGLYRP2 | SEPP1 | TAGLN2 | 0.868 |
| APOA4 | CD14 | CLU | TLN1 | 0.867 |
| CLU | PFN1 | PGLYRP2 | VASN | 0.867 |
| CD14 | CPN2 | TLN1 | VCAM1 | 0.867 |
| CD14 | PFN1 | SEPP1 | VASN | 0.867 |
| APOA1 | MST1 | S100A8 | TAGLN2 | 0.867 |
| APOA4 | CD14 | CPN2 | S100A9 | 0.867 |
| APOA1 | IGFBP6 | S100A8 | S100A9 | 0.867 |
| APOA4 | CD163 | MST1 | VASN | 0.867 |
| CD14 | CLU | TLN1 | VCAM1 | 0.867 |
| APOA1 | PFN1 | PGLYRP2 | S100A8 | 0.866 |
| CD14 | IGFBP6 | MST1 | PFN1 | 0.866 |
| APOA1 | CD14 | PFN1 | S100A9 | 0.866 |
| APOA4 | CLU | MST1 | PFN1 | 0.866 |
| APOA1 | MST1 | S100A8 | S100A9 | 0.866 |
| APOA4 | PFN1 | PGLYRP2 | S100A8 | 0.866 |
| CD14 | SEPP1 | TAGLN2 | VASN | 0.866 |
| CPN2 | PGLYRP2 | S100A9 | TAGLN2 | 0.866 |
| CD14 | CD163 | MST1 | VASN | 0.865 |
| CD14 | S100A8 | SEPP1 | TAGLN2 | 0.865 |
| IGFBP6 | S100A9 | TAGLN2 | VCAM1 | 0.865 |
| CPN2 | IGFBP6 | PGLYRP2 | TAGLN2 | 0.865 |
| APOA4 | CPN2 | MST1 | VASN | 0.865 |
| APOA4 | CD163 | S100A9 | TAGLN2 | 0.864 |
| APOA4 | CLU | PFN1 | S100A8 | 0.864 |
| CD14 | CLU | IGFBP6 | TLN1 | 0.864 |
| CD14 | CLU | S100A9 | TLN1 | 0.864 |
| APOA1 | CPN2 | PGLYRP2 | TLN1 | 0.863 |
| APOA1 | CD163 | TAGLN2 | TLN1 | 0.863 |
| PFN1 | PGLYRP2 | TAGLN2 | VASN | 0.863 |
| CD14 | CLU | TLN1 | VASN | 0.862 |
| CD14 | CPN2 | PGLYRP2 | TLN1 | 0.862 |
| CLU | IGFBP6 | MST1 | PFN1 | 0.862 |
| IGFBP6 | S100A8 | TAGLN2 | VASN | 0.862 |
| CD163 | IGFBP6 | S100A8 | VASN | 0.862 |
| MST1 | PGLYRP2 | TAGLN2 | TLN1 | 0.862 |
| MST1 | PFN1 | PGLYRP2 | SEPP1 | 0.862 |
| CD163 | PFN1 | PGLYRP2 | TAGLN2 | 0.862 |
| PFN1 | PGLYRP2 | S100A8 | TLN1 | 0.861 |
| APOA1 | S100A9 | TAGLN2 | VCAM1 | 0.861 |
| CD163 | CPN2 | IGFBP6 | VASN | 0.861 |
| APOA4 | CD14 | SEPP1 | TAGLN2 | 0.861 |
| PGLYRP2 | S100A8 | S100A9 | VASN | 0.861 |
| APOA1 | PFN1 | VASN | VCAM1 | 0.860 |
| MST1 | PGLYRP2 | S100A9 | TAGLN2 | 0.859 |
| PFN1 | PGLYRP2 | S100A9 | TLN1 | 0.859 |
| CD14 | CD163 | CPN2 | S100A9 | 0.859 |
| CLU | CPN2 | IGFBP6 | PGLYRP2 | 0.859 |
| APOA4 | MST1 | PFN1 | S100A9 | 0.859 |
| CD163 | IGFBP6 | S100A9 | VASN | 0.859 |
| CD14 | CLU | CPN2 | TLN1 | 0.858 |
| APOA1 | CPN2 | PFN1 | S100A8 | 0.858 |
| APOA4 | CD14 | CPN2 | S100A8 | 0.858 |
| APOA1 | APOA4 | CD163 | PFN1 | 0.857 |
| IGFBP6 | S100A8 | S100A9 | TLN1 | 0.857 |
| CD163 | PGLYRP2 | TAGLN2 | TLN1 | 0.857 |
| CD14 | CD163 | CPN2 | S100A8 | 0.857 |
| IGFBP6 | PGLYRP2 | S100A8 | TAGLN2 | 0.857 |
| PFN1 | PGLYRP2 | SEPP1 | VASN | 0.857 |
| MST1 | PGLYRP2 | S100A8 | TAGLN2 | 0.856 |
| CD14 | CPN2 | PGLYRP2 | SEPP1 | 0.856 |
| APOA1 | CD163 | CPN2 | PFN1 | 0.856 |
| APOA1 | PGLYRP2 | S100A8 | S100A9 | 0.856 |
| CD14 | CLU | PGLYRP2 | TLN1 | 0.856 |
| CLU | S100A8 | SEPP1 | TAGLN2 | 0.856 |
| PGLYRP2 | TAGLN2 | TLN1 | VASN | 0.855 |
| APOA1 | PFN1 | S100A8 | TLN1 | 0.855 |
| CPN2 | IGFBP6 | PGLYRP2 | VCAM1 | 0.855 |
| PGLYRP2 | TLN1 | VASN | VCAM1 | 0.854 |
| MST1 | TLN1 | VASN | VCAM1 | 0.854 |
| APOA1 | CD163 | PFN1 | VCAM1 | 0.853 |
| APOA1 | CD163 | PFN1 | SEPP1 | 0.853 |
| CD163 | CLU | IGFBP6 | TAGLN2 | 0.853 |
| APOA4 | MST1 | S100A8 | TAGLN2 | 0.853 |
| CD14 | CLU | MST1 | VCAM1 | 0.853 |
| CD14 | PFN1 | TLN1 | VASN | 0.853 |
| CD14 | CPN2 | S100A9 | VCAM1 | 0.852 |
| CD14 | CPN2 | S100A9 | VASN | 0.852 |
| APOA1 | PFN1 | S100A9 | TLN1 | 0.852 |
| CPN2 | S100A8 | SEPP1 | TAGLN2 | 0.852 |
| APOA4 | PFN1 | PGLYRP2 | S100A9 | 0.852 |
| CD163 | CLU | TAGLN2 | TLN1 | 0.851 |
| APOA4 | CD163 | IGFBP6 | VASN | 0.851 |
| CD14 | CPN2 | S100A9 | SEPP1 | 0.851 |
| CD14 | CPN2 | S100A8 | VASN | 0.851 |
| APOA4 | CPN2 | S100A8 | S100A9 | 0.851 |
| CD163 | IGFBP6 | SEPP1 | VASN | 0.851 |
| CD163 | CLU | SEPP1 | TLN1 | 0.851 |
| CLU | S100A9 | SEPP1 | TAGLN2 | 0.850 |
| APOA4 | PFN1 | S100A9 | VCAM1 | 0.850 |
| IGFBP6 | S100A8 | SEPP1 | TAGLN2 | 0.850 |
| APOA1 | CD14 | S100A8 | S100A9 | 0.850 |
| CD14 | CD163 | CLU | MST1 | 0.850 |
| APOA1 | MST1 | S100A9 | TAGLN2 | 0.850 |
| APOA1 | PFN1 | S100A8 | VASN | 0.850 |
| CPN2 | IGFBP6 | S100A9 | VCAM1 | 0.849 |
| APOA4 | CD14 | CPN2 | PGLYRP2 | 0.849 |
| APOA4 | S100A8 | S100A9 | TAGLN2 | 0.849 |
| APOA1 | PFN1 | PGLYRP2 | S100A9 | 0.849 |
| CLU | IGFBP6 | MST1 | VCAM1 | 0.849 |
| CD14 | PFN1 | S100A9 | VCAM1 | 0.849 |
| APOA4 | CPN2 | IGFBP6 | VCAM1 | 0.849 |
| IGFBP6 | MST1 | S100A9 | TAGLN2 | 0.849 |
| CD14 | CD163 | PFN1 | SEPP1 | 0.848 |
| CPN2 | PGLYRP2 | TAGLN2 | TLN1 | 0.848 |
| APOA4 | PGLYRP2 | S100A8 | S100A9 | 0.848 |
| APOA4 | CD163 | PFN1 | SEPP1 | 0.848 |

TABLE 12-continued

HIV+ panels
Combination of Four Candidate Biomarkers

| protein.1 | protein.2 | protein.3 | protein.4 | AUC |
|---|---|---|---|---|
| APOA1 | CLU | PFN1 | S100A8 | 0.848 |
| CD163 | CPN2 | IGFBP6 | S100A9 | 0.848 |
| APOA1 | CD163 | CPN2 | TLN1 | 0.847 |
| CLU | IGFBP6 | S100A8 | TAGLN2 | 0.847 |
| IGFBP6 | MST1 | TAGLN2 | VASN | 0.847 |
| CLU | IGFBP6 | S100A9 | TAGLN2 | 0.846 |
| APOA4 | CD163 | PGLYRP2 | VASN | 0.846 |
| CD163 | CLU | TLN1 | VCAM1 | 0.846 |
| CD14 | CPN2 | PGLYRP2 | VASN | 0.846 |
| CD14 | S100A9 | SEPP1 | TAGLN2 | 0.846 |
| CLU | MST1 | PGLYRP2 | VCAM1 | 0.846 |
| MST1 | PGLYRP2 | VASN | VCAM1 | 0.846 |
| CD163 | IGFBP6 | PGLYRP2 | VASN | 0.845 |
| APOA4 | CD163 | IGFBP6 | TAGLN2 | 0.845 |
| CPN2 | IGFBP6 | S100A8 | VCAM1 | 0.845 |
| CD14 | CLU | CPN2 | S100A8 | 0.845 |
| CPN2 | PGLYRP2 | TLN1 | VCAM1 | 0.845 |
| CLU | MST1 | SEPP1 | TAGLN2 | 0.845 |
| CLU | PGLYRP2 | S100A8 | S100A9 | 0.844 |
| CD14 | CPN2 | S100A8 | VCAM1 | 0.844 |
| APOA1 | CLU | PFN1 | S100A9 | 0.844 |
| CD14 | CD163 | IGFBP6 | VASN | 0.844 |
| CD163 | CLU | PGLYRP2 | TAGLN2 | 0.844 |
| CD14 | CD163 | CPN2 | PGLYRP2 | 0.843 |
| CD14 | CPN2 | PGLYRP2 | VCAM1 | 0.843 |
| APOA4 | CD14 | PFN1 | TLN1 | 0.843 |
| MST1 | PFN1 | SEPP1 | VASN | 0.843 |
| CLU | IGFBP6 | MST1 | TAGLN2 | 0.843 |
| PFN1 | S100A9 | TAGLN2 | VASN | 0.842 |
| APOA1 | CD14 | S100A9 | TAGLN2 | 0.842 |
| CLU | MST1 | S100A8 | TLN1 | 0.842 |
| CLU | MST1 | S100A9 | TLN1 | 0.842 |
| APOA4 | PFN1 | S100A8 | VASN | 0.842 |
| IGFBP6 | PGLYRP2 | S100A8 | S100A9 | 0.842 |
| CPN2 | PGLYRP2 | SEPP1 | TLN1 | 0.841 |
| APOA1 | CD14 | S100A8 | TAGLN2 | 0.840 |
| APOA1 | PGLYRP2 | TAGLN2 | VASN | 0.840 |
| CLU | MST1 | S100A8 | S100A9 | 0.840 |
| APOA1 | CD14 | CPN2 | S100A9 | 0.840 |
| MST1 | S100A8 | VASN | VCAM1 | 0.839 |
| CD163 | CLU | IGFBP6 | MST1 | 0.839 |
| CD163 | CPN2 | IGFBP6 | S100A8 | 0.839 |
| APOA1 | CD163 | IGFBP6 | VASN | 0.839 |
| APOA4 | CLU | PFN1 | S100A9 | 0.839 |
| APOA4 | CD163 | CLU | MST1 | 0.839 |
| CPN2 | S100A9 | SEPP1 | TAGLN2 | 0.839 |
| CD14 | CD163 | VASN | VCAM1 | 0.838 |
| PFN1 | S100A8 | S100A9 | VASN | 0.838 |
| CD163 | CLU | MST1 | PGLYRP2 | 0.838 |
| CD163 | CLU | IGFBP6 | PFN1 | 0.838 |
| S100A8 | S100A9 | SEPP1 | TLN1 | 0.838 |
| CD14 | CPN2 | VASN | VCAM1 | 0.838 |
| S100A8 | SEPP1 | TAGLN2 | TLN1 | 0.837 |
| CD14 | CD163 | IGFBP6 | PFN1 | 0.837 |
| APOA1 | CD163 | PGLYRP2 | VASN | 0.836 |
| APOA4 | CPN2 | IGFBP6 | S100A8 | 0.836 |
| APOA4 | CD14 | S100A8 | TAGLN2 | 0.836 |
| CD163 | IGFBP6 | VASN | VCAM1 | 0.836 |
| IGFBP6 | MST1 | VASN | VCAM1 | 0.835 |
| CLU | CPN2 | PFN1 | PGLYRP2 | 0.835 |
| APOA4 | CD14 | CD163 | TAGLN2 | 0.835 |
| CLU | IGFBP6 | PFN1 | VCAM1 | 0.835 |
| APOA4 | MST1 | VASN | VCAM1 | 0.835 |
| APOA4 | CD14 | CD163 | PFN1 | 0.835 |
| APOA4 | CPN2 | TAGLN2 | VCAM1 | 0.834 |
| APOA4 | CD163 | PGLYRP2 | TLN1 | 0.833 |
| CD14 | S100A8 | TAGLN2 | VCAM1 | 0.833 |
| CD14 | MST1 | PFN1 | SEPP1 | 0.832 |
| CD163 | CPN2 | PFN1 | SEPP1 | 0.832 |
| IGFBP6 | PFN1 | PGLYRP2 | SEPP1 | 0.831 |
| APOA1 | MST1 | PGLYRP2 | TAGLN2 | 0.831 |
| PGLYRP2 | SEPP1 | TAGLN2 | VASN | 0.830 |
| CPN2 | PGLYRP2 | SEPP1 | TAGLN2 | 0.830 |
| CD163 | MST1 | SEPP1 | TAGLN2 | 0.830 |
| IGFBP6 | PGLYRP2 | TAGLN2 | VASN | 0.830 |
| APOA1 | CD163 | SEPP1 | TAGLN2 | 0.829 |
| CPN2 | IGFBP6 | PGLYRP2 | SEPP1 | 0.829 |
| APOA4 | CD163 | MST1 | TAGLN2 | 0.829 |
| PGLYRP2 | SEPP1 | VASN | VCAM1 | 0.829 |
| IGFBP6 | S100A9 | TAGLN2 | VASN | 0.829 |
| APOA1 | CPN2 | S100A8 | S100A9 | 0.829 |
| CD163 | CLU | IGFBP6 | VASN | 0.829 |
| CD163 | PGLYRP2 | S100A8 | VASN | 0.829 |
| CD163 | PGLYRP2 | S100A9 | TAGLN2 | 0.828 |
| CLU | S100A8 | S100A9 | TAGLN2 | 0.828 |
| S100A8 | S100A9 | TAGLN2 | TLN1 | 0.828 |
| CD14 | CD163 | PGLYRP2 | VASN | 0.828 |
| CD14 | PGLYRP2 | TLN1 | VASN | 0.828 |
| CD163 | PGLYRP2 | S100A9 | TLN1 | 0.827 |
| PGLYRP2 | S100A9 | TAGLN2 | VASN | 0.827 |
| CLU | PGLYRP2 | TAGLN2 | VASN | 0.827 |
| CPN2 | PFN1 | PGLYRP2 | SEPP1 | 0.827 |
| CPN2 | PGLYRP2 | S100A9 | TLN1 | 0.827 |
| APOA4 | MST1 | PFN1 | PGLYRP2 | 0.827 |
| MST1 | SEPP1 | TAGLN2 | VASN | 0.827 |
| APOA4 | MST1 | PFN1 | VASN | 0.827 |
| CPN2 | PGLYRP2 | TLN1 | VASN | 0.827 |
| APOA1 | APOA4 | S100A8 | S100A9 | 0.827 |
| CPN2 | S100A8 | S100A9 | TLN1 | 0.827 |
| APOA1 | CD14 | CPN2 | VASN | 0.827 |
| CLU | IGFBP6 | TLN1 | VCAM1 | 0.826 |
| APOA4 | CPN2 | IGFBP6 | S100A9 | 0.826 |
| IGFBP6 | MST1 | PFN1 | VASN | 0.825 |
| S100A9 | SEPP1 | TAGLN2 | TLN1 | 0.825 |
| CLU | PFN1 | S100A8 | VASN | 0.824 |
| CD163 | PGLYRP2 | S100A9 | VASN | 0.824 |
| CD163 | CPN2 | IGFBP6 | PFN1 | 0.824 |
| CD163 | PFN1 | SEPP1 | TLN1 | 0.824 |
| APOA1 | MST1 | VASN | VCAM1 | 0.824 |
| CLU | MST1 | PFN1 | SEPP1 | 0.824 |
| CD14 | IGFBP6 | PFN1 | VCAM1 | 0.824 |
| APOA4 | CD163 | MST1 | PFN1 | 0.823 |
| APOA4 | CD163 | SEPP1 | TAGLN2 | 0.823 |
| CPN2 | PGLYRP2 | S100A8 | TLN1 | 0.823 |
| MST1 | S100A8 | TAGLN2 | VCAM1 | 0.823 |
| CD163 | MST1 | PFN1 | SEPP1 | 0.823 |
| APOA4 | SEPP1 | TAGLN2 | VCAM1 | 0.823 |
| CD14 | CLU | CPN2 | PGLYRP2 | 0.823 |
| APOA1 | PFN1 | S100A9 | VASN | 0.822 |
| CD14 | CLU | CPN2 | VASN | 0.822 |
| APOA4 | PFN1 | S100A9 | VASN | 0.822 |
| CD14 | CD163 | CPN2 | SEPP1 | 0.822 |
| MST1 | PGLYRP2 | TLN1 | VASN | 0.822 |
| APOA4 | CD163 | IGFBP6 | PFN1 | 0.821 |
| CD163 | CLU | CPN2 | PGLYRP2 | 0.821 |
| CD14 | CLU | SEPP1 | VCAM1 | 0.821 |
| APOA1 | CD14 | CD163 | CPN2 | 0.821 |
| APOA1 | CPN2 | PFN1 | PGLYRP2 | 0.821 |
| APOA4 | S100A9 | TAGLN2 | VASN | 0.821 |
| APOA1 | S100A8 | S100A9 | SEPP1 | 0.821 |
| CD14 | CD163 | IGFBP6 | TAGLN2 | 0.821 |
| CD14 | MST1 | S100A8 | TAGLN2 | 0.820 |
| CPN2 | S100A8 | S100A9 | VASN | 0.820 |
| IGFBP6 | PFN1 | PGLYRP2 | TAGLN2 | 0.820 |
| CD14 | CD163 | PFN1 | S100A9 | 0.820 |
| PGLYRP2 | S100A8 | TAGLN2 | VASN | 0.820 |
| CD14 | IGFBP6 | TAGLN2 | TLN1 | 0.820 |
| CPN2 | PFN1 | TAGLN2 | VCAM1 | 0.820 |
| IGFBP6 | PGLYRP2 | S100A9 | TAGLN2 | 0.820 |
| MST1 | PFN1 | TAGLN2 | VASN | 0.820 |
| APOA1 | IGFBP6 | PFN1 | PGLYRP2 | 0.819 |
| CD14 | TLN1 | VASN | VCAM1 | 0.819 |
| APOA4 | PFN1 | S100A8 | TLN1 | 0.819 |
| APOA4 | MST1 | PGLYRP2 | TAGLN2 | 0.819 |
| CLU | MST1 | PGLYRP2 | TLN1 | 0.819 |
| CD163 | CLU | PFN1 | S100A9 | 0.819 |
| APOA4 | CPN2 | PFN1 | PGLYRP2 | 0.819 |
| APOA4 | IGFBP6 | TAGLN2 | VCAM1 | 0.819 |
| CD14 | CD163 | CPN2 | VCAM1 | 0.819 |
| APOA4 | IGFBP6 | PFN1 | PGLYRP2 | 0.819 |

TABLE 12-continued

HIV+ panels
Combination of Four Candidate Biomarkers

| protein.1 | protein.2 | protein.3 | protein.4 | AUC |
|---|---|---|---|---|
| CD14 | MST1 | PFN1 | S100A9 | 0.819 |
| IGFBP6 | TLN1 | VASN | VCAM1 | 0.818 |
| APOA4 | MST1 | PFN1 | SEPP1 | 0.818 |
| APOA1 | CPN2 | IGFBP6 | PGLYRP2 | 0.818 |
| S100A8 | S100A9 | TAGLN2 | VASN | 0.818 |
| CPN2 | PFN1 | S100A8 | TLN1 | 0.818 |
| APOA1 | CD14 | PFN1 | SEPP1 | 0.817 |
| APOA1 | CD163 | CPN2 | TAGLN2 | 0.817 |
| CLU | CPN2 | PGLYRP2 | TAGLN2 | 0.817 |
| APOA4 | CD163 | SEPP1 | TLN1 | 0.817 |
| APOA1 | IGFBP6 | PGLYRP2 | TAGLN2 | 0.817 |
| CD163 | SEPP1 | TAGLN2 | TLN1 | 0.817 |
| CLU | IGFBP6 | TAGLN2 | VCAM1 | 0.816 |
| APOA4 | IGFBP6 | PGLYRP2 | TAGLN2 | 0.816 |
| IGFBP6 | S100A9 | SEPP1 | TAGLN2 | 0.816 |
| CD14 | MST1 | VASN | VCAM1 | 0.816 |
| APOA1 | APOA4 | PFN1 | S100A8 | 0.816 |
| MST1 | SEPP1 | VASN | VCAM1 | 0.816 |
| CD14 | IGFBP6 | MST1 | TAGLN2 | 0.816 |
| TAGLN2 | TLN1 | VASN | VCAM1 | 0.816 |
| IGFBP6 | PGLYRP2 | SEPP1 | TAGLN2 | 0.815 |
| APOA4 | CD14 | TAGLN2 | TLN1 | 0.815 |
| APOA1 | CPN2 | IGFBP6 | VCAM1 | 0.815 |
| CD14 | CD163 | SEPP1 | VASN | 0.815 |
| IGFBP6 | SEPP1 | VASN | VCAM1 | 0.815 |
| IGFBP6 | PGLYRP2 | VASN | VCAM1 | 0.815 |
| APOA1 | CD14 | PGLYRP2 | TLN1 | 0.815 |
| CD163 | CPN2 | PFN1 | S100A9 | 0.814 |
| CPN2 | IGFBP6 | PGLYRP2 | VASN | 0.814 |
| APOA4 | PGLYRP2 | SEPP1 | TAGLN2 | 0.814 |
| CD14 | IGFBP6 | PFN1 | TLN1 | 0.814 |
| CLU | CPN2 | PGLYRP2 | VCAM1 | 0.814 |
| CPN2 | PFN1 | S100A8 | VASN | 0.814 |
| APOA4 | CD14 | PGLYRP2 | TLN1 | 0.814 |
| APOA1 | CD14 | CD163 | VASN | 0.814 |
| APOA1 | CD14 | CPN2 | VCAM1 | 0.813 |
| CD14 | CLU | MST1 | VASN | 0.813 |
| CD14 | IGFBP6 | TAGLN2 | VCAM1 | 0.813 |
| APOA1 | CD163 | CPN2 | IGFBP6 | 0.813 |
| CD163 | PFN1 | S100A8 | TLN1 | 0.813 |
| CLU | IGFBP6 | S100A8 | S100A9 | 0.812 |
| APOA4 | IGFBP6 | MST1 | PFN1 | 0.812 |
| CD163 | CLU | PGLYRP2 | VASN | 0.812 |
| CLU | MST1 | PFN1 | VASN | 0.812 |
| APOA4 | PFN1 | PGLYRP2 | SEPP1 | 0.812 |
| CD163 | MST1 | S100A8 | TAGLN2 | 0.812 |
| APOA4 | MST1 | S100A9 | TAGLN2 | 0.812 |
| APOA4 | S100A9 | SEPP1 | TAGLN2 | 0.812 |
| CD163 | CPN2 | IGFBP6 | TAGLN2 | 0.811 |
| APOA4 | CD14 | CPN2 | VASN | 0.811 |
| CPN2 | IGFBP6 | PGLYRP2 | S100A9 | 0.811 |
| CD14 | CLU | MST1 | PGLYRP2 | 0.811 |
| CD14 | MST1 | PFN1 | VASN | 0.811 |
| APOA1 | PGLYRP2 | VASN | VCAM1 | 0.811 |
| MST1 | PFN1 | S100A9 | VCAM1 | 0.811 |
| APOA1 | APOA4 | CD14 | CPN2 | 0.810 |
| CLU | CPN2 | IGFBP6 | PFN1 | 0.810 |
| APOA1 | IGFBP6 | S100A8 | TAGLN2 | 0.810 |
| CD14 | PFN1 | SEPP1 | VCAM1 | 0.810 |
| APOA4 | PFN1 | PGLYRP2 | TLN1 | 0.810 |
| APOA4 | PGLYRP2 | TLN1 | VCAM1 | 0.810 |
| CD163 | PGLYRP2 | S100A8 | TAGLN2 | 0.810 |
| CLU | IGFBP6 | PGLYRP2 | TAGLN2 | 0.810 |
| IGFBP6 | PFN1 | PGLYRP2 | TLN1 | 0.809 |
| CLU | CPN2 | MST1 | VASN | 0.809 |
| APOA4 | IGFBP6 | S100A8 | S100A9 | 0.809 |
| APOA4 | PGLYRP2 | TAGLN2 | VASN | 0.809 |
| PGLYRP2 | S100A8 | SEPP1 | TAGLN2 | 0.809 |
| APOA4 | CD14 | CD163 | VASN | 0.809 |
| PFN1 | TLN1 | VASN | VCAM1 | 0.808 |
| CLU | CPN2 | PGLYRP2 | TLN1 | 0.808 |
| APOA1 | IGFBP6 | VASN | VCAM1 | 0.808 |
| CD14 | IGFBP6 | VASN | VCAM1 | 0.808 |
| APOA4 | S100A8 | S100A9 | SEPP1 | 0.808 |
| APOA1 | CLU | S100A8 | S100A9 | 0.808 |
| CD14 | MST1 | SEPP1 | TAGLN2 | 0.807 |
| CD163 | CLU | CPN2 | IGFBP6 | 0.807 |
| CD14 | CLU | IGFBP6 | MST1 | 0.807 |
| CD14 | CD163 | CLU | CPN2 | 0.806 |
| CD14 | PFN1 | S100A9 | TLN1 | 0.805 |
| APOA1 | CD14 | CLU | MST1 | 0.805 |
| APOA4 | CLU | CPN2 | PGLYRP2 | 0.805 |
| APOA4 | MST1 | S100A8 | S100A9 | 0.805 |
| CD163 | CPN2 | PGLYRP2 | VASN | 0.805 |
| CD163 | CPN2 | IGFBP6 | VCAM1 | 0.805 |
| CD14 | CPN2 | SEPP1 | VASN | 0.804 |
| CD14 | CLU | S100A9 | VCAM1 | 0.804 |
| APOA4 | CPN2 | PFN1 | S100A8 | 0.804 |
| PGLYRP2 | S100A8 | S100A9 | SEPP1 | 0.804 |
| CLU | PGLYRP2 | TLN1 | VCAM1 | 0.804 |
| APOA4 | PGLYRP2 | SEPP1 | TLN1 | 0.804 |
| APOA4 | IGFBP6 | PGLYRP2 | TLN1 | 0.803 |
| CD14 | CD163 | PGLYRP2 | S100A9 | 0.803 |
| APOA1 | CD163 | IGFBP6 | S100A9 | 0.803 |
| CPN2 | PFN1 | SEPP1 | VCAM1 | 0.803 |
| CLU | CPN2 | PGLYRP2 | S100A9 | 0.803 |
| CD163 | PGLYRP2 | VASN | VCAM1 | 0.803 |
| CPN2 | IGFBP6 | PGLYRP2 | S100A8 | 0.802 |
| CLU | IGFBP6 | PFN1 | PGLYRP2 | 0.802 |
| CD14 | S100A8 | S100A9 | TLN1 | 0.802 |
| APOA4 | CD163 | TAGLN2 | TLN1 | 0.802 |
| APOA4 | S100A8 | S100A9 | TLN1 | 0.802 |
| APOA4 | CD14 | IGFBP6 | TLN1 | 0.801 |
| CLU | CPN2 | PFN1 | S100A8 | 0.801 |
| MST1 | PFN1 | SEPP1 | TLN1 | 0.801 |
| APOA4 | CD14 | CD163 | CPN2 | 0.801 |
| APOA1 | CD14 | SEPP1 | TAGLN2 | 0.800 |
| MST1 | PGLYRP2 | S100A8 | S100A9 | 0.800 |
| CD14 | CLU | MST1 | SEPP1 | 0.800 |
| CD163 | IGFBP6 | PFN1 | TLN1 | 0.800 |
| CPN2 | PFN1 | S100A9 | VASN | 0.800 |
| APOA4 | CD14 | TLN1 | VASN | 0.799 |
| CLU | IGFBP6 | MST1 | TLN1 | 0.799 |
| APOA1 | S100A8 | S100A9 | TLN1 | 0.799 |
| APOA1 | CD14 | TLN1 | VASN | 0.798 |
| CD163 | PFN1 | S100A9 | VCAM1 | 0.798 |
| CD163 | IGFBP6 | PGLYRP2 | S100A9 | 0.798 |
| PFN1 | S100A9 | TLN1 | VCAM1 | 0.798 |
| APOA1 | CD14 | TAGLN2 | VCAM1 | 0.798 |
| CLU | MST1 | PGLYRP2 | VASN | 0.798 |
| APOA1 | CLU | PGLYRP2 | TLN1 | 0.797 |
| IGFBP6 | S100A9 | VASN | VCAM1 | 0.797 |
| APOA4 | CLU | TAGLN2 | VCAM1 | 0.797 |
| APOA4 | CD163 | PFN1 | TLN1 | 0.797 |
| APOA1 | CPN2 | PFN1 | VCAM1 | 0.797 |
| APOA4 | MST1 | TAGLN2 | TLN1 | 0.797 |
| APOA1 | CD14 | MST1 | PFN1 | 0.797 |
| CD14 | CLU | IGFBP6 | S100A9 | 0.797 |
| S100A8 | SEPP1 | TAGLN2 | VASN | 0.796 |
| APOA1 | CD14 | PFN1 | TAGLN2 | 0.796 |
| APOA1 | IGFBP6 | S100A9 | TAGLN2 | 0.796 |
| CD163 | IGFBP6 | PFN1 | SEPP1 | 0.796 |
| APOA4 | CLU | MST1 | VCAM1 | 0.796 |
| APOA1 | CD14 | PFN1 | VCAM1 | 0.796 |
| APOA1 | S100A8 | S100A9 | VASN | 0.796 |
| CD14 | CPN2 | SEPP1 | VCAM1 | 0.796 |
| CD163 | IGFBP6 | PGLYRP2 | S100A8 | 0.796 |
| APOA4 | CPN2 | PFN1 | VCAM1 | 0.796 |
| CLU | MST1 | S100A8 | VCAM1 | 0.796 |
| APOA4 | CD14 | CPN2 | SEPP1 | 0.796 |
| APOA1 | CD163 | CLU | TLN1 | 0.796 |
| CD14 | CPN2 | S100A8 | SEPP1 | 0.796 |
| CLU | CPN2 | PGLYRP2 | S100A8 | 0.796 |
| APOA1 | APOA4 | CD14 | PFN1 | 0.795 |
| APOA1 | CD163 | CPN2 | SEPP1 | 0.795 |
| APOA1 | CPN2 | IGFBP6 | TAGLN2 | 0.795 |
| IGFBP6 | S100A8 | S100A9 | SEPP1 | 0.795 |
| CLU | IGFBP6 | VASN | VCAM1 | 0.795 |
| CPN2 | S100A8 | TAGLN2 | TLN1 | 0.795 |

TABLE 12-continued

HIV+ panels
Combination of Four Candidate Biomarkers

| protein.1 | protein.2 | protein.3 | protein.4 | AUC |
|---|---|---|---|---|
| CLU | MST1 | SEPP1 | VCAM1 | 0.795 |
| IGFBP6 | MST1 | PFN1 | SEPP1 | 0.794 |
| CD163 | IGFBP6 | SEPP1 | TAGLN2 | 0.794 |
| CD163 | MST1 | PFN1 | S100A9 | 0.794 |
| APOA4 | MST1 | PFN1 | TLN1 | 0.794 |
| CLU | CPN2 | IGFBP6 | TAGLN2 | 0.794 |
| CD14 | CLU | PGLYRP2 | S100A9 | 0.793 |
| S100A9 | SEPP1 | TAGLN2 | VASN | 0.793 |
| CLU | PFN1 | PGLYRP2 | TLN1 | 0.793 |
| CLU | S100A8 | S100A9 | TLN1 | 0.793 |
| APOA4 | CPN2 | PFN1 | S100A9 | 0.793 |
| S100A8 | TLN1 | VASN | VCAM1 | 0.793 |
| APOA4 | CD14 | MST1 | PFN1 | 0.793 |
| APOA4 | MST1 | SEPP1 | TAGLN2 | 0.792 |
| CPN2 | PFN1 | TLN1 | VCAM1 | 0.792 |
| CD163 | PFN1 | SEPP1 | TAGLN2 | 0.792 |
| CD14 | CLU | CPN2 | S100A8 | 0.792 |
| CLU | MST1 | PGLYRP2 | SEPP1 | 0.792 |
| APOA4 | IGFBP6 | VASN | VCAM1 | 0.792 |
| APOA4 | CD14 | PFN1 | TAGLN2 | 0.792 |
| APOA1 | APOA4 | PFN1 | PGLYRP2 | 0.791 |
| APOA4 | IGFBP6 | S100A8 | TAGLN2 | 0.791 |
| PGLYRP2 | S100A9 | SEPP1 | TAGLN2 | 0.791 |
| APOA1 | APOA4 | PFN1 | S100A9 | 0.791 |
| IGFBP6 | SEPP1 | TAGLN2 | VCAM1 | 0.791 |
| APOA4 | PFN1 | S100A9 | TLN1 | 0.790 |
| APOA4 | CD14 | S100A9 | TAGLN2 | 0.790 |
| APOA4 | CD14 | CLU | MST1 | 0.790 |
| APOA1 | S100A8 | SEPP1 | TAGLN2 | 0.790 |
| APOA4 | CLU | IGFBP6 | TLN1 | 0.790 |
| APOA4 | CD14 | PFN1 | VCAM1 | 0.790 |
| PFN1 | PGLYRP2 | SEPP1 | TAGLN2 | 0.789 |
| APOA4 | IGFBP6 | S100A8 | TLN1 | 0.789 |
| APOA1 | APOA4 | CD163 | VASN | 0.789 |
| CD14 | CLU | IGFBP6 | VCAM1 | 0.789 |
| IGFBP6 | S100A8 | VASN | VCAM1 | 0.789 |
| S100A9 | TLN1 | VASN | VCAM1 | 0.789 |
| CPN2 | PFN1 | S100A9 | TLN1 | 0.789 |
| APOA1 | CPN2 | PFN1 | S100A9 | 0.789 |
| MST1 | S100A8 | S100A9 | TLN1 | 0.789 |
| CD163 | MST1 | PGLYRP2 | S100A9 | 0.789 |
| CD163 | SEPP1 | TAGLN2 | VCAM1 | 0.788 |
| CD163 | CLU | MST1 | S100A9 | 0.788 |
| CPN2 | S100A8 | TLN1 | VCAM1 | 0.788 |
| CD163 | CLU | MST1 | S100A8 | 0.787 |
| CD163 | PGLYRP2 | SEPP1 | TLN1 | 0.787 |
| CD163 | CLU | S100A8 | TAGLN2 | 0.787 |
| CD163 | PFN1 | S100A9 | TLN1 | 0.787 |
| CD163 | CLU | SEPP1 | TAGLN2 | 0.787 |
| APOA4 | CD163 | CLU | PFN1 | 0.787 |
| APOA4 | CD14 | TAGLN2 | VCAM1 | 0.787 |
| APOA1 | CPN2 | TAGLN2 | VCAM1 | 0.787 |
| APOA4 | MST1 | PGLYRP2 | TLN1 | 0.787 |
| IGFBP6 | MST1 | SEPP1 | TAGLN2 | 0.787 |
| CD14 | PGLYRP2 | VASN | VCAM1 | 0.787 |
| CPN2 | IGFBP6 | PFN1 | TAGLN2 | 0.786 |
| APOA4 | CD163 | IGFBP6 | TLN1 | 0.786 |
| APOA1 | IGFBP6 | MST1 | TAGLN2 | 0.786 |
| CD163 | CPN2 | S100A8 | TAGLN2 | 0.786 |
| CLU | S100A8 | TLN1 | VCAM1 | 0.786 |
| CD163 | CLU | PFN1 | SEPP1 | 0.786 |
| CPN2 | PGLYRP2 | VASN | VCAM1 | 0.785 |
| MST1 | S100A8 | TLN1 | VASN | 0.785 |
| APOA1 | CD163 | TAGLN2 | VCAM1 | 0.785 |
| IGFBP6 | S100A8 | TAGLN2 | TLN1 | 0.785 |
| PGLYRP2 | S100A9 | VASN | VCAM1 | 0.785 |
| IGFBP6 | S100A8 | S100A9 | VASN | 0.784 |
| CPN2 | IGFBP6 | PFN1 | VASN | 0.784 |
| APOA4 | IGFBP6 | MST1 | TAGLN2 | 0.784 |
| IGFBP6 | MST1 | S100A8 | S100A9 | 0.784 |
| CLU | PFN1 | S100A8 | TLN1 | 0.784 |
| APOA4 | IGFBP6 | S100A9 | TLN1 | 0.784 |
| CLU | CPN2 | IGFBP6 | S100A8 | 0.784 |
| APOA4 | CD14 | S100A8 | S100A9 | 0.783 |
| APOA4 | IGFBP6 | MST1 | TLN1 | 0.783 |
| APOA1 | CD163 | CLU | MST1 | 0.783 |
| S100A8 | S100A9 | SEPP1 | VASN | 0.783 |
| S100A8 | S100A9 | TLN1 | VASN | 0.783 |
| APOA4 | CPN2 | PGLYRP2 | TAGLN2 | 0.783 |
| IGFBP6 | PGLYRP2 | TAGLN2 | TLN1 | 0.783 |
| APOA1 | CD14 | MST1 | TAGLN2 | 0.783 |
| APOA1 | CPN2 | IGFBP6 | PFN1 | 0.783 |
| MST1 | SEPP1 | TAGLN2 | VCAM1 | 0.782 |
| MST1 | S100A8 | S100A9 | SEPP1 | 0.782 |
| APOA1 | MST1 | PFN1 | SEPP1 | 0.782 |
| APOA1 | PGLYRP2 | S100A8 | TAGLN2 | 0.781 |
| CD14 | CLU | S100A8 | S100A9 | 0.781 |
| PFN1 | PGLYRP2 | TAGLN2 | TLN1 | 0.781 |
| CLU | IGFBP6 | MST1 | PGLYRP2 | 0.781 |
| MST1 | PFN1 | SEPP1 | VCAM1 | 0.781 |
| CLU | IGFBP6 | S100A8 | TLN1 | 0.781 |
| CLU | MST1 | PGLYRP2 | S100A9 | 0.781 |
| APOA1 | MST1 | TAGLN2 | VASN | 0.781 |
| CD14 | CD163 | CLU | IGFBP6 | 0.781 |
| APOA4 | PGLYRP2 | S100A8 | TAGLN2 | 0.780 |
| APOA4 | CPN2 | S100A8 | TAGLN2 | 0.780 |
| CLU | PFN1 | S100A9 | VASN | 0.780 |
| MST1 | PFN1 | S100A9 | TLN1 | 0.780 |
| APOA1 | IGFBP6 | MST1 | PFN1 | 0.780 |
| CD163 | CLU | MST1 | SEPP1 | 0.779 |
| APOA4 | CD163 | CPN2 | IGFBP6 | 0.779 |
| CLU | SEPP1 | TAGLN2 | VCAM1 | 0.779 |
| CLU | MST1 | PFN1 | TAGLN2 | 0.779 |
| APOA1 | PGLYRP2 | S100A9 | TAGLN2 | 0.779 |
| MST1 | S100A9 | TLN1 | VASN | 0.779 |
| MST1 | S100A8 | TAGLN2 | TLN1 | 0.779 |
| APOA4 | CLU | S100A8 | TAGLN2 | 0.779 |
| APOA1 | APOA4 | CD14 | TAGLN2 | 0.779 |
| MST1 | S100A8 | S100A9 | VASN | 0.778 |
| PFN1 | S100A8 | TLN1 | VASN | 0.778 |
| CLU | MST1 | PGLYRP2 | S100A8 | 0.778 |
| APOA1 | CD163 | PGLYRP2 | TLN1 | 0.778 |
| APOA1 | S100A9 | SEPP1 | TAGLN2 | 0.778 |
| IGFBP6 | PFN1 | SEPP1 | VCAM1 | 0.778 |
| APOA4 | TLN1 | VASN | VCAM1 | 0.778 |
| APOA4 | IGFBP6 | TLN1 | VASN | 0.777 |
| IGFBP6 | PGLYRP2 | TLN1 | VCAM1 | 0.777 |
| APOA4 | PGLYRP2 | S100A9 | TLN1 | 0.777 |
| CD163 | CPN2 | SEPP1 | TAGLN2 | 0.777 |
| CPN2 | S100A8 | TAGLN2 | VASN | 0.776 |
| CD14 | CD163 | S100A8 | TAGLN2 | 0.776 |
| APOA4 | CD163 | TAGLN2 | VCAM1 | 0.776 |
| CLU | PFN1 | TLN1 | VCAM1 | 0.775 |
| APOA4 | TAGLN2 | TLN1 | VCAM1 | 0.775 |
| PGLYRP2 | S100A8 | VASN | VCAM1 | 0.775 |
| CLU | IGFBP6 | MST1 | S100A8 | 0.775 |
| IGFBP6 | MST1 | PFN1 | TAGLN2 | 0.775 |
| CLU | PFN1 | PGLYRP2 | S100A9 | 0.775 |
| CD163 | PGLYRP2 | S100A8 | TLN1 | 0.775 |
| CLU | MST1 | S100A9 | VCAM1 | 0.774 |
| CLU | MST1 | S100A8 | VASN | 0.774 |
| CLU | PGLYRP2 | VASN | VCAM1 | 0.774 |
| APOA1 | CD163 | TLN1 | VCAM1 | 0.774 |
| CD163 | CPN2 | S100A9 | TAGLN2 | 0.774 |
| CPN2 | S100A9 | TAGLN2 | TLN1 | 0.774 |
| APOA4 | PGLYRP2 | S100A8 | TLN1 | 0.774 |
| APOA1 | CPN2 | PGLYRP2 | TAGLN2 | 0.774 |
| APOA4 | CLU | PGLYRP2 | TLN1 | 0.774 |
| APOA4 | CD163 | CPN2 | PFN1 | 0.773 |
| APOA4 | MST1 | TAGLN2 | VASN | 0.773 |
| APOA1 | CPN2 | IGFBP6 | S100A9 | 0.773 |
| CLU | IGFBP6 | PGLYRP2 | TLN1 | 0.773 |
| CPN2 | PGLYRP2 | SEPP1 | VCAM1 | 0.773 |
| CD14 | SEPP1 | TAGLN2 | VCAM1 | 0.773 |
| APOA1 | CD14 | CPN2 | SEPP1 | 0.773 |
| CD163 | S100A8 | TAGLN2 | VCAM1 | 0.773 |
| APOA4 | CD14 | MST1 | TAGLN2 | 0.773 |
| CLU | PGLYRP2 | TAGLN2 | TLN1 | 0.773 |
| CD14 | S100A8 | S100A9 | SEPP1 | 0.772 |
| CD163 | MST1 | PGLYRP2 | SEPP1 | 0.772 |

TABLE 12-continued

HIV+ panels
Combination of Four Candidate Biomarkers

| protein.1 | protein.2 | protein.3 | protein.4 | AUC |
|---|---|---|---|---|
| S100A8 | TAGLN2 | TLN1 | VCAM1 | 0.772 |
| CLU | MST1 | PFN1 | TLN1 | 0.772 |
| CLU | IGFBP6 | MST1 | VASN | 0.772 |
| CD14 | CLU | VASN | VCAM1 | 0.771 |
| APOA4 | IGFBP6 | S100A9 | TAGLN2 | 0.771 |
| CLU | MST1 | SEPP1 | VASN | 0.771 |
| CD163 | CLU | MST1 | VCAM1 | 0.771 |
| APOA1 | MST1 | PFN1 | VASN | 0.771 |
| CD14 | PGLYRP2 | SEPP1 | TLN1 | 0.771 |
| APOA1 | CPN2 | IGFBP6 | S100A8 | 0.771 |
| CLU | MST1 | S100A9 | VASN | 0.770 |
| APOA4 | CPN2 | S100A9 | TAGLN2 | 0.770 |
| CLU | CPN2 | PFN1 | S100A9 | 0.770 |
| CD14 | PGLYRP2 | S100A8 | S100A9 | 0.770 |
| CD14 | CLU | PGLYRP2 | SEPP1 | 0.770 |
| IGFBP6 | S100A9 | TAGLN2 | TLN1 | 0.770 |
| APOA4 | MST1 | PFN1 | VCAM1 | 0.770 |
| CLU | PFN1 | S100A9 | TLN1 | 0.770 |
| CPN2 | SEPP1 | TAGLN2 | VCAM1 | 0.770 |
| CPN2 | IGFBP6 | S100A8 | SEPP1 | 0.769 |
| APOA4 | PFN1 | SEPP1 | VCAM1 | 0.769 |
| CPN2 | IGFBP6 | S100A9 | SEPP1 | 0.769 |
| CD14 | CLU | IGFBP6 | S100A8 | 0.769 |
| CD14 | PGLYRP2 | S100A9 | TLN1 | 0.769 |
| CD14 | CD163 | S100A9 | TAGLN2 | 0.769 |
| CPN2 | PGLYRP2 | S100A8 | VCAM1 | 0.769 |
| CLU | CPN2 | IGFBP6 | S100A9 | 0.768 |
| APOA1 | CD163 | SEPP1 | VASN | 0.768 |
| CD14 | PFN1 | SEPP1 | TAGLN2 | 0.768 |
| MST1 | SEPP1 | TLN1 | VASN | 0.768 |
| CD163 | S100A8 | SEPP1 | TLN1 | 0.768 |
| APOA4 | PGLYRP2 | S100A9 | TAGLN2 | 0.767 |
| IGFBP6 | MST1 | TLN1 | VASN | 0.767 |
| CD163 | CLU | SEPP1 | VASN | 0.767 |
| PFN1 | S100A9 | TAGLN2 | TLN1 | 0.767 |
| CD14 | S100A8 | S100A9 | VASN | 0.767 |
| CLU | IGFBP6 | S100A9 | TLN1 | 0.767 |
| MST1 | PGLYRP2 | SEPP1 | TLN1 | 0.767 |
| APOA4 | CD14 | CPN2 | VCAM1 | 0.767 |
| CD163 | CLU | IGFBP6 | PGLYRP2 | 0.766 |
| APOA4 | PGLYRP2 | VASN | VCAM1 | 0.766 |
| CD163 | MST1 | S100A9 | TAGLN2 | 0.766 |
| APOA4 | CD14 | CLU | CPN2 | 0.766 |
| APOA4 | CLU | S100A9 | TAGLN2 | 0.766 |
| APOA4 | MST1 | TAGLN2 | VCAM1 | 0.766 |
| APOA1 | CD14 | CPN2 | S100A8 | 0.766 |
| APOA4 | IGFBP6 | PFN1 | VCAM1 | 0.766 |
| CD163 | PFN1 | SEPP1 | VCAM1 | 0.766 |
| CD14 | CLU | IGFBP6 | SEPP1 | 0.766 |
| CPN2 | IGFBP6 | TAGLN2 | VASN | 0.766 |
| CLU | PGLYRP2 | SEPP1 | TLN1 | 0.765 |
| CD14 | S100A9 | TAGLN2 | VCAM1 | 0.765 |
| CD14 | CLU | CPN2 | VCAM1 | 0.765 |
| CD14 | PGLYRP2 | S100A8 | TLN1 | 0.764 |
| CD163 | IGFBP6 | PGLYRP2 | SEPP1 | 0.764 |
| CLU | S100A8 | S100A9 | VASN | 0.764 |
| CD163 | IGFBP6 | PGLYRP2 | TLN1 | 0.764 |
| CD14 | MST1 | S100A9 | TAGLN2 | 0.764 |
| CLU | IGFBP6 | MST1 | SEPP1 | 0.764 |
| APOA4 | PFN1 | PGLYRP2 | TAGLN2 | 0.764 |
| APOA1 | CD163 | IGFBP6 | MST1 | 0.763 |
| APOA4 | CD14 | CLU | S100A8 | 0.763 |
| CLU | PGLYRP2 | TLN1 | VASN | 0.763 |
| MST1 | PFN1 | SEPP1 | TAGLN2 | 0.763 |
| CPN2 | IGFBP6 | S100A9 | VASN | 0.763 |
| CD163 | IGFBP6 | MST1 | SEPP1 | 0.763 |
| CPN2 | S100A9 | TAGLN2 | VASN | 0.763 |
| CLU | MST1 | TAGLN2 | VASN | 0.763 |
| CD163 | IGFBP6 | TAGLN2 | TLN1 | 0.763 |
| APOA1 | CD14 | CLU | IGFBP6 | 0.762 |
| CLU | PGLYRP2 | S100A8 | TAGLN2 | 0.762 |
| APOA1 | IGFBP6 | TAGLN2 | VCAM1 | 0.762 |
| APOA4 | CPN2 | SEPP1 | TLN1 | 0.762 |
| CLU | IGFBP6 | MST1 | S100A9 | 0.762 |
| IGFBP6 | MST1 | PGLYRP2 | VASN | 0.762 |
| CD14 | CD163 | PGLYRP2 | TLN1 | 0.762 |
| CD14 | CLU | PGLYRP2 | S100A8 | 0.762 |
| CD14 | CLU | IGFBP6 | PGLYRP2 | 0.762 |
| CPN2 | IGFBP6 | S100A8 | VASN | 0.762 |
| APOA1 | PGLYRP2 | SEPP1 | VCAM1 | 0.761 |
| APOA1 | SEPP1 | TAGLN2 | VCAM1 | 0.761 |
| CD14 | IGFBP6 | S100A8 | S100A9 | 0.761 |
| APOA1 | CPN2 | S100A8 | TAGLN2 | 0.761 |
| APOA1 | CD163 | CLU | VASN | 0.761 |
| CLU | TAGLN2 | TLN1 | VCAM1 | 0.761 |
| APOA1 | APOA4 | PGLYRP2 | TAGLN2 | 0.760 |
| CLU | CPN2 | S100A8 | S100A9 | 0.760 |
| CPN2 | PGLYRP2 | S100A9 | VASN | 0.760 |
| APOA4 | CPN2 | TLN1 | VCAM1 | 0.760 |
| CLU | IGFBP6 | PFN1 | TLN1 | 0.760 |
| CPN2 | PGLYRP2 | S100A8 | VASN | 0.760 |
| CPN2 | TLN1 | VASN | VCAM1 | 0.760 |
| CLU | TLN1 | VASN | VCAM1 | 0.759 |
| APOA4 | CD163 | CPN2 | VASN | 0.759 |
| APOA1 | CLU | IGFBP6 | MST1 | 0.759 |
| CD14 | S100A9 | TLN1 | VASN | 0.759 |
| CD14 | IGFBP6 | PGLYRP2 | TLN1 | 0.759 |
| CLU | PGLYRP2 | SEPP1 | TAGLN2 | 0.759 |
| APOA4 | CLU | MST1 | TLN1 | 0.759 |
| APOA1 | CLU | MST1 | PGLYRP2 | 0.759 |
| CLU | IGFBP6 | S100A9 | VCAM1 | 0.758 |
| APOA4 | PFN1 | TLN1 | VCAM1 | 0.758 |
| CD163 | S100A8 | TAGLN2 | TLN1 | 0.758 |
| APOA4 | PGLYRP2 | TLN1 | VASN | 0.758 |
| APOA1 | CD163 | PGLYRP2 | SEPP1 | 0.758 |
| CD14 | CD163 | CLU | PGLYRP2 | 0.758 |
| CLU | MST1 | TLN1 | VASN | 0.758 |
| CPN2 | PGLYRP2 | SEPP1 | VASN | 0.758 |
| APOA4 | IGFBP6 | TLN1 | VCAM1 | 0.758 |
| CD14 | CD163 | CLU | S100A9 | 0.758 |
| PFN1 | S100A9 | TLN1 | VASN | 0.758 |
| CD163 | PGLYRP2 | TLN1 | VCAM1 | 0.758 |
| CD14 | S100A8 | TLN1 | VASN | 0.757 |
| CLU | PGLYRP2 | S100A9 | TAGLN2 | 0.757 |
| APOA1 | CD163 | PGLYRP2 | S100A9 | 0.757 |
| APOA4 | CLU | TLN1 | VCAM1 | 0.757 |
| CPN2 | S100A8 | SEPP1 | TLN1 | 0.757 |
| APOA1 | PFN1 | PGLYRP2 | SEPP1 | 0.757 |
| APOA1 | PGLYRP2 | TLN1 | VCAM1 | 0.757 |
| APOA4 | PFN1 | TAGLN2 | VCAM1 | 0.757 |
| CD14 | CD163 | CLU | SEPP1 | 0.757 |
| MST1 | S100A9 | TAGLN2 | VCAM1 | 0.757 |
| APOA4 | CD14 | CLU | IGFBP6 | 0.756 |
| CLU | IGFBP6 | PGLYRP2 | VCAM1 | 0.756 |
| APOA1 | PFN1 | PGLYRP2 | TAGLN2 | 0.756 |
| PGLYRP2 | SEPP1 | TLN1 | VASN | 0.756 |
| APOA4 | S100A8 | S100A9 | VASN | 0.756 |
| APOA4 | CPN2 | PGLYRP2 | VASN | 0.756 |
| CPN2 | PGLYRP2 | S100A8 | SEPP1 | 0.756 |
| PGLYRP2 | SEPP1 | TLN1 | VCAM1 | 0.756 |
| CD163 | IGFBP6 | MST1 | TAGLN2 | 0.756 |
| APOA4 | CD163 | CLU | TAGLN2 | 0.755 |
| CD14 | CLU | S100A9 | VASN | 0.755 |
| APOA1 | CPN2 | S100A9 | TAGLN2 | 0.755 |
| APOA1 | MST1 | PGLYRP2 | TLN1 | 0.755 |
| CD14 | CLU | PGLYRP2 | VCAM1 | 0.755 |
| CD163 | CPN2 | PGLYRP2 | S100A9 | 0.755 |
| CD163 | CLU | S100A9 | TAGLN2 | 0.755 |
| CD14 | MST1 | PGLYRP2 | VASN | 0.754 |
| APOA1 | APOA4 | VASN | VCAM1 | 0.754 |
| IGFBP6 | PGLYRP2 | TLN1 | VASN | 0.754 |
| IGFBP6 | S100A8 | TLN1 | VASN | 0.754 |
| CD14 | MST1 | PGLYRP2 | TLN1 | 0.754 |
| PGLYRP2 | S100A9 | TLN1 | VCAM1 | 0.754 |
| APOA1 | CD163 | IGFBP6 | S100A8 | 0.754 |
| CD14 | S100A8 | TAGLN2 | TLN1 | 0.753 |
| PGLYRP2 | S100A8 | TLN1 | VCAM1 | 0.753 |
| CD163 | CPN2 | PGLYRP2 | SEPP1 | 0.753 |
| IGFBP6 | MST1 | PGLYRP2 | TLN1 | 0.753 |
| CD14 | CLU | PGLYRP2 | VASN | 0.753 |

TABLE 12-continued

HIV+ panels
Combination of Four Candidate Biomarkers

| protein.1 | protein.2 | protein.3 | protein.4 | AUC |
|---|---|---|---|---|
| APOA4 | S100A8 | SEPP1 | TLN1 | 0.752 |
| APOA1 | PGLYRP2 | SEPP1 | TAGLN2 | 0.752 |
| APOA4 | CD14 | SEPP1 | TLN1 | 0.752 |
| CLU | MST1 | SEPP1 | TLN1 | 0.752 |
| IGFBP6 | PGLYRP2 | SEPP1 | VCAM1 | 0.751 |
| APOA1 | CD14 | CLU | S100A9 | 0.751 |
| CD14 | S100A9 | VASN | VCAM1 | 0.751 |
| CLU | IGFBP6 | S100A8 | VCAM1 | 0.751 |
| CD163 | S100A9 | SEPP1 | TLN1 | 0.751 |
| APOA4 | CLU | MST1 | PGLYRP2 | 0.751 |
| IGFBP6 | MST1 | SEPP1 | VASN | 0.751 |
| APOA1 | CD163 | MST1 | PGLYRP2 | 0.751 |
| CPN2 | S100A9 | TLN1 | VCAM1 | 0.751 |
| CD14 | IGFBP6 | TLN1 | VASN | 0.751 |
| PGLYRP2 | SEPP1 | TAGLN2 | TLN1 | 0.751 |
| APOA4 | MST1 | SEPP1 | TLN1 | 0.751 |
| CD163 | CLU | IGFBP6 | S100A8 | 0.750 |
| APOA4 | CD163 | S100A8 | TLN1 | 0.750 |
| CD14 | PGLYRP2 | SEPP1 | VASN | 0.750 |
| APOA4 | MST1 | TLN1 | VASN | 0.750 |
| PFN1 | PGLYRP2 | SEPP1 | TLN1 | 0.750 |
| CD163 | IGFBP6 | MST1 | PFN1 | 0.750 |
| APOA4 | CPN2 | PGLYRP2 | S100A9 | 0.750 |
| CD163 | IGFBP6 | PFN1 | TAGLN2 | 0.749 |
| CLU | CPN2 | S100A8 | TAGLN2 | 0.749 |
| CD14 | S100A8 | VASN | VCAM1 | 0.749 |
| CD14 | MST1 | S100A8 | S100A9 | 0.749 |
| CD14 | CLU | MST1 | S100A9 | 0.749 |
| APOA4 | CD163 | PGLYRP2 | S100A9 | 0.749 |
| CPN2 | TAGLN2 | TLN1 | VCAM1 | 0.749 |
| APOA1 | CLU | PFN1 | PGLYRP2 | 0.749 |
| APOA1 | APOA4 | TAGLN2 | VCAM1 | 0.749 |
| APOA1 | CPN2 | PGLYRP2 | SEPP1 | 0.749 |
| APOA1 | CD14 | PGLYRP2 | VASN | 0.748 |
| APOA1 | PGLYRP2 | TLN1 | VASN | 0.748 |
| APOA1 | CD14 | IGFBP6 | TLN1 | 0.748 |
| APOA4 | CLU | PFN1 | PGLYRP2 | 0.748 |
| APOA4 | S100A8 | TAGLN2 | TLN1 | 0.748 |
| CD14 | CLU | S100A8 | VASN | 0.748 |
| CD163 | CPN2 | PGLYRP2 | S100A8 | 0.747 |
| CD14 | PGLYRP2 | TLN1 | VCAM1 | 0.747 |
| APOA4 | CD14 | VASN | VCAM1 | 0.747 |
| APOA1 | IGFBP6 | PFN1 | VCAM1 | 0.747 |
| CD14 | CLU | CPN2 | SEPP1 | 0.747 |
| CD14 | IGFBP6 | MST1 | VASN | 0.747 |
| APOA1 | CLU | MST1 | TAGLN2 | 0.747 |
| CD14 | CD163 | CLU | S100A8 | 0.747 |
| CD14 | SEPP1 | TLN1 | VASN | 0.747 |
| PGLYRP2 | S100A9 | SEPP1 | TLN1 | 0.747 |
| APOA1 | CD163 | IGFBP6 | PGLYRP2 | 0.747 |
| APOA1 | PFN1 | SEPP1 | VCAM1 | 0.746 |
| APOA1 | APOA4 | CPN2 | PGLYRP2 | 0.746 |
| CD14 | IGFBP6 | PGLYRP2 | SEPP1 | 0.746 |
| APOA4 | PGLYRP2 | TAGLN2 | TLN1 | 0.746 |
| CD163 | CPN2 | S100A8 | VASN | 0.746 |
| CD14 | PGLYRP2 | S100A9 | VASN | 0.746 |
| CD14 | IGFBP6 | PGLYRP2 | VASN | 0.745 |
| APOA4 | CD14 | PGLYRP2 | S100A9 | 0.745 |
| APOA1 | CLU | IGFBP6 | TLN1 | 0.745 |
| IGFBP6 | S100A8 | TLN1 | VCAM1 | 0.745 |
| APOA1 | CD163 | MST1 | S100A8 | 0.745 |
| CD14 | CLU | IGFBP6 | VASN | 0.745 |
| CPN2 | PGLYRP2 | S100A9 | VCAM1 | 0.745 |
| APOA1 | CPN2 | PGLYRP2 | VASN | 0.745 |
| IGFBP6 | PGLYRP2 | SEPP1 | TLN1 | 0.745 |
| CLU | PFN1 | PGLYRP2 | TAGLN2 | 0.745 |
| IGFBP6 | PGLYRP2 | S100A9 | VCAM1 | 0.745 |
| CD163 | CLU | IGFBP6 | S100A9 | 0.745 |
| CLU | PFN1 | PGLYRP2 | SEPP1 | 0.745 |
| APOA1 | CPN2 | S100A8 | TLN1 | 0.745 |
| APOA1 | MST1 | PGLYRP2 | VASN | 0.744 |
| CLU | CPN2 | PGLYRP2 | SEPP1 | 0.744 |
| APOA1 | CD14 | CLU | PGLYRP2 | 0.744 |
| APOA1 | IGFBP6 | MST1 | TLN1 | 0.744 |
| CPN2 | S100A8 | VASN | VCAM1 | 0.744 |
| APOA1 | IGFBP6 | PGLYRP2 | VASN | 0.744 |
| APOA4 | CD163 | S100A9 | TLN1 | 0.744 |
| MST1 | PGLYRP2 | SEPP1 | VASN | 0.744 |
| CLU | S100A9 | TLN1 | VCAM1 | 0.744 |
| APOA4 | CD163 | CPN2 | TAGLN2 | 0.744 |
| APOA1 | CD163 | CPN2 | PGLYRP2 | 0.743 |
| CLU | CPN2 | S100A9 | TAGLN2 | 0.743 |
| APOA1 | CLU | MST1 | S100A9 | 0.743 |
| CD163 | PGLYRP2 | S100A9 | SEPP1 | 0.743 |
| APOA1 | CD163 | CPN2 | VASN | 0.742 |
| IGFBP6 | MST1 | PGLYRP2 | SEPP1 | 0.742 |
| CLU | PGLYRP2 | S100A8 | TLN1 | 0.742 |
| CD163 | IGFBP6 | SEPP1 | TLN1 | 0.742 |
| CD14 | CD163 | CLU | VCAM1 | 0.742 |
| APOA1 | CD163 | IGFBP6 | TLN1 | 0.742 |
| APOA1 | CLU | MST1 | S100A8 | 0.742 |
| CD163 | IGFBP6 | MST1 | PGLYRP2 | 0.742 |
| APOA4 | IGFBP6 | MST1 | PGLYRP2 | 0.742 |
| PGLYRP2 | S100A8 | SEPP1 | TLN1 | 0.742 |
| CLU | CPN2 | PFN1 | VCAM1 | 0.741 |
| IGFBP6 | PGLYRP2 | S100A9 | VASN | 0.741 |
| APOA1 | CD14 | CD163 | CLU | 0.741 |
| APOA4 | CD14 | CD163 | TLN1 | 0.741 |
| APOA4 | CLU | IGFBP6 | VCAM1 | 0.741 |
| IGFBP6 | MST1 | TAGLN2 | VCAM1 | 0.741 |
| APOA1 | CD14 | PGLYRP2 | S100A9 | 0.741 |
| APOA1 | CD14 | VASN | VCAM1 | 0.741 |
| APOA4 | CLU | PGLYRP2 | TAGLN2 | 0.741 |
| CLU | S100A8 | S100A9 | SEPP1 | 0.741 |
| CD163 | CLU | VASN | VCAM1 | 0.741 |
| CD14 | SEPP1 | VASN | VCAM1 | 0.740 |
| APOA4 | IGFBP6 | MST1 | VCAM1 | 0.740 |
| IGFBP6 | MST1 | S100A8 | VASN | 0.740 |
| APOA1 | CPN2 | PGLYRP2 | S100A8 | 0.740 |
| IGFBP6 | MST1 | PGLYRP2 | VCAM1 | 0.740 |
| APOA4 | CPN2 | S100A8 | TLN1 | 0.740 |
| APOA1 | MST1 | PGLYRP2 | SEPP1 | 0.740 |
| APOA4 | CD14 | CLU | PGLYRP2 | 0.740 |
| PGLYRP2 | S100A8 | TLN1 | VASN | 0.740 |
| CD14 | CD163 | MST1 | PFN1 | 0.740 |
| APOA4 | CD14 | CLU | VCAM1 | 0.740 |
| APOA1 | CD14 | IGFBP6 | PGLYRP2 | 0.740 |
| APOA4 | CPN2 | PFN1 | TLN1 | 0.739 |
| IGFBP6 | PFN1 | TAGLN2 | VCAM1 | 0.739 |
| APOA1 | CPN2 | PGLYRP2 | S100A9 | 0.739 |
| CD163 | IGFBP6 | PGLYRP2 | VCAM1 | 0.739 |
| CD14 | CLU | MST1 | S100A8 | 0.739 |
| IGFBP6 | PGLYRP2 | SEPP1 | VASN | 0.739 |
| APOA4 | CLU | IGFBP6 | MST1 | 0.739 |
| APOA4 | CD163 | IGFBP6 | MST1 | 0.739 |
| IGFBP6 | S100A9 | TLN1 | VASN | 0.738 |
| APOA1 | APOA4 | PGLYRP2 | TLN1 | 0.738 |
| APOA4 | S100A9 | TAGLN2 | TLN1 | 0.738 |
| APOA1 | CLU | PGLYRP2 | TAGLN2 | 0.738 |
| APOA4 | CPN2 | PGLYRP2 | S100A8 | 0.738 |
| APOA1 | CD14 | CLU | VCAM1 | 0.738 |
| CPN2 | IGFBP6 | SEPP1 | TAGLN2 | 0.738 |
| MST1 | SEPP1 | TAGLN2 | TLN1 | 0.738 |
| CD163 | MST1 | PGLYRP2 | TLN1 | 0.738 |
| APOA1 | CLU | TLN1 | VCAM1 | 0.738 |
| CD163 | CPN2 | VASN | VCAM1 | 0.737 |
| APOA1 | APOA4 | CD163 | TLN1 | 0.737 |
| APOA4 | CD14 | CD163 | CLU | 0.737 |
| APOA4 | CD163 | TLN1 | VCAM1 | 0.737 |
| APOA1 | CD14 | CLU | SEPP1 | 0.737 |
| APOA4 | CLU | PFN1 | VCAM1 | 0.737 |
| APOA4 | CPN2 | PGLYRP2 | VCAM1 | 0.737 |
| IGFBP6 | PGLYRP2 | S100A8 | VASN | 0.737 |
| MST1 | PGLYRP2 | S100A8 | VASN | 0.737 |
| APOA4 | IGFBP6 | SEPP1 | TLN1 | 0.736 |
| APOA1 | IGFBP6 | MST1 | VASN | 0.736 |
| MST1 | PGLYRP2 | TLN1 | VCAM1 | 0.736 |
| CD14 | CD163 | PGLYRP2 | S100A8 | 0.736 |
| APOA4 | CPN2 | S100A9 | TLN1 | 0.736 |
| CLU | PGLYRP2 | S100A9 | TLN1 | 0.736 |

TABLE 12-continued

HIV+ panels
Combination of Four Candidate Biomarkers

| protein.1 | protein.2 | protein.3 | protein.4 | AUC |
|---|---|---|---|---|
| APOA4 | CD14 | CLU | S100A8 | 0.736 |
| APOA1 | CPN2 | PGLYRP2 | VCAM1 | 0.736 |
| APOA1 | CD163 | MST1 | S100A9 | 0.736 |
| CD163 | S100A9 | TAGLN2 | VCAM1 | 0.736 |
| APOA4 | CD163 | MST1 | TLN1 | 0.735 |
| APOA1 | CLU | CPN2 | IGFBP6 | 0.735 |
| CD14 | IGFBP6 | PGLYRP2 | VCAM1 | 0.735 |
| CPN2 | IGFBP6 | PFN1 | SEPP1 | 0.735 |
| APOA4 | CD14 | IGFBP6 | PGLYRP2 | 0.735 |
| APOA1 | PFN1 | PGLYRP2 | TLN1 | 0.735 |
| PGLYRP2 | S100A9 | TLN1 | VASN | 0.734 |
| CLU | S100A8 | VASN | VCAM1 | 0.734 |
| APOA4 | CD163 | CPN2 | PGLYRP2 | 0.734 |
| APOA4 | CD14 | CD163 | S100A9 | 0.734 |
| CD163 | MST1 | S100A8 | SEPP1 | 0.734 |
| APOA1 | CLU | CPN2 | PGLYRP2 | 0.734 |
| APOA1 | CD163 | MST1 | VCAM1 | 0.734 |
| APOA4 | S100A9 | SEPP1 | TLN1 | 0.734 |
| APOA1 | CLU | MST1 | PFN1 | 0.734 |
| IGFBP6 | PGLYRP2 | S100A8 | TLN1 | 0.733 |
| CD14 | CLU | S100A8 | SEPP1 | 0.733 |
| CD163 | S100A9 | TAGLN2 | TLN1 | 0.733 |
| APOA1 | CLU | MST1 | VCAM1 | 0.733 |
| MST1 | PGLYRP2 | SEPP1 | VCAM1 | 0.733 |
| APOA4 | CD14 | PGLYRP2 | VASN | 0.733 |
| CD163 | CPN2 | PGLYRP2 | VCAM1 | 0.732 |
| APOA1 | IGFBP6 | MST1 | PGLYRP2 | 0.732 |
| APOA4 | SEPP1 | TAGLN2 | TLN1 | 0.732 |
| CD14 | IGFBP6 | MST1 | PGLYRP2 | 0.732 |
| MST1 | PGLYRP2 | S100A9 | VASN | 0.732 |
| APOA1 | TLN1 | VASN | VCAM1 | 0.731 |
| CD163 | IGFBP6 | S100A8 | TLN1 | 0.731 |
| CLU | IGFBP6 | TAGLN2 | TLN1 | 0.731 |
| CLU | MST1 | TAGLN2 | TLN1 | 0.731 |
| IGFBP6 | S100A8 | SEPP1 | TLN1 | 0.731 |
| S100A9 | TAGLN2 | TLN1 | VCAM1 | 0.731 |
| APOA1 | MST1 | SEPP1 | TAGLN2 | 0.731 |
| IGFBP6 | MST1 | PGLYRP2 | S100A9 | 0.731 |
| CD163 | IGFBP6 | TAGLN2 | VCAM1 | 0.731 |
| CD163 | MST1 | PGLYRP2 | S100A8 | 0.731 |
| CD14 | PGLYRP2 | S100A8 | VASN | 0.730 |
| CD163 | CPN2 | PFN1 | VCAM1 | 0.730 |
| CD163 | MST1 | SEPP1 | TLN1 | 0.730 |
| APOA1 | CD163 | MST1 | TLN1 | 0.730 |
| APOA4 | CLU | MST1 | S100A9 | 0.730 |
| IGFBP6 | MST1 | S100A8 | TLN1 | 0.730 |
| CD14 | S100A9 | TAGLN2 | TLN1 | 0.730 |
| APOA4 | IGFBP6 | MST1 | VASN | 0.730 |
| CD14 | CLU | S100A9 | SEPP1 | 0.730 |
| CPN2 | PFN1 | SEPP1 | TLN1 | 0.730 |
| IGFBP6 | PGLYRP2 | S100A9 | TLN1 | 0.730 |
| APOA4 | MST1 | PGLYRP2 | SEPP1 | 0.730 |
| IGFBP6 | MST1 | S100A9 | VASN | 0.729 |
| S100A8 | SEPP1 | VASN | VCAM1 | 0.729 |
| APOA4 | CLU | MST1 | S100A8 | 0.729 |
| APOA1 | CD163 | MST1 | SEPP1 | 0.729 |
| CD14 | CD163 | IGFBP6 | PGLYRP2 | 0.729 |
| APOA4 | CLU | S100A8 | S100A9 | 0.729 |
| APOA4 | CD163 | IGFBP6 | PGLYRP2 | 0.729 |
| CLU | S100A9 | VASN | VCAM1 | 0.729 |
| APOA1 | IGFBP6 | PGLYRP2 | SEPP1 | 0.729 |
| SEPP1 | TLN1 | VASN | VCAM1 | 0.729 |
| APOA1 | MST1 | PGLYRP2 | S100A9 | 0.729 |
| APOA1 | CD163 | SEPP1 | TLN1 | 0.728 |
| PFN1 | SEPP1 | TLN1 | VCAM1 | 0.728 |
| APOA4 | IGFBP6 | PGLYRP2 | VCAM1 | 0.728 |
| CLU | MST1 | S100A8 | SEPP1 | 0.728 |
| CLU | IGFBP6 | PGLYRP2 | VASN | 0.728 |
| APOA1 | CD163 | CLU | PGLYRP2 | 0.728 |
| APOA1 | CLU | MST1 | TLN1 | 0.727 |
| CPN2 | S100A9 | VASN | VCAM1 | 0.727 |
| APOA4 | MST1 | S100A8 | TLN1 | 0.727 |
| CD14 | CLU | SEPP1 | VASN | 0.727 |
| APOA1 | IGFBP6 | PGLYRP2 | TLN1 | 0.727 |
| IGFBP6 | MST1 | SEPP1 | VCAM1 | 0.727 |
| APOA1 | CD14 | CD163 | IGFBP6 | 0.727 |
| IGFBP6 | MST1 | PGLYRP2 | S100A8 | 0.727 |
| APOA4 | CD14 | PGLYRP2 | S100A8 | 0.727 |
| APOA1 | CD163 | VASN | VCAM1 | 0.726 |
| APOA1 | APOA4 | CD14 | CLU | 0.726 |
| IGFBP6 | PGLYRP2 | S100A9 | SEPP1 | 0.726 |
| APOA4 | CPN2 | IGFBP6 | TAGLN2 | 0.726 |
| APOA1 | APOA4 | CD14 | TLN1 | 0.726 |
| APOA1 | APOA4 | MST1 | PGLYRP2 | VASN | 0.726 |
| IGFBP6 | MST1 | PFN1 | VCAM1 | 0.726 |
| APOA4 | CD163 | PFN1 | VCAM1 | 0.726 |
| CD14 | CD163 | PGLYRP2 | SEPP1 | 0.726 |
| APOA1 | CD14 | IGFBP6 | MST1 | 0.726 |
| S100A8 | TAGLN2 | TLN1 | VASN | 0.725 |
| IGFBP6 | PGLYRP2 | S100A8 | SEPP1 | 0.725 |
| APOA4 | IGFBP6 | PGLYRP2 | S100A9 | 0.725 |
| CD163 | IGFBP6 | S100A8 | SEPP1 | 0.725 |
| APOA4 | CLU | SEPP1 | TLN1 | 0.725 |
| CLU | IGFBP6 | PGLYRP2 | SEPP1 | 0.725 |
| APOA1 | CD14 | MST1 | PGLYRP2 | 0.725 |
| APOA4 | IGFBP6 | PGLYRP2 | VASN | 0.725 |
| APOA4 | IGFBP6 | S100A9 | VCAM1 | 0.725 |
| CPN2 | S100A8 | TLN1 | VASN | 0.724 |
| APOA4 | IGFBP6 | PGLYRP2 | S100A8 | 0.724 |
| CD14 | PGLYRP2 | S100A9 | VCAM1 | 0.724 |
| APOA4 | SEPP1 | TLN1 | VCAM1 | 0.724 |
| APOA1 | S100A8 | TAGLN2 | VASN | 0.724 |
| CLU | IGFBP6 | SEPP1 | VCAM1 | 0.724 |
| APOA4 | S100A8 | TAGLN2 | VASN | 0.724 |
| CD14 | CD163 | SEPP1 | TLN1 | 0.723 |
| MST1 | S100A8 | SEPP1 | VASN | 0.723 |
| APOA4 | CD14 | CLU | SEPP1 | 0.723 |
| CPN2 | PGLYRP2 | S100A9 | SEPP1 | 0.723 |
| APOA1 | CD163 | S100A8 | TLN1 | 0.723 |
| APOA1 | CPN2 | IGFBP6 | VASN | 0.723 |
| APOA1 | IGFBP6 | MST1 | S100A9 | 0.723 |
| APOA1 | PGLYRP2 | S100A9 | VCAM1 | 0.723 |
| CD163 | S100A9 | VASN | VCAM1 | 0.723 |
| CD163 | IGFBP6 | PFN1 | VCAM1 | 0.722 |
| APOA1 | IGFBP6 | PGLYRP2 | VCAM1 | 0.722 |
| APOA1 | CD14 | IGFBP6 | S100A9 | 0.722 |
| CD163 | MST1 | S100A9 | SEPP1 | 0.722 |
| APOA4 | PGLYRP2 | S100A9 | VCAM1 | 0.722 |
| APOA4 | CD163 | MST1 | PGLYRP2 | 0.722 |
| APOA1 | CD163 | S100A9 | VASN | 0.722 |
| APOA4 | CD163 | VASN | VCAM1 | 0.722 |
| CD163 | CPN2 | SEPP1 | VASN | 0.722 |
| APOA4 | CLU | MST1 | VASN | 0.722 |
| APOA4 | CPN2 | TAGLN2 | TLN1 | 0.721 |
| SEPP1 | TAGLN2 | TLN1 | VCAM1 | 0.721 |
| APOA4 | CLU | S100A8 | TLN1 | 0.721 |
| APOA4 | CD163 | PFN1 | TAGLN2 | 0.721 |
| APOA1 | IGFBP6 | MST1 | S100A8 | 0.721 |
| CD163 | SEPP1 | VASN | VCAM1 | 0.721 |
| APOA4 | CD14 | IGFBP6 | MST1 | 0.721 |
| APOA4 | MST1 | SEPP1 | VCAM1 | 0.721 |
| PFN1 | SEPP1 | TAGLN2 | VCAM1 | 0.721 |
| APOA1 | PGLYRP2 | SEPP1 | VASN | 0.721 |
| CD14 | PGLYRP2 | S100A9 | SEPP1 | 0.721 |
| APOA1 | CPN2 | IGFBP6 | SEPP1 | 0.720 |
| CLU | PFN1 | SEPP1 | VCAM1 | 0.720 |
| APOA1 | CD14 | IGFBP6 | VASN | 0.720 |
| IGFBP6 | PGLYRP2 | S100A8 | VCAM1 | 0.720 |
| APOA4 | CLU | VASN | VCAM1 | 0.720 |
| APOA1 | CLU | IGFBP6 | PGLYRP2 | 0.719 |
| APOA1 | IGFBP6 | PGLYRP2 | S100A9 | 0.719 |
| APOA1 | MST1 | S100A8 | TLN1 | 0.719 |
| APOA1 | CD163 | PGLYRP2 | S100A8 | 0.719 |
| MST1 | S100A9 | TAGLN2 | TLN1 | 0.719 |
| CD14 | MST1 | PGLYRP2 | VCAM1 | 0.719 |
| CPN2 | SEPP1 | TAGLN2 | TLN1 | 0.719 |
| CLU | CPN2 | IGFBP6 | VASN | 0.719 |
| APOA4 | S100A8 | TLN1 | VASN | 0.719 |
| APOA1 | CD163 | CLU | IGFBP6 | 0.719 |
| CLU | CPN2 | IGFBP6 | SEPP1 | 0.718 |

TABLE 12-continued

HIV+ panels
Combination of Four Candidate Biomarkers

| protein.1 | protein.2 | protein.3 | protein.4 | AUC |
|---|---|---|---|---|
| MST1 | PGLYRP2 | S100A8 | SEPP1 | 0.718 |
| APOA1 | CPN2 | TLN1 | VCAM1 | 0.718 |
| APOA4 | CPN2 | IGFBP6 | PFN1 | 0.718 |
| MST1 | S100A9 | SEPP1 | VASN | 0.718 |
| APOA4 | CD14 | PGLYRP2 | SEPP1 | 0.718 |
| MST1 | PGLYRP2 | S100A9 | SEPP1 | 0.717 |
| CD14 | CD163 | MST1 | PGLYRP2 | 0.717 |
| APOA1 | CD14 | PGLYRP2 | SEPP1 | 0.717 |
| CLU | IGFBP6 | TAGLN2 | VASN | 0.717 |
| CD14 | IGFBP6 | PGLYRP2 | S100A9 | 0.717 |
| APOA4 | IGFBP6 | PGLYRP2 | SEPP1 | 0.717 |
| CD163 | PGLYRP2 | S100A8 | SEPP1 | 0.717 |
| CD14 | CD163 | MST1 | TAGLN2 | 0.716 |
| APOA1 | CD14 | CD163 | TLN1 | 0.716 |
| APOA4 | CD14 | CD163 | PGLYRP2 | 0.716 |
| CLU | IGFBP6 | TLN1 | VASN | 0.716 |
| APOA4 | IGFBP6 | MST1 | SEPP1 | 0.716 |
| APOA4 | CPN2 | PGLYRP2 | SEPP1 | 0.716 |
| S100A8 | SEPP1 | TLN1 | VASN | 0.716 |
| CD14 | PGLYRP2 | SEPP1 | VCAM1 | 0.716 |
| APOA4 | CD14 | S100A8 | TLN1 | 0.716 |
| APOA1 | CLU | TAGLN2 | VCAM1 | 0.716 |
| APOA1 | PGLYRP2 | TAGLN2 | TLN1 | 0.716 |
| APOA4 | CD14 | S100A9 | TLN1 | 0.716 |
| APOA1 | CLU | S100A8 | TAGLN2 | 0.716 |
| APOA4 | CD14 | CLU | VASN | 0.715 |
| APOA4 | MST1 | PGLYRP2 | VCAM1 | 0.715 |
| APOA1 | CLU | MST1 | VASN | 0.715 |
| APOA4 | CD14 | MST1 | TLN1 | 0.715 |
| CD14 | IGFBP6 | SEPP1 | VASN | 0.715 |
| APOA1 | MST1 | S100A8 | VASN | 0.715 |
| CD14 | MST1 | S100A9 | VASN | 0.715 |
| CD163 | PGLYRP2 | S100A8 | VCAM1 | 0.715 |
| APOA1 | CD163 | S100A8 | VASN | 0.715 |
| APOA4 | CD163 | PGLYRP2 | S100A8 | 0.715 |
| CD163 | SEPP1 | TLN1 | VCAM1 | 0.715 |
| MST1 | PGLYRP2 | S100A9 | TLN1 | 0.714 |
| APOA4 | CD163 | IGFBP6 | S100A9 | 0.714 |
| CD163 | S100A8 | VASN | VCAM1 | 0.714 |
| APOA1 | MST1 | PGLYRP2 | S100A8 | 0.713 |
| CPN2 | IGFBP6 | SEPP1 | VASN | 0.713 |
| APOA1 | CD14 | PGLYRP2 | S100A8 | 0.713 |
| APOA4 | S100A8 | TLN1 | VCAM1 | 0.713 |
| CLU | S100A8 | TAGLN2 | VASN | 0.713 |
| APOA4 | CLU | S100A9 | TLN1 | 0.712 |
| CD14 | IGFBP6 | S100A8 | TLN1 | 0.712 |
| APOA1 | CLU | IGFBP6 | VCAM1 | 0.712 |
| CD14 | CLU | S100A8 | VCAM1 | 0.712 |
| CD14 | MST1 | PGLYRP2 | S100A9 | 0.712 |
| APOA1 | IGFBP6 | PGLYRP2 | S100A8 | 0.712 |
| APOA1 | SEPP1 | VASN | VCAM1 | 0.712 |
| APOA4 | MST1 | S100A9 | TLN1 | 0.712 |
| CLU | IGFBP6 | PGLYRP2 | S100A9 | 0.712 |
| APOA4 | CD14 | IGFBP6 | S100A9 | 0.712 |
| APOA4 | CLU | IGFBP6 | PGLYRP2 | 0.711 |
| CD14 | MST1 | PFN1 | VCAM1 | 0.711 |
| CPN2 | SEPP1 | TLN1 | VCAM1 | 0.711 |
| IGFBP6 | TAGLN2 | TLN1 | VCAM1 | 0.711 |
| IGFBP6 | MST1 | S100A9 | VCAM1 | 0.711 |
| CLU | IGFBP6 | PFN1 | VASN | 0.711 |
| CD14 | CD163 | PGLYRP2 | VCAM1 | 0.711 |
| APOA4 | S100A9 | TAGLN2 | VASN | 0.711 |
| MST1 | PGLYRP2 | S100A9 | VCAM1 | 0.711 |
| APOA1 | IGFBP6 | S100A8 | TLN1 | 0.711 |
| APOA1 | IGFBP6 | S100A9 | VCAM1 | 0.711 |
| APOA4 | CPN2 | VASN | VCAM1 | 0.711 |
| APOA1 | APOA4 | CPN2 | IGFBP6 | 0.711 |
| IGFBP6 | TAGLN2 | TLN1 | VASN | 0.711 |
| CD163 | PGLYRP2 | S100A9 | VCAM1 | 0.710 |
| APOA1 | CD14 | S100A8 | TLN1 | 0.710 |
| MST1 | PGLYRP2 | S100A8 | TLN1 | 0.710 |
| APOA4 | IGFBP6 | TAGLN2 | TLN1 | 0.710 |
| APOA4 | IGFBP6 | MST1 | S100A8 | 0.710 |
| CD14 | IGFBP6 | S100A9 | VASN | 0.710 |
| APOA1 | CLU | PFN1 | VCAM1 | 0.710 |
| APOA1 | CD14 | CD163 | PGLYRP2 | 0.709 |
| APOA4 | CD14 | MST1 | PGLYRP2 | 0.709 |
| APOA4 | CD163 | CLU | VASN | 0.709 |
| APOA1 | CD14 | CLU | VASN | 0.709 |
| APOA1 | S100A8 | VASN | VCAM1 | 0.708 |
| IGFBP6 | PFN1 | TAGLN2 | VASN | 0.708 |
| APOA4 | S100A9 | TLN1 | VASN | 0.708 |
| CD14 | MST1 | S100A8 | VASN | 0.708 |
| IGFBP6 | PFN1 | TLN1 | VCAM1 | 0.708 |
| APOA1 | CD163 | PGLYRP2 | VCAM1 | 0.708 |
| S100A9 | SEPP1 | TLN1 | VASN | 0.707 |
| APOA4 | CLU | CPN2 | IGFBP6 | 0.707 |
| APOA1 | APOA4 | IGFBP6 | PGLYRP2 | 0.707 |
| APOA4 | CD14 | TLN1 | VCAM1 | 0.707 |
| APOA4 | CD14 | MST1 | VASN | 0.707 |
| APOA1 | MST1 | S100A9 | TLN1 | 0.707 |
| APOA1 | MST1 | S100A9 | VASN | 0.707 |
| APOA4 | CD14 | S100A9 | VASN | 0.707 |
| APOA4 | IGFBP6 | S100A8 | VCAM1 | 0.707 |
| IGFBP6 | S100A8 | SEPP1 | VCAM1 | 0.707 |
| IGFBP6 | MST1 | S100A8 | SEPP1 | 0.706 |
| APOA4 | CD14 | IGFBP6 | SEPP1 | 0.706 |
| CD163 | MST1 | PGLYRP2 | VCAM1 | 0.706 |
| CD163 | CLU | CPN2 | VASN | 0.706 |
| CD163 | IGFBP6 | TLN1 | VCAM1 | 0.706 |
| APOA4 | CD163 | CLU | IGFBP6 | 0.706 |
| APOA1 | S100A9 | TAGLN2 | VASN | 0.706 |
| CD14 | MST1 | PGLYRP2 | SEPP1 | 0.706 |
| APOA4 | PFN1 | TAGLN2 | TLN1 | 0.706 |
| IGFBP6 | MST1 | S100A8 | VCAM1 | 0.706 |
| APOA4 | IGFBP6 | MST1 | S100A9 | 0.705 |
| APOA4 | CLU | MST1 | SEPP1 | 0.705 |
| CLU | MST1 | S100A9 | SEPP1 | 0.705 |
| APOA4 | PGLYRP2 | S100A8 | VCAM1 | 0.705 |
| APOA4 | PFN1 | SEPP1 | TLN1 | 0.705 |
| APOA1 | MST1 | SEPP1 | VASN | 0.705 |
| APOA4 | CD14 | CD163 | IGFBP6 | 0.705 |
| APOA4 | CPN2 | TLN1 | VASN | 0.705 |
| APOA4 | SEPP1 | VASN | VCAM1 | 0.705 |
| APOA4 | MST1 | TLN1 | VCAM1 | 0.705 |
| IGFBP6 | MST1 | SEPP1 | TLN1 | 0.705 |
| APOA4 | CD163 | MST1 | SEPP1 | 0.705 |
| MST1 | PGLYRP2 | S100A8 | VCAM1 | 0.704 |
| MST1 | SEPP1 | TLN1 | VCAM1 | 0.704 |
| CD163 | CPN2 | S100A9 | VASN | 0.704 |
| APOA4 | CD163 | IGFBP6 | S100A8 | 0.704 |
| CPN2 | S100A9 | TLN1 | VASN | 0.704 |
| CD14 | IGFBP6 | SEPP1 | TLN1 | 0.704 |
| CLU | IGFBP6 | SEPP1 | TLN1 | 0.704 |
| APOA1 | APOA4 | PGLYRP2 | SEPP1 | 0.704 |
| APOA1 | CPN2 | VASN | VCAM1 | 0.704 |
| APOA4 | CPN2 | VASN | VCAM1 | 0.704 |
| APOA1 | PGLYRP2 | S100A8 | VASN | 0.703 |
| APOA1 | IGFBP6 | TAGLN2 | VASN | 0.703 |
| CLU | CPN2 | S100A8 | TLN1 | 0.703 |
| APOA1 | CD14 | IGFBP6 | SEPP1 | 0.703 |
| CPN2 | S100A9 | SEPP1 | TLN1 | 0.703 |
| CLU | S100A9 | TAGLN2 | VASN | 0.703 |
| APOA1 | APOA4 | CPN2 | TLN1 | 0.703 |
| APOA1 | CD14 | MST1 | TLN1 | 0.703 |
| APOA4 | MST1 | PGLYRP2 | S100A9 | 0.703 |
| APOA1 | IGFBP6 | S100A9 | TLN1 | 0.703 |
| APOA1 | IGFBP6 | PFN1 | VASN | 0.703 |
| CD163 | CLU | PGLYRP2 | SEPP1 | 0.702 |
| PGLYRP2 | S100A8 | TAGLN2 | TLN1 | 0.702 |
| APOA1 | APOA4 | IGFBP6 | MST1 | 0.702 |
| APOA1 | PGLYRP2 | S100A9 | TLN1 | 0.702 |
| APOA1 | PGLYRP2 | S100A9 | VASN | 0.702 |
| APOA1 | CD14 | PGLYRP2 | VCAM1 | 0.702 |
| CLU | IGFBP6 | PFN1 | TAGLN2 | 0.701 |
| APOA4 | CLU | CPN2 | TLN1 | 0.701 |
| APOA1 | CPN2 | SEPP1 | TLN1 | 0.701 |
| CD14 | IGFBP6 | S100A8 | VASN | 0.701 |
| APOA1 | CD14 | S100A9 | VASN | 0.701 |
| CD14 | IGFBP6 | PGLYRP2 | S100A8 | 0.701 |

TABLE 12-continued

HIV+ panels
Combination of Four Candidate Biomarkers

| protein.1 | protein.2 | protein.3 | protein.4 | AUC |
|---|---|---|---|---|
| CD14 | PGLYRP2 | S100A8 | VCAM1 | 0.701 |
| CD14 | CD163 | IGFBP6 | SEPP1 | 0.700 |
| CD163 | CLU | IGFBP6 | SEPP1 | 0.700 |
| APOA1 | CD14 | CLU | S100A8 | 0.700 |
| CD163 | CLU | S100A9 | VASN | 0.700 |
| CD14 | MST1 | SEPP1 | VASN | 0.700 |
| APOA4 | CD14 | IGFBP6 | VASN | 0.700 |
| CD14 | MST1 | PGLYRP2 | S100A8 | 0.700 |
| APOA1 | PGLYRP2 | S100A8 | TLN1 | 0.700 |
| APOA1 | MST1 | PFN1 | TLN1 | 0.700 |
| APOA4 | PGLYRP2 | S100A9 | VASN | 0.700 |
| CLU | S100A8 | TAGLN2 | TLN1 | 0.700 |
| PGLYRP2 | S100A9 | TAGLN2 | TLN1 | 0.700 |
| CLU | S100A8 | SEPP1 | TLN1 | 0.699 |
| S100A9 | TAGLN2 | TLN1 | VASN | 0.699 |
| IGFBP6 | PFN1 | TLN1 | VASN | 0.699 |
| CLU | PFN1 | TAGLN2 | VCAM1 | 0.699 |
| APOA1 | CD14 | CLU | CPN2 | 0.699 |
| APOA1 | IGFBP6 | S100A8 | VCAM1 | 0.699 |
| APOA1 | CD163 | IGFBP6 | SEPP1 | 0.698 |
| CLU | IGFBP6 | PGLYRP2 | S100A8 | 0.698 |
| APOA1 | APOA4 | MST1 | PGLYRP2 | 0.698 |
| APOA4 | IGFBP6 | PFN1 | TLN1 | 0.698 |
| APOA1 | CD163 | S100A9 | TLN1 | 0.698 |
| APOA1 | MST1 | TAGLN2 | TLN1 | 0.698 |
| APOA1 | IGFBP6 | PFN1 | TAGLN2 | 0.698 |
| APOA1 | APOA4 | MST1 | TLN1 | 0.698 |
| CD163 | CPN2 | TAGLN2 | VCAM1 | 0.697 |
| APOA1 | CLU | IGFBP6 | S100A8 | 0.697 |
| CD14 | IGFBP6 | MST1 | VCAM1 | 0.697 |
| CLU | IGFBP6 | S100A8 | SEPP1 | 0.697 |
| CLU | PGLYRP2 | S100A8 | VASN | 0.697 |
| CLU | IGFBP6 | S100A9 | SEPP1 | 0.697 |
| IGFBP6 | S100A9 | TLN1 | VCAM1 | 0.697 |
| APOA4 | CD163 | S100A8 | VASN | 0.697 |
| CD163 | IGFBP6 | MST1 | VCAM1 | 0.697 |
| MST1 | S100A8 | SEPP1 | TLN1 | 0.697 |
| APOA4 | CD163 | S100A9 | VASN | 0.697 |
| CD163 | CLU | S100A8 | VASN | 0.697 |
| APOA1 | APOA4 | IGFBP6 | TLN1 | 0.697 |
| MST1 | TAGLN2 | TLN1 | VASN | 0.697 |
| APOA1 | APOA4 | CD163 | PGLYRP2 | 0.697 |
| CD163 | IGFBP6 | MST1 | S100A8 | 0.697 |
| APOA4 | PGLYRP2 | SEPP1 | VASN | 0.696 |
| CLU | PGLYRP2 | SEPP1 | VASN | 0.696 |
| APOA4 | CLU | IGFBP6 | S100A8 | 0.696 |
| APOA1 | APOA4 | PFN1 | VCAM1 | 0.696 |
| APOA1 | APOA4 | CD14 | PGLYRP2 | 0.696 |
| APOA1 | PGLYRP2 | SEPP1 | TLN1 | 0.696 |
| CLU | CPN2 | TAGLN2 | VCAM1 | 0.696 |
| APOA4 | CD14 | IGFBP6 | S100A8 | 0.696 |
| APOA1 | CPN2 | PFN1 | TLN1 | 0.695 |
| IGFBP6 | PFN1 | SEPP1 | TAGLN2 | 0.695 |
| APOA1 | IGFBP6 | S100A8 | VASN | 0.695 |
| APOA4 | CD14 | IGFBP6 | VCAM1 | 0.695 |
| APOA1 | CD14 | IGFBP6 | S100A8 | 0.695 |
| APOA4 | MST1 | PFN1 | TAGLN2 | 0.695 |
| PGLYRP2 | S100A9 | SEPP1 | VASN | 0.694 |
| CD163 | CLU | IGFBP6 | VCAM1 | 0.694 |
| IGFBP6 | PFN1 | TAGLN2 | TLN1 | 0.694 |
| APOA4 | S100A9 | TLN1 | VCAM1 | 0.694 |
| APOA4 | CLU | IGFBP6 | PFN1 | 0.694 |
| APOA1 | APOA4 | PGLYRP2 | VASN | 0.694 |
| APOA1 | APOA4 | TLN1 | VCAM1 | 0.694 |
| CD14 | PGLYRP2 | S100A8 | SEPP1 | 0.694 |
| APOA4 | CD163 | SEPP1 | VASN | 0.694 |
| CLU | SEPP1 | TLN1 | VCAM1 | 0.693 |
| APOA1 | CD163 | CLU | CPN2 | 0.693 |
| APOA4 | PGLYRP2 | S100A9 | SEPP1 | 0.693 |
| CLU | S100A9 | SEPP1 | VASN | 0.693 |
| CLU | PGLYRP2 | SEPP1 | VCAM1 | 0.693 |
| APOA1 | CLU | S100A9 | TAGLN2 | 0.693 |
| APOA1 | MST1 | PGLYRP2 | VCAM1 | 0.692 |
| APOA1 | CLU | MST1 | SEPP1 | 0.692 |
| APOA1 | PGLYRP2 | S100A9 | SEPP1 | 0.692 |
| APOA4 | MST1 | S100A9 | VASN | 0.692 |
| CLU | IGFBP6 | S100A8 | VASN | 0.692 |
| APOA1 | CLU | IGFBP6 | S100A9 | 0.692 |
| APOA1 | CLU | PGLYRP2 | VCAM1 | 0.692 |
| APOA1 | CPN2 | TAGLN2 | TLN1 | 0.692 |
| APOA4 | CD14 | PGLYRP2 | VCAM1 | 0.692 |
| IGFBP6 | SEPP1 | TLN1 | VCAM1 | 0.691 |
| PGLYRP2 | S100A8 | SEPP1 | VASN | 0.691 |
| CD14 | CD163 | S100A8 | SEPP1 | 0.691 |
| CD14 | CD163 | S100A9 | SEPP1 | 0.691 |
| APOA1 | CLU | IGFBP6 | PFN1 | 0.691 |
| APOA1 | IGFBP6 | MST1 | VCAM1 | 0.691 |
| APOA1 | APOA4 | MST1 | PFN1 | 0.691 |
| APOA1 | S100A9 | VASN | VCAM1 | 0.691 |
| APOA1 | MST1 | S100A8 | SEPP1 | 0.691 |
| APOA4 | MST1 | PGLYRP2 | S100A8 | 0.691 |
| APOA4 | CD163 | IGFBP6 | SEPP1 | 0.690 |
| APOA1 | APOA4 | S100A8 | TAGLN2 | 0.690 |
| CD14 | IGFBP6 | MST1 | S100A8 | 0.690 |
| APOA4 | MST1 | S100A8 | VASN | 0.690 |
| CD14 | CD163 | PFN1 | TAGLN2 | 0.690 |
| APOA4 | CD163 | PGLYRP2 | SEPP1 | 0.689 |
| APOA4 | PGLYRP2 | S100A8 | VASN | 0.689 |
| APOA1 | CLU | IGFBP6 | TAGLN2 | 0.689 |
| APOA1 | CD163 | CPN2 | SEPP1 | 0.688 |
| APOA1 | CD14 | SEPP1 | TLN1 | 0.688 |
| APOA1 | CD14 | CD163 | S100A8 | 0.688 |
| APOA4 | CLU | IGFBP6 | TAGLN2 | 0.688 |
| IGFBP6 | MST1 | TAGLN2 | TLN1 | 0.688 |
| APOA1 | APOA4 | S100A8 | TLN1 | 0.688 |
| APOA1 | APOA4 | S100A9 | TAGLN2 | 0.688 |
| CLU | S100A9 | TAGLN2 | TLN1 | 0.688 |
| APOA4 | CD163 | CLU | PGLYRP2 | 0.688 |
| IGFBP6 | MST1 | PFN1 | TLN1 | 0.687 |
| CLU | CPN2 | VASN | VCAM1 | 0.687 |
| APOA4 | S100A9 | VASN | VCAM1 | 0.687 |
| APOA1 | CPN2 | S100A9 | TLN1 | 0.687 |
| APOA1 | PGLYRP2 | S100A8 | VASN | 0.687 |
| APOA1 | MST1 | SEPP1 | VCAM1 | 0.687 |
| APOA1 | MST1 | TAGLN2 | VCAM1 | 0.687 |
| APOA1 | MST1 | SEPP1 | TLN1 | 0.686 |
| CD163 | IGFBP6 | MST1 | S100A9 | 0.686 |
| CD14 | CD163 | TAGLN2 | VCAM1 | 0.686 |
| APOA4 | CLU | PGLYRP2 | VASN | 0.686 |
| CD14 | MST1 | SEPP1 | TLN1 | 0.685 |
| CPN2 | SEPP1 | VASN | VCAM1 | 0.685 |
| CD163 | IGFBP6 | S100A8 | VCAM1 | 0.685 |
| IGFBP6 | SEPP1 | TAGLN2 | TLN1 | 0.685 |
| APOA1 | APOA4 | S100A9 | TLN1 | 0.685 |
| IGFBP6 | PFN1 | SEPP1 | TLN1 | 0.685 |
| APOA4 | IGFBP6 | TAGLN2 | VASN | 0.684 |
| APOA1 | MST1 | TLN1 | VASN | 0.684 |
| APOA1 | S100A8 | TAGLN2 | TLN1 | 0.684 |
| CLU | PGLYRP2 | S100A9 | VCAM1 | 0.684 |
| CD14 | S100A8 | SEPP1 | VASN | 0.683 |
| IGFBP6 | S100A8 | SEPP1 | VASN | 0.683 |
| CD163 | IGFBP6 | S100A9 | TLN1 | 0.683 |
| APOA4 | CPN2 | IGFBP6 | SEPP1 | 0.683 |
| APOA4 | CD14 | S100A8 | VASN | 0.683 |
| APOA1 | IGFBP6 | S100A9 | VASN | 0.683 |
| CLU | SEPP1 | VASN | VCAM1 | 0.682 |
| CLU | IGFBP6 | SEPP1 | TAGLN2 | 0.682 |
| APOA4 | CLU | IGFBP6 | S100A9 | 0.682 |
| APOA1 | PFN1 | TAGLN2 | VCAM1 | 0.682 |
| CD163 | S100A9 | SEPP1 | VASN | 0.682 |
| CD14 | MST1 | TLN1 | VASN | 0.682 |
| APOA1 | CLU | VASN | VCAM1 | 0.682 |
| CD14 | IGFBP6 | S100A8 | SEPP1 | 0.682 |
| MST1 | S100A9 | SEPP1 | TLN1 | 0.682 |
| CLU | IGFBP6 | S100A9 | VASN | 0.682 |
| APOA1 | TAGLN2 | TLN1 | VCAM1 | 0.682 |
| APOA4 | CLU | PGLYRP2 | VCAM1 | 0.682 |
| CD14 | S100A9 | SEPP1 | VASN | 0.682 |
| APOA1 | IGFBP6 | TLN1 | VCAM1 | 0.682 |
| CLU | CPN2 | TLN1 | VCAM1 | 0.682 |

TABLE 12-continued

HIV+ panels
Combination of Four Candidate Biomarkers

| protein.1 | protein.2 | protein.3 | protein.4 | AUC |
|---|---|---|---|---|
| APOA4 | IGFBP6 | PFN1 | VASN | 0.681 |
| CD163 | CPN2 | PFN1 | TAGLN2 | 0.681 |
| APOA4 | MST1 | SEPP1 | VASN | 0.681 |
| IGFBP6 | SEPP1 | TAGLN2 | VASN | 0.681 |
| APOA4 | PGLYRP2 | S100A8 | SEPP1 | 0.681 |
| APOA4 | SEPP1 | TLN1 | VASN | 0.681 |
| CD163 | CLU | PGLYRP2 | S100A9 | 0.681 |
| APOA1 | APOA4 | CLU | TLN1 | 0.681 |
| CD163 | S100A8 | SEPP1 | VASN | 0.681 |
| APOA1 | APOA4 | SEPP1 | TLN1 | 0.681 |
| CD163 | CPN2 | S100A8 | SEPP1 | 0.681 |
| APOA1 | IGFBP6 | SEPP1 | TAGLN2 | 0.681 |
| APOA1 | CD14 | S100A8 | VASN | 0.680 |
| APOA1 | APOA4 | PGLYRP2 | VCAM1 | 0.680 |
| APOA1 | CLU | PGLYRP2 | VASN | 0.680 |
| APOA1 | CLU | PGLYRP2 | S100A8 | 0.680 |
| IGFBP6 | MST1 | S100A9 | TLN1 | 0.680 |
| APOA1 | APOA4 | MST1 | TAGLN2 | 0.680 |
| APOA1 | CD163 | CPN2 | S100A8 | 0.679 |
| APOA1 | PGLYRP2 | S100A8 | SEPP1 | 0.679 |
| APOA1 | CLU | PGLYRP2 | S100A9 | 0.679 |
| APOA1 | IGFBP6 | SEPP1 | VCAM1 | 0.679 |
| APOA1 | IGFBP6 | MST1 | SEPP1 | 0.679 |
| APOA4 | IGFBP6 | SEPP1 | VCAM1 | 0.678 |
| CLU | IGFBP6 | PFN1 | SEPP1 | 0.678 |
| CD163 | CPN2 | S100A9 | SEPP1 | 0.678 |
| APOA1 | CD14 | CD163 | MST1 | 0.678 |
| APOA1 | CD14 | CD163 | S100A9 | 0.677 |
| APOA4 | PGLYRP2 | SEPP1 | VCAM1 | 0.677 |
| CD14 | CD163 | MST1 | SEPP1 | 0.677 |
| APOA1 | CD14 | TLN1 | VCAM1 | 0.677 |
| APOA4 | CD14 | SEPP1 | VASN | 0.676 |
| APOA1 | APOA4 | CD14 | IGFBP6 | 0.676 |
| APOA4 | PFN1 | TLN1 | VASN | 0.676 |
| CD14 | CD163 | PFN1 | VCAM1 | 0.676 |
| APOA1 | PFN1 | TLN1 | VCAM1 | 0.675 |
| IGFBP6 | S100A9 | SEPP1 | TLN1 | 0.675 |
| CD14 | IGFBP6 | MST1 | SEPP1 | 0.675 |
| PFN1 | SEPP1 | TAGLN2 | TLN1 | 0.675 |
| CLU | PGLYRP2 | S100A8 | VCAM1 | 0.675 |
| APOA1 | CD14 | SEPP1 | VASN | 0.675 |
| CD163 | PGLYRP2 | SEPP1 | VCAM1 | 0.674 |
| APOA4 | CLU | PGLYRP2 | S100A9 | 0.674 |
| IGFBP6 | PFN1 | SEPP1 | VASN | 0.674 |
| CPN2 | PFN1 | TAGLN2 | TLN1 | 0.674 |
| CLU | S100A9 | SEPP1 | TLN1 | 0.674 |
| CD14 | IGFBP6 | SEPP1 | VCAM1 | 0.674 |
| APOA4 | IGFBP6 | S100A8 | VASN | 0.673 |
| CD14 | S100A8 | SEPP1 | TLN1 | 0.672 |
| APOA4 | TAGLN2 | TLN1 | VASN | 0.672 |
| APOA4 | IGFBP6 | PFN1 | TAGLN2 | 0.672 |
| APOA4 | S100A8 | VASN | VCAM1 | 0.672 |
| IGFBP6 | S100A9 | SEPP1 | VASN | 0.672 |
| MST1 | S100A8 | SEPP1 | VCAM1 | 0.672 |
| APOA1 | APOA4 | CD163 | MST1 | 0.672 |
| S100A8 | SEPP1 | TLN1 | VCAM1 | 0.672 |
| APOA1 | CD14 | S100A9 | TLN1 | 0.672 |
| CD14 | IGFBP6 | TLN1 | VCAM1 | 0.672 |
| CD14 | MST1 | PFN1 | TAGLN2 | 0.671 |
| CD14 | IGFBP6 | S100A8 | VCAM1 | 0.671 |
| CD163 | IGFBP6 | S100A9 | SEPP1 | 0.671 |
| CD163 | CLU | PGLYRP2 | S100A8 | 0.670 |
| APOA1 | MST1 | SEPP1 | VCAM1 | 0.670 |
| APOA4 | CLU | PGLYRP2 | S100A8 | 0.670 |
| CD14 | SEPP1 | TLN1 | VCAM1 | 0.670 |
| APOA4 | CD163 | CPN2 | SEPP1 | 0.669 |
| APOA1 | MST1 | PFN1 | TAGLN2 | 0.669 |
| IGFBP6 | SEPP1 | TLN1 | VASN | 0.669 |
| APOA1 | IGFBP6 | S100A9 | SEPP1 | 0.669 |
| CD14 | PFN1 | TAGLN2 | VCAM1 | 0.669 |
| APOA4 | CD14 | CD163 | S100A8 | 0.669 |
| APOA1 | IGFBP6 | TLN1 | VASN | 0.668 |
| APOA1 | IGFBP6 | PFN1 | SEPP1 | 0.668 |
| APOA4 | CLU | TLN1 | VASN | 0.668 |
| CD163 | CLU | PGLYRP2 | VCAM1 | 0.667 |
| APOA1 | IGFBP6 | S100A8 | SEPP1 | 0.667 |
| CD163 | MST1 | SEPP1 | VCAM1 | 0.667 |
| IGFBP6 | MST1 | S100A9 | SEPP1 | 0.667 |
| CLU | S100A8 | TLN1 | VASN | 0.667 |
| APOA1 | CLU | S100A8 | TLN1 | 0.667 |
| APOA1 | APOA4 | CLU | PGLYRP2 | 0.666 |
| APOA4 | IGFBP6 | S100A9 | VASN | 0.666 |
| APOA1 | CLU | SEPP1 | TLN1 | 0.666 |
| APOA1 | MST1 | S100A8 | VCAM1 | 0.666 |
| APOA1 | APOA4 | PGLYRP2 | S100A9 | 0.666 |
| CD14 | CD163 | IGFBP6 | S100A8 | 0.666 |
| APOA4 | IGFBP6 | S100A9 | SEPP1 | 0.665 |
| APOA1 | CD14 | MST1 | S100A8 | 0.665 |
| APOA1 | S100A9 | TAGLN2 | TLN1 | 0.665 |
| APOA4 | IGFBP6 | S100A8 | SEPP1 | 0.665 |
| PGLYRP2 | S100A8 | SEPP1 | VCAM1 | 0.665 |
| CPN2 | S100A8 | SEPP1 | VASN | 0.664 |
| APOA4 | IGFBP6 | SEPP1 | TAGLN2 | 0.664 |
| APOA1 | CD14 | CD163 | SEPP1 | 0.664 |
| APOA1 | CD14 | IGFBP6 | VCAM1 | 0.664 |
| MST1 | PFN1 | TLN1 | VASN | 0.664 |
| CPN2 | SEPP1 | TLN1 | VASN | 0.664 |
| APOA1 | APOA4 | IGFBP6 | TAGLN2 | 0.664 |
| S100A9 | SEPP1 | VASN | VCAM1 | 0.664 |
| IGFBP6 | S100A9 | SEPP1 | VCAM1 | 0.663 |
| APOA1 | SEPP1 | TLN1 | VCAM1 | 0.663 |
| APOA1 | CD163 | CPN2 | S100A9 | 0.663 |
| CD163 | CPN2 | S100A8 | VCAM1 | 0.663 |
| APOA1 | APOA4 | CLU | MST1 | 0.663 |
| CD14 | TAGLN2 | TLN1 | VCAM1 | 0.663 |
| CD14 | MST1 | TAGLN2 | VCAM1 | 0.661 |
| APOA1 | APOA4 | CD163 | CPN2 | 0.661 |
| APOA1 | CD163 | IGFBP6 | VCAM1 | 0.661 |
| CD14 | CD163 | TAGLN2 | TLN1 | 0.660 |
| CPN2 | PFN1 | SEPP1 | TAGLN2 | 0.660 |
| APOA1 | IGFBP6 | PFN1 | TLN1 | 0.660 |
| APOA4 | CD14 | S100A9 | VCAM1 | 0.660 |
| APOA4 | CLU | PFN1 | TLN1 | 0.659 |
| CD14 | IGFBP6 | S100A9 | TLN1 | 0.659 |
| APOA1 | APOA4 | IGFBP6 | PFN1 | 0.659 |
| CLU | CPN2 | SEPP1 | TLN1 | 0.659 |
| PFN1 | SEPP1 | TLN1 | VASN | 0.658 |
| CD14 | IGFBP6 | MST1 | TLN1 | 0.658 |
| CLU | CPN2 | PFN1 | SEPP1 | 0.658 |
| APOA4 | CLU | TAGLN2 | TLN1 | 0.658 |
| APOA4 | PFN1 | SEPP1 | TAGLN2 | 0.658 |
| APOA4 | MST1 | S100A8 | SEPP1 | 0.657 |
| APOA1 | APOA4 | CD163 | IGFBP6 | 0.657 |
| CD163 | IGFBP6 | SEPP1 | VCAM1 | 0.657 |
| APOA4 | CD163 | CPN2 | S100A8 | 0.657 |
| CD163 | CLU | PFN1 | VCAM1 | 0.657 |
| CD14 | CD163 | IGFBP6 | TLN1 | 0.657 |
| APOA1 | APOA4 | PGLYRP2 | S100A8 | 0.657 |
| CD14 | PFN1 | TLN1 | VCAM1 | 0.656 |
| PGLYRP2 | S100A9 | SEPP1 | VCAM1 | 0.656 |
| APOA1 | S100A8 | SEPP1 | TLN1 | 0.656 |
| CD14 | S100A9 | SEPP1 | TLN1 | 0.656 |
| APOA1 | APOA4 | CD14 | VASN | 0.656 |
| APOA4 | CD14 | CD163 | SEPP1 | 0.656 |
| APOA4 | MST1 | S100A9 | SEPP1 | 0.655 |
| CLU | PGLYRP2 | S100A8 | SEPP1 | 0.655 |
| APOA4 | CPN2 | PFN1 | SEPP1 | 0.655 |
| APOA4 | CD163 | CPN2 | S100A9 | 0.655 |
| APOA1 | CD14 | SEPP1 | VCAM1 | 0.655 |
| CLU | PFN1 | SEPP1 | TLN1 | 0.654 |
| APOA4 | CD163 | PGLYRP2 | VCAM1 | 0.654 |
| IGFBP6 | MST1 | TLN1 | VCAM1 | 0.654 |
| CD163 | IGFBP6 | S100A9 | VCAM1 | 0.654 |
| S100A9 | SEPP1 | TLN1 | VCAM1 | 0.653 |
| APOA1 | S100A8 | TLN1 | VCAM1 | 0.653 |
| APOA1 | IGFBP6 | TAGLN2 | TLN1 | 0.653 |
| APOA1 | APOA4 | IGFBP6 | S100A9 | 0.652 |
| CD14 | MST1 | SEPP1 | VCAM1 | 0.652 |
| APOA1 | CPN2 | TLN1 | VASN | 0.652 |
| CD163 | CPN2 | SEPP1 | VCAM1 | 0.652 |

TABLE 12-continued

HIV+ panels
Combination of Four Candidate Biomarkers

| protein.1 | protein.2 | protein.3 | protein.4 | AUC |
|---|---|---|---|---|
| CLU | CPN2 | SEPP1 | TAGLN2 | 0.651 |
| APOA1 | APOA4 | IGFBP6 | S100A8 | 0.651 |
| APOA1 | APOA4 | MST1 | VASN | 0.651 |
| APOA1 | APOA4 | TAGLN2 | TLN1 | 0.651 |
| APOA1 | APOA4 | MST1 | S100A8 | 0.651 |
| SEPP1 | TAGLN2 | TLN1 | VASN | 0.651 |
| APOA4 | IGFBP6 | PFN1 | SEPP1 | 0.650 |
| APOA1 | CPN2 | S100A9 | VCAM1 | 0.650 |
| CD163 | CLU | TAGLN2 | VCAM1 | 0.650 |
| CD163 | IGFBP6 | MST1 | TLN1 | 0.649 |
| APOA1 | MST1 | S100A9 | SEPP1 | 0.649 |
| CD163 | CPN2 | S100A9 | VCAM1 | 0.649 |
| APOA1 | CPN2 | S100A8 | VCAM1 | 0.649 |
| APOA4 | CLU | PGLYRP2 | SEPP1 | 0.648 |
| APOA1 | CD14 | MST1 | S100A9 | 0.648 |
| MST1 | S100A9 | SEPP1 | VCAM1 | 0.647 |
| APOA4 | CLU | PFN1 | SEPP1 | 0.647 |
| CD14 | CD163 | IGFBP6 | MST1 | 0.647 |
| APOA1 | CLU | PGLYRP2 | SEPP1 | 0.647 |
| APOA1 | APOA4 | MST1 | SEPP1 | 0.647 |
| CLU | SEPP1 | TAGLN2 | TLN1 | 0.647 |
| CLU | PGLYRP2 | S100A9 | SEPP1 | 0.647 |
| CD14 | PFN1 | TAGLN2 | TLN1 | 0.646 |
| APOA1 | SEPP1 | TLN1 | VASN | 0.646 |
| APOA1 | CD163 | S100A9 | SEPP1 | 0.646 |
| CLU | S100A9 | TLN1 | VASN | 0.646 |
| APOA4 | CD163 | MST1 | S100A8 | 0.645 |
| APOA1 | APOA4 | TLN1 | VASN | 0.645 |
| APOA1 | CLU | CPN2 | PFN1 | 0.645 |
| APOA4 | CPN2 | S100A8 | VCAM1 | 0.645 |
| APOA1 | APOA4 | MST1 | S100A9 | 0.645 |
| APOA1 | CD14 | MST1 | VASN | 0.645 |
| APOA1 | CPN2 | SEPP1 | VCAM1 | 0.645 |
| CPN2 | S100A8 | SEPP1 | VCAM1 | 0.644 |
| APOA1 | CD163 | CPN2 | VCAM1 | 0.644 |
| APOA4 | CD14 | MST1 | SEPP1 | 0.643 |
| APOA4 | CPN2 | SEPP1 | VCAM1 | 0.643 |
| APOA1 | APOA4 | CPN2 | VCAM1 | 0.643 |
| APOA1 | CLU | IGFBP6 | VASN | 0.642 |
| CPN2 | PFN1 | TLN1 | VASN | 0.642 |
| APOA4 | CD163 | MST1 | S100A9 | 0.642 |
| APOA4 | CLU | SEPP1 | TAGLN2 | 0.642 |
| CD14 | MST1 | PFN1 | TLN1 | 0.641 |
| APOA1 | IGFBP6 | SEPP1 | TLN1 | 0.641 |
| APOA1 | S100A9 | TLN1 | VCAM1 | 0.641 |
| APOA1 | S100A8 | TLN1 | VASN | 0.641 |
| APOA1 | PFN1 | SEPP1 | TLN1 | 0.641 |
| CLU | PFN1 | SEPP1 | TAGLN2 | 0.641 |
| APOA1 | PFN1 | SEPP1 | TAGLN2 | 0.640 |
| APOA4 | CPN2 | SEPP1 | TAGLN2 | 0.640 |
| APOA4 | CD163 | S100A9 | SEPP1 | 0.639 |
| CD163 | CLU | CPN2 | TAGLN2 | 0.639 |
| APOA4 | CPN2 | PFN1 | TAGLN2 | 0.639 |
| APOA4 | CD163 | IGFBP6 | VCAM1 | 0.638 |
| CD14 | IGFBP6 | S100A9 | VCAM1 | 0.638 |
| CD163 | CLU | PFN1 | TAGLN2 | 0.638 |
| APOA1 | CD14 | S100A8 | SEPP1 | 0.638 |
| APOA4 | CPN2 | S100A9 | VCAM1 | 0.638 |
| APOA1 | APOA4 | CD163 | S100A9 | 0.638 |
| APOA1 | CPN2 | PFN1 | TAGLN2 | 0.637 |
| APOA1 | APOA4 | CD163 | SEPP1 | 0.637 |
| APOA1 | APOA4 | PFN1 | TLN1 | 0.636 |
| CPN2 | S100A9 | SEPP1 | VCAM1 | 0.636 |
| CD163 | CLU | CPN2 | SEPP1 | 0.636 |
| CLU | IGFBP6 | SEPP1 | VASN | 0.636 |
| APOA1 | CLU | S100A9 | TLN1 | 0.636 |
| CD14 | IGFBP6 | S100A9 | SEPP1 | 0.636 |
| APOA4 | CD163 | MST1 | VCAM1 | 0.635 |
| CD163 | CLU | CPN2 | PFN1 | 0.635 |
| CD14 | CD163 | PFN1 | TLN1 | 0.635 |
| APOA1 | PFN1 | SEPP1 | VASN | 0.635 |
| APOA1 | CD163 | S100A8 | SEPP1 | 0.634 |
| APOA1 | S100A9 | SEPP1 | TLN1 | 0.634 |
| CD14 | CD163 | IGFBP6 | VCAM1 | 0.634 |
| APOA4 | CD163 | S100A8 | SEPP1 | 0.634 |
| APOA1 | MST1 | TLN1 | VCAM1 | 0.633 |
| APOA1 | CPN2 | PFN1 | SEPP1 | 0.633 |
| APOA4 | CLU | IGFBP6 | VASN | 0.633 |
| APOA4 | CD14 | CD163 | MST1 | 0.632 |
| APOA1 | APOA4 | PFN1 | TAGLN2 | 0.632 |
| APOA4 | CD163 | CPN2 | VCAM1 | 0.632 |
| APOA1 | CD163 | CLU | SEPP1 | 0.631 |
| APOA1 | CLU | CPN2 | TLN1 | 0.631 |
| APOA4 | CD14 | S100A8 | VCAM1 | 0.631 |
| CPN2 | TAGLN2 | TLN1 | VASN | 0.631 |
| APOA1 | CLU | IGFBP6 | SEPP1 | 0.630 |
| CLU | CPN2 | S100A9 | TLN1 | 0.630 |
| APOA1 | SEPP1 | TAGLN2 | VASN | 0.630 |
| APOA4 | MST1 | S100A8 | VCAM1 | 0.630 |
| APOA1 | CLU | CPN2 | TAGLN2 | 0.629 |
| CLU | PFN1 | TAGLN2 | TLN1 | 0.629 |
| APOA1 | CD14 | S100A8 | VCAM1 | 0.628 |
| APOA1 | APOA4 | CLU | IGFBP6 | 0.628 |
| APOA1 | PFN1 | TLN1 | VASN | 0.628 |
| APOA4 | PFN1 | TAGLN2 | VASN | 0.627 |
| APOA4 | MST1 | S100A9 | VCAM1 | 0.627 |
| APOA4 | CLU | PFN1 | VASN | 0.627 |
| APOA1 | APOA4 | CD14 | S100A9 | 0.626 |
| CD163 | CLU | CPN2 | S100A8 | 0.626 |
| APOA1 | S100A9 | TLN1 | VASN | 0.625 |
| CD14 | IGFBP6 | MST1 | S100A9 | 0.625 |
| CLU | CPN2 | TAGLN2 | TLN1 | 0.625 |
| APOA1 | SEPP1 | TAGLN2 | TLN1 | 0.624 |
| APOA4 | CLU | CPN2 | PFN1 | 0.624 |
| CD163 | S100A8 | TLN1 | VCAM1 | 0.624 |
| APOA4 | CD14 | SEPP1 | VCAM1 | 0.624 |
| APOA1 | CD163 | SEPP1 | VCAM1 | 0.624 |
| CD14 | CD163 | SEPP1 | VCAM1 | 0.623 |
| APOA1 | IGFBP6 | SEPP1 | VASN | 0.623 |
| APOA1 | CD14 | MST1 | SEPP1 | 0.623 |
| APOA1 | APOA4 | CD163 | S100A8 | 0.623 |
| APOA4 | CD163 | CLU | CPN2 | 0.623 |
| CD14 | CD163 | IGFBP6 | S100A9 | 0.623 |
| APOA4 | CLU | CPN2 | VCAM1 | 0.623 |
| APOA4 | CD163 | CLU | S100A8 | 0.623 |
| APOA1 | APOA4 | IGFBP6 | VCAM1 | 0.623 |
| APOA4 | CLU | SEPP1 | VCAM1 | 0.622 |
| APOA1 | MST1 | S100A9 | VCAM1 | 0.621 |
| APOA4 | CD14 | S100A9 | SEPP1 | 0.621 |
| CD14 | MST1 | TAGLN2 | TLN1 | 0.621 |
| APOA4 | CLU | PFN1 | TAGLN2 | 0.620 |
| CLU | SEPP1 | TLN1 | VASN | 0.620 |
| CLU | TAGLN2 | TLN1 | VASN | 0.620 |
| APOA1 | CLU | PFN1 | SEPP1 | 0.619 |
| APOA4 | CPN2 | TAGLN2 | VASN | 0.619 |
| APOA4 | PFN1 | SEPP1 | VASN | 0.619 |
| APOA1 | PFN1 | TAGLN2 | TLN1 | 0.619 |
| CD14 | CD163 | S100A8 | TLN1 | 0.618 |
| CLU | PFN1 | SEPP1 | VASN | 0.618 |
| CLU | CPN2 | PFN1 | TLN1 | 0.618 |
| APOA4 | CPN2 | PFN1 | VASN | 0.618 |
| APOA1 | CLU | SEPP1 | VCAM1 | 0.618 |
| APOA4 | CD163 | CLU | S100A9 | 0.618 |
| APOA1 | APOA4 | PFN1 | SEPP1 | 0.617 |
| CPN2 | SEPP1 | TAGLN2 | VASN | 0.617 |
| APOA4 | CLU | CPN2 | TAGLN2 | 0.616 |
| APOA4 | CLU | TAGLN2 | VASN | 0.616 |
| CD14 | S100A8 | TLN1 | VCAM1 | 0.616 |
| APOA4 | CLU | IGFBP6 | SEPP1 | 0.616 |
| APOA1 | APOA4 | PFN1 | VASN | 0.615 |
| PFN1 | SEPP1 | TAGLN2 | VASN | 0.615 |
| CPN2 | S100A9 | SEPP1 | VASN | 0.615 |
| APOA1 | S100A8 | SEPP1 | VCAM1 | 0.615 |
| APOA4 | CD163 | S100A9 | VCAM1 | 0.615 |
| APOA4 | CD163 | CLU | SEPP1 | 0.615 |
| CPN2 | PFN1 | SEPP1 | VASN | 0.614 |
| CPN2 | PFN1 | TAGLN2 | VASN | 0.614 |
| APOA4 | CLU | S100A8 | VCAM1 | 0.614 |
| CLU | CPN2 | TLN1 | VASN | 0.614 |
| APOA1 | APOA4 | CD14 | CD163 | 0.614 |

TABLE 12-continued

HIV+ panels
Combination of Four Candidate Biomarkers

| protein.1 | protein.2 | protein.3 | protein.4 | AUC |
|---|---|---|---|---|
| APOA1 | CD14 | S100A9 | VCAM1 | 0.613 |
| APOA4 | CD14 | S100A8 | SEPP1 | 0.613 |
| APOA1 | CPN2 | SEPP1 | TAGLN2 | 0.613 |
| CLU | CPN2 | PFN1 | TAGLN2 | 0.613 |
| CLU | CPN2 | PFN1 | VASN | 0.613 |
| APOA1 | CD14 | S100A9 | SEPP1 | 0.611 |
| APOA1 | APOA4 | CPN2 | PFN1 | 0.611 |
| CD163 | CLU | S100A9 | SEPP1 | 0.610 |
| APOA1 | APOA4 | IGFBP6 | VASN | 0.610 |
| APOA1 | PFN1 | TAGLN2 | VASN | 0.610 |
| CLU | SEPP1 | TAGLN2 | VASN | 0.609 |
| APOA1 | CD163 | CLU | S100A8 | 0.609 |
| CD14 | S100A9 | SEPP1 | VCAM1 | 0.609 |
| APOA1 | APOA4 | CD14 | S100A8 | 0.608 |
| CLU | CPN2 | SEPP1 | VCAM1 | 0.608 |
| APOA4 | CD14 | MST1 | VCAM1 | 0.608 |
| CLU | CPN2 | S100A8 | VCAM1 | 0.608 |
| APOA1 | CD14 | CD163 | VCAM1 | 0.608 |
| CD163 | CLU | S100A8 | SEPP1 | 0.608 |
| APOA4 | IGFBP6 | SEPP1 | VASN | 0.608 |
| APOA1 | CPN2 | PFN1 | VASN | 0.608 |
| CD14 | S100A8 | SEPP1 | VCAM1 | 0.607 |
| MST1 | S100A8 | TLN1 | VCAM1 | 0.607 |
| APOA4 | CD14 | MST1 | S100A9 | 0.607 |
| APOA4 | SEPP1 | TAGLN2 | VASN | 0.606 |
| APOA1 | CLU | CPN2 | VCAM1 | 0.606 |
| CD163 | MST1 | PFN1 | TAGLN2 | 0.606 |
| APOA1 | TAGLN2 | TLN1 | VASN | 0.606 |
| APOA1 | APOA4 | CD163 | CLU | 0.605 |
| CLU | S100A8 | SEPP1 | VCAM1 | 0.605 |
| APOA1 | CD163 | S100A8 | VCAM1 | 0.604 |
| APOA4 | CD14 | MST1 | S100A8 | 0.604 |
| APOA1 | CLU | PFN1 | TAGLN2 | 0.603 |
| APOA1 | CLU | S100A8 | VCAM1 | 0.603 |
| APOA1 | CLU | PFN1 | TLN1 | 0.603 |
| APOA1 | CLU | SEPP1 | TAGLN2 | 0.603 |
| APOA4 | CLU | S100A9 | VCAM1 | 0.603 |
| APOA1 | CLU | PFN1 | VASN | 0.602 |
| APOA4 | S100A9 | SEPP1 | VCAM1 | 0.602 |
| APOA1 | APOA4 | SEPP1 | TAGLN2 | 0.601 |
| APOA1 | CD163 | CLU | VCAM1 | 0.601 |
| CLU | PFN1 | TLN1 | VASN | 0.601 |
| APOA1 | CPN2 | TAGLN2 | VASN | 0.600 |
| APOA4 | CD14 | CD163 | VCAM1 | 0.600 |
| APOA1 | S100A9 | SEPP1 | VCAM1 | 0.600 |
| CLU | CPN2 | TAGLN2 | VASN | 0.600 |
| APOA1 | CD163 | S100A9 | VCAM1 | 0.600 |
| APOA1 | APOA4 | MST1 | VCAM1 | 0.600 |
| APOA1 | APOA4 | SEPP1 | VCAM1 | 0.600 |
| CD163 | CLU | CPN2 | S100A9 | 0.600 |
| APOA1 | CD163 | CLU | S100A9 | 0.599 |
| APOA4 | CPN2 | S100A8 | SEPP1 | 0.599 |
| APOA1 | CD14 | MST1 | VCAM1 | 0.599 |
| APOA1 | APOA4 | S100A9 | VCAM1 | 0.599 |
| APOA4 | CD163 | S100A8 | VCAM1 | 0.599 |
| APOA1 | APOA4 | CD14 | MST1 | 0.598 |
| PFN1 | TAGLN2 | TLN1 | VASN | 0.598 |
| CD14 | CD163 | TLN1 | VCAM1 | 0.598 |
| APOA4 | S100A8 | SEPP1 | VCAM1 | 0.598 |
| APOA1 | CPN2 | S100A8 | VASN | 0.598 |
| CD163 | CLU | SEPP1 | VCAM1 | 0.597 |
| CD163 | MST1 | S100A8 | TLN1 | 0.597 |
| APOA4 | CPN2 | S100A8 | VASN | 0.597 |
| APOA1 | CLU | TAGLN2 | TLN1 | 0.595 |
| APOA1 | APOA4 | CLU | PFN1 | 0.594 |
| CD163 | MST1 | TAGLN2 | VCAM1 | 0.594 |
| APOA1 | APOA4 | IGFBP6 | SEPP1 | 0.593 |
| APOA1 | CPN2 | S100A9 | VASN | 0.593 |
| CD14 | CD163 | S100A9 | TLN1 | 0.593 |
| APOA1 | CLU | TLN1 | VASN | 0.593 |
| APOA1 | APOA4 | TAGLN2 | VASN | 0.592 |
| APOA1 | APOA4 | CD14 | SEPP1 | 0.591 |
| APOA1 | APOA4 | CLU | VCAM1 | 0.591 |
| APOA1 | APOA4 | CPN2 | S100A8 | 0.590 |
| CD163 | S100A9 | TLN1 | VCAM1 | 0.589 |
| APOA1 | APOA4 | S100A8 | VCAM1 | 0.589 |
| APOA4 | CPN2 | S100A9 | VASN | 0.588 |
| APOA1 | APOA4 | CPN2 | TAGLN2 | 0.588 |
| CD14 | MST1 | S100A8 | SEPP1 | 0.588 |
| CD14 | MST1 | S100A9 | SEPP1 | 0.588 |
| CD163 | CLU | CPN2 | VCAM1 | 0.587 |
| APOA1 | APOA4 | CLU | TAGLN2 | 0.587 |
| CD14 | S100A9 | TLN1 | VCAM1 | 0.587 |
| CLU | S100A9 | SEPP1 | VCAM1 | 0.586 |
| CLU | CPN2 | S100A9 | VCAM1 | 0.586 |
| CD163 | PFN1 | TAGLN2 | TLN1 | 0.585 |
| MST1 | PFN1 | TAGLN2 | VCAM1 | 0.585 |
| APOA1 | CPN2 | SEPP1 | VASN | 0.585 |
| CD163 | CLU | S100A8 | VCAM1 | 0.584 |
| APOA4 | CD163 | SEPP1 | VCAM1 | 0.584 |
| CD163 | TAGLN2 | TLN1 | VCAM1 | 0.584 |
| APOA4 | CPN2 | S100A9 | SEPP1 | 0.584 |
| CLU | CPN2 | S100A8 | SEPP1 | 0.583 |
| APOA4 | CD163 | CLU | VCAM1 | 0.582 |
| CLU | PFN1 | TAGLN2 | VASN | 0.581 |
| CD163 | PFN1 | TAGLN2 | VCAM1 | 0.581 |
| APOA1 | CPN2 | S100A8 | SEPP1 | 0.581 |
| APOA4 | CPN2 | SEPP1 | VASN | 0.580 |
| APOA1 | CLU | S100A9 | VCAM1 | 0.580 |
| APOA1 | APOA4 | CPN2 | S100A9 | 0.579 |
| APOA1 | APOA4 | CD14 | VCAM1 | 0.578 |
| APOA1 | CLU | TAGLN2 | VASN | 0.578 |
| CD14 | MST1 | S100A8 | TLN1 | 0.577 |
| CD163 | MST1 | PFN1 | TLN1 | 0.576 |
| CD163 | MST1 | PFN1 | VCAM1 | 0.576 |
| CLU | CPN2 | S100A9 | SEPP1 | 0.576 |
| APOA1 | APOA4 | CD163 | VCAM1 | 0.575 |
| APOA1 | S100A8 | SEPP1 | VASN | 0.574 |
| CD163 | MST1 | TAGLN2 | TLN1 | 0.574 |
| APOA1 | CPN2 | S100A9 | SEPP1 | 0.571 |
| CD163 | PFN1 | TLN1 | VCAM1 | 0.570 |
| CLU | S100A8 | SEPP1 | VASN | 0.570 |
| APOA4 | S100A8 | SEPP1 | VASN | 0.570 |
| CLU | CPN2 | SEPP1 | VASN | 0.569 |
| CD163 | CLU | S100A9 | VCAM1 | 0.569 |
| APOA4 | S100A9 | SEPP1 | VASN | 0.569 |
| MST1 | PFN1 | TAGLN2 | TLN1 | 0.568 |
| MST1 | S100A9 | TLN1 | VCAM1 | 0.567 |
| CLU | S100A9 | SEPP1 | VASN | 0.566 |
| MST1 | TAGLN2 | TLN1 | VCAM1 | 0.566 |
| APOA1 | S100A9 | SEPP1 | VASN | 0.566 |
| CD163 | MST1 | S100A9 | TLN1 | 0.564 |
| APOA1 | CLU | CPN2 | VASN | 0.564 |
| CD14 | CD163 | MST1 | TLN1 | 0.564 |
| PFN1 | TAGLN2 | TLN1 | VCAM1 | 0.563 |
| CD163 | S100A8 | SEPP1 | VCAM1 | 0.562 |
| APOA1 | CLU | CPN2 | S100A8 | 0.562 |
| CD163 | S100A9 | SEPP1 | VCAM1 | 0.561 |
| APOA1 | CLU | SEPP1 | VASN | 0.559 |
| APOA1 | APOA4 | CPN2 | VASN | 0.558 |
| APOA1 | APOA4 | S100A8 | SEPP1 | 0.556 |
| CLU | CPN2 | S100A8 | VASN | 0.556 |
| CD14 | MST1 | TLN1 | VCAM1 | 0.552 |
| APOA4 | CLU | CPN2 | S100A8 | 0.550 |
| APOA1 | CLU | CPN2 | S100A9 | 0.550 |
| APOA1 | CLU | CPN2 | SEPP1 | 0.550 |
| APOA4 | CLU | CPN2 | SEPP1 | 0.549 |
| APOA1 | APOA4 | S100A9 | SEPP1 | 0.547 |
| APOA1 | APOA4 | S100A8 | VASN | 0.547 |
| APOA1 | APOA4 | SEPP1 | VASN | 0.546 |
| MST1 | PFN1 | TLN1 | VCAM1 | 0.545 |
| APOA4 | CLU | SEPP1 | VASN | 0.544 |
| APOA1 | APOA4 | CPN2 | SEPP1 | 0.544 |
| CD14 | MST1 | S100A8 | VCAM1 | 0.543 |
| APOA4 | CLU | CPN2 | S100A9 | 0.543 |
| APOA1 | APOA4 | S100A9 | VASN | 0.543 |
| APOA1 | APOA4 | CLU | CPN2 | 0.543 |
| APOA1 | CLU | S100A8 | SEPP1 | 0.542 |
| APOA4 | CLU | S100A8 | SEPP1 | 0.542 |
| CLU | CPN2 | S100A9 | VASN | 0.542 |

TABLE 12-continued

HIV+ panels
Combination of Four Candidate Biomarkers

| protein.1 | protein.2 | protein.3 | protein.4 | AUC |
|---|---|---|---|---|
| CD14 | MST1 | S100A9 | TLN1 | 0.540 |
| APOA4 | CLU | CPN2 | VASN | 0.540 |
| APOA4 | CLU | S100A9 | SEPP1 | 0.537 |
| APOA4 | CLU | S100A8 | VASN | 0.536 |
| CD163 | MST1 | TLN1 | VCAM1 | 0.530 |
| APOA4 | CLU | S100A9 | VASN | 0.529 |
| CD14 | MST1 | S100A9 | VCAM1 | 0.529 |
| APOA1 | CLU | S100A9 | SEPP1 | 0.529 |
| APOA1 | CLU | S100A8 | VASN | 0.523 |
| CD14 | CD163 | S100A8 | VCAM1 | 0.519 |
| CD14 | CD163 | MST1 | S100A8 | 0.514 |
| APOA1 | CLU | S100A9 | VASN | 0.514 |
| CD14 | CD163 | S100A9 | VCAM1 | 0.513 |
| APOA1 | APOA4 | CLU | S100A8 | 0.511 |
| APOA1 | APOA4 | CLU | SEPP1 | 0.509 |
| APOA1 | APOA4 | CLU | S100A9 | 0.508 |
| CD163 | MST1 | S100A8 | VCAM1 | 0.507 |
| CD14 | CD163 | MST1 | VCAM1 | 0.504 |
| APOA1 | APOA4 | CLU | VASN | 0.502 |
| CD14 | CD163 | MST1 | S100A9 | 0.490 |
| CD163 | MST1 | S100A9 | VCAM1 | 0.471 |

EQUIVALENTS

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2, etc., or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

INCORPORATION BY REFERENCE

The contents of all references, including patents and patent applications, cited throughout this application are hereby incorporated herein by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

We claim:

1. A method for determining whether a subject suspected of having active tuberculosis (TB) has active TB, the method comprising
determining the level of three or more markers selected from the group consisting of SELL, QSOX1, CD14, PEPD, PFN1, CPN2, TAGLN2, VASN, PGLYRP2, IGFBP6, SEPP1, and LGALS3BP in a fluid sample(s) obtained from the subject
wherein the determining of the level of the three or more markers in the subject sample(s) is performed using mass spectrometry or immunoassay; and
comparing the level of the three or more markers in the subject sample(s) with a control level of the three or more markers, wherein the control level of the three or more markers is the level of the three or more markers in a fluid sample that is the same type of fluid sample as the subject fluid sample and is the level in a subject that has latent TB; the level in a subject that has an other respiratory disease (ORD); an average level in a fluid sample from a subject that has latent TB; an average level in a fluid sample from a subject that has an ORD; and/or the level in a fluid sample previously obtained from the subject,
wherein a difference in the level of the three or more markers in the subject sample(s) as compared to the control level of the three or more markers indicates that the subject has active TB;
wherein the difference in the level is an increased level of SELL, CD14, PFN1, IGFBP6, LGALS3BP, and/or TAGLN2 in the subject sample(s) relative to the control level of the corresponding marker, and/or a decreased level of PEPD, QSOX1, CPN2, VASN, PGLYRP2, and/or SEPP1 in the subject sample(s) relative to the control level of the corresponding marker,
thereby determining whether the subject suspected of having active TB has active TB.

2. A method for monitoring the effectiveness of a treatment in a subject having active tuberculosis (TB), the method comprising
determining the level of three or more markers selected from the group consisting of SELL, QSOX1, CD14, PEPD, PFN1, CPN2, TAGLN2, VASN, PGLYRP2, IGFBP6, SEPP1, and LGALS3BP in a first fluid sample(s) obtained from the subject prior to the initiation of the treatment;
wherein the determining of the level of the three or more markers in the first fluid sample(s) is performed using mass spectrometry or immunoassay;
determining the level of the three or more markers in a second fluid sample(s) obtained from the subject after at least a portion of the treatment has been administered, wherein the second fluid sample is the same type of fluid sample as the first fluid sample;
wherein the determining of the level of the three or more markers in the second fluid sample(s) is performed using a technique selected from the group consisting of mass spectrometry or immunoassay; and
comparing the level of the three or more markers in the first fluid sample(s) with a level of the three or more markers in the second fluid sample(s), wherein a difference in the level of the three or more markers in the first fluid sample(s) as compared to the level of the three or more markers in the second fluid sample(s) indicates that the treatment is effective;
wherein the difference in the level is a decreased level of SELL, CD14, PFN1, IGFBP6, LGALS3BP, and/or TAGLN2 in the second sample(s) relative to the level of the corresponding marker in the first sample(s), and/or an increased level of PEPD, QSOX1, CPN2, VASN, PGLYRP2, and/or SEPP1 in the second sample(s) relative to the level of the corresponding marker in the first sample(s), thereby monitoring the effectiveness of a treatment in the subject having active TB.

3. The method of claim 1 or 2, wherein the subject is HIV negative (HIV−).

4. The method of claim 1 or 2, wherein the subject resides in North America or Europe.

5. The method of claim 1 or 2, further comprising determining the level of one or more markers selected from the group consisting of APOE, SELL, TNXB, COMP, LUM, PGLYRP2, HABP2, LRG1, QSOX1, S100A8, APOC3, LCP1, VASN, PFN1, IGFBP6, LRG1, PGLYRP2, APOA4, BCHE, PI16, SEPP1, APOA1, IGFALS, CD14, TAGLN2, CPN2, APOC1, PEPD, GP1BA and PTGDS in a sample(s) obtained from the subject.

6. The method of claim 1 or 2, further comprising determining the level of one or more markers selected from the group consisting of CPB2, GP1BA, GP5, GPX3, PROCR, VWF, ATRN, CD14, DBH, SELL, VCAM1, S100A8, S100A9, CD163, CPN1, FCN3, HIST2H2BE, KNG1, MASP1, MASP2, PROS1, YWHAZ, CA1, ORM1, PDLIM1, PGLYRP2, LCAT, LPA, PCSK9, PON1, PTGDS, APOA1, APOA4, APOC1, APOC3, APOE, ANPEP, BCHE, BTD, CDH5, CLEC3B, CLU, CNTN1, ECM1, GPLD1, HABP2, HGFAC, HYOU1, IGFALS, IGFBP3, IGFBP6, LCP1, LGALS3BP, LUM, MINPP1, MST1, NCAM1, NID1, PEPD, PFN1, PRG4, QSOX1, SEPP1, SHBG, SPARC, TGFBI, THBS1, TLN1, TNXB, VASN, VTN, YWHAE, CA2, CKM, CNDP1, COMP, IGF2, LRG1, PI16, PRDX2, PTPRG, SPP2, TAGLN2, ZYX, MTB81, MTB51, CACNA2D1, CPN2, and MAN1A1 in a sample(s) obtained from the subject.

7. The method of claim 1 or 2, wherein the combination of markers has an area under the curve (AUC) of about 0.85 to about 1.00.

8. The method of claim 1 or 2, wherein the immunoassay comprises contacting the subject sample(s) with antibodies, or antigen-binding fragments thereof, that specifically bind to the corresponding three or more markers.

9. The method of claim 1 or 2, wherein the mass spectrometry comprises ionizing the three or more markers in the subject sample(s).

10. The method of claim 1, wherein the subject suspected of having active TB was previously diagnosed as having latent TB.

11. The method of claim 1 or 2, wherein the subject is HIV positive (HIV+).

12. The method of claim 1 or 2, wherein the subject is HIV negative (HIV−) and the markers comprise SELL, QSOX1, CD14, and PEPD.

13. The method of claim 1 or 2, wherein the subject is HIV positive (HIV+) and the markers comprise SELL, QSOX1, CD14, PFN1, CPN2, TAGLN2, VASN, PGLYRP2, IGFBP6, SEPP1, and LGALS3BP.

* * * * *